(12) United States Patent
Stevens et al.

(10) Patent No.: US 8,252,899 B2
(45) Date of Patent: Aug. 28, 2012

(54) METHODS AND COMPOSITIONS FOR OBTAINING HIGH-RESOLUTION CRYSTALS OF MEMBRANE PROTEINS

(75) Inventors: Raymond C. Stevens, La Jolla, CA (US); Michael A. Hanson, San Marcos, CA (US); Vadim Cherezov, San Diego, CA (US); Peter Kuhn, Solana Beach, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 12/739,134

(22) PCT Filed: Oct. 22, 2008

(86) PCT No.: PCT/US2008/080847
§ 371 (c)(1),
(2), (4) Date: Sep. 23, 2010

(87) PCT Pub. No.: WO2009/055512
PCT Pub. Date: Apr. 30, 2009

(65) Prior Publication Data
US 2011/0031438 A1 Feb. 10, 2011

Related U.S. Application Data

(60) Provisional application No. 60/999,951, filed on Oct. 22, 2007, provisional application No. 61/000,325, filed on Oct. 24, 2007, provisional application No. 61/060,107, filed on Jun. 9, 2008, provisional application No. 61/194,961, filed on Oct. 1, 2008.

(51) Int. Cl.
*C07K 1/00* (2006.01)
*C07K 14/00* (2006.01)
*C12N 9/00* (2006.01)

(52) U.S. Cl. .................. 530/350; 530/419; 435/183

(58) Field of Classification Search .................. None
See application file for complete search history.

(56) References Cited

U.S. PATENT DOCUMENTS

| 6,448,377 | B1 | 9/2002 | Kobilka et al. |
| 7,790,850 | B2 * | 9/2010 | Kobilka et al. ............... 530/350 |
| 2005/0124792 | A1 | 6/2005 | Palczewski et al. |
| 2006/0094119 | A1 | 5/2006 | Ismagilov et al. |
| 2006/0188964 | A1 | 8/2006 | Mancia et al. |
| 2007/0031926 | A1 | 2/2007 | Linden et al. |

FOREIGN PATENT DOCUMENTS
WO    WO 2006/036772    * 6/2006

OTHER PUBLICATIONS

European Extended Search Report, European Application No. 08841630.0, Jul. 18, 2011, 7 pages.

(Continued)

*Primary Examiner* — Nashaat Nashed
(74) *Attorney, Agent, or Firm* — Fenwick & West LLP

(57) ABSTRACT

The invention describes compositions and method useful for the crystallization of membrane proteins.

**14 Claims, 27 Drawing Sheets
(11 of 27 Drawing Sheet(s) Filed in Color)**

OTHER PUBLICATIONS

Katona, G. et al., "Lipidic Cubic Phase Crystal Structure of the Photosynthetic Reaction Centre from Rhodobacter Sphaeroides at 2.35Å Resolution," Journal of Molecular Biology, Aug. 15, 2003, pp. 681-692, vol. 331, No. 3.

Navarro, J. et al., "Receptor-Dependent G-Protein Activation in Lipidic Cubic Phase," Biopolymers, Jan. 2002, pp. 167-177, vol. 67, No. 3.

Rummel, G., "Lipidic Cubic Phases: New Matrices for the Three-Dimensional Crystallization of Membrane Proteins," Journal of Structural Biology, Jan. 1998, pp. 82-91, vol. 121, No. 2.

Angers, D. et al., "Detection of $\beta_2$-Adrenergic Receptor Dimerization in Living Cells Using Bioluminescence Resonance Energy Transfer (BRET)," Proc. Natl. Acad. Sci., Mar. 28, 2000, pp. 3684-3689, vol. 97, No. 7.

Bissantz, C. et al., "Protein-Based Virtual Screening of Chemical Databases. II. Are Homology Models of G-Protein Coupled Receptors Suitable Targets?" Protein: Structure, Function, and Genetics, 2003, pp. 5-25, vol. 50.

Caffrey, M., "A Lipid's Eye View of Membrane Protein Crystallization in Mesophases," Current Opinion in Structural Biology, 2000, pp. 486-497. vol. 10.

Caron, M.C. et al., "Catecholamine Receptors: Structure, Function, and Regulation," Recent Progress in Hormone Research, 1993, pp. 277-290, vol. 48.

Chelikani, P. et al., "Role of Group-Conserved Residues in the Helical Core of $\beta_2$-Adrenergic Receptor," PNAS, Apr. 24, 2007, pp. 7027-7032, vol. 104, No. 17.

Cheng, A. et al., "A Simple Mechanical Mixer for Small Viscous Lipid-Containing Samples," Chemistry and Physics of Lipids, 1998, pp. 11-21, vol. 95.

Cherezov, V. et al., "Membrane Protein Crystallization in Meso: Lipid Type-Tailoring of the Cubic Phase," Biophysical Journal, Dec. 2002, pp. 3393-3407, vol. 83.

Cherezov, V. et al., "A Robotic System for Crystallizing Membrane and Soluble Proteins in Lipidic Mesophases," Acta Crystallographica Section D, Biological Crystallography, 2004, pp. 1795-1807, vol. D 60.

Cherezov, V. et al., "Nano-Volume Plates with Excellent Optical Properties for Fast, Inexpensive Crystallization Screening of Membrane Proteins," Journal of Applied Crystallography, 2003, pp. 1372-1377, vol. 36.

Cherezov, V. et al., "Room to Move: Crystallizing Membrane Proteins in Swollen Lipidic Mesophases," J. Mol. Bol., 2006, pp. 1605-1618, vol. 357.

Cherezov, V. et al., "In Meso Structure of the Cobalamin Transporter, BtuB, at 1.96 Å Resolution," J. Mol. Biol., 2006, pp. 716-734, vol. 364.

Cherezov, V. et al., "High Resolution Crystal Structure of an Engineered Human $\beta_2$-Adrenergic G Protein-Coupled Receptor," Science, Nov. 23, 2007, pp. 1258-1265, vol. 318, No. 5854.

Deisenhofer, J., "The Photosynthetic Reaction Centre from the Purple Bacterium *Rhodopseudomonas viridis*," The EMBO Journal, 1989, pp. 2149-2170, vol. 8, No. 8.

Deupi, X. et al., "Activation of G Protein-Coupled Receptors," Advances in Protein Chemistry, 2007, pp. 137-166, vol. 74.

Engel, C.K. et al., "Insertion of Carrier Proteins into Hydrophilic Loops of the *Escherichia coli* Lactose Permease," Biochimica et Biophysica Acta, 2002, pp. 38-46, vol. 1564, Issue 1.

Freddolino, P.L. et al., "Predicted 3D Structure for the Human $\beta_2$ Adrenergic Receptor and Its Binding Site for Agonists and Antagonists," PNAS, Mar. 2, 2004, pp. 2736-2741, vol. 101, No. 9.

Fredriksson, R. et al., "The G-Protein-Coupled Receptors in the Human Genome Form Five Main Families. Phylogenetic Analysis, Paralogon Groups, and Fingerprints," Molecular Pharmacology, 2003, pp. 1256-1272, vol. 63, No. 6.

Furse, K.E. et al., "Three-Dimensional Models for $\beta_2$-Adrenergic Receptor Complexes with Agonists and Antagonists," J. Med. Chem., 2003, pp. 4450-4462, vol. 46.

Gouldson, P.R. et al., "Toward the Active Conformations of Rhodopsin and the $\beta_2$-Adrenergic Receptor," Proteins: Structure, Function, and Bioinformatics, 2004, pp. 67-84, vol. 56.

Hanson et al., "A Specific Cholesterol Binding Site is Established by the 2.8A Structure of the Human Beta-2-Andrenergic Receptor in an Alternate Crystal Form," Structure, Jun. 2008, pp. 897-905, vol. 16, No. 6.

Hein, L. et al., "Adrenergic Receptors, From Molecular Structure to in vivo Function," Trends Cardiovasc. Med., 1997, pp. 137-145, vol. 7, No. 5.

Horn, F. et al., "GPCRDB Information System for G Protein-Coupled Receptors," Nucleic Acids Research, 2003, pp. 294-297, vol. 31, No. 1.

Jaakola, B. et al., "The 2.6 Angstrom Crystal Structure of a Human $A_{2A}$ Adenosine Receptor Bound to an Antagonist," Science, Nov. 21, 2008, pp. 1211-1217, vol. 322, No. 5905.

Javitch, J.A., "The Ants Go Marching Two by Two: Oligomeric Structure of G-Protein-Coupled Receptors," Molecular Pharmacology, 2004, pp. 1077-1082, vol. 66, No. 5.

Katragadda, M. et al., "Structural Studies of the Putative Helix 8 in the Human $\beta_2$ Adrenergic Receptor: an NMR Study," Biochimica et Biophysica Acta, 2004, pp. 74-81, vol. 1663.

Kobilka, B., Adrenergic Receptors as Models for G Protein-Coupled Receptors, Annu. Rev. Neurosci., 1992, pp. 87-114, vol. 15.

Kobilka, B.K. et al, "Conformational Complexity of G-Protein-Coupled Receptors," Trends in Pharmacological Sciences, Epub Jul. 13, 2007, Aug. 2007, pp. 397-406, vol. 28, No. 8.

Kobilka, B.K., "G Protein Coupled Receptor Structure and Activation," Biochimica et Biophysica Acta, Epub Nov. 15, 2006, 2007, pp. 794-807, vol. 1768, No. 4.

Landau, E.M. et al., "Lipidic Cubic Phases: A Novel Concept for the Crystallization of Membrane Proteins," Proc. Natl. Acad. Sci., Dec. 1996, pp. 14532-14535, vol. 93.

Lefkowitz, R.J., "The Superfamily of Heptahelical Receptors," Nature Cell Biology, Jul. 2000, pp. E133-E136, vol. 2.

Luecke, H. et al., "Crystal Structure of Sensory Rhodopsin II at 2.4 A: Insights into Color Tuning and Transducer Interaction," Sciencexpress, Jul. 21, 2001, 8 pages.

Mercier, J.-F. et al., "Quantitative Assessment of $\beta_1$- and $\beta_2$-Adrenergic Receptor Homo- and Heterodimerization by Bioluminescence Resonance Energy Transfer," The Journal of Biological Chemistry, Nov. 22, 2002, pp. 44925-44931, vol. 277, No. 47.

Mialet-Perez, J. et al., "A Primate-Dominant Third Glycosylation Site of the $\beta_2$-Adrenergic Receptor Routes Receptors to Degradation During Agonist Regulation," The Journal of Biological Chemistry, Sep. 10, 2004, pp. 38603-38607, vol. 279, No. 37.

Ostrom, R.S. et al., "The Evolving Role of Lipid Rafts and Caveolae in G Protein-Coupled Receptor Signaling: Implications for Molecular Pharmacology," British Journal of Pharmacology, Sep. 2004, pp. 235-245, vol. 143.

Palczewski, K., "G Protein-Coupled Receptor Rhodopsin," Annu Rev Biochem., 2006, pp. 743-767, vol. 75.

Pardo, L. et al., "The Role of Internal Water Molecules in the Structure and Function of the Rhodopsin Family of G Protein-Coupled Receptors," ChemBioChem, 2007, pp. 19-24, vol. 8.

PCT International Search Report and Written Opinion, PCT Application No. PCT/US2009/059289, Oct. 4, 2010, 10 pages.

PCT International Search Report and Written Opinion, PCT Application No. PCT/US08/80847, Sep. 10, 2009, 12 pages.

PCT International Search Report and Written Opinion, PCT Application No. PCT/US08/80844, 9 pages.

Pierce, K.L. et al., "Seven-Transmembrane Receptors," Nature Reviews Molecular Cell Biology, Sep. 2002, pp. 639-650, vol. 3.

Rasmussen, S.G.F. et al., "Crystal Structure of the human $\beta_2$ Adrenergic G-Protein-Coupled Receptor," Nature, Nov. 15, 2007, pp. 383-388, vol. 450.

Rasmussen, S.G.F. et al., "Crystal Structure of the human $\beta_2$ Adrenergic G-Protein-Coupled Receptor—Online Methods," 2 pages, [Online] [Retrieved on Mar. 15, 2011] Retrieved from the Internet<URL:www.nature.com>.

Rasmussen, S.G.F. et al., "Crystal Structure of the human $\beta_2$ Adrenergic G-Protein-Coupled Receptor—Supplementary Information," pp. 1-8, [Online] [Retrieved on Mar. 15, 2011] Retrieved from the Internet<URL:www.nature.com>.

Rohrer, D.K., "Physiological Consequences of $\beta$-Adrenergic Receptor Disruption," J. Mol. Med., 1998, pp. 764-772, vol. 76.

Rosenbaum, D.M. et al., "GPCR Engineering Yields High-Resolution Structural Insights into β₂-Adrenergic Receptor Function," Epub Oct. 25, 2007, 2007, pp. 1266-1273 vol. 318.

Salom, D. et al., "Crystal Structure of a Photoactivated Deprotonated Intermediate of Rhodopsin," PNAS, Oct. 13, 2006, pp. 16123-16128, vol. 103, No. 44.

Schertler, G. FX., "Structure of Rhodopsin and the Metarhodopsin I Photointermediate," Current Opinion in Structural Biology, 2005, pp. 408-415, vol. 15.

Schwartz, T.W. et al., "Molecular Mechanism of 7TM Receptor Activation—A Global Toggle Switch Model," Annu. Rev. Pharmacol. Toxicol., 2006, pp. 481-519, vol. 46.

Shi, L. et al., "β₂ Adrenergic Receptor Activation," The Journal of Biological Chemistry, Oct. 25, 2002, pp. 40989-10996, vol. 277, No. 43.

Smyth, D.R. et al., "Crystal Structures of Fusion Proteins with Large-Affinity Tags," Protein Science, 2003, pp. 1313-1322, vol. 12.

Sprang, S.R., "A Receptor Unlocked," Nature, Nov. 15, 2007, pp. 355-356, vol. 450.

Strosberg, A.D., "Structure, Function, and Regulation of Adrenergic Receptors," Protein Science, 1993, pp. 1198-1209, vol. 2.

Sugimoto, Y. et al., "β₁-Selective Agonist (−)-1-(3,4-Dimethoxyphenetylamino)-3-(3,4-dihydroxy)-2-propanol [(−)-RO363] Differentially Interacts with Key Amino Acids Responsible for β₁-Selective Binding in Resting and Active States," The Journal of Pharmacology and Experimental Therapeutics, 2002, pp. 51-58, vol. 301, No. 1.

Wadsten, P. et al., "Lipidic Sponge Phase Crystallization of Membrane Proteins," J. Mol. Biol., 2006, pp. 44-53, vol. 364.

Wieland, K. et al., "Involvement of Asn-293 in Stereospecific Agonist Recognition and in Activation of the β₂-Adrenergic Receptor," Proc. Natl. Acad. Sci., Aug. 1996, pp. 9276-9281, vol. 93.

Xiang, Y. et al., "The β-Adrenergic Receptors," Chapter 10, *The Adrenergic Receptors*, 2006, ed. D. Perez, pp. 267-291.

Xiang, Y. et al., "Caveolar Localization Dictates Physiologic Signaling of β₂-Adrenoceptors in Neonatal Cardiac Myocytes," The Journal of Biological Chemistry, Sep. 13, 2002, pp. 34280-34286, vol. 277, No. 37.

Yohannan, S. et al., "The Evolution of Transmembrane Helix Kinks and the Structural Diversity of G Protein-Coupled Receptors," PNAS, Jan. 27, 2004, pp. 959-963, vol. 101, No. 4.

Zhang, Y. et al., "Structure Modeling of All Identified G Protein-Coupled Receptors in the Human Genome," PLoS Comput Biol, 2006, pp. 88-99, vol. 2, Issue 2, e13.

* cited by examiner

SEQUENCE LISTING

<160> NUMBER OF SEQ ID NOS: 9

<210> SEQ ID NO 1
<211> LENGTH: 7
<212> TYPE: PRT
<213> ORGANISM: Homo sapiens

<400> SEQUENCE: 1

Asp Tyr Lys Asp Asp Asp Ala
1               5

<210> SEQ ID NO 2
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Cys Asp Phe Phe Thr Asn Gln Ala Tyr Ala Ile Ala Ser Ser Ile
1               5                   10                  15

Val Ser Phe Tyr Val Pro Leu Val Ile Met Val Phe Val Tyr Ser Arg
            20                  25                  30

Val Phe Gln Glu Ala Lys Arg Gln Leu Gln Lys Ile Asp Lys Ser Glu
        35                  40                  45

Gly Arg Phe His Val Gln Asn Leu Ser Gln Val Glu Gln Asp Gly Arg
    50                  55                  60

Thr Gly His Gly Leu Arg Arg Ser Ser Lys Phe Cys Leu Lys Glu His
65                  70                  75                  80

Lys Ala Leu Lys Thr Leu Gly Ile Ile Met Gly Thr Phe Thr Leu Cys
                85                  90                  95

Trp Leu Pro Phe Phe Ile Val Asn Ile Val His Val Ile Gln Asp Asn
            100                 105                 110

Leu Ile Arg Lys Glu Val Tyr Ile Leu Leu Asn Trp Ile Gly Tyr Val
        115                 120                 125

Asn Ser Gly Phe Asn Pro Leu Ile Tyr Cys Arg Ser Pro Asp Phe Arg
    130                 135                 140

Ile Ala Phe Gln Glu Leu Leu Cys Leu Arg Arg Ser Ser Leu Lys Ala
145                 150                 155                 160

```
Tyr Gly Asn Gly Tyr Ser Ser Asn Gly Asn Thr Gly Glu Gln Ser Gly
                165                 170                 175

Tyr His Val Glu Gln Glu Lys Glu Asn Lys Leu Leu Cys Glu Asp Leu
            180                 185                 190

Pro Gly Thr Glu Asp Phe Val Gly His Gln Gly Thr Val Pro Ser Asp
        195                 200                 205

Asn Ile Asp Ser Gln Gly Arg Asn Cys Ser Thr Asn Asp Ser Leu Leu
    210                 215                 220

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Asn Lys Tyr Ala Asp Trp Thr
1               5

<210> SEQ ID NO 4
<211> LENGTH: 35
<212> TYPE: PRT
<213> ORGANISM: Homo sapiens

<400> SEQUENCE: 4

Asp Tyr Lys Asp Asp Asp Ala Met Gly Gln Pro Gly Asn Gly Ser Ala
1               5                   10                  15

Phe Leu Leu Ala Pro Asn Arg Ser His Ala Pro Asp His Asp Val Thr
            20                  25                  30

Gln Gln Arg
        35

<210> SEQ ID NO 5
<211> LENGTH: 23
<212> TYPE: PRT
<213> ORGANISM: Homo sapiens

<400> SEQUENCE: 5

Arg Arg Ser Ser Leu Lys Ala Tyr Gly Asn Gly Tyr Ser Ser Asn Gly
1               5                   10                  15

Asn Thr Gly Glu Gln Ser Gly
            20

<210> SEQ ID NO 6
<211> LENGTH: 500
<212> TYPE: PRT
<213> ORGANISM: Homo sapiens

<400> SEQUENCE: 6

Asp Tyr Lys Asp Asp Asp Ala Met Gly Gln Pro Gly Asn Gly Ser Ala
1               5                   10                  15

Phe Leu Leu Ala Pro Asn Arg Ser His Ala Pro Asp His Asp Val Thr
            20                  25                  30

Gln Gln Arg Asp Glu Val Trp Val Val Gly Met Gly Ile Val Met Ser
        35                  40                  45

Leu Ile Val Leu Ala Ile Val Phe Gly Asn Val Leu Val Ile Thr Ala
    50                  55                  60

Ile Ala Lys Phe Glu Arg Leu Gln Thr Val Thr Asn Tyr Phe Ile Thr
65                  70                  75                  80
```

```
Ser Leu Ala Cys Ala Asp Leu Val Met Gly Leu Ala Val Val Pro Phe
                85                  90                  95

Gly Ala Ala His Ile Leu Met Lys Met Trp Thr Phe Gly Asn Phe Trp
                100                 105                 110

Cys Glu Phe Trp Thr Ser Ile Asp Val Leu Cys Val Thr Ala Ser Ile
                115                 120                 125

Glu Thr Leu Cys Val Ile Ala Val Asp Arg Tyr Phe Ala Ile Thr Ser
    130                 135                 140

Pro Phe Lys Tyr Gln Ser Leu Leu Thr Lys Asn Lys Ala Arg Val Ile
145                 150                 155                 160

Ile Leu Met Val Trp Ile Val Ser Gly Leu Thr Ser Phe Leu Pro Ile
                165                 170                 175

Gln Met His Trp Tyr Arg Ala Thr His Gln Glu Ala Ile Asn Cys Tyr
                180                 185                 190

Ala Glu Glu Thr Cys Cys Asp Phe Phe Thr Asn Gln Ala Tyr Ala Ile
                195                 200                 205

Ala Ser Ser Ile Val Ser Phe Tyr Val Pro Leu Val Ile Met Val Phe
                210                 215                 220

Val Tyr Ser Arg Val Phe Gln Glu Ala Lys Arg Gln Leu Asn Ile Phe
225                 230                 235                 240

Glu Met Leu Arg Ile Asp Glu Gly Leu Arg Leu Lys Ile Tyr Lys Asp
                245                 250                 255

Thr Glu Gly Tyr Tyr Thr Ile Gly Ile Gly His Leu Leu Thr Lys Ser
                260                 265                 270

Pro Ser Leu Asn Ala Ala Lys Ser Glu Leu Asp Lys Ala Ile Gly Arg
                275                 280                 285

Asn Thr Asn Gly Val Ile Thr Lys Asp Glu Ala Glu Lys Leu Phe Asn
                290                 295                 300

Gln Asp Val Asp Ala Ala Val Arg Gly Ile Leu Arg Asn Ala Lys Leu
305                 310                 315                 320

Lys Pro Val Tyr Asp Ser Leu Asp Ala Val Arg Arg Ala Ala Leu Ile
                325                 330                 335

Asn Met Val Phe Gln Met Gly Glu Thr Gly Val Ala Gly Phe Thr Asn
                340                 345                 350

Ser Leu Arg Met Leu Gln Gln Lys Arg Trp Asp Glu Ala Ala Val Asn
                355                 360                 365

Leu Ala Lys Ser Arg Trp Tyr Asn Gln Thr Pro Asn Arg Ala Lys Arg
                370                 375                 380

Val Ile Thr Thr Phe Arg Thr Gly Thr Trp Asp Ala Tyr Lys Phe Cys
385                 390                 395                 400

Leu Lys Glu His Lys Ala Leu Lys Thr Leu Gly Ile Ile Met Gly Thr
                405                 410                 415

Phe Thr Leu Cys Trp Leu Pro Phe Phe Ile Val Asn Ile Val His Val
                420                 425                 430

Ile Gln Asp Asn Leu Ile Arg Lys Glu Val Tyr Ile Leu Leu Asn Trp
                435                 440                 445

Ile Gly Tyr Val Asn Ser Gly Phe Asn Pro Leu Ile Tyr Cys Arg Ser
                450                 455                 460

Pro Asp Phe Arg Ile Ala Phe Gln Glu Leu Leu Cys Leu Arg Arg Ser
465                 470                 475                 480

Ser Leu Lys Ala Tyr Gly Asn Gly Tyr Ser Ser Asn Gly Asn Thr Gly
                485                 490                 495

Glu Gln Ser Gly
```

-continued

```
<210> SEQ ID NO 7
<211> LENGTH: 202
<212> TYPE: PRT
<213> ORGANISM: Homo sapiens

<400> SEQUENCE: 7

Asp Glu Val Trp Val Gly Met Gly Ile Val Met Ser Leu Ile Val
1               5                   10                  15

Leu Ala Ile Val Phe Gly Asn Val Leu Val Ile Thr Ala Ile Ala Lys
                20                  25                  30

Phe Glu Arg Leu Gln Thr Val Thr Asn Tyr Phe Ile Thr Ser Leu Ala
                35                  40                  45

Cys Ala Asp Leu Val Met Gly Leu Ala Val Val Pro Phe Gly Ala Ala
        50                  55                  60

His Ile Leu Met Lys Met Trp Thr Phe Gly Asn Phe Trp Cys Glu Phe
65                  70                  75                  80

Trp Thr Ser Ile Asp Val Leu Cys Val Thr Ala Ser Ile Glu Thr Leu
                85                  90                  95

Cys Val Ile Ala Val Asp Arg Tyr Phe Ala Ile Thr Ser Pro Phe Lys
            100                 105                 110

Tyr Gln Ser Leu Leu Thr Lys Asn Lys Ala Arg Val Ile Ile Leu Met
        115                 120                 125

Val Trp Ile Val Ser Gly Leu Thr Ser Phe Leu Pro Ile Gln Met His
130                 135                 140

Trp Tyr Arg Ala Thr His Gln Glu Ala Ile Asn Cys Tyr Ala Glu Glu
145                 150                 155                 160

Thr Cys Cys Asp Phe Phe Thr Asn Gln Ala Tyr Ala Ile Ala Ser Ser
                165                 170                 175

Ile Val Ser Phe Tyr Val Pro Leu Val Ile Met Val Phe Val Tyr Ser
            180                 185                 190

Arg Val Phe Gln Glu Ala Lys Arg Gln Leu
        195                 200

<210> SEQ ID NO 8
<211> LENGTH: 160
<212> TYPE: PRT
<213> ORGANISM: Homo sapiens

<400> SEQUENCE: 8

Asn Ile Phe Glu Met Leu Arg Ile Asp Glu Gly Leu Arg Leu Lys Ile
1               5                   10                  15

Tyr Lys Asp Thr Glu Gly Tyr Tyr Thr Ile Gly Ile Gly His Leu Leu
                20                  25                  30

Thr Lys Ser Pro Ser Leu Asn Ala Ala Lys Ser Glu Leu Asp Lys Ala
            35                  40                  45

Ile Gly Arg Asn Thr Asn Gly Val Ile Thr Lys Asp Glu Ala Glu Lys
        50                  55                  60

Leu Phe Asn Gln Asp Val Asp Ala Ala Val Arg Gly Ile Leu Arg Asn
65                  70                  75                  80

Ala Lys Leu Lys Pro Val Tyr Asp Ser Leu Asp Ala Val Arg Arg Ala
                85                  90                  95

Ala Leu Ile Asn Met Val Phe Gln Met Gly Glu Thr Gly Val Ala Gly
            100                 105                 110

Phe Thr Asn Ser Leu Arg Met Leu Gln Gln Lys Arg Trp Asp Glu Ala
        115                 120                 125
```

-continued

```
Ala Val Asn Leu Ala Lys Ser Arg Trp Tyr Asn Gln Thr Pro Asn Arg
        130                 135                 140

Ala Lys Arg Val Ile Thr Thr Phe Arg Thr Gly Thr Trp Asp Ala Tyr
145                 150                 155                 160

<210> SEQ ID NO 9
<211> LENGTH: 80
<212> TYPE: PRT
<213> ORGANISM: Homo sapiens

<400> SEQUENCE: 9

Lys Phe Cys Leu Lys Glu His Lys Ala Leu Lys Thr Leu Gly Ile Ile
1               5                   10                  15

Met Gly Thr Phe Thr Leu Cys Trp Leu Pro Phe Phe Ile Val Asn Ile
            20                  25                  30

Val His Val Ile Gln Asp Asn Leu Ile Arg Lys Glu Val Tyr Ile Leu
        35                  40                  45

Leu Asn Trp Ile Gly Tyr Val Asn Ser Gly Phe Asn Pro Leu Ile Tyr
    50                  55                  60

Cys Arg Ser Pro Asp Phe Arg Ile Ala Phe Gln Glu Leu Leu Cys Leu
65                  70                  75                  80
```

METHODS AND COMPOSITIONS FOR OBTAINING HIGH-RESOLUTION CRYSTALS OF MEMBRANE PROTEINS

RELATED APPLICATIONS

This invention claims the benefit of U.S. provisional applications 60/999,951, filed Oct. 22, 2007; U.S. provisional application 61/000,325, filed Oct. 24, 2007; U.S. provisional application 61/060,107, filed Jun. 9, 2008; and U.S. provisional application 61/194,961, filed Oct. 1, 2008, each of which is incorporated herein by reference, in its entirety, for all purposes.

STATEMENT AS TO FEDERALLY SPONSORED RESEARCH

This invention was made with government support under Grant Nos. GM73197 awarded by the National Institutes of Health; GM74691 and GM62411 awarded by the Protein Structure Initiative; Y1-CO-1020 awarded by the National Cancer Institute; and yl-GM-1104 awarded by the National Institute of General Medical Sciences. The government has certain rights in this invention.

Coordinates and structure factors have been deposited in the Protein Data Bank with identification code 2RH1.

REFERENCE TO SEQUENCE LISTING

This application contains a computer-readable Sequence Listing which has been submitted via EFS-Web and is hereby incorporated by reference in its entirety. Said ASCII copy, created on Apr. 21, 2010, is named "14675_US_Sequence Listing.txt", lists 9 sequences, and is 12 kb in size.

BACKGROUND OF THE INVENTION

Naturally occurring polypeptides or proteins often fold into complex, three-dimensional shapes that determine both chemical and physiological functionality. Thus a thorough understanding of proteins necessarily involves a detailed representation of their spatial topography. The field of protein crystallography has flourished over the last 20 years resulting in a rapid increase in the knowledge bas of protein structure enabling great strides in other disciplines including biochemistry, pharmaceutical development and cell biology. However, the structural biology field has largely been restrained to working with protein that is naturally soluble in aqueous media, or made soluble by incorporation into surfactant micelles. The present invention provides methods and compositions that allow for the study of membrane-embedded proteins (i.e., integral membrane proteins) in a more natural membrane bilayer environment. The present invention enable a more detailed analysis of important classes of membrane-embedded polypeptides that play key roles in a variety of cellular processes including energy and signal transduction.

SUMMARY OF THE INVENTION

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

All publications, patents, and patent applications mentioned in this specification are herein incorporated by reference for all purposes and to the same extent as if each individual publication or patent application was specifically and individually indicated to be incorporated by reference.

In one aspect the invention provides compositions, e.g., useful for the crystallization of membrane protein. In some embodiments, the composition is suitable for lipidic cubic phase crystallization. In some embodiments the compositions contain 10-60% v/v of a polyethylene glycol, 0.01-0.5 M of a salt, 1-20% v/v of an organic compound, and 1-50% w/w of a lipid additive in a host lipid. In some embodiments of the compositions, the protein to be crystallized is present at a concentration of 1 to 100 mg/mL. In some embodiments, the protein to be crystallized is present at a concentration of 50 mg/mL.

In some embodiments of the compositions of the inventions, the polyethylene glycol is PEG or modified PEG at a molecular size of 10-8000. In some embodiments, the PEG or modified PEG has an average molecular weight of 400-8000. In some embodiments, the PEG or modified PEG has an average molecular weight of 400-2000. In some embodiments, the PEG or modified PEG has an average molecular weight of 400-1000. In some embodiments, the PEG or modified PEG has an average molecular weight of 400. Examples of modified PEG include but are not limited to PEG laurate, PEG dilaurate, PEG oleate, PEG dioleate, PEG stearate, PEG distearate, PEG glyceryl trioleate, PEG glyceryl laurate, PEG glyceryl stearate, PEG glyceryl oleate, PEG palm kernel oil, PEG hydrogenated castor oil, PEG castor oil, PEGcorn oil, PEG caprate/caprylate glycerides, PEG caprate/caprylate glycerides, PEG cholesterol, PEG phyto sterol, PEG soya sterol, PEG trioleate, PEG sorbitan oleate, PEG sorbitan laurate, PEG succinate, PEG nonyl phenol series, PEG octyl phenol series, Methyl-PEG, PEG-Maleimide, PEG4-NHS Ester and methoxypoly(ethylene glycol) (mPEG).

In some embodiments of the compositions, the salt is a sulfate salt. In some embodiments, the sulfate salt is sodium sulfate. In some embodiments, the salt is present at a concentration of 0.1-0.5 M. In some embodiments, the salt is present at a concentration of 0.1-0.2 M. In some embodiments, the compositions of the invention contain a buffer. In some embodiments, the buffer is present at a concentration of 0.01-0.5 M. In some embodiments, the buffer is present at a concentration of 0.1-0.2 M. In some embodiments, the buffer is present at a concentration of 0.1 M. In some embodiments, the buffer is Bis-tris propane. In some embodiments, the buffer has a pH 6.5-7.0. In some embodiments of the compositions, an organic compound is present at a concentration of 1-10% v/v. In some embodiments, the organic compound is present at a concentration of 5-7% v/v. In some embodiments, the organic compound is 1,4-butanediol.

In some embodiments of the compositions, the lipid additive is present at a concentration of 1-20% w/w in a host lipid. In some embodiments, the lipid additive is present at a concentration of 8-10% w/w in a host lipid. Examples of lipid additives include but are not limited to cholesterol, DOPE, DOPE-Me, DOPC, and Asolectin. In some embodiments, the lipid additive is cholesterol. Examples of host lipids include, but are not limited to monopalmitolein, monovaccenin and monoolein. In some embodiments, the host lipid is monoolein.

In some embodiments of this aspect, the composition of the invention comprises 30-35% v/v PEG400, 0.1-0.2 M Na sulfate, 0.1 M Bis-tris propane pH 6.5-7.0, 5-7% v/v 1,4-butanediol using 8-10% w/w cholesterol in monoolein as the host lipid.

In another aspect the invention includes compositions suitable for lipidic cubic phase crystallization. In some embodiments, the compositions of the inventions contain a lipid additive. In some embodiments, the lipid additive is present at a concentration of 1-50% w/w in a host lipid. In some embodiments, the lipid additive is present at a concentration of 1-20% w/w in a host lipid. In some embodiments, the lipid additive is present at a concentration of 8-10% w/w in a host lipid. Examples of lipid additives include, but are not limited to, cholesterol, DOPE, DOPE-Me, DOPC, and Asolectin. In some embodiments, the lipid additive is cholesterol. Examples of host lipids include, but are not limited to monopalmitolein, monovaccenin and monoolein. In some embodiments the host lipid is monoolein.

In another aspect the invention includes methods for crystallization of membrane proteins. In some embodiments, the method for crystallization of membrane proteins comprises adding a lipid additive to a lipidic cubic phase. Examples of lipid additives include, but are not limited to, cholesterol, DOPE, DOPE-Me, DOPC, and Asolectin. In some embodiments, the lipid additive is cholesterol. In some embodiments, the lipid additive is present at a concentration of 1-50% w/w in a host lipid. In some embodiments, the lipid additive is present at a concentration of 1-20% w/w in a host lipid. In some embodiments, the lipid additive is present at a concentration of 8-10% w/w in a host lipid. Examples of host lipids include, but are not limited to monopalmitolein, monovaccenin and monoolein. In some embodiments the host lipid is monoolein.

In another aspect, the invention provides for methods of crystallization of a protein. In some embodiments of this aspect, the method comprises, providing said protein in a lipidic cubic phase composition, filling a plate comprising a material that does not interfere with imaging (such as, e.g., a transparent glass or plastic) with said composition, placing said plate containing said composition under conditions suitable for crystallization of said protein and detecting the presence of a crystal of said protein in said plate. In some embodiments, the method further comprises covering said plate with a second plate comprising a material that does not interfere with imaging (such as, e.g., a transparent glass or plastic).

In some embodiments of the methods, the protein is a non-colored protein. In some embodiments, the protein is a G protein-coupled receptor (GPCR). In some embodiments, the protein comprises a $\beta_2AR$, a CXCR4, or a human adenosine $A_{2A}$ receptor. In some embodiments the protein comprises a stabilizing point mutation or a T4 lysozyme fusion or both.

In some embodiments of the methods, the lipidic cubic phase composition comprises a lipid additive. Examples of lipid additives include, but are not limited to, cholesterol, DOPE, DOPE-Me, DOPC, and Asolectin. In some embodiments, the lipid additive is cholesterol. In some embodiments, the lipid additive is present at a concentration of 1-50% w/w in a host lipid. In some embodiments, the lipid additive is present at a concentration of 1-20% w/w in a host lipid. In some embodiments, the lipid additive is present at a concentration of 8-10% w/w in a host lipid. Examples of host lipids include, but are not limited to monopalmitolein, monovaccenin and monoolein. In some embodiments the host lipid is monoolein.

In some embodiments of the methods, the first plate and second plate are made of glass. In some embodiments, the plate allows for the control of crystallization conditions, such as the humidity and temperature of said lipidic cubic phase composition.

In some embodiments of the methods, the crystals are harvested directly from the plate. In some embodiments of the methods, the crystals are harvested between the cubic and the sponge phase of the lipidic cubic phase composition. In some embodiments of the methods, the crystals are harvested directly from said lipidic cubic phase composition and placing said crystals in liquid nitrogen.

In another aspect the invention provides methods for screening a crystal present in a liquid cubic phase composition. In some embodiments, the method comprises exposing the composition to a first beam and determining a change of the first beam, exposing the composition to a second beam and determining a change of the second beam, and identifying an area where the crystal is present in said composition. Examples of changes in the beams, include but are not limited to, change in direction and/or intensity of the beams. In some embodiments the crystals are non-colored.

In some embodiments of the methods, the first beam and second beam are attenuated. In some embodiments the beams are attenuated 10 times. In some embodiments, the first beam is a slitted 100×25 µm beam. In some embodiments, the methods comprise exposing said lipidic cubic phase composition to a third beam. In some embodiments, the methods comprise exposing said lipidic cubic phase composition to up to ten extra beams. In some embodiments, the exposure of composition to the beams is 2 seconds. In some embodiments, the beams are beams of visible light.

In another aspect the invention includes a crystal of a membrane protein. In some embodiments, the invention includes a crystal of a G protein-coupled receptor (i.e., a "GPCR") non-covalently bound to a ligand. In some embodiments, the extracellular domain of said crystalline GPCR is resolvable by X-Ray crystallography. In some embodiments, the ligand is a diffusible ligand.

In some embodiments of this aspect, the volume of the crystal is greater than 15×5×1 µm. In some embodiments, the volume of said crystal is greater than 30×5×5 µm. In some embodiments of this aspect, the volume of crystal is greater than 40×20×5 µm. In some embodiments, volume of the crystal is estimated assuming that each of the stated dimensions are orthogonal so that the volume estimate is the product of the dimensions. In some embodiments, the crystal is suitable for X-ray crystallography. In some embodiments, X-ray crystallographic analysis can be carried out to determine the structure of a protein comprising said crystal.

In some embodiments of this aspect, the crystal is crystallized using liquid cubic phase crystallization. In some embodiments, the crystal is obtainable by harvesting the crystal from a glass sandwich plate. In some embodiments, the crystal diffract to a resolution of 1.0 to 10.0 Å. In some embodiments, the crystal diffract to a resolution of 2.0 to 5.0 Å. In some embodiments, the crystal diffract to a resolution of 2.2 Å. In some embodiments, the structure of said crystal is solved and refined at resolution of less than about 3.2, 2.8, 2.6 or 2.4 Å. In some embodiments, the structure of said crystal is solved and refined at resolution of less than about 2.8, 2.6 or 2.4 Å. In some embodiments, the structure of said crystal is solved and refined at resolution of less than about 2.4 Å.

In some embodiments, the G protein-coupled receptor is a $\beta_2AR$ protein, a CXCR4 protein, or a human adenosine $A_{2A}$ receptor protein.

In another aspect the invention provides for a crystal of $\beta_2AR$. In some embodiments, the structure of an extracellular domain of said crystal is capable of being resolved by X-ray crystallography. In some embodiments, the crystal comprises 442 amino acids, a palmitic acid covalently bound to Cys341 and an acetamide molecule bound to $Cys265^{6.27}$, a diffusible ligand, up to 10 molecules a lipid additive, up to five salt ions and up to 10 butanediol molecules. In some embodiments, the lipid additive is cholesterol. In some embodiments, the crystal comprises three cholesterol molecules. In some embodiments, the salt ion is a sulfate ion. In some embodiments, the crystal comprises two sulfate ions. In some embodiments, the diffusible ligand is carazol. In some embodiments the crystal comprises two butanediol molecules. In some embodiments of this aspect, the volume of the crystal is greater than 15×5×1 µm. In some embodiments, the volume of said crystal is greater than 30×5×5 µm. In some embodiments of this aspect, the volume of the crystal is greater than 40×20×5 µm. In some embodiments the volume of the crystal is estimated by assuming that each dimension is orthogonal to the other dimensions so that the volume is the product of the three lengths. In some embodiments, the crystal is suitable for X-ray crystallography. In some embodiments, the structure of a $\beta_2AR$ protein can be determined from said crystal using X-ray crystallographic analysis. In some embodiments, the crystal is crystallized using liquid cubic phase crystallization. In some embodiments, the crystal is obtainable by harvesting the crystal from a glass sandwich plate. In some embodiments of this aspect, the crystal is crystallized using liquid cubic phase crystallization. In some embodiments, the crystal is obtainable by harvesting the crystal from a glass sandwich plate. In some embodiments, the crystal diffract to a resolution of 1.0 to 10.0 Å. In some embodiments, the crystals diffract to a resolution of 2.0 to 5.0 Å. In some embodiments, the crystal diffract to a resolution of 2.2 Å. In some embodiments, the structure of said crystal is solved and refined at resolution of less than about 3.2, 2.8, 2.6 or 2.4 Å. In some embodiments, the structure of said crystal is solved and refined at resolution of less than about 2.8, 2.6 or 2.4 Å. In some embodiments, the structure of said crystal is solved and refined at resolution of less than about 2.4 Å.

In another embodiment, the invention provides a composition for lipidic cubic phase crystallization of a membrane protein, comprising a polyethylene glycol or modified polyethylene glycol; 0.01-1M of a salt; a host lipid; a lipid additive, wherein said lipid additive is present at 10-60% v/v ratio relative to the host lipid; a buffer; and 1 to 100 mg/ml of a membrane protein. In a related embodiment, the polyethylene glycol is PEG or modified PEG, wherein said PEG or modified PEG has an average molecular weight of 200-20,000, 400-8000, or 400-2000. In yet another related embodiment, the PEG or modified PEG in the composition has an average molecular weight of 400. In another related embodiment, the salt is selected from the group consisting of a sulfate salt, a citrate salt, a malonate salt, a tartrate salt, an acetate salt, and a formate salt. In certain embodiments of the composition, the salt is present at a concentration of 0.1-0.2 M. In another related embodiment, the buffer is present at a concentration of 0.05-0.5 M in the composition. In certain embodiments, the buffer is Bis-tris propane or sodium citrate. In other related embodiments of the composition, the buffer has a pH between 4.5-8.0.

In still other related embodiments of the composition for lipidic cubic phase crystallization of a membrane protein, the composition further comprising an alcohol present at a concentration of 1-10% v/v or 5-7% v/v. In certain embodiments, the alcohol is a diol or triol. In other embodiments, the alcohol is 1,4-butanediol or 2,6-hexanediol.

In still other related embodiments of the composition for lipidic cubic phase crystallization of a membrane protein, the lipid additive is present at a concentration of 1-20% w/w in a host lipid or 8-10% w/w in a host lipid. In yet another related embodiment of the composition, the lipid additive is selected from the group consisting of 2-monoolein, phosphotidylcholine, cardiolipin, lyso-PC, a polyethylene glyocol-lipid, dioleoylphosphatidylethanolamine ("DOPE"), DOPE-Me, dioleoyl phosphatidylcholine ("DOPC"), Asolectin, and a sterol. In still other embodiments, the lipid additive is a sterol. In related embodiments, the lipid additive is cholesterol.

In still another related embodiment of the composition for lipidic cubic phase crystallization of a membrane protein, the host lipid is selected from the group consisting of monopalmitolein, monovaccenin and monoolein. In a related embodiment, the host lipid is monoolein. In still another related embodiment, the membrane protein to be crystallized in said composition is present at a concentration of 1 to 100 mg/mL. In yet another embodiment, the memrane protein to be crystallized in said composition is present at a concentration of 40-60 mg/mL.

In still another related embodiment of the composition for lipidic cubic phase crystallization of a membrane protein membrane protein is a G-protein coupled receptor, such as a $\beta_2AR$ protein, a human adenosine A2A receptor protein, a CXCR4-T4L protein, or a $\beta_2AR$-T4L protein. In related embodiments, the G-protein coupled receptor is a protein comprising or consisting of a $\beta_2AR^{(E122W)}$, a $\beta_2AR^{(E122W)}$-T4L, a human adenosine A2A receptor-T4L, a CXCR4-T4L or $\beta_2AR$-T4L. In still another related embodiment of the composition for lipidic cubic phase crystallization of a membrane protein, the composition comprises a ligand selected from the group consisting of carazolol, timolol, alprenolol, and clenbutorol.

In another embodiment, the invention provides a method of generating crystals of a membrane protein comprising: mixing a lipid additive with a host lipid to form a lipid mixture, wherein said lipid additive is selected from the group consisting of a sterol, DOPE, DOPE-Me, DOPC, and Asolectin, and wherein said lipid additive is 5 to 20% w/w in said host lipid; and combining said lipid mixture with a membrane protein solution under conditions suitable for the formation of a lipidic cubic phase composition. In a related embodiment of the method, said protein is a non-colored protein. In a related embodiment, the amount of said lipid additive is 8 to 10% w/w in said lipid. In another related embodiment, the invention further comprises: filling a plate with said lipidic cubic phase composition, wherein said plate is compatible with imaging; placing said plate containing said lipic cubic phase composition under conditions suitable for crystallization of said protein; and detecting the presence of a crystal of said protein in said plate. In another embodiment, the method further comprises covering said plate with a second plate.

In a related embodiment of the method of generating crystals of a membrane protein, the protein is a GPCR. In yet another related embodiments, the protein comprises a $\beta_2AR$. In yet another related embodiment, the $\beta_2AR$ protein is selected from the group consisting of $\beta_2AR^{(E122W)}$, $\beta_2AR^{(E122W)}$-T4L, and $\beta_2AR$-T4L. In yet another related embodiment, the GPCR is a human adenosine A2A receptor or a CXCR4 receptor where the proteins may comprise, in still other related embodiments, a T4 lysozome.

In yet another related embodiment of method of generating crystals of a membrane protein, the lipid additive is present at a concentration of 1-20% w/w or 8-10% w/w in a host lipid. In yet another related embodiment of the method, the second plate comprises a glass. In yet another related embodiment, the method further comprises harvesting crystals directly from said plate. Another related embodiment of the method comprises harvesting crystals from between the cubic and the sponge phase of said lipidic cubic phase composition. In another related embodiment, the method comprises harvesting crystals directly from said lipidic cubic phase composition and placing said crystals in liquid nitrogen. In yet another related embodiment, the method comprising a step of soaking into said crystal a diffusable ligand or candidate ligand.

The invention also provides a method of screening a crystal of a GPCR present in a liquid cubic phase composition comprising: preparing a liquid cubic phase composition comprising a GPCR protein, a host lipid, and a lipid additive; exposing said composition to a first X-ray beam and determining a change in direction or intensity of said first X-ray beam; exposing said composition to a second beam and determining a change in direction or intensity of said second X-ray beam; identifying an area where said GPCR crystal is present in said composition; and exposing said identified area to at least a third X-ray beam. In a related embodiment, the first beam is a slitted 100×25 µm beam. In another related embodiment, the crystal is colorless. In yet another embodiment, the GPCR crystal is $\beta_2AR^{(E122W)}$-T4L, $\beta_2AR^{(E122W)}$, $\beta_2AR$, or $\beta_2AR$-T4L protein. In related embodiments, the crystal is human adenosine A2A receptor or a CXCR4 receptor where the proteins may comprise, in still other related embodiments, a T4 lysozome.

In another embodiment, the invention provides a crystal of a human $\beta_2AR$ protein wherein the extracellular loop ECL2 of said $\beta_2AR$ is sufficiently ordered to produce interpretable electron density in a crystallographically-derived electron density map. In yet another related embodiment, each $\beta_2AR$ molecule in said crystal comprises three non-covalently bound cholesterol molecules and at least one salt ion. In yet another related embodiment, the at least one salt ion is a sulfate ion. In yet another embodiment, each $\beta_2AR$ molecule in said crystal said crystal comprises two sulfate ions. In yet another related embodiment, each $\beta_2AR$ molecule in said crystal said crystal further comprises carazol. In yet another related embodiment of the crystal, each $\beta_2AR$ molecule in said crystal comprises between 1 and 10 butanediol molecules. In yet another related embodiment of the crystal, the volume of said crystal exceeds 15×5×1 µm, 30×5×5 µm or 40×20×5 µm. In yet another related embodiment, the specific surface area of the crystal is 0.0001-5 $m^2/g$. In yet another related embodiment, the crystal is crystallized using liquid cubic phase crystallization. In yet another related embodiment, the crystal is obtainable by harvesting the crystal from a glass sandwich plate. In yet another related embodiment, the crystal diffracts to a resolution of 2.0 to 10.0 Å, 2.0 to 5.0 Å, or 2.2 to 2.4 Å. In yet another related embodiment, the structure of said crystal is solved and refined at a resolution higher than about 3.2, higher than about 2.8, or higher than about 2.4 Å.

In yet another embodiment, the invention provides a crystalline form of a human $\beta_2AR$ protein having an atomic arrangement of coordinates comprising the $\beta_2AR$ coordinates set forth in Appendix I (SEQ ID NOS 4-5, 1 and 6-9, respectively in order of appearance).

In another embodiment, the invention provides a crystalline form of a human $\beta_2AR$ protein, where said form has unit cell dimensions of a=106.3 Angstroms, b=169.2 Angstroms, and c=40.2 Angstroms. In a related embodiment, said $\beta_2AR$ protein is $\beta_2AR$-T4L. In another related embodiment, the $\beta_2AR$-T4L crystal further comprises a carazolol ligand.

In another embodiment, the invention provides a crystalline form of a human $\beta_2AR$ protein, wherein said space group of said crystalline form is C2. In a related embodiment, said $\beta_2AR$ protein is $\beta_2AR$-T4L. In another related embodiment, the $\beta_2AR$-T4L crystal further comprises a carazolol ligand.

In another embodiment, the invention provides a crystalline form of a human $\beta_2AR$ protein, wherein said crystalline form diffracts X-rays to a resolution of 2.4 Angstroms. In a related embodiment, said $\beta_2AR$ protein comprises a point mutation that stabilizes said $\beta_2AR$ protein. In another related embodiment, said $\beta_2AR$ protein is $\beta_2AR$-T4L. In a related embodiment, the $\beta_2AR$-T4L crystal further comprises a carazolol ligand.

In another embodiment, the invention provides a crystalline form of a human $\beta_2AR$ protein wherein each $\beta_2AR$ molecule in said crystal comprises 442 amino acids, a palmitic acid covalently bound to Cys341, an acetamide molecule bound to $Cys265^{6.27}$, a diffusible ligand, one to ten molecules of a lipid additive, one to five salt ions and one to ten butanediol molecules.

In another embodiment, the invention provides a method of identifying a compound that binds to a ligand binding site of a human $\beta_2AR$ protein, comprising comparing a set of three-dimensional structures representing a set of candidate compounds with a three-dimensional molecular model of said ligand binding site, comprising: receiving a three-dimensional model of a ligand binding site on said human $\beta_2AR$ protein, wherein said three-dimensional model of said ligand binding site comprises atomic co-ordinates for a plurality of ligand-binding residues, wherein said atomic co-ordinates are taken from Appendix I (SEQ ID NOS 4-5, 1 and 6-9, respectively in order of appearance); determining, for each of the set of compound three-dimensional models, a plurality of distance values indicating distances between said atomic co-ordinates of said candidate compound of the set of candidate compounds and said atomic coordinates of said ligand-binding residues comprising said ligand binding site; determining, for each of the set of compound three-dimensional models, a binding strength value based on the plurality of distance values determined for the compound three-dimensional model, wherein the binding strength value indicates the stability of a complex formed by said human $\beta_2AR$ protein and a compound represented by the compound three-dimensional model; and storing a set of results indicating whether each candidate compound binds to the three-dimensional model based on the binding strength values. In a related embodiment, said ligand-binding residues comprise a plurality of residues selected from the group consisting of Y199, A200, S204, T118, V117, W286, Y316, F290, F289, N293, W109, F193, and Y308. In another related embodiment, said ligand-binding residues comprise a plurality of residues selected from the group consisting of W109, V117, T118, F193, Y199, A200, W286, F289, F290, Y316. In another related embodiment of the method of identifying a compound that binds to a ligand binding site of a human $\beta_2AR$ protein, said binding strength value is based on one or more of a hydrogen bonding strength, a hydrophobic interaction strength, or a Coulombic interaction binding strength. In another related embodiment, one or more of said receiving, determining, or storing steps is carried out using a commercially-available software program. In yet another related embodiment, the commercially-available software program is selected from the group consisting of DOCK, QUANTA, Sybyl, CHARMM, AMBER, GRID, MCSS, AUTODOCK, CERIUS II, Flexx, CAVEAT, MACCS-3D, HOOK, LUDI, LEGEND, LeapFrog, Gaussian 92, QUANTA/CHARMM, Insight II/Discover, and ICM. In yet another related embodiment, the method further comprising the step of contacting a human $\beta_2AR$ protein with a molecule comprising an identified candidate compound. In yet another related embodiment, the molecule further comprises a moiety capable of competitively displacing a ligand from said human β₂AR protein, wherein said ligand binds to said ligand binding site of said human β₂AR protein. In yet another related embodiment, the method further comprising characterizing a binding interaction between said human β₂AR protein and said molecule comprising said identified candidate compound, and storing a result of said characterizing. In yet another related embodiment, said characterization comprises determining an activation of a function of said human β₂AR protein, an inhibition of a function of said human β₂AR protein, an increase in expression of said human β₂AR protein, a decrease in expression of said human β₂AR protein, a displacement of a ligand bound to said ligand binding site, or a stability measure for said human β₂AR protein.

In another embodiment, the invention provides a method for selecting a library of potential modulators of β₂AR to be screened, comprising calculating a structure of a first potential modulator using at least a portion of the structure co-ordinates of Appendix I (SEQ ID NOS 4-5, 1 and 6-9, respectively in order of appearance), correlating said structure of said first potential modulator with a library of modulators identified as comprising said structure said first potential modulator, and storing or transmitting information about the identified library.

In yet another embodiment, the invention provides a method of solving the structure of a crystalline form of a protein, comprising: using at least a portion of the structure co-ordinates of Appendix I (SEQ ID NOS 4-5, 1 and 6-9, respectively in order of appearance) to solve the structure of the crystalline form of a test protein, wherein said test protein has significant amino acid sequence homology to any functional domain of β₂AR; and transmitting or storing data descriptive of the structure of said test protein.

In another embodiment, the invention provides a method of identifying from a set of candidate compound three-dimensional models a compound that binds to a ligand binding site of a GPCR or β₂AR protein comprising: receiving a three-dimensional model of a ligand binding site on said GPCR or β₂AR protein, wherein said three-dimensional model of said ligand binding site comprises atomic co-ordinates for a plurality of ligand binding residues; determining, for each candidate compound of the set of candidate compound three-dimensional models, a plurality of distance and angle values indicating distances and angles between atomic co-ordinates of said candidate compound of the set of candidate compound three-dimensional models and said ligand binding site comprising atomic coordinates of said ligand-binding residues; determining, for each of the set of candidate compound three-dimensional models, a binding strength value based on the plurality of distance and angle values determined for the candidate compound three-dimensional model, wherein the binding strength value indicates the stability of a complex formed by said human GPCR or β₂AR protein and a compound represented by the compound three-dimensional model; storing a set of results indicating whether each candidate compound binds to the three-dimensional model based on the binding strength values; searching a database of small organic molecules for compounds exhibiting shape, chemistry, or electrostatic similarity with the candidate compounds indicated to bind to the three-dimensional model based on the binding strength values; and identifying the set of small organic molecules exhibiting shape, chemistry, or electrostatic similarity with the candidate compounds indicated to bind to the three-dimensional model based on binding strength values as likely to also bind to the GPCR or β₂AR the database of small organic molecules is the available chemicals database. In a related embodiment, the shape, chemistry or electrostatic similarity is determined using a program selected from the group consisting of BROOD (openeye), EON (openeye), ROCS (openeye), ISIS Base, and SciFinder.

In another embodiment, the invention provides a method of identifying a ligand that binds to a membrane protein comprising: preparing a lipid meso phase, wherein said lipid meso phase composition comprises (1) a host lipid; (2) said membrane protein; (3) a lipid additive selected from the group consisting of consisting of a sterol, cholesterol, DOPE, DOPE-Me, DOPC, and Asolectin, wherein said lipid additive is 1 to 50% w/w in a lipid host; subjecting said lipid meso phase to humidity and temperature conditions to grow crystals of said membrane protein; contacting said membrane protein crystals with diffusible ligands or a mixture of diffusible ligands; determining the three-dimensional structure of said diffusible ligand contacted membrane protein crystals by X-ray crystallography to obtain an electron density map; and identifying bound ligands by inspection of the electron density map. In a related embodiment, the ligands are substantially insoluble in water.

BRIEF DESCRIPTION OF THE DRAWINGS

The patent or application file contains at least one drawing executed in color. Copies of this patent application publication with color drawing(s) will be Provided by the Office upon request and payment of the necessary fee.

A better understanding of the features and advantages of the present invention will be obtained by reference to the following detailed description that sets forth illustrative embodiments, in which the principles of the invention are utilized, and the accompanying drawings of which:

FIG. 1. Crystals of β₂AR-T4L obtained in 30-35% v/v PEG400, 0.1-0.2 M Na sulfate, 0.1 M Bis-tris propane pH 6.5-7.0, 5-7% v/v 1,4-butanediol using 8-10% w/w cholesterol in monoolein as the host lipid.

FIG. 7A, B, and C are representations of the electron density of the ligand binding site at three different orientations. Residues are labeled by their Ballesteros-Weinstein numbers as superscripts. Elecon density is contoured at 1σ from a 2 $F_o$-$F_c$ difference map. Both B and C are generated by rotating the field of view 90° about the y-axis clockwise and counterclockwise respectively.

Movements of helices III, IV and VI. D. Ligand binding site representation. Carazolol is shown with yellow carbons. Entire helices are assigned a single designation based on their divergence from the rhodopsin position in the area of the ligand binding site as shown. Helix I is highly divergent, Helices II and VI are similar to rhodopsin. Helices IV and VII are moderately constant. Helices III and V are moderately divergent.

Figure 15:
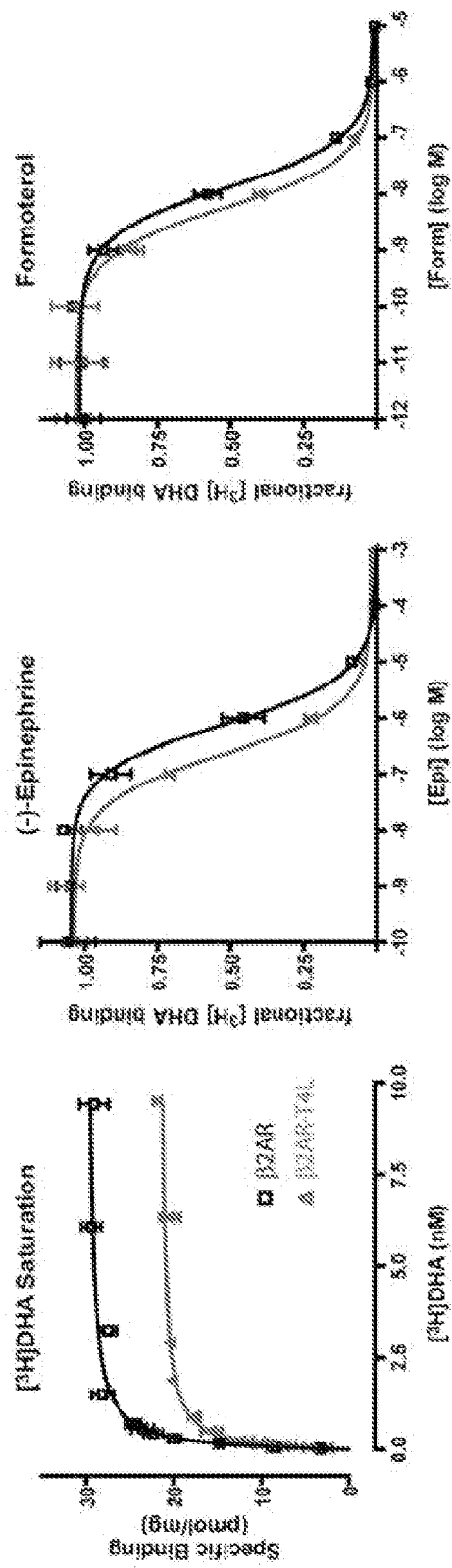

FIG. 15. Affinity curves for adrenergic ligands binding to $\beta_2$AR-T4L and wildtype $\beta_2$AR. Saturation curves for the antagonist [$^3$H]DHA is shown at left, next to competition binding curves for the natural ligand (−)-Epinephrine and the high-affinity synthetic agonist Formoterol. Binding experiments on membranes isolated from Sf9 insect cells expressing the receptors were performed as described above.

Figure 16:
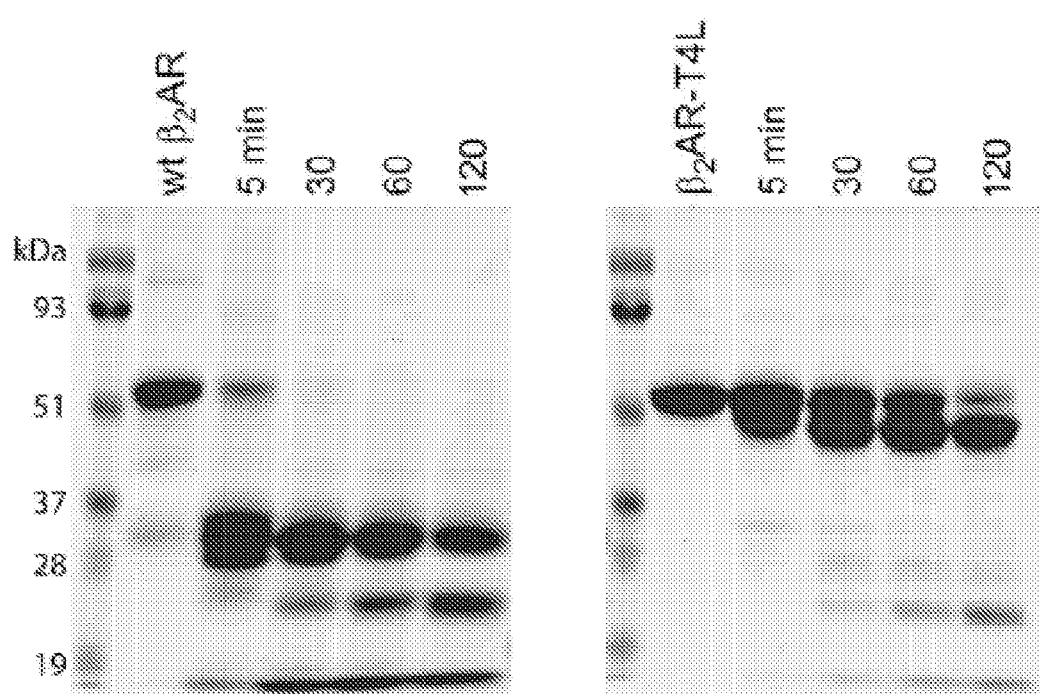

FIG. 16. Comparison of the proteolytic stability between the wild-type $\beta_2$AR and $\beta_2$AR-T4L in a limited trypsin proteolysis assay. TPCK-trypsin was added to carazolol-bound, purified, dodecylmaltoside-solubilized receptor at a 1:1000 ratio (wt:wt), and samples were analyzed by SDS-PAGE. Intact $\beta_2$AR-T4L (56.7 kD) and FLAG-tagged wild-type $\beta_2$AR (47.4 kD) migrate similarly as ~55 kD bands. Markers are Biorad low-range SDS-PAGE protein standards.

Figure 17:
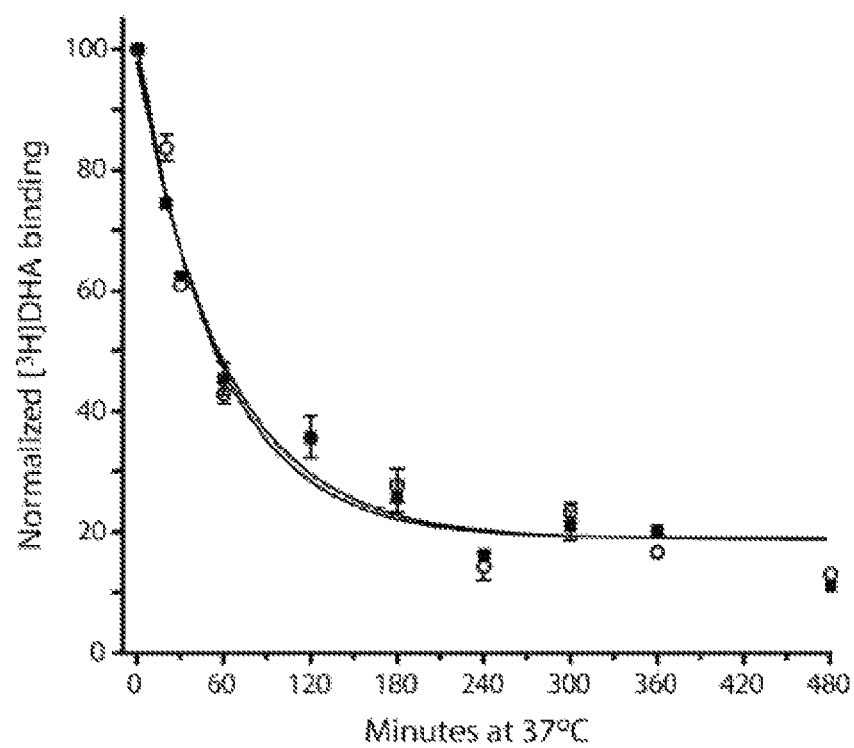

FIG. 17. Stability comparison of unliganded $\beta_2$AR365 and $\beta_2$AR-T4L. For dodecylmaltoside-solubilized receptor preparations, maintenance of the ability to specifically bind [$^3$H]DHA after incubation at 37° C. is taken as a measure of stability.

Figure 18:
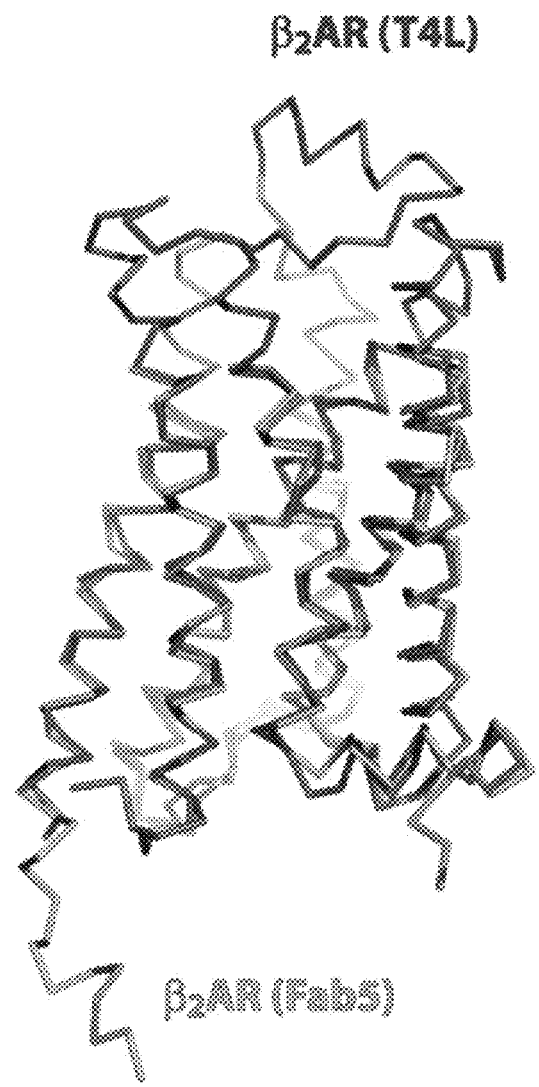

FIG. 18. Superimposed Cα traces of the receptor component of $\beta_2$AR-T4L (in blue) and $\beta_2$AR365 (in yellow). Common modeled transmembrane helix regions 41-58, 67-87, 108-137, 147-164, 204-230, 267-291, 312-326, 332-339 were used in the superposition by the program Lsqkab (The CCP4 Suite, *Acta Crystallogr D Biol Crystallogr* 50, 760 (1994)) (RMSD=0.8 Å).

Figure 19:
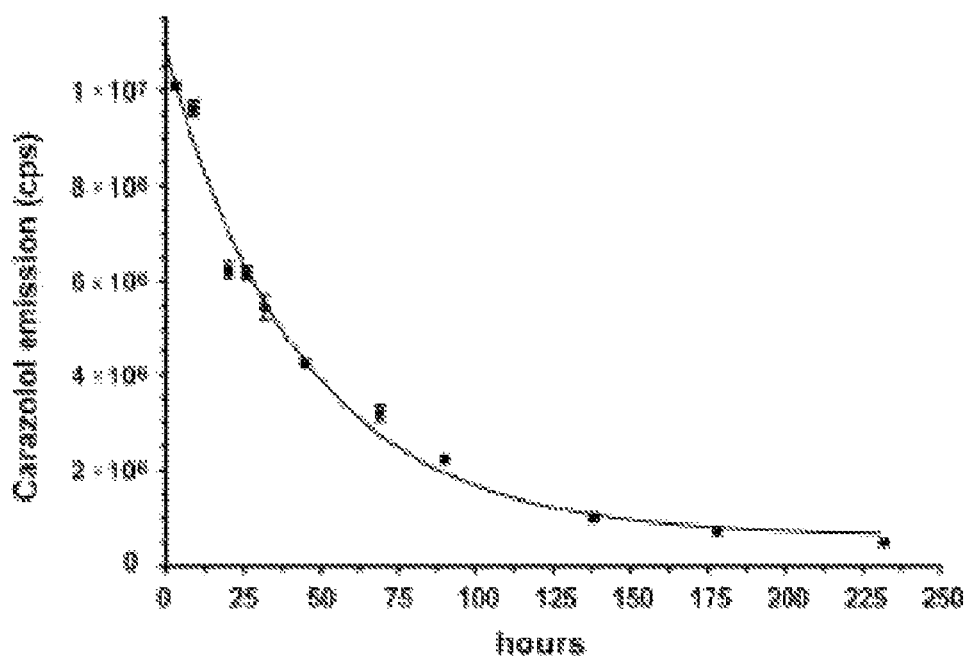

FIG. 19. Carazolol dissociation from $\beta_2$AR365. Dodecylmaltoside-solubilized carazolol-bound receptor (at 50 μM) was dialyzed in a large volume of buffer containing 300 micromolar alprenonol as a competing ligand, and aliquots were removed from the dialysis cassette at different time points. Remaining bound carazolol was measured (in a relative sense) by collecting fluorescence emission with excitation at 330 nm and emission from 335 to 400 nm. For each carazolol fluorescence measurement, data was normalized for the protein concentration in the dialysis cassette (measured with the Bio-Rad Protein DC kit). The Y-axis represents carazolol fluorescence emission Intensity (in cps) at 341 nm. The exponential decay of carazolol concentration in the receptor dialysis cassette was fit using Graphpad Prism software, giving a half-life of 30.4 hrs.

Figure 20:
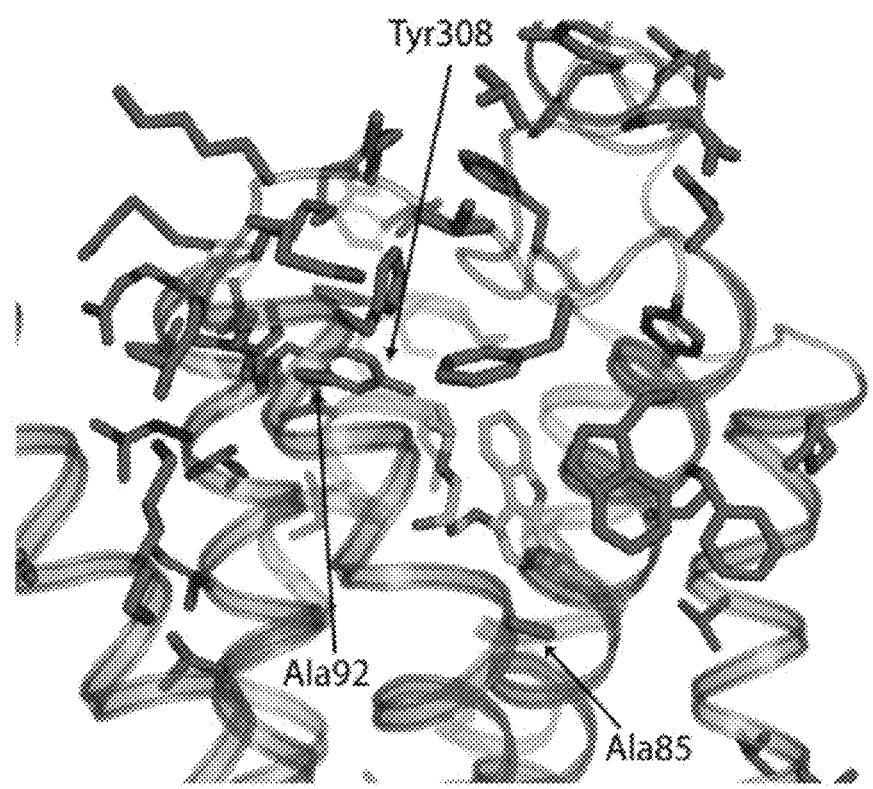

FIG. 20. Comparison of $\beta_1$ and $\beta_2$AR sequences. After aligning the $\beta_1$ and $\beta_2$AR sequences, positions that have different amino acids between the two receptors were mapped onto the high-resolution structure of $\beta_2$ART4L (shown as red sticks). The carazolol ligand is shown as green sticks (with nitrogens in blue and oxygens in red). Highlighted residues Ala85$^{2.56}$, Ala92$^{2.63}$ and Tyr308$^{7.35}$ are homologous to amino acids Leu110$^{2.56}$, Thr117$^{2.63}$ and Phe359$^{7.35}$ of the PAR, which were shown to be primarily responsible for its selectivity over $\beta_2$AR for the compound RO363 (Sugimoto et al., *J Pharmacol Exp Ther* 301, 51 (2002)). In the $\beta_2$AR-T4L structure, only Tyr308$^{7.35}$ faces the ligand, while Ala85$^{2.56}$ lies at the interface between helices II and III. Of all the divergent amino acids, only Tyr308$^{7.35}$ is found within 4 Å of any atom of carazolol.

Figure 21:
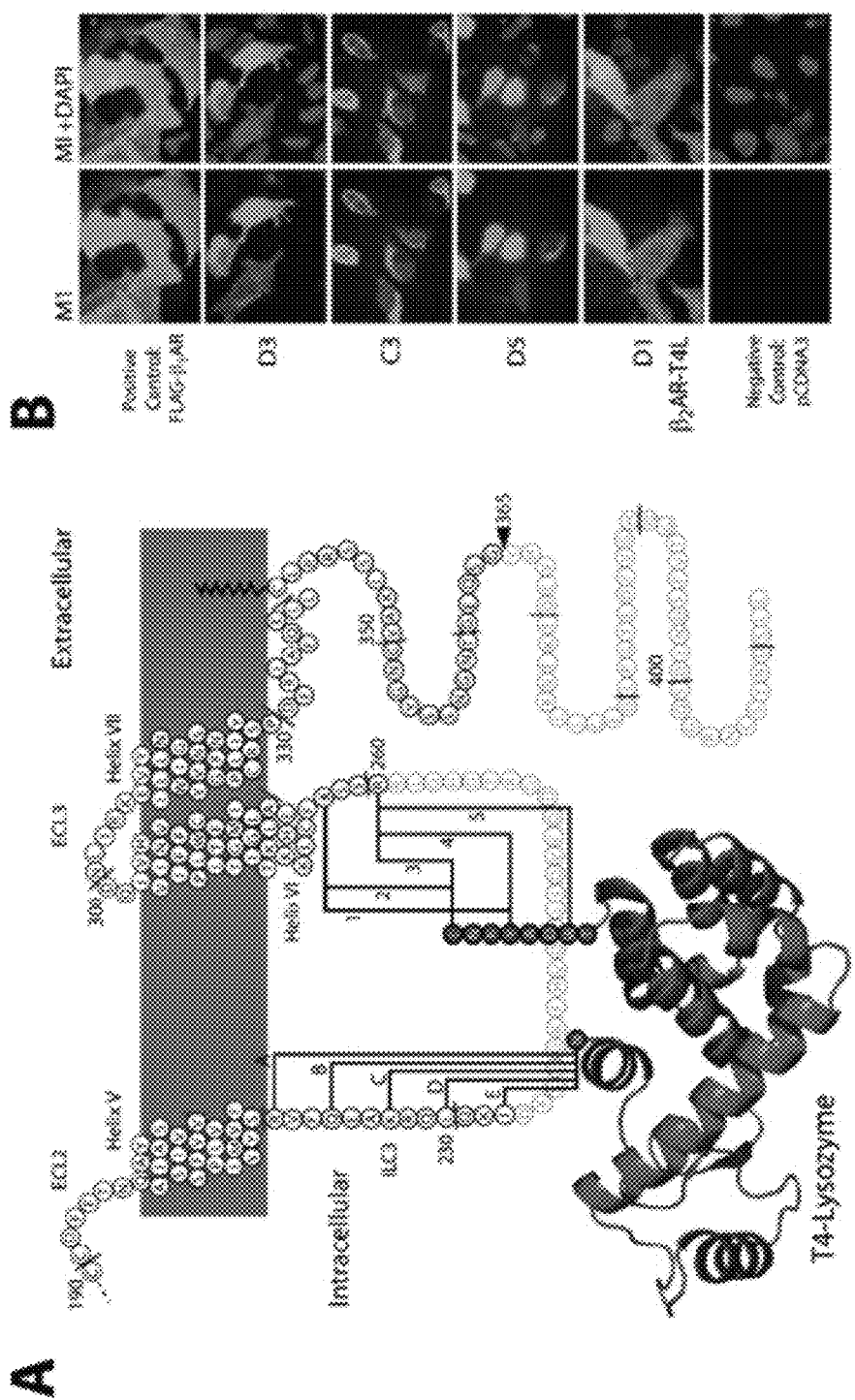

FIG. 21. Design and optimization of the $\beta_2$AR-T4L fusion protein A. The sequence of the region of the $\beta_2$AR targeted for insertion of a crystallizable domain is shown (SEQ ID NO:2), and the positions of the junctions between the receptor and T4L (in red) for various constructs are indicated. The sequences that were initially replaced or removed are faded. Red lines are shown after every tenth residue. Peptide 'LNKYADWT' disclosed as SEQ ID NO 3 B Immunofluorescence images of HEK293 cells expressing selected fusion constructs. Panels on the left shows M1 anti-FLAG signal corresponding to antibody bound to the N-terminus of the receptor. Panels on the right show the same signal merged with blue emission from DAPI (nuclear staining for all cells). Plasma membrane staining is observed in the positive control, D3 and D1, while C3 and D5 are retained in the endoplasmic reticulum.

Figure 22:
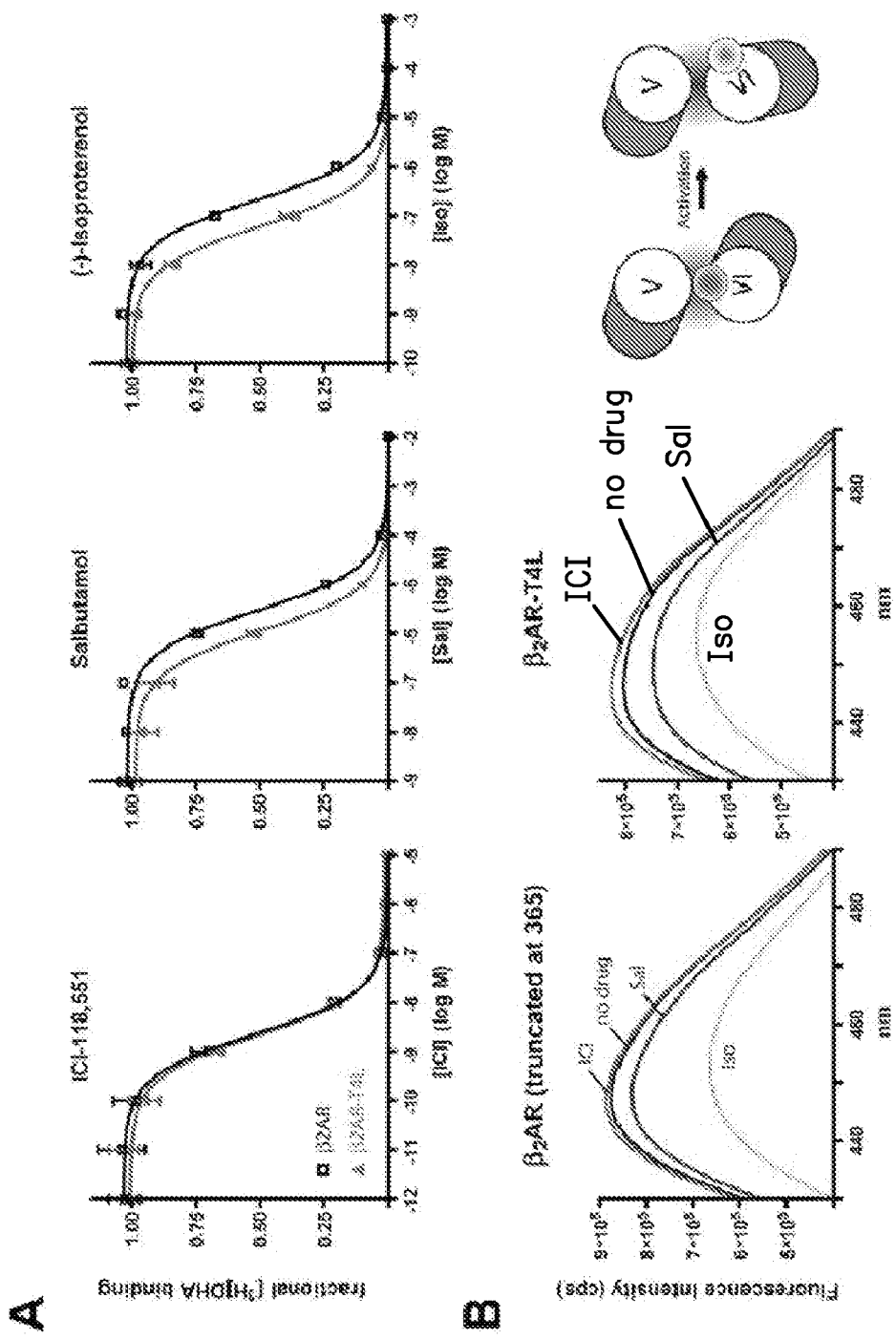

FIG. 22. Functional characterization of $\beta_2$AR-T4L. A. Affinity competition curves for adrenergic ligands binding to $\beta_2$AR-T4L and wild-type $\beta_2$AR. Binding experiments on membranes isolated from Sf9 insect cells expressing the receptors were performed as described in the methods section of Example 4. B. $\beta_2$AR-T4L is still able to undergo ligand-induced conformational changes. Bimane fluorescence spectra (excitation at 350 nm) of detergent-solubilized $\beta_2$AR-T4L and wild-type $\beta_2$AR truncated at 365, labeled under conditions that selectively modify Cys265$^{6.27}$ (see methods section of Example 4), were measured after incubating unliganded receptor with compounds for 15 min at room temperature. The cartoon illustrates that the observed changes in fluorescence can be interpreted as a movement of the bimane probe from a more buried, hydrophobic environment to a more polar, solvent-exposed position.

Figure 23:
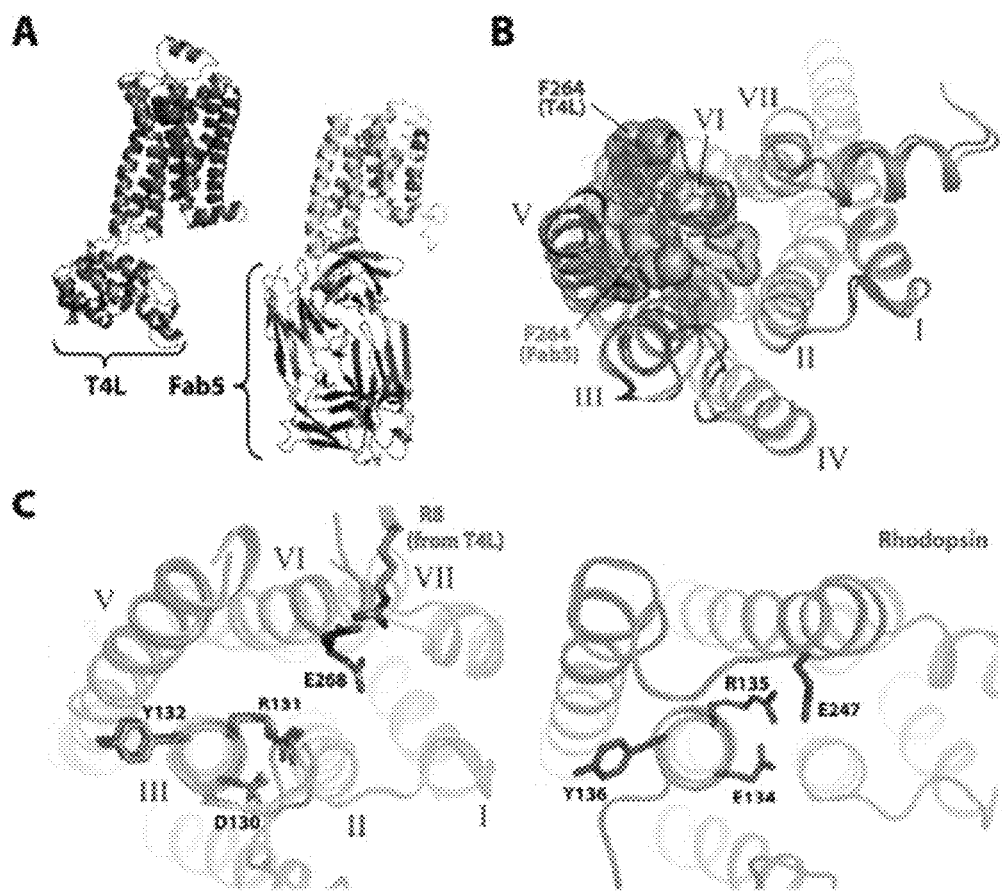

FIG. 23. A. Side-by-side comparison of the crystal structures of the $\beta_2$AR-T4L fusion protein and the complex between $\beta_2$AR365 and a Fab fragment. The receptor component of the fusion protein is shown as a blue cartoon (with modeled carazolol as red spheres), while the receptor bound to Fab5 is in yellow. B. Differences in the environment surrounding Phe264$^{6.26}$ (shown as spheres) for the two proteins. C. The analogous interactions to the "ionic lock" between the E(D)RY motif and Glu247$^{6.30}$ seen in rhodopsin (right panel, darkened) are broken in both structures of the $\beta_2$AR (left panel). Pymol (W. L. DeLano, *The PyMOL Molecular Graphics System* (2002) on the World Wide Web http://www.pymol.org) was used for the preparation of all figures.

Figure 24:
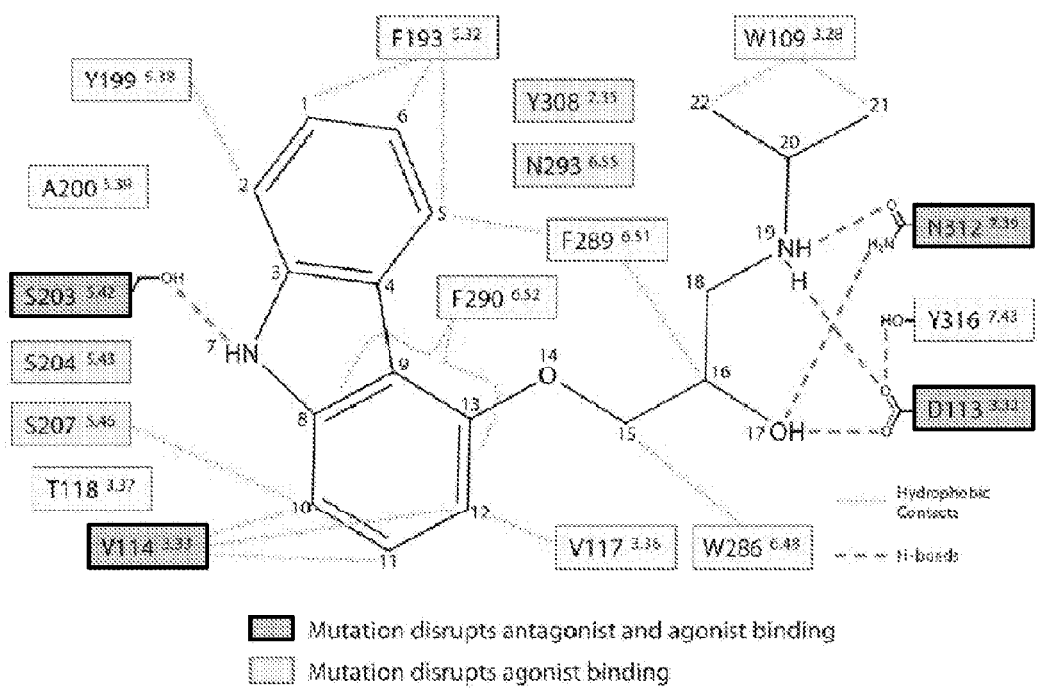

FIG. 24. Schematic representation of the interactions between $\beta_2$AR-T4L and carazolol at the ligand binding pocket. Residues shown have at least one atom within 4 Å of the ligand in the 2.4 Å resolution crystal structure.

Figure 25:
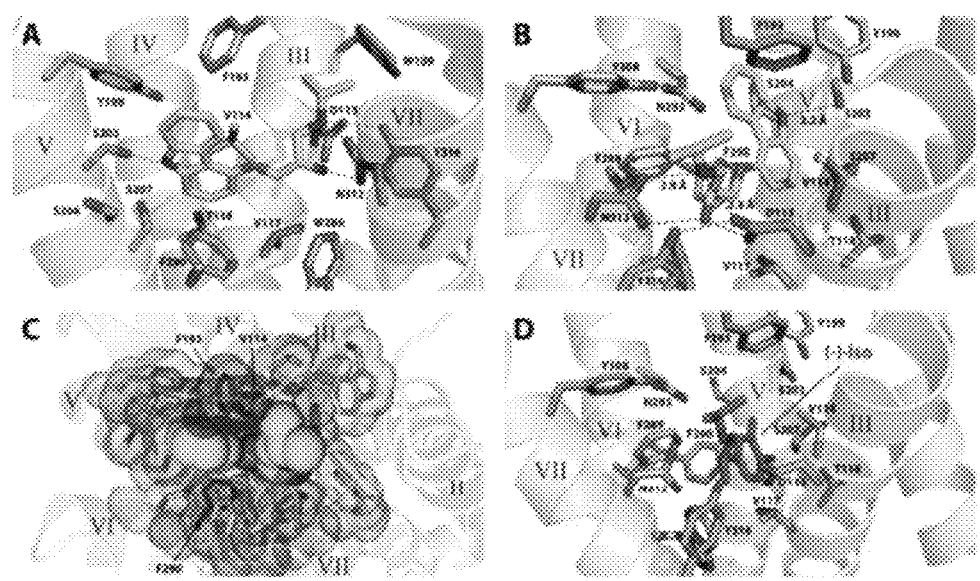

FIG. 25. The ligand binding pocket of $\beta_2$AR-T4L with carazolol bound. A. Residues within 4 Å of the ligand are shown as sticks, with the exception of A200, N293, F289, and Y308. Residues that form polar contacts with the ligand (distance cutoff 3.5 Å) are in green, other residues are gray (in all panels, oxygens are colored red and nitrogens are blue). B. Same as panel A, except that the ligand is oriented with its amine facing out of the page. W109 is not shown. C. Packing interactions between carazolol and all residues within 5 Å of the ligand. View is from the extracellular side of the membrane. Carazolol is shown as yellow spheres, receptor residues are shown as sticks within van der Waals dot surfaces. D. Model of (−)-isoproterenol (magenta sticks) in the ligand binding pocket observed in the crystal structure. A model of the agonist with optimal bond lengths and angles was obtained from the PRODRG server (Schuettelkopf, et al., *Acta Crystallogr D Biol Crystallogr* D60, 1355 (2004)), and the dihedral angles were adjusted to the values observed in the homologous atoms of bound carazolol (16-22 in FIG. 24). The one remaining unaccounted dihedral in (−)-isoproterenol was adjusted in order to place the catechol ring in the same plane as the $C_{16}$—$C_{15}$—$O_{14}$ plane in carazolol. Residues known to specifically interact with agonists are shown as green sticks.

Figure 26:
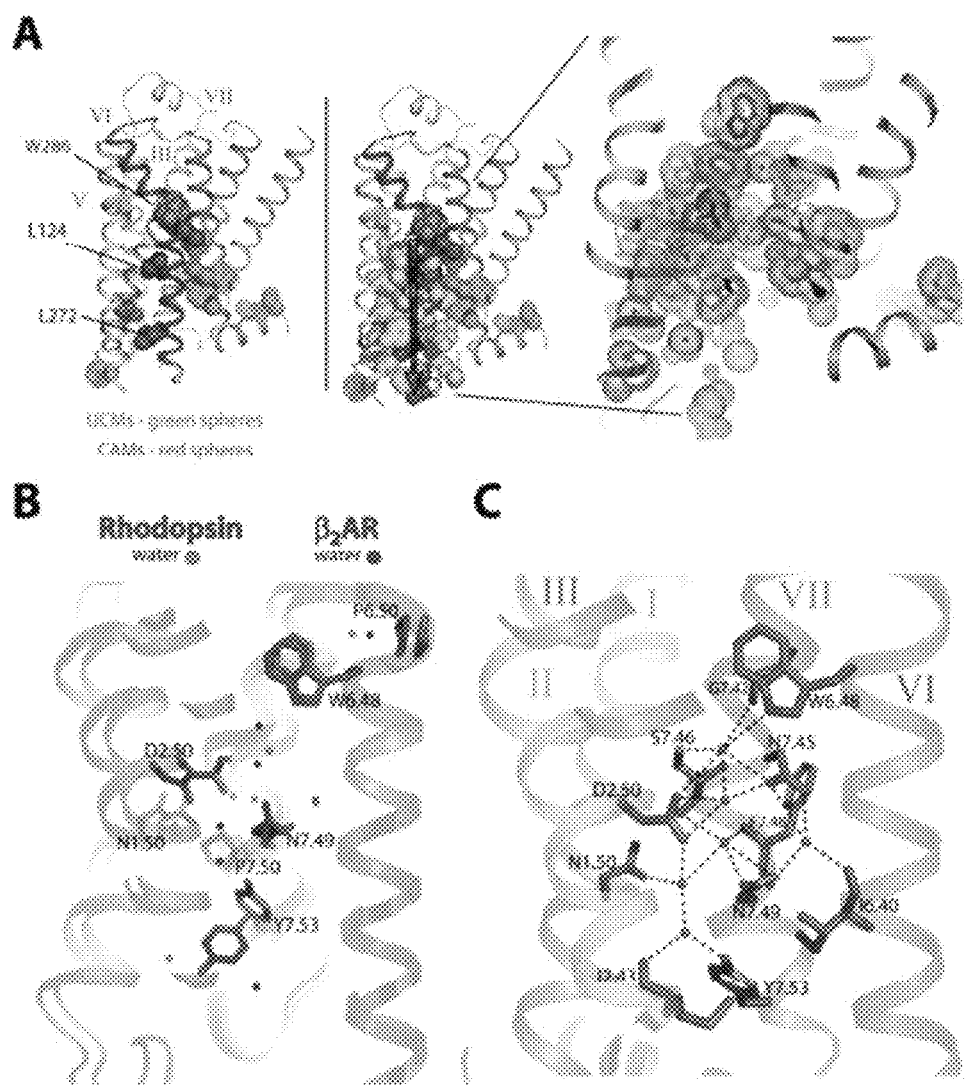

FIG. 26. Packing interactions in the $\beta_2AR$ that are likely to be modulated during the activation process. A. On the left, residues previously demonstrated to be CAMs (Rasmussen et al., *Mol Pharmacol* 56, 175 (1999); Tao, et. al., *Mol Endocrinol* 14, 1272 (2000); Jensen et al., *J Biol Chem* 276, 9279 (2001); Shi et al., *J Biol Chem* 277, 40989 (2002); Zuscik, et. al., (1998)) or UCMs (Strader et al., *Proc Natl Acad Sci USA* 84, 4384 (1987); Chung, et al., *J Biol Chem* 263, 4052 (1988); Moro, et. al., *J Biol Chem* 269, 6651 (1994); Green, et. al., *J Biol Chem* 268, 23116 (1993); Gabilondo et al., *Proc Natl Acad Sci USA* 94, 12285 (1997)) are shown as van der Waals spheres mapped onto a backbone cartoon of the $\beta_2AR$-T4L structure. On the right, residues that are found within 4 Å of the CAMs Leu124$^{3.43}$ and Leu272$^{6.34}$ are shown as yellow spheres or dot surfaces. A vertical cross-section through the structure illustrates that these surrounding residues connect the CAMs on helices III and VI with the UCMs on helix VII through packing interactions. B. In both $\beta_2AR$-T4L (blue) and rhodopsin (purple), a network of ordered water molecules is found at the interface between the transmembrane helices at their cytoplasmic ends. C. Network of hydrogen bonding interactions between water molecules and $\beta_2AR$-T4L residues (sidechains as blue sticks), notably the UCMs on helix VII (orange cartoon).

DETAILED DESCRIPTION OF THE INVENTION

The invention described herein provides methods and compositions for generating crystal structures of membrane proteins that diffract to resolutions as low as 2 to 3 Ångstroms. In one embodiment, the methods involve the crystallization of proteins in a lipidic cubic phase, wherein the host lipid comprises an additive, e.g., a sterol, such as cholesterol. The invention also provides the crystallized membrane proteins themselves, wherein the crystallized membrane proteins include GPCRs or modified GPCRs. The crystallized proteins can also include bound ligands, natural agonists, antagonists, and/or allosteric effectors. The invention additionally provides methods of using the 3-dimensional structures of the proteins (obtained from the crystals) to screen for novel ligands, drugs, and other useful molecules that affect the conformation and/or activity of the proteins in vitro or in vivo.

More specifically, the invention provides particular crystal forms of GPCRs diffracting to high resolutions. GPCRs have been grouped into five classes (Fredriksson, et al., *Mol Pharmacol* 63, 1256 (2003)) based on sequence conservation, with class A GPCRs, including $\beta_2AR$, being the largest and most studied. $\beta_2AR$ agonists are used in the treatment of asthma and preterm labor (DeLano, *The PyMOL Molecular Graphics System* (2002) on World Wide Web at pymol.org). The crystal forms provided by the invention include several diffraction-quality class A GPCR crystals, including crystals comprising β2AR and crystals comprising the human adenosine $A_{2A}$ receptor.

The invention provides a three-dimensional structure of a human $\beta_2AR$ protein comprising a T4-lysozyme (T4L) in place of the third intracellular loop ($\beta_2AR$-T4L") that has been solved in the presence of carazolol (2-propanol, 1-(9H-carbazol-4-yloxy)-3-[(1-methylethyl)amino] at 2.4 Å resolution. Additional class A GPCR structures make it possible to correlate sequence differences between GPCRs, e.g., between rhodopsin and β2AR, with emperically determined structural differences and extrapolate to other class A GPCRs. Highlighting interactions that constrain class A receptors into each of the two observed states allows a more comprehensive analysis of structural divergence and, therefore, more accurate models. Furthermore, GPCR structures provide an alternative signaling state on which to base homology models that will be more relevant For virtual ligand screening and structure-based drug design (Bissantz, et. al, *Proteins* 50, 5 (2003); Gouldson et al., *Proteins* 56, 67 (2004)).

DEFINITIONS

Terms used in the claims and specification are defined as set forth below unless otherwise specified. Unless defined otherwise, all technical and scientific terms used herein have the same meaning as is commonly understood by one of skill in the art to which this invention belongs.

As used herein, the term "binding site" or "binding pocket" refers to a region of a protein that binds or interacts with a particular compound.

As used herein, the terms "binding" or "interaction" refers to a condition of proximity between a chemical entity, compound, or portions thereof, with another chemical entity, compound or portion thereof. The association or interaction can be non-covalent—wherein the juxtaposition is energetically favored by hydrogen bonding or van der Waals or electrostatic interactions—or it can be covalent.

As used herein, the term "residue" refers to an amino acid that is joined to another by a peptide bond. Residue is referred to herein to describe both an amino acid and its position in a polypeptide sequence.

As used herein, the term "surface residue" refers to a residue located on a surface of a polypeptide. In contrast, a buried residue is a residue that is not located on the surface of a polypeptide. A surface residue usually includes a hydrophilic side chain. Operationally, a surface residue can be identified computationally from a structural model of a polypeptide as a residue that contacts a sphere of hydration rolled over the surface of the molecular structure. A surface residue also can be identified experimentally through the use of deuterium exchange studies, or accessibility to various labeling reagents such as, e.g., hydrophilic alkylating agents.

As used herein, the term "polypeptide" refers to a single linear chain of 2 or more amino acids. A protein is an example of a polypeptide.

As used herein, the term "homolog" refers to a gene related to a second gene by descent from a common ancestral DNA sequence. The term, homolog, can apply to the relationship between genes separated by the event of speciation or to the relationship between genes separated by the event of genetic duplication.

As used herein, the term "conservation" refers to a high degree of similarity in the primary or secondary structure of molecules between homologs. This similarity is thought to confer functional importance to a conserved region of the molecule. In reference to an individual residue or amino acid, conservation is used to refer to a computed likelihood of substitution or deletion based on comparison with homologous molecules.

As used herein, the term "distance matrix" refers to the method used to present the results of the calculation of an optimal pairwise alignment score. The matrix field (i,j) is the score assigned to the optimal alignment between two residues (up to a total of i by j residues) from the input sequences. Each entry is calculated from the top-left neighboring entries by way of a recursive equation.

As used herein, the term "substitution matrix" refers to a matrix that defines scores for amino acid substitutions, reflecting the similarity of physicochemical properties, and observed substitution frequencies. These matrices are the foundation of statistical techniques for finding alignments.

As used herein, the term "pharmacophore" refers to an ensemble of steric and electronic features that is necessary to ensure the optimal supramolecular interactions with a specific biological target structure and to trigger or block a biological response. A pharmacophore can be used to design one or more candidate compounds that comprise all or most of the ensemble of steric and electronic features present in the pharmacophore and that are expected to bind to a site and trigger or block a biological response.

As used herein, the term "G-protein coupled receptor" (or "GPCR") refers to a member of a family of heterotrimeric guanine-nucleotide binding protein ("G-protein") coupled receptors (Pierce, et al., *Nat. Rev. Mol. Cell. Biol.* 3:630 (2002)). GPCRs share a common structural signature of seven membrane-spanning helices with an extra-cellular N terminus and an intracellular C terminus. The family has been grouped into at least five classes (designated A, B, C, D, E, etc.; see, e.g., Fredriksson, et al., *Mol Pharmacol* 63, 1256 (2003)) based on sequence conservation. When used without a descriptive limitation, the term "a G-protein couple receptor" includes GPCRs with native amino acid sequences as well as genetically engineered or otherwise mutated GPCR proteins. Mutated GPCR proteins include those comprising point mutations, truncations, inserted sequences or other chemical modifications, while retaining ligand binding activity. One example of a GPCR referred to herein that comprises a point mutation is $\beta 2AR^{E122W}$. An example of a GPCR referred to herein that comprises an inserted T4 lysozyme sequence is the human $A_{2a}$ receptor-T4L.

Adrenergic receptors in the class A or amine group are some of the most thoroughly investigated GPCRs (Kobilka, *Annu Rev Neurosci* 15, 87 (1992); Caron, et al., *Recent Prog Horm Res* 48, 277 (1993); Strosberg, *Protein Sci* 2, 1198 (1993); Hein, et al., *Trends Cardiovasc Med* 7, 137 (1997); Rohrer, *J Mol Med* 76, 764 (1998); Xiang, et al., *Adrenergic Receptors*, 267 (2006)), and are composed of two main sub-families, α and β, which differ in tissue localization and ligand specificity, as well as in G protein coupling and downstream effector mechanisms (Milligan, et al., *Biochem Pharmacol* 48, 1059 (1994)). Some representative class A receptors include the human $A_{2A}$ adenosine receptor and the beta-2 adrenergic receptor. The term "beta-2 adrenergic receptor" (or "$\beta_2 AR$" or "β2AR") refers to a class A GPCR that responds to diffusable hormones and neurotransmitters and resides predominantly in smooth muscles throughout the body. When used without a descriptive limitation, the term "β2AR" includes β2ARs with native amino acid sequences as well as genetically engineered or otherwise mutated β2AR proteins. Mutated β2AR proteins include those comprising point mutations, truncations, inserted sequences or other chemical modifications, while retaining ligand binding activity. One example of a β2AR referred to herein that comprises a point mutation is $\beta 2AR^{E122W}$. An example of a β2AR referred to herein that comprises an inserted T4 lysozyme sequence is the human adenosine receptor $\beta 2AR^{E122W}$-T4L.

The term "diffracts to a resolution of xx-yy Angstroms" means that diffraction data exceeding a predetermined signal to noise ratio can be obtained within the stated resolution range. In some embodiments, that diffraction data can be obtained using synchrotron radiation. Also, in some embodiments, that diffraction data can be obtained following freezing of the crystal in liquid nitrogen.

As used herein, the term "atomic co-ordinates" refers to a set of three-dimensional co-ordinates for atoms within a molecular structure. In one embodiment, atomic-co-ordinates are obtained using X-ray crystallography according to methods well-known to those of ordinarily skill in the art of biophysics. Briefly described, X-ray diffraction patterns can be obtained by diffracting X-rays off a crystal. The diffraction data are used to calculate an electron density map of the unit cell comprising the crystal; said maps are used to establish the positions of the atoms (i.e., the atomic co-ordinates) within the unit cell. Those of skill in the art understand that a set of structure co-ordinates determined by X-ray crystallography contains standard errors. In other embodiments, atomic co-ordinates can be obtained using other experimental biophysical structure determination methods that can include electron diffraction (also known as electron crystallography) and nuclear magnetic resonance (NMR) methods. In yet other embodiments, atomic co-ordinates can be obtained using molecular modeling tools which can be based on one or more of ab initio protein folding algorithms, energy minimization, and homology-based modeling. These techniques are well known to persons of ordinary skill in the biophysical and bioinformatic arts, and are described in greater detail below.

Atomic co-ordinates for binding pockets, such as, e.g., the ligand binding pocket of β2AR, and/or other agonist/antagonist binding sites of the present invention are intended to encompass those co-ordinates set out in the .pdb file (Appendix I; SEQ ID NOS 4-5, 1 and 6-9, respectively in order of appearance) incorporated into this specification, as well as co-ordinates that are substantially equivalent. Substantially equivalent co-ordinates are those that can be related to a reference set of co-ordinates by transformation reflecting differences in the choice of origin or inter-axis angels for one or more axes used to define the coordinate system. Operationally, co-ordinates are "substantially equivalent" when the structures represented by those co-ordinates can be superimposed in a manner such that root mean square deviations (RMSD) of atomic positions for the structures differs by less than a predetermined threshold. In some embodiments that threshold is less than about 5 Angstroms, or less than about 4 Angstroms, or less than about 3 Angstroms, or less than about 2 Angstroms, or less than about 1 Angstrom, or less than about 0.9 Angstrom, or less than about 0.8 Angstrom, or less than about 0.7 Angstrom, or less than about 0.6 Angstrom, or less than about 0.5 Angstrom, or less than about 0.4 Angstrom, or less than about 0.3 Angstrom. Preferably, co-ordinates are considered "substantially equivalent" when the RMSD is less than about 1 Angstrom. Methods for structure superpositioning and RMSD calculations are well known to those of ordinary skill in the art, and can be carried out using programs such as, e.g., the programs listed in Table 5 below.

Structural similarity can be inferred from, e.g., sequence similarity, which can be determined by one of ordinary skill through visual inspection and comparison of the sequences, or through the use of well-known alignment software programs such as CLUSTAL (Wilbur et al., *J. Proc. Natl. Acad. Sci. USA*, 80, 726 730 (1983)) or CLUSTALW (Thompson et al., *Nucleic Acids Research*, 22:4673 4680 (1994)) or BLAST® (Altschul et al., *J Mol. Biol.*, October 5; 215(3):403 10 (1990)), a set of similarity search programs designed to explore all of the available sequence databases regardless of whether the query is protein or DNA. CLUSTAL W is available at the EMBL-EBI website (http://www.ebi.ac.uk/clustalw/); BLAST is available from the National Center for Biotechnology website (http://www.ncbi.nlm.nih.gov/BLAST/). A residue within a first protein or nucleic acid sequence corresponds to a residue within a second protein or nucleic acid sequence if the two residues occupy the same position when the first and second sequences are aligned.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence co-ordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (NCBI web-site).

The term "sterol" refers to a subgroup of steroids with a hydroxyl group at the 3-position of the A-ring. See Fahy E. Subramaniam S et al., "A comprehensive classification system for lipids," *J. Lipid Res.* 46 (5):839-861 (2005)). Sterols are amphipathic lipids synthesized from acetyl-coenzyme A via the HMG-CoA reductase pathway. The overall molecule is quite flat. Sterols can include, e.g., cholesterol or cholesteryl hemisuccinate ("CHS").

The term "atomic co-ordinates for residues" refers to co-ordinates for all atoms associated with a residue, or for some of the atoms such as, e.g., side chain atoms.

The term "atomic co-ordinates of a candidate compound" refers to co-ordinates for all atoms comprising the compound or a subset of atoms comprising the compound.

The term "characterizing a binding interaction" refers to characterizing any observable property of a first molecule and determining an whether there is a change in that observable property after contacting the first molecule with a second molecule under conditions in which said first and second molecules can potentially bind.

The term "antagonist" refers to molecules that bind to and block the active site of a protein, but do not affect the equilibrium between inactive and active states. In contrast, an "agonist" is a ligand that shifts the equilibrium to an active receptor state. An "inverse agonist" is a ligand that acts to reduce the basal activity of a receptor through interactions that shift the equilibrium to more of an inactive state.

Ballesteros-Weinstein numbering appears in the text and Figures as superscripts to the protein numbering. Within each helix is a single most conserved residue among the class A GPCRs. This residue is designated X.50, where x is the number of the transmembrane helix. All other residues on that helix are numbered relative to this conserved position.

It must be noted that, as used in the specification and the appended claims, the singular forms "a," "an" and "the" include plural referents unless the context clearly dictates otherwise.

Method for Producing Diffraction Quality Crystals of Membrane Proteins

In one aspect, the present invention discloses a modified lipidic cubic mesophase method for crystallizing proteins (see, e.g., Cherezov et al., *Biophysical J.*, v. 83, 3393-3407 (2002)). The novel method described herein yields diffraction quality crystals of membrane proteins and is particularly useful for generating crystals of G-protein coupled receptor proteins ("GPCRs"). The method has now been successfully applied to diverse members of this important family of proteins, yielding crystals that diffract to resolutions in the 2.5 Å range. Among other advantages, this method allows diffraction-quality crystals of membrane proteins to be generated in the absence of any stabilizing antibodies bound to the protein in the crystal.

The LCP/sterol crystallization method described herein includes a step of mixing a solution containing the protein of interest with a host lipid or a host lipid mixture that includes a lipid additive. Given the teaching provided herein, one skilled in the art will recognize that a variety of host lipids may suffice for the generation of a cubic mesophase, e.g., hydrated monounsaturated monoacylglycerols such as monoolein, monopalmitolein, and/or monovacennin. The host lipid 1-monoolein is a preferred host lipid for certain applications of the method. In embodiments utilizing a lipid mixture, a lipid additive that is distinct from the host lipid is included, e.g., monounsaturated monoacylglycerols or other hydrophobic molecules known to interact with membranes or membrane-associated proteins such as, 2-monoolein, phosphotidylcholine, cardiolipin, lyso-PC, a polyethylene glycol-lipid, dioleoylphosphatidylethanolamine ("DOPE"), DOPE-Me, dioleoyl phosphatidylcholine ("DOPC"), Asolectin, or a sterol (e.g., cholesterol, ergosterol, etc.). An example of a lipid mixture for GPCR crystallization is one comprising cholesterol as lipid additive in a ratio between 1 and 50% w/w relative to the host lipid, more preferably between 5 and 20%, and even more preferably between 8 and 12%. The protein mixture may include ligands of physiological interest and/or ligands that stabilize the protein. In the case of GPCRs, the ligands may include various agonists and antagonists known to the artisan, including well-known agonists such as carazolol (an inverse agonist), timolol, and other molecules including, without limitation, Examples of ligands, include but are not limited to carazolol, light and olfactory stimulatory molecules; adenosine, bombesin, bradykinin, endothelin, γ-aminobutyric acid (GABA), hepatocyte growth factor, melanocortins, neuropeptide Y, opioid peptides, opsins, somatostatin, tachykinins, vasoactive intestinal polypeptide family, and vasopressin; biogenic amines (e.g., dopamine, epinephrine and norepinephrine, histamine, glutamate (metabotropic effect), glucagon, acetylcholine (muscarinic effect), and serotonin); chemokines; lipid mediators of inflammation (e.g., prostaglandins and prostanoids, platelet activating factor, and leukotrienes); and peptide hormones (e.g., calcitonin, C5a anaphylatoxin, follicle stimulating hormone (FSH), gonadotropic-releasing hormone (GnRH), neurokinin, and thyrotropin releasing hormone (TRH), and oxytocin).

A typical concentration of protein in the protein mixture is 25-75 mgs/ml but this concentration may vary according to protein identity and purification methods. As will be recognized by the skilled artisan, the concentration must be high enough to result in a degree of insolubility sufficient for nucleation to occur after a precipitation solution is combined with the protein-laden lipid solution; on the other hand, concentrations of protein that are too high may prevent the orderly growth of high-quality crystals.

The lipid mixture is preferably combined with the protein mixture and homogenized, e.g., using a syringe mixer, spontaneously yielding a homogenous cubic phase. Typically, the lipid mixture is added to the protein solution at a ratio of 1:1, 3:2, 4:2 w/w lipid:protein, but this ratio may be varied by the skilled artisan as desired, depending on various parameters, e.g., the concentration of protein in the protein mixture. The protein-laden lipidic cubic phase preparation thus obtained is then combined with precipitation solution (also referred to as crystallization solution) on or in an appropriate surface or container, e.g., a glass sandwich plate with wells where the mixed solutions can incubate while crystallization occurs. A typical volume of the protein-laden lipidic cubic phase used in the method is between 10 and 100 mL, with 40 to 60 mL preferred in certain embodiments. A typical volume of precipitation solution is 20 to 100 times greater, e.g., for a 20 mL volume of protein-laden lipidic cubic phase, approximately 1 µL of precipitation solution would be added to initiate crystallization.

The precipitation solution used in the crystallization method is an appropriately buffered solution (i.e., buffered to approximate the physiological conditions of the native protein) comprising polyethylene glycol, a salt, and optionally a small soluble molecule such as an alcohol.

With respect to the polyethylene glycol in the precipitation solution, useful PEG molecules include PEG 300, PEG 400, PEG 550, PEG 550 mme, PEG 1000, and PEG 1500, as well as other PEG molecules with average molecular weights less than 2000. In certain embodiments, larger average molecular weight PEG molecules (up to 20,000) or modified PEG molecules may be preferred. In some embodiments, the PEG or modified PEG has an average molecular weight of 400. Examples of modified PEG include but are not limited to PEG laurate, PEG dilaurate, PEG oleate, PEG dioleate, PEG stearate, PEG distearate, PEG glyceryl trioleate, PEG glyceryl laurate, PEG glyceryl stearate, PEG glyceryl oleate, PEG palm kernel oil, PEG hydrogenated castor oil, PEG castor oil, PEGcorn oil, PEG caprate/caprylate glycerides, PEG caprate/caprylate glycerides, PEG cholesterol, PEG phyto sterol, PEG soya sterol, PEG trioleate, PEG sorbitan oleate, PEG sorbitan laurate, PEG succinate, PEG nonyl phenol series, PEG octyl phenol series, Methyl-PEG, PEG-Maleimide, PEG4-NHS Ester and methoxypoly(ethylene glycol) (mPEG).

PEG may be present in the crystallization solution in concentrations between 10-60% v/v, and most typically between 20-40% v/v. The preferred concentration will vary depending on the average molecular weight of PEG utilized, i.e., 10-60% v/v of PEG will be preferred for PEG<1000 whereas 10-30% w/v will be preferred for PEG>1000 (larger average molecular weight PEG formulations are described in % w/v rather than % v/v).

With respect to the salt used in the method, an optimum cation can usually be found for a given crystal. Both sodium and lithium sulfate have proven useful for obtaining high resolution proteins of GPCRs. Again, the concentrations may be varied up to 1M, with lower concentrations of approximately 50-200 mM typically preferred. Other organic salts, e.g., citrate, malonate, tartrate, formate and acetate, may also be screened for their effects on crystal formation. In certain embodiments, the precipitation solution additionally comprises a small organic molecule such as an alcohol, a diol or a triol, e.g., a hexanediol, a butanediol, or derivative thereof. These molecules may be present in the precipitation solution in various concentrations, as appropriate, but typically in the range of 1-20% v/v, more typically in the 5-10% v/v range. In certain embodiments, preferred combinations of lipid additives (in the protein-laden lipidic cubic phase mixture) and small molecules (in the precipitation solution) yield optimal results. Examples of such combinations include 1,4-butanediol in combination with DOPE or cholesterol, and 2,6-hexanediol in combination with cholesterol.

In optimizing the conditions from micro-crystals to larger crystals for a given system (e.g., a protein/ligand system), the choice and concentration of a specific sterol(s) and specific lipid(s), as well the pH, buffer system, salt, and salt concentration may be varied, as in other types of crystallization formats. As noted above, small organic additives, especially alcohols and diols such as 1,4 butanediol, 1,6 hexanediol, etc., can be particularly useful in generating large diffraction quality crystals. Also, due to the membrane fluidity-altering properties of cholesterol and other sterols, sterol and precipitant concentration should be treated as dependent variables. For example, increasing concentrations of cholesterol in monoolein serve to rigidify the membranes, potentially slowing diffusion of the membrane protein within the lipid matrix. Conversely, increasing concentrations of PEG 400 swell the cubic phase, thereby increasing the lattice parameter of the matrix and speeding diffusion within the lipid. The former scenario would slow the rate of crystallization while the latter would increase the rate. The two effects should therefore be balanced for optimal nucleation and also for optimal growth of large, well-ordered crystals that diffract to a high resolution.

The mixing of the protein-laden lipidic cubic phase solution and the precipitation solution typically occurs at room temperatures. After set-up, the plates containing the mixed crystallization solutions can be monitored as often as desired for the appearance of crystal growth. One skilled in the art will recognize that further optimization of these conditions may be desirable, for example, to maximize the size and number of diffraction quality crystals that are obtained. In making determinations as to the preferred molecules and conditions for crystallization, the skilled artisan may rely on well-known phase diagrams and other previously determined physical constants, in addition to the novel methodology and Examples described herein. For certain lipid mixtures, pre-screening their phase behavior by microscope visualization and/or by X-ray prior to being mixed with the protein solution may facilitate the process of optimization. An in meso crystallization robot and automatic imager combined with multiple 96-well optimization screens can be used to run thousands of trials in a relatively facile manner.

It also possible to achieve additional stabilization of proteins and improve the yield of diffraction-quality crystals using the LCP/sterol method described herein by modification of the protein. For example, an unstable region of the protein may be replaced or stabilized by incorporation of a portion of a stable protein, e.g., a T4 lysozyme, whose structure is previously known but which does not (when fused) significantly affect the biochemical activity of the protein of interest. For example, the ECL2 and ECL3 regions of a β2AR can be stabilized by such modifications, as described herein (Examples 3 and 4). Other modifications include one or more point mutations that do not significantly alter the properties of the protein of interest except to increase its stability and/or tendency to crystallize well. For example, $\beta 2AR^{(E122W)}$ comprises an E122W point mutation and yields crystals with the LPC/sterol method. Analogous residues in other GPCRs could be modified in the same way. One advantage of the LCP method applied to both modified and unmodified proteins, as noted above, is that it allows (but does not preclude) the crystallization of proteins in the absence of heterologous proteins, such as antibodies, that may not be of interest to the crystallographer.

Method of Ligand Screening by Lipidic Cubic Phase Crystallization

Aspects of the lipidic cubic phase crystallization methodology described above can be modified for the purpose of determining low affinity lipid binding sites within integral membrane proteins through co-crystallization trials within a lipidic cubic phase matrix. In this method various lipids of different composition are incorporated at a variety of concentrations into monoolein, wherein the monoolein is solubilized in chloroform or heated to its fluid isotropic phase. Crystal growth is then assessed by visual inspections and diffraction data collected on any crystalline material within the experiment. Because the lipid is low affinity the method requires an environment conducive for free exchange of lipid from annular to non-annular protein binding sites. The presence of interpretable electron density not associated with crystal packing interfaces allows the inference of specific binding sites for a particular lipid within the context of the membrane protein in a membrane environment. Because the binding occurs within a membrane the complicating factor of detergent partitioning is eliminated and thermodynamics of association are more realistic. The method thus allows one to characterize in detail previously inaccessible regions of membrane proteins, as well as describe and exploit binding interactions that might otherwise remain undetected. Furthermore, the technique can be applied to ligand binding studies where the ligand occupies a site on the membrane protein that is juxtaposed to the lipid plane relying on partitioning into the aqueous phase to enable saturation of the site. This limits the exposure of the protein to harsh organic co-solvents and may also find utility for soluble proteins that crystallize within the lipidic cubic phase solvent channels.

By wan of example, existing crystallization conditions for a protein can be utilized as a starting point for screening novel ligands to the β2-adrenergic receptor. In the first instance, cholesterol solubilized in chloroform can be incorporated into chloroform-solubilized monoolein at weight ratio of 10%. After drying and desiccating the mixture, protein at 30-80 mg/mL can incorporated at 2/3 volume ratio and used for crystallization trials. A similar protocol was used for other lipid like molecules, including cholesteryl hemisuccinate and a variety of other cholesterol analogs. In each case protein was incorporated into the resulting mixture and screened for crystallization. Binding of the novel ligand to the receptor is indicated by diffraction quality crystals and ultimately by three-dimensional structural data. By incorporating analogues of cholesterol we are able to map out the binding specificities based on the unique structural features of their respective sterol rings and polar moieties and, if their incorporation led to diffraction quality crystals, the interactions between the protein and cholesterol analogue are determined.

This method of ligand screening is not limited to lipid-like molecules, as we can use the lipidic cubic phase as a host for other highly hydrophobic molecules that act at orthosteric binding sites. One problem with structure based or fragment based design of novel ligands is the hydrophobicity often associated with potential drug leads. This is a problem in aqueous based crystallization schemes because the solubility of the ligand is often less than 1 mM and unless there is a slow off rate from the protein of interest the binding site will be in a ligand depleted state at crystallization conditions which often involve protein concentrations between 0.5 and 1 mM. One can attempt to co-solubilize the hydrophobic ligand in aqueous miscible organic solvent such as dimethyl sulfoxide (DMSO) or dimethyl formamide (DMF). However, these often interfere with the stability or crystallization properties of the protein and their usefulness is not general. Therefore, this method allows one to incorporate the hydrophobic ligand directly into the lipidic cubic phase where its accessibility to the protein will be limited by the partitioning between the lipid and aqueous phase and/or the accessibility of the binding.

Additional guidance relating to these methods is provided by the working and prophetic examples of protein crystallization presented herein.

The Crystal Structure of Human β2AR Bound to Carazolol and Uses Thereof

G-protein coupled receptors are cell surface receptors that indirectly transduce extracellular signals to downstream effectors, e.g., intracellular signaling proteins, enzymes, or channels. G-protein coupled receptor membrane proteins are grouped into one of at least 6 classes (i.e., A, B, C, D, E, and F). An example of a mammalian G-protein coupled receptor is the β2A receptor, a receptor in the Class A subfamily of GPCRs.

Class A GPCRs function in a variety of physiological processes such as vasodilation, bronchodilation, neurotransmitter signaling, stimulation of endocrine secretions, gut peristalsis, development, mitogenesis, cell proliferation, cell migration, immune system function, and oncogenesis. Accordingly, class A GPCRs can be used as screening targets to identify modulators of these processes which can then function to ameliorate diseases associated with these processes, e.g., cancer and autoimmunity.

The 2.4 Angstrom structure of β2AR bound to carazolol, described herein (PDB coordinates appear in Appendix I; SEQ ID NOS 4-5, 1 and 6-9, respectively in order of appearance) can be used as a model for rationally designing pharmacophore and/or candidate compounds, either de novo or by modification of known compounds. As noted below, the multiple ligand binding sites in this structure include amino acids that are highly conserved across a large number of class A G protein coupled receptors (GPCRs) indicating that the 2.4 Angstrom structure of β2AR can be used for the rational designing of ligands (e.g., therapeutic compounds) that bind to this receptor and others. Pharmacophore and candidate compounds identified through the use of the crystal structure co-ordinates will have utility as pharmaceuticals due to their ability to alter the structure and/or binding properties of β2AR. Pharmacophores and candidate compounds can be determined according to any method known in the art, including the methods described in U.S. Pat. No. 5,888,738 to Hendry, and the methods described in U.S. Pat. No. 5,856,116 to Wilson et al. the disclosures of which both are incorporated by reference in their entirety for all purposes.

The structure data provided herein can be used in conjunction with computer-modeling techniques to develop models of sites on the human β2AR or related GPCRs selected by analysis of the crystal structure data. The site models characterize the three-dimensional topography of site surface, as well as factors including van der Waals contacts, electrostatic interactions, and hydrogen-bonding opportunities. Computer simulation techniques can be used to map interaction positions for functional groups including protons, hydroxyl groups, amine groups, divalent cations, aromatic and aliphatic functional groups, amide groups, alcohol groups, etc. that are designed to interact with the model site. These groups can be designed into a pharmacophore or candidate compound with the expectation that the candidate compound will specifically bind to the site. Pharmacophore design thus involves a consideration of the ability of the candidate compounds falling within the pharmacophore to interact with a site through any or all of the available types of chemical interactions, including hydrogen bonding, van der Waals, electrostatic, and covalent interactions, although, in general, and preferably, pharmacophores interact with a site through non-covalent mechanisms.

The ability of a pharmacophore or candidate compound to bind to the human β2AR can be analyzed prior to actual synthesis using computer modeling techniques. Only those candidates that are indicated by computer modeling to bind the target with sufficient binding energy (i.e., binding energy corresponding to a dissociation constant with the target on the order of $10^{-2}$M or tighter) can be synthesized and tested for their ability to bind to the human β2AR using binding assays or functional assays known to those of skill in the art. The computational evaluation step thus avoids the unnecessary synthesis of compounds that are unlikely to bind β2AR or one or more of its constitutive binding sites, or the related binding sites of another GPCR with adequate affinity.

A human β2AR or candidate compound(s) can be computationally evaluated and designed by means of a series of steps in which chemical entities or fragments are screened and selected for their ability to associate with individual binding target sites on β2AR or binding site thereof, including, but not limited to a binding pocket of the human β2AR. One skilled in the art can use one of several methods to screen chemical entities or fragments for their ability to associate with one or more of these human β2AR binding sites. For example, increased affinity and specificity may be designed into caffeine and other xanthine molecules by combining interactions with both xanthine and non-xanthine binding sites.

The process can begin by visual inspection of, for example a target site on a computer screen, based on the human β2AR co-ordinates, or a subset of those co-ordinates (e.g., binding pocket residues V117, T118, F193, Y199, A200, W286, F289, F290, and Y316), as set forth in Appendix I (SEQ ID NOS 4-5, 1 and 6-9, respectively in order of appearance). Selected fragments or chemical entities can then be positioned in a variety of orientations or "docked" within a target site of the human β2AR as defined from analysis of the crystal structure data Docking can be accomplished using software such as Quanta (Molecular Simulations, Inc., San Diego, Calif.) and Sybyl (Tripos, Inc. St. Louis, Mo.) followed by energy minimization and molecular dynamics with standard molecular mechanics forcefields such as CHARMM (Molecular Simulations, Inc., San Diego, Calif.), ICM (Molsoft, San Diego, Calif.), and AMBER (University of California, San Francisco).

Specialized computer programs can also assist in the process of selecting fragments or chemical entities. These include but are not limited to: GRID (Goodford, P. J., "A Computational Procedure for Determining Energetically Favorable Binding Sites on Biologically Important Macromolecules," *J. Med. Chem.*, 28, pp. 849 857 (1985)); GRID is available from Oxford University, Oxford, UK; MCSS (Miranker, A. and M. Karplus, "Functionality Maps of Binding Sites: A Multiple Copy Simultaneous Search Method," *Proteins: Structure, Function and Genetics*, 11, pp. 29 34 (1991)); MCSS is available from Molecular Simulations, Inc., San Diego, Calif.; AUTODOCK (Goodsell, D. S, and A. J. Olsen, "Automated Docking of Substrates to Proteins by Simulated Annealing," Proteins: Structure, Function, and Genetics, 8, pp. 195 202 (1990)); AUTODOCK is available from Scripps Research Institute, La Jolla, Calif.; DOCK (Kuntz, I. D., et al. "A Geometric Approach to Macromolecule-Ligand Interactions," *J. Mol. Biol.*, 161, pp. 269 288 (1982)); DOCK is available from University of California, San Francisco, Calif.; CERIUS II (available from Molecular Simulations, Inc., San Diego, Calif.); and Flexx (Raret, et al. *J. Mol. Biol.* 261, pp. 470 489 (1996)).

After selecting suitable chemical entities or fragments, they can be assembled into a single compound. Assembly can proceed by visual inspection of the relationship of the fragments to each other on a three-dimensional image of the fragments in relation to the human β2AR or its binding sites or those of a related GPCR receptor structure or portion thereof displayed on a computer screen. Visual inspection can be followed by manual model building using software such as the Quanta or Sybyl programs described above.

Software programs also can be used to aid one skilled in the art in connecting the individual chemical entities or fragments. These include, but are not limited to CAVEAT (Bartlett, P. A., et al. "CAVEAT: A Program to Facilitate the Structure-Derived Design of Biologically Active Molecules" In "Molecular Recognition in Chemical and Biological Problems," Special Publ, *Royal Chem. Soc.*, 78, pp. 182 196 (1989)); CAVEAT is available from the University of California, Berkeley, Calif.; 3D Database systems such as MACCS-3D (MDL Information Systems, San Leandro, Calif.); this area is reviewed in Martin, Y. C., "3D Database Searching in Drug Design," *J. Med. Chem.*, 35:2145 2154 (1992)); and HOOK (available from Molecular Simulations Inc., San Diego, Calif.).

As an alternative to building candidate pharmacophores or candidate compounds up from individual fragments or chemical entities, they can be designed de novo using the structure of the β2AR, its constituent ligand binding pocket, or the homologous cavities in a related GPCR, optionally, including information from co-factor(s) or known activators or inhibitor(s) that bind to the target site. De novo design can be implemented by programs including, but not limited to LUDI (Bohm, H. J., "The Computer Program LUDI: A New Method for the De Novo Design of Enzyme Inhibitors," *J. Comp. Aid. Molec. Design*, 6, pp. 61 78 (1992)); LUDI is available from Molecular Simulations, Inc., San Diego, Calif.; LEGEND (Nishibata, Y., and Itai, A., *Tetrahedron* 47, p. 8985 (1991); LEGEND is available from Molecular Simulations, San Diego, Calif.; and LeapFrog (available from Tripos Associates, St. Louis, Mo.).

The functional effects of known β2AR also can be altered through the use of the molecular modeling and design techniques described herein. This can be carried out by docking the structure of the known ligand on a human $A_{2A}$ adenosine receptor or a model structure of one or more binding sites of the human β2AR (e.g., the binding pocket described herein) and modifying the shape and charge distribution of the ligand or protein model structure to optimize the binding interactions between the ligand and protein. The modified structure can be synthesized or obtained from a library of compounds and tested for its binding affinity and/or effect on ribosome function. Of course, where the crystal structure of a complex between a human β2AR (or subunit thereof) and a ligand is known, comparisons between said complex and the structures of the present invention can be made to gain additional information about alterations in human β2AR conformation that occur upon ligand binding. This information can be used in design of optimized ligands. Compounds that interfere or activate human β2AR function (e.g., by interacting with a binding pocket) are especially well suited for the docking, co-crystallization, and optimization applications of the present invention.

Additional molecular modeling techniques also can be employed in accordance with the invention. See, e.g., Cohen, N. C., et al. "Molecular Modeling Software and Methods for Medicinal Chemistry," *J. Med. Chem.*, 33, pp. 883 894 (1990); Hubbard, Roderick E., "Can drugs be designed?" *Curr. Opin. Biotechnol.* 8, pp. 696 700 (1997); and Afshar, et al. "Structure-Based and Combinatorial Search for New RNA-Binding Drugs," *Curr. Opin. Biotechnol.* 10, pp. 59 63 (1999).

Following pharmacophore or candidate compound design or selection according to any of the above methods or other methods known to one skilled in the art, the efficiency with which a candidate compound falling within the pharmacophore definition binds to the human β2AR or its ligand binding site, or alternatively binds to a related GPCR or homologous portions thereof, can be tested and optimized using computational evaluation. A candidate compound can be optimized, e.g., so that in its bound state it would preferably lack repulsive electrostatic interaction with the target site. These repulsive electrostatic interactions include repulsive charge-charge, dipole-dipole, and charge-dipole interactions. It is preferred that the sum of all electrostatic interactions between the candidate compound and the human β2AR, including its ligand binding site when the candidate compound is bound to the target make a neutral or favorable contribution to the binding enthalpy or free energy.

Specific computer software is available in the art to evaluate compound deformation energy and electrostatic interactions. Examples of programs designed for such uses include, but are not limited to Gaussian 92, revision C (Frisch, M. J., Gaussian, Inc., Pittsburgh, Pa. (1992)); AMBER, version 4.0 (Kollman, P. A., University of California at San Francisco, (1994)); QUANTA/CHARMM (Molecular Simulations, Inc., San Diego, Calif. (1994)); and Insight II/Discover (Biosym Technologies Inc., San Diego, Calif. (1994)). These programs can be run, using, e.g., a Silicon Graphics workstation, Indigo, 02-R10000 or IBM RISC/6000 workstation model 550. Other hardware and software combinations can be used to carry out the above described functions, and are known to those of skill in the art. In general, the methods described herein, particularly computer-implemented methods, comprise a step of recording or storing data onto a medium, wherein the medium can include a computer-readable medium. Additionally, or alternatively, the methods comprise a step of reporting or communicating the data to a user of interest, e.g., an operator of the device and/or computer that is employed in the method; or the computer can perform an additional useful task, e.g., alert the operator of the computer that a function has been completed, upon completing one or more determining steps of the method.

Once a pharmacophore or candidate compound has been optimally selected or designed, as described above, substitutions can then be made in some of its atoms or side groups to improve or modify its binding properties. Generally, initial substitutions are conservative in that the replacement group will have approximately the same size, shape, hydrophobicity and charge as the original group. Components known in the art to alter conformation should be avoided in making substitutions. Substituted candidates can be analyzed for efficiency of fit to the human β2AR (or one or more binding sites of the humanβ2AR) using the same methods described above.

Assays

Any one of a number of assays of function known to those of skill in the art can be used to determine the biological activity of candidate compounds.

Candidate compound interaction with the human β2AR (or one or more binding sites of human β2AR) or to a related GPCR or portion thereof can be evaluated using direct binding assays including filter binding assays, such as are known to those skilled in the art. Binding assays can be modified to evaluate candidate compounds that competitively inhibit the binding of, e.g., known human β2AR binding compounds including xanthine and xanthine-based compounds such as theophylline, theobromine and caffeine. These and other assays are described in International Publication WO 00/69391, the entire disclosure of which is incorporated by reference in its entirety for all purposes. Methods of assaying for modulators of ligand binding and signal transduction include in vitro ligand binding assays using GPCRs, such as human β2AR (or one or more binding sites selected from the binding pockets I, II and III of the human β2AR), portions thereof such as the extracellular domain, or chimeric proteins comprising one or more domains of a GPCR, oocyte GPCR expression or tissue culture cell GPCR expression, either naturally occurring or recombinant; membrane expression of a GPCR, either naturally occurring or recombinant; tissue expression of a GPCR; expression of a GPCR in a transgenic animal, etc.

As noted above, GPCRs and their alleles and polymorphic variants are G-protein coupled receptors that participate in signal transduction and are associated with cellular function in a variety of cells, e.g., neurons, immune system cells, kidney, liver, colon, adipose, and other cells. The activity of GPCR polypeptides can be assessed using a variety of in vitro and in vivo assays to determine functional, chemical, and physical effects, e.g., measuring ligand binding, (e.g., radioactive ligand binding), second messengers (e.g., cAMP, cGMP, $IP_3$, DAG, or $Ca^{2+}$), ion flux, phosphorylation levels, transcription levels, neurotransmitter levels, and the like. Such assays can be used to test for inhibitors and activators of a GPCR. In particular, the assays can be used to test for compounds that modulate natural ligand-induced GPCR activity, for example, by modulating the binding of the natural ligand to the receptor and/or by modulating the ability of the natural ligand to activate the receptor. Typically in such assays, the test compound is contacted with the GPCR in the presence of the natural ligand. The natural ligand can be added to the assay before, after, or concurrently with the test compound. The results of the assay, for example, the level of binding, calcium mobilization, etc. is then compared to the level in a control assay that comprises the GPCR and natural ligand in the absence of the test compound.

Screening assays of the invention are used to identify modulators that can be used as therapeutic agents, e.g., antagonists of GPCR activity. For example, carazolol is a known high-affinity inverse agonist of human β2AR.

The effects of test compounds upon the function of the GPCR polypeptides can be measured by examining any of the parameters described above. Any suitable physiological change that affects GPCR activity can be used to assess the influence of a test compound on the GPCRs and natural ligand-mediated GPCR activity. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, $IP_3$ or cAMP.

For a general review of GPCR signal transduction and methods of assaying signal transduction, see, e.g., Methods in Enzymology, vols. 237 and 238 (1994) and volume 96 (1983); Bourne et al., Nature 10:349:117-27 (1991); Bourne et al., Nature 348:125-32 (1990); Pitcher et al., Annu. Rev. Biochem. 67:653-92 (1998).

Modulators of GPCR activity are tested using GPCR polypeptides, either recombinant or naturally occurring. The protein can be isolated, expressed in a cell, expressed in a membrane derived from a cell, expressed in tissue or in an animal, either recombinant or naturally occurring. For example, neurons, cells of the immune system, adipocytes, kidney cells, transformed cells, or membranes can be used. Modulation is tested using one of the in vitro or in vivo assays described herein or others as generally known in the art. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of the protein of interest can be used in vitro in soluble or solid state reactions to assay for ligand binding.

Ligand binding to a human β2AR (or one or more binding sites thereof) or a chimeric protein derivative can be tested in a number of formats. For example, binding can be performed in solution, in a bilayer membrane, attached to a solid phase, in a lipid monolayer, or in vesicles. Typically, in an assay of the invention, the binding of the natural ligand to its receptor is measured in the presence of a candidate modulator. Alternatively, the binding of the candidate modulator can be measured in the presence of the natural ligand. Often, competitive assay that measure the ability of a compound to compete with binding of the natural ligand to the receptor are used. Binding can be measured by assessing GPCR activity or by other assays: binding can be tested by measuring e.g., changes in spectroscopic characteristics (e.g., fluorescence, absorbance, refractive index), hydrodynamic (e.g., shape) changes, or changes in chromatographic or solubility properties.

Receptor-G-protein interactions can also be used to assay for modulators. For example, in the absence of GTP, binding of an activator such as the natural ligand will lead to the formation of a tight complex of a G protein (all three subunits) with the receptor. This complex can be detected in a variety of ways, as noted above. Such an assay can be modified to search for inhibitors. For example, a ligand can be added to the human β2AR and G protein in the absence of GTP to form a tight complex. Inhibitors can be identified by looking at dissociation of the receptor-G protein complex. In the presence of GTP, release of the alpha subunit of the G protein from the other two G protein subunits serves as a criterion of activation.

An activated or inhibited G-protein will in turn alter the properties of downstream effectors such as proteins, enzymes, and channels. The classic examples are the activation of cGMP phosphodiesterase by transducin in the visual system, adenylate cyclase by the stimulatory G-protein, phospholipase C by $G_q$ and other cognate G proteins, and modulation of diverse channels by Gi and other G proteins. Downstream consequences such as generation of diacyl glycerol and $IP_3$ by phospholipase C, and in turn, for calcium mobilization e.g., by $IP_3$ can also be examined. Thus, modulators can be evaluated for the ability to stimulate or inhibit ligand-mediated downstream effects. In other examples, the ability of a modulator to activate a GPCR expressed in adipocytes in comparison to the ability of a natural ligand, can be determined using assays such as lipolysis (see, e.g., WO01/61359).

Activated GPCRs become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. Modulators can therefore also be identified using assays involving beta-arrestin recruitment. Beta-arrestin serves as a regulatory protein that is distributed throughout the cytoplasm in unactivated cells. Ligand binding to an appropriate GPCR is associated with redistribution of beta-arrestin from the cytoplasm to the cell surface, where it associates with the GPCR. Thus, receptor activation and the effect of candidate modulators on ligand-induced receptor activation, can be assessed by monitoring beta-arrestin recruitment to the cell surface. This is frequently performed by transfecting a labeled beta-arrestin fusion protein (e.g., beta-arrestin-green fluorescent protein (GFP)) into cells and monitoring its distribution using confocal microscopy (see, e.g., Groarke et al., J. Biol. Chem. 274(33):23263-69 (1999)).

Receptor internalization assays can also be used to assess receptor function. Upon ligand binding, the G-protein coupled receptor—ligand complex is internalized from the plasma membrane by a clathrin-coated vesicular endocytic process; internalization motifs on the receptors bind to adaptor protein complexes and mediate the recruitment of the activated receptors into clathrin-coated pits and vesicles. Because only activated receptors are internalized, it is possible to detect ligand-receptor binding by determining the amount of internalized receptor. In one assay format, cells are transiently transfected with radiolabeled receptor and incubated for an appropriate period of time to allow for ligand binding and receptor internalization. Thereafter, surface-bound radioactivity is removed by washing with an acid solution, the cells are solubilized, and the amount of internalized radioactivity is calculated as a percentage of ligand binding. See, e.g., Vrecl et al., Mol. Endocrinol. 12:1818-29 (1988) and Conway et al., J. Cell Physiol. 189(3):341-55 (2001). In addition, receptor internalization approaches have allowed real-time optical measurements of GPCR interactions with other cellular components in living cells (see, e.g., Barak et al., Mol. Pharmacol. 51(2)177-84 (1997)). Modulators can be identified by comparing receptor internalization levels in control cells and cells contacted with candidate compounds. For example, candidate modulators the human β2AR are assayed by examining their effects on receptor internalization upon binding of the natural ligand.

Another technology that can be used to evaluate GPCR-protein interactions in living cells involves bioluminescence resonance energy transfer (BRET). A detailed discussion regarding BRET can be found in Kroeger et al., J. Biol. Chem., 276(16):12736-43 (2001).

Receptor-stimulated guanosine 5'-O-(γ-Thio)-Triphosphate ([$^{35}$S]GTPγS) binding to G-proteins can also be used as an assay for evaluating modulators of GPCRs. [$^{35}$S]GTPγS is a radiolabeled GTP analog that has a high affinity for all types of G-proteins, is available with a high specific activity and, although unstable in the unbound form, is not hydrolyzed when bound to the G-protein. Thus, it is possible to quantitatively assess ligand-bound receptor by comparing stimulated versus unstimulated [$^{35}$S]GTPγS binding utilizing, for example, a liquid scintillation counter. Inhibitors of the receptor-ligand interactions would result in decreased [$^{35}$S]GTPγS binding. Descriptions of [$^{35}$S]GTPγS binding assays are provided in Traynor and Nahorski, Mol. Pharmacol. 47(4):848-54 (1995) and Bohn et al., Nature 408:720-23 (2000).

The ability of modulators to affect ligand-induced ion flux can also be determined. Ion flux can be assessed by determining changes in polarization (i.e., electrical potential) of the cell or membrane expressing a GPCR. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., New Engl. J. Med. 336:1575-1595 (1997)). Whole cell currents are conveniently determined using the standard methodology (see, e.g., Hamil et al., Pflügers. Archiv. 391:85 (1981). Other known assays include: radiolabeled ion flux assays and fluorescence assays using voltage-sensitive dyes (see, e.g., Vestergarrd-Bogind et al., J. Membrane Biol. 88:67-75 (1988); Gonzales & Tsien, Chem. Biol. 4:269-277 (1997); Daniel et al., J. Pharmacol. Meth. 25:185-193 (1991); Holevinsky et al., J. Membrane Biology 137:59-70 (1994)). Generally, the compounds to be tested are present in the range from 1 pM to 100 mM.

Preferred assays for G-protein coupled receptors include cells that are loaded with ion or voltage sensitive dyes to report receptor activity. Assays for determining activity of such receptors can also use known agonists and antagonists for other G-protein coupled receptors and the natural ligands disclosed herein as negative or positive controls to assess activity of tested compounds. In assays for identifying modulatory compounds (e.g., agonists, antagonists), changes in the level of ions in the cytoplasm or membrane voltage are monitored using an ion sensitive or membrane voltage fluorescent indicator, respectively. Among the ion-sensitive indicators and voltage probes that can be employed are those disclosed in the Molecular Probes 1997 Catalog. For G-protein coupled receptors, promiscuous G-proteins such as Gα15 and Gα16 can be used in the assay of choice (Wilkie et al., Proc. Nat'l Acad. Sci. USA 88:10049-10053 (1991)). Such promiscuous G-proteins allow coupling of a wide range of receptors to signal transduction pathways in heterologous cells.

Receptor activation by ligand binding typically initiates subsequent intracellular events, e.g., increases in second messengers such as IP$_3$, which releases intracellular stores of calcium ions. Activation of some G-protein coupled receptors stimulates the formation of inositol triphosphate (IP$_3$) through phospholipase C-mediated hydrolysis of phosphatidylinositol (Berridge & Irvine, Nature 312:315-21 (1984)). IP$_3$ in turn stimulates the release of intracellular calcium ion stores. Thus, a change in cytoplasmic calcium ion levels, or a change in second messenger levels such as IP$_3$ can be used to assess G-protein coupled receptor function. Cells expressing such G-protein coupled receptors can exhibit increased cytoplasmic calcium levels as a result of contribution from both intracellular stores and via activation of ion channels, in which case it can be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated by ligand binding, result in a change in the level of intracellular cyclic nucleotides, e.g., cAMP or cGMP, by activating or inhibiting downstream effectors such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., Proc. Natl. Acad. Sci. U.S.A. 88:9868-9872 (1991) and Dhallan et al., Nature 347:184-187 (1990)). In cases where activation of the receptor results in a decrease in cyclic nucleotide levels, it can be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In one embodiment, changes in intracellular cAMP or cGMP can be measured using immunoassays. The method described in Offermanns & Simon, J. Biol. Chem. 270:15175-15180 (1995) can be used to determine the level of cAMP. Also, the method described in Felley-Bosco et al., Am. J. Resp. Cell and Mol. Biol., 11:159-164 (1994) can be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with $^3$H-myoinositol for 48 or more hrs. The labeled cells are treated with a test compound for one hour. The treated cells are lysed and extracted in chloroform-methanol-water after which the inositol phosphates are separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which can or can not contain an agonist).

In another embodiment, transcription levels can be measured to assess the effects of a test compound on ligand-induced signal transduction. A host cell containing the protein of interest is contacted with a test compound in the presence of the natural ligand for a sufficient time to effect any interactions, and then the level of gene expression is measured. The amount of time to effect such interactions can be empirically determined, such as by running a time course and measuring the level of transcription as a function of time. The amount of transcription can be measured by using any method known to those of skill in the art to be suitable. For example, mRNA expression of the protein of interest can be detected using northern blots or their polypeptide products can be identified using immunoassays. Alternatively, transcription based assays using reporter genes can be used as described in U.S. Pat. No. 5,436,128, herein incorporated by reference. The reporter genes can be, e.g., chloramphenicol acetyltransferase, firefly luciferase, bacterial luciferase, beta-galactosidase and alkaline phosphatase. Furthermore, the protein of interest can be used as an indirect reporter via attachment to a second reporter such as green fluorescent protein (see, e.g., Mistili & Spector, Nature Biotechnology 15:961-964 (1997)).

The amount of transcription is then compared to the amount of transcription in either the same cell in the absence of the test compound, or it can be compared with the amount of transcription in a substantially identical cell that lacks the protein of interest. A substantially identical cell can be derived from the same cells from which the recombinant cell was prepared but which had not been modified by introduction of heterologous DNA. Any difference in the amount of transcription indicates that the test compound has in some manner altered the activity of the protein of interest.

Samples that are treated-with a potential GPCR inhibitor or activator are compared to control samples comprising the natural ligand without the test compound to examine the extent of modulation. Control samples (untreated with activators or inhibitors) are assigned a relative GPCR activity value of 100. Inhibition of a GPCR is achieved when the GPCR activity value relative to the control is about 90%, optionally 50%, optionally 25-0%. Activation of a GPCR is achieved when the GPCR activity value relative to the control is 110%, optionally 150%, 200-500%, or 1000-2000%.

In one embodiment the invention provides soluble assays using molecules such as a domain, e.g., a ligand binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; a GPCR; or a cell or tissue expressing a GPCR, either naturally occurring or recombinant. In another embodiment, the invention provides solid phase based in vitro assays in a high throughput format, where the domain, chimeric molecule, GPCR, or cell or tissue expressing a GPCR is attached to a solid phase substrate.

Certain screening methods involve screening for a compound that modulates the expression of the GPCRs described herein, or the levels of natural ligands, e.g., ASP and stanniocalcins. Such methods generally involve conducting cell-based assays in which test compounds are contacted with one or more cells expressing the GPCR or ligand and then detecting an increase or decrease in expression (either transcript or translation product). Such assays are typically performed with cells that express the endogenous GPCR or ligand. Expression can be detected in a number of different ways. As described herein, the expression levels of the protein in a cell can be determined by probing the mRNA expressed in a cell with a probe that specifically hybridizes with a transcript (or complementary nucleic acid derived therefrom) of the GPCR or protein ligand. Probing can be conducted by lysing the cells and conducting Northern blots or without lysing the cells using in situ-hybridization techniques (see above). Alternatively, protein can be detected using immunological methods in which a cell lysate is probed with antibodies that specifically bind to the protein.

Other cell-based assays are reporter assays conducted with cells that do not express the protein. Certain of these assays are conducted with a heterologous nucleic acid construct that includes a promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, beta-glucuronidase, CAT (chloramphenicol acetyl transferase), luciferase, beta-galactosidase and alkaline phosphatase.

In these assays, cells harboring the reporter construct are contacted with a test compound. A test compound that either modulates the activity of the promoter by binding to it or triggers a cascade that produces a molecule that modulates the promoter causes expression of the detectable reporter. Certain other reporter assays are conducted with cells that harbor a heterologous construct that includes a transcriptional control element that activates expression of the GPCR or ligand and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

In one embodiment the invention provides soluble assays using molecules such as a domain, e.g., a ligand binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; a GPCR; or a cell or tissue expressing a GPCR, either naturally occurring or recombinant. In another embodiment, the invention provides solid phase based in vitro assays in a high throughput format, where the domain, chimeric molecule, GPCR, or cell or tissue expressing a GPCR is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-1500 different compounds. It is possible to assay several different plates per day; assay screens for up to about 6,000-20,000 different compounds are possible using the integrated systems of the invention.

The molecule of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the signal transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and are appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book I (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups Aminoalkylsilanes and hydroxyalkylsilanes can be used to functionalize a variety of surfaces, such as glass surfaces. The construction of such solid phase biopolymer arrays is well described in the literature. See, e.g., Merrifield, J. Am. Chem. Soc. 85:2149-2154 (1963) (describing solid phase synthesis of, e.g., peptides); Geysen et al., J. Immun Meth. 102:259-274 (1987) (describing synthesis of solid phase components on pins); Frank & Doring, Tetrahedron 44:60316040 (1988) (describing synthesis of various peptide sequences on cellulose disks); Fodor et al., Science, 251:767-777 (1991); Sheldon et al., Clinical Chemistry 39(4):718-719 (1993); and Kozal et al., Nature Medicine 2(7):753759 (1996) (all describing arrays of biopolymers fixed to solid substrates). Non-chemical approaches for fixing tag binders to substrates include other common methods, such as heat, cross-linking by UV radiation, and the like.

Modulators

Inhibitors and/or activators identified according to the methods of the invention can be provided from libraries of compounds available from a number of sources or can be derived by combinatorial chemistry approaches known in the art. Such libraries include but are not limited to the available Chemical Director, Maybridge, and natural product collections. In one embodiment of the invention libraries of compounds with known or predicted structures can be docked to the human β2AR structures of the invention. In another embodiment, the libraries for ligands binding to the ligand binding site can include carazolol and related compounds. In another embodiment, the libraries can include a linker component or moiety. In some embodiments, the linker can include from about 10-22 atoms and can include one or more of C, O, N, S, and/or H atoms. In another embodiment, the libraries can include a ligand binding site (also known as the ligand, agonist, or antagonist binding pocket) component or moiety. In some embodiments, the libraries can include drug-like molecules, i.e., molecules having structural attributes of one or more compounds known to bind to and/or affect a physiologic function of a GPCR.

In some embodiments, the invention includes compounds that can be tested as modulators of GPCR activity. Compounds tested as modulators of GPCRs can be any small chemical compound or biological entity. Typically, test compounds will be small chemical molecules and peptides. Essentially any chemical compound can be used as a potential modulator or ligand in the assays of the invention, although most often compounds can be dissolved in aqueous or organic (especially DMSO-based) solutions. The assays are designed to screen large chemical libraries by automating the assay steps. The assays are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or ligand libraries are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Russell & Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. Nos. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

It is noted that modulators that compete with the binding and/or activity of the known ligands for to human β2AR can be used to treat various diseases including, but not limited to, coronary artery disease, atherosclerosis, thrombosis, obesity, diabetes, stroke, and other diseases.

In one embodiment, a modulator binds to a site on a GPCR, e.g., a human β2AR. In one aspect, the site is a carazolol binding site. In a related aspect, the site is a ligand binding site. In another aspect, the modulator has a first moiety that binds to a binding site. In another aspect, the first moiety is connected to a linker. In another aspect, the first moiety and the linker are connected to at least one additional moiety that binds to a site other than that bound by the first moiety. In another aspect, the two or more moieties are not connected by a linker and are both present in a composition.

Computer-Based Modeling of β2AR

Protein-ligand docking aims to employ principles by which protein receptors, e.g., human β2AR, recognize, interact, and associate with molecular substrates and compounds to predict the structure arising from the association between a given compound and a target protein of known three-dimensional structure.

In protein-ligand docking, the search algorithm can allow the degrees of freedom of the protein-ligand system to be sampled sufficiently as to include the true binding modes. Three general categories of algorithms have been developed to address this problem of ligand flexibility: systematic methods; random or stochastic methods; and simulation methods.

Systematic search algorithms attempt to explore all degrees of freedom in a molecule. These algorithms can be further divided into three types: conformational search methods, fragmentation methods, and database methods.

In conformational search methods, all rotatable bonds in the ligand are systematically rotated through 360° using a fixed increment, until all possible combinations have been generated and evaluated. As the number of structures generated increases immensely with the number of rotatable bonds (combinatorial explosion), the application of this type of method, in its purest form, is very limited.

Fragmentation methods use two different approaches to incrementally grow the ligands into the active site. One approach is by docking the several fragments into a site and linking them covalently to recreate the initial ligand ("the place-and-join approach"). Another approach is by dividing the ligand into a rigid core-fragment that is docked in first place and flexible regions that are subsequently and successively added ("the incremental approach"). DOCK (see above) is an example of s docking programs that use a fragmentation search method.

Database methods using libraries of pre-generated conformations or conformational ensembles to address the combinatorial explosion problem. A example of a docking program using database methods is FLOG which generates a small set of 25 database conformations per molecule based on distance geometry, that are subsequently subject to a rigid docking protocol.

Random search algorithms sample the conformational space by performing random changes to a single ligand or a population of ligands. At each step, the alteration performed is accepted or rejected based on a predefined probability function. There are three basic types of methods based on random algorithms: Monte Carlo methods (MC), Genetic Algorithm methods (GA), and Tabu Search methods.

Simulation methods employ a rather different approach to the docking problem, based on the calculation of the solutions to Newton's equations of motion. Two major types exist: molecular dynamics (MD) and pure energy minimization methods.

Scoring functions normally employed in protein-ligand docking are generally able to predict binding free energies within 7-10 kJ/mol and can be divided into three major classes: force field-based, empirical, and knowledge-based scoring functions.

In force-field based scoring, standard force fields quantify the sum of two energies: the interaction energy between the receptor and the ligand, and the internal energy of the ligand. The energies are normally accounted through a combination of a van der Waals with an electrostatic energy terms. A Lennard-Jones potential is used to describe the van der Waals energy term, whereas the electrostatic term is given by a Coulombic formulation with a distance-dependent dielectric function that lessens the contribution from charge-charge interactions.

Empirical scoring functions are based on the idea that binding energies can be approximated by a sum of several individual uncorrelated terms. Experimentally determined binding energies and sometimes a training set of experimentally resolved receptor-ligand complexes are used to determine the coefficients for the various terms by means of a regression analysis.

Knowledge-based scoring functions focus on following the rules and general principles statistically derived that aim to reproduce experimentally determined structures, instead of binding energies, trying to implicitly capture binding effects that are difficult to model explicitly. Typically, these methods use very simple atomic interactions-pair potentials, allowing large compound databases to be efficiently screened. These potentials are based on the frequency of occurrence of different atom-atom pair contacts and other typical interactions in large datasets of protein-ligand complexes of known structure. Therefore, their derivation is dependent on the information available in limited sets of structures.

Consensus Scoring combines the information obtained from different scores to compensate for errors from individual scoring functions, therefore improving the probability of finding the correct solution. Several studies have demonstrated the success of consensus scoring methods in relation to the use of individual functions schemes.

Using the Protein-ligand docking methods described above, a predicted association can be made between a selected chemical library compound (see above for examples) and the binding sites in the human β2AR structure described in Appendix I (SEQ ID NOS 4-5, 1 and 6-9, respectively in order of appearance). These methods will therefore allow the generation of a binding profile for any known compound in any of the binding sites or cavities of the human β2AR based on the simulated docking of the compound.

In another embodiment, a form of computer-assisted drug design is employed in which a computer system is used to generate a three-dimensional structure of the candidate class A GPCR based on the structural information encoded by the amino acid sequence. This will allow use of the methods described above to identify candidate compounds based on their ability to dock in one or more of the predicted GPCR structure binding sites. In one aspect, the input amino acid sequence of the GPCR interacts directly and actively with a pre-established algorithm in a computer program to yield secondary, tertiary, and quaternary structural models of the class A GPCR. The models of the class A GPCR structure are then examined to identify the position and structure of the binding sites, e.g., a binding pocket. The position and structure of the predicted binding site(s) is then used to identify various compounds that modulate ligand-receptor binding using the methods described above.

The three-dimensional structural model of the GPCR is generated by entering protein amino acid sequences of at least 10 amino acid residues or corresponding nucleic acid sequences encoding a GPCR polypeptide into the computer system. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the GPCR is then generated by the interaction of the amino acid sequence and the computer system, using software known to those of skill in the art. Any method of protein structure modeling such as ab-initio modeling, threading or sequence-sequence based methods of fold recognition. In one embodiment, the AS2TS system of protein structure modeling is used. In other embodiments, a sequence alignment in combination with a threshold protein sequence similarity to determine a set of protein sequences for which to model protein structure is used. In one aspect, sequence alignments are generated for the set of sequences to be modeled with sequences of proteins with solved empirical structure in a protein structure databank known to one of skill in the art. If the sequences to be modeled have a sufficient similarity to one or more sequences with known protein structure, then the three dimensional structure of the sequence can be modeled.

The amino acid sequence represents a primary structure that encodes the information necessary to form the secondary, tertiary and quaternary structure of the GPCR of interest. In one embodiment, software can look at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

In another embodiment, protein structure alignments can be used to determine the structure of GPCRs using the known structure of the β2AR (Appendix I) (SEQ ID NOS 4-5, 1 and 6-9, respectively in order of appearance). Protein structure alignments preferably are sets of correspondences between spatial co-ordinates of sets of carbon alpha atoms which form the 'backbone' of the three-dimensional structure of polypeptides, although alignments of other backbone or side chain atoms also can be envisioned. These correspondences are generated by computationally aligning or superimposing two sets of atoms order to minimize distance between the two sets of carbon alpha atoms. The root mean square deviation (RMSD) of all the corresponding carbon alpha atoms in the backbone is commonly used as a quantitative measure of the quality of alignment. Another quantitative measure of alignment is the number of equivalent or structurally aligned residues.

In another embodiment, a GPCR structure is calculated based on the solved structure of the human β2AR by computationally aligning or superimposing two sets of atoms to minimize distance between the two sets of carbon alpha atoms (i.e., the alpha carbon atoms of the human β2AR and an unknown GPCR structure), followed by one or more of simulated annealing and energy minimization. The result of this calculation is a computed structure for a GPCR that provides atomic co-ordinates for the alpha carbon backbone as well as side chain atoms.

A variety of methods for generating an optimal set of correspondences can be used in the present invention. Some methods use the calculation of distance matrices to generate an optimal alignment. Other methods maximize the number of equivalent residues while RMSD is kept close to a constant value.

In the calculation of correspondences, various cutoff values can be specified to increase or decrease the stringency of the alignment. These cutoffs can be specified using distance in Angstroms. Depending on the level of stringency employed in the present invention, the distance cutoff used is less than 10 Angstroms or less than 5 Angstroms, or less than 4 Angstroms, or less than 3 Angstroms. One of ordinary skill will recognize that the utility of stringency criterion depends on the resolution of the structure determination.

In another embodiment of the present invention, the set of residue-residue correspondences are created using a local-global alignment (LGA), as described in US Patent Publication Number 2004/0185486. In this method, a set of local superpositions are created in order to detect regions which are most similar. The LGA scoring function has two components, LCS (longest continuous segments) and GDT (global distance test), established for the detection of regions of local and global structure similarities between proteins. In comparing two protein structures, the LCS procedure is able to localize and superimpose the longest segments of residues that can fit under a selected RMSD cutoff. The GDT algorithm is designed to complement evaluations made with LCS searching for the largest (not necessary continuous) set of 'equivalent' residues that deviate by no more than a specified distance cutoff.

Using the protein structure alignments described above, the structure of human β2AR in Appendix I (SEQ ID NOS 4-5, 1 and 6-9, respectively in order of appearance) can be used as a model on which to discern the structure of other GPCRs and/or their predicted ligand-binding sites.

Once the GPCR structure has been generated, a binding pocket can be identified by the computer system. Computational models seek to identify the regions by characterization of the three dimensional structure of the GPCR. Some methods of identifying a binding pocket use triangulation such as weighted Delaunay triangulation to determine pocket volumes (castP). Other methods use spheres to determining protein pocket volumes (Q-site-finder, UniquePocket). Conserved binding-site identification seeks to identify conserved regions such as a binding pocket through associating the residues which form the aforementioned regions with conserved residues in homologous protein sequences or structures, e.g., through the use of sequence alignments.

One method of identifying a binding pocket in a GPCR entails filling the three dimensional protein structures with spheres, creating a "negative image" of the structure. A cutoff distance, such as 8 Angstroms, is used to determine spheres which interact with residues. Spheres are labeled as conserved or not-conserved based on their interaction with residues which form a conserved binding site. The conserved spheres are clustered based on their three dimensional coordinates to identify a set of spheres with interact with conserved residues and are proximal in three dimensional space forming a cluster. Three-dimensional structures for potential compounds are generated by entering chemical formulas of compounds. The three-dimensional structure of the potential compound is then compared to that of the GPCR protein ligand-binding site(s) (e.g., a binding pocket) to identify compounds that bind to the GPCR binding site(s). Binding affinity between the GPCR binding site(s) and the compound is determined using energy terms to determine which ligands have an enhanced probability of binding to the protein.

It should be noted that the language used in the specification has been principally selected for readability and instructional purposes, and can not have been selected to delineate or circumscribe the inventive subject matter. Accordingly, the disclosure of the present invention is intended to be illustrative, but not limiting, of the scope of the invention, which is set forth in the claims.

Reference will now be made in detail to particularly preferred embodiments of the invention. Examples of the preferred embodiments are illustrated in the following Examples section.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols. A and B (1992).

Example 1

Crystallization of a β2AR Protein Using a Lipidic Cubic Phase/Sterol Method This Example describes the generation of diffraction-quality crystals of a β2AR protein, specifically crystals of β2AR-T4L, a fusion protein of human β2AR with T4 lysozyme, bound to carazolol. A detailed description of the protein and its synthesis is provided in Example 4. Briefly, T4 lysozyme was generated by three distinct modifications to β2AR: (1) a fusion protein was created by replacement of the third intracellular loop with T4L, (2) the carboxyl terminal 48 amino acids were deleted, and (3) a glycosylation site at Asn187 was eliminated through a glutamate substitution. β2AR-T4L was expressed in Sf9 insect cells, solubilized in 1% dodecylmaltoside, and purified by sequential antibody and ligand affinity chromatography.

LCP Crystallization Setup

Protein solution (30 mg/ml) was mixed with a host lipid or lipid mixture typically in 2:3 ratio by volume ratio using a syringe mixer (Cheng, et al., *Chem Phys Lipids* 95, 11 (1998). Upon mixing (~100 passages, 2-3 min) the sample spontaneously formed homogeneous transparent cubic phase, which was directly used in crystallization trials. Robotic trials were performed using an in meso crystallization robot (Cherezov, et al., *Acta Cryst D* 60, 1795 (2004)). Six-well glass sandwich plates (Cherezov, et al., *Acta Cryst D* 60, 1795 (2004); Cherezov, *J Appl Cryst* 36, 1372 (2003)), were filled with 25 or 50 mL protein-laden lipidic cubic phase drops overlaid by 800 μL of precipitant solution in each well and sealed with a glass coverslip. Manual setups were performed in Impact microbatch plates (Hampton Research cat# HR3-293), Innovaplate SD-2 sitting drop plates (Hampton Research cat# HR3-083) or VDX48 hanging drop plates (Hampton Research cat# HR3-275). Modified repetitive syringe dispenser (Cherezov, et al., *J Appl Cryst* 38, 398 (2005)), coupled with a gas-tight 10 μL syringe was used to deliver 70 mL of cubic phase drops per well to which 1-2 μL of precipitant solution was added with a microvolume pipette. Reservoirs of the Innovaplate and VDX48 plates were filed with 50 and 100 μL of precipitant respectively. All operations starting from mixing lipid and protein were performed at room temperature (~21-23° C.). After setup, plates were transferred into an automatic incubator/imager (RockImager 1000, Formulatrix Inc.) maintained at 20° C. Plates were imaged every 12 hours for the first 3 days, then every day until 7 days and after that on the 10th and on the 14th day.

Initial Hits

Initial trials were performed using protein solution at a concentration of 30 mg/mL mixed with monoolein as a host lipid against a set of 6 commercial screens (Index HT, SaltRxHT and MemFac HT from Hampton Research, JCSG+ and MbClass from Nextal, and MemSys&MemStart from Molecular Dimensions) set up in duplicates. Initial hits detected in three different wells contained extremely small, <5 μm, needle-like birefringent crystal showers. The detection of such small colorless protein crystals in LCP was made feasible by specially developed glass sandwich plates with optimized optical properties (Cherezov, et al., *Acta Cryst D* 60, 1795 (2004); Cherezov et al., *J Appl Cryst* 36, 1372 (2003)). Hit conditions were similar by chemical composition containing 30% v/v PEG 400 as a precipitant, low concentration of Li sulfate and a buffer at pH 6.5 or 7.5.

Optimization

Crystal condition optimization is well known to practioners in the art of x-ray crystallography. What follows is a specific example of a generally applicable optimization approach in which one or more of the crystallization mixture components is systematically varied in concentration or substituted by a chemical analog. Initial rounds of optimization were focused on varying concentration of the main precipitant, PEG 400, buffer pH and identity, and salt identity and concentration. As a result, Li sulfate was replaced with Na sulfate and useful concentration and pH ranges were established. Crystals were still rather small reaching ~15×5×1 µm in size.

Further, lipid and soluble additives were searched for and optimized simultaneously. Three different host lipids (monopalmitolein, monovaccenin and monoolein), five lipid additives to monoolein host (DOPE, DOPE-Me, DOPC, Asolectin and cholesterol) and 96-well soluble additives screen were tried in different combinations along with the previously found basic crystallization conditions. One of the soluble additives, 1,4-butanediol, stood out, but only when it was used in combination with lipid additives, DOPE or cholesterol. When DOPE was used as an additive the crystals grew as thin plates (40×7×2 µm), while when cholesterol was used the crystals grew as small rods (30×5×5 µm). DOPE was dropped out in favor of cholesterol in the subsequent optimization steps.

Final optimization required fine tuning concentrations of all components (protein, PEG 400, Na sulfate, 1,4-butanediol, cholesterol, buffer pH). At the final stages of optimization, higher concentrations of protein, e.g., 50 mg/mL protein solution, were preferred. Decreasing the volume of lipidic cubic phase per trial from 50 to 20 mL consistently produced larger crystals. The best crystals (40×20×5 µm; FIG. 1) were obtained in 30-35% v/v PEG400, 0.1-0.2 M Na sulfate, 0.1 M Bis-tris propane pH 6.5-7.0, 5-7% v/v 1,4-butanediol using 8-10% w/w cholesterol in monoolein as the host lipid. Thus, in another aspect, the invention provides a method of directly adding a lipid additive (e.g., cholesterol, DOPE) to the host lipid prior to combining with the protein mixture, thereby significantly improving the size and quality of LCP grown crystals. Previously, exogenous lipid had been added only to the protein solution prior to combining the protein solution with the host lipid (Luecke, et al., *Science* 293, 1499 (2001)).

To limit the range of precipitant and additives concentrations used for screening, previously published phased diagrams were used, e.g., for monoolein (Qiu, et al., *Biomaterials* 21, 223 (2000)), and monovaccenin (Qiu, et al., *J. Phys. Chem. B* 102, 4819 (1998)), and the effects on monoolein phase behavior of soluble (Cherezov, et al., *Biophys J* 81, 225 (2001)), and lipid additives (Cherezov, et al., Biophys J 83, 3393 (2002)). Certain lipid mixtures required pre-screening their phase behavior by microscope visualization and by X-ray, prior to being mixed with the protein for crystallization trials. Thirty-three 96-well optimization screens were used in combinations with different lipid mixtures, resulting in over 15,000 trials. This throughput was made feasible through the use of an in meso crystallization robot and automatic imager.

Typically, the best crystals grown under lipidic cubic phase conditions appear at the boundary between the cubic and the sponge phase (Cherezov, et al., *J Mol Biol* 357, 1605 (2006); Wadsten, et al., *J Mol Biol* 364, 44 (2006)). When crystals are close to the phase boundary, equally good crystals are obtained in either phase.

Crystal Harvesting

Figure 2:
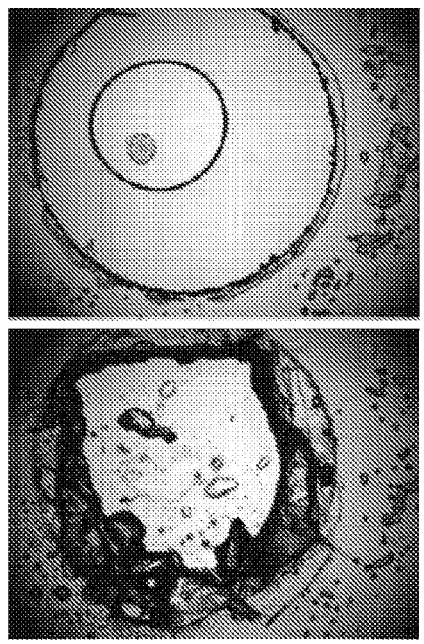
FIG. 2. Before (top) and after (bottom) images of a lipidic cubic phase crystal harvested directly from a well in a previously sealed glass sandwich plate, according to the method described herein (see, e.g., Example 1).

Crystals were harvested directly from the glass sandwich plates (FIG. 2) because this method provided results superior to those obtained with microbatch or vapor diffusion plates. These plates have been specifically designed to perform optimally only at the screening and optimization stages (Cherezov, et al., *Acta Cryst D* 60, 1795 (2004); Cherezov and M. Caffrey, *J Appl Cryst* 36, 1372 (2003)). No harvesting has been previously attempted from them, due to the difficulties in separating glass slides strongly bound by a high performance double sticky tape. Thus, in another aspect, the invention disclosed herein provides a special technique for opening individual wells and harvesting crystals from them. A corner of a capillary cutting stone (in this instance, from Hampton Research) was used to scratch the top glass around the perimeter of the well. Gently pressing the glass slide just outside the scratch allows propagation of the scratch through the depth of the glass. The glass slide was then broken in one point just outside of the scratched perimeter using a sharp needle. This hole was used to lift up the glass slide and expose the cubic phase for harvesting. An extra drop of ~5 µL of precipitant was added to the well to reduce dehydration. Using this technique, it was possible to open up and harvest crystals successfully from more than 80% of attempted wells.

Crystals were scooped directly from the lipidic cubic phase using 30 µm aperture MiTeGen MicroMounts and plunged into liquid nitrogen. Care was taken to drag as little as possible lipid around the crystal to decrease the unwanted background. Attempts to dissolve the lipids, either by increasing concentration of PEG400 or using a mineral oil, typically resulted in decreasing the diffraction power of the crystals.

Data Collection

Figure 1A:
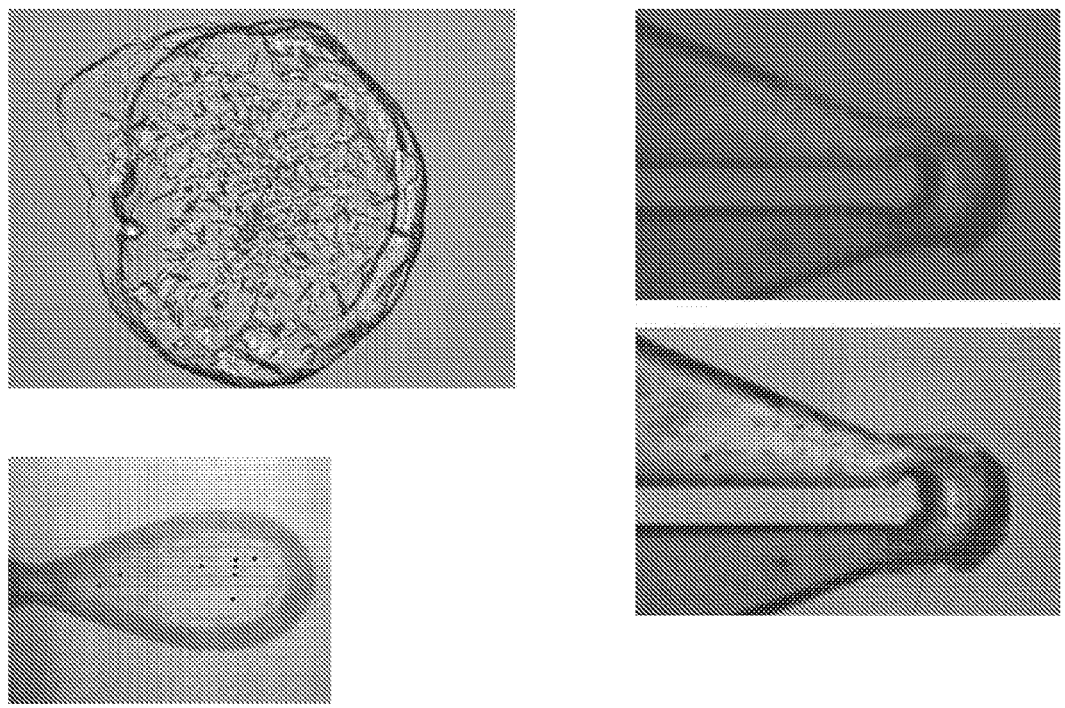
FIG. 1a shows β₂AR-T4L crystals in the crystallization mixture drop (upper left) and in the loop.
Figure 1B:
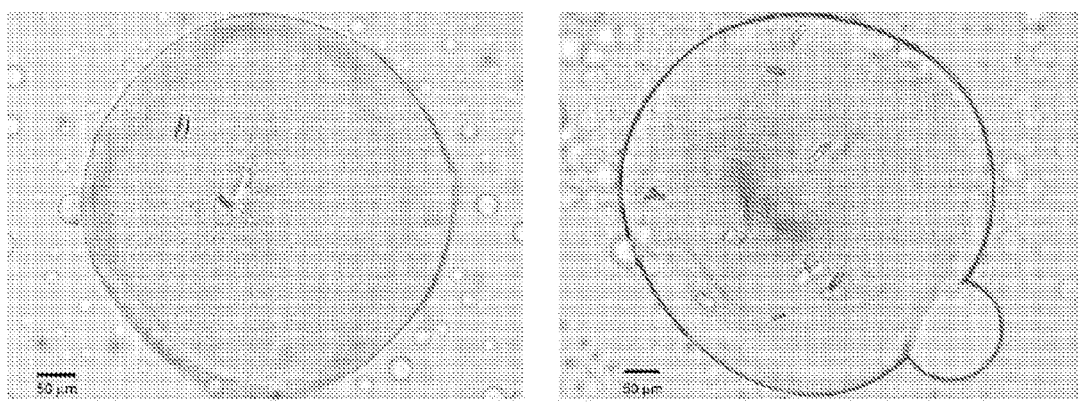
FIG. 1b shows crystals in the "sponge" phase.
Figure 3:
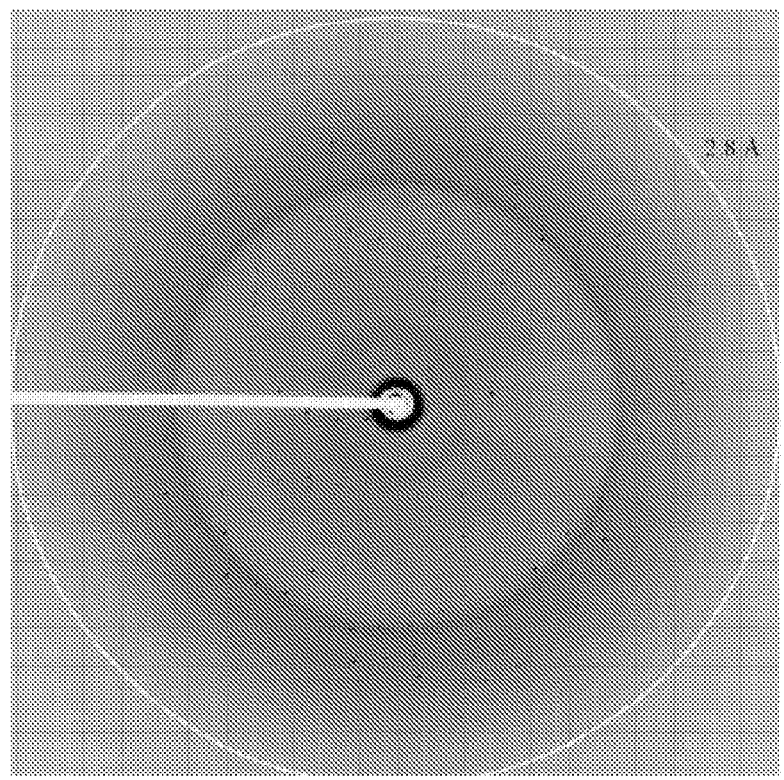
FIG. 3. Diffraction pattern (2.8 Å resolution) from β₂AR-T4L crystals grown in lipid cubic phase. The crystal size was approximately 25×5×5 Å; space group C2 (a=106.8 Å, b=169.5 Å, c=40.5 Å; β=105.3°, α=γ=90°. Beam diameter was 10 µm, exposure 10 s, oscillation: 1°.

During screening for diffraction of these crystals at APS beamline GM/CA CAT (FIG. 3), the crystals themselves could not be observed in the mounted loops (FIG. 1a). Therefore, a systematic screening of the loop material with varying beams was conducted to identify the crystal in the loop. Optimization of the diffraction with a low x-ray dose was then used to center the crystals and eventually allow for complete data collection using the 10 µm×10 µm minibeam setup at GM/CA CAT. The complete data set is then compared to data filtered by a sigma cutoff (see Table 1). All of the data was used in structure solution and refinement.

TABLE 1

| Resolution | # Observed refl | # Unique refl | Redundancy | Completeness | $R_{sym}$ | I/SIGMA | R-meas | Rmrgd-F |
|---|---|---|---|---|---|---|---|---|
| | | | Signal/noise −3 | | | | | |
| 10 | 3352 | 333 | 10.1 | 87.40% | 6.60% | 23.25 | 6.90% | 2.70% |
| 8 | 3591 | 354 | 10.1 | 99.40% | 7.60% | 22.6 | 8.00% | 2.80% |
| 6 | 10480 | 1003 | 10.4 | 99.60% | 9.90% | 20.01 | 10.50% | 4.00% |
| 3 | 126008 | 11968 | 10.5 | 99.80% | 13.30% | 14.01 | 14.00% | 6.60% |
| 2.8 | 33158 | 3130 | 10.6 | 100.10% | 38.00% | 6.42 | 39.90% | 18.70% |
| 2.7 | 19702 | 1893 | 10.4 | 99.70% | 49.50% | 4.96 | 52.10% | 24.90% |
| 2.6 | 23772 | 2275 | 10.4 | 99.90% | 60.20% | 4.07 | 63.40% | 30.10% |

TABLE 1-continued

| Resolution | # Observed refl | # Unique refl | Redundancy | Completeness | $R_{sym}$ | I/SIGMA | R-meas | Rmrgd-F |
|---|---|---|---|---|---|---|---|---|
| 2.5 | 14108 | 2558 | 5.5 | 99.30% | 58.90% | 2.69 | 65.10% | 51.80% |
| 2.4 | 14672 | 3060 | 4.8 | 99.10% | 67.80% | 2.18 | 75.70% | 62.80% |
| Total | 248843 | 26574 | 9.4 | 99.50% | 12.70% | 9.62 | 13.40% | 11.40% |
| | | | | Signal/noise 0 | | | | |
| 10 | 3352 | 333 | 10.1 | 87.40% | 6.60% | 23.25 | 6.90% | 2.70% |
| 8 | 3591 | 354 | 10.1 | 99.40% | 7.60% | 22.6 | 8.00% | 2.80% |
| 6 | 10480 | 1003 | 10.4 | 99.60% | 9.90% | 20.01 | 10.50% | 4.00% |
| 3 | 125628 | 11923 | 10.5 | 99.40% | 13.30% | 14.06 | 14.00% | 6.50% |
| 2.8 | 32679 | 3077 | 10.6 | 98.40% | 37.60% | 6.54 | 39.50% | 17.70% |
| 2.7 | 19346 | 1849 | 10.5 | 97.40% | 48.80% | 5.08 | 51.30% | 23.40% |
| 2.6 | 23201 | 2210 | 10.5 | 97.00% | 58.90% | 4.2 | 62.00% | 28.00% |
| 2.5 | 13461 | 2406 | 5.6 | 93.40% | 56.40% | 2.88 | 62.30% | 45.90% |
| 2.4 | 13833 | 2827 | 4.9 | 91.50% | 64.10% | 2.4 | 71.50% | 54.30% |
| Total | 245571 | 25982 | 9.5 | 97.30% | 12.60% | 9.85 | 13.30% | 10.80% |

Example 2

Using the LCP/Sterol Method to Generate Additional Membrane Protein Crysals

In addition to the $\beta_2$AR-T4L/carazolol structure (Examples 1, 3, and 4), the LCP/sterol matrix has successfully been used to crystallize a diversity of receptor-ligand systems.

Figure 4:
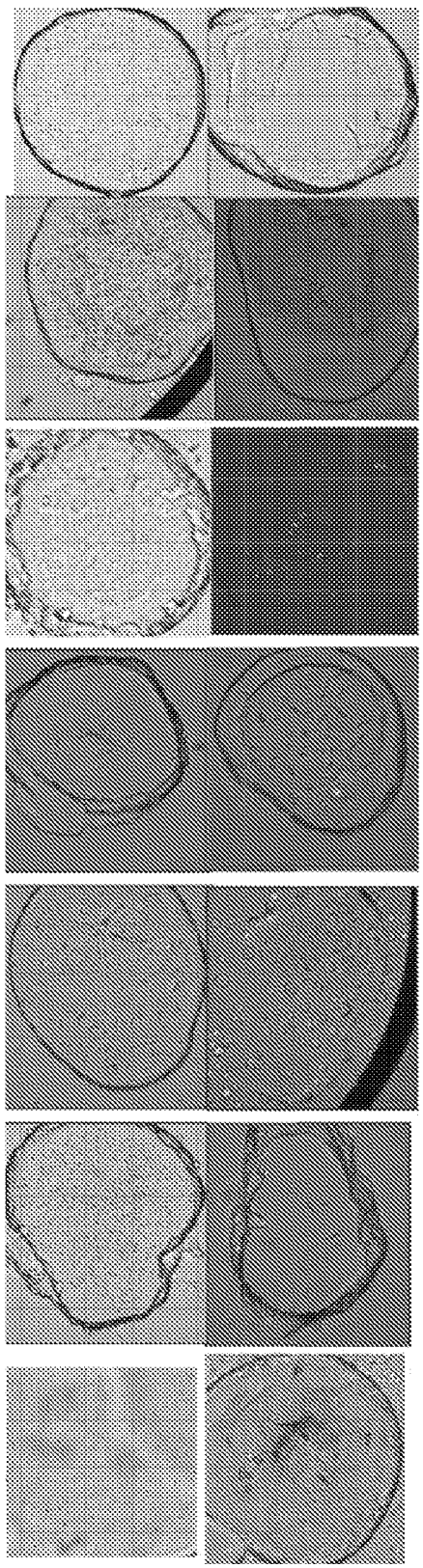
FIG. 4. Gallery of crystals of various GPCRs obtained using LCP/cholesterol mixtures and in combination with a variety of ligands. The top panel corresponds to non-optimized initial hits, whereas the bottom panel shows diffraction quality for optimized crystals. From left to right, β₂AR-T4L (bound to carazolol), diffracted to 2.4 Å resolution; β₂AR (E122W)T4L (bound to carazolol), diffracted to 3.5 Å resolution; β₂AR(E122W)T4L (bound to alprenolol), diffracted to 3.5 Å resolution; β₂AR(E122W)T4L (bound to timolol), diffracted to 2.8 Å resolution; β₂AR(E122W) (bound to carazolol); β₂AR(E122W)T4L (bound to clenbuterol), diffracted to 6 Å, anisotropic; human $A_{2A}$ adenosine receptor-T4L (bound to ZM241385), diffracted to 2.6 Å resolution.

1. $\beta_2$AR-T4L$^{(E122W)}$ A thermally-stabilized construct of $\beta_2$AR-T4L comprising an E122W mutation has been crystallized in the presence of both agonist and antagonist ligands including: alprenolol, timolol, clenbuterol and carazolol. For lipidic cubic phase (LCP) crystallization of $\beta_2$AR-T4L$^{(E122W)}$, robotic trials were performed using an in meso crystallization robot (Cherezov et al., 2004). Glass sandwich plates in 96-well format (Cherezov and Caffrey, 2003; Cherezov et al., 2004) were filled with 25 or 50 mL protein-laden LCP drops overlaid by 0.8 µL of precipitant solution in each well and sealed with a glass coverslip. All operations starting from mixing lipid and protein were performed at room temperature (~21-23° C.). Crystals were obtained in 28% (v/v) PEG 400, 0.3 M potassium formate, 0.1 M Bis-tris propane pH 7.0 and saturating concentrations of ligand (e.g., 2 mM in the case of timolol) using 10% (w/w) cholesterol in monoolein as the host lipid. Diffraction data were collected on all four ligand complexes (see FIG. 4), and structures were determined for alprenolol (3.2 Å), timolol (2.8 Å), and carazolol (2.8 Å).

2. $A_{2A}$R-T4L The applicability of the monoolein cholesterol system in the crystallization of non-biogenic amine receptors has also been demonstrated with the structural determination of the human $A_{2A}$ adenosine receptor ($A_{2A}$R-T4L) bound to a high affinity selective antagonist, ZM241385, to 2.6 Å resolution. See FIG. 4. For lipidic cubic phase (LCP) crystallization of the human A2A adenosine receptor in meso, glass sandwich plates (Cherezov, et al., *Acta Crystallogr D Biol Crystallogr,* 60, 1795 (2004)) were filled with 50 nl receptor-cholesterol-monoolein LCP drops overlaid by 0.8 µl of precipitant solution in each well and sealed with a glass coverslip. Lipid:receptor LCP mixture typically contained monoolein:cholesterol (54%:6% (w/w)) and receptor (40% (w/w)). Crystallization set-ups were performed at ambient temperature (22±2° C.). Plates were incubated and imaged at 20° C. using an automated incubator/imager (RockImager 1000, Formulatrix). Data-collection quality crystals (~100 µm×10 µm×5 µm) were obtained in 30% (v/v) PEG 400 (range of 28-32%), 186 mM Lithium sulfate (range of 180 to 220 mM), 100 mM Sodium citrate (pH 6.5) (Range of 5.5 to 6.5) and 200 µM ZM241385. The protein crystallized in the primitive monoclinic space group $P2_1$ with one molecule per asymmetric unit and an estimated solvent content of 52%.

3. $\beta_2$AR$^{(E122W)}$ Initial crystals of $\beta_2$AR$^{(E122W)}$, lacking inserted T4 lysozyme, have also been obtained. The protein was extracted from insect cell membranes using a mixture of 0.5% w/v dodecyl maltoside (DDM), 0.1% w/v cholesteryl hemisuccinate (CHS) and 1 mM timolol. Timolol was maintained at 1 mM throughout the first steps of the purification. The extracted protein was purified by binding overnight to Talon™ immobilized metal affinity resin followed by a standard washing and elution with 200 mM imidazole. Adenosine triphosphate at 5 mM in combination with 10 mM $MgCl_2$ was used to eliminate chaperone protein contamination. Eluted protein was concentrated to 2.5 mL and desalted into a 0 mM imidazole buffer using a PD10 desalting column (GE-Biosciences). Protein was then bound to 100 µL of Ni-sepharose immobilized metal affinity resin in the presence of PNGase (New England Biolabs) to remove glycosylation, and incubated overnight. After incubation the protein was washed on the column and timolol was replaced by carazolol for structure solution. The protein bound to carazolol was eluted from the Ni-Sepharose column, treated with 100 mM Nacitrate pH 7.5, and concentrated to 50 mg/mL.

The protein solution was then mixed with monoolein containing 10% cholesterol at a ration of 40:60% w/w protein to lipid to generate the lipidic cubic phase used in crystallization trials. The LCP lipid containing protein was dispensed onto glass sandwich crystallization plates at a volume of 20 mL to which 1 µL of crystallization solution was added. The entire experiment in 96 well format was then covered by an additional glass plate which was fastened to the first by virtue of double back sticky tape. Initial crystals have been obtained after 24 hours by addition of a solution containing 35% v/v PEG 400, 100 mM NaSO4 100 mM Bis tris propane pH 7 and 8% 2,6 hexanediol.

By way of a prophetic example, optimized crystals of $\beta_2$AR$^{(E122W)}$ obtained by this method are screened for their ability to diffract at high resolution, e.g., less than 3.5 Å or, more preferably, less than 3 Å. Guidance for optimization is provided by the optimization protocols set forth herein and in the examples. In combination with the teaching provided 4. CXCR4-T4L CXCR4, also called fusin, is a GPCR protein specific for stromal-derived-factor-1 (SDF-1 also called CXCL12), a molecule endowed with potent chemotactic activity for lymphocytes. This Example teaches prophetically how the methods of the invention may be used to generate diffraction quality crystals of a fusion protein comprising CXCR4 (CXCR4-T4L).

The cDNA encoding CXCR4 is synthesized by outsourcing to DNA2.0 where the DNA was optimized for human codon usage, elimination of transcribed RNA secondary structure, elimination of ribosome binding sites and avoidance of common restrictions sites used in subsequent cloning procedures. Two initial variants are contracted to be synthesized, the first encoding a wild-type full-length receptor and the second a full length receptor with a fusion protein located between transmembrane helix V and helix VI, effectively eliminating the third intracellular loop (3IL) region of the receptor. In the case of CXCR4, T4-lysozyme (T4L) is the fusion protein fused in the place of the 3IL. A set of guidelines is followed for the incorporation of T4L into the fusion protein which minimizes the possibility of structural disruption and concomitant effects on protein expression and stability. Briefly, the 5' insertion point for the fusion protein takes precedence over the 3' insertion point and is located 66 nucleotides (22 residues) downstream of the codon for a conserved proline on helix V of the receptor. If the 3IL section of the receptor is large, the 3' fusion point is set 87 nucleotides (29 residues) upstream from the codon for the family conserved proline on helix VI. However, as is the case for CXCR4, where the 3IL loop is small, cDNA for the fusion protein is inserted directly into the 3IL loop position dictated by spacing from helix V with no resulting excision of intervening nucleotides. Specifically, T4L is inserted into CXCR4 based on spacing between a conserved proline on helix V and a C-terminal truncation was generated based on literature precedence. Each synthesized cDNA is flanked by an out of frame AscI (GGCGCGCCG) restriction site on the 5' end and an in frame FseI (GGCCGGCC) on the 3' end for sub-cloning into a set of four expression vectors. Viral DNA is then generated, amplified from these vectors according to standard protocols and titered using flow cytometry to measure the population of cells expressing the virally encoded GP64 protein.

Protein Expression of CXCR4-T4L

With titered virus in hand, small scale expression trials are carried out in a volume of 5 mL/experiment. Expression levels are assessed using flow cytometry to measure the mean fluorescence intensity (MFI) and percentage of cells expressing the FLAG epitope encoded by the expression screening vectors. Expressing cells are tested with and without permeabilization to generate a ratio between protein inserted in the plasma membrane and protein inside the cellular trafficking machinery. A correlation between cell surface expression and overall protein expression is demonstrated, as well as a correlation between stability and the ratio of cell surface expression/total expression. In addition to these assays, small scale purification after solubilization with dodecyl maltoside (DDM) is carried out to determine the quantity of recoverable protein as well as the quality as measured by size exclusion chromatography. Based on these data it was apparent that the T4L fused receptor is expressing and that it is dimerizing in a ligand independent manner, an indicator of C-terminal non-specific interactions in other receptors. Thus, a C-terminal truncation mutant of CXCR4 is generated.

Protein Purification

The C-terminal truncation of T4L fused CXCR4 was scaled up to production sized expression (5-10L of cell culture) and further processed by large scale purification efforts intended for crystallization trials. Briefly 5-10 L of cells culture are centrifuged and washed with PBS followed by freezing at $-80°$ C. The frozen cellular material is then resuspended in 820 mL of lysis buffer (10 mM Hepes pH 7.5, 10 mM $MgCl_2$, 20 mM KCl) supplemented with protease inhibitor (Roche). The cell suspension is lysed by 20 strokes of a dounce homogenizer and centrifuged at 45,000 rpm in Ti45 ultracentrifuge for 30 minutes. The resulted pellet was separated from the supernatant, resuspended and the process repeated six times to ensure complete removal of soluble protein material. On the final resuspension step the membranes were resuspended in 100 mL of lysis buffer containing 40% v/v glycerol, homogenized with 20 strokes of a dounce homogenizer and frozen in 10 mL aliquots at $-80°$ C. for indefinite storage.

For solubilization and purification, each 10 mL aliquot of frozen membranes is resuspended to 25 mL using lysis buffer to which 100 uM AMD070 ligand is added in addition to protease inhibitor at 2× working concentration and 2 mg/mL iodoacetamide. The membranes are allowed to thaw and incubate with ligand at an appropriate temperature for at least 30 minutes. After the incubation the mixture is diluted two-fold with a 2× solubilization buffer containing 100 mM Hepes pH 7.5, 1M NaCl, 2% w/v DDM 0.2% w/v CHS. The solubilization is allowed to proceed with agitation for at least 2 hours at $4°$ C. after which insoluble material is separated by centrifugation and discarded. The supernatant is isolated and allowed to bind to 0.5 mL of Talon (Clontech) IMAC resin charged with $Co^{2+}$ in the presence of 20 mM imidizole buffered to 7.5 and 800 mM NaCl. Binding to the Talon IMAC resin is allowed to proceed with agitation at least 4 hours but most commonly overnight. After binding, the slurry is poured into a gravity column and the resin is separated from the supernatant. The resin is then washed with 80 column volumes (CV) of wash buffer (50 mM Hepes pH 7.5, 800 mM NaCl, 20 mM Imidizole, 0.1% w/v DDM, 0.01% w/v CHS and 100 uM AMD070 (or receptor appropriate ligand). After the initial wash the resin is further treated to adjust the NaCl concentration to 500 mM and to increase the ligand concentration to 300 uM. The protein is then eluted from the resin using 200 mM Imidazole and concentrated to 2.5 mL for removal of the excess imidazole with a PD10 desalting column (GE Biosciences). The ligand concentration is increased to 500 uM and the protein is bound to 100 uL of Ni-Sepharose IMAC resin in the presence of 20,000 units of PNGase (NEB) an endoglycosidase capable of removing N-linked glycosylation. The protein is allowed to bind to the resin and deglycosylate for 6 hours after which the resin is washed with imidizole free elution buffer (50 mM Hepes pH 7.5, 500 mM NaCl, 0.05% w/v DDM, 0.01% w/v CHS and 1 mM AMD 070). After the washing step the protein was eluted from the resin using the same buffer but including 200 mM imidazole. After elution the protein is normally concentrated to approximately 50 mg/mL and tested for integrity by SEC. Crystallizable protein should be >90% free of heterogeneity as judged by SDS-PAGE and contain no detectable aggregated species at high protein concentrations as judged by SEC. If the protein remains of high quality it is reconstituted into lipidic cubic phase containing cholesterol. The reconstituted protein is then dispensed onto glass sandwich crystallization plates and tested for crystallization using the screening methodology described in this Example and Example 1. After mixing, the protein-laden lipidid cubic phase mixture will comprise 3.6-7.2% w/w sterol, 56.5-52.8 w/w % Monoolein and 40% w/w protein solution (a 3:2 ratio of lipid mixture to protein). Initial crystallization conditions use PEG 400 between 25-35%, a salt between 50-500 mM, and a pH between 5.0-7.5.

Example 3

High Resolution Crystal Structure of a Human $\beta_2$-Adrenergic G protein-Coupled Receptor T4 Lysozyme Fusion Protein The engineering, functional properties, expression and purification of crystallization grade β2AR-T4L protein are described in more detail in Example 4. Briefly, β2AR-T4L was generated by three distinct modifications to β2AR: (1) a fusion protein was created by replacement of the third intracellular loop with T4L, (2) the carboxyl terminal 48 amino acids were deleted, and (3) a glycosylation site at Asn187 was eliminated through a glutamate substitution. β2AR-T4L was expressed in Sf9 insect cells, solubilized in 1% dodecylmaltoside, and purified by sequential antibody and ligand affinity chromatography. Using the modified lipidic cubic phase (LCP) crystallization procedure described herein, wherein crystals are grown from a cholesterol-doped monoolein cubic phase, β2AR-T4L crystals were obtained that diffract to a resolution of 2.2 Å. The structure was solved at 2.4 Å resolution. Compared to crystallization in detergents, LCP provides a more native, lipid environment for crystallization, as well as a confinement of protein molecules to two-dimensional membrane sheets that may facilitate the crystallization process through the formation of Type I packing interactions (Caffrey, *Curr Opin Struct Biol* 10, 486 (2000); Deisenhofer, *EMBO J.* 8, 2149 (1989); Landau et al., *Proc Natl Acad Sci USA* 93, 14532 (1996)).

Methods

Figure 5:
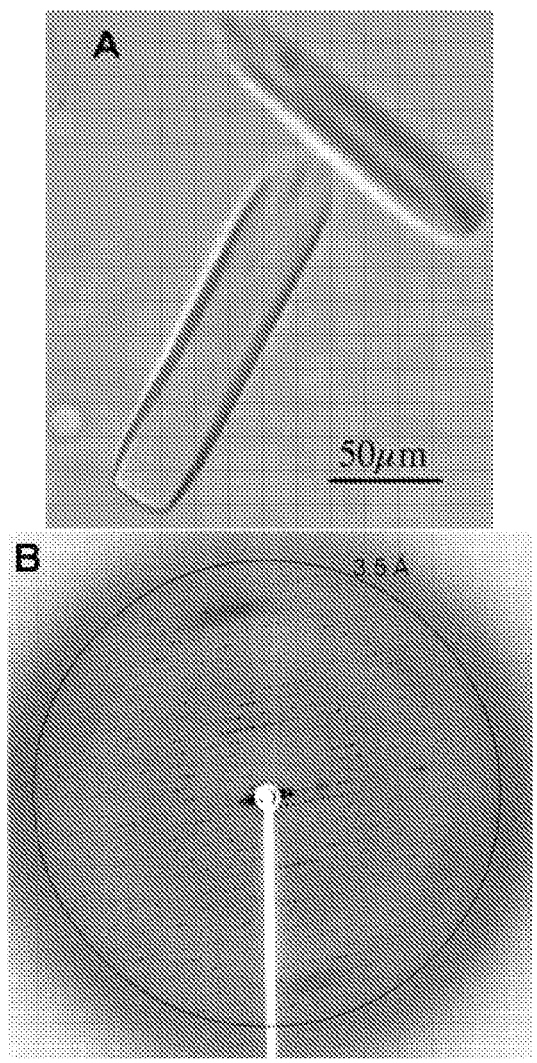
FIG. 5. A. β₂AR-T4L Crystals grown from bicelle conditions. B. Diffraction image from bicelle grown microcrystals of β₂AR-T4L recorded using 10 µm minibeam on 23ID-B beamline at APS. Black circle is drawn at resolution 3.5 Å.
Figure 6:
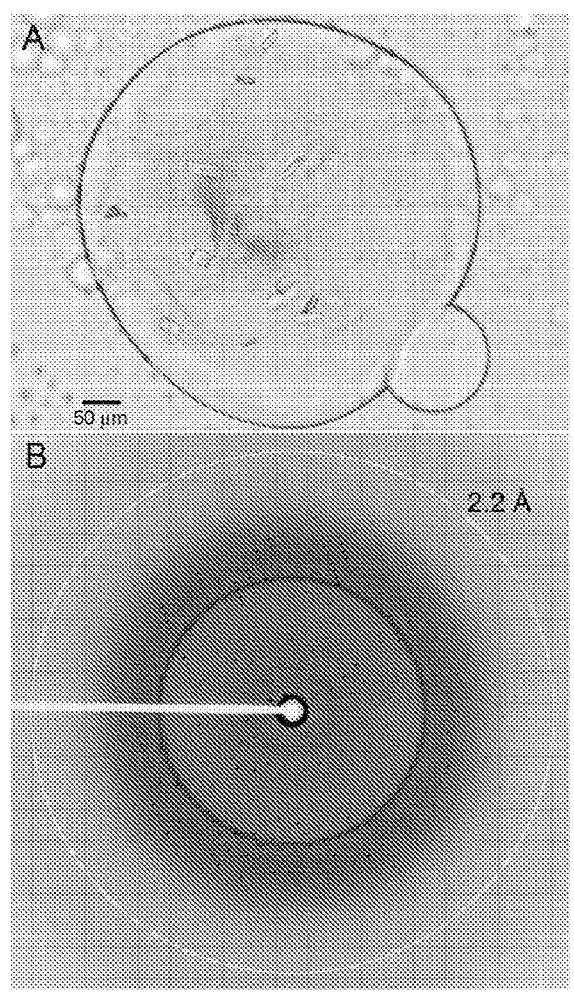
FIG. 6. A. Microcrystals of β₂AR-T4L grown in lipidic mesophase. B. Diffraction image from lipidic cubic phase grown microcrystals of β₂AR-T4L recorded using a 10 μm minibeam on 23ID-B beamline at APS. The white circle is drawn at resolution 2.2 Å.

Lipidic cubic phase crystallization. Crystals of engineered human β2AR (β2AR-T4L) grown from bicelles could not be optimized beyond 3.5 Å resolution (FIG. 5). Lipidic cubic phase (LCP) crystallization trials were therefore performed using an in meso crystallization robot (Cherezov, et al., *Acta Crystallogr D Biol Crystallogr* 60, 1795 (2004)). 96-well glass sandwich plates (Cherezov, et al., *Acta Crystallogr D Biol Crystallogr* 60, 1795 (2004); Cherezov, et al, *J Membr Biol* 195, 165 (2003)) were filled with 25 or 50 mL protein-laden LCP drops overlaid by 0.8 μL of precipitant solution in each well and sealed with a glass coverslip. All operations starting from mixing lipid and protein were performed at room temperature (~21-23° C.). Crystals were obtained in 30-35% (v/v) PEG 400, 0.1-0.2 M sodium sulfate, 0.1 M Bis-tris propane pH 6.5-7.0 and 5-7% (v/v) 1,4-butanediol using 8-10% (w/w) cholesterol in monoolein as the host lipid (FIG. 6A). Addition of cholesterol and 1,4-butanediol dramatically improved crystals size and shape, thereby enabling high-resolution diffraction. In this instance, additions of phospholipids (dioleoylphosphatidylcholine, dioleoylphosphatidylethanolamine, asolectin) to the main host LCP lipid monoolein (either alone or in combination with cholesterol) failed to improve crystal quality.

Crystal Harvesting

The average size of the harvested crystals was 30×15×5 μm (largest crystal was 40×20×7 μm). Crystals were harvested directly from the glass sandwich plates, even though these plates have been specifically designed for screening and optimization (Cherezov, et al., *Acta Crystallogr D Biol Crystallogr* 60, 1795 (2004); Cherezov, et al, *J Membr Biol* 195, 165 (2003)). Crystals were scooped directly from the LCP using 30 or 50 μm aperture MiTeGen MicroMounts and plunged into liquid nitrogen. Care was taken to drag as little as possible lipid around the crystal to decrease unwanted background scattering. Attempts to dissolve the lipids, either by increasing concentration of PEG 400 or using a mineral oil, typically resulted in a decrease in diffraction power of the crystals.

Data Collection

X-ray data were collected on the 23ID-B beamline (GM/CA CAT) at the Advanced Photon Source, Argonne, Ill. using a 10 μm minibeam (wavelength 1.0332 Å) and a MarMosaic 300 CCD detector (FIG. 6B). Several complete datasets were collected from single crystals at resolution between 2.8 and 3.5 Å using 5× attenuated beam, 5 s exposure and 1° oscillation per frame. However, some crystals diffracted to a maximum of 2.2 Å resolution upon 5 s exposure with 1× attenuated beam. Therefore, 10-20° wedges of high-resolution data were collected from more than 40 crystals (some of the crystals were large enough to allow 2-3 translations). 31 of the best datasets from 27 independent crystals were then combined and scaled against the lower resolution full dataset to obtain complete 2.4 Å data.

One of the challenges during data collection was visualization of colorless microcrystals within an opaque frozen lipid phase and aligning them with the 10 μm minibeam. Because the crystals could not be adequately visualized through the inline optics at the beamline, alignment-by-diffraction techniques were employed. The present invention provides, in one aspect, an optimized crystal search algorithm to locate the crystals without the minibeam. First, the area of the loop containing lipid was scanned in the vertical direction with a highly attenuated and slitted 100×25 μm beam. When diffraction was found, the crystal location was further confined by two additional exposures to an area of ~50×25 μm. This area was further coarse-scanned with the collimated and 10× attenuated minibeam using 15 μm steps, following by fine-tuning the position using 5 and 2 μm steps. After locating the crystal in one orientation the loop was rotated 90° and the procedure was repeated. Typically during alignment the crystal was exposed ~10 times using 10× attenuated beam and 2 s exposures.

Data Processing

A 90% complete, 2-fold redundant monoclinic dataset was processed from one crystal diffracting to 2.8 Å resolution. Initial indexing of lattice parameters in spacegroup C2 and crystal orientation were performed using HKL2000 (Otwinowski, et al, in *Methods in Enzymology* C. W. J. Carter, R. M. Sweet, Eds. (Academic Press, New York, 1997), vol. 276, pp. 307-326). The refined lattice parameters and space group were implemented in the data processing program XDS for spot integration which models error explicitly for radiation decay, absorption, and rotation (Kabsch, *J Appl Crystallogr* 26, 795 (1993)). Because data was collected using a 10 μm beam from microcrystals, maintaining the crystal orientation at the beam center during data collection was especially problematic. It appeared that XDS modeled the crystal orientation error upon rotation about the phi axis better than other data processing programs that were tried, resulting in better merging statistics. In addition to rotational error, the radiation decay was also an issue that was partially corrected by the XDS processing program, enabling a more reliable scaling of datasets from different crystals and translations of crystals. The 2.8 Å data was used as a scaling reference for incorporation of additional wedges of data collected at a much higher exposure. Each new dataset was indexed in XDS using the original unit cell parameters as constants which were then refined along with the crystal orientation, beam geometry, and mosaicity parameters. The refinement was generally stable, resulting in very similar unit cell constants which enabled subsequent scaling. All of the integrated wedges of data were then tested individually against the scaling reference set and included in the final scaled dataset if the merging statistics remained acceptable upon incorporation of the data. In total, 31 wedges of data from 27 crystals were combined with the scaling reference dataset, 22 of which diffracted to a resolution of 2.4 Å or better. Each of the higher resolution datasets were exposed to a much larger dose of radiation resulting in a rapid decay in intensity. Typically 10°-20° wedges were collected from each crystal or translation, 5°-7° of which had diffraction data to 2.4 Å. The final merging statistics for the dataset are shown in Table 2. Based on the mean $F/\sigma(F)$ of reflections near the three crystallographic axes, the effective resolution is estimated to be 2.4 Å along b* and c* and 2.7 Å along a*. The anisotropy results in the high merging R factors in the last few resolution shells despite the significant $I/\sigma(I)$ values. The anisotropy is either an inherent property of the crystals or the result of a preferential orientation of the crystals within the mounting loop. Thus, the higher resolution shells were filled in anisotropically by incorporation of the additional data at high exposure levels, while the lower resolution shells have a very high redundancy and low anisotropy.

Structure Solution and Refinement

Initial phases for β2AR-T4L were obtained by molecular replacement using both T4-lysozyme (PDB ID Code 2LZM) and a polyalanine model of the rhodopsin seven-transmembrane bundle (PDB ID Code 1U19) as search models. It was necessary to trim the lysozyme search model to remove residues 12-71 as that domain had shifted conformations relative to the larger section. This domain was later reintroduced to the model by fitting into observed density. Molecular replacement was carried out using the program Phaser by first placing the truncated lysozyme (RFZ=3.74; TFZ=3.65) followed by the rhodopsin model (RFZ=5.2; TFZ=7) (McCoy, *Acta Crystallogr D Biol Crystallogr* 63, 32 (2007)). In order to optimize placement of the receptor each of the seven helices was refined independently by rigid body maximum likelihood refinement as implemented in Refmac (Initial Rwork/Rfree=0.50/0.51) (Murshudov, et al, *Acta Crystallogr D* D53, 240 (1997)).

Figure 7:
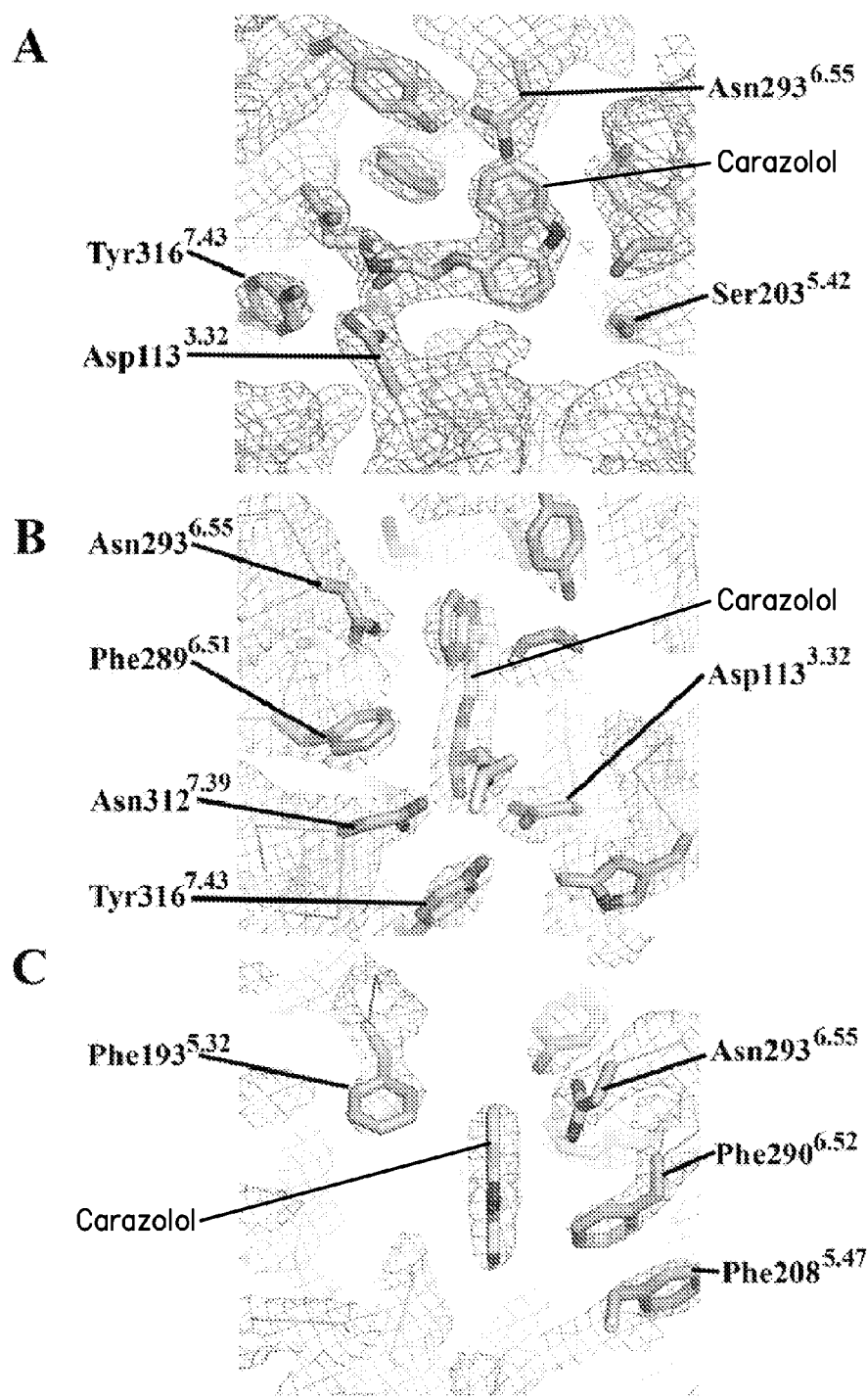
FIG. 7. Detailed representation of the carazolol binding site in β₂AR-T4L.
Figure 8:
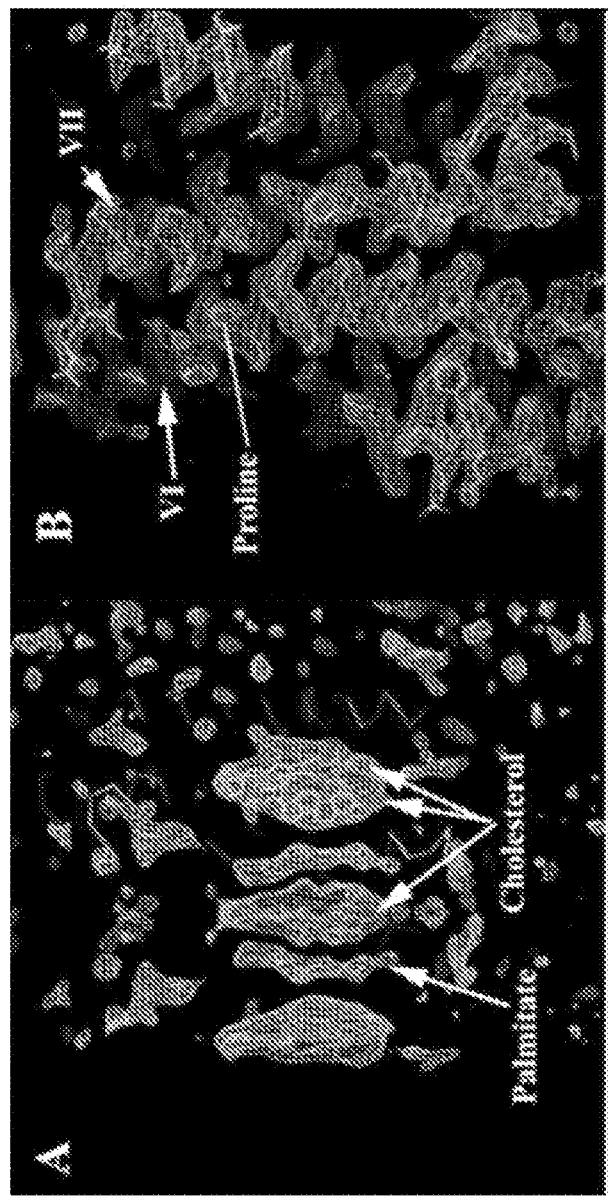
FIG. 8. Electron density of: A. Cholesterol molecules shown with a $F_o$-$F_c$ electron density contoured at 2σ omitting the lipid from phase calculation, palmitic acid is also shown. B. Helix-kinked region with 2$F_o$—$F_c$ electron density contoured at 1.5σ.

Initial rounds of refinement were carried out using restrained parameters in Refmac. Model rebuilding was performed in Coot utilizing 2 Fo–Fc sigma-A weighted maps, as well as density modified maps calculated using Resolve prime-and-switch phasing which reduces model bias introduced by model based phasing methods (Terwilliger, *Acta Crystallogr D* D56, 965 (2000)). The Resolve calculated maps were superior to the sigma-A weighted ones in that more of the main chain density could be traced. Density for the bound ligand was visible early in the refinement but was not modeled immediately to allow an unbiased assessment of the phase quality through the improvement of the signal/noise of the observed ligand density. The structure quality is excellent (Table 3), with strong electron density in particular observed in the ligand binding site (FIG. 7), cholesterol binding sites (FIG. 8A), and the proline helix kinks (FIG. 8B).

TABLE 2

Data processing statistics from XDS. A comparison is made between data filtered by a sigma cutoff and the complete set. All of the data was used in structure solution and refinement.

| Resolution | # Observed refl | # Unique refl | Redundancy | Completeness | $R_{sym}$ | I/SIGMA | R-meas | Rmrgd-F |
|---|---|---|---|---|---|---|---|---|
| Signal/noise ≧ −3 | | | | | | | | |
| 10 | 3352 | 333 | 10.1 | 87.40% | 6.60% | 23.25 | 6.90% | 2.70% |
| 8 | 3591 | 354 | 10.1 | 99.40% | 7.60% | 22.6 | 8.00% | 2.80% |
| 6 | 10480 | 1003 | 10.4 | 99.60% | 9.90% | 20.01 | 10.50% | 4.00% |
| 3 | 126008 | 11968 | 10.5 | 99.80% | 13.30% | 14.01 | 14.00% | 6.60% |
| 2.8 | 33158 | 3130 | 10.6 | 100.10% | 38.00% | 6.42 | 39.90% | 18.70% |
| 2.7 | 19702 | 1893 | 10.4 | 99.70% | 49.50% | 4.96 | 52.10% | 24.90% |
| 2.6 | 23772 | 2275 | 10.4 | 99.90% | 60.20% | 4.07 | 63.40% | 30.10% |
| 2.5 | 14108 | 2558 | 5.5 | 99.30% | 58.90% | 2.69 | 65.10% | 51.80% |
| 2.4 | 14672 | 3060 | 4.8 | 99.10% | 67.80% | 2.18 | 75.70% | 62.80% |
| Total | 248843 | 26574 | 9.4 | 99.50% | 12.70% | 9.62 | 13.40% | 11.40% |
| Signal/noise ≧ 0 | | | | | | | | |
| 10 | 3352 | 333 | 10.1 | 87.40% | 6.60% | 23.25 | 6.90% | 2.70% |
| 8 | 3591 | 354 | 10.1 | 99.40% | 7.60% | 22.6 | 8.00% | 2.80% |
| 6 | 10480 | 1003 | 10.4 | 99.60% | 9.90% | 20.01 | 10.50% | 4.00% |
| 3 | 125628 | 11923 | 10.5 | 99.40% | 13.30% | 14.06 | 14.00% | 6.50% |
| 2.8 | 32679 | 3077 | 10.6 | 98.40% | 37.60% | 6.54 | 39.50% | 17.70% |
| 2.7 | 19346 | 1849 | 10.5 | 97.40% | 48.80% | 5.08 | 51.30% | 23.40% |
| 2.6 | 23201 | 2210 | 10.5 | 97.00% | 58.90% | 4.2 | 62.00% | 28.00% |
| 2.5 | 13461 | 2406 | 5.6 | 93.40% | 56.40% | 2.88 | 62.30% | 45.90% |
| 2.4 | 13833 | 2827 | 4.9 | 91.50% | 64.10% | 2.4 | 71.50% | 54.30% |
| Total | 245571 | 25982 | 9.5 | 97.30% | 12.60% | 9.85 | 13.30% | 10.80% |

$R_{sym} = \Sigma_{hkl}|I(hkl) - <I(hkl)>|/\Sigma_{hkl}(hkl)$, where $<I(hkl)>$ is the mean of the symmetry equivalent reflections of I(hkl); R-meas = redundancy independent Rsym; Rmrgd-F = indication of amplitude quality. See, e.g., Murshudov, et al, Acta Crystallogr D D53, 240 (1997).

TABLE 3

Data collection and refinement statistics

| | β₂AR-T4L |
|---|---|
| Data collection (APS GM/CA CAT 23ID-B, 10 μm beam)* | |
| Space group | C2 |
| Cell dimensions | |
| a, b, c (Å) | 106.32, 169.24, 40.15 |
| β (°) | 105.62 |
| No. of reflections processed | 245,571 |
| No. unique reflections | 26,574 |
| Resolution (Å) | 50-2.4 (2.5-2.4) |
| $R_{sym}$ | 12.7 (67.8) |
| Mean I/σ(I) | 9.6 (2.2) |
| Completeness (%) | 99.5 (99.1) |
| Redundancy | 9.4 (4.8) |
| Refinement* | |
| Resolution (Å) | 20-2.4 (2.46-2.4) |
| No. reflections (test set) | 25,247 (1,310) |
| $R_{work}/R_{free}$ | 19.8 (27.0)/23.2 (30.1) |
| No. atoms | 3,805 |
| Protein | 3,544 |
| Ions, lipids, ligand and other | 213 |
| Water | 48 |
| Overall B-values (Å²) | 82 |
| β₂AR | 77 |
| T4-Lysozyme | 75 |
| Carazolol | 55 |
| Lipid | 100 |
| R.m.s deviations | |
| Bond lengths (Å) | 0.013 |
| Bond angles (°) | 1.5 |
| Ramachandran plot statistics (%) (excl. Gly, Pro): | |
| Most favored regions | 94.8 |
| Additionally allowed regions | 5.0 |
| Generously allowed regions | 0.2 |
| Disallowed regions | 0 |

*Highest resolution shell is shown in parenthesis. $R_{sym} = \Sigma_{hkl}|I(hkl) - <I(hkl)>|/\Sigma_{hkl}(hkl)$, where <I(hkl)> is the mean of the symmetry equivalent reflections of I(hkl).

Analysis of β2A Receptor Topology

The final model of β2AR-T4L includes 442 amino acids. β2AR-T4L was treated with iodoacetamide during purification to eliminate free thiols. The model includes a palmitic acid covalently bound to Cys341 (GPCRs are frequently post-translationally modified with palmitoylate on cysteine residues at the C-terminal tail) and an acetamide molecule bound to Cys265$^{6.27}$. Throughout the description, residues are designated by their position within the β2AR sequence and their Ballesteros-Weinstein designation as a superscript where applicable. Ballesteros-Weinstein numbering is used throughout the text as superscripts to the protein numbering. Within each helix is a single most conserved residue among the class A GPCRs. This residue is designated x.50 where x is the number of the transmembrane helix. All other residues on that helix are numbered relative to this conserved position. The model also includes one carazolol molecule, three cholesterol molecules, two sulfate ions and two butanediol molecules that interact with β2AR. There are also four sulfate ions, a putative disaccharide (modeled as maltose) and a molecule of PEG 400 bound to T4L. For β2AR, excellent electron density is observed for residues 29-342, including the ligand carazolol and the two disulfide bonds Cys106$^{3.25}$-Cys191$^{5.30}$ and Cys184$^{4.26}$-Cys190$^{5.29}$. The palmitic acid at Cys341 is clearly visible in Fo–Fc omit maps; however, the quality of the electron density is lower than for the rest of the receptor. The N-terminus (residues 1 to 28) and the majority of the C-terminus (residues 343 to 365) are disordered and not visible in the structure.

Figure 9:
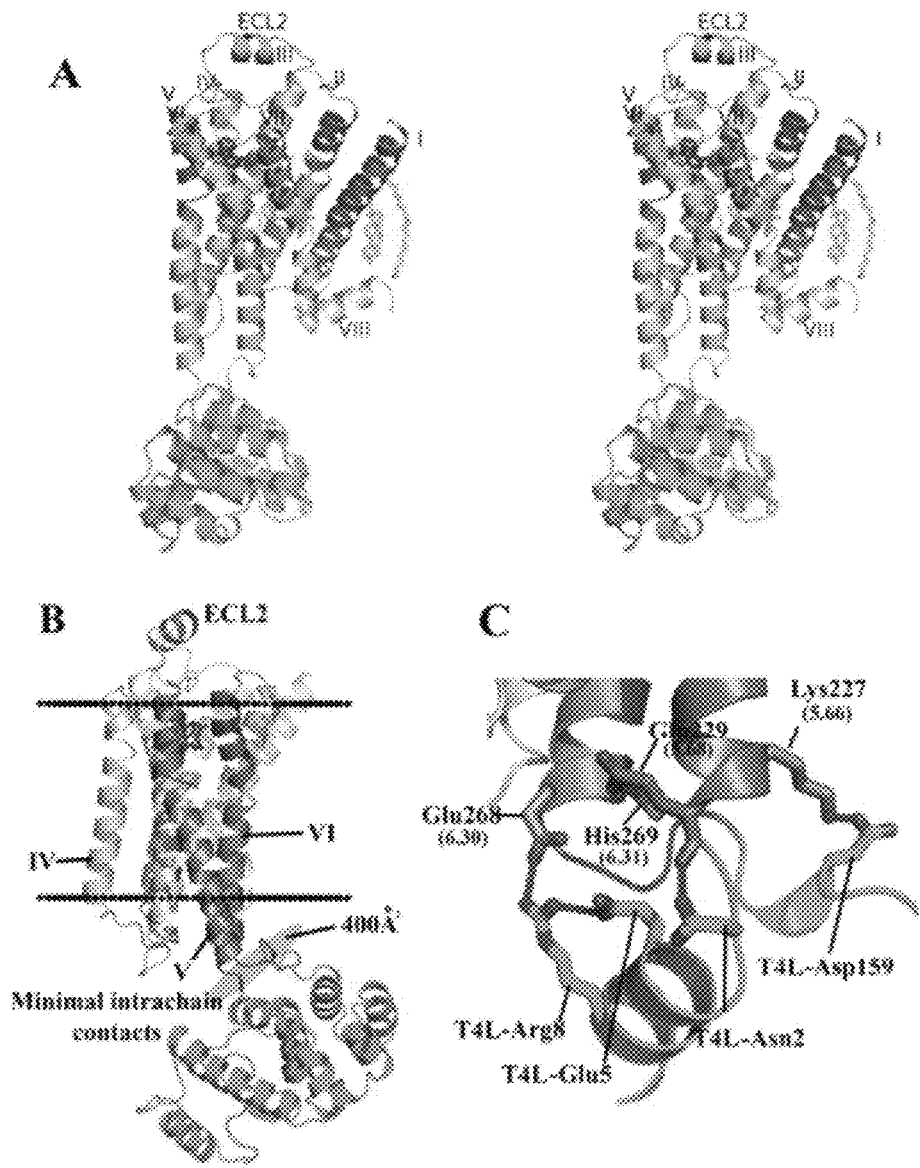
FIG. 9. Overall fold of the β₂AR-T4L fusion with its predicted orientation in the plasma membrane and key intramolecular interactions. A. Stereoview of the overall fold of β₂AR-T4L. The receptor and T4L are colored gray and green, respectively. Carazolol is colored blue and the lipid molecules bound to the receptor are colored yellow. B. The receptor is aligned to a rhodopsin model that was positioned in a lipid membrane (boundaries indicated by horizontal black lines) as found in the orientations of proteins in membranes (OPM) database (M. A. Lomize et al., *Bioinformatics* 22, 623 (2006)). T4L is fused internally into the third intracellular loop of β₂AR and maintains minimal intramolecular packing interactions by tilting away from the receptor. C. Specific intramolecular interactions between β₂AR and T4L are represented.

The β2AR has a fold composed of seven transmembrane helices forming a helical bundle (FIG. 9A). The residues that make up the helices (I to VII) in β2AR are as follows: helix I 29$^{1.28}$ to 60$^{1.59}$ helix II 67$^{2.38}$ to 96$^{2.67}$, helix III 103$^{3.22}$ to 136$^{3.55}$, helix IV 147$^{4.39}$ to 171$^{4.63}$, helix V 197$^{5.36}$ to 229$^{5.68}$, helix VI 267$^{6.29}$ to 298$^{6.60}$, and helix VII 305$^{7.32}$ to 328$^{7.55}$. The residues forming the intracellular loops (ICL) and extracellular loops (ECL) of β2AR are: ICL1.61$^{1.60}$ to 66$^{2.37}$, ECL1.97$^{2.68}$ to 102$^{3.21}$, ICL2 137$^{3.56}$ to 146$^{4.38}$, ECL2 172$^{4.64}$ to 196$^{5.35}$, ICL3 230$^{5.69}$ to 266$^{6.28}$ (residues 231 to 262 are replaced by T4-lysozyme residues 2 to 161), and ECL3 299$^{6.61}$ to 304$^{7.31}$. Helices II, V, VI and VII each have a proline-induced kink at conserved positions along the span of the transmembrane segments. These kinks are thought to enable the structural rearrangements required for activation of G protein effectors (Yohannan et al., *Proc Natl Acad Sci USA* 101, 959 (2004)). In addition to the seven membrane spanning helices, β2AR possesses two other helical segments: helix VIII, which is believed to be common to all rhodopsin-like GPCRs (Katragadda et al., *Biochim Biophys Acta* 1663, 74 (2004)), and an unexpected, short helical segment in the middle of ECL2, which is not present in rhodopsin, and was not predicted by computational secondary structure analysis (FIG. 9A).

In the β2AR-T4L construct, T4L is fused to the truncated cytoplasmic ends of helices V and VI. In the crystal structure, the T4L moiety is tilted slightly away from the center axis of β2AR drawn normal to the membrane (FIG. 9B). As a result, interactions between T4L and β2AR are minimal, with only 400 Å2 of surface area buried between them. The intramolecular contacts between T4L and β2AR include salt bridges between the side chains of T4L-Asp159 and the side-chain amine of β2AR-Lys227$^{5.66}$ (distance 3.4 Å) and between the guanidinium group of T4L-Arg8 with the side-chain carboxyl of β2AR-Glu268$^{6.30}$ on helix VI (distance 3.2 Å) (FIG. 9C, Table 4). The latter interaction is noteworthy because it differs from rhodopsin where Glu6.30 forms an ionic bond with Arg3.50 of the conserved D(E)RY motif. This interaction is postulated to be important for maintaining rhodopsin in the inactive state, but the charged groups of the two residues [Arg131$^{3.50}$ (NH1) and Glu268$^{6.30}$ (OE1)] are 10 Å apart in the β2AR-T4L structure. The remainder of the lysozyme molecule provides important crystal packing interactions, but does not appear to influence significantly the receptor structure.

TABLE 4

Direct contacts between β₂AR and T4L

| β₂AR atom | T4 Lysozyme | Distance (Å) |
|---|---|---|
| van der Waals Contacts | | |
| Leu230$^{5.69}$ | Trp 158 | |
| Lys263$^{6.25}$ | Asp159 | |
| Cys265$^{6.27}$ | Ile9 | |
| Leu266$^{6.28}$ | Ile9 | |
| Leu266$^{6.28}$ | Glu5 | |
| Hydrogen Bond and Salt Bridge Contacts | | |
| Lys227$^{5.66}$ (NZ) | Asp159(OD1) | 3.4 |
| Gln229$^{5.68}$ (O) | Asn2 (N) | 3.1 |
| Gln229$^{5.68}$ (O) | Asn2 (ND2) | 3.2 |
| Gln268$^{6.30}$ (OE2) | Arg8 (NH2) | 3.2 |
| Covalent bonds | | |
| Leu230$^{5.69}$ | Asn2 | |
| Lys263$^{6.25}$ | Tyr161 | |

Crystal Packing Interactions

Figure 10:
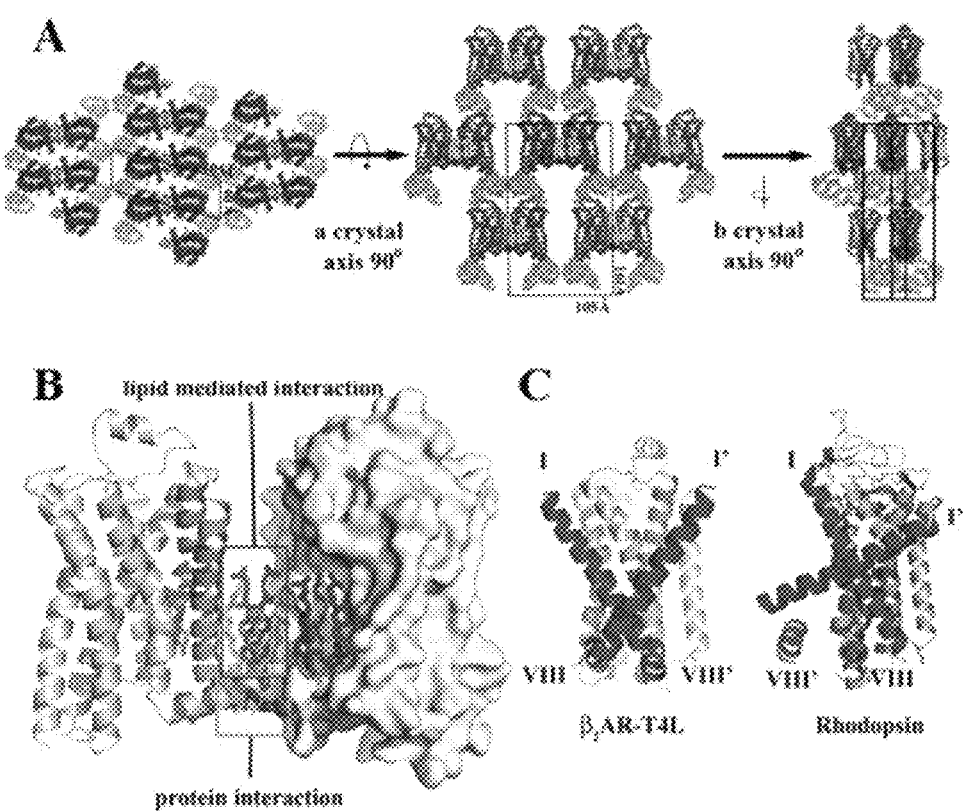
FIG. 10. Crystal packing interactions in the lipidic mesophase crystallized β₂AR-T4L. A. There are four main contact areas, two of which are mediated by T4L in the plane of the membrane with itself through a two-fold symmetry axis and translation. The third interaction is normal to the membrane plane between T4L and lumen exposed loops of β₂AR. The fourth interaction is generated by the two-fold symmetry axis, packing one receptor to receptor in the plane of the membrane. B. The receptor crystal packing interface is composed mainly of lipids with two cholesterol molecules and two palmitic acid molecules forming the majority of the interactions. A network of ionic charge interactions exists on the cytoplasmic end of the interface forming the only inter-receptor protein contacts. C. Comparison between β₂AR-T4L and rhodopsin (PDB ID Code 2I35) parallel receptor association interface. Helices I (blue) and VIII (magenta) are highlighted in both structures. Only one monomer is shown for each receptor representation along with helices I' and VIII' only from the opposing symmetry related molecule. The rhodopsin interface is twisted significantly relative to β₂AR-T4L resulting in a significant offset from the parallel orientation required for a physiological dimer interface. β₂AR-T4L associated monomers are in a highly parallel orientation.

The β2AR-T4L protein is packed in a C-centered monoclinic lattice with one molecule per asymmetric unit (FIG. 10A). Membrane protein generally can form two types of crystal packing: Type I represents stacks of two dimensional crystals ordered in the third dimension via interactions of hydrophilic parts of membrane proteins. Type II crystals are composed of membrane proteins whose hydrophobic part is shielded by a detergent micelle and all crystal contacts are formed through hydrophilic, solvent exposed parts of protein molecules. As observed in all previous lipidic mesophase grown crystals (Schwartz, et al., *Annu Rev Pharmacol Toxicol* 46, 481 (2006)), the β2AR-T4L crystals adopt Type I packing, featuring a multilayered arrangement in accordance with proposed crystallization mechanism (Caffrey, *Curr Opin Struct Biol* 10, 486 (2000); P. Nollert, et al., *FEBS Lett* 504, 179 (2001)). Within each layer, protein molecules form arrays of parallel, symmetry-related dimers. There are four distinct crystal-packing interactions within each layer, three of which are mediated by T4L. The fourth interaction in the array is between two receptor molecules related by a crystallographic two-fold rotation axis. This is the sole interaction between symmetry-related receptors, and is mediated primarily by ordered lipids consisting of six cholesterol and two palmitic acid molecules, the latter being covalently attached to Cys341 in the C-terminal portion of the receptor (O'Dowd et al., *J Biol Chem* 264, 7564 (1989)) (FIG. 10B). These eight lipid molecules form a two-fold symmetric sheet between receptors. The only direct receptor-receptor contact involves a 2.7 Å pair of ionic interactions between the charged amine group of Lys60$^{1.59}$ in helix I and the carboxylate of Glu$^{338}$ in helix VIII from the symmetry-related receptor. Remarkably, of the 515 Å2 buried at the receptor symmetry interface, 73% of the crystal contact surface area is mediated by ordered lipid, while only 27% is contributed by protein-protein contacts. The stacking interactions between layers are formed between T4L and extracellular loops ECL2 and ECL3 of the receptor (FIG. 10A). It is unlikely that these contacts affect the orientation of these loops due to the small size of ECL3 and the rigid architecture of ECL2.

Lipid Mediated Receptor Association

Many GPCRs including β2AR are thought to exist as dimers in the plasma membrane, although the location of the dimer interface and the functional significance of dimerization is not clear (Milligan, *Mol Pharmacol* 66, 1 (2004)). The observation of ordered lipids in the helix I and VIII interface between two symmetry related molecules suggests the association is physiologically relevant (Angers, et al., *Proc Natl Acad Sci USA* 97, 3684 (2000); Javitch, *Mol Pharmacol* 66, 1077 (2004); Mercier, et al., *J Biol Chem* 277, 44925 (2002)). Associations between the equivalent regions of rhodopsin have been found in crystal structures (Salom et al., *Proc Natl Acad Sci USA* 103, 16123 (2006); Schertler, *Curr Opin Struct Biol* 15, 408 (2005)) (FIG. 10C).

The role of cholesterol in the physiologic function of β2AR is well documented. Depletion of cholesterol from the membranes of neonatal cardiac myocytes alters the signaling behavior of endogenous β2AR (Xiang, et al., *J Biol Chem* 277, 34280 (2002)). In untreated cells, activation of β2AR results in sequential coupling to the G proteins Gs and Gi, producing a biphasic effect on myocyte contraction rate. Upon depletion of cholesterol, the β2AR couples more strongly to Gs. This effect may be due to a role of cholesterol in regulating interactions between the β2AR and G proteins, or an effect of cholesterol on β2AR dimerization. The β2AR couples efficiently to Gs as a monomer (Mialet-Perez, et al., *J Biol Chem* 279, 38603 (2004)), so cholesterol mediated association (dimerization) may reduce the efficiency of β2AR coupling to Gs. The effects of cholesterol depletion on β2AR signaling may also be a secondary effect of altering subcellular signaling compartments. There is evidence that cells may concentrate signaling molecules, such as GPCRs and their cognate G proteins, by way of membrane microdomains or compartments, such as caveolae (Ostrom, et al., *Br J Pharmacol* 143, 235 (September, 2004)). This compartmentalization may be a major regulator of receptor-effector coupling. Thus, the importance of cholesterol in forming the observed crystallographic association is consistent with its role in β2AR signaling.

Electrostatic Charge Distribution

Figure 11:
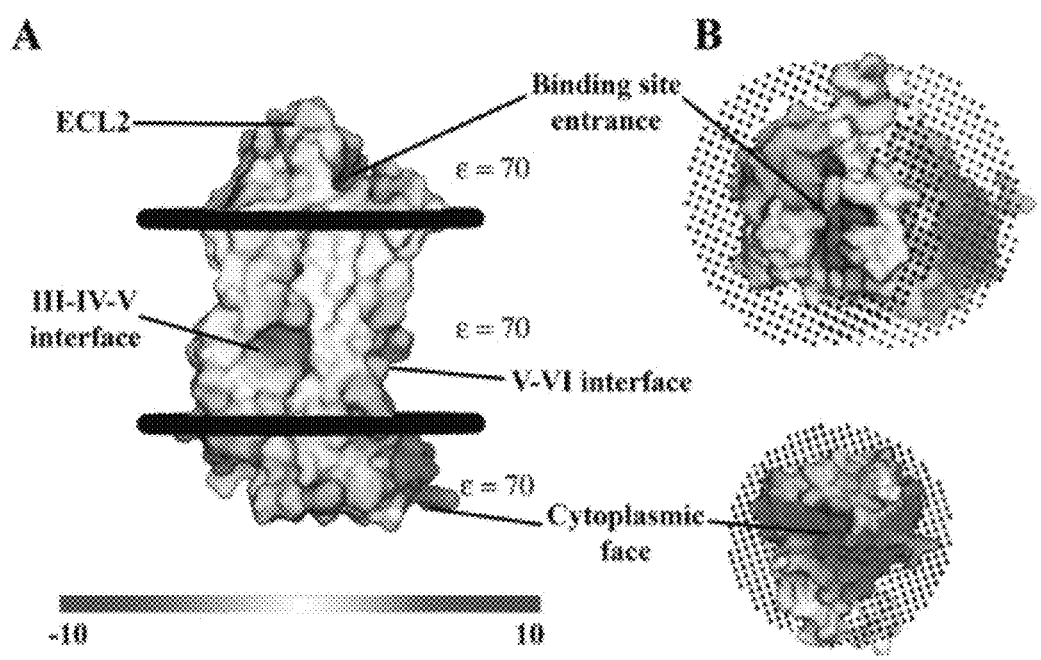
FIG. 11. Surface representation of β₂AR colored by calculated charge from red (−10 $k_bT/e_c$) to blue (+10 $k_bT/e_c$) using a dielectric constant of 70. A. Three main areas of interest are indicated. The binding site cleft is negatively charged as is a groove between helices III, IV and V. The third region is an overall positive charge in the region of the ionic lock and DRY motif on the cytoplasmic face. The overall result is a highly polarized molecule that may utilize its negative charge to facilitate binding of catecholamine ligands. The presence of a negative charge in the groove between helices III, IV and V is unexpected as it is in the middle of the lipid membrane. This charge may be partially derived from the presence of an unpaired glutamate at position 122[3,41]. The effective charge in this region is likely greater than shown here due to its location in the low dielectric environment of the lipid membrane. B. View rotated 90° from A. Showing both the negatively charged binding site cleft (top) and positively charged cytoplasmic face (bottom). Poisson-Boltzmann electrostatics were calculated using the program APBS (Baker et al., *Proc Natl Acad Sci USA*, 98, 10037 (2001)) as implemented in Pymol (The PyMOL Molecular Graphics System (2002) on World Wide Web http://www.pymol.org). Pymol was used exclusively in the preparation of all figures.

Electrostatic charge distribution was calculated using APBS (Gether, *Endocr Rev* 21, 90 (2000)) and mapped onto a molecular surface representation of β2AR. The analysis reveals three polarized areas within the molecule (FIG. 11A). First, the cytoplasmic face of the receptor is involved in G protein interaction and carries a net positive charge even in the absence of ICL3, which also has a predicted overall positive charge (FIG. 11B). The second site is an electrostatically negative region located within the membrane between helices III, IV and V potentially exposed to the lipid alkyl chains, which is unexpected as the burial of charge within the plasma membrane is thermodynamically unfavorable. A glutamate residue at position 122$^{3.41}$ may partially account for the observed charge distribution. Finally, the binding site cleft is negatively charged and exposed to solvent by an unusual ECL2 architecture and lack of N-terminal interactions. This negative charge may facilitate ligand binding through electrostatic funneling of positively charged catecholamines (FIG. 11B).

Extracellular Region

Figure 12:
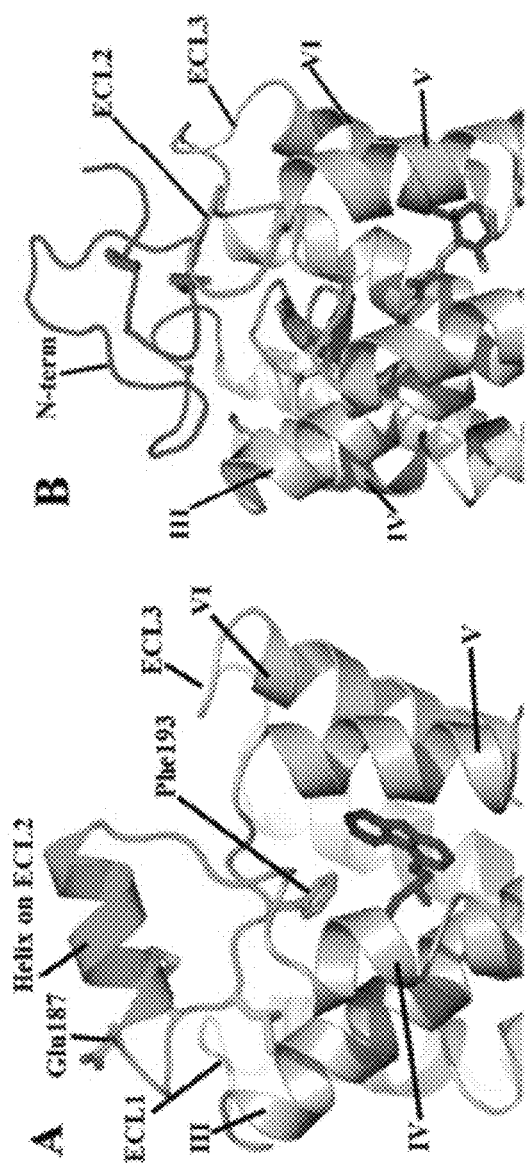
FIG. 12. Comparison of the extracellular sides of β₂AR-T4L and rhodopsin. A. The N-terminus is missing from the experimental density in the β₂AR-T4L structure and is not shown. ECL2 is shown in green and contains a short α-helix and two disulfide bonds (yellow). The intraloop disulfide bond constrains the tip of ECL2 which interacts with ECL1. The second disulfide bond links ECL2 with helix III. There is one interaction between ECL2 and carazolol (blue) through Phe193[5.32]. The entire loop is held out of the ligand binding site by a combination of the rigid helical segment and the two disulfide bonds. B. In contrast, ECL2 (green) in rhodopsin assumes a lower position in the structure that occludes direct access to the retinal-binding site and forms a small β-sheet in combination with the N-terminal region (magenta) directly above the bound retinal (pink).

The ECLs and amino termini of GPCRs, together with the extracellular halves of the transmembrane helices, are believed to define the ligand-binding site of each receptor (Angers et al., *Proc Natl Acad Sci USA* 97, 3684 (2000)); Gether, *Endocr Rev* 21, 90 (2000)). Mutagenesis studies suggest that the β2AR binds its ligand deep within the transmembrane helix bundle, which may be related to the observation that the extracellular regions have a rather simple structure with short loops connecting transmembrane helices II and III, and VI and VII (FIG. 12A). ECL2, which links helices IV and V, has a somewhat more extensive architecture that is unanticipated. In contrast to the buried, β-sheet structure of this loop in rhodopsin (FIG. 12B), ECL2 in β2AR is more exposed to the solvent and contains an extra helical segment. Additionally, there is an intra-loop disulfide bond between Cys184$^{4.76}$ and Cys190$^{5.29}$ that may help stabilize the more exposed ECL2. A second disulfide bond between Cys191$^{5.30}$ and Cys106$^{3.25}$ in helix III effectively ties ECL2 to the transmembrane core (Noda, et al., *J Biol Chem* 269, 6743 (1994)). The distal portion of ECL2 makes close contacts with ECL1 and contains a glycosylation site at Asn187$^{5.26}$ (Mialet-Perez, et al., *J Biol Chem* 279, 38603 (2004)), which may serve to mask a grouping of aromatic residues on ECL1; in this construct, Asn1875.26 has been mutated to glutamate to aid in crystallization.

Figure 13:
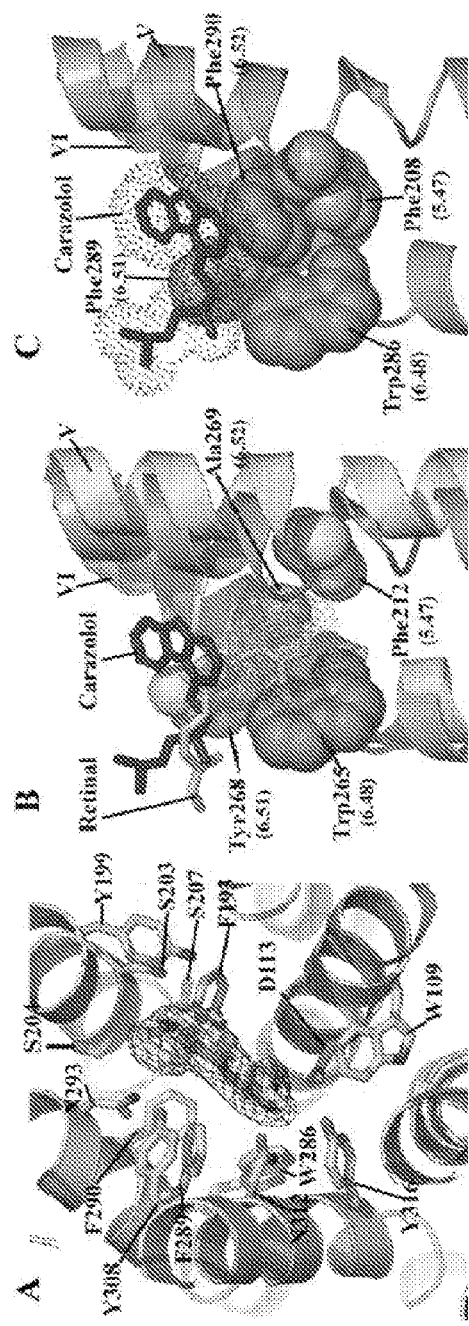
FIG. 13. Ligand binding characterization and comparison to rhodopsin. A. A view looking down on the plane of the membrane from the extracellular surface showing a detailed representation of the carazolol binding site in β₂AR-T4L. Carazolol is shown as sticks with carbon atoms colored yellow. β₂AR-T4L residues contributing to carazolol binding are shown in green and labeled. Electron density is contoured at 5σ from an $F_o$-$F_c$ omit map calculated without the contribution of carazolol. B. Binding orientation comparison between 11-cis-retinal in rhodopsin and carazolol in β₂AR-T4L. Van der Waals' surfaces for carazolol and retinal are represented as dots to accentuate the close packing interactions. Retinal in the all-cis conformation (pink), binds deep in the active site of rhodopsin as compared to carazolol (blue), packing its β-ionone ring between Tyr268[6.51] and Phe212[5.47] (cyan), blocking movement of Trp265[6.48] (magenta) into the space. The β-ionone ring of trans-retinal in activated rhodopsin would not block Trp265[6.48] from rotating into the space allowing a rotameric shift into its proposed active form. C. There are four residues involved in the toggle switch mechanism of β₂AR-T4L as shown. Phe290[6.52] (magenta) is sandwiched between Phe208[5.47] (tan) and Phe289[6.51] (tan) forming a ring-face aromatic interaction. Like rhodopsin, an activation step is thought to occur by a rotameric change of Trp286[6.48] (magenta) which would displace Phe290[6.52]. Carazolol is shown to interact extensively with the sandwich motif as shown: however, few interactions are seen with Trp286[6.48]. The 6.52 position in β₂AR-T4L is occupied by Phe290[6.52] as opposed to Ala269[6.52] in rhodopsin where the β-ionone ring replaces an aromatic protein side chain in forming the sandwich interactions. The aromatic character of the sandwich is otherwise maintained by Phe289[6.51] and Phe208[5.47] in β₂AR-T4L.

Electron density corresponding to the N-terminus was not apparent in the maps and, therefore, residues 1-28 are not included in the model. This disorder contrasts with rhodopsin, in which the N-terminus interacts extensively with the ECLs, forming a small four-strand β-sheet in conjunction with ECL2. This sheet structure forms a cap that effectively isolates the retinal binding site in a hydrophobic pocket (FIG. 13B). The lack of interactions between the N-terminus of β2AR and ECL2 further enables diffusible ligand access to the binding site. However a completely disordered N-terminus may be an artifact induced by the presence of the N-terminal Flag tag which carries an overall positive charge and may disrupt N-terminal interactions.

The short helical region on ECL2 adds a rigid structural element that, along with the two disulfide bonds, constrains the loop to a small range of conformations and helps stabilize the receptor by linking three transmembrane helices (FIG. 13A). This rigid conformation may help to stabilize the core of the receptor and lock ECL2 in a conformation that does not hinder access to the binding pocket.

Ligand Binding Site and Comparison to Rhodopsin

Carazolol is a partial inverse agonist that binds with picomolar affinity to β2AR-T4L producing a reduction of the basal activity of the receptor. The crystal structure reveals extensive interactions between the receptor and carazolol that position the carbazole moiety adjacent to Phe289$^{6.51}$, Phe290$^{6.52}$, and Trp286$^{6.48}$ (FIG. 13A, FIG. 7, and Table 5). In contrast, cis-retinal is a full inverse agonist covalently bound to rhodopsin, which suppresses all activity towards transducin (Palczewski, *Annu Rev Biochem* 75, 743 (2006)). Carazolol and retinal occupy similar spaces in their respective receptors, with significant overlap of the non-aromatic regions of carazolol. However, the β-ionone ring of retinal extends deep into the binding pocket of rhodopsin and contacts residues on helix V and VI, where it is sandwiched between Phe212$^{5.47}$ and Tyr268$^{6.51}$, and interacts with the highly conserved Trp265$^{6.48}$ (FIG. 13B). It has been proposed that changes in the rotamer of Trp265$^{6.48}$ occur upon activation of rhodopsin and related family members, and constitutes the "toggle switch" for receptor activation (Schwartz, et al., *Annu Rev Pharmacol Toxicol* 46, 481 (2006)). Accordingly, the interactions between c/s-retinal and Trp265$^{6.48}$ are likely to contribute to the absence of basal activity in rhodopsin. Carazolol does not interact directly with the toggle switch on helix VI, however it lowers the basal activity of the receptor, and may do so by interacting with Phe289$^{6.51}$ and Phe290$^{6.52}$, which form an extended aromatic network surrounding the highly conserved Trp286$^{6.48}$. As a result, Trp286$^{6.48}$ adopts the rotamer associated with the inactive state. Thus, the steric constraints imposed by Phe290$^{6.52}$ appear to structurally mimic the interaction of the β-ionone ring of retinal with the conserved Trp265$^{6.48}$ and Phe212$^{5.47}$ on rhodopsin (Shi et al., *J Biol Chem* 277, 40989 (2002)) (FIG. 13C).

TABLE 5

Direct contacts between β2AR and carazolol.

| β2AR atom | Carazolol | Distance (Å) |
|---|---|---|
| Hydrogen Bond and Salt Bridge Contacts | | |
| Asp113$^{3.32}$ (OD2) | N19 | 2.9 |
| Asp113$^{3.32}$ (OD1) | O17 | 2.6 |
| Ser203$^{5.42}$ (OG) | N7 | 3.2 |
| Asn312$^{7.39}$ (ND2) | O17 | 2.9 |
| Asn312$^{7.39}$ (OD1) | N19 | 2.9 |
| Tyr316$^{7.43}$ (OH) | N19 | 3.4 |
| Hydrophobic and Aromatic Interactions (closest distance for each residue, <4 Å) | | |
| Trp109$^{3.28}$ (CH2) | C21 | 3.8 |
| Val114$^{3.33}$ (CG1) | C11 | 3.9 |
| Val117$^{3.36}$ (CG1) | C12 | 4.0 |
| Thr118$^{3.37}$ (OG1) | C11 | 3.9 |

TABLE 5-continued

Direct contacts between β2AR and carazolol.

| β2AR atom | Carazolol | Distance (Å) |
|---|---|---|
| Phe193$^{5.32}$ (CE2) | C6 | 3.5 |
| Tyr199$^{5.38}$ (CE2) | C2 | 3.9 |
| Ser207$^{5.46}$ (CB) | C10 | 3.6 |
| Trp286$^{6.48}$ (CH2) | O17 | 3.4 |
| Phe289$^{6.51}$ (CE2) | O14 | 3.7 |
| Phe290$^{6.52}$ (CZ) | C12 | 3.5 |
| Asn293$^{6.55}$ (ND2) | C5 | 3.6 |
| Tyr308$^{7.35}$ (OH) | C6 | 3.6 |

Structural Alignment and Helix Bundle Reorganization

It has long been thought that class A GPCRs share a similar architecture due to their predicted seven transmembrane helical bundles and sequence conservation within the membrane spanning regions (Lefkowitz, *Nat Cell Biol* 2, E133 (2000)). We aligned the structure of β2AR-T4L to highest resolution structure of rhodopsin (PDB ID Code 1U19) to evaluate the similarities and differences in ligand binding modes. We used difference distance matrices to select non-divergent areas between the two structures that align to reveal the differences in helix orientation between β2AR-T4L and rhodopsin. For the alignment, residues on β2AR were aligned to equivalent residues on Rhodopsin, respectively: 43-59 to 47-63; 67-95 to 71-99; 122-135 to 126-139; 285-296 to 264-275.

Figure 14:
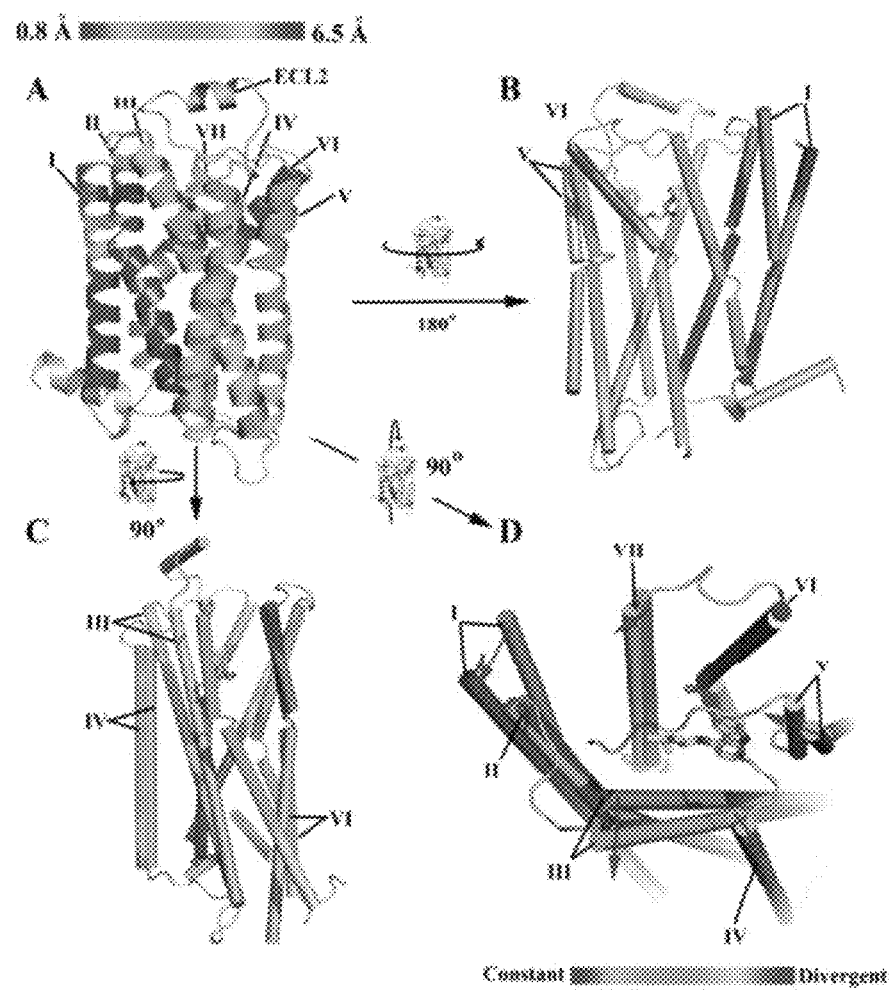
FIG. 14. Comparison of β₂AR-T4L helical orientations with rhodopsin (PDB ID Code 1U19). A. β₂AR-T4L is rendered as a ribbon trace colored with a blue to red spectrum corresponding to observed distances between Cα positions in the two structures (RMSD 2.7 Å between all residues in the transmembrane region). Helix II shows very little movement, whereas the entire lengths of helices III, IV, V shift significantly. Helix VIII and loops were not included in the comparison and are colored in tan. B. Movements of helices I and V of rhodopsin (grey) are shown relative to β₂AR-T4L. C.

Relative to rhodopsin, the following helical shifts are seen in β2AR-T4L: the extracellular portions of helices I and III angle away from the center of the receptor, helix IV is translated away from the center of the receptor, helix V is translated closer to the center of the receptor and helix VI angles away from the receptor on the cytoplasmic end (FIG. 14). The largest difference is in helix I, which lacks a proline-induced kink found in rhodopsin and is comparatively straight. The angle between the rhodopsin and β2AR positions of helix I is approximately 18° with a shift of 7 Å at the apex on the extracellular face. This structural difference may arise from the need for an accessible binding site in β2AR, which is provided in part by a lack of interactions between the N-terminus and extracellular loop segments. In contrast the N-terminal region in rhodopsin occludes the retinal-binding site through extensive interactions with the extracellular loops (FIG. 12B). Helix V of β2AR is closer to the binding pocket by approximately 3.5 Å on average and its lumenal end is angled more towards helix VI. Helix IV of β2AR is further from the binding site, possibly to remove steric clashes resulting from the modified position of helix V (FIG. 14B, 14C). Helix III pivots further from the binding site about a fulcrum located close to the cytoplasmic end (FIG. 14C). The angle formed between rhodopsin helix III and the β2AR helix III is approximately 7°, yielding a 4 Å displacement out of the binding pocket at the cytoplasmic end of the helix. Helix VI is positioned further from the center of the receptor at the cytoplasmic end as compared to rhodopsin, which is caused by a slight difference in the angle about the proline-induced kink in the helix (FIG. 14C).

The ligand-binding pocket is formed by both structurally conserved and divergent helices as compared to rhodopsin (FIG. 14D). Helices III and V are two of the most conformationally shifted helices and contain the canonical catecholamine binding residues associated with activation of adrenergic family of receptors (Strader et al., *J Biol Chem* 263, 10267 (1988); Strader, et al., *J Biol Chem* 264, 13572 (1989); Liapakis et al., *J Biol Chem* 275, 37779 (2000)). The comparison with rhodopsin shows that the structurally conserved helices provide a common core present throughout the class A GPCRs, whereas the variable helices confer binding site plasticity with a resulting architecture capable of binding a large spectrum of ligands.

Comparison to Rhodopsin-Based GPCR Models

Since the determination of the inactive dark-state rhodopsin structure (Palczewski et al., *Science* 289, 739 (2000)), a number of homology models of other class A GPCRs have been reported (Bissantz, et al., *Proteins* 50, 5 (2003); Fano, et al., *J Chem Inf Model* 46, 1223 (2006); Hobrath, et al., *J Med Chem* 49, 4470 (2006); Nowak, et al., *J Med Chem* 49, 205 (2006); Zhang, et al., *PLoS Comput Biol* 2, e13 (2006)). Typically, homology models start by alignment of so-called fingerprint motifs that are common among the family. These fingerprint motifs are extrapolated to assign coordinates for the entire helical bundle. Loop regions are either ignored or modeled based on databases of loop conformations depending on the application (Bissantz, et. al, *Proteins* 50, 5 (2003)). A number of models exist for β2AR, some of which have been improved upon with supporting biochemical data (Bissantz, et. al, *Proteins* 50, 5 (2003); Zhang, et al., *PLoS Comput Biol* 2, e13 (2006); Freddolino et al., *Proc Natl Acad Sci USA* 101, 2736 (2004); Furse, et al., *J Med Chem* 46, 4450 (2003); Gouldson et al., *Proteins* 56, 67 (2004)). When compared to the β2AR structure reported here (according to the methods described above in this Example), however, all of these models were more similar to rhodopsin, as were models for other receptors (e.g. dopamine, muscarinic, and chemokine). This highlights a general shortcoming in homology models generated from a single structural template. The structural divergence between β2AR and rhodopsin would be quite difficult to predict accurately using only rhodopsin as a template.

Example 4

Structural Insights into $\beta_2$ Adrenergic Receptor Function

Methods

Molecular Biology for Generation of Mammalian and Sf9 Expression Constructs.

The insect cell expression plasmid that was used as a template for modification of the human β2AR gene has been described previously (Yao et al., *Nat Chem Biol* 2, 417 (2006)): the wild-type coding sequence of the human β2AR (starting at Gly2) was cloned into the pFastbac1 Sf-9 expression vector (Invitrogen) with the HA signal sequence followed by the Flag epitope tag at the amino terminus and the third glycosylation site mutated as N187E. Using this template, a TAA stop codon was placed between Gly365 and Tyr366, terminating translation without the 48 C-terminal residues of the wild-type β2AR ("β2AR365"). A synthetic DNA cassette encoding the T4 Lysozyme (WT*-C54T, C97A) protein was made by overlapping extension PCR of 50-base oligonucleotides. This cassette was amplified and inserted into the β2AR365 construct between Ile233$^{5.72}$ and Arg260$^{6.22}$ (FIG. 21A), using the Quickchange Multi protocol (Stratagene). The corresponding mammalian cell expression plasmid was made by amplifying the entire fusion gene and cloning it into pcDNA3 (Invitrogen). Further deletions in the Sf9 and mammalian cell constructs were made using appropriate synthetic oligonucleotides in the Quickchange Multi protocol (Stratagene). All constructs were confirmed by sequencing.

HEK293 Cell Staining and Immunofluorescence Staining.

HEK293 cells were cultured on plastic dishes at 37° C. with 5% $CO_2$ in Dulbecco's modified Eagle's medium (Cell-gro) with 5% fetal bovine serum. For an individual expression experiment, cells at confluency were split, and approximately 100,000 cells were used to seed glass cover slips in the same medium. After 2 d, cells were transfected with the addition of 1 μg of a given pcDNA3-receptor plasmid and 3 μl of Fugene 6 reagent (Roche). 48 h after transfection, cells were washed with PBS, fixed with 4% paraformaldehyde, blocked with PBS+2% goat serum, permeabilized with PBS+2% goat serum+0.5% Nonidet P-40 (Sigma), stained with Alexa488-conjugated M1 anti-FLAG antibody (for receptor) plus DAPI (nuclear) in blocking buffer, and washed with blocking buffer. Cover slips were mounted on microscope slides with Vectashield (Vector Labs) and dried overnight. Staining was visualized with an Axioplan 2 fluorescence imaging system, using a 63× objective and either green (Alexa488/FITC) or blue (DAPI/Hoechst) filter sets. A plasmid pcDNA3-β1AR, expressing an N-terminal FLAG-tagged β1 adrenergic receptor, was used as a positive control for cell-surface staining. Empty pcDNA3 was used as a negative control to assess background staining.

Expression and Purification of $\beta_2$AR-T4L from Baculovirus-Infected Sf9 Cells.

Recombinant baculovirus was made from pFastbac1-β2AR-T4L using the Bac-to-Bac system (Invitrogen), as described previously (Yao et al., *Nat Chem Biol* 2, 417 (2006)). The β2AR-T4L protein was expressed in Sf9 insect cells infected with this baculovirus, and solubilized according to previously described methods (Kobilka, *Anal Biochem* 231, 269 (1995)). Dodecylmaltoside-solubilized receptor with the N-terminal FLAG epitope (DYKDDDA) (SEQ ID NO: 1) was purified by M1 antibody affinity chromatography (Sigma), treated with TCEP/iodoacetamide, and further purified by alprenolol-Sepharose chromatography (Kobilka, *Anal Biochem* 231, 269 (1995)) to isolate only functional GPCR. Eluted alprenolol-bound receptor was re-bound to M1 FLAG resin, and ligand exchange with 30 μM carazolol was performed on the column. β2AR-T4L was eluted from this final column with 0.2 mg/ml FLAG peptide in HLS buffer (0.1% dodecylmaltoside, 20 mM Hepes, 100 mM NaCl, pH 7.5) plus 30 μM carazolol and 5 mM EDTA. N-linked glycosylations were removed by treatment with PNGaseF (NEB). Protein was concentrated from ~5 mg/ml to 50 mg/ml with a 100 kDa molecular weight cut-off Vivaspin concentrator (Vivascience), and dialyzed against HLS buffer plus 10 μM carazolol.

Binding Measurements on Wild-Type $\beta_2$AR and $\beta_2$AR-T4L from Membranes.

Membrane preparation from baculovirus-infected Sf9 cells was performed as described previously (Swaminath, et al., *Mol Pharmacol* 61, 65 (2002)). For each binding reaction, membranes containing 0.7 μg total membrane protein were used. Saturation binding of [$^3$H]-dihydroalprenolol (DHA) was measured by incubating membranes resuspended in 500 μl binding buffer (75 mM Tris, 12.5 mM $MgCl_2$, 1 mM EDTA, pH 7.4, supplemented with 0.4 mg/ml BSA) with 12 different concentrations of [$^3$H]DHA (Perkin Elmer) between 20 pM and 10 nM. After 1 h incubation with shaking at 230 rpm, membranes were filtered from the binding reactions with a Brandel harvester, washed with binding buffer, and measured for bound [$^3$H]DHA with a Beckman LS6000 scintillation counter. Non-specific binding was assessed by performing identical reactions in the presence of 1 μM alprenolol. For competition binding, membranes resuspended in 500 μl binding buffer were incubated with 0.5 nM [$^3$H]DHA plus increasing concentrations of the competing ligand (all compounds were purchased from Sigma). For (−)-isoproterenol and (−)-epinephrine, concentrations were 100 pM-1 mM, each increasing by a factor of 10. For salbutamol, concentrations were 1 nM-10 mM. For ICI-118,551 and formoterol, concentrations were 1 pM-10 µM. Non-specific binding was measured by using 1 µM unlabeled alprenolol as competing ligand. Each data point in the curves in FIGS. 2A and S1 represents the mean of three separate experiments, each done in triplicate. Binding data were analyzed by nonlinear regression analysis using Graphpad Prism. The values for $K_d$ of [$^3$H]DHA and K, of other ligands are shown in Table 6.

TABLE 6

Saturation Binding

| [$^3$H]DHA | $K_d$ ± SE (nM) | Bmax (pmol/mg) |
|---|---|---|
| $\beta_2$AR | 0.161 ± 0.012 | 30.0 ± 0.5 |
| $\beta_2$AR-T4L | 0.180 ± 0.016 | 21.6 ± 0.5 |

Competition Binding

| Ligand | $K_i$ [S.E. interval] for $\beta_2$AR (nM) | $K_i$ [S.E. interval] for $\beta_2$AR-T4L (nM) |
|---|---|---|
| (−)-isoproteronol | 50.6 [48.9-52.3] | 15.7 [15.2-16.2] |
| (−)-epinephrine | 175 [163-188] | 56.0 [52.8-59.4] |
| salbutamol | 728 [708-750] | 307 [291-323] |
| ICI-118,551 | 0.617 [0.570-0.668] | 0.626 [0.591-0.662] |
| formoterol | 3.60 [3.39-3.83] | 1.68 [1.55-1.81] |

Binding affinities of different ligands for the wild-type $\beta_2$AR and the fusion protein $\beta_2$AR-T4L. The saturation and competition binding curves shown in FIG. 22 were fit to theoretical saturation and one-site competition binding models, using the program Graphpad Prism. $K_i$ values were calculated using the Cheng-Prusoff equation: $K_i = IC_{50}/(1 + [\text{ligand}]/K_d)$.

Bimane Fluorescence Experiments on Purified, Detergent-Solubilized Receptors $\beta_2$AR-T4L and $\beta_2$AR365 were purified as described above, with two important differences. First, prior to iodoacetamide treatment, FLAG-pure receptor at 2.5 µM (measured by soluble [$^3$H]DHA binding) was incubated with 5 µM monobromobimane for 1 h at 4° C. Second, after binding the bimane-labeled alprenolol-Sepharose-purified receptor to M1 antibody resin, the column was washed extensively with ligand-free buffer before elution. Based on previous precedent (Ghanouni, et al., Proc Natl Acad Sci USA 98, 5997 (2001)), this protocol is expected to target primarily Cys265[6,27] for fluorophore derivitization. Fluorescence spectroscopy was performed on a Spex FluoroMax-3 spectrofluorometer (Jobin Yvon Inc.) with photon-counting mode, using an excitation and emission bandpass of 5 nm. All experiments were done at 25° C. For emission scans, we set excitation at 350 nm and measured emission from 417 to 530 nm with an integration time of 1.0 s nm$^{-1}$. To determine the effect of ligands, spectra were measured after 15 min incubation with different compounds (at saturating concentrations: [(−)-isoproterenol]=100 µM; [ICI-118,551]=10 µM; [salbutamol]=500 µM). Fluorescence intensity was corrected for background fluorescence from buffer and ligands in all experiments. The curves shown in FIG. 22B are each the average of triplicate experiments performed in parallel. $\lambda_{max}$ values and intensity changes for $\beta_2$AR-T4L and $\beta_2$AR365, each incubated with different ligands, are tabulated in Table 7.

TABLE 7

| Ligand | λmax ± SD for ($\beta_2$AR365 (nm) | λmax ± SD for $\beta_2$AR-T4L (nm) |
|---|---|---|
| none | 448 ± 2 | 447 ± 2 |
| (−)-isoproteronol | 453 ± 2 | 455 ± 2 |

TABLE 7-continued

| | | |
|---|---|---|
| ICI-118,551 | 447 ± 1 | 446 ± 1 |
| salbutamol | 449 ± 1 | 449 ± 1 |

Intensity at λmax$_{Ligand}$/Intensity at λmax$_{none}$

| Ligand | $\beta_2$AR365 | $\beta_2$AR-T4L |
|---|---|---|
| (−)-isoproteronol | 0.758 ± 0.007 | 0.824 ± 0.006 |
| ICI-118,551 | 1.013 ± 0.008 | 1.028 ± 0.008 |
| salbutamol | 0.950 ± 0.013 | 0.928 ± 0.009 |

Bimane fluorescence responses for unliganded $\beta_2$AR365 and $\beta_2$AR-T4L, incubated for 15 min with different ligands. Top panel shows the $\lambda_{max}$ for fluorescence emission spectra (excitation at 350 nm and emission from 417 to 530 nm) collected after 15 min incubation with ligand. Each value is mean ± standard deviation for triplicate experiments performed in parallel. Bottom panel shows the change in fluorescence intensity after incubation with ligand, represented as the ratio of Intensity at λmax of the ligand to Intensity at $\lambda_{max}$ of the control no ligand ("none") response.

Comparing the proteolytic stability of unliganded $\beta_2$AR and $\beta_2$AR-T4L.

The limited trypsin proteolysis protocol was adapted from Jiang et al., Biochemistry 44, 1163 (2005). Carazolol-bound $\beta_2$AR-T4L or wild-type $\beta_2$AR (each at 30 mg/ml) were diluted 10-fold into HLS buffer (see above) and TPCK-trypsin was added at a 1:1000 ratio (wt:wt). The digests were incubated at room temperature. At various time points, aliquots were removed and flash frozen on dry ice/ethanol. After the last aliquot was removed, all samples were thawed, and an equal volume of 10% SDS/PAGE loading buffer was added to each. Samples were then analyzed by electrophoresis on 12% polyacrylamide gels, followed by staining with Coomassie blue (FIG. 16).

Comparing the Stability of Unliganded $\beta_2$AR and $\beta_2$AR-T4L

Unliganded β2AR365 and β2AR-T4L were each purified as described above for the bimane experiments. 200 µl 0.02 mg/ml receptor in HLS buffer was incubated at 37° C. on a heating block. At the time points indicated in FIG. 17, samples were briefly spun and gently vortexed and 16.5 µl was removed and diluted 18.2-fold in HLS (300 µl total). Then 4×5 µl was removed for determination of total binding and 2×5 µl was removed for nonspecific binding. To measure soluble binding, 5 µl diluted receptor was added to 105 µl HLS (400-fold final dilution of receptor) containing 10 nM [3H]DHA±10 µM cold alprenolol. Reactions were incubated 30 min at RT, then on ice until processing. 100 µl of each reaction was applied to a 1 ml G50 column to separate protein from residual unbound [3H]DHA, and receptor was eluted using 1.1 ml ice-cold HLS. Bound [3H]DHA was quantified on a Beckman LS6000 scintillation counter.

Carazolol Dissociation from the "Wild-Type" Receptor NAR365

β2AR365 was purified with carazolol bound, according to the protocol described above for β2ART4L. Carazolol-bound receptor (at approximately 50 µM concentration) was dialyzed in the dark against 1L dialysis buffer (20 mM HEPES pH7.5, 100 mM NaCl, 0.1% dodecylmaltoside, 300 micromolar alprenolol) at room temperature with stirring. At indicated time points, two samples were removed from the parafilm-sealed open-ended dialysis chamber, diluted into fresh dialysis buffer, and carazolol emission spectra were obtained on a Spex FluoroMax spectrofluorometer (using excitation at 330 nm and emission from 335 to 400 nm). As internal standards for every time point, samples were removed for determination of protein concentration using the Bio-Rad Protein DC kit (FIG. 19).

CAM and UCM Mutants

The CAMs (constitutively active mutants) described in the literature that are the basis for FIG. 26A and the associated discussion are: L124A (Tao, et al., Mol Endocrinol 14, 1272 (2000)), C116F (Zuscik, et al., J Biol Chem 273, 3401 (1998)), D130A (Rasmussen et al., Mol Pharmacol 56, 175 (1999)), L272C (Jensen et al., J Biol Chem 276, 9279 (2001)), and C285T (Shi et al., J Biol Chem 277, 40989 (2002)). The UCMs (uncoupling mutations) from the literature that were used for FIG. 26C are: D79N (Chung, et al., J Biol Chem 263, 4052 (1988)), F139A (Moro, et al., J Biol Chem 269, 6651 (1994)), T164I (Green, et al., J Biol Chem 268, 23116 (1993)), N318K (Strader et al., Proc Natl Acad Sci USA 84, 4384 (1987)), N322A (Barak, et al., Biochemistry 34, 15407 (1995)), P323A (Barak, et al., Biochemistry 34, 15407 (1995)), Y326A (Barak, et al., Biochemistry 34, 15407 (1995)), L339A (Gabilondo et al., Proc Natl Acad Sci USA 94, 12285 (1997)), and L340A (Gabilondo et al., Proc Natl Acad Sci USA 94, 12285 (1997)).

Biochemical and Structural Analysis of $\beta_2$AR-T4L

The $\beta_2$AR fusion protein in which T4 Lysozyme replaces most of the third intracellular loop of the GPCR ("$\beta_2$AR-T4L") retains near-native pharmacologic properties. The $\beta_2$AR-T4L protein was crystallized in lipidic cubic phase, as described in the Examples above, and the resulting 2.4 Å resolution crystal structure reveals the interface between the receptor and the ligand carazolol, a partial inverse agonist. The efficacy of a ligand describes the effect of the ligand on the functional properties of a GPCR. For purposes of the Examples only, agonists are defined as ligands that fully activate the receptor; partial agonists induce submaximal activation even at saturating concentrations; inverse agonists inhibit basal receptor activity, and antagonists have no effect on basal activity, but competitively block access of other ligands. Carazolol, is defined as a partial inverse agonist because it suppresses only 50% of the basal activity of the $\beta_2$AR. Analysis of mutagenesis data in light of the structure clarifies the roles of different amino acids in inverse agonist binding, and implies that rearrangement of the binding pocket accompanies agonist binding. In addition, the structure reveals how mutations known to cause constitutive activity or uncoupling of agonist binding and G-protein activation are distributed between the ligand-binding pocket and the cytoplasmic surface of the protein, such that changes in side chains due to interaction with the ligand can be transmitted through the structure to the site of G protein interaction.

Cloning of $\beta_2$AR-T4L

DNA encoding the T4L protein (C54T, C97A) (Matsumura, et al., Proc Natl Acad Sci USA 86, 6562 (1989)) was initially cloned into the human $\beta_2$AR gene, guided by comparison of ICL3 length and sequence among class A GPCRs (Horn et al., Nucleic Acids Res 31, 294 (2003)): residues $234^{5.73}$-$259^{6.21}$ of the $\beta_2$AR were replaced by residues 2-164 of T4L (construct "E3" in FIG. 21A). In addition, the receptor was truncated at position 365, which aligns approximately with the position of the rhodopsin carboxyl terminus. Although these modifications resulted in a receptor that was expressed efficiently in Sf9 cells, further optimization was carried out to reduce the length of the junction between the receptor and the T4L termini, as described in the methods above. Several candidate constructs are illustrated in FIG. 21A, and selected immunofluorescence images of transfected, permeabilized HEK293 cells are shown in FIG. 21B. Relative to the initial construct, we could remove three residues from the cytoplasmic end of helix V, three residues from the C-terminal end of T4L, and three residues from the N terminus of helix VI, all without losing significant cell-surface expression. The final construct used for crystallization trials ("$\beta$2AR-T4L") has residues $231^{5.70}$-$262^{6.24}$ of the $\beta$2AR replaced by amino acids 2-161 of T4L ("1D" in FIG. 21A). Similar reduction of flexibility through minimization of linker length has been important in previous crystallization studies on soluble fusion proteins (Smyth, et al., Protein Sci 12, 1313 (2003)).

Functional Properties of $\beta_2$AR-T4L

We measured saturation binding of [3H]DHA to the $\beta_2$AR-T4L, as well as competition binding of the inverse agonist ICI-118,551 and several agonists (FIG. 22A, FIG. 15 and Table 6). The results show that $\beta$2AR-T4L has wild-type affinity for the antagonist [3H]DHA and the inverse agonist ICI-118,551, whereas the affinity for both agonists (isoproterenol, epinephrine, formoterol) and a partial agonist (salbutamol) is two to three-fold higher relative to wild-type $\beta$2AR. Higher agonist binding affinity is a property associated with constitutively active mutants (CAMs) of GPCRs. CAMs of the $\beta$2AR also exhibit elevated basal, agonist-independent activation of Gs, and typically have lower expression levels and reduced stability (Gether et al., J Biol Chem 272, 2587 (1997); Rasmussen et al., Mol Pharmacol 56, 175 (1999)). $\beta$2ART4L exhibits binding properties of a CAM, but it expresses at levels exceeding 1 mg per liter of Sf9 cell culture, is more resistant to trypsin proteolysis than the wild-type $\beta$2AR (FIG. 16), and retains binding activity in detergent at 37° C. as well as the wild-type receptor (FIG. 17).

$\beta$2AR-T4L did not couple to Gs, as expected due to the replacement of ICL3 by T4L. To assess whether the fused protein alters receptor function at the level of its ability to undergo conformational changes, we used a covalently attached fluorescent probe as a reporter for ligand-induced structural changes. Fluorophores attached at $Cys265^{6.27}$, at the cytoplasmic end of helix VI, detect agonist-induced conformational changes that correlate with the efficacy of the agonist towards G protein activation (Ghanouni et al., J Biol Chem 276, 24433 (2001); Ghanouni, et al., Proc Natl Acad Sci USA 98, 5997 (2001); Swaminath et al., J Biol Chem 279, 686 (2004); Swaminath et al., J Biol Chem 280, 22165 (2005)). Detergent-solubilized $\beta$2AR365 (wild-type receptor truncated at 365) and $\beta$2AR-T4L were each labeled with monobromobimane. Addition of the agonist isoproterenol to purified $\beta$2AR365 induces a decrease in fluorescence intensity and a shift in $\lambda$max for the attached bimane probe (FIG. 22B and Table 7). These changes in intensity and $\lambda$max are consistent with an agonist-induced increase in polarity around bimane. A smaller change is observed with the partial agonist salbutamol, while the inverse agonist ICI-118,551 had little effect. For the $\beta$2AR-T4L, there are subtle differences in the baseline spectrum of the bimane-labeled fusion protein, as might be expected if the environment around $Cys265^{6.27}$ is altered by T4L. However, the full agonist isoproterenol induces a qualitatively similar decrease in intensity and rightward shift in $\lambda$max. Thus the presence of the fused T4L does not prevent agonist-induced conformational changes. The partial agonist salbutamol induced larger responses in $\beta$2AR-T4L than were observed in wild-type $\beta$2AR, and there was a small increase in fluorescence in response to the inverse agonist ICI-118,551. These are properties observed in CAMs (Gether et al., J Biol Chem 272, 2587 (1997); Samama, et al., J Biol Chem 268, 4625 (1993)) and are consistent with the higher affinities for agonists and partial agonists exhibited by $\beta$2AR-T4L. Therefore, we conclude that the T4L fusion induces a partial constitutively active phenotype in the $\beta$2AR, likely caused by changes at the cytoplasmic ends of helices V and VI.

Comparison between $\beta_2$AR-T4L and $\beta_2$AR-Fab Structures

The $\beta_2$AR-T4L fusion strategy is validated by comparison of its structure to the structure of wild-type $\beta_2$AR complexed with a Fab that recognizes a three dimensional epitope consisting of the amino and carboxyl-terminal ends of ICL3, determined at an anisotropic resolution of 3.4 Å/3.7 Å (Rasmussen et al., *Nature*, 7168:355-6 (2007)). FIG. 23A illustrates the similarity between the fusion and antibody complex approaches to $\beta_2$AR crystallization, in that both strategies rely on attachment (covalent or non-covalent, respectively) of a soluble protein partner between helices V and VI. A major difference between the two structures is that the extracellular loops and the carazolol ligand could not be modeled in the $\beta_2$AR-Fab complex, whereas these regions are resolved in the structure of $\beta_2$AR-T4L. Nonetheless, it is clear that the T4L insertion does not significantly alter the receptor. Superposition of the two structures (FIG. 18) illustrates that the transmembrane helices of the receptor components are very similar (RMSD=0.8 Å for 154 common modeled transmembrane Cα positions, versus 2.3 Å between $\beta_2$AR-T4L and the 154 equivalent residues in rhodopsin), especially when the modest resolution of the Fab complex is taken into account.

There is one significant difference between the Fab-complex and chimeric receptor structures that can be attributed to the presence of T4L. The cytoplasmic end of helix VI is pulled outward as a result of the fusion to the carboxyl terminus of T4L, which alters the packing of Phe264$^{6.26}$ at the end of helix VI (FIG. 23B). In the Fab-complex $\beta_2$AR, interactions between Phe264$^{6.26}$ and residues in helix V, helix VI, and ICL2 may be important in maintaining the $\beta_2$AR in the basal state. The loss of these packing interactions in $\beta_2$AR-T4L could contribute to the higher agonist binding affinity characteristic of a CAM.

An unexpected difference between the structure of rhodopsin and the $\beta_2$AR-T4L involves the sequence E/DRY found at the cytoplasmic end of helix III in 71% of class A GPCRs. In rhodopsin, Glu134$^{3.49}$ and Arg135$^{3.50}$ form a network of hydrogen bond and ionic interactions with Glu247$^{6.30}$ at the cytoplasmic end of helix VI. These interactions have been referred to as an "ionic lock" that stabilizes the inactive state of rhodopsin and other class A members (Ballesteros et al., *J Biol Chem* 276, 29171 (2001)). However, the arrangement of the homologous residues is significantly different in $\beta_2$AR-T4L: Arg131$^{3.50}$ interacts primarily with Asp130$^{3.49}$ and a sulfate ion rather than with Glu268$^{6.30}$, and the distance between helix III and helix VI is greater than in rhodopsin (FIG. 23C). The fact that similar ionic lock structures were obtained using two different approaches suggests that a broken ionic lock is a genuine feature of the carazolol-bound state of the receptor.

Ligand Binding to the $\beta_2$AR

The $\beta_2$AR-T4L fusion protein was purified and crystallized in complex with the inverse agonist carazolol. Carazolol stabilizes the $\beta_2$AR against extremes of pH and temperature, perhaps related to its unusually high binding affinity ($K_d$<0.1 nM) and slow dissociation kinetics ($t_{1/2}$~30 h) (FIG. 19). The interactions between carazolol and $\beta_2$AR-T4L are depicted schematically in FIG. 24. The carbazole ring system is oriented roughly perpendicular to the plane of the membrane, and the alkylamine chain (atoms 15-22 in the model) is nearly parallel to the heterocycle (FIGS. 25A-B). As described in Example 3, above, carazolol was modeled into the electron density as the (S)-(−) isomer due to the higher affinity of this enantiomer, despite the fact that a racemic mixture of the ligand was used in crystallization. Asp113$^{3.32}$, Tyr316$^{7.43}$, and Asn312$^{7.39}$ present a constellation of polar functional groups to the alkylamine and alcohol moieties of the ligand, with Asp113$^{3.32}$ and Asn312$^{7.39}$ sidechains forming close contacts (<3 Å) with $O_{17}$ and $N_{19}$ atoms of carazolol (FIGS. 24 and 25A-B). Asp113$^{3.32}$ was one of the first $\beta_2$AR residues shown to be important for ligand binding; notably the D113N mutation causes complete loss of detectable affinity for antagonists (Strader et al., *Proc Natl Acad Sci USA* 84, 4384 (1987)) and a decrease in the potency of agonists towards cell-based G protein activation by over 4 orders of magnitude (Strader et al., *J Biol Chem* 263, 10267 (1988)). Likewise, mutations of Asn312$^{7.39}$ perturb $\beta_2$AR binding to agonists and antagonists: changes to nonpolar amino acids (Ala or Phe) reduce affinities to undetectable levels, while retention of a polar functionality (Thr or Gln) gives partial affinity (Suryanarayana, et al., *Mol Pharmacol* 44, 111 (1993)). On the opposite end of the ligand near helix V, $N_7$ of the carbazole heterocycle forms a hydrogen bond with the side chain hydroxyl of Ser203$^{5.42}$. Interestingly, mutations of Ser203$^{5.42}$ specifically decrease $\beta_2$AR affinity towards catecholamine agonists and aryloxyalkylamine ligands with nitrogen-containing heterocycles such as pindolol (Liapakis et al., *J Biol Chem* 275, 37779 (2000)), and by implication carazolol. Thus, the polar interactions between carazolol and the receptor observed in the crystal structure agree with the known biochemical data. The contribution of Tyr316$^{7.43}$ to antagonist and agonist affinity remains to be tested; this residue is conserved as tyrosine in all sequenced adrenergic receptor genes (Horn et al., *Nucleic Acids Res* 31, 294 (2003)).

FIG. 25C shows the tight packing between carazolol and surrounding amino acids that buries 790 Å$^2$ of surface area from solvent; specific contacts are depicted schematically in FIG. 24. Notable among the hydrophobic residues contacting carazolol are Val114$^{3.33}$, Phe290$^{6.52}$, and Phe193$^{5.32}$. The side chain of Val114$^{3.33}$ from helix III makes multiple contacts with the $C_8$—$C_{13}$ ring of the carbazole heterocycle, and Phe290$^{6.52}$ from helix VI forms an edge-to-face aromatic interaction with the same ring. As a result, these two amino acids form a hydrophobic "sandwich" with the portion of the aryl moiety that is common to many adrenergic antagonists. Mutation of Val114$^{3.33}$ to alanine was shown to decrease $\beta_2$AR affinity towards the antagonist alprenolol by an order of magnitude, as well as lowering affinity for the agonist epinephrine 300-fold (P. Chelikani et al., *Proc Natl Acad Sci USA* 104, 7027 (2007)). Phe193$^{5.32}$ is different from other carazolol contact residues in that it is located on the ECL2, in the path of hormone accessibility to the binding pocket. This amino acid contributes more buried surface area than any other residue to the interface between $\beta_2$AR-T4L and carazolol (see Table 8). Therefore, Phe193$^{5.32}$ is likely to contribute significantly to the energy of $\beta_2$AR-carazolol complex formation, and the position of this residue on the extracellular side of the binding site may allow it to act as a gate that contributes to the unusually slow dissociation of the ligand (FIG. 19).

TABLE 8

| $\beta_2$AR residue | Surface area buried (Å$^2$) |
|---|---|
| Trp109$^{3.28}$ | 21.4 |
| Thr110$^{3.29}$ | 5.7 |
| Asp113$^{3.32}$ | 19.3 |
| Val114$^{3.33}$ | 25.5 |
| Val117$^{3.36}$ | 8.5 |
| Thr118$^{3.37}$ | 1.9 |
| Phe193$^{5.32}$ | 51.2 |
| Thr195$^{5.34}$ | 7.4 |
| Tyr199$^{5.38}$ | 7.6 |
| Ala200$^{5.39}$ | 10.0 |
| Ser203$^{5.42}$ | 9.0 |
| Ser204$^{5.43}$ | 4.6 |
| Ser207$^{5.46}$ | 6.3 |
| Trp286$^{6.48}$ | 3.1 |
| Phe289$^{6.51}$ | 20.0 |

TABLE 8-continued

| $\beta_2$AR residue | Surface area buried (Å$^2$) |
|---|---|
| Phe290$^{6.52}$ | 19.0 |
| Phe293$^{6.55}$ | 18.7 |
| Tyr308$^{7.35}$ | 14.4 |
| Asn312$^{7.39}$ | 22.5 |
| Tyr316$^{7.43}$ | 6.5 |

Buried surface area contributions at the $\beta_2$AR-T4L/carazolol interface. Solvent accessible surface area calculations were done with the CNS software package (Brunger et al., Acta Crystallogr D Biol Crystallogr 54, 905 (1998)), using a probe radius of 1.4 Å. Buried surface area contributions of individual residues were determined by calculating solvent-accessible surface area per residue for the full $\beta_2$ART4L/carazolol model, and subtracting these numbers from the calculated values for the receptor model without carazolol.

Analysis of the binding pocket provides insights into the structural basis for pharmacologic selectivity between the $\beta_2$AR and closely related adrenergic receptors such as the $\beta_1$AR. The affinities of these two receptors for certain ligands, such as ICI-118,551, betaxolol and RO363 (Sugimoto et al., J Pharmacol Exp Ther 301, 51 (2002)), differ by up to 100-fold. Curiously, all of the amino acids in the carazolol binding pocket are conserved between the $\beta_1$AR and $\beta_2$AR (see FIG. 20). The majority of the 94 amino acid differences between the $\beta_1$AR and $\beta_2$AR are found in the cytoplasmic and extracellular loops. While residues that differ in the transmembrane segments generally face the lipid bilayer, eight residues lie at the interface between helices and may influence helix packing. The structural basis for pharmacologic differences between $\beta_1$AR and $\beta_2$AR must, therefore, arise from amino acid differences in the entrance to the binding pocket or subtle differences in the packing of helices. Evidence for the latter comes from chimeric receptor studies (Frielle, et al., Proc Natl Acad Sci USA 85, 9494 (1988)) in which successive exchange of helices between $\beta_1$AR and $\beta_2$ARs led to a gradual change in affinity for the $\beta_2$AR selective ICI-118,551 and the $\beta_1$AR selective betaxolol.

As discussed above, $\beta_2$AR-T4L shows CAM-like properties with respect to agonist binding affinities, suggesting that the unliganded $\beta_2$AR-T4L may exist in a more active conformation than the wild type-$\beta_2$AR. Nevertheless, as shown in FIG. 22B, $\beta_2$AR-T4L can be stabilized in an inactive conformation by an inverse agonist. Since $\beta_2$AR-T4L was crystallized with bound carazolol, a partial inverse agonist, the structure most likely represents an inactive state. This is consistent with the similarity of the $\beta_2$AR-T4L and $\beta_2$AR-Fab5 carazolol-bound structures. To assess whether conformational changes are required to accommodate catecholamines, a model of isoproterenol was placed in the binding site such that common atoms (16-22 in FIG. 24) were superimposed onto the analogous carazolol coordinates in the crystal structure (FIG. 25D). Residues Ser204$^{5.43}$ and Ser207$^{5.46}$ are critical for catecholamine binding and activation of the $\beta_2$AR, with Ser204$^{5.43}$ hydrogen bonding to the meta-hydroxyl and Ser207$^{5.46}$ to the para-hydroxyl of the catechol ring, respectively (Strader, et al., J Biol Chem 264, 13572 (1989)). In our model, the catechol hydroxyls of isoproterenol face the appropriate serines on helix V, but the distances are too long for hydrogen bonding (6.8 Å from meta-hydroxyl oxygen to the sidechain oxygen of Ser204$^{5.43}$, 4.8 Å from the para-hydroxyl oxygen to the sidechain oxygen of Ser207$^{5.46}$). In addition, Asn293$^{6.55}$ and Tyr308$^{7.35}$, two residues expected to form selective interactions with agonists based on the literature (Wieland, et al., Proc Natl Acad Sci USA 93, 9276 (1996); Kikkawa, et al., Mol Pharmacol 53, 128 (1998)), are too distant to form productive polar or hydrophobic contacts with the modeled isoproterenol molecule. These observations suggest that agonist binding requires changes in the binding site relative to the carazolol-bound structure, unless common structural components of agonists and inverse agonists bind in a significantly different manner.

Structural Insights into $\beta_2$AR Activation

Analysis of mutations that affect $\beta_2$AR function provides insights into structural rearrangements that are likely to occur during receptor activation. FIG. 26A illustrates the location of amino acids for which mutations lead to elevated basal, agonist-independent activity (constitutively active mutations, CAMs), as well as amino acids for which mutations impair agonist activation (uncoupling mutations, UCMs). Residues for which CAMs have been described are likely to be involved in interactions that maintain the receptor in the inactive conformation. These amino acids are centrally located on helices III and VI. In contrast, positions in which UCMs have been observed are likely to form intramolecular interactions that stabilize the active state. A cluster of UCMs are found at the cytoplasmic end of helix VII. Neither CAMs nor UCMs are directly involved in agonist binding. Although the CAMs and UCMs are not directly connected in sequence, it is evident from the structure that they are linked through packing interactions, such that movements in one will likely affect the packing of others. For example, FIG. 26A (right panel) shows all amino acids with atoms within 4 Å of the two centrally located CAMs, Leu124$^{3.43}$ (Tao, et al., Mol Endocrinol 14, 1272 (2000)) and Leu272$^{6.34}$ (Jensen et al., J Biol Chem 276, 9279 (2001)). Several amino acids that pack against these CAMs also interact with one or more UCMs. Trp286$^{6.48}$ lies at the base of the binding pocket. It has been proposed that agonist binding leads to a change in the rotameric state of Trp286$^{6.48}$ with subsequent changes in the angle of the helical kink formed by Pro288$^{6.50}$ (Shi et al., J Biol Chem 277, 40989 (2002)). It is likely that an agonist-induced change in the rotameric state of Trp286$^{6.48}$ will be linked to changes in sidechains of CAMs and UCMs through packing interactions and propagated to the cytoplasmic ends of the helices and the associated intracellular loops that interact with G proteins and other signaling molecules.

In the structures of both rhodopsin and the $\beta_2$AR, a cluster of water molecules lies near the most highly conserved class A GPCR residues (FIG. 26B). It has been proposed that these water molecules may play a role in the structural changes involved in receptor activation (Pardo, et al., Chembiochem 8, 19 (2007)). FIG. 26C shows the network of potential hydrogen bonding interactions that link Trp286$^{6.48}$ with conserved amino acids extending to the cytoplasmic ends of helices. UCMs have been identified for three amino acids linked by this network—N322$^{7.49}$, P323$^{7.50}$, and Y326$^{7.53}$ (Barak et al., Biochemistry 34, 15407 (1995)). This relatively loose-packed, water filled region is likely to be important in allowing conformational transitions, as there will be fewer steric restraints to sidechain repacking.

All references, issued patents and patent applications cited within the body of the instant specification are hereby incorporated by reference in their entirety, for all purposes.

APPENDIX 1

| HEADER | MEMBRANE PROTEIN/HYDROLASE | 05-OCT-07 | 2RH1 |
|---|---|---|---|
| TITLE | HIGH RESOLUTION CRYSTAL STRUCTURE OF HUMAN B2-ADRENERGIC G | | |
| TITLE | 2 PROTEIN-COUPLED RECEPTOR | | |

APPENDIX 1-continued

```
COMPND        MOL_ID: 1;
COMPND      2 MOLECULE: BETA-2-ADRENERGIC RECEPTOR/T4-LYSOZYME CHIMERA;
COMPND      3 CHAIN: A;
COMPND      4 SYNONYM: BETA-2 ADRENERGIC RECEPTOR, BETA-2 ADRENOCEPTOR,
COMPND      5 BETA-2 ADRENORECEPTOR/LYSIS PROTEIN, MURAMIDASE,
COMPND      6 ENDOLYSIN;
COMPND      7 ENGINEERED: YES;
COMPND      8 MUTATION: YES
SOURCE        MOL_ID: 1;
SOURCE      2 ORGANISM_SCIENTIFIC: *HOMO SAPIENS*, ENTEROBACTERIA PHAGE T4;
SOURCE      3 ORGANISM_COMMON: HUMAN,;
SOURCE      4 STRAIN: ,;
SOURCE      5 GENE: ADRB2, ADRB2R, B2AR/E;
SOURCE      6 EXPRESSION_SYSTEM: *SPODOPTERA FRUGIPERDA;*
SOURCE      7 EXPRESSION_SYSTEM_COMMON: FALL ARMYWORM;
SOURCE      8 EXPRESSION_SYSTEM_VECTOR_TYPE: PLASMID;
SOURCE      9 EXPRESSION_SYSTEM_PLASMID: PFASTBAC1;
SOURCE     10 OTHER_DETAILS: THE CONSTRUCT HAS BEEN OBTAINED BY
SOURCE     11 OVERLAPPING EXTENSION PCR
KEYWDS        GPCR, 7TM, ADRENERGIC, FUSION, LIPIDIC CUBIC PHASE, LIPIDIC,
KEYWDS      2 MESOPHASE, CHOLESTEROL, MEMBRANE PROTEIN, MEMBRANE
KEYWDS      3 PROTEIN/HYDROLASE COMPLEX
EXPDTA     X-RAY DIFFRACTION
AUTHOR        V. CHEREZOV, D. M. ROSENBAUM, M. A. HANSON, S. G. F. RASMUSSEN,
AUTHOR      2 F. S. THIAN, T. S. KOBILKA, H. J. CHOI, P. KUHN, W. I. WEIS, B. K. KOBILKA,
AUTHOR      3 R. C. STEVENS
REVDAT      5 07-OCT-08    2RH1 1    REMARK
REVDAT      4 11-DEC-07    2RH1 1    REMARK
REVDAT      3 04-DEC-07    2RH1 1    JRNL
REVDAT      2 06-NOV-07    2RH1 1    JRNL HELIX SHEET
REVDAT      1 30-OCT-07    2RH1 0
JRNL          AUTH     V. CHEREZOV, D. M. ROSENBAUM, M. A. HANSON, S. G. RASMUSSEN,
JRNL          AUTH 2   F. S. THIAN, T. S. KOBILKA, H. J. CHOI, P. KUHN, W. I. WEIS,
JRNL          AUTH 3   B. K. KOBILKA, R. C. STEVENS
JRNL          TITL     HIGH-RESOLUTION CRYSTAL STRUCTURE OF AN ENGINEERED
JRNL          TITL 2   HUMAN BETA2-ADRENERGIC G PROTEIN-COUPLED RECEPTOR.
JRNL          REF      SCIENCE        V. 318 1258 2007
JRNL          REFN     ASTM SCIEAS    US ISSN 0036-8075
REMARK        1
REMARK      1 REFERENCE 1
REMARK      1 AUTH     D. M. ROSENBAUM, V. CHEREZOV, M. A. HANSON,
REMARK      1 AUTH 2   S. G. F. RASMUSSEN, F. S. THIAN, T. S. KOBILKA, H. J. CHOI,
REMARK      1 AUTH 3   X. J. YAO, W. I. WEIS, R. C. STEVENS, B. K. KOBILKA
REMARK      1 TITL     GPCR ENGINEERING YIELDS HIGH-RESOLUTION STRUCTURAL
REMARK      1 TITL 2   INSIGHTS INTO BETA2 ADRENERGIC RECEPTOR FUNCTION.
REMARK      1 REF      TO BE PUBLISHED
REMARK      1 REFN
REMARK        2
REMARK      2 RESOLUTION. 2.40 ANGSTROMS.
REMARK        3
REMARK      3 REFINEMENT.
REMARK      3 PROGRAM: REFMAC 5.2.0019
REMARK      3 AUTHORS: MURSHUDOV, VAGIN, DODSON
REMARK        3
REMARK      3 REFINEMENT TARGET: MAXIMUM LIKELIHOOD
REMARK        3
REMARK      3 DATA USED IN REFINEMENT.
REMARK      3 RESOLUTION RANGE HIGH (ANGSTROMS):         2.40
REMARK      3 RESOLUTION RANGE LOW  (ANGSTROMS):        19.95
REMARK      3 DATA CUTOFF            (SIGMA(F)):          0.000
REMARK      3 COMPLETENESS FOR RANGE        (%):         99.8
REMARK      3 NUMBER OF REFLECTIONS:                    26506
REMARK        3
REMARK      3 FIT TO DATA USED IN REFINEMENT.
REMARK      3 CROSS-VALIDATION METHOD:          THROUGHOUT
REMARK      3 FREE R VALUE TEST SET SELECTION:  RANDOM
REMARK      3 R VALUE   (WORKING + TEST SET):    0.198
REMARK      3 R VALUE            (WORKING SET):  0.196
REMARK      3 FREE R VALUE:                      0.232
REMARK      3 FREE R VALUE TEST SET SIZE   (%):  4.900
REMARK      3 FREE R VALUE TEST SET COUNT:      1310
REMARK        3
REMARK      3 FIT IN THE HIGHEST RESOLUTION BIN.
REMARK      3 TOTAL NUMBER OF BINS USED:                  20
REMARK      3 BIN RESOLUTION RANGE HIGH:                2.40
REMARK      3 BIN RESOLUTION RANGE LOW:                 2.46
REMARK      3 REFLECTION IN BIN  (WORKING SET):         1829
REMARK      3 BIN COMPLETENESS (WORKING + TEST) (%):   98.76
REMARK      3 BIN R VALUE        (WORKING SET):        0.2700
REMARK      3 BIN FREE R VALUE SET COUNT:                 78
```

APPENDIX 1-continued

| | | | | |
|---|---|---|---|---|
| REMARK | 3 BIN FREE R VALUE: | 0.3010 | | |
| REMARK | 3 | | | |
| REMARK | 3 NUMBER OF NON-HYDROGEN ATOMS USED IN REFINEMENT. | | | |
| REMARK | 3 ALL ATOMS: 3804 | | | |
| REMARK | 3 | | | |
| REMARK | 3 B VALUES. | | | |
| REMARK | 3 FROM WILSON PLOT (A**2): | 63.91 | | |
| REMARK | 3 MEAN B VALUE (OVERALL, A**2): 63.91 | | | |
| REMARK | 3 OVERALL ANISOTROPIC B VALUE. | | | |
| REMARK | 3 B11 (A**2): 0.43000 | | | |
| REMARK | 3 B22 (A**2): −3.46000 | | | |
| REMARK | 3 B33 (A**2): 4.25000 | | | |
| REMARK | 3 B12 (A**2): 0.00000 | | | |
| REMARK | 3 B13 (A**2): 2.26000 | | | |
| REMARK | 3 B23 (A**2): 0.00000 | | | |
| REMARK | 3 | | | |
| REMARK | 3 ESTIMATED OVERALL COORDINATE ERROR. | | | |
| REMARK | 3 ESU BASED ON R VALUE (A): | | 0.295 | |
| REMARK | 3 ESU BASED ON FREE R VALUE (A): | | 0.220 | |
| REMARK | 3 ESU BASED ON MAXIMUM LIKELIHOOD (A): | | 0.203 | |
| REMARK | 3 ESU FOR B VALUES BASED ON MAXIMUM LIKELIHOOD (A**2): 18.501 | | | |
| REMARK | 3 | | | |
| REMARK | 3 CORRELATION COEFFICIENTS. | | | |
| REMARK | 3 CORRELATION COEFFICIENT FO-FC: | 0.963 | | |
| REMARK | 3 CORRELATION COEFFICIENT FO-FC FREE: | 0.944 | | |
| REMARK | 3 | | | |
| REMARK | 3 RMS DEVIATIONS FROM IDEAL VALUES | COUNT | RMS | WEIGHT |
| REMARK | 3 BOND LENGTHS REFINED ATOMS (A): | 3843; | 0.013; | 0.022 |
| REMARK | 3 BOND LENGTHS OTHERS (A): | 2622; | 0.000; | 0.020 |
| REMARK | 3 BOND ANGLES REFINED ATOMS (DEGREES): | 5219; | 1.500; | 2.000 |
| REMARK | 3 BOND ANGLES OTHERS (DEGREES): | 6377; | 4.099; | 3.002 |
| REMARK | 3 TORSION ANGLES, PERIOD 1 (DEGREES): | 441; | 3.876; | 5.000 |
| REMARK | 3 TORSION ANGLES, PERIOD 2 (DEGREES): | 154; | 31.604; | 23.182 |
| REMARK | 3 TORSION ANGLES, PERIOD 3 (DEGREES): | 627; | 11.383; | 15.000 |
| REMARK | 3 TORSION ANGLES, PERIOD 4 (DEGREES): | 22; | 12.164; | 15.000 |
| REMARK | 3 CHIRAL-CENTER RESTRAINTS (A**3): | 610; | 0.060; | 0.200 |
| REMARK | 3 GENERAL PLANES REFINED ATOMS (A): | 4008; | 0.001; | 0.020 |
| REMARK | 3 GENERAL PLANES OTHERS (A): | 804; | 0.001; | 0.020 |
| REMARK | 3 NON-BONDED CONTACTS REFINED ATOMS (A): | 926; | 0.187; | 0.300 |
| REMARK | 3 NON-BONDED CONTACTS OTHERS (A): | 2443; | 0.194; | 0.300 |
| REMARK | 3 NON-BONDED TORSION REFINED ATOMS (A): | 1935; | 0.180; | 0.500 |
| REMARK | 3 NON-BONDED TORSION OTHERS (A): | 1580; | 0.107; | 0.500 |
| REMARK | 3 H-BOND (X . . . Y) REFINED ATOMS (A): | 194; | 0.164; | 0.500 |
| REMARK | 3 H-BOND (X . . . Y) OTHERS (A): | NULL; | NULL; | NULL |
| REMARK | 3 POTENTIAL METAL-ION REFINED ATOMS (A): | NULL; | NULL; | NULL |
| REMARK | 3 POTENTIAL METAL-ION OTHERS (A): | NULL; | NULL; | NULL |
| REMARK | 3 SYMMETRY VDW REFINED ATOMS (A): | 7; | 0.155; | 0.300 |
| REMARK | 3 SYMMETRY VDW OTHERS (A): | 29; | 0.140; | 0.300 |
| REMARK | 3 SYMMETRY H-BOND REFINED ATOMS (A): | 6; | 0.192; | 0.500 |
| REMARK | 3 SYMMETRY H-BOND OTHERS (A): | NULL; | NULL; | NULL |
| REMARK | 3 SYMMETRY METAL-ION REFINED ATOMS (A): | NULL; | NULL; | NULL |
| REMARK | 3 SYMMETRY METAL-ION OTHERS (A): | NULL; | NULL; | NULL |
| REMARK | 3 | | | |
| REMARK | 3 ISOTROPIC THERMAL FACTOR RESTRAINTS. | COUNT | RMS | WEIGHT |
| REMARK | 3 MAIN-CHAIN BOND REFINED ATOMS (A**2): | 2884; | 2.352; | 2.000 |
| REMARK | 3 MAIN-CHAIN BOND OTHER ATOMS (A**2): | 896; | 0.097; | 2.000 |
| REMARK | 3 MAIN-CHAIN ANGLE REFINED ATOMS (A**2): | 3571; | 2.767; | 2.500 |
| REMARK | 3 SIDE-CHAIN BOND REFINED ATOMS (A**2): | 1974; | 4.582; | 2.000 |
| REMARK | 3 SIDE-CHAIN ANGLE REFINED ATOMS (A**2): | 1648; | 5.849; | 2.500 |
| REMARK | 3 | | | |
| REMARK | 3 ANISOTROPIC THERMAL FACTOR RESTRAINTS. | COUNT | RMS | WEIGHT |
| REMARK | 3 RIGID-BOND RESTRAINTS (A**2): | NULL; | NULL; | NULL |
| REMARK | 3 SPHERICITY; FREE ATOMS (A**2): | NULL; | NULL; | NULL |
| REMARK | 3 SPHERICITY; BONDED ATOMS (A**2): | NULL; | NULL; | NULL |
| REMARK | 3 | | | |
| REMARK | 3 NCS RESTRAINTS STATISTICS | | | |
| REMARK | 3 NUMBER OF DIFFERENT NCS GROUPS: NULL | | | |
| REMARK | 3 | | | |
| REMARK | 3 TLS DETAILS | | | |
| REMARK | 3 NUMBER OF TLS GROUPS: 3 | | | |
| REMARK | 3 | | | |
| REMARK | 3 TLS GROUP: 1 | | | |
| REMARK | 3 NUMBER OF COMPONENTS GROUP: 2 | | | |
| REMARK | 3 COMPONENTS      C    SSSEQI TO   C    SSSEQI | | | |
| REMARK | 3 RESIDUE RANGE:   A    1002       A    1011 | | | |
| REMARK | 3 RESIDUE RANGE:   A    1062       A    1161 | | | |
| REMARK | 3 ORIGIN FOR THE GROUP (A): −23.6840   58.4050   30.4850 | | | |
| REMARK | 3 T TENSOR | | | |
| REMARK | 3 T11: −0.2208   T22: −0.2598 | | | |
| REMARK | 3 T33: −0.7033   T12:  0.0432 | | | |

APPENDIX 1-continued

```
REMARK    3 T13:  -0.0594  T23:  -0.0241
REMARK    3 L TENSOR
REMARK    3 L11:   3.1220  L22:   2.6914
REMARK    3 L33:   5.9787  L12:   0.8643
REMARK    3 L13:   0.6146  L23:  -0.8632
REMARK    3 S TENSOR
REMARK    3 S11:  -0.1453  S12:  -0.2225  S13:   0.2116
REMARK    3 S21:   0.0984  S22:  -0.0656  S23:  -0.0133
REMARK    3 S31:  -0.1849  S32:  -0.1761  S33:   0.2109
REMARK    3
REMARK    3 TLS GROUP: 2
REMARK    3 NUMBER OF COMPONENTS GROUP: 1
REMARK    3 COMPONENTS      C   SSSEQI TO   C    SSSEQI
REMARK    3 RESIDUE RANGE:  A    1012        A    1061
REMARK    3 ORIGIN FOR THE GROUP (A): -35.0580   69.0010   11.9610
REMARK    3 T TENSOR
REMARK    3 T11:   0.0414  T22:  -0.0871
REMARK    3 T33:  -0.4908  T12:   0.0577
REMARK    3 T13:  -0.1559  T23:  -0.0085
REMARK    3 L TENSOR
REMARK    3 L11:   9.6406  L22:  16.6501
REMARK    3 L33:   7.1133  L12:  -6.5961
REMARK    3 L13:  -0.9803  L23:   3.2882
REMARK    3 S TENSOR
REMARK    3 S11:  -0.1628  S12:  -0.1008  S13:   0.4114
REMARK    3 S21:  -0.7585  S22:  -0.1058  S23:   0.7355
REMARK    3 S31:  -0.6590  S32:  -0.6073  S33:   0.2686
REMARK    3
REMARK    3 TLS GROUP: 3
REMARK    3 NUMBER OF COMPONENTS GROUP: 2
REMARK    3 COMPONENTS       C   SSSEQI TO   C    SSSEQI
REMARK    3 RESIDUE RANGE:   A    29         A    230
REMARK    3 RESIDUE RANGE:   A    263        A    342
REMARK    3 ORIGIN FOR THE GROUP (A): -33.0740   20.0130    7.1220
REMARK    3 T TENSOR
REMARK    3 T11:  -0.0103  T22:  -0.2341
REMARK    3 T33:  -0.5401  T12:  -0.0025
REMARK    3 T13:  -0.0974  T23:  -0.0034
REMARK    3 L TENSOR
REMARK    3 L11:   2.3670  L22:   6.1551
REMARK    3 L33:   1.9314  L12:   2.1068
REMARK    3 L13:   0.8591  L23:   0.7864
REMARK    3 S TENSOR
REMARK    3 S11:  -0.0346  S12:   0.0267  S13:  -0.2068
REMARK    3 S21:  -0.5009  S22:   0.0712  S23:   0.2388
REMARK    3 S31:   0.3208  S32:   0.0002  S33:  -0.0366
REMARK    3
REMARK    3 BULK SOLVENT MODELLING.
REMARK    3 METHOD USED: MASK
REMARK    3 PARAMETERS FOR MASK CALCULATION
REMARK    3 VDW PROBE RADIUS:        1.40
REMARK    3 ION PROBE RADIUS:        0.80
REMARK    3 SHRINKAGE RADIUS:        0.80
REMARK    3
REMARK    3 OTHER REFINEMENT REMARKS: HYDROGENS HAVE BEEN ADDED IN THE
REMARK    3 RIDING POSITIONS. WATER #548 HAS STRONG DIFFERENCE DENSITY BUT
REMARK    3 WEAK 2FO-FC DENSITY.
REMARK    4
REMARK    4 2RH1 COMPLIES WITH FORMAT V. 3.1, 01-AUG-2007
REMARK  100
REMARK  100 THIS ENTRY HAS BEEN PROCESSED BY RCSB.
REMARK  100 THE RCSB ID CODE IS RCSB044849.
REMARK  200
REMARK  200 EXPERIMENTAL DETAILS
REMARK  200 EXPERIMENT TYPE:                  X-RAY DIFFRACTION
REMARK  200 DATE OF DATA COLLECTION:          22-JUN-2007; 18-JUL-2007
REMARK  200 TEMPERATURE (KELVIN):             78; 78
REMARK  200 PH:                               6.75
REMARK  200 NUMBER OF CRYSTALS USED:          27
REMARK  200
REMARK  200 SYNCHROTRON (Y/N):                Y; Y
REMARK  200 RADIATION SOURCE:                 APS; APS
REMARK  200 BEAMLINE:                         23-ID-B; 23-ID-B
REMARK  200 X-RAY GENERATOR MODEL:            NULL
REMARK  200 MONOCHROMATIC OR LAUE (M/L):      M
REMARK  200 WAVELENGTH OR RANGE (A):          1.03321; 1.03321
REMARK  200 MONOCHROMATOR:                    DOUBLE CRYSTAL
REMARK  200 OPTICS:                           MIRRORS; MIRRORS
REMARK  200
REMARK  200 DETECTOR TYPE:                    CCD; CCD
```

APPENDIX 1-continued

```
REMARK   200 DETECTOR MANUFACTURER:          MARMOSAIC 300 MM CCD;
REMARK   200                                 MARMOSAIC 300 MM CCD
REMARK   200 INTENSITY-INTEGRATION SOFTWARE: XDS
REMARK   200 DATA SCALING SOFTWARE:          XDS
REMARK   200
REMARK   200 NUMBER OF UNIQUE REFLECTIONS:    26506
REMARK   200 RESOLUTION RANGE HIGH (A):        2.400
REMARK   200 RESOLUTION RANGE LOW  (A):       20.000
REMARK   200 REJECTION CRITERIA (SIGMA(I)):   -3.000
REMARK   200
REMARK   200 OVERALL.
REMARK   200 COMPLETENESS FOR RANGE (%):     99.2
REMARK   200 DATA REDUNDANCY:                NULL
REMARK   200 R MERGE (I):                     0.12700
REMARK   200 R SYM (I):                      NULL
REMARK   200 <I/SIGMA(I)> FOR THE DATA SET:   9.6200
REMARK   200
REMARK   200 IN THE HIGHEST RESOLUTION SHELL.
REMARK   200 HIGHEST RESOLUTION SHELL, RANGE HIGH (A):   2.40
REMARK   200 HIGHEST RESOLUTION SHELL, RANGE LOW  (A):   2.50
REMARK   200 COMPLETENESS FOR SHELL (%):                99.1
REMARK   200 DATA REDUNDANCY IN SHELL:                  NULL
REMARK   200 R MERGE FOR SHELL (I):                      0.67800
REMARK   200 R SYM FOR SHELL (I):                       NULL
REMARK   200 <I/SIGMA(I)> FOR SHELL:                     2.200
REMARK   200
REMARK   200 DIFFRACTION PROTOCOL: SINGLE WAVELENGTH
REMARK   200 METHOD USED TO DETERMINE THE STRUCTURE: MOLECULAR REPLACEMENT
REMARK   200 SOFTWARE USED: PHASER
REMARK   200 STARTING MODEL: PDB ENTRIES 1U19, 2LZM
REMARK   200
REMARK   200 REMARK: THIS STRUCTURE IS A PART OF THE ROADMAP/PSI COMMUNITY
REMARK   200 OUTREACH PROGRAM, NOT A SPECIFIC PSI TARGET.
REMARK   280
REMARK   280 CRYSTAL
REMARK   280 SOLVENT CONTENT, VS (%):                   59.98
REMARK   280 MATTHEWS COEFFICIENT, VM (ANGSTROMS-3/DA):  3.07
REMARK   280
REMARK   280 CRYSTALLIZATION CONDITIONS: 30-35% V/V PEG 400, 0.1-0.2M
REMARK   280 NA2SO4, 0.1M BIS-TRIS PROPANE PH 6.5-7.0, 5-7% 1,4-
REMARK   280 BUTANEDIOL, 8-10% CHOLESTEROL, 52-50% MONOOLEIN, PH 6.75,
REMARK   280 LIPIDIC MESOPHASE, TEMPERATURE 293 K
REMARK   290
REMARK   290 CRYSTALLOGRAPHIC SYMMETRY
REMARK   290 SYMMETRY OPERATORS FOR SPACE GROUP:      C 1 2 1
REMARK   290
REMARK   290 SYMOP       SYMMETRY
REMARK   290 NNNMMM      OPERATOR
REMARK   290 1555        X, Y, Z
REMARK   290 2555        -X, Y, -Z
REMARK   290 3555        1/2 + X, 1/2 + Y, Z
REMARK   290 4555        1/2 - X, 1/2 + Y, -Z
REMARK   290
REMARK   290 WHERE NNN -> OPERATOR NUMBER
REMARK   290 MMM -> TRANSLATION VECTOR
REMARK   290
REMARK   290 CRYSTALLOGRAPHIC SYMMETRY TRANSFORMATIONS
REMARK   290 THE FOLLOWING TRANSFORMATIONS OPERATE ON THE ATOM/HETATM
REMARK   290 RECORDS IN THIS ENTRY TO PRODUCE CRYSTALLOGRAPHICALLY
REMARK   290 RELATED MOLECULES.
REMARK   290 SMTRY1    1     1.000000   0.000000   0.000000    0.00000
REMARK   290 SMTRY2    1     0.000000   1.000000   0.000000    0.00000
REMARK   290 SMTRY3    1     0.000000   0.000000   1.000000    0.00000
REMARK   290 SMTRY1    2    -1.000000   0.000000   0.000000    0.00000
REMARK   290 SMTRY2    2     0.000000   1.000000   0.000000    0.00000
REMARK   290 SMTRY3    2     0.000000   0.000000  -1.000000    0.00000
REMARK   290 SMTRY1    3     1.000000   0.000000   0.000000   53.15900
REMARK   290 SMTRY2    3     0.000000   1.000000   0.000000   84.62000
REMARK   290 SMTRY3    3     0.000000   0.000000   1.000000    0.00000
REMARK   290 SMTRY1    4    -1.000000   0.000000   0.000000   53.15900
REMARK   290 SMTRY2    4     0.000000   1.000000   0.000000   84.62000
REMARK   290 SMTRY3    4     0.000000   0.000000  -1.000000    0.00000
REMARK   290
REMARK   290 REMARK: NULL
REMARK   300
REMARK   300 BIOMOLECULE: 1
REMARK   300 SEE REMARK 350 FOR THE AUTHOR PROVIDED AND/OR PROGRAM
REMARK   300 GENERATED ASSEMBLY INFORMATION FOR THE STRUCTURE IN
REMARK   300 THIS ENTRY. THE REMARK MAY ALSO PROVIDE INFORMATION ON
REMARK   300 BURIED SURFACE AREA.
```

APPENDIX 1-continued

```
REMARK   300
REMARK   300 REMARK: AUTHORS STATE THAT THE BIOLOGICAL UNIT IS UNKNOWN
REMARK   350
REMARK   350 COORDINATES FOR A COMPLETE MULTIMER REPRESENTING THE KNOWN
REMARK   350 BIOLOGICALLY SIGNIFICANT OLIGOMERIZATION STATE OF THE
REMARK   350 MOLECULE CAN BE GENERATED BY APPLYING BIOMT TRANSFORMATIONS
REMARK   350 GIVEN BELOW. BOTH NON-CRYSTALLOGRAPHIC AND
REMARK   350 CRYSTALLOGRAPHIC OPERATIONS ARE GIVEN.
REMARK   350
REMARK   350 BIOMOLECULE: 1
REMARK   350 SOFTWARE DETERMINED QUATERNARY STRUCTURE: MONOMERIC
REMARK   350 SOFTWARE USED: PISA
REMARK   350 APPLY THE FOLLOWING TO CHAINS: A
REMARK   350 BIOMT1   1   1.000000   0.000000   0.000000   0.00000
REMARK   350 BIOMT2   1   0.000000   1.000000   0.000000   0.00000
REMARK   350 BIOMT3   1   0.000000   0.000000   1.000000   0.00000
REMARK   375
REMARK   375 SPECIAL POSITION
REMARK   375 THE FOLLOWING ATOMS ARE FOUND TO BE WITHIN 0.15 ANGSTROMS
REMARK   375 OF A SYMMETRY RELATED ATOM AND ARE ASSUMED TO BE ON SPECIAL
REMARK   375 POSITIONS.
REMARK   375
REMARK   375 ATOM RES      CSSEQI
REMARK   375 HOH          A 520      LIES ON A SPECIAL POSITION.
REMARK   465
REMARK   465 MISSING RESIDUES
REMARK   465 THE FOLLOWING RESIDUES WERE NOT LOCATED IN THE
REMARK   465 EXPERIMENT. (M = MODEL NUMBER; RES = RESIDUE NAME; C = CHAIN
REMARK   465 IDENTIFIER; SSEQ = SEQUENCE NUMBER; I = INSERTION CODE.)
REMARK   465
REMARK   465   M RES    C    SSEQI
REMARK   465     ASP    A     -6
REMARK   465     TYR    A     -5
REMARK   465     LYS    A     -4
REMARK   465     ASP    A     -3
REMARK   465     ASP    A     -2
REMARK   465     ASP    A     -1
REMARK   465     ALA    A      0
REMARK   465     MET    A      1
REMARK   465     GLY    A      2
REMARK   465     GLN    A      3
REMARK   465     PRO    A      4
REMARK   465     GLY    A      5
REMARK   465     ASN    A      6
REMARK   465     GLY    A      7
REMARK   465     SER    A      8
REMARK   465     ALA    A      9
REMARK   465     PHE    A     10
REMARK   465     LEU    A     11
REMARK   465     LEU    A     12
REMARK   465     ALA    A     13
REMARK   465     PRO    A     14
REMARK   465     ASN    A     15
REMARK   465     ARG    A     16
REMARK   465     SER    A     17
REMARK   465     HIS    A     18
REMARK   465     ALA    A     19
REMARK   465     PRO    A     20
REMARK   465     ASP    A     21
REMARK   465     HIS    A     22
REMARK   465     ASP    A     23
REMARK   465     VAL    A     24
REMARK   465     THR    A     25
REMARK   465     GLN    A     26
REMARK   465     GLN    A     27
REMARK   465     ARG    A     28
REMARK   465     ARG    A    343
REMARK   465     ARG    A    344
REMARK   465     SER    A    345
REMARK   465     SER    A    346
REMARK   465     LEU    A    347
REMARK   465     LYS    A    348
REMARK   465     ALA    A    349
REMARK   465     TYR    A    350
REMARK   465     GLY    A    351
REMARK   465     ASN    A    352
REMARK   465     GLY    A    353
REMARK   465     TYR    A    354
REMARK   465     SER    A    355
REMARK   465     SER    A    356
```

APPENDIX 1-continued

```
REMARK   465   ASN   A   357
REMARK   465   GLY   A   358
REMARK   465   ASN   A   359
REMARK   465   THR   A   360
REMARK   465   GLY   A   361
REMARK   465   GLU   A   362
REMARK   465   GLN   A   363
REMARK   465   SER   A   364
REMARK   465   GLY   A   365
REMARK   470
REMARK   470 MISSING ATOM
REMARK   470 THE FOLLOWING RESIDUES HAVE MISSING ATOMS (M = MODEL NUMBER;
REMARK   470 RES = RESIDUE NAME; C = CHAIN IDENTIFIER; SSEQ = SEQUENCE NUMBER;
REMARK   470 I = INSERTION CODE):
REMARK   470 M    RES    CSSEQI         ATOMS
REMARK   470       ASP    A 29          CG OD1 OD2
REMARK   500
REMARK   500 GEOMETRY AND STEREOCHEMISTRY
REMARK   500 SUBTOPIC: CLOSE CONTACTS IN SAME ASYMMETRIC UNIT
REMARK   500
REMARK   500 THE FOLLOWING ATOMS ARE IN CLOSE CONTACT.
REMARK   500
REMARK   500 ATM1    RES    C    SSEQI    ATM2    RES    C    SSEQI
REMARK   500 SG      CYS    A    341      O2      PLM    A    415    1.88
REMARK   500
REMARK   500 REMARK: NULL
REMARK   500
REMARK   500 GEOMETRY AND STEREOCHEMISTRY
REMARK   500 SUBTOPIC: TORSION ANGLES
REMARK   500
REMARK   500 TORSION ANGLES OUTSIDE THE EXPECTED RAMACHANDRAN REGIONS:
REMARK   500 (M = MODEL NUMBER; RES = RESIDUE NAME; C = CHAIN IDENTIFIER;
REMARK   500 SSEQ = SEQUENCE NUMBER; I = INSERTION CODE).
REMARK   500
REMARK   500 STANDARD TABLE:
REMARK   500 FORMAT: (10X, I3, 1X, A3, 1X, A1, I4, A1, 4X, F7.2, 3X, F7.2)
REMARK   500
REMARK   500 EXPECTED VALUES: GJ KLEYWEGT AND TA JONES (1996). PHI/PSI-
REMARK   500 CHOLOGY: RAMACHANDRAN REVISITED. STRUCTURE 4, 1395-1400
REMARK   500
REMARK   500 M    RES    CSSEQI     PSI       PHI
REMARK   500      VAL    A 86      −64.27    −100.05
REMARK   500      TYR    A 141     −22.19     73.12
REMARK   500
REMARK   500 REMARK: NULL
REMARK   600
REMARK   600 HETEROGEN
REMARK   600 THE PALMITIC ACID (PLM) AND ACETAMIDE (ACM) GROUPS ARE
REMARK   600 COVALENTLY LINKED TO THEIR RESPECTIVE CYSTEINE RESIDUES.
REMARK   610
REMARK   610 MISSING HETEROATOM
REMARK   610 THE FOLLOWING RESIDUES HAVE MISSING ATOMS (M = MODEL NUMBER;
REMARK   610 RES = RESIDUE NAME; C = CHAIN IDENTIFIER; SSEQ = SEQUENCE NUMBER;
REMARK   610 I = INSERTION CODE):
REMARK   610 M    RES    C    SSEQI
REMARK   610      12P    A    416
REMARK   800
REMARK   800 SITE
REMARK   800 SITE_IDENTIFIER: AC1
REMARK   800 SITE_DESCRIPTION: BINDING SITE FOR RESIDUE    12P    A    416
REMARK   800 SITE_IDENTIFIER: AC2
REMARK   800 SITE_DESCRIPTION: BINDING SITE FOR RESIDUE    ACM    A    411
REMARK   800 SITE_IDENTIFIER: AC3
REMARK   800 SITE_DESCRIPTION: BINDING SITE FOR RESIDUE    BU1    A    409
REMARK   800 SITE_IDENTIFIER: AC5
REMARK   800 SITE_DESCRIPTION: BINDING SITE FOR RESIDUE    CAU    A    408
REMARK   800 SITE_IDENTIFIER: AC6
REMARK   800 SITE_DESCRIPTION: BINDING SITE FOR RESIDUE    CLR    A    412
REMARK   800 SITE_IDENTIFIER: AC7
REMARK   800 SITE_DESCRIPTION: BINDING SITE FOR RESIDUE    CLR    A    413
REMARK   800 SITE_IDENTIFIER: AC9
REMARK   800 SITE_DESCRIPTION: BINDING SITE FOR RESIDUE    MAL    A    401
REMARK   800 SITE_IDENTIFIER: BC1
REMARK   800 SITE_DESCRIPTION: BINDING SITE FOR RESIDUE    PLM    A    415
REMARK   800 SITE_IDENTIFIER: BC2
REMARK   800 SITE_DESCRIPTION: BINDING SITE FOR RESIDUE    SO4    A    402
REMARK   800 SITE_IDENTIFIER: BC3
REMARK   800 SITE_DESCRIPTION: BINDING SITE FOR RESIDUE    SO4    A    403
REMARK   800 SITE_IDENTIFIER: BC4
REMARK   800 SITE_DESCRIPTION: BINDING SITE FOR RESIDUE    SO4    A    404
```

APPENDIX 1-continued

```
REMARK   800 SITE_IDENTIFIER: BC5
REMARK   800 SITE_DESCRIPTION: BINDING SITE FOR RESIDUE   SO4   A    405
REMARK   800 SITE_IDENTIFIER: BC6
REMARK   800 SITE_DESCRIPTION: BINDING SITE FOR RESIDUE   SO4   A    406
REMARK   800 SITE_IDENTIFIER: BC7
REMARK   800 SITE_DESCRIPTION: BINDING SITE FOR RESIDUE   SO4   A    407
REMARK   999
REMARK   999 SEQUENCE THE STRUCTURE IS AN INTERNAL FUSION PROTEIN WITH
REMARK   999 LYSOZYME. AN OFFSET 1000 HAS BEEN ADDED TO ORIGINAL
REMARK   999 SEQUENCE DATABASE RESIDUE NUMBERS (2-161) OF THE LYSOZYME
REMARK   999 PART IN COORDINATES TO DISTINGUISH THE LYSOZYME PART IN THE
REMARK   999 CHAIN. THEREFORE THE RESIDUES OF LYSOZYME PART HAVE NUMBERS
REMARK   999 A1002-A1161.
DBREF    2RH1 A      1    230  UNP    P07550  ADRB2_HUMAN      1    230
DBREF    2RH1 A   1002   1161  UNP    P00720  LYS_BPT4         2    161
DBREF    2RH1 A    263    365  UNP    P07550  ADRB2_HUMAN    263    365
SEQADV   2RH1 ASP  A     -6  UNP  P07550  EXPRESSION TAG
SEQADV   2RH1 TYR  A     -5  UNP  P07550  EXPRESSION TAG
SEQADV   2RH1 LYS  A     -4  UNP  P07550  EXPRESSION TAG
SEQADV   2RH1 ASP  A     -3  UNP  P07550  EXPRESSION TAG
SEQADV   2RH1 ASP  A     -2  UNP  P07550  EXPRESSION TAG
SEQADV   2RH1 ASP  A     -1  UNP  P07550  EXPRESSION TAG
SEQADV   2RH1 ALA  A      0  UNP  P07550  EXPRESSION TAG
SEQADV   2RH1 GLU  A    187  UNP  P07550  ASN  187  ENGINEERED
SEQADV   2RH1 THR  A   1054  UNP  P00720  CYS   54  ENGINEERED
SEQADV   2RH1 ALA  A   1097  UNP  P00720  CYS   97  ENGINEERED
SEQRES    1 A  500   ASP  TYR  LYS  ASP  ASP  ASP  ALA  MET  GLY  GLN  PRO  GLY  ASN
SEQRES    2 A  500   GLY  SER  ALA  PHE  LEU  LEU  ALA  PRO  ASN  ARG  SER  HIS  ALA
SEQRES    3 A  500   PRO  ASP  HIS  ASP  VAL  THR  GLN  GLN  ARG  ASP  GLU  VAL  TRP
SEQRES    4 A  500   VAL  VAL  GLY  MET  GLY  ILE  VAL  MET  SER  LEU  ILE  VAL  LEU
SEQRES    5 A  500   ALA  ILE  VAL  PHE  GLY  ASN  VAL  LEU  VAL  ILE  THR  ALA  ILE
SEQRES    6 A  500   ALA  LYS  PHE  GLU  ARG  LEU  GLN  THR  VAL  THR  ASN  TYR  PHE
SEQRES    7 A  500   ILE  THR  SER  LEU  ALA  CYS  ALA  ASP  LEU  VAL  MET  GLY  LEU
SEQRES    8 A  500   ALA  VAL  VAL  PRO  PHE  GLY  ALA  ALA  HIS  ILE  LEU  MET  LYS
SEQRES    9 A  500   MET  TRP  THR  PHE  GLY  ASN  PHE  TRP  CYS  GLU  PHE  TRP  THR
SEQRES   10 A  500   SER  ILE  ASP  VAL  LEU  CYS  VAL  THR  ALA  SER  ILE  GLU  THR
SEQRES   11 A  500   LEU  CYS  VAL  ILE  ALA  VAL  ASP  ARG  TYR  PHE  ALA  ILE  THR
SEQRES   12 A  500   SER  PRO  PHE  LYS  TYR  GLN  SER  LEU  LEU  THR  LYS  ASN  LYS
SEQRES   13 A  500   ALA  ARG  VAL  ILE  ILE  LEU  MET  VAL  TRP  ILE  VAL  SER  GLY
SEQRES   14 A  500   LEU  THR  SER  PHE  LEU  PRO  ILE  GLN  MET  HIS  TRP  TYR  ARG
SEQRES   15 A  500   ALA  THR  HIS  GLN  GLU  ALA  ILE  ASN  CYS  TYR  ALA  GLU  GLU
SEQRES   16 A  500   THR  CYS  CYS  ASP  PHE  PHE  THR  ASN  GLN  ALA  TYR  ALA  ILE
SEQRES   17 A  500   ALA  SER  SER  ILE  VAL  SER  PHE  TYR  VAL  PRO  LEU  VAL  ILE
SEQRES   18 A  500   MET  VAL  PHE  VAL  TYR  SER  ARG  VAL  PHE  GLN  GLU  ALA  LYS
SEQRES   19 A  500   ARG  GLN  LEU  ASN  ILE  PHE  GLU  MET  LEU  ARG  ILE  ASP  GLU
SEQRES   20 A  500   GLY  LEU  ARG  LEU  LYS  ILE  TYR  LYS  ASP  THR  GLU  GLY  TYR
SEQRES   21 A  500   TYR  THR  ILE  GLY  ILE  GLY  HIS  LEU  LEU  THR  LYS  SER  PRO
SEQRES   22 A  500   SER  LEU  ASN  ALA  ALA  LYS  SER  GLU  LEU  ASP  LYS  ALA  ILE
SEQRES   23 A  500   GLY  ARG  ASN  THR  ASN  GLY  VAL  ILE  THR  LYS  ASP  GLU  ALA
SEQRES   24 A  500   GLU  LYS  LEU  PHE  ASN  GLN  ASP  VAL  ASP  ALA  ALA  VAL  ARG
SEQRES   25 A  500   GLY  ILE  LEU  ARG  ASN  ALA  LYS  LEU  LYS  PRO  VAL  TYR  ASP
SEQRES   26 A  500   SER  LEU  ASP  ALA  VAL  ARG  ARG  ALA  ALA  LEU  ILE  ASN  MET
SEQRES   27 A  500   VAL  PHE  GLN  MET  GLY  GLU  THR  GLY  VAL  ALA  GLY  PHE  THR
SEQRES   28 A  500   ASN  SER  LEU  ARG  MET  LEU  GLN  LYS  ARG  TRP  ASP  PHE  GLU
SEQRES   29 A  500   ALA  ALA  VAL  ASN  LEU  ALA  LYS  SER  ARG  TRP  TYR  ASN  GLN
SEQRES   30 A  500   THR  PRO  ASN  ARG  ALA  LYS  ARG  VAL  ILE  THR  THR  PHE  ARG
SEQRES   31 A  500   THR  GLY  THR  TRP  ASP  ALA  TYR  LYS  PHE  CYS  LEU  LYS  GLU
SEQRES   32 A  500   HIS  LYS  ALA  LEU  LYS  THR  LEU  GLY  ILE  ILE  MET  GLY  THR
SEQRES   33 A  500   PHE  THR  LEU  CYS  TRP  LEU  PRO  PHE  PHE  ILE  VAL  ASN  ILE
SEQRES   34 A  500   VAL  HIS  VAL  ILE  GLN  ASP  ASN  LEU  ILE  ARG  LYS  GLU  VAL
SEQRES   35 A  500   TYR  ILE  LEU  LEU  ASN  TRP  ILE  GLY  TYR  VAL  ASN  SER  GLY
SEQRES   36 A  500   PHE  ASN  PRO  LEU  ILE  TYR  CYS  ARG  SER  PRO  ASP  PHE  ARG
SEQRES   37 A  500   ILE  ALA  PHE  GLN  GLU  LEU  LEU  CYS  LEU  ARG  ARG  SER  SER
SEQRES   38 A  500   LEU  LYS  ALA  TYR  GLY  ASN  GLY  TYR  SER  SER  ASN  GLY  ASN
SEQRES   39 A  500   THR  GLY  GLU  GLN  SER  GLY
HET      MAL  A   401    23
HET      SO4  A   402     5
HET      SO4  A   403     5
HET      SO4  A   404     5
HET      SO4  A   405     5
HET      SO4  A   406     5
HET      SO4  A   407     5
HET      CAU  A   408    22
HET      BU1  A   409     6
HET      BU1  A   410     6
HET      ACM  A   411     4
HET      CLR  A   412    28
HET      CLR  A   413    28
HET      CLR  A   414    28
HET      PLM  A   415    17
```

APPENDIX 1-continued

```
HET        12P   A  416      21
HETNAM          MAL  MALTOSE
HETNAM          SO4  SULFATE ION
HETNAM          CAU  (2S)-1-(9H-CARBAZOL-4-YLOXY)-3-(ISOPROPYLAMINO)PROPAN-
HETNAM        2 CAU  2-OL
HETNAM          BU1  1,4-BUTANEDIOL
HETNAM          ACM  ACETAMIDE
HETNAM          CLR  CHOLESTEROL
HETNAM          PLM  PALMITIC ACID
HETNAM          12P  DODECAETHYLENE GLYCOL
HETSYN          CAU  (S)-CARAZOLOL
HETSYN          12P  POLYETHYLENE GLYCOL PEG400
FORMUL       2  MAL  C12 H22 O11
FORMUL       3  SO4  6(O4 S 2-)
FORMUL       9  CAU  C18 H22 N2 O2
FORMUL      10  BU1  2(C4 H10 O2)
FORMUL      12  ACM  C2 H5 N O
FORMUL      13  CLR  3(C27 H46 O)
FORMUL      16  PLM  C16 H32 O2
FORMUL      17  12P  C24 H50 O13
FORMUL      18  HOH  *48(H2 O)
HELIX        1   1 ASP A    29  LYS A    60  1    32
HELIX        2   2 VAL A    67  MET A    96  1    30
HELIX        3   3 ASN A   103  THR A   136  1    34
HELIX        4   4 LYS A   147  MET A   171  1    25
HELIX        5   5 HIS A   178  GLU A   187  1    10
HELIX        6   6 GLN A   197  GLN A   229  1    33
HELIX        7   7 LYS A   267  ILE A   298  1    32
HELIX        8   8 LYS A   305  ARG A   328  1    24
HELIX        9   9 PRO A   330  CYS A   341  1    12
HELIX       10  10 ILE A  1003  GLU A  1011  1     9
HELIX       11  11 LEU A  1039  ILE A  1050  1    12
HELIX       12  12 LYS A  1060  ARG A  1080  1    21
HELIX       13  13 ALA A  1082  SER A  1090  1     9
HELIX       14  14 ALA A  1093  MET A  1106  1    14
HELIX       15  15 GLU A  1108  GLY A  1113  1     6
HELIX       16  16 THR A  1115  GLN A  1123  1     9
HELIX       17  17 TRP A  1126  ALA A  1134  1     9
HELIX       18  18 ARG A  1137  GLN A  1141  1     5
HELIX       19  19 PRO A  1143  THR A  1155  1    13
SHEET        1   1 4 LYS A  1016  ASP A  1020  0
SHEET        2   1 4 TYR A  1024  GLY A  1028  0
SHEET        3   1 4 HIS A  1031  THR A  1034  0
SHEET        4   1 4 GLY A  1056  THR A  1059  0
SSBOND       1 CYS A   106   CYS A   191   1555  1555  2.05
SSBOND       2 CYS A   184   CYS A   190   1555  1555  2.06
LINK        SG CYS A   265   C2 ACM A   411  1555  1555  1.61
LINK        SG CYS A   341   C1 PLM A   415  1555  1555  1.62
SITE         1 AC1  2   ASP A  1072 HOH A   538
SITE         1 AC2  1   CYS A   265
SITE         1 AC3  4   LYS A   263 PHE A   264 HIS A   269 HOH A   502
SITE         1 AC5  4   ASP A   113 PHE A   193 ASN A   312 TYR A   316
SITE         1 AC6  1   ILE A   112
SITE         1 AC7  1   HOH A   520
SITE         1 AC9  7   GLU A  1011 GLY A  1030 LEU A  1032 ASP A  1070
SITE         2 AC9  7   VAL A  1103 PHE A  1104 ARG A  1145
SITE         1 BC1  2   LEU A   339 CYS A   341
SITE         1 BC2  5   VAL A    67 THR A    68 ARG A   131 TYR A   141
SITE         2 BC2  5   SER A   143
SITE         1 BC3  4   PHE A   264 LYS A   270 LYS A   273 ARG A   328
SITE         1 BC4  5   PHE A  1114 THR A  1115 ASN A  1116 SER A  1117
SITE         2 BC4  5   ASN A  1132
SITE         1 BC5  6   PRO A  1143 ASN A  1144 ARG A  1145 HOH A   512
SITE         2 BC5  6   HOH A   526 HOH A   531
SITE         1 BC6  1   ARG A  1095
SITE         1 BC7  2   LEU A  1015 LYS A  1016
CRYST1   106.318  169.240   40.154  90.00  105.62  90.00   C 1 2 1     4
ORIGX1    1.000000   0.000000   0.000000       0.00000
ORIGX2    0.000000   1.000000   0.000000       0.00000
ORIGX3    0.000000   0.000000   1.000000       0.00000
SCALE1    0.009406   0.000000   0.002630       0.00000
SCALE2    0.000000   0.005909   0.000000       0.00000
SCALE3    0.000000   0.000000   0.025859       0.00000
ATOM         1  N    ASP  A    29    -52.822   -1.611   23.137  1.00  98.48   N
ATOM         2  CA   ASP  A    29    -51.922   -2.262   22.148  1.00  98.06   C
ATOM         3  C    ASP  A    29    -52.178   -1.713   20.742  1.00  97.74   C
ATOM         4  O    ASP  A    29    -51.291   -1.100   20.143  1.00  96.54   O
ATOM         5  CB   ASP  A    29    -52.106   -3.786   22.184  1.00  97.64   C
ATOM         6  N    GLU  A    30    -53.394   -1.944   20.236  1.00  98.37   N
ATOM         7  CA   GLU  A    30    -53.821   -1.515   18.887  1.00  98.17   C
```

APPENDIX 1-continued

| ATOM | 8 | C | GLU | A | 30 | −54.424 | −0.104 | 18.879 | 1.00 | 98.57 | C |
|---|---|---|---|---|---|---|---|---|---|---|---|
| ATOM | 9 | O | GLU | A | 30 | −54.197 | 0.649 | 17.943 | 1.00 | 99.79 | O |
| ATOM | 10 | CB | GLU | A | 30 | −54.840 | −2.498 | 18.305 | 1.00 | 99.00 | C |
| ATOM | 11 | CG | GLU | A | 30 | −54.377 | −3.969 | 18.286 | 1.00 | 99.46 | C |
| ATOM | 12 | CD | GLU | A | 30 | −55.432 | −4.928 | 17.733 | 1.00 | 98.77 | C |
| ATOM | 13 | OE1 | GLU | A | 30 | −56.228 | −4.527 | 16.853 | 1.00 | 97.60 | O |
| ATOM | 14 | OE2 | GLU | A | 30 | −55.463 | −6.092 | 18.185 | 1.00 | 99.75 | O |
| ATOM | 15 | N | VAL | A | 31 | −55.190 | 0.248 | 19.918 | 1.00 | 97.89 | N |
| ATOM | 16 | CA | VAL | A | 31 | −55.757 | 1.618 | 20.079 | 1.00 | 96.48 | C |
| ATOM | 17 | C | VAL | A | 31 | −54.643 | 2.678 | 20.185 | 1.00 | 95.12 | C |
| ATOM | 18 | O | VAL | A | 31 | −54.838 | 3.837 | 19.803 | 1.00 | 93.37 | O |
| ATOM | 19 | CB | VAL | A | 31 | −56.729 | 1.697 | 21.306 | 1.00 | 96.71 | C |
| ATOM | 20 | CG1 | VAL | A | 31 | −57.185 | 3.135 | 21.580 | 1.00 | 96.80 | C |
| ATOM | 21 | CG2 | VAL | A | 31 | −57.948 | 0.806 | 21.077 | 1.00 | 96.80 | C |
| ATOM | 22 | N | TRP | A | 32 | −53.486 | 2.259 | 20.709 | 1.00 | 95.21 | N |
| ATOM | 23 | CA | TRP | A | 32 | −52.267 | 3.063 | 20.735 | 1.00 | 94.60 | C |
| ATOM | 24 | C | TRP | A | 32 | −51.837 | 3.491 | 19.319 | 1.00 | 93.60 | C |
| ATOM | 25 | O | TRP | A | 32 | −51.335 | 4.603 | 19.140 | 1.00 | 91.48 | O |
| ATOM | 26 | CB | TRP | A | 32 | −51.129 | 2.273 | 21.427 | 1.00 | 96.93 | C |
| ATOM | 27 | CG | TRP | A | 32 | −49.770 | 2.899 | 21.304 | 1.00 | 98.27 | C |
| ATOM | 28 | CD1 | TRP | A | 32 | −49.169 | 3.734 | 22.197 | 1.00 | 100.48 | C |
| ATOM | 29 | CD2 | TRP | A | 32 | −48.844 | 2.737 | 20.216 | 1.00 | 100.89 | C |
| ATOM | 30 | NE1 | TRP | A | 32 | −47.924 | 4.105 | 21.737 | 1.00 | 101.70 | N |
| ATOM | 31 | CE2 | TRP | A | 32 | −47.700 | 3.507 | 20.523 | 1.00 | 102.25 | C |
| ATOM | 32 | CE3 | TRP | A | 32 | −48.874 | 2.013 | 19.010 | 1.00 | 100.84 | C |
| ATOM | 33 | CZ2 | TRP | A | 32 | −46.587 | 3.578 | 19.667 | 1.00 | 101.34 | C |
| ATOM | 34 | CZ3 | TRP | A | 32 | −47.771 | 2.082 | 18.158 | 1.00 | 100.68 | C |
| ATOM | 35 | CH2 | TRP | A | 32 | −46.640 | 2.860 | 18.493 | 1.00 | 101.20 | C |
| ATOM | 36 | N | VAL | A | 33 | −52.036 | 2.600 | 18.332 | 1.00 | 92.39 | N |
| ATOM | 37 | CA | VAL | A | 33 | −51.667 | 2.852 | 16.922 | 1.00 | 91.10 | C |
| ATOM | 38 | C | VAL | A | 33 | −52.435 | 4.017 | 16.332 | 1.00 | 89.89 | C |
| ATOM | 39 | O | VAL | A | 33 | −51.827 | 4.918 | 15.748 | 1.00 | 88.01 | O |
| ATOM | 40 | CB | VAL | A | 33 | −51.920 | 1.621 | 16.012 | 1.00 | 91.28 | C |
| ATOM | 41 | CG1 | VAL | A | 33 | −51.625 | 1.950 | 14.553 | 1.00 | 93.68 | C |
| ATOM | 42 | CG2 | VAL | A | 33 | −51.080 | 0.443 | 16.467 | 1.00 | 93.38 | C |
| ATOM | 43 | N | VAL | A | 34 | −53.762 | 3.986 | 16.490 | 1.00 | 88.20 | N |
| ATOM | 44 | CA | VAL | A | 34 | −54.638 | 5.078 | 16.041 | 1.00 | 87.62 | C |
| ATOM | 45 | C | VAL | A | 34 | −54.145 | 6.388 | 16.649 | 1.00 | 87.34 | C |
| ATOM | 46 | O | VAL | A | 34 | −53.871 | 7.334 | 15.921 | 1.00 | 88.42 | O |
| ATOM | 47 | CB | VAL | A | 34 | −56.126 | 4.852 | 16.422 | 1.00 | 87.61 | C |
| ATOM | 48 | CG1 | VAL | A | 34 | −56.972 | 6.064 | 16.046 | 1.00 | 87.66 | C |
| ATOM | 49 | CG2 | VAL | A | 34 | −56.684 | 3.592 | 15.755 | 1.00 | 85.12 | C |
| ATOM | 50 | N | GLY | A | 35 | −54.036 | 6.413 | 17.981 | 1.00 | 86.61 | N |
| ATOM | 51 | CA | GLY | A | 35 | −53.524 | 7.576 | 18.738 | 1.00 | 86.08 | C |
| ATOM | 52 | C | GLY | A | 35 | −52.123 | 8.048 | 18.358 | 1.00 | 85.30 | C |
| ATOM | 53 | O | GLY | A | 35 | −51.837 | 9.245 | 18.408 | 1.00 | 85.51 | O |
| ATOM | 54 | N | MET | A | 36 | −51.257 | 7.110 | 17.981 | 1.00 | 85.55 | N |
| ATOM | 55 | CA | MET | A | 36 | −49.919 | 7.431 | 17.486 | 1.00 | 84.86 | C |
| ATOM | 56 | C | MET | A | 36 | −50.004 | 7.888 | 16.029 | 1.00 | 85.06 | C |
| ATOM | 57 | O | MET | A | 36 | −49.216 | 8.733 | 15.590 | 1.00 | 86.04 | O |
| ATOM | 58 | CB | MET | A | 36 | −49.001 | 6.214 | 17.596 | 1.00 | 86.69 | C |
| ATOM | 59 | CG | MET | A | 36 | −47.509 | 6.496 | 17.400 | 1.00 | 88.99 | C |
| ATOM | 60 | SD | MET | A | 36 | −46.800 | 7.642 | 18.613 | 1.00 | 102.42 | S |
| ATOM | 61 | CE | MET | A | 36 | −47.213 | 6.857 | 20.179 | 1.00 | 100.39 | C |
| ATOM | 62 | N | GLY | A | 37 | −50.959 | 7.324 | 15.287 | 1.00 | 83.06 | N |
| ATOM | 63 | CA | GLY | A | 37 | −51.227 | 7.713 | 13.911 | 1.00 | 82.58 | C |
| ATOM | 64 | C | GLY | A | 37 | −51.710 | 9.144 | 13.811 | 1.00 | 81.74 | C |
| ATOM | 65 | O | GLY | A | 37 | −51.171 | 9.912 | 13.024 | 1.00 | 83.08 | O |
| ATOM | 66 | N | ILE | A | 38 | −52.724 | 9.494 | 14.611 | 1.00 | 81.34 | N |
| ATOM | 67 | CA | ILE | A | 38 | −53.260 | 10.869 | 14.659 | 1.00 | 80.88 | C |
| ATOM | 68 | C | ILE | A | 38 | −52.153 | 11.874 | 15.003 | 1.00 | 80.13 | C |
| ATOM | 69 | O | ILE | A | 38 | −52.121 | 12.964 | 14.453 | 1.00 | 81.84 | O |
| ATOM | 70 | CB | ILE | A | 38 | −54.432 | 11.032 | 15.686 | 1.00 | 81.07 | C |
| ATOM | 71 | CG1 | ILE | A | 38 | −55.635 | 10.132 | 15.356 | 1.00 | 81.29 | C |
| ATOM | 72 | CG2 | ILE | A | 38 | −54.912 | 12.479 | 15.745 | 1.00 | 80.45 | C |
| ATOM | 73 | CD1 | ILE | A | 38 | −56.310 | 10.413 | 14.026 | 1.00 | 85.05 | C |
| ATOM | 74 | N | VAL | A | 39 | −51.255 | 11.496 | 15.911 | 1.00 | 79.45 | N |
| ATOM | 75 | CA | VAL | A | 39 | −50.128 | 12.346 | 16.306 | 1.00 | 79.67 | C |
| ATOM | 76 | C | VAL | A | 39 | −49.166 | 12.575 | 15.154 | 1.00 | 79.83 | C |
| ATOM | 77 | O | VAL | A | 39 | −48.803 | 13.717 | 14.863 | 1.00 | 81.09 | O |
| ATOM | 78 | CB | VAL | A | 39 | −49.352 | 11.740 | 17.496 | 1.00 | 81.11 | C |
| ATOM | 79 | CG1 | VAL | A | 39 | −47.996 | 12.425 | 17.671 | 1.00 | 78.01 | C |
| ATOM | 80 | CG2 | VAL | A | 39 | −50.185 | 11.843 | 18.770 | 1.00 | 81.49 | C |
| ATOM | 81 | N | MET | A | 40 | −48.754 | 11.492 | 14.506 | 1.00 | 80.50 | N |
| ATOM | 82 | CA | MET | A | 40 | −47.881 | 11.589 | 13.320 | 1.00 | 80.67 | C |
| ATOM | 83 | C | MET | A | 40 | −48.575 | 12.333 | 12.155 | 1.00 | 80.62 | C |
| ATOM | 84 | O | MET | A | 40 | −47.915 | 13.033 | 11.390 | 1.00 | 78.80 | O |
| ATOM | 85 | CB | MET | A | 40 | −47.405 | 10.197 | 12.870 | 1.00 | 80.79 | C |
| ATOM | 86 | CG | MET | A | 40 | −46.294 | 9.613 | 13.745 | 1.00 | 80.56 | C |
| ATOM | 87 | SD | MET | A | 40 | −45.995 | 7.863 | 13.419 | 1.00 | 83.92 | S |

APPENDIX 1-continued

| | | | | | | | | | | |
|---|---|---|---|---|---|---|---|---|---|---|
| ATOM | 88 | CE | MET | A | 40 | −44.486 | 7.588 | 14.344 | 1.00 | 83.67 | C |
| ATOM | 89 | N | SER | A | 41 | −49.896 | 12.177 | 12.034 | 1.00 | 79.41 | N |
| ATOM | 90 | CA | SER | A | 41 | −50.672 | 12.898 | 11.020 | 1.00 | 79.83 | C |
| ATOM | 91 | C | SER | A | 41 | −50.651 | 14.403 | 11.269 | 1.00 | 80.21 | C |
| ATOM | 92 | O | SER | A | 41 | −50.521 | 15.181 | 10.324 | 1.00 | 82.42 | O |
| ATOM | 93 | CB | SER | A | 41 | −52.104 | 12.394 | 10.976 | 1.00 | 79.47 | C |
| ATOM | 94 | OG | SER | A | 41 | −52.128 | 11.044 | 10.561 | 1.00 | 82.68 | O |
| ATOM | 95 | N | LEU | A | 42 | −50.778 | 14.805 | 12.534 | 1.00 | 79.85 | N |
| ATOM | 96 | CA | LEU | A | 42 | −50.675 | 16.219 | 12.908 | 1.00 | 79.83 | C |
| ATOM | 97 | C | LEU | A | 42 | −49.256 | 16.752 | 12.687 | 1.00 | 78.29 | C |
| ATOM | 98 | O | LEU | A | 42 | −49.093 | 17.917 | 12.355 | 1.00 | 80.15 | O |
| ATOM | 99 | CB | LEU | A | 42 | −51.106 | 16.448 | 14.364 | 1.00 | 80.71 | C |
| ATOM | 100 | CG | LEU | A | 42 | −52.586 | 16.242 | 14.714 | 1.00 | 81.76 | C |
| ATOM | 101 | CD1 | LEU | A | 42 | −52.774 | 16.400 | 16.213 | 1.00 | 83.86 | C |
| ATOM | 102 | CD2 | LEU | A | 42 | −53.508 | 17.191 | 13.956 | 1.00 | 82.80 | C |
| ATOM | 103 | N | ILE | A | 43 | −48.243 | 15.902 | 12.876 | 1.00 | 77.38 | N |
| ATOM | 104 | CA | ILE | A | 43 | −46.850 | 16.274 | 12.593 | 1.00 | 77.38 | C |
| ATOM | 105 | C | ILE | A | 43 | −46.683 | 16.604 | 11.112 | 1.00 | 77.46 | C |
| ATOM | 106 | O | ILE | A | 43 | −46.072 | 17.608 | 10.771 | 1.00 | 77.58 | O |
| ATOM | 107 | CB | ILE | A | 43 | −45.845 | 15.155 | 12.995 | 1.00 | 78.54 | C |
| ATOM | 108 | CG1 | ILE | A | 43 | −45.698 | 15.080 | 14.520 | 1.00 | 80.06 | C |
| ATOM | 109 | CG2 | ILE | A | 43 | −44.473 | 15.387 | 12.366 | 1.00 | 74.64 | C |
| ATOM | 110 | CD1 | ILE | A | 43 | −44.923 | 13.845 | 15.002 | 1.00 | 77.13 | C |
| ATOM | 111 | N | VAL | A | 44 | −47.229 | 15.750 | 10.247 | 1.00 | 77.58 | N |
| ATOM | 112 | CA | VAL | A | 44 | −47.195 | 15.967 | 8.801 | 1.00 | 76.60 | C |
| ATOM | 113 | C | VAL | A | 44 | −47.951 | 17.251 | 8.416 | 1.00 | 78.14 | C |
| ATOM | 114 | O | VAL | A | 44 | −47.445 | 18.053 | 7.629 | 1.00 | 76.84 | O |
| ATOM | 115 | CB | VAL | A | 44 | −47.769 | 14.755 | 8.041 | 1.00 | 76.85 | C |
| ATOM | 116 | CG1 | VAL | A | 44 | −47.967 | 15.079 | 6.567 | 1.00 | 75.75 | C |
| ATOM | 117 | CG2 | VAL | A | 44 | −46.856 | 13.533 | 8.219 | 1.00 | 70.47 | C |
| ATOM | 118 | N | LEU | A | 45 | −49.150 | 17.434 | 8.972 | 1.00 | 78.66 | N |
| ATOM | 119 | CA | LEU | A | 45 | −49.954 | 18.638 | 8.719 | 1.00 | 78.89 | C |
| ATOM | 120 | C | LEU | A | 45 | −49.219 | 19.901 | 9.163 | 1.00 | 79.68 | C |
| ATOM | 121 | O | LEU | A | 45 | −49.246 | 20.900 | 8.460 | 1.00 | 80.46 | O |
| ATOM | 122 | CB | LEU | A | 45 | −51.306 | 18.555 | 9.433 | 1.00 | 80.42 | C |
| ATOM | 123 | CG | LEU | A | 45 | −52.374 | 19.590 | 9.062 | 1.00 | 83.12 | C |
| ATOM | 124 | CD1 | LEU | A | 45 | −52.835 | 19.414 | 7.616 | 1.00 | 86.47 | C |
| ATOM | 125 | CD2 | LEU | A | 45 | −53.555 | 19.485 | 10.008 | 1.00 | 82.85 | C |
| ATOM | 126 | N | ALA | A | 46 | −48.571 | 19.830 | 10.330 | 1.00 | 78.89 | N |
| ATOM | 127 | CA | ALA | A | 46 | −47.783 | 20.933 | 10.893 | 1.00 | 76.32 | C |
| ATOM | 128 | C | ALA | A | 46 | −46.639 | 21.352 | 9.985 | 1.00 | 75.76 | C |
| ATOM | 129 | O | ALA | A | 46 | −46.453 | 22.539 | 9.731 | 1.00 | 78.99 | O |
| ATOM | 130 | CB | ALA | A | 46 | −47.227 | 20.535 | 12.244 | 1.00 | 75.15 | C |
| ATOM | 131 | N | ILE | A | 47 | −45.885 | 20.371 | 9.505 | 1.00 | 72.82 | N |
| ATOM | 132 | CA | ILE | A | 47 | −44.751 | 20.613 | 8.596 | 1.00 | 72.71 | C |
| ATOM | 133 | C | ILE | A | 47 | −45.206 | 21.216 | 7.267 | 1.00 | 69.65 | C |
| ATOM | 134 | O | ILE | A | 47 | −44.651 | 22.209 | 6.815 | 1.00 | 68.44 | O |
| ATOM | 135 | CB | ILE | A | 47 | −43.984 | 19.310 | 8.290 | 1.00 | 73.57 | C |
| ATOM | 136 | CG1 | ILE | A | 47 | −43.276 | 18.777 | 9.540 | 1.00 | 73.61 | C |
| ATOM | 137 | CG2 | ILE | A | 47 | −42.961 | 19.534 | 7.179 | 1.00 | 73.63 | C |
| ATOM | 138 | CD1 | ILE | A | 47 | −42.811 | 17.358 | 9.399 | 1.00 | 71.65 | C |
| ATOM | 139 | N | VAL | A | 48 | −46.216 | 20.606 | 6.659 | 1.00 | 68.32 | N |
| ATOM | 140 | CA | VAL | A | 48 | −46.721 | 21.051 | 5.360 | 1.00 | 69.33 | C |
| ATOM | 141 | C | VAL | A | 48 | −47.390 | 22.440 | 5.463 | 1.00 | 71.00 | C |
| ATOM | 142 | O | VAL | A | 48 | −47.115 | 23.305 | 4.638 | 1.00 | 72.48 | O |
| ATOM | 143 | CB | VAL | A | 48 | −47.692 | 20.011 | 4.722 | 1.00 | 69.55 | C |
| ATOM | 144 | CG1 | VAL | A | 48 | −48.178 | 20.489 | 3.364 | 1.00 | 64.85 | C |
| ATOM | 145 | CG2 | VAL | A | 48 | −47.008 | 18.642 | 4.585 | 1.00 | 66.28 | C |
| ATOM | 146 | N | PHE | A | 49 | −48.248 | 22.640 | 6.468 | 1.00 | 70.84 | N |
| ATOM | 147 | CA | PHE | A | 49 | −48.951 | 23.916 | 6.654 | 1.00 | 69.45 | C |
| ATOM | 148 | C | PHE | A | 49 | −47.994 | 25.077 | 6.803 | 1.00 | 71.34 | C |
| ATOM | 149 | O | PHE | A | 49 | −48.039 | 26.025 | 6.017 | 1.00 | 71.00 | O |
| ATOM | 150 | CB | PHE | A | 49 | −49.869 | 23.866 | 7.886 | 1.00 | 70.88 | C |
| ATOM | 151 | CG | PHE | A | 49 | −50.669 | 25.123 | 8.103 | 1.00 | 71.45 | C |
| ATOM | 152 | CD1 | PHE | A | 49 | −51.932 | 25.254 | 7.554 | 1.00 | 72.92 | C |
| ATOM | 153 | CD2 | PHE | A | 49 | −50.161 | 26.176 | 8.855 | 1.00 | 75.73 | C |
| ATOM | 154 | CE1 | PHE | A | 49 | −52.678 | 26.414 | 7.751 | 1.00 | 73.41 | C |
| ATOM | 155 | CE2 | PHE | A | 49 | −50.905 | 27.336 | 9.052 | 1.00 | 74.53 | C |
| ATOM | 156 | CZ | PHE | A | 49 | −52.162 | 27.450 | 8.498 | 1.00 | 69.47 | C |
| ATOM | 157 | N | GLY | A | 50 | −47.133 | 24.985 | 7.821 | 1.00 | 71.43 | N |
| ATOM | 158 | CA | GLY | A | 50 | −46.193 | 26.040 | 8.158 | 1.00 | 67.82 | C |
| ATOM | 159 | C | GLY | A | 50 | −45.210 | 26.409 | 7.066 | 1.00 | 68.17 | C |
| ATOM | 160 | O | GLY | A | 50 | −44.952 | 27.592 | 6.852 | 1.00 | 67.71 | O |
| ATOM | 161 | N | ASN | A | 51 | −44.662 | 25.402 | 6.381 | 1.00 | 66.99 | N |
| ATOM | 162 | CA | ASN | A | 51 | −43.713 | 25.636 | 5.273 | 1.00 | 67.98 | C |
| ATOM | 163 | C | ASN | A | 51 | −44.414 | 26.145 | 3.998 | 1.00 | 71.16 | C |
| ATOM | 164 | O | ASN | A | 51 | −43.847 | 26.968 | 3.274 | 1.00 | 69.41 | O |
| ATOM | 165 | CB | ASN | A | 51 | −42.890 | 24.395 | 4.997 | 1.00 | 68.88 | C |
| ATOM | 166 | CG | ASN | A | 51 | −41.927 | 24.083 | 6.134 | 1.00 | 71.66 | C |
| ATOM | 167 | OD1 | ASN | A | 51 | −40.914 | 24.758 | 6.305 | 1.00 | 69.08 | O |

APPENDIX 1-continued

| | | | | | | | | | | |
|---|---|---|---|---|---|---|---|---|---|---|
| ATOM | 168 | ND2 | ASN | A | 51 | −42.241 | 23.063 | 6.913 | 1.00 | 68.08 | N |
| ATOM | 169 | N | VAL | A | 52 | −45.631 | 25.656 | 3.730 | 1.00 | 67.56 | N |
| ATOM | 170 | CA | VAL | A | 52 | −46.453 | 26.245 | 2.687 | 1.00 | 70.68 | C |
| ATOM | 171 | C | VAL | A | 52 | −46.616 | 27.731 | 2.994 | 1.00 | 71.64 | C |
| ATOM | 172 | O | VAL | A | 52 | −46.463 | 28.558 | 2.108 | 1.00 | 72.88 | O |
| ATOM | 173 | CB | VAL | A | 52 | −47.860 | 25.599 | 2.575 | 1.00 | 69.27 | C |
| ATOM | 174 | CG1 | VAL | A | 52 | −48.837 | 26.549 | 1.903 | 1.00 | 71.90 | C |
| ATOM | 175 | CG2 | VAL | A | 52 | −47.784 | 24.286 | 1.829 | 1.00 | 67.05 | C |
| ATOM | 176 | N | LEU | A | 53 | −46.921 | 28.049 | 4.256 | 1.00 | 73.15 | N |
| ATOM | 177 | CA | LEU | A | 53 | −47.156 | 29.441 | 4.688 | 1.00 | 72.57 | C |
| ATOM | 178 | C | LEU | A | 53 | −45.913 | 30.335 | 4.500 | 1.00 | 73.72 | C |
| ATOM | 179 | O | LEU | A | 53 | −46.043 | 31.494 | 4.120 | 1.00 | 76.55 | O |
| ATOM | 180 | CB | LEU | A | 53 | −47.632 | 29.482 | 6.147 | 1.00 | 72.34 | C |
| ATOM | 181 | CG | LEU | A | 53 | −48.422 | 30.705 | 6.593 | 1.00 | 74.13 | C |
| ATOM | 182 | CD1 | LEU | A | 53 | −49.812 | 30.716 | 5.973 | 1.00 | 73.24 | C |
| ATOM | 183 | CD2 | LEU | A | 53 | −48.530 | 30.738 | 8.109 | 1.00 | 76.12 | C |
| ATOM | 184 | N | VAL | A | 54 | −44.723 | 29.789 | 4.765 | 1.00 | 72.68 | N |
| ATOM | 185 | CA | VAL | A | 54 | −43.458 | 30.517 | 4.563 | 1.00 | 70.92 | C |
| ATOM | 186 | C | VAL | A | 54 | −43.183 | 30.795 | 3.076 | 1.00 | 72.46 | C |
| ATOM | 187 | O | VAL | A | 54 | −42.786 | 31.903 | 2.711 | 1.00 | 72.67 | O |
| ATOM | 188 | CB | VAL | A | 54 | −42.255 | 29.741 | 5.161 | 1.00 | 73.28 | C |
| ATOM | 189 | CG1 | VAL | A | 54 | −40.937 | 30.380 | 4.769 | 1.00 | 72.16 | C |
| ATOM | 190 | CG2 | VAL | A | 54 | −42.376 | 29.647 | 6.682 | 1.00 | 69.63 | C |
| ATOM | 191 | N | ILE | A | 55 | −43.395 | 29.787 | 2.233 | 1.00 | 69.98 | N |
| ATOM | 192 | CA | ILE | A | 55 | −43.164 | 29.906 | 0.791 | 1.00 | 68.58 | C |
| ATOM | 193 | C | ILE | A | 55 | −44.076 | 30.960 | 0.177 | 1.00 | 69.05 | C |
| ATOM | 194 | O | ILE | A | 55 | −43.606 | 31.844 | −0.552 | 1.00 | 65.40 | O |
| ATOM | 195 | CB | ILE | A | 55 | −43.379 | 28.569 | 0.090 | 1.00 | 68.25 | C |
| ATOM | 196 | CG1 | ILE | A | 55 | −42.253 | 27.591 | 0.454 | 1.00 | 71.45 | C |
| ATOM | 197 | CG2 | ILE | A | 55 | −43.430 | 28.766 | −1.409 | 1.00 | 72.11 | C |
| ATOM | 198 | CD1 | ILE | A | 55 | −42.573 | 26.152 | 0.127 | 1.00 | 71.51 | C |
| ATOM | 199 | N | THR | A | 56 | −45.369 | 30.840 | 0.491 | 1.00 | 70.28 | N |
| ATOM | 200 | CA | THR | A | 56 | −46.403 | 31.770 | 0.067 | 1.00 | 69.62 | C |
| ATOM | 201 | C | THR | A | 56 | −46.078 | 33.211 | 0.454 | 1.00 | 71.19 | C |
| ATOM | 202 | O | THR | A | 56 | −46.188 | 34.089 | −0.372 | 1.00 | 72.89 | O |
| ATOM | 203 | CB | THR | A | 56 | −47.780 | 31.399 | 0.686 | 1.00 | 71.36 | C |
| ATOM | 204 | OG1 | THR | A | 56 | −48.082 | 30.019 | 0.434 | 1.00 | 65.43 | O |
| ATOM | 205 | CG2 | THR | A | 56 | −48.896 | 32.281 | 0.110 | 1.00 | 69.44 | C |
| ATOM | 206 | N | ALA | A | 57 | −45.678 | 33.423 | 1.714 | 1.00 | 71.45 | N |
| ATOM | 207 | CA | ALA | A | 57 | −45.368 | 34.762 | 2.263 | 1.00 | 70.84 | C |
| ATOM | 208 | C | ALA | A | 57 | −44.180 | 35.464 | 1.584 | 1.00 | 71.90 | C |
| ATOM | 209 | O | ALA | A | 57 | −44.220 | 36.665 | 1.339 | 1.00 | 70.99 | O |
| ATOM | 210 | CB | ALA | A | 57 | −45.119 | 34.666 | 3.767 | 1.00 | 67.19 | C |
| ATOM | 211 | N | ILE | A | 58 | −43.128 | 34.712 | 1.289 | 1.00 | 71.62 | N |
| ATOM | 212 | CA | ILE | A | 58 | −41.960 | 35.250 | 0.586 | 1.00 | 71.02 | C |
| ATOM | 213 | C | ILE | A | 58 | −42.294 | 35.462 | −0.910 | 1.00 | 76.54 | C |
| ATOM | 214 | O | ILE | A | 58 | −41.898 | 36.471 | −1.503 | 1.00 | 79.19 | O |
| ATOM | 215 | CB | ILE | A | 58 | −40.758 | 34.321 | 0.745 | 1.00 | 69.83 | C |
| ATOM | 216 | CG1 | ILE | A | 58 | −40.343 | 34.235 | 2.227 | 1.00 | 69.16 | C |
| ATOM | 217 | CG2 | ILE | A | 58 | −39.585 | 34.805 | −0.082 | 1.00 | 69.14 | C |
| ATOM | 218 | CD1 | ILE | A | 58 | −39.371 | 33.129 | 2.513 | 1.00 | 70.35 | C |
| ATOM | 219 | N | ALA | A | 59 | −43.016 | 34.511 | −1.505 | 1.00 | 74.84 | N |
| ATOM | 220 | CA | ALA | A | 59 | −43.420 | 34.599 | −2.913 | 1.00 | 75.72 | C |
| ATOM | 221 | C | ALA | A | 59 | −44.422 | 35.722 | −3.174 | 1.00 | 76.56 | C |
| ATOM | 222 | O | ALA | A | 59 | −44.416 | 36.311 | −4.256 | 1.00 | 77.62 | O |
| ATOM | 223 | CB | ALA | A | 59 | −43.999 | 33.268 | −3.385 | 1.00 | 72.21 | C |
| ATOM | 224 | N | LYS | A | 60 | −45.271 | 36.012 | −2.184 | 1.00 | 76.98 | N |
| ATOM | 225 | CA | LYS | A | 60 | −46.336 | 37.010 | −2.323 | 1.00 | 76.24 | C |
| ATOM | 226 | C | LYS | A | 60 | −45.932 | 38.438 | −1.965 | 1.00 | 77.94 | C |
| ATOM | 227 | O | LYS | A | 60 | −46.282 | 39.371 | −2.694 | 1.00 | 75.40 | O |
| ATOM | 228 | CB | LYS | A | 60 | −47.532 | 36.605 | −1.466 | 1.00 | 75.25 | C |
| ATOM | 229 | CG | LYS | A | 60 | −48.667 | 37.578 | −1.530 | 1.00 | 77.75 | C |
| ATOM | 230 | CD | LYS | A | 60 | −49.959 | 36.950 | −1.164 | 1.00 | 78.52 | C |
| ATOM | 231 | CE | LYS | A | 60 | −51.028 | 37.983 | −1.189 | 1.00 | 79.74 | C |
| ATOM | 232 | NZ | LYS | A | 60 | −52.299 | 37.333 | −1.081 | 1.00 | 83.19 | N |
| ATOM | 233 | N | PHE | A | 61 | −45.209 | 38.597 | −0.856 | 1.00 | 78.18 | N |
| ATOM | 234 | CA | PHE | A | 61 | −44.861 | 39.919 | −0.334 | 1.00 | 79.67 | C |
| ATOM | 235 | C | PHE | A | 61 | −43.457 | 40.379 | −0.743 | 1.00 | 81.98 | C |
| ATOM | 236 | O | PHE | A | 61 | −42.443 | 39.855 | −0.253 | 1.00 | 78.47 | O |
| ATOM | 237 | CB | PHE | A | 61 | −45.055 | 39.943 | 1.185 | 1.00 | 78.50 | C |
| ATOM | 238 | CG | PHE | A | 61 | −46.488 | 39.744 | 1.589 | 1.00 | 77.03 | C |
| ATOM | 239 | CD1 | PHE | A | 61 | −46.946 | 38.513 | 2.013 | 1.00 | 74.37 | C |
| ATOM | 240 | CD2 | PHE | A | 61 | −47.385 | 40.799 | 1.536 | 1.00 | 79.08 | C |
| ATOM | 241 | CE1 | PHE | A | 61 | −48.267 | 38.334 | 2.380 | 1.00 | 77.21 | C |
| ATOM | 242 | CE2 | PHE | A | 61 | −48.708 | 40.621 | 1.903 | 1.00 | 77.13 | C |
| ATOM | 243 | CZ | PHE | A | 61 | −49.141 | 39.382 | 2.326 | 1.00 | 75.36 | C |
| ATOM | 244 | N | GLU | A | 62 | −43.450 | 41.369 | −1.648 | 1.00 | 84.43 | N |
| ATOM | 245 | CA | GLU | A | 62 | −42.247 | 42.031 | −2.208 | 1.00 | 86.75 | C |
| ATOM | 246 | C | GLU | A | 62 | −41.256 | 42.491 | −1.122 | 1.00 | 89.37 | C |
| ATOM | 247 | O | GLU | A | 62 | −40.040 | 42.414 | −1.313 | 1.00 | 90.84 | O |

APPENDIX 1-continued

| ATOM | 248 | CB | GLU | A | 62 | −42.699 | 43.219 | −3.080 | 1.00 | 86.58 | C |
|---|---|---|---|---|---|---|---|---|---|---|---|
| ATOM | 249 | CG | GLU | A | 62 | −41.641 | 43.860 | −3.967 | 1.00 | 87.94 | C |
| ATOM | 250 | CD | GLU | A | 62 | −42.234 | 44.940 | −4.911 | 1.00 | 90.76 | C |
| ATOM | 251 | OE1 | GLU | A | 62 | −43.321 | 44.720 | −5.505 | 1.00 | 96.67 | O |
| ATOM | 252 | OE2 | GLU | A | 62 | −41.611 | 46.016 | −5.065 | 1.00 | 89.94 | O |
| ATOM | 253 | N | ARG | A | 63 | −41.798 | 42.964 | 0.003 | 1.00 | 90.60 | N |
| ATOM | 254 | CA | ARG | A | 63 | −41.036 | 43.318 | 1.207 | 1.00 | 88.93 | C |
| ATOM | 255 | C | ARG | A | 63 | −40.139 | 42.177 | 1.705 | 1.00 | 88.02 | C |
| ATOM | 256 | O | ARG | A | 63 | −39.007 | 42.409 | 2.131 | 1.00 | 88.49 | O |
| ATOM | 257 | CB | ARG | A | 63 | −42.028 | 43.691 | 2.309 | 1.00 | 91.49 | C |
| ATOM | 258 | CG | ARG | A | 63 | −41.443 | 43.980 | 3.698 | 1.00 | 95.03 | C |
| ATOM | 259 | CD | ARG | A | 63 | −42.573 | 44.340 | 4.643 | 1.00 | 99.84 | C |
| ATOM | 260 | NE | ARG | A | 63 | −42.113 | 44.841 | 5.939 | 1.00 | 103.70 | N |
| ATOM | 261 | CZ | ARG | A | 63 | −42.903 | 45.373 | 6.882 | 1.00 | 105.87 | C |
| ATOM | 262 | NH1 | ARG | A | 63 | −44.231 | 45.491 | 6.708 | 1.00 | 107.12 | N |
| ATOM | 263 | NH2 | ARG | A | 63 | −42.362 | 45.796 | 8.028 | 1.00 | 109.62 | N |
| ATOM | 264 | N | LEU | A | 64 | −40.658 | 40.955 | 1.648 | 1.00 | 85.74 | N |
| ATOM | 265 | CA | LEU | A | 64 | −39.932 | 39.775 | 2.097 | 1.00 | 82.11 | C |
| ATOM | 266 | C | LEU | A | 64 | −39.032 | 39.168 | 1.011 | 1.00 | 81.55 | C |
| ATOM | 267 | O | LEU | A | 64 | −38.378 | 38.184 | 1.272 | 1.00 | 78.38 | O |
| ATOM | 268 | CB | LEU | A | 64 | −40.923 | 38.712 | 2.602 | 1.00 | 80.82 | C |
| ATOM | 269 | CG | LEU | A | 64 | −41.851 | 39.090 | 3.769 | 1.00 | 79.80 | C |
| ATOM | 270 | CD1 | LEU | A | 64 | −42.899 | 37.999 | 4.007 | 1.00 | 70.96 | C |
| ATOM | 271 | CD2 | LEU | A | 64 | −41.056 | 39.337 | 5.038 | 1.00 | 73.56 | C |
| ATOM | 272 | N | GLN | A | 65 | −38.992 | 39.745 | −0.198 | 1.00 | 82.04 | N |
| ATOM | 273 | CA | GLN | A | 65 | −38.174 | 39.189 | −1.308 | 1.00 | 83.43 | C |
| ATOM | 274 | C | GLN | A | 65 | −36.720 | 39.672 | −1.264 | 1.00 | 83.31 | C |
| ATOM | 275 | O | GLN | A | 65 | −36.305 | 40.518 | −2.060 | 1.00 | 86.84 | O |
| ATOM | 276 | CB | GLN | A | 65 | −38.820 | 39.500 | −2.662 | 1.00 | 82.54 | C |
| ATOM | 277 | CG | GLN | A | 65 | −40.120 | 38.749 | −2.856 | 1.00 | 84.91 | C |
| ATOM | 278 | CD | GLN | A | 65 | −40.789 | 39.016 | −4.182 | 1.00 | 88.24 | C |
| ATOM | 279 | OE1 | GLN | A | 65 | −40.516 | 40.018 | −4.857 | 1.00 | 97.81 | O |
| ATOM | 280 | NE2 | GLN | A | 65 | −41.681 | 38.114 | −4.569 | 1.00 | 97.75 | N |
| ATOM | 281 | N | THR | A | 66 | −35.973 | 39.113 | −0.320 | 1.00 | 80.37 | N |
| ATOM | 282 | CA | THR | A | 66 | −34.561 | 39.413 | −0.090 | 1.00 | 79.80 | C |
| ATOM | 283 | C | THR | A | 66 | −33.747 | 38.170 | −0.355 | 1.00 | 79.26 | C |
| ATOM | 284 | O | THR | A | 66 | −34.306 | 37.105 | −0.428 | 1.00 | 82.12 | O |
| ATOM | 285 | CB | THR | A | 66 | −34.334 | 39.778 | 1.353 | 1.00 | 79.66 | C |
| ATOM | 286 | OG1 | THR | A | 66 | −34.641 | 38.639 | 2.177 | 1.00 | 79.38 | O |
| ATOM | 287 | CG2 | THR | A | 66 | −35.218 | 40.953 | 1.753 | 1.00 | 75.58 | C |
| ATOM | 288 | N | VAL | A | 67 | −32.431 | 38.303 | −0.492 | 1.00 | 76.86 | N |
| ATOM | 289 | CA | VAL | A | 67 | −31.561 | 37.138 | −0.771 | 1.00 | 76.42 | C |
| ATOM | 290 | C | VAL | A | 67 | −31.679 | 36.080 | 0.342 | 1.00 | 76.58 | C |
| ATOM | 291 | O | VAL | A | 67 | −31.869 | 34.888 | 0.050 | 1.00 | 76.26 | O |
| ATOM | 292 | CB | VAL | A | 67 | −30.087 | 37.543 | −0.956 | 1.00 | 77.31 | C |
| ATOM | 293 | CG1 | VAL | A | 67 | −29.185 | 36.325 | −0.914 | 1.00 | 75.37 | C |
| ATOM | 294 | CG2 | VAL | A | 67 | −29.900 | 38.301 | −2.270 | 1.00 | 72.45 | C |
| ATOM | 295 | N | THR | A | 68 | −31.568 | 36.512 | 1.597 | 1.00 | 71.98 | N |
| ATOM | 296 | CA | THR | A | 68 | −31.754 | 35.609 | 2.736 | 1.00 | 72.07 | C |
| ATOM | 297 | C | THR | A | 68 | −33.028 | 34.797 | 2.566 | 1.00 | 71.33 | C |
| ATOM | 298 | O | THR | A | 68 | −33.001 | 33.564 | 2.645 | 1.00 | 69.01 | O |
| ATOM | 299 | CB | THR | A | 68 | −31.810 | 36.372 | 4.062 | 1.00 | 71.58 | C |
| ATOM | 300 | OG1 | THR | A | 68 | −30.546 | 37.009 | 4.283 | 1.00 | 73.28 | O |
| ATOM | 301 | CG2 | THR | A | 68 | −32.098 | 35.420 | 5.213 | 1.00 | 71.59 | C |
| ATOM | 302 | N | ASN | A | 69 | −34.139 | 35.488 | 2.321 | 1.00 | 71.44 | N |
| ATOM | 303 | CA | ASN | A | 69 | −35.438 | 34.810 | 2.146 | 1.00 | 70.87 | C |
| ATOM | 304 | C | ASN | A | 69 | −35.534 | 33.842 | 0.957 | 1.00 | 71.14 | C |
| ATOM | 305 | O | ASN | A | 69 | −36.425 | 32.981 | 0.941 | 1.00 | 73.32 | O |
| ATOM | 306 | CB | ASN | A | 69 | −36.571 | 35.835 | 2.123 | 1.00 | 68.01 | C |
| ATOM | 307 | CG | ASN | A | 69 | −36.794 | 36.501 | 3.503 | 1.00 | 72.26 | C |
| ATOM | 308 | OD1 | ASN | A | 69 | −36.311 | 36.018 | 4.539 | 1.00 | 66.06 | O |
| ATOM | 309 | ND2 | ASN | A | 69 | −37.525 | 37.606 | 3.513 | 1.00 | 72.74 | N |
| ATOM | 310 | N | TYR | A | 70 | −34.640 | 33.969 | −0.023 | 1.00 | 72.21 | N |
| ATOM | 311 | CA | TYR | A | 70 | −34.578 | 33.002 | −1.133 | 1.00 | 73.01 | C |
| ATOM | 312 | C | TYR | A | 70 | −33.995 | 31.695 | −0.599 | 1.00 | 73.34 | C |
| ATOM | 313 | O | TYR | A | 70 | −34.479 | 30.630 | −0.942 | 1.00 | 77.66 | O |
| ATOM | 314 | CB | TYR | A | 70 | −33.781 | 33.529 | −2.341 | 1.00 | 74.09 | C |
| ATOM | 315 | CG | TYR | A | 70 | −34.536 | 34.496 | −3.245 | 1.00 | 75.84 | C |
| ATOM | 316 | CD1 | TYR | A | 70 | −35.265 | 35.553 | −2.732 | 1.00 | 82.81 | C |
| ATOM | 317 | CD2 | TYR | A | 70 | −34.514 | 34.348 | −4.620 | 1.00 | 84.86 | C |
| ATOM | 318 | CE1 | TYR | A | 70 | −35.957 | 36.444 | −3.555 | 1.00 | 84.18 | C |
| ATOM | 319 | CE2 | TYR | A | 70 | −35.200 | 35.229 | −5.453 | 1.00 | 85.94 | C |
| ATOM | 320 | CZ | TYR | A | 70 | −35.921 | 36.278 | −4.918 | 1.00 | 84.44 | C |
| ATOM | 321 | OH | TYR | A | 70 | −36.603 | 37.149 | −5.771 | 1.00 | 85.23 | O |
| ATOM | 322 | N | PHE | A | 71 | −32.961 | 31.788 | 0.238 | 1.00 | 75.67 | N |
| ATOM | 323 | CA | PHE | A | 71 | −32.384 | 30.609 | 0.904 | 1.00 | 73.91 | C |
| ATOM | 324 | C | PHE | A | 71 | −33.360 | 30.004 | 1.903 | 1.00 | 75.76 | C |
| ATOM | 325 | O | PHE | A | 71 | −33.426 | 28.779 | 2.046 | 1.00 | 72.03 | O |
| ATOM | 326 | CB | PHE | A | 71 | −31.108 | 30.949 | 1.666 | 1.00 | 74.63 | C |
| ATOM | 327 | CG | PHE | A | 71 | −30.024 | 31.535 | 0.817 | 1.00 | 72.11 | C |

APPENDIX 1-continued

| ATOM | 328 | CD1 | PHE | A | 71 | −29.584 | 30.876 | −0.311 | 1.00 | 69.28 | C |
|------|-----|-----|-----|---|----|---------|--------|--------|------|-------|---|
| ATOM | 329 | CD2 | PHE | A | 71 | −29.438 | 32.748 | 1.158 | 1.00 | 70.30 | C |
| ATOM | 330 | CE1 | PHE | A | 71 | −28.583 | 31.413 | −1.095 | 1.00 | 74.96 | C |
| ATOM | 331 | CE2 | PHE | A | 71 | −28.449 | 33.285 | 0.396 | 1.00 | 72.37 | C |
| ATOM | 332 | CZ | PHE | A | 71 | −28.013 | 32.613 | −0.749 | 1.00 | 76.19 | C |
| ATOM | 333 | N | ILE | A | 72 | −34.111 | 30.863 | 2.595 | 1.00 | 71.39 | N |
| ATOM | 334 | CA | ILE | A | 72 | −35.160 | 30.393 | 3.485 | 1.00 | 71.36 | C |
| ATOM | 335 | C | ILE | A | 72 | −36.192 | 29.597 | 2.692 | 1.00 | 73.02 | C |
| ATOM | 336 | O | ILE | A | 72 | −36.652 | 28.546 | 3.151 | 1.00 | 70.62 | O |
| ATOM | 337 | CB | ILE | A | 72 | −35.868 | 31.541 | 4.197 | 1.00 | 68.07 | C |
| ATOM | 338 | CG1 | ILE | A | 72 | −34.924 | 32.236 | 5.203 | 1.00 | 79.57 | C |
| ATOM | 339 | CG2 | ILE | A | 72 | −37.089 | 31.044 | 4.929 | 1.00 | 67.38 | C |
| ATOM | 340 | CD1 | ILE | A | 72 | −34.499 | 31.384 | 6.367 | 1.00 | 74.31 | C |
| ATOM | 341 | N | THR | A | 73 | −36.554 | 30.100 | 1.506 | 1.00 | 70.93 | N |
| ATOM | 342 | CA | THR | A | 73 | −37.500 | 29.397 | 0.644 | 1.00 | 71.88 | C |
| ATOM | 343 | C | THR | A | 73 | −36.937 | 28.040 | 0.264 | 1.00 | 73.34 | C |
| ATOM | 344 | O | THR | A | 73 | −37.663 | 27.045 | 0.296 | 1.00 | 77.13 | O |
| ATOM | 345 | CB | THR | A | 73 | −37.840 | 30.208 | −0.618 | 1.00 | 73.11 | C |
| ATOM | 346 | OG1 | THR | A | 73 | −38.491 | 31.424 | −0.228 | 1.00 | 71.91 | O |
| ATOM | 347 | CG2 | THR | A | 73 | −38.747 | 29.418 | −1.548 | 1.00 | 72.28 | C |
| ATOM | 348 | N | SER | A | 74 | −35.654 | 28.000 | −0.091 | 1.00 | 73.09 | N |
| ATOM | 349 | CA | SER | A | 74 | −34.981 | 26.740 | −0.409 | 1.00 | 74.48 | C |
| ATOM | 350 | C | SER | A | 74 | −35.030 | 25.775 | 0.800 | 1.00 | 74.98 | C |
| ATOM | 351 | O | SER | A | 74 | −35.270 | 24.570 | 0.638 | 1.00 | 78.94 | O |
| ATOM | 352 | CB | SER | A | 74 | −33.546 | 27.014 | −0.877 | 1.00 | 74.59 | C |
| ATOM | 353 | OG | SER | A | 74 | −32.820 | 25.829 | −1.084 | 1.00 | 73.96 | O |
| ATOM | 354 | N | LEU | A | 75 | −34.810 | 26.318 | 1.995 | 1.00 | 73.74 | N |
| ATOM | 355 | CA | LEU | A | 75 | −34.911 | 25.567 | 3.255 | 1.00 | 72.08 | C |
| ATOM | 356 | C | LEU | A | 75 | −36.351 | 25.067 | 3.482 | 1.00 | 71.55 | C |
| ATOM | 357 | O | LEU | A | 75 | −36.565 | 23.897 | 3.819 | 1.00 | 71.52 | O |
| ATOM | 358 | CB | LEU | A | 75 | −34.437 | 26.455 | 4.418 | 1.00 | 72.86 | C |
| ATOM | 359 | CG | LEU | A | 75 | −34.085 | 25.884 | 5.771 | 1.00 | 78.35 | C |
| ATOM | 360 | CD1 | LEU | A | 75 | −33.026 | 24.797 | 5.661 | 1.00 | 80.50 | C |
| ATOM | 361 | CD2 | LEU | A | 75 | −33.614 | 27.061 | 6.695 | 1.00 | 77.36 | C |
| ATOM | 362 | N | ALA | A | 76 | −37.326 | 25.958 | 3.290 | 1.00 | 69.20 | N |
| ATOM | 363 | CA | ALA | A | 76 | −38.758 | 25.610 | 3.373 | 1.00 | 70.43 | C |
| ATOM | 364 | C | ALA | A | 76 | −39.206 | 24.520 | 2.362 | 1.00 | 70.45 | C |
| ATOM | 365 | O | ALA | A | 76 | −40.112 | 23.747 | 2.658 | 1.00 | 73.21 | O |
| ATOM | 366 | CB | ALA | A | 76 | −39.613 | 26.864 | 3.200 | 1.00 | 67.40 | C |
| ATOM | 367 | N | CYS | A | 77 | −38.578 | 24.461 | 1.184 | 1.00 | 72.62 | N |
| ATOM | 368 | CA | CYS | A | 77 | −38.911 | 23.411 | 0.176 | 1.00 | 72.54 | C |
| ATOM | 369 | C | CYS | A | 77 | −38.399 | 22.039 | 0.601 | 1.00 | 71.97 | C |
| ATOM | 370 | O | CYS | A | 77 | −39.084 | 21.047 | 0.401 | 1.00 | 75.84 | O |
| ATOM | 371 | CB | CYS | A | 77 | −38.350 | 23.752 | −1.195 | 1.00 | 71.94 | C |
| ATOM | 372 | SG | CYS | A | 77 | −39.135 | 25.162 | −1.970 | 1.00 | 78.85 | S |
| ATOM | 373 | N | ALA | A | 78 | −37.197 | 22.000 | 1.181 | 1.00 | 71.07 | N |
| ATOM | 374 | CA | ALA | A | 78 | −36.609 | 20.774 | 1.704 | 1.00 | 70.88 | C |
| ATOM | 375 | C | ALA | A | 78 | −37.457 | 20.206 | 2.846 | 1.00 | 71.74 | C |
| ATOM | 376 | O | ALA | A | 78 | −37.644 | 18.997 | 2.947 | 1.00 | 72.80 | O |
| ATOM | 377 | CB | ALA | A | 78 | −35.174 | 21.031 | 2.172 | 1.00 | 68.59 | C |
| ATOM | 378 | N | ASP | A | 79 | −37.964 | 21.083 | 3.698 | 1.00 | 71.88 | N |
| ATOM | 379 | CA | ASP | A | 79 | −38.859 | 20.676 | 4.783 | 1.00 | 71.72 | C |
| ATOM | 380 | C | ASP | A | 79 | −40.240 | 20.312 | 4.244 | 1.00 | 70.22 | C |
| ATOM | 381 | O | ASP | A | 79 | −40.872 | 19.384 | 4.743 | 1.00 | 70.23 | O |
| ATOM | 382 | CB | ASP | A | 79 | −38.934 | 21.775 | 5.847 | 1.00 | 68.87 | C |
| ATOM | 383 | CG | ASP | A | 79 | −37.609 | 21.931 | 6.630 | 1.00 | 82.57 | C |
| ATOM | 384 | OD1 | ASP | A | 79 | −36.914 | 20.899 | 6.889 | 1.00 | 83.92 | O |
| ATOM | 385 | OD2 | ASP | A | 79 | −37.258 | 23.081 | 6.992 | 1.00 | 79.92 | O |
| ATOM | 386 | N | LEU | A | 80 | −40.712 | 21.034 | 3.237 | 1.00 | 67.28 | N |
| ATOM | 387 | CA | LEU | A | 80 | −42.008 | 20.683 | 2.616 | 1.00 | 68.96 | C |
| ATOM | 388 | C | LEU | A | 80 | −41.960 | 19.284 | 2.009 | 1.00 | 65.98 | C |
| ATOM | 389 | O | LEU | A | 80 | −42.889 | 18.505 | 2.184 | 1.00 | 70.25 | O |
| ATOM | 390 | CB | LEU | A | 80 | −42.430 | 21.705 | 1.562 | 1.00 | 63.48 | C |
| ATOM | 391 | CG | LEU | A | 80 | −43.828 | 21.494 | 0.969 | 1.00 | 70.22 | C |
| ATOM | 392 | CD1 | LEU | A | 80 | −44.896 | 21.346 | 2.048 | 1.00 | 68.20 | C |
| ATOM | 393 | CD2 | LEU | A | 80 | −44.193 | 22.645 | −0.015 | 1.00 | 74.86 | C |
| ATOM | 394 | N | VAL | A | 81 | −40.877 | 18.972 | 1.302 | 1.00 | 66.65 | N |
| ATOM | 395 | CA | VAL | A | 81 | −40.686 | 17.628 | 0.713 | 1.00 | 68.44 | C |
| ATOM | 396 | C | VAL | A | 81 | −40.559 | 16.537 | 1.815 | 1.00 | 68.93 | C |
| ATOM | 397 | O | VAL | A | 81 | −41.066 | 15.426 | 1.647 | 1.00 | 71.60 | O |
| ATOM | 398 | CB | VAL | A | 81 | −39.475 | 17.608 | −0.253 | 1.00 | 68.36 | C |
| ATOM | 399 | CG1 | VAL | A | 81 | −39.202 | 16.216 | −0.740 | 1.00 | 65.96 | C |
| ATOM | 400 | CG2 | VAL | A | 81 | −39.713 | 18.581 | −1.445 | 1.00 | 63.74 | C |
| ATOM | 401 | N | MET | A | 82 | −39.889 | 16.859 | 2.923 | 1.00 | 67.67 | N |
| ATOM | 402 | CA | MET | A | 82 | −39.862 | 15.968 | 4.099 | 1.00 | 69.67 | C |
| ATOM | 403 | C | MET | A | 82 | −41.282 | 15.658 | 4.578 | 1.00 | 67.76 | C |
| ATOM | 404 | O | MET | A | 82 | −41.632 | 14.503 | 4.804 | 1.00 | 66.68 | O |
| ATOM | 405 | CB | MET | A | 82 | −39.088 | 16.603 | 5.245 | 1.00 | 70.60 | C |
| ATOM | 406 | CG | MET | A | 82 | −37.580 | 16.550 | 5.089 | 1.00 | 76.37 | C |
| ATOM | 407 | SD | MET | A | 82 | −36.812 | 15.024 | 5.666 | 1.00 | 86.09 | S |

APPENDIX 1-continued

| | | | | | | | | | | | |
|---|---|---|---|---|---|---|---|---|---|---|---|
| ATOM | 408 | CE  | MET | A | 82 | −37.447 | 15.024 | 7.316  | 1.00 | 88.14 | C |
| ATOM | 409 | N   | GLY | A | 83 | −42.089 | 16.703 | 4.725  | 1.00 | 66.27 | N |
| ATOM | 410 | CA  | GLY | A | 83 | −43.480 | 16.564 | 5.170  | 1.00 | 68.36 | C |
| ATOM | 411 | C   | GLY | A | 83 | −44.416 | 15.795 | 4.250  | 1.00 | 71.02 | C |
| ATOM | 412 | O   | GLY | A | 83 | −45.350 | 15.161 | 4.730  | 1.00 | 72.14 | O |
| ATOM | 413 | N   | LEU | A | 84 | −44.169 | 15.853 | 2.939  | 1.00 | 71.19 | N |
| ATOM | 414 | CA  | LEU | A | 84 | −45.010 | 15.170 | 1.939  | 1.00 | 73.59 | C |
| ATOM | 415 | C   | LEU | A | 84 | −44.469 | 13.816 | 1.460  | 1.00 | 73.92 | C |
| ATOM | 416 | O   | LEU | A | 84 | −45.224 | 12.859 | 1.294  | 1.00 | 72.70 | O |
| ATOM | 417 | CB  | LEU | A | 84 | −45.195 | 16.069 | 0.702  | 1.00 | 72.52 | C |
| ATOM | 418 | CG  | LEU | A | 84 | −45.901 | 17.406 | 0.885  | 1.00 | 75.09 | C |
| ATOM | 419 | CD1 | LEU | A | 84 | −45.933 | 18.147 | −0.445 | 1.00 | 78.12 | C |
| ATOM | 420 | CD2 | LEU | A | 84 | −47.316 | 17.232 | 1.430  | 1.00 | 77.53 | C |
| ATOM | 421 | N   | ALA | A | 85 | −43.166 | 13.751 | 1.237  | 1.00 | 73.21 | N |
| ATOM | 422 | CA  | ALA | A | 85 | −42.540 | 12.584 | 0.628  | 1.00 | 73.60 | C |
| ATOM | 423 | C   | ALA | A | 85 | −41.858 | 11.673 | 1.615  | 1.00 | 72.66 | C |
| ATOM | 424 | O   | ALA | A | 85 | −41.825 | 10.482 | 1.377  | 1.00 | 78.23 | O |
| ATOM | 425 | CB  | ALA | A | 85 | −41.533 | 13.043 | −0.426 | 1.00 | 74.36 | C |
| ATOM | 426 | N   | VAL | A | 86 | −41.319 | 12.218 | 2.710  | 1.00 | 74.33 | N |
| ATOM | 427 | CA  | VAL | A | 86 | −40.544 | 11.419 | 3.678  | 1.00 | 71.85 | C |
| ATOM | 428 | C   | VAL | A | 86 | −41.349 | 11.025 | 4.910  | 1.00 | 71.02 | C |
| ATOM | 429 | O   | VAL | A | 86 | −41.584 | 9.860  | 5.132  | 1.00 | 73.11 | O |
| ATOM | 430 | CB  | VAL | A | 86 | −39.254 | 12.136 | 4.110  | 1.00 | 71.51 | C |
| ATOM | 431 | CG1 | VAL | A | 86 | −38.400 | 11.213 | 4.969  | 1.00 | 68.65 | C |
| ATOM | 432 | CG2 | VAL | A | 86 | −38.467 | 12.587 | 2.885  | 1.00 | 70.81 | C |
| ATOM | 433 | N   | VAL | A | 87 | −41.773 | 11.995 | 5.707  | 1.00 | 71.04 | N |
| ATOM | 434 | CA  | VAL | A | 87 | −42.455 | 11.692 | 7.002  | 1.00 | 71.84 | C |
| ATOM | 435 | C   | VAL | A | 87 | −43.718 | 10.799 | 6.915  | 1.00 | 72.51 | C |
| ATOM | 436 | O   | VAL | A | 87 | −43.894 | 9.940  | 7.783  | 1.00 | 76.50 | O |
| ATOM | 437 | CB  | VAL | A | 87 | −42.798 | 12.999 | 7.819  | 1.00 | 72.70 | C |
| ATOM | 438 | CG1 | VAL | A | 87 | −43.506 | 12.655 | 9.148  | 1.00 | 65.72 | C |
| ATOM | 439 | CG2 | VAL | A | 87 | −41.549 | 13.826 | 8.093  | 1.00 | 69.80 | C |
| ATOM | 440 | N   | PRO | A | 88 | −44.588 | 10.984 | 5.886  | 1.00 | 74.57 | N |
| ATOM | 441 | CA  | PRO | A | 88 | −45.792 | 10.131 | 5.828  | 1.00 | 73.89 | C |
| ATOM | 442 | C   | PRO | A | 88 | −45.514 | 8.629  | 5.696  | 1.00 | 74.31 | C |
| ATOM | 443 | O   | PRO | A | 88 | −46.204 | 7.831  | 6.322  | 1.00 | 72.95 | O |
| ATOM | 444 | CB  | PRO | A | 88 | −46.529 | 10.654 | 4.580  | 1.00 | 72.19 | C |
| ATOM | 445 | CG  | PRO | A | 88 | −46.040 | 12.026 | 4.413  | 1.00 | 70.91 | C |
| ATOM | 446 | CD  | PRO | A | 88 | −44.581 | 11.922 | 4.748  | 1.00 | 75.19 | C |
| ATOM | 447 | N   | PHE | A | 89 | −44.517 | 8.266  | 4.895  | 1.00 | 75.27 | N |
| ATOM | 448 | CA  | PHE | A | 89 | −44.153 | 6.857  | 4.707  | 1.00 | 76.82 | C |
| ATOM | 449 | C   | PHE | A | 89 | −43.325 | 6.300  | 5.850  | 1.00 | 75.58 | C |
| ATOM | 450 | O   | PHE | A | 89 | −43.466 | 5.124  | 6.182  | 1.00 | 76.46 | O |
| ATOM | 451 | CB  | PHE | A | 89 | −43.434 | 6.665  | 3.380  | 1.00 | 81.35 | C |
| ATOM | 452 | CG  | PHE | A | 89 | −44.258 | 7.080  | 2.177  | 1.00 | 87.88 | C |
| ATOM | 453 | CD1 | PHE | A | 89 | −45.600 | 6.699  | 2.046  | 1.00 | 93.20 | C |
| ATOM | 454 | CD2 | PHE | A | 89 | −43.709 | 7.840  | 1.186  | 1.00 | 87.00 | C |
| ATOM | 455 | CE1 | PHE | A | 89 | −46.350 | 7.082  | 0.940  | 1.00 | 93.35 | C |
| ATOM | 456 | CE2 | PHE | A | 89 | −44.469 | 8.219  | 0.076  | 1.00 | 92.27 | C |
| ATOM | 457 | CZ  | PHE | A | 89 | −45.780 | 7.839  | −0.040 | 1.00 | 91.97 | C |
| ATOM | 458 | N   | GLY | A | 90 | −42.468 | 7.125  | 6.444  | 1.00 | 74.71 | N |
| ATOM | 459 | CA  | GLY | A | 90 | −41.738 | 6.731  | 7.650  | 1.00 | 75.06 | C |
| ATOM | 460 | C   | GLY | A | 90 | −42.728 | 6.369  | 8.749  | 1.00 | 74.16 | C |
| ATOM | 461 | O   | GLY | A | 90 | −42.572 | 5.341  | 9.402  | 1.00 | 77.84 | O |
| ATOM | 462 | N   | ALA | A | 91 | −43.747 | 7.223  | 8.939  | 1.00 | 72.72 | N |
| ATOM | 463 | CA  | ALA | A | 91 | −44.835 | 6.994  | 9.912  | 1.00 | 72.43 | C |
| ATOM | 464 | C   | ALA | A | 91 | −45.543 | 5.664  | 9.680  | 1.00 | 74.22 | C |
| ATOM | 465 | O   | ALA | A | 91 | −45.668 | 4.853  | 10.604 | 1.00 | 74.73 | O |
| ATOM | 466 | CB  | ALA | A | 91 | −45.849 | 8.129  | 9.849  | 1.00 | 69.78 | C |
| ATOM | 467 | N   | ALA | A | 92 | −45.999 | 5.464  | 8.437  | 1.00 | 73.35 | N |
| ATOM | 468 | CA  | ALA | A | 92 | −46.699 | 4.241  | 8.013  | 1.00 | 74.78 | C |
| ATOM | 469 | C   | ALA | A | 92 | −45.850 | 2.998  | 8.219  | 1.00 | 73.86 | C |
| ATOM | 470 | O   | ALA | A | 92 | −46.355 | 1.985  | 8.671  | 1.00 | 76.34 | O |
| ATOM | 471 | CB  | ALA | A | 92 | −47.131 | 4.348  | 6.541  | 1.00 | 73.00 | C |
| ATOM | 472 | N   | HIS | A | 93 | −44.566 | 3.098  | 7.881  | 1.00 | 75.22 | N |
| ATOM | 473 | CA  | HIS | A | 93 | −43.592 | 2.022  | 8.080  | 1.00 | 75.74 | C |
| ATOM | 474 | C   | HIS | A | 93 | −43.521 | 1.575  | 9.543  | 1.00 | 76.69 | C |
| ATOM | 475 | O   | HIS | A | 93 | −43.429 | 0.383  | 9.818  | 1.00 | 80.31 | O |
| ATOM | 476 | CB  | HIS | A | 93 | −42.216 | 2.487  | 7.579  | 1.00 | 77.29 | C |
| ATOM | 477 | CG  | HIS | A | 93 | −41.151 | 1.442  | 7.633  | 1.00 | 75.35 | C |
| ATOM | 478 | ND1 | HIS | A | 93 | −39.816 | 1.752  | 7.759  | 1.00 | 74.50 | N |
| ATOM | 479 | CD2 | HIS | A | 93 | −41.220 | 0.094  | 7.579  | 1.00 | 76.44 | C |
| ATOM | 480 | CE1 | HIS | A | 93 | −39.110 | 0.635  | 7.779  | 1.00 | 78.85 | C |
| ATOM | 481 | NE2 | HIS | A | 93 | −39.939 | −0.386 | 7.671  | 1.00 | 74.19 | N |
| ATOM | 482 | N   | ILE | A | 94 | −43.568 | 2.533  | 10.464 | 1.00 | 77.24 | N |
| ATOM | 483 | CA  | ILE | A | 94 | −43.534 | 2.243  | 11.901 | 1.00 | 77.99 | C |
| ATOM | 484 | C   | ILE | A | 94 | −44.855 | 1.668  | 12.417 | 1.00 | 78.57 | C |
| ATOM | 485 | O   | ILE | A | 94 | −44.853 | 0.680  | 13.162 | 1.00 | 80.24 | O |
| ATOM | 486 | CB  | ILE | A | 94 | −43.193 | 3.506  | 12.720 | 1.00 | 78.41 | C |
| ATOM | 487 | CG1 | ILE | A | 94 | −41.745 | 3.911  | 12.482 | 1.00 | 78.28 | C |

APPENDIX 1-continued

| | | | | | | | | | | |
|---|---|---|---|---|---|---|---|---|---|---|
| ATOM | 488 | CG2 | ILE | A | 94 | −43.404 | 3.262 | 14.201 | 1.00 | 79.28 | C |
| ATOM | 489 | CD1 | ILE | A | 94 | −41.379 | 5.210 | 13.108 | 1.00 | 77.39 | C |
| ATOM | 490 | N | LEU | A | 95 | −45.967 | 2.283 | 12.024 | 1.00 | 78.45 | N |
| ATOM | 491 | CA | LEU | A | 95 | −47.302 | 1.855 | 12.478 | 1.00 | 79.09 | C |
| ATOM | 492 | C | LEU | A | 95 | −47.729 | 0.492 | 11.925 | 1.00 | 80.71 | C |
| ATOM | 493 | O | LEU | A | 95 | −48.401 | −0.271 | 12.626 | 1.00 | 82.74 | O |
| ATOM | 494 | CB | LEU | A | 95 | −48.347 | 2.916 | 12.119 | 1.00 | 79.29 | C |
| ATOM | 495 | CG | LEU | A | 95 | −48.202 | 4.255 | 12.843 | 1.00 | 78.03 | C |
| ATOM | 496 | CD1 | LEU | A | 95 | −49.033 | 5.334 | 12.164 | 1.00 | 77.81 | C |
| ATOM | 497 | CD2 | LEU | A | 95 | −48.587 | 4.110 | 14.306 | 1.00 | 75.72 | C |
| ATOM | 498 | N | MET | A | 96 | −47.346 | 0.195 | 10.685 | 1.00 | 80.36 | N |
| ATOM | 499 | CA | MET | A | 96 | −47.635 | −1.103 | 10.066 | 1.00 | 80.57 | C |
| ATOM | 500 | C | MET | A | 96 | −46.592 | −2.157 | 10.421 | 1.00 | 78.70 | C |
| ATOM | 501 | O | MET | A | 96 | −46.849 | −3.336 | 10.242 | 1.00 | 75.20 | O |
| ATOM | 502 | CB | MET | A | 96 | −47.727 | −0.965 | 8.552 | 1.00 | 80.83 | C |
| ATOM | 503 | CG | MET | A | 96 | −48.948 | −0.212 | 8.114 | 1.00 | 83.20 | C |
| ATOM | 504 | SD | MET | A | 96 | −48.947 | 0.080 | 6.357 | 1.00 | 91.34 | S |
| ATOM | 505 | CE | MET | A | 96 | −50.698 | 0.372 | 6.060 | 1.00 | 92.81 | C |
| ATOM | 506 | N | LYS | A | 97 | −45.429 | −1.717 | 10.918 | 1.00 | 80.00 | N |
| ATOM | 507 | CA | LYS | A | 97 | −44.302 | −2.598 | 11.317 | 1.00 | 81.41 | C |
| ATOM | 508 | C | LYS | A | 97 | −43.720 | −3.385 | 10.128 | 1.00 | 79.08 | C |
| ATOM | 509 | O | LYS | A | 97 | −43.216 | −4.494 | 10.294 | 1.00 | 78.90 | O |
| ATOM | 510 | CB | LYS | A | 97 | −44.705 | −3.535 | 12.483 | 1.00 | 82.51 | C |
| ATOM | 511 | CG | LYS | A | 97 | −45.084 | −2.800 | 13.750 | 1.00 | 85.16 | C |
| ATOM | 512 | CD | LYS | A | 97 | −45.946 | −3.663 | 14.664 | 1.00 | 86.38 | C |
| ATOM | 513 | CE | LYS | A | 97 | −46.262 | −2.937 | 15.971 | 1.00 | 90.74 | C |
| ATOM | 514 | NZ | LYS | A | 97 | −46.864 | −1.569 | 15.763 | 1.00 | 92.55 | N |
| ATOM | 515 | N | MET | A | 98 | −43.797 | −2.788 | 8.941 | 1.00 | 78.37 | N |
| ATOM | 516 | CA | MET | A | 98 | −43.317 | −3.387 | 7.703 | 1.00 | 78.62 | C |
| ATOM | 517 | C | MET | A | 98 | −43.508 | −2.378 | 6.592 | 1.00 | 78.05 | C |
| ATOM | 518 | O | MET | A | 98 | −44.326 | −1.458 | 6.720 | 1.00 | 80.11 | O |
| ATOM | 519 | CB | MET | A | 98 | −44.045 | −4.706 | 7.375 | 1.00 | 79.92 | C |
| ATOM | 520 | CG | MET | A | 98 | −45.573 | −4.628 | 7.326 | 1.00 | 84.42 | C |
| ATOM | 521 | SD | MET | A | 98 | −46.226 | −4.350 | 5.681 | 1.00 | 96.30 | S |
| ATOM | 522 | CE | MET | A | 98 | −45.936 | −5.962 | 4.938 | 1.00 | 95.48 | C |
| ATOM | 523 | N | TRP | A | 99 | −42.754 | −2.552 | 5.510 | 1.00 | 77.49 | N |
| ATOM | 524 | CA | TRP | A | 99 | −42.823 | −1.681 | 4.333 | 1.00 | 75.69 | C |
| ATOM | 525 | C | TRP | A | 99 | −43.856 | −2.268 | 3.372 | 1.00 | 73.64 | C |
| ATOM | 526 | O | TRP | A | 99 | −43.802 | −3.441 | 3.079 | 1.00 | 77.31 | O |
| ATOM | 527 | CB | TRP | A | 99 | −41.444 | −1.587 | 3.691 | 1.00 | 74.33 | C |
| ATOM | 528 | CG | TRP | A | 99 | −41.339 | −0.599 | 2.633 | 1.00 | 74.05 | C |
| ATOM | 529 | CD1 | TRP | A | 99 | −41.293 | −0.838 | 1.306 | 1.00 | 70.83 | C |
| ATOM | 530 | CD2 | TRP | A | 99 | −41.262 | 0.821 | 2.788 | 1.00 | 73.53 | C |
| ATOM | 531 | NE1 | TRP | A | 99 | −41.195 | 0.331 | 0.624 | 1.00 | 73.91 | N |
| ATOM | 532 | CE2 | TRP | A | 99 | −41.172 | 1.368 | 1.505 | 1.00 | 73.77 | C |
| ATOM | 533 | CE3 | TRP | A | 99 | −41.262 | 1.680 | 3.887 | 1.00 | 74.17 | C |
| ATOM | 534 | CZ2 | TRP | A | 99 | −41.083 | 2.737 | 1.277 | 1.00 | 75.99 | C |
| ATOM | 535 | CZ3 | TRP | A | 99 | −41.172 | 3.054 | 3.664 | 1.00 | 71.44 | C |
| ATOM | 536 | CH2 | TRP | A | 99 | −41.083 | 3.564 | 2.370 | 1.00 | 77.11 | C |
| ATOM | 537 | N | THR | A | 100 | −44.795 | −1.451 | 2.892 | 1.00 | 73.03 | N |
| ATOM | 538 | CA | THR | A | 100 | −45.840 | −1.896 | 1.924 | 1.00 | 72.98 | C |
| ATOM | 539 | C | THR | A | 100 | −45.766 | −1.236 | 0.546 | 1.00 | 71.23 | C |
| ATOM | 540 | O | THR | A | 100 | −46.562 | −1.571 | −0.333 | 1.00 | 71.17 | O |
| ATOM | 541 | CB | THR | A | 100 | −47.266 | −1.597 | 2.444 | 1.00 | 73.76 | C |
| ATOM | 542 | OG1 | THR | A | 100 | −47.509 | −0.178 | 2.405 | 1.00 | 76.78 | O |
| ATOM | 543 | CG2 | THR | A | 100 | −47.446 | −2.076 | 3.842 | 1.00 | 78.02 | C |
| ATOM | 544 | N | PHE | A | 101 | −44.829 | −0.312 | 0.355 | 1.00 | 70.30 | N |
| ATOM | 545 | CA | PHE | A | 101 | −44.748 | 0.499 | −0.870 | 1.00 | 72.26 | C |
| ATOM | 546 | C | PHE | A | 101 | −43.772 | −0.083 | −1.920 | 1.00 | 74.09 | C |
| ATOM | 547 | O | PHE | A | 101 | −43.621 | 0.485 | −3.018 | 1.00 | 74.48 | O |
| ATOM | 548 | CB | PHE | A | 101 | −44.414 | 1.947 | −0.481 | 1.00 | 72.34 | C |
| ATOM | 549 | CG | PHE | A | 101 | −45.268 | 2.457 | 0.663 | 1.00 | 70.71 | C |
| ATOM | 550 | CD1 | PHE | A | 101 | −44.766 | 2.495 | 1.965 | 1.00 | 71.75 | C |
| ATOM | 551 | CD2 | PHE | A | 101 | −46.572 | 2.887 | 0.438 | 1.00 | 68.75 | C |
| ATOM | 552 | CE1 | PHE | A | 101 | −45.552 | 2.961 | 3.028 | 1.00 | 71.54 | C |
| ATOM | 553 | CE2 | PHE | A | 101 | −47.364 | 3.354 | 1.493 | 1.00 | 70.01 | C |
| ATOM | 554 | CZ | PHE | A | 101 | −46.853 | 3.391 | 2.789 | 1.00 | 68.99 | C |
| ATOM | 555 | N | GLY | A | 102 | −43.122 | −1.207 | −1.581 | 1.00 | 73.14 | N |
| ATOM | 556 | CA | GLY | A | 102 | −42.234 | −1.922 | −2.502 | 1.00 | 73.21 | C |
| ATOM | 557 | C | GLY | A | 102 | −40.821 | −1.391 | −2.546 | 1.00 | 72.86 | C |
| ATOM | 558 | O | GLY | A | 102 | −40.552 | −0.299 | −2.091 | 1.00 | 72.40 | O |
| ATOM | 559 | N | ASN | A | 103 | −39.916 | −2.184 | −3.114 | 1.00 | 74.31 | N |
| ATOM | 560 | CA | ASN | A | 103 | −38.484 | −1.824 | −3.165 | 1.00 | 74.88 | C |
| ATOM | 561 | C | ASN | A | 103 | −38.129 | −0.574 | −3.956 | 1.00 | 74.74 | C |
| ATOM | 562 | O | ASN | A | 103 | −37.251 | 0.175 | −3.515 | 1.00 | 76.17 | O |
| ATOM | 563 | CB | ASN | A | 103 | −37.626 | −2.998 | −3.690 | 1.00 | 74.34 | C |
| ATOM | 564 | CG | ASN | A | 103 | −37.420 | −4.108 | −2.651 | 1.00 | 74.79 | C |
| ATOM | 565 | OD1 | ASN | A | 103 | −37.242 | −5.271 | −3.012 | 1.00 | 76.47 | O |
| ATOM | 566 | ND2 | ASN | A | 103 | −37.444 | −3.753 | −1.363 | 1.00 | 74.57 | N |
| ATOM | 567 | N | PHE | A | 104 | −38.782 | −0.339 | −5.098 | 1.00 | 74.65 | N |

APPENDIX 1-continued

| | | | | | | | | | | |
|---|---|---|---|---|---|---|---|---|---|---|
| ATOM | 568 | CA | PHE | A | 104 | −38.478 | 0.860 | −5.884 | 1.00 | 75.28 | C |
| ATOM | 569 | C | PHE | A | 104 | −38.644 | 2.100 | −5.041 | 1.00 | 75.71 | C |
| ATOM | 570 | O | PHE | A | 104 | −37.710 | 2.895 | −4.906 | 1.00 | 77.93 | O |
| ATOM | 571 | CB | PHE | A | 104 | −39.367 | 1.020 | −7.116 | 1.00 | 78.02 | C |
| ATOM | 572 | CG | PHE | A | 104 | −39.279 | 2.408 | −7.727 | 1.00 | 79.37 | C |
| ATOM | 573 | CD1 | PHE | A | 104 | −38.129 | 2.802 | −8.421 | 1.00 | 80.42 | C |
| ATOM | 574 | CD2 | PHE | A | 104 | −40.337 | 3.321 | −7.603 | 1.00 | 81.51 | C |
| ATOM | 575 | CE1 | PHE | A | 104 | −38.031 | 4.072 | −8.984 | 1.00 | 79.83 | C |
| ATOM | 576 | CE2 | PHE | A | 104 | −40.248 | 4.598 | −8.164 | 1.00 | 83.42 | C |
| ATOM | 577 | CZ | PHE | A | 104 | −39.091 | 4.975 | −8.857 | 1.00 | 82.52 | C |
| ATOM | 578 | N | TRP | A | 105 | −39.839 | 2.255 | −4.478 | 1.00 | 76.21 | N |
| ATOM | 579 | CA | TRP | A | 105 | −40.134 | 3.416 | −3.670 | 1.00 | 75.91 | C |
| ATOM | 580 | C | TRP | A | 105 | −39.295 | 3.456 | −2.357 | 1.00 | 76.37 | C |
| ATOM | 581 | O | TRP | A | 105 | −38.972 | 4.534 | −1.899 | 1.00 | 74.11 | O |
| ATOM | 582 | CB | TRP | A | 105 | −41.645 | 3.562 | −3.386 | 1.00 | 78.05 | C |
| ATOM | 583 | CG | TRP | A | 105 | −41.870 | 4.799 | −2.623 | 1.00 | 82.40 | C |
| ATOM | 584 | CD1 | TRP | A | 105 | −42.157 | 4.889 | −1.318 | 1.00 | 83.43 | C |
| ATOM | 585 | CD2 | TRP | A | 105 | −41.810 | 6.147 | −3.120 | 1.00 | 87.60 | C |
| ATOM | 586 | NE1 | TRP | A | 105 | −42.288 | 6.182 | −0.950 | 1.00 | 83.52 | N |
| ATOM | 587 | CE2 | TRP | A | 105 | −42.082 | 6.994 | −2.033 | 1.00 | 84.67 | C |
| ATOM | 588 | CE3 | TRP | A | 105 | −41.556 | 6.716 | −4.381 | 1.00 | 86.42 | C |
| ATOM | 589 | CZ2 | TRP | A | 105 | −42.109 | 8.401 | −2.155 | 1.00 | 81.05 | C |
| ATOM | 590 | CZ3 | TRP | A | 105 | −41.583 | 8.115 | −4.507 | 1.00 | 84.49 | C |
| ATOM | 591 | CH2 | TRP | A | 105 | −41.860 | 8.938 | −3.391 | 1.00 | 85.45 | C |
| ATOM | 592 | N | CYS | A | 106 | −38.952 | 2.302 | −1.775 | 1.00 | 74.15 | N |
| ATOM | 593 | CA | CYS | A | 106 | −38.086 | 2.278 | −0.573 | 1.00 | 75.23 | C |
| ATOM | 594 | C | CYS | A | 106 | −36.763 | 2.982 | −0.834 | 1.00 | 74.63 | C |
| ATOM | 595 | O | CYS | A | 106 | −36.332 | 3.831 | −0.045 | 1.00 | 72.22 | O |
| ATOM | 596 | CB | CYS | A | 106 | −37.827 | 0.848 | −0.097 | 1.00 | 75.82 | C |
| ATOM | 597 | SG | CYS | A | 106 | −36.530 | 0.694 | 1.167 | 1.00 | 75.27 | S |
| ATOM | 598 | N | GLU | A | 107 | −36.137 | 2.618 | −1.946 | 1.00 | 74.18 | N |
| ATOM | 599 | CA | GLU | A | 107 | −34.882 | 3.219 | −2.380 | 1.00 | 73.95 | C |
| ATOM | 600 | C | GLU | A | 107 | −35.054 | 4.698 | −2.773 | 1.00 | 73.77 | C |
| ATOM | 601 | O | GLU | A | 107 | −34.185 | 5.521 | −2.469 | 1.00 | 69.11 | O |
| ATOM | 602 | CB | GLU | A | 107 | −34.337 | 2.411 | −3.542 | 1.00 | 74.75 | C |
| ATOM | 603 | CG | GLU | A | 107 | −33.001 | 2.841 | −4.117 | 1.00 | 78.43 | C |
| ATOM | 604 | CD | GLU | A | 107 | −32.677 | 2.072 | −5.397 | 1.00 | 82.58 | C |
| ATOM | 605 | OE1 | GLU | A | 107 | −32.915 | 0.843 | −5.452 | 1.00 | 87.52 | O |
| ATOM | 606 | OE2 | GLU | A | 107 | −32.186 | 2.688 | −6.352 | 1.00 | 90.13 | O |
| ATOM | 607 | N | PHE | A | 108 | −36.166 | 5.025 | −3.445 | 1.00 | 72.86 | N |
| ATOM | 608 | CA | PHE | A | 108 | −36.458 | 6.414 | −3.816 | 1.00 | 70.73 | C |
| ATOM | 609 | C | PHE | A | 108 | −36.705 | 7.236 | −2.556 | 1.00 | 68.58 | C |
| ATOM | 610 | O | PHE | A | 108 | −36.073 | 8.275 | −2.357 | 1.00 | 66.92 | O |
| ATOM | 611 | CB | PHE | A | 108 | −37.676 | 6.506 | −4.729 | 1.00 | 70.86 | C |
| ATOM | 612 | CG | PHE | A | 108 | −37.744 | 7.783 | −5.526 | 1.00 | 72.80 | C |
| ATOM | 613 | CD1 | PHE | A | 108 | −37.339 | 7.799 | −6.868 | 1.00 | 78.82 | C |
| ATOM | 614 | CD2 | PHE | A | 108 | −38.205 | 8.965 | −4.961 | 1.00 | 74.96 | C |
| ATOM | 615 | CE1 | PHE | A | 108 | −37.396 | 8.977 | −7.621 | 1.00 | 76.80 | C |
| ATOM | 616 | CE2 | PHE | A | 108 | −38.262 | 10.149 | −5.720 | 1.00 | 74.68 | C |
| ATOM | 617 | CZ | PHE | A | 108 | −37.858 | 10.148 | −7.043 | 1.00 | 76.41 | C |
| ATOM | 618 | N | TRP | A | 109 | −37.628 | 6.752 | −1.723 | 1.00 | 66.71 | N |
| ATOM | 619 | CA | TRP | A | 109 | −37.960 | 7.358 | −0.431 | 1.00 | 68.89 | C |
| ATOM | 620 | C | TRP | A | 109 | −36.701 | 7.635 | 0.361 | 1.00 | 69.04 | C |
| ATOM | 621 | O | TRP | A | 109 | −36.504 | 8.752 | 0.807 | 1.00 | 68.71 | O |
| ATOM | 622 | CB | TRP | A | 109 | −38.866 | 6.437 | 0.371 | 1.00 | 71.86 | C |
| ATOM | 623 | CG | TRP | A | 109 | −39.102 | 6.855 | 1.747 | 1.00 | 70.49 | C |
| ATOM | 624 | CD1 | TRP | A | 109 | −39.862 | 7.878 | 2.149 | 1.00 | 72.33 | C |
| ATOM | 625 | CD2 | TRP | A | 109 | −38.569 | 6.248 | 2.938 | 1.00 | 74.86 | C |
| ATOM | 626 | NE1 | TRP | A | 109 | −39.847 | 7.967 | 3.516 | 1.00 | 76.09 | N |
| ATOM | 627 | CE2 | TRP | A | 109 | −39.062 | 6.979 | 4.025 | 1.00 | 72.44 | C |
| ATOM | 628 | CE3 | TRP | A | 109 | −37.720 | 5.156 | 3.187 | 1.00 | 77.42 | C |
| ATOM | 629 | CZ2 | TRP | A | 109 | −38.747 | 6.669 | 5.347 | 1.00 | 75.85 | C |
| ATOM | 630 | CZ3 | TRP | A | 109 | −37.404 | 4.849 | 4.532 | 1.00 | 74.21 | C |
| ATOM | 631 | CH2 | TRP | A | 109 | −37.919 | 5.602 | 5.575 | 1.00 | 73.66 | C |
| ATOM | 632 | N | THR | A | 110 | −35.861 | 6.607 | 0.518 | 1.00 | 64.06 | N |
| ATOM | 633 | CA | THR | A | 110 | −34.570 | 6.747 | 1.190 | 1.00 | 66.65 | C |
| ATOM | 634 | C | THR | A | 110 | −33.707 | 7.863 | 0.621 | 1.00 | 68.41 | C |
| ATOM | 635 | O | THR | A | 110 | −33.116 | 8.624 | 1.385 | 1.00 | 71.70 | O |
| ATOM | 636 | CB | THR | A | 110 | −33.757 | 5.477 | 1.102 | 1.00 | 66.89 | C |
| ATOM | 637 | OG1 | THR | A | 110 | −34.491 | 4.404 | 1.699 | 1.00 | 70.60 | O |
| ATOM | 638 | CG2 | THR | A | 110 | −32.427 | 5.645 | 1.830 | 1.00 | 64.09 | C |
| ATOM | 639 | N | SER | A | 111 | −33.636 | 7.959 | −0.709 | 1.00 | 69.98 | N |
| ATOM | 640 | CA | SER | A | 111 | −32.849 | 9.017 | −1.387 | 1.00 | 70.65 | C |
| ATOM | 641 | C | SER | A | 111 | −33.343 | 10.443 | −1.092 | 1.00 | 73.21 | C |
| ATOM | 642 | O | SER | A | 111 | −32.524 | 11.356 | −0.899 | 1.00 | 76.91 | O |
| ATOM | 643 | CB | SER | A | 111 | −32.825 | 8.802 | −2.909 | 1.00 | 72.35 | C |
| ATOM | 644 | OG | SER | A | 111 | −32.247 | 7.565 | −3.262 | 1.00 | 69.46 | O |
| ATOM | 645 | N | ILE | A | 112 | −34.669 | 10.626 | −1.063 | 1.00 | 72.31 | N |
| ATOM | 646 | CA | ILE | A | 112 | −35.290 | 11.938 | −0.786 | 1.00 | 70.06 | C |
| ATOM | 647 | C | ILE | A | 112 | −35.011 | 12.365 | 0.650 | 1.00 | 69.36 | C |

APPENDIX 1-continued

| ATOM | 648 | O | ILE | A | 112 | −34.706 | 13.535 | 0.916 | 1.00 | 68.07 | O |
| --- | --- | --- | --- | --- | --- | --- | --- | --- | --- | --- | --- |
| ATOM | 649 | CB | ILE | A | 112 | −36.819 | 11.916 | −1.006 | 1.00 | 68.74 | C |
| ATOM | 650 | CG1 | ILE | A | 112 | −37.174 | 11.632 | −2.476 | 1.00 | 75.90 | C |
| ATOM | 651 | CG2 | ILE | A | 112 | −37.426 | 13.234 | −0.645 | 1.00 | 72.66 | C |
| ATOM | 652 | CD1 | ILE | A | 112 | −38.665 | 11.518 | −2.704 | 1.00 | 73.21 | C |
| ATOM | 653 | N | ASP | A | 113 | −35.126 | 11.403 | 1.557 | 1.00 | 68.09 | N |
| ATOM | 654 | CA | ASP | A | 113 | −34.823 | 11.584 | 2.973 | 1.00 | 69.93 | C |
| ATOM | 655 | C | ASP | A | 113 | −33.435 | 12.218 | 3.102 | 1.00 | 68.24 | C |
| ATOM | 656 | O | ASP | A | 113 | −33.311 | 13.328 | 3.600 | 1.00 | 69.08 | O |
| ATOM | 657 | CB | ASP | A | 113 | −34.916 | 10.225 | 3.681 | 1.00 | 71.22 | C |
| ATOM | 658 | CG | ASP | A | 113 | −35.001 | 10.325 | 5.163 | 1.00 | 71.94 | C |
| ATOM | 659 | OD1 | ASP | A | 113 | −34.453 | 11.263 | 5.771 | 1.00 | 73.99 | O |
| ATOM | 660 | OD2 | ASP | A | 113 | −35.644 | 9.419 | 5.727 | 1.00 | 78.39 | O |
| ATOM | 661 | N | VAL | A | 114 | −32.415 | 11.501 | 2.640 | 1.00 | 69.76 | N |
| ATOM | 662 | CA | VAL | A | 114 | −31.016 | 11.951 | 2.687 | 1.00 | 69.79 | C |
| ATOM | 663 | C | VAL | A | 114 | −30.790 | 13.289 | 1.934 | 1.00 | 70.38 | C |
| ATOM | 664 | O | VAL | A | 114 | −30.022 | 14.132 | 2.409 | 1.00 | 66.61 | O |
| ATOM | 665 | CB | VAL | A | 114 | −30.070 | 10.827 | 2.158 | 1.00 | 71.48 | C |
| ATOM | 666 | CG1 | VAL | A | 114 | −28.657 | 11.338 | 1.891 | 1.00 | 71.98 | C |
| ATOM | 667 | CG2 | VAL | A | 114 | −30.054 | 9.643 | 3.147 | 1.00 | 68.67 | C |
| ATOM | 668 | N | LEU | A | 115 | −31.455 | 13.467 | 0.780 | 1.00 | 69.66 | N |
| ATOM | 669 | CA | LEU | A | 115 | −31.356 | 14.717 | −0.015 | 1.00 | 70.60 | C |
| ATOM | 670 | C | LEU | A | 115 | −31.817 | 15.929 | 0.773 | 1.00 | 72.08 | C |
| ATOM | 671 | O | LEU | A | 115 | −31.084 | 16.909 | 0.895 | 1.00 | 71.75 | O |
| ATOM | 672 | CB | LEU | A | 115 | −32.193 | 14.621 | −1.314 | 1.00 | 73.84 | C |
| ATOM | 673 | CG | LEU | A | 115 | −32.357 | 15.859 | −2.238 | 1.00 | 73.55 | C |
| ATOM | 674 | CD1 | LEU | A | 115 | −31.014 | 16.399 | −2.735 | 1.00 | 72.28 | C |
| ATOM | 675 | CD2 | LEU | A | 115 | −33.278 | 15.542 | −3.431 | 1.00 | 66.35 | C |
| ATOM | 676 | N | CYS | A | 116 | −33.039 | 15.841 | 1.297 | 1.00 | 72.44 | N |
| ATOM | 677 | CA | CYS | A | 116 | −33.670 | 16.941 | 2.034 | 1.00 | 73.77 | C |
| ATOM | 678 | C | CYS | A | 116 | −32.868 | 17.364 | 3.251 | 1.00 | 74.35 | C |
| ATOM | 679 | O | CYS | A | 116 | −32.711 | 18.570 | 3.492 | 1.00 | 75.14 | O |
| ATOM | 680 | CB | CYS | A | 116 | −35.112 | 16.586 | 2.437 | 1.00 | 72.52 | C |
| ATOM | 681 | SG | CYS | A | 116 | −36.268 | 16.557 | 1.013 | 1.00 | 80.97 | S |
| ATOM | 682 | N | VAL | A | 117 | −32.365 | 16.391 | 4.010 | 1.00 | 72.36 | N |
| ATOM | 683 | CA | VAL | A | 117 | −31.509 | 16.695 | 5.167 | 1.00 | 73.25 | C |
| ATOM | 684 | C | VAL | A | 117 | −30.188 | 17.351 | 4.725 | 1.00 | 75.09 | C |
| ATOM | 685 | O | VAL | A | 117 | −29.729 | 18.311 | 5.369 | 1.00 | 76.15 | O |
| ATOM | 686 | CB | VAL | A | 117 | −31.217 | 15.439 | 6.020 | 1.00 | 73.55 | C |
| ATOM | 687 | CG1 | VAL | A | 117 | −30.199 | 15.737 | 7.098 | 1.00 | 69.89 | C |
| ATOM | 688 | CG2 | VAL | A | 117 | −32.503 | 14.916 | 6.641 | 1.00 | 73.99 | C |
| ATOM | 689 | N | THR | A | 118 | −29.592 | 16.837 | 3.635 | 1.00 | 71.84 | N |
| ATOM | 690 | CA | THR | A | 118 | −28.329 | 17.366 | 3.096 | 1.00 | 71.32 | C |
| ATOM | 691 | C | THR | A | 118 | −28.501 | 18.788 | 2.575 | 1.00 | 73.72 | C |
| ATOM | 692 | O | THR | A | 118 | −27.710 | 19.656 | 2.916 | 1.00 | 78.08 | O |
| ATOM | 693 | CB | THR | A | 118 | −27.767 | 16.482 | 1.949 | 1.00 | 72.20 | C |
| ATOM | 694 | OG1 | THR | A | 118 | −27.512 | 15.161 | 2.433 | 1.00 | 75.03 | O |
| ATOM | 695 | CG2 | THR | A | 118 | −26.471 | 17.066 | 1.389 | 1.00 | 65.55 | C |
| ATOM | 696 | N | ALA | A | 119 | −29.534 | 19.013 | 1.752 | 1.00 | 72.84 | N |
| ATOM | 697 | CA | ALA | A | 119 | −29.857 | 20.351 | 1.220 | 1.00 | 71.95 | C |
| ATOM | 698 | C | ALA | A | 119 | −30.142 | 21.361 | 2.334 | 1.00 | 71.48 | C |
| ATOM | 699 | O | ALA | A | 119 | −29.750 | 22.521 | 2.226 | 1.00 | 73.66 | O |
| ATOM | 700 | CB | ALA | A | 119 | −31.054 | 20.284 | 0.243 | 1.00 | 69.50 | C |
| ATOM | 701 | N | SER | A | 120 | −30.818 | 20.920 | 3.394 | 1.00 | 71.79 | N |
| ATOM | 702 | CA | SER | A | 120 | −31.124 | 21.803 | 4.531 | 1.00 | 71.94 | C |
| ATOM | 703 | C | SER | A | 120 | −29.861 | 22.374 | 5.153 | 1.00 | 73.64 | C |
| ATOM | 704 | O | SER | A | 120 | −29.724 | 23.598 | 5.252 | 1.00 | 74.21 | O |
| ATOM | 705 | CB | SER | A | 120 | −31.927 | 21.071 | 5.584 | 1.00 | 71.95 | C |
| ATOM | 706 | OG | SER | A | 120 | −33.202 | 20.758 | 5.077 | 1.00 | 75.41 | O |
| ATOM | 707 | N | ILE | A | 121 | −28.945 | 21.500 | 5.562 | 1.00 | 74.66 | N |
| ATOM | 708 | CA | ILE | A | 121 | −27.694 | 21.946 | 6.223 | 1.00 | 72.09 | C |
| ATOM | 709 | C | ILE | A | 121 | −26.767 | 22.684 | 5.253 | 1.00 | 74.47 | C |
| ATOM | 710 | O | ILE | A | 121 | −26.066 | 23.606 | 5.668 | 1.00 | 72.06 | O |
| ATOM | 711 | CB | ILE | A | 121 | −26.922 | 20.782 | 6.903 | 1.00 | 72.33 | C |
| ATOM | 712 | CG1 | ILE | A | 121 | −25.776 | 21.297 | 7.823 | 1.00 | 75.07 | C |
| ATOM | 713 | CG2 | ILE | A | 121 | −26.349 | 19.826 | 5.858 | 1.00 | 69.34 | C |
| ATOM | 714 | CD1 | ILE | A | 121 | −26.149 | 22.421 | 8.816 | 1.00 | 75.41 | C |
| ATOM | 715 | N | GLU | A | 122 | −26.758 | 22.289 | 3.977 | 1.00 | 71.61 | N |
| ATOM | 716 | CA | GLU | A | 122 | −25.957 | 23.013 | 2.976 | 1.00 | 73.61 | C |
| ATOM | 717 | C | GLU | A | 122 | −26.477 | 24.430 | 2.815 | 1.00 | 71.97 | C |
| ATOM | 718 | O | GLU | A | 122 | −25.684 | 25.357 | 2.719 | 1.00 | 73.76 | O |
| ATOM | 719 | CB | GLU | A | 122 | −25.936 | 22.298 | 1.619 | 1.00 | 71.23 | C |
| ATOM | 720 | CG | GLU | A | 122 | −25.042 | 21.050 | 1.616 | 1.00 | 78.82 | C |
| ATOM | 721 | CD | GLU | A | 122 | −24.898 | 20.393 | 0.249 | 1.00 | 76.68 | C |
| ATOM | 722 | OE1 | GLU | A | 122 | −25.210 | 21.034 | −0.777 | 1.00 | 81.34 | O |
| ATOM | 723 | OE2 | GLU | A | 122 | −24.464 | 19.221 | 0.208 | 1.00 | 82.37 | O |
| ATOM | 724 | N | THR | A | 123 | −27.804 | 24.585 | 2.788 | 1.00 | 71.94 | N |
| ATOM | 725 | CA | THR | A | 123 | −28.437 | 25.916 | 2.693 | 1.00 | 71.90 | C |
| ATOM | 726 | C | THR | A | 123 | −28.141 | 26.762 | 3.909 | 1.00 | 71.32 | C |
| ATOM | 727 | O | THR | A | 123 | −27.722 | 27.903 | 3.768 | 1.00 | 70.52 | O |

APPENDIX 1-continued

| ATOM | 728 | CB  | THR | A | 123 | −29.940 | 25.819 | 2.596 | 1.00 | 69.91 | C |
| --- | --- | --- | --- | --- | --- | --- | --- | --- | --- | --- | --- |
| ATOM | 729 | OG1 | THR | A | 123 | −30.275 | 24.924 | 1.534 | 1.00 | 70.66 | O |
| ATOM | 730 | CG2 | THR | A | 123 | −30.539 | 27.214 | 2.354 | 1.00 | 68.19 | C |
| ATOM | 731 | N   | LEU | A | 124 | −28.364 | 26.197 | 5.099 | 1.00 | 69.53 | N |
| ATOM | 732 | CA  | LEU | A | 124 | −28.044 | 26.877 | 6.330 | 1.00 | 70.49 | C |
| ATOM | 733 | C   | LEU | A | 124 | −26.624 | 27.353 | 6.294 | 1.00 | 69.98 | C |
| ATOM | 734 | O   | LEU | A | 124 | −26.349 | 28.465 | 6.684 | 1.00 | 72.08 | O |
| ATOM | 735 | CB  | LEU | A | 124 | −28.230 | 25.963 | 7.561 | 1.00 | 72.66 | C |
| ATOM | 736 | CG  | LEU | A | 124 | −29.654 | 25.655 | 7.991 | 1.00 | 71.44 | C |
| ATOM | 737 | CD1 | LEU | A | 124 | −29.643 | 24.635 | 9.128 | 1.00 | 74.54 | C |
| ATOM | 738 | CD2 | LEU | A | 124 | −30.358 | 26.930 | 8.384 | 1.00 | 68.04 | C |
| ATOM | 739 | N   | CYS | A | 125 | −25.726 | 26.509 | 5.822 | 1.00 | 72.50 | N |
| ATOM | 740 | CA  | CYS | A | 125 | −24.319 | 26.880 | 5.727 | 1.00 | 75.56 | C |
| ATOM | 741 | C   | CYS | A | 125 | −24.087 | 28.030 | 4.746 | 1.00 | 73.80 | C |
| ATOM | 742 | O   | CYS | A | 125 | −23.222 | 28.868 | 4.985 | 1.00 | 74.28 | O |
| ATOM | 743 | CB  | CYS | A | 125 | −23.474 | 25.682 | 5.322 | 1.00 | 76.67 | C |
| ATOM | 744 | SG  | CYS | A | 125 | −21.781 | 25.957 | 5.620 | 1.00 | 84.21 | S |
| ATOM | 745 | N   | VAL | A | 126 | −24.860 | 28.059 | 3.652 | 1.00 | 76.58 | N |
| ATOM | 746 | CA  | VAL | A | 126 | −24.803 | 29.161 | 2.654 | 1.00 | 74.32 | C |
| ATOM | 747 | C   | VAL | A | 126 | −25.327 | 30.458 | 3.269 | 1.00 | 74.06 | C |
| ATOM | 748 | O   | VAL | A | 126 | −24.820 | 31.529 | 2.959 | 1.00 | 74.99 | O |
| ATOM | 749 | CB  | VAL | A | 126 | −25.612 | 28.848 | 1.381 | 1.00 | 73.89 | C |
| ATOM | 750 | CG1 | VAL | A | 126 | −25.614 | 30.050 | 0.435 | 1.00 | 78.42 | C |
| ATOM | 751 | CG2 | VAL | A | 126 | −25.056 | 27.612 | 0.682 | 1.00 | 75.52 | C |
| ATOM | 752 | N   | ILE | A | 127 | −26.341 | 30.352 | 4.138 | 1.00 | 73.19 | N |
| ATOM | 753 | CA  | ILE | A | 127 | −26.902 | 31.527 | 4.840 | 1.00 | 71.30 | C |
| ATOM | 754 | C   | ILE | A | 127 | −25.846 | 32.137 | 5.724 | 1.00 | 69.71 | C |
| ATOM | 755 | O   | ILE | A | 127 | −25.706 | 33.342 | 5.750 | 1.00 | 73.08 | O |
| ATOM | 756 | CB  | ILE | A | 127 | −28.150 | 31.200 | 5.671 | 1.00 | 70.82 | C |
| ATOM | 757 | CG1 | ILE | A | 127 | −29.301 | 30.720 | 4.782 | 1.00 | 74.13 | C |
| ATOM | 758 | CG2 | ILE | A | 127 | −28.636 | 32.429 | 6.410 | 1.00 | 72.22 | C |
| ATOM | 759 | CD1 | ILE | A | 127 | −30.450 | 30.161 | 5.540 | 1.00 | 73.97 | C |
| ATOM | 760 | N   | ALA | A | 128 | −25.105 | 31.298 | 6.440 | 1.00 | 70.03 | N |
| ATOM | 761 | CA  | ALA | A | 128 | −24.031 | 31.756 | 7.323 | 1.00 | 70.78 | C |
| ATOM | 762 | C   | ALA | A | 128 | −22.929 | 32.481 | 6.577 | 1.00 | 70.23 | C |
| ATOM | 763 | O   | ALA | A | 128 | −22.493 | 33.544 | 7.004 | 1.00 | 70.16 | O |
| ATOM | 764 | CB  | ALA | A | 128 | −23.443 | 30.585 | 8.092 | 1.00 | 72.00 | C |
| ATOM | 765 | N   | VAL | A | 129 | −22.480 | 31.905 | 5.463 | 1.00 | 73.67 | N |
| ATOM | 766 | CA  | VAL | A | 129 | −21.415 | 32.529 | 4.657 | 1.00 | 70.68 | C |
| ATOM | 767 | C   | VAL | A | 129 | −21.923 | 33.853 | 4.062 | 1.00 | 70.47 | C |
| ATOM | 768 | O   | VAL | A | 129 | −21.212 | 34.853 | 4.092 | 1.00 | 73.60 | O |
| ATOM | 769 | CB  | VAL | A | 129 | −20.878 | 31.595 | 3.556 | 1.00 | 70.74 | C |
| ATOM | 770 | CG1 | VAL | A | 129 | −19.835 | 32.328 | 2.689 | 1.00 | 65.41 | C |
| ATOM | 771 | CG2 | VAL | A | 129 | −20.285 | 30.331 | 4.172 | 1.00 | 66.69 | C |
| ATOM | 772 | N   | ASP | A | 130 | −23.149 | 33.836 | 3.536 | 1.00 | 72.22 | N |
| ATOM | 773 | CA  | ASP | A | 130 | −23.812 | 35.034 | 2.993 | 1.00 | 69.02 | C |
| ATOM | 774 | C   | ASP | A | 130 | −23.965 | 36.125 | 4.036 | 1.00 | 68.79 | C |
| ATOM | 775 | O   | ASP | A | 130 | −23.668 | 37.270 | 3.758 | 1.00 | 66.69 | O |
| ATOM | 776 | CB  | ASP | A | 130 | −25.195 | 34.686 | 2.460 | 1.00 | 71.35 | C |
| ATOM | 777 | CG  | ASP | A | 130 | −25.925 | 35.902 | 1.916 | 1.00 | 78.10 | C |
| ATOM | 778 | OD1 | ASP | A | 130 | −25.369 | 36.570 | 1.008 | 1.00 | 76.18 | O |
| ATOM | 779 | OD2 | ASP | A | 130 | −27.049 | 36.181 | 2.399 | 1.00 | 90.58 | O |
| ATOM | 780 | N   | ARG | A | 131 | −24.434 | 35.770 | 5.243 | 1.00 | 69.55 | N |
| ATOM | 781 | CA  | ARG | A | 131 | −24.520 | 36.762 | 6.342 | 1.00 | 67.36 | C |
| ATOM | 782 | C   | ARG | A | 131 | −23.143 | 37.268 | 6.778 | 1.00 | 67.63 | C |
| ATOM | 783 | O   | ARG | A | 131 | −23.021 | 38.445 | 7.169 | 1.00 | 65.43 | O |
| ATOM | 784 | CB  | ARG | A | 131 | −25.291 | 36.222 | 7.544 | 1.00 | 67.67 | C |
| ATOM | 785 | CG  | ARG | A | 131 | −26.791 | 35.942 | 7.317 | 1.00 | 70.59 | C |
| ATOM | 786 | CD  | ARG | A | 131 | −27.581 | 37.208 | 7.051 | 1.00 | 78.70 | C |
| ATOM | 787 | NE  | ARG | A | 131 | −27.386 | 37.707 | 5.685 | 1.00 | 80.63 | N |
| ATOM | 788 | CZ  | ARG | A | 131 | −27.690 | 38.934 | 5.244 | 1.00 | 84.09 | C |
| ATOM | 789 | NH1 | ARG | A | 131 | −28.227 | 39.861 | 6.051 | 1.00 | 88.30 | N |
| ATOM | 790 | NH2 | ARG | A | 131 | −27.454 | 39.237 | 3.969 | 1.00 | 81.21 | N |
| ATOM | 791 | N   | TYR | A | 132 | −22.112 | 36.414 | 6.716 | 1.00 | 66.25 | N |
| ATOM | 792 | CA  | TYR | A | 132 | −20.772 | 36.872 | 7.091 | 1.00 | 66.91 | C |
| ATOM | 793 | C   | TYR | A | 132 | −20.300 | 37.951 | 6.123 | 1.00 | 69.24 | C |
| ATOM | 794 | O   | TYR | A | 132 | −19.816 | 38.995 | 6.553 | 1.00 | 74.15 | O |
| ATOM | 795 | CB  | TYR | A | 132 | −19.744 | 35.746 | 7.153 | 1.00 | 64.41 | C |
| ATOM | 796 | CG  | TYR | A | 132 | −18.362 | 36.288 | 7.466 | 1.00 | 65.53 | C |
| ATOM | 797 | CD1 | TYR | A | 132 | −17.989 | 36.601 | 8.780 | 1.00 | 73.29 | C |
| ATOM | 798 | CD2 | TYR | A | 132 | −17.433 | 36.492 | 6.460 | 1.00 | 66.44 | C |
| ATOM | 799 | CE1 | TYR | A | 132 | −16.716 | 37.102 | 9.068 | 1.00 | 69.45 | C |
| ATOM | 800 | CE2 | TYR | A | 132 | −16.170 | 36.989 | 6.731 | 1.00 | 66.23 | C |
| ATOM | 801 | CZ  | TYR | A | 132 | −15.809 | 37.293 | 8.025 | 1.00 | 71.49 | C |
| ATOM | 802 | OH  | TYR | A | 132 | −14.542 | 37.787 | 8.266 | 1.00 | 69.82 | O |
| ATOM | 803 | N   | PHE | A | 133 | −20.435 | 37.715 | 4.827 | 1.00 | 69.93 | N |
| ATOM | 804 | CA  | PHE | A | 133 | −20.010 | 38.759 | 3.860 | 1.00 | 70.80 | C |
| ATOM | 805 | C   | PHE | A | 133 | −20.920 | 39.992 | 3.920 | 1.00 | 69.98 | C |
| ATOM | 806 | O   | PHE | A | 133 | −20.427 | 41.103 | 3.794 | 1.00 | 70.63 | O |
| ATOM | 807 | CB  | PHE | A | 133 | −19.846 | 38.184 | 2.456 | 1.00 | 67.77 | C |

APPENDIX 1-continued

| ATOM | 808 | CG  | PHE | A | 133 | −18.650 | 37.278 | 2.342  | 1.00 | 69.98  | C |
|------|-----|-----|-----|---|-----|---------|--------|--------|------|--------|---|
| ATOM | 809 | CD1 | PHE | A | 133 | −17.352 | 37.802 | 2.445  | 1.00 | 72.82  | C |
| ATOM | 810 | CD2 | PHE | A | 133 | −18.799 | 35.914 | 2.140  | 1.00 | 69.69  | C |
| ATOM | 811 | CE1 | PHE | A | 133 | −16.228 | 36.981 | 2.345  | 1.00 | 70.61  | C |
| ATOM | 812 | CE2 | PHE | A | 133 | −17.667 | 35.081 | 2.039  | 1.00 | 71.02  | C |
| ATOM | 813 | CZ  | PHE | A | 133 | −16.385 | 35.620 | 2.143  | 1.00 | 68.76  | C |
| ATOM | 814 | N   | ALA | A | 134 | −22.221 | 39.790 | 4.120  | 1.00 | 69.44  | N |
| ATOM | 815 | CA  | ALA | A | 134 | −23.141 | 40.911 | 4.273  | 1.00 | 68.56  | C |
| ATOM | 816 | C   | ALA | A | 134 | −22.724 | 41.816 | 5.416  | 1.00 | 68.68  | C |
| ATOM | 817 | O   | ALA | A | 134 | −22.633 | 43.022 | 5.229  | 1.00 | 71.94  | O |
| ATOM | 818 | CB  | ALA | A | 134 | −24.562 | 40.422 | 4.491  | 1.00 | 67.16  | C |
| ATOM | 819 | N   | ILE | A | 135 | −22.465 | 41.241 | 6.589  | 1.00 | 68.84  | N |
| ATOM | 820 | CA  | ILE | A | 135 | −22.145 | 42.039 | 7.792  | 1.00 | 70.46  | C |
| ATOM | 821 | C   | ILE | A | 135 | −20.732 | 42.639 | 7.824  | 1.00 | 73.76  | C |
| ATOM | 822 | O   | ILE | A | 135 | −20.483 | 43.567 | 8.604  | 1.00 | 77.85  | O |
| ATOM | 823 | CB  | ILE | A | 135 | −22.361 | 41.205 | 9.107  | 1.00 | 68.09  | C |
| ATOM | 824 | CG1 | ILE | A | 135 | −22.694 | 42.122 | 10.290 | 1.00 | 70.69  | C |
| ATOM | 825 | CG2 | ILE | A | 135 | −21.151 | 40.315 | 9.387  | 1.00 | 54.90  | C |
| ATOM | 826 | CD1 | ILE | A | 135 | −23.130 | 41.371 | 11.531 | 1.00 | 69.39  | C |
| ATOM | 827 | N   | THR | A | 136 | −19.819 | 42.123 | 6.998  | 1.00 | 72.13  | N |
| ATOM | 828 | CA  | THR | A | 136 | −18.450 | 42.658 | 6.911  | 1.00 | 72.48  | C |
| ATOM | 829 | C   | THR | A | 136 | −18.272 | 43.602 | 5.722  | 1.00 | 73.00  | C |
| ATOM | 830 | O   | THR | A | 136 | −17.205 | 44.194 | 5.560  | 1.00 | 76.38  | O |
| ATOM | 831 | CB  | THR | A | 136 | −17.408 | 41.523 | 6.791  | 1.00 | 71.33  | C |
| ATOM | 832 | OG1 | THR | A | 136 | −17.656 | 40.755 | 5.612  | 1.00 | 69.78  | O |
| ATOM | 833 | CG2 | THR | A | 136 | −17.478 | 40.622 | 7.980  | 1.00 | 76.96  | C |
| ATOM | 834 | N   | SER | A | 137 | −19.312 | 43.743 | 4.890  | 1.00 | 73.57  | N |
| ATOM | 835 | CA  | SER | A | 137 | −19.224 | 44.546 | 3.673  | 1.00 | 71.50  | C |
| ATOM | 836 | C   | SER | A | 137 | −19.370 | 46.004 | 4.020  | 1.00 | 70.30  | C |
| ATOM | 837 | O   | SER | A | 137 | −20.079 | 46.302 | 4.923  | 1.00 | 72.29  | O |
| ATOM | 838 | CB  | SER | A | 137 | −20.327 | 44.159 | 2.678  | 1.00 | 70.57  | C |
| ATOM | 839 | OG  | SER | A | 137 | −20.402 | 45.088 | 1.612  | 1.00 | 73.10  | O |
| ATOM | 840 | N   | PRO | A | 138 | −18.693 | 46.924 | 3.292  | 1.00 | 73.40  | N |
| ATOM | 841 | CA  | PRO | A | 138 | −18.908 | 48.362 | 3.552  | 1.00 | 71.10  | C |
| ATOM | 842 | C   | PRO | A | 138 | −20.342 | 48.823 | 3.196  | 1.00 | 72.24  | C |
| ATOM | 843 | O   | PRO | A | 138 | −20.791 | 49.845 | 3.689  | 1.00 | 73.27  | O |
| ATOM | 844 | CB  | PRO | A | 138 | −17.875 | 49.042 | 2.656  | 1.00 | 72.76  | C |
| ATOM | 845 | CG  | PRO | A | 138 | −16.952 | 47.966 | 2.220  | 1.00 | 75.11  | C |
| ATOM | 846 | CD  | PRO | A | 138 | −17.713 | 46.719 | 2.207  | 1.00 | 70.99  | C |
| ATOM | 847 | N   | PHE | A | 139 | −21.030 | 48.053 | 2.343  | 1.00 | 75.02  | N |
| ATOM | 848 | CA  | PHE | A | 139 | −22.436 | 48.228 | 2.012  | 1.00 | 75.94  | C |
| ATOM | 849 | C   | PHE | A | 139 | −23.097 | 47.194 | 2.924  | 1.00 | 81.11  | C |
| ATOM | 850 | O   | PHE | A | 139 | −23.703 | 46.209 | 2.451  | 1.00 | 82.84  | O |
| ATOM | 851 | CB  | PHE | A | 139 | −22.686 | 47.948 | 0.517  | 1.00 | 70.64  | C |
| ATOM | 852 | CG  | PHE | A | 139 | −21.537 | 48.366 | −0.376 | 1.00 | 68.22  | C |
| ATOM | 853 | CD1 | PHE | A | 139 | −20.705 | 47.417 | −0.943 | 1.00 | 64.99  | C |
| ATOM | 854 | CD2 | PHE | A | 139 | −21.291 | 49.686 | −0.634 | 1.00 | 54.92  | C |
| ATOM | 855 | CE1 | PHE | A | 139 | −19.676 | 47.789 | −1.736 | 1.00 | 53.34  | C |
| ATOM | 856 | CE2 | PHE | A | 139 | −20.261 | 50.061 | −1.427 | 1.00 | 55.02  | C |
| ATOM | 857 | CZ  | PHE | A | 139 | −19.448 | 49.112 | −1.982 | 1.00 | 59.66  | C |
| ATOM | 858 | N   | LYS | A | 140 | −22.970 | 47.430 | 4.239  | 1.00 | 82.78  | N |
| ATOM | 859 | CA  | LYS | A | 140 | −23.326 | 46.437 | 5.288  | 1.00 | 86.29  | C |
| ATOM | 860 | C   | LYS | A | 140 | −24.732 | 45.890 | 5.161  | 1.00 | 84.99  | C |
| ATOM | 861 | O   | LYS | A | 140 | −25.668 | 46.622 | 4.835  | 1.00 | 84.00  | O |
| ATOM | 862 | CB  | LYS | A | 140 | −23.144 | 47.003 | 6.710  | 1.00 | 86.05  | C |
| ATOM | 863 | CG  | LYS | A | 140 | −21.716 | 47.263 | 7.104  | 1.00 | 93.56  | C |
| ATOM | 864 | CD  | LYS | A | 140 | −21.533 | 47.754 | 8.540  | 1.00 | 92.32  | C |
| ATOM | 865 | CE  | LYS | A | 140 | −20.068 | 48.178 | 8.748  | 1.00 | 94.63  | C |
| ATOM | 866 | NZ  | LYS | A | 140 | −19.803 | 48.731 | 10.115 | 1.00 | 103.84 | N |
| ATOM | 867 | N   | TYR | A | 141 | −24.836 | 44.589 | 5.424  | 1.00 | 85.69  | N |
| ATOM | 868 | CA  | TYR | A | 141 | −26.070 | 43.783 | 5.383  | 1.00 | 87.34  | C |
| ATOM | 869 | C   | TYR | A | 141 | −26.642 | 43.451 | 3.984  | 1.00 | 87.45  | C |
| ATOM | 870 | O   | TYR | A | 141 | −27.393 | 42.477 | 3.859  | 1.00 | 87.44  | O |
| ATOM | 871 | CB  | TYR | A | 141 | −27.154 | 44.369 | 6.294  | 1.00 | 89.48  | C |
| ATOM | 872 | CG  | TYR | A | 141 | −26.773 | 44.254 | 7.729  | 1.00 | 86.02  | C |
| ATOM | 873 | CD1 | TYR | A | 141 | −27.055 | 43.095 | 8.434  | 1.00 | 82.79  | C |
| ATOM | 874 | CD2 | TYR | A | 141 | −26.132 | 45.293 | 8.380  | 1.00 | 87.79  | C |
| ATOM | 875 | CE1 | TYR | A | 141 | −26.717 | 42.968 | 9.747  | 1.00 | 95.42  | C |
| ATOM | 876 | CE2 | TYR | A | 141 | −25.777 | 45.189 | 9.716  | 1.00 | 94.16  | C |
| ATOM | 877 | CZ  | TYR | A | 141 | −26.071 | 44.020 | 10.400 | 1.00 | 97.24  | C |
| ATOM | 878 | OH  | TYR | A | 141 | −25.728 | 43.897 | 11.720 | 1.00 | 91.49  | O |
| ATOM | 879 | N   | GLN | A | 142 | −26.313 | 44.220 | 2.958  | 1.00 | 83.88  | N |
| ATOM | 880 | CA  | GLN | A | 142 | −26.686 | 43.826 | 1.640  | 1.00 | 87.53  | C |
| ATOM | 881 | C   | GLN | A | 142 | −25.823 | 42.632 | 1.368  | 1.00 | 85.35  | C |
| ATOM | 882 | O   | GLN | A | 142 | −24.602 | 42.682 | 1.609  | 1.00 | 85.83  | O |
| ATOM | 883 | CB  | GLN | A | 142 | −26.375 | 44.883 | 0.590  | 1.00 | 86.73  | C |
| ATOM | 884 | CG  | GLN | A | 142 | −27.186 | 46.134 | 0.674  | 1.00 | 87.65  | C |
| ATOM | 885 | CD  | GLN | A | 142 | −26.769 | 47.145 | −0.388 | 1.00 | 91.57  | C |
| ATOM | 886 | OE1 | GLN | A | 142 | −26.382 | 46.780 | −1.508 | 1.00 | 90.57  | O |
| ATOM | 887 | NE2 | GLN | A | 142 | −26.847 | 48.425 | −0.040 | 1.00 | 99.82  | N |

APPENDIX 1-continued

| ATOM | 888 | N | SER | A | 143 | −26.446 | 41.562 | 0.879 | 1.00 | 81.37 | N |
|---|---|---|---|---|---|---|---|---|---|---|---|
| ATOM | 889 | CA | SER | A | 143 | −25.716 | 40.420 | 0.415 | 1.00 | 78.53 | C |
| ATOM | 890 | C | SER | A | 143 | −24.884 | 40.866 | −0.772 | 1.00 | 77.76 | C |
| ATOM | 891 | O | SER | A | 143 | −25.320 | 41.731 | −1.554 | 1.00 | 76.92 | O |
| ATOM | 892 | CB | SER | A | 143 | −26.662 | 39.315 | −0.030 | 1.00 | 79.11 | C |
| ATOM | 893 | OG | SER | A | 143 | −25.960 | 38.321 | −0.743 | 1.00 | 79.05 | O |
| ATOM | 894 | N | LEU | A | 144 | −23.695 | 40.284 | −0.913 | 1.00 | 75.59 | N |
| ATOM | 895 | CA | LEU | A | 144 | −22.854 | 40.541 | −2.082 | 1.00 | 78.96 | C |
| ATOM | 896 | C | LEU | A | 144 | −23.461 | 39.937 | −3.371 | 1.00 | 77.36 | C |
| ATOM | 897 | O | LEU | A | 144 | −23.012 | 40.278 | −4.477 | 1.00 | 79.84 | O |
| ATOM | 898 | CB | LEU | A | 144 | −21.433 | 40.007 | −1.867 | 1.00 | 80.08 | C |
| ATOM | 899 | CG | LEU | A | 144 | −20.660 | 40.517 | −0.639 | 1.00 | 82.77 | C |
| ATOM | 900 | CD1 | LEU | A | 144 | −19.218 | 40.045 | −0.740 | 1.00 | 84.51 | C |
| ATOM | 901 | CD2 | LEU | A | 144 | −20.714 | 42.055 | −0.474 | 1.00 | 77.04 | C |
| ATOM | 902 | N | LEU | A | 145 | −24.466 | 39.056 | −3.210 | 1.00 | 74.06 | N |
| ATOM | 903 | CA | LEU | A | 145 | −25.162 | 38.394 | −4.293 | 1.00 | 75.14 | C |
| ATOM | 904 | C | LEU | A | 145 | −26.417 | 39.116 | −4.759 | 1.00 | 74.57 | C |
| ATOM | 905 | O | LEU | A | 145 | −27.158 | 39.675 | −3.951 | 1.00 | 76.73 | O |
| ATOM | 906 | CB | LEU | A | 145 | −25.610 | 36.999 | −3.836 | 1.00 | 74.59 | C |
| ATOM | 907 | CG | LEU | A | 145 | −24.572 | 36.016 | −3.326 | 1.00 | 73.05 | C |
| ATOM | 908 | CD1 | LEU | A | 145 | −25.249 | 34.715 | −2.973 | 1.00 | 75.64 | C |
| ATOM | 909 | CD2 | LEU | A | 145 | −23.502 | 35.785 | −4.364 | 1.00 | 79.94 | C |
| ATOM | 910 | N | THR | A | 146 | −26.645 | 39.095 | −6.070 | 1.00 | 74.52 | N |
| ATOM | 911 | CA | THR | A | 146 | −27.901 | 39.539 | −6.654 | 1.00 | 76.04 | C |
| ATOM | 912 | C | THR | A | 146 | −28.928 | 38.413 | −6.482 | 1.00 | 75.70 | C |
| ATOM | 913 | O | THR | A | 146 | −28.574 | 37.282 | −6.104 | 1.00 | 75.21 | O |
| ATOM | 914 | CB | THR | A | 146 | −27.772 | 39.850 | −8.156 | 1.00 | 76.46 | C |
| ATOM | 915 | OG1 | THR | A | 146 | −27.440 | 38.650 | −8.860 | 1.00 | 79.82 | O |
| ATOM | 916 | CG2 | THR | A | 146 | −26.702 | 40.917 | −8.423 | 1.00 | 71.60 | C |
| ATOM | 917 | N | LYS | A | 147 | −30.193 | 38.719 | −6.760 | 1.00 | 77.16 | N |
| ATOM | 918 | CA | LYS | A | 147 | −31.279 | 37.718 | −6.687 | 1.00 | 77.11 | C |
| ATOM | 919 | C | LYS | A | 147 | −30.999 | 36.539 | −7.633 | 1.00 | 76.19 | C |
| ATOM | 920 | O | LYS | A | 147 | −31.219 | 35.383 | −7.267 | 1.00 | 73.96 | O |
| ATOM | 921 | CB | LYS | A | 147 | −32.646 | 38.315 | −7.052 | 1.00 | 78.39 | C |
| ATOM | 922 | CG | LYS | A | 147 | −33.107 | 39.543 | −6.264 | 1.00 | 81.83 | C |
| ATOM | 923 | CD | LYS | A | 147 | −33.377 | 39.263 | −4.815 | 1.00 | 87.01 | C |
| ATOM | 924 | CE | LYS | A | 147 | −33.758 | 40.559 | −4.072 | 1.00 | 89.91 | C |
| ATOM | 925 | NZ | LYS | A | 147 | −35.048 | 41.155 | −4.556 | 1.00 | 91.41 | N |
| ATOM | 926 | N | ASN | A | 148 | −30.512 | 36.843 | −8.843 | 1.00 | 76.47 | N |
| ATOM | 927 | CA | ASN | A | 148 | −30.199 | 35.809 | −9.849 | 1.00 | 77.14 | C |
| ATOM | 928 | C | ASN | A | 148 | −29.023 | 34.912 | −9.476 | 1.00 | 76.20 | C |
| ATOM | 929 | O | ASN | A | 148 | −29.113 | 33.689 | −9.647 | 1.00 | 74.96 | O |
| ATOM | 930 | CB | ASN | A | 148 | −29.958 | 36.431 | −11.244 | 1.00 | 79.53 | C |
| ATOM | 931 | CG | ASN | A | 148 | −31.254 | 36.824 | −11.956 | 1.00 | 84.32 | C |
| ATOM | 932 | OD1 | ASN | A | 148 | −32.355 | 36.395 | −11.586 | 1.00 | 89.19 | O |
| ATOM | 933 | ND2 | ASN | A | 148 | −31.121 | 37.648 | −12.993 | 1.00 | 85.88 | N |
| ATOM | 934 | N | LYS | A | 149 | −27.933 | 35.503 | −8.976 | 1.00 | 73.79 | N |
| ATOM | 935 | CA | LYS | A | 149 | −26.801 | 34.706 | −8.474 | 1.00 | 76.59 | C |
| ATOM | 936 | C | LYS | A | 149 | −27.254 | 33.809 | −7.319 | 1.00 | 76.35 | C |
| ATOM | 937 | O | LYS | A | 149 | −26.822 | 32.672 | −7.232 | 1.00 | 81.05 | O |
| ATOM | 938 | CB | LYS | A | 149 | −25.662 | 35.562 | −7.950 | 1.00 | 79.46 | C |
| ATOM | 939 | CG | LYS | A | 149 | −25.007 | 36.526 | −8.914 | 1.00 | 82.58 | C |
| ATOM | 940 | CD | LYS | A | 149 | −24.001 | 37.409 | −8.129 | 1.00 | 83.85 | C |
| ATOM | 941 | CE | LYS | A | 149 | −23.690 | 38.747 | −8.790 | 1.00 | 89.02 | C |
| ATOM | 942 | NZ | LYS | A | 149 | −23.014 | 39.645 | −7.773 | 1.00 | 88.17 | N |
| ATOM | 943 | N | ALA | A | 150 | −28.120 | 34.331 | −6.441 | 1.00 | 73.36 | N |
| ATOM | 944 | CA | ALA | A | 150 | −28.684 | 33.545 | −5.325 | 1.00 | 74.46 | C |
| ATOM | 945 | C | ALA | A | 150 | −29.457 | 32.309 | −5.827 | 1.00 | 75.42 | C |
| ATOM | 946 | O | ALA | A | 150 | −29.337 | 31.239 | −5.245 | 1.00 | 79.11 | O |
| ATOM | 947 | CB | ALA | A | 150 | −29.572 | 34.416 | −4.440 | 1.00 | 68.50 | C |
| ATOM | 948 | N | ARG | A | 151 | −30.243 | 32.465 | −6.900 | 1.00 | 77.55 | N |
| ATOM | 949 | CA | ARG | A | 151 | −30.945 | 31.314 | −7.511 | 1.00 | 77.51 | C |
| ATOM | 950 | C | ARG | A | 151 | −29.983 | 30.249 | −8.022 | 1.00 | 77.61 | C |
| ATOM | 951 | O | ARG | A | 151 | −30.272 | 29.057 | −7.913 | 1.00 | 77.15 | O |
| ATOM | 952 | CB | ARG | A | 151 | −31.836 | 31.709 | −8.690 | 1.00 | 83.00 | C |
| ATOM | 953 | CG | ARG | A | 151 | −33.284 | 32.095 | −8.376 | 1.00 | 89.58 | C |
| ATOM | 954 | CD | ARG | A | 151 | −33.576 | 33.556 | −8.598 | 1.00 | 95.56 | C |
| ATOM | 955 | NE | ARG | A | 151 | −34.990 | 33.794 | −8.884 | 1.00 | 93.67 | N |
| ATOM | 956 | CZ | ARG | A | 151 | −35.510 | 34.981 | −9.220 | 1.00 | 98.85 | C |
| ATOM | 957 | NH1 | ARG | A | 151 | −34.743 | 36.084 | −9.325 | 1.00 | 97.06 | N |
| ATOM | 958 | NH2 | ARG | A | 151 | −36.820 | 35.073 | −9.458 | 1.00 | 102.25 | N |
| ATOM | 959 | N | VAL | A | 152 | −28.852 | 30.684 | −8.579 | 1.00 | 77.11 | N |
| ATOM | 960 | CA | VAL | A | 152 | −27.825 | 29.767 | −9.081 | 1.00 | 77.01 | C |
| ATOM | 961 | C | VAL | A | 152 | −27.144 | 29.030 | −7.919 | 1.00 | 76.31 | C |
| ATOM | 962 | O | VAL | A | 152 | −26.878 | 27.845 | −8.023 | 1.00 | 73.81 | O |
| ATOM | 963 | CB | VAL | A | 152 | −26.806 | 30.502 | −9.987 | 1.00 | 78.53 | C |
| ATOM | 964 | CG1 | VAL | A | 152 | −25.612 | 29.617 | −10.311 | 1.00 | 85.33 | C |
| ATOM | 965 | CG2 | VAL | A | 152 | −27.486 | 30.934 | −11.274 | 1.00 | 75.42 | C |
| ATOM | 966 | N | ILE | A | 153 | −26.874 | 29.734 | −6.824 | 1.00 | 76.01 | N |
| ATOM | 967 | CA | ILE | A | 153 | −26.278 | 29.102 | −5.632 | 1.00 | 76.47 | C |

APPENDIX 1-continued

| ATOM | 968 | C | ILE | A | 153 | −27.235 | 28.053 | −5.074 | 1.00 | 75.66 | C |
|---|---|---|---|---|---|---|---|---|---|---|---|
| ATOM | 969 | O | ILE | A | 153 | −26.812 | 26.945 | −4.733 | 1.00 | 74.99 | O |
| ATOM | 970 | CB | ILE | A | 153 | −25.954 | 30.101 | −4.523 | 1.00 | 75.93 | C |
| ATOM | 971 | CG1 | ILE | A | 153 | −24.899 | 31.127 | −4.966 | 1.00 | 78.94 | C |
| ATOM | 972 | CG2 | ILE | A | 153 | −25.402 | 29.373 | −3.320 | 1.00 | 75.34 | C |
| ATOM | 973 | CD1 | ILE | A | 153 | −23.488 | 30.564 | −5.063 | 1.00 | 84.91 | C |
| ATOM | 974 | N | ILE | A | 154 | −28.517 | 28.416 | −4.990 | 1.00 | 75.41 | N |
| ATOM | 975 | CA | ILE | A | 154 | −29.570 | 27.497 | −4.545 | 1.00 | 75.93 | C |
| ATOM | 976 | C | ILE | A | 154 | −29.645 | 26.286 | −5.461 | 1.00 | 72.61 | C |
| ATOM | 977 | O | ILE | A | 154 | −29.565 | 25.159 | −5.001 | 1.00 | 70.17 | O |
| ATOM | 978 | CB | ILE | A | 154 | −30.943 | 28.192 | −4.490 | 1.00 | 75.92 | C |
| ATOM | 979 | CG1 | ILE | A | 154 | −30.975 | 29.183 | −3.328 | 1.00 | 79.46 | C |
| ATOM | 980 | CG2 | ILE | A | 154 | −32.072 | 27.170 | −4.312 | 1.00 | 73.88 | C |
| ATOM | 981 | CD1 | ILE | A | 154 | −32.130 | 30.133 | −3.371 | 1.00 | 81.26 | C |
| ATOM | 982 | N | LEU | A | 155 | −29.793 | 26.521 | −6.754 | 1.00 | 75.14 | N |
| ATOM | 983 | CA | LEU | A | 155 | −29.826 | 25.411 | −7.725 | 1.00 | 75.92 | C |
| ATOM | 984 | C | LEU | A | 155 | −28.604 | 24.497 | −7.543 | 1.00 | 75.22 | C |
| ATOM | 985 | O | LEU | A | 155 | −28.744 | 23.279 | −7.543 | 1.00 | 73.02 | O |
| ATOM | 986 | CB | LEU | A | 155 | −29.912 | 25.930 | −9.158 | 1.00 | 71.84 | C |
| ATOM | 987 | CG | LEU | A | 155 | −29.837 | 24.903 | −10.297 | 1.00 | 79.20 | C |
| ATOM | 988 | CD1 | LEU | A | 155 | −30.845 | 23.769 | −10.095 | 1.00 | 82.92 | C |
| ATOM | 989 | CD2 | LEU | A | 155 | −30.038 | 25.585 | −11.666 | 1.00 | 75.89 | C |
| ATOM | 990 | N | MET | A | 156 | −27.423 | 25.100 | −7.384 | 1.00 | 76.89 | N |
| ATOM | 991 | CA | MET | A | 156 | −26.186 | 24.339 | −7.184 | 1.00 | 77.43 | C |
| ATOM | 992 | C | MET | A | 156 | −26.181 | 23.568 | −5.871 | 1.00 | 76.37 | C |
| ATOM | 993 | O | MET | A | 156 | −25.571 | 22.504 | −5.801 | 1.00 | 78.59 | O |
| ATOM | 994 | CB | MET | A | 156 | −24.945 | 25.247 | −7.281 | 1.00 | 81.89 | C |
| ATOM | 995 | CG | MET | A | 156 | −24.609 | 25.744 | −8.716 | 1.00 | 83.04 | C |
| ATOM | 996 | SD | MET | A | 156 | −24.284 | 24.442 | −9.942 | 1.00 | 100.97 | S |
| ATOM | 997 | CE | MET | A | 156 | −24.128 | 25.398 | −11.458 | 1.00 | 89.68 | C |
| ATOM | 998 | N | VAL | A | 157 | −26.851 | 24.094 | −4.841 | 1.00 | 76.00 | N |
| ATOM | 999 | CA | VAL | A | 157 | −27.000 | 23.370 | −3.572 | 1.00 | 74.39 | C |
| ATOM | 1000 | C | VAL | A | 157 | −27.835 | 22.098 | −3.784 | 1.00 | 74.09 | C |
| ATOM | 1001 | O | VAL | A | 157 | −27.447 | 21.022 | −3.327 | 1.00 | 74.06 | O |
| ATOM | 1002 | CB | VAL | A | 157 | −27.624 | 24.250 | −2.448 | 1.00 | 73.43 | C |
| ATOM | 1003 | CG1 | VAL | A | 157 | −28.152 | 23.382 | −1.321 | 1.00 | 69.33 | C |
| ATOM | 1004 | CG2 | VAL | A | 157 | −26.613 | 25.269 | −1.942 | 1.00 | 68.63 | C |
| ATOM | 1005 | N | TRP | A | 158 | −28.969 | 22.227 | −4.472 | 1.00 | 74.10 | N |
| ATOM | 1006 | CA | TRP | A | 158 | −29.817 | 21.046 | −4.777 | 1.00 | 74.40 | C |
| ATOM | 1007 | C | TRP | A | 158 | −29.131 | 20.024 | −5.683 | 1.00 | 75.32 | C |
| ATOM | 1008 | O | TRP | A | 158 | −29.313 | 18.824 | −5.482 | 1.00 | 78.30 | O |
| ATOM | 1009 | CB | TRP | A | 158 | −31.188 | 21.469 | −5.310 | 1.00 | 70.20 | C |
| ATOM | 1010 | CG | TRP | A | 158 | −31.961 | 21.950 | −4.183 | 1.00 | 74.02 | C |
| ATOM | 1011 | CD1 | TRP | A | 158 | −32.015 | 23.217 | −3.719 | 1.00 | 80.00 | C |
| ATOM | 1012 | CD2 | TRP | A | 158 | −32.803 | 21.173 | −3.333 | 1.00 | 72.24 | C |
| ATOM | 1013 | NE1 | TRP | A | 158 | −32.842 | 23.290 | −2.632 | 1.00 | 79.53 | N |
| ATOM | 1014 | CE2 | TRP | A | 158 | −33.342 | 22.050 | −2.371 | 1.00 | 79.45 | C |
| ATOM | 1015 | CE3 | TRP | A | 158 | −33.157 | 19.822 | −3.292 | 1.00 | 73.80 | C |
| ATOM | 1016 | CZ2 | TRP | A | 158 | −34.220 | 21.625 | −1.374 | 1.00 | 71.01 | C |
| ATOM | 1017 | CZ3 | TRP | A | 158 | −34.026 | 19.396 | −2.307 | 1.00 | 73.95 | C |
| ATOM | 1018 | CH2 | TRP | A | 158 | −34.549 | 20.299 | −1.358 | 1.00 | 74.98 | C |
| ATOM | 1019 | N | ILE | A | 159 | −28.354 | 20.495 | −6.663 | 1.00 | 76.28 | N |
| ATOM | 1020 | CA | ILE | A | 159 | −27.572 | 19.595 | −7.526 | 1.00 | 75.87 | C |
| ATOM | 1021 | C | ILE | A | 159 | −26.509 | 18.840 | −6.713 | 1.00 | 76.85 | C |
| ATOM | 1022 | O | ILE | A | 159 | −26.416 | 17.626 | −6.830 | 1.00 | 76.71 | O |
| ATOM | 1023 | CB | ILE | A | 159 | −26.892 | 20.332 | −8.696 | 1.00 | 73.88 | C |
| ATOM | 1024 | CG1 | ILE | A | 159 | −27.933 | 20.757 | −9.735 | 1.00 | 75.94 | C |
| ATOM | 1025 | CG2 | ILE | A | 159 | −25.861 | 19.431 | −9.354 | 1.00 | 76.05 | C |
| ATOM | 1026 | CD1 | ILE | A | 159 | −27.359 | 21.529 | −10.923 | 1.00 | 71.99 | C |
| ATOM | 1027 | N | VAL | A | 160 | −25.725 | 19.564 | −5.903 | 1.00 | 74.32 | N |
| ATOM | 1028 | CA | VAL | A | 160 | −24.672 | 18.947 | −5.073 | 1.00 | 74.37 | C |
| ATOM | 1029 | C | VAL | A | 160 | −25.257 | 17.970 | −4.047 | 1.00 | 76.12 | C |
| ATOM | 1030 | O | VAL | A | 160 | −24.738 | 16.864 | −3.877 | 1.00 | 72.86 | O |
| ATOM | 1031 | CB | VAL | A | 160 | −23.805 | 20.011 | −4.357 | 1.00 | 75.98 | C |
| ATOM | 1032 | CG1 | VAL | A | 160 | −22.910 | 19.378 | −3.297 | 1.00 | 70.80 | C |
| ATOM | 1033 | CG2 | VAL | A | 160 | −22.962 | 20.777 | −5.377 | 1.00 | 72.65 | C |
| ATOM | 1034 | N | SER | A | 161 | −26.332 | 18.388 | −3.376 | 1.00 | 76.74 | N |
| ATOM | 1035 | CA | SER | A | 161 | −27.052 | 17.522 | −2.436 | 1.00 | 76.33 | C |
| ATOM | 1036 | C | SER | A | 161 | −27.588 | 16.253 | −3.127 | 1.00 | 80.12 | C |
| ATOM | 1037 | O | SER | A | 161 | −27.565 | 15.175 | −2.540 | 1.00 | 81.12 | O |
| ATOM | 1038 | CB | SER | A | 161 | −28.203 | 18.277 | −1.783 | 1.00 | 77.19 | C |
| ATOM | 1039 | OG | SER | A | 161 | −27.721 | 19.391 | −1.043 | 1.00 | 76.25 | O |
| ATOM | 1040 | N | GLY | A | 162 | −28.067 | 16.399 | −4.367 | 1.00 | 78.97 | N |
| ATOM | 1041 | CA | GLY | A | 162 | −28.559 | 15.268 | −5.165 | 1.00 | 77.45 | C |
| ATOM | 1042 | C | GLY | A | 162 | −27.418 | 14.346 | −5.559 | 1.00 | 75.17 | C |
| ATOM | 1043 | O | GLY | A | 162 | −27.536 | 13.134 | −5.495 | 1.00 | 72.75 | O |
| ATOM | 1044 | N | LEU | A | 163 | −26.313 | 14.958 | −5.965 | 1.00 | 76.45 | N |
| ATOM | 1045 | CA | LEU | A | 163 | −25.098 | 14.253 | −6.355 | 1.00 | 78.44 | C |
| ATOM | 1046 | C | LEU | A | 163 | −24.517 | 13.473 | −5.171 | 1.00 | 79.50 | C |
| ATOM | 1047 | O | LEU | A | 163 | −23.962 | 12.407 | −5.356 | 1.00 | 80.46 | O |

APPENDIX 1-continued

| | | | | | | | | | | |
|---|---|---|---|---|---|---|---|---|---|---|
| ATOM | 1048 | CB | LEU | A | 163 | −24.044 | 15.248 | −6.908 | 1.00 | 79.15 | C |
| ATOM | 1049 | CG | LEU | A | 163 | −23.153 | 14.848 | −8.081 | 1.00 | 79.51 | C |
| ATOM | 1050 | CD1 | LEU | A | 163 | −23.978 | 14.520 | −9.308 | 1.00 | 75.74 | C |
| ATOM | 1051 | CD2 | LEU | A | 163 | −22.183 | 15.984 | −8.386 | 1.00 | 78.31 | C |
| ATOM | 1052 | N | THR | A | 164 | −24.650 | 14.007 | −3.958 | 1.00 | 82.19 | N |
| ATOM | 1053 | CA | THR | A | 164 | −24.150 | 13.328 | −2.751 | 1.00 | 84.31 | C |
| ATOM | 1054 | C | THR | A | 164 | −25.196 | 12.399 | −2.061 | 1.00 | 85.47 | C |
| ATOM | 1055 | O | THR | A | 164 | −24.814 | 11.585 | −1.225 | 1.00 | 83.60 | O |
| ATOM | 1056 | CB | THR | A | 164 | −23.560 | 14.350 | −1.758 | 1.00 | 84.63 | C |
| ATOM | 1057 | OG1 | THR | A | 164 | −24.500 | 15.405 | −1.514 | 1.00 | 86.96 | O |
| ATOM | 1058 | CG2 | THR | A | 164 | −22.291 | 14.950 | −2.337 | 1.00 | 82.27 | C |
| ATOM | 1059 | N | SER | A | 165 | −26.485 | 12.525 | −2.415 | 1.00 | 87.63 | N |
| ATOM | 1060 | CA | SER | A | 165 | −27.562 | 11.705 | −1.832 | 1.00 | 88.01 | C |
| ATOM | 1061 | C | SER | A | 165 | −28.057 | 10.621 | −2.778 | 1.00 | 90.10 | C |
| ATOM | 1062 | O | SER | A | 165 | −28.029 | 9.438 | −2.432 | 1.00 | 94.95 | O |
| ATOM | 1063 | CB | SER | A | 165 | −28.745 | 12.583 | −1.454 | 1.00 | 92.00 | C |
| ATOM | 1064 | OG | SER | A | 165 | −29.324 | 13.166 | −2.614 | 1.00 | 96.93 | O |
| ATOM | 1065 | N | PHE | A | 166 | −28.512 | 11.027 | −3.967 | 1.00 | 87.60 | N |
| ATOM | 1066 | CA | PHE | A | 166 | −29.078 | 10.078 | −4.951 | 1.00 | 85.74 | C |
| ATOM | 1067 | C | PHE | A | 166 | −28.042 | 9.150 | −5.573 | 1.00 | 85.31 | C |
| ATOM | 1068 | O | PHE | A | 166 | −28.313 | 7.967 | −5.704 | 1.00 | 85.33 | O |
| ATOM | 1069 | CB | PHE | A | 166 | −29.884 | 10.789 | −6.073 | 1.00 | 85.68 | C |
| ATOM | 1070 | CG | PHE | A | 166 | −31.350 | 10.954 | −5.753 | 1.00 | 84.00 | C |
| ATOM | 1071 | CD1 | PHE | A | 166 | −32.307 | 10.148 | −6.362 | 1.00 | 82.71 | C |
| ATOM | 1072 | CD2 | PHE | A | 166 | −31.773 | 11.910 | −4.847 | 1.00 | 78.83 | C |
| ATOM | 1073 | CE1 | PHE | A | 166 | −33.659 | 10.302 | −6.066 | 1.00 | 84.17 | C |
| ATOM | 1074 | CE2 | PHE | A | 166 | −33.124 | 12.065 | −4.551 | 1.00 | 79.25 | C |
| ATOM | 1075 | CZ | PHE | A | 166 | −34.062 | 11.265 | −5.155 | 1.00 | 80.39 | C |
| ATOM | 1076 | N | LEU | A | 167 | −26.870 | 9.673 | −5.954 | 1.00 | 83.84 | N |
| ATOM | 1077 | CA | LEU | A | 167 | −25.839 | 8.813 | −6.579 | 1.00 | 83.08 | C |
| ATOM | 1078 | C | LEU | A | 167 | −25.510 | 7.568 | −5.738 | 1.00 | 83.34 | C |
| ATOM | 1079 | O | LEU | A | 167 | −25.725 | 6.477 | −6.235 | 1.00 | 84.70 | O |
| ATOM | 1080 | CB | LEU | A | 167 | −24.543 | 9.568 | −6.947 | 1.00 | 82.52 | C |
| ATOM | 1081 | CG | LEU | A | 167 | −24.431 | 10.342 | −8.250 | 1.00 | 81.28 | C |
| ATOM | 1082 | CD1 | LEU | A | 167 | −23.003 | 10.847 | −8.415 | 1.00 | 76.32 | C |
| ATOM | 1083 | CD2 | LEU | A | 167 | −24.815 | 9.492 | −9.427 | 1.00 | 75.15 | C |
| ATOM | 1084 | N | PRO | A | 168 | −25.003 | 7.727 | −4.480 | 1.00 | 82.18 | N |
| ATOM | 1085 | CA | PRO | A | 168 | −24.657 | 6.540 | −3.663 | 1.00 | 81.22 | C |
| ATOM | 1086 | C | PRO | A | 168 | −25.803 | 5.561 | −3.419 | 1.00 | 80.15 | C |
| ATOM | 1087 | O | PRO | A | 168 | −25.578 | 4.352 | −3.439 | 1.00 | 79.49 | O |
| ATOM | 1088 | CB | PRO | A | 168 | −24.226 | 7.145 | −2.321 | 1.00 | 80.06 | C |
| ATOM | 1089 | CG | PRO | A | 168 | −23.858 | 8.515 | −2.614 | 1.00 | 82.53 | C |
| ATOM | 1090 | CD | PRO | A | 168 | −24.720 | 8.968 | −3.734 | 1.00 | 83.35 | C |
| ATOM | 1091 | N | ILE | A | 169 | −27.007 | 6.086 | −3.191 | 1.00 | 80.34 | N |
| ATOM | 1092 | CA | ILE | A | 169 | −28.181 | 5.246 | −2.931 | 1.00 | 81.83 | C |
| ATOM | 1093 | C | ILE | A | 169 | −28.670 | 4.542 | −4.207 | 1.00 | 83.09 | C |
| ATOM | 1094 | O | ILE | A | 169 | −28.974 | 3.347 | −4.167 | 1.00 | 85.69 | O |
| ATOM | 1095 | CB | ILE | A | 169 | −29.316 | 6.029 | −2.245 | 1.00 | 80.40 | C |
| ATOM | 1096 | CG1 | ILE | A | 169 | −28.845 | 6.522 | −0.876 | 1.00 | 82.52 | C |
| ATOM | 1097 | CG2 | ILE | A | 169 | −30.538 | 5.150 | −2.069 | 1.00 | 80.48 | C |
| ATOM | 1098 | CD1 | ILE | A | 169 | −29.913 | 7.192 | −0.059 | 1.00 | 83.50 | C |
| ATOM | 1099 | N | GLN | A | 170 | −28.743 | 5.274 | −5.322 | 1.00 | 83.76 | N |
| ATOM | 1100 | CA | GLN | A | 170 | −29.161 | 4.691 | −6.617 | 1.00 | 83.63 | C |
| ATOM | 1101 | C | GLN | A | 170 | −28.056 | 3.817 | −7.243 | 1.00 | 83.39 | C |
| ATOM | 1102 | O | GLN | A | 170 | −28.374 | 2.864 | −7.960 | 1.00 | 86.11 | O |
| ATOM | 1103 | CB | GLN | A | 170 | −29.606 | 5.780 | −7.616 | 1.00 | 84.12 | C |
| ATOM | 1104 | CG | GLN | A | 170 | −30.766 | 6.740 | −7.123 | 1.00 | 84.07 | C |
| ATOM | 1105 | CD | GLN | A | 170 | −32.159 | 6.134 | −7.119 | 1.00 | 80.98 | C |
| ATOM | 1106 | OE1 | GLN | A | 170 | −32.370 | 5.018 | −7.557 | 1.00 | 77.62 | O |
| ATOM | 1107 | NE2 | GLN | A | 170 | −33.123 | 6.895 | −6.614 | 1.00 | 76.26 | N |
| ATOM | 1108 | N | MET | A | 171 | −26.777 | 4.134 | −6.981 | 1.00 | 82.82 | N |
| ATOM | 1109 | CA | MET | A | 171 | −25.636 | 3.286 | −7.436 | 1.00 | 83.78 | C |
| ATOM | 1110 | C | MET | A | 171 | −25.340 | 2.113 | −6.493 | 1.00 | 83.40 | C |
| ATOM | 1111 | O | MET | A | 171 | −24.487 | 1.279 | −6.816 | 1.00 | 79.60 | O |
| ATOM | 1112 | CB | MET | A | 171 | −24.336 | 4.104 | −7.631 | 1.00 | 84.08 | C |
| ATOM | 1113 | CG | MET | A | 171 | −24.315 | 5.014 | −8.854 | 1.00 | 84.82 | C |
| ATOM | 1114 | SD | MET | A | 171 | −24.372 | 4.141 | −10.445 | 1.00 | 93.60 | S |
| ATOM | 1115 | CE | MET | A | 171 | −22.962 | 3.018 | −10.356 | 1.00 | 86.88 | C |
| ATOM | 1116 | N | HIS | A | 172 | −26.032 | 2.056 | −5.346 | 1.00 | 83.18 | N |
| ATOM | 1117 | CA | HIS | A | 172 | −25.909 | 0.954 | −4.373 | 1.00 | 83.41 | C |
| ATOM | 1118 | C | HIS | A | 172 | −24.544 | 0.943 | −3.621 | 1.00 | 83.06 | C |
| ATOM | 1119 | O | HIS | A | 172 | −24.082 | −0.107 | −3.168 | 1.00 | 83.35 | O |
| ATOM | 1120 | CB | HIS | A | 172 | −26.218 | −0.415 | −5.050 | 1.00 | 82.96 | C |
| ATOM | 1121 | CG | HIS | A | 172 | −27.640 | −0.563 | −5.505 | 1.00 | 83.78 | C |
| ATOM | 1122 | ND1 | HIS | A | 172 | −28.273 | −1.780 | −5.517 | 1.00 | 79.73 | N |
| ATOM | 1123 | CD2 | HIS | A | 172 | −28.552 | 0.332 | −5.957 | 1.00 | 82.46 | C |
| ATOM | 1124 | CE1 | HIS | A | 172 | −29.509 | −1.639 | −5.954 | 1.00 | 77.50 | C |
| ATOM | 1125 | NE2 | HIS | A | 172 | −29.705 | −0.364 | −6.229 | 1.00 | 81.47 | N |
| ATOM | 1126 | N | TRP | A | 173 | −23.915 | 2.116 | −3.495 | 1.00 | 83.44 | N |
| ATOM | 1127 | CA | TRP | A | 173 | −22.647 | 2.253 | −2.758 | 1.00 | 83.86 | C |

APPENDIX 1-continued

| ATOM | 1128 | C | TRP | A | 173 | −22.823 | 2.178 | −1.244 | 1.00 | 83.60 | C |
|---|---|---|---|---|---|---|---|---|---|---|---|
| ATOM | 1129 | O | TRP | A | 173 | −21.888 | 1.843 | −0.520 | 1.00 | 83.83 | O |
| ATOM | 1130 | CB | TRP | A | 173 | −21.953 | 3.576 | −3.084 | 1.00 | 83.86 | C |
| ATOM | 1131 | CG | TRP | A | 173 | −21.492 | 3.720 | −4.491 | 1.00 | 84.03 | C |
| ATOM | 1132 | CD1 | TRP | A | 173 | −21.496 | 2.766 | −5.475 | 1.00 | 84.91 | C |
| ATOM | 1133 | CD2 | TRP | A | 173 | −20.939 | 4.893 | −5.079 | 1.00 | 82.79 | C |
| ATOM | 1134 | NE1 | TRP | A | 173 | −20.988 | 3.281 | −6.631 | 1.00 | 84.59 | N |
| ATOM | 1135 | CE2 | TRP | A | 173 | −20.636 | 4.585 | −6.419 | 1.00 | 81.34 | C |
| ATOM | 1136 | CE3 | TRP | A | 173 | −20.671 | 6.184 | −4.602 | 1.00 | 84.75 | C |
| ATOM | 1137 | CZ2 | TRP | A | 173 | −20.079 | 5.517 | −7.291 | 1.00 | 85.31 | C |
| ATOM | 1138 | CZ3 | TRP | A | 173 | −20.115 | 7.115 | −5.470 | 1.00 | 84.09 | C |
| ATOM | 1139 | CH2 | TRP | A | 173 | −19.825 | 6.777 | −6.799 | 1.00 | 86.15 | C |
| ATOM | 1140 | N | TYR | A | 174 | −24.018 | 2.505 | −0.777 | 1.00 | 81.87 | N |
| ATOM | 1141 | CA | TYR | A | 174 | −24.330 | 2.478 | 0.643 | 1.00 | 82.95 | C |
| ATOM | 1142 | C | TYR | A | 174 | −24.461 | 1.103 | 1.261 | 1.00 | 84.39 | C |
| ATOM | 1143 | O | TYR | A | 174 | −24.328 | 0.993 | 2.451 | 1.00 | 85.16 | O |
| ATOM | 1144 | CB | TYR | A | 174 | −25.646 | 3.224 | 0.916 | 1.00 | 82.89 | C |
| ATOM | 1145 | CG | TYR | A | 174 | −26.913 | 2.473 | 0.522 | 1.00 | 80.98 | C |
| ATOM | 1146 | CD1 | TYR | A | 174 | −27.679 | 1.794 | 1.475 | 1.00 | 79.89 | C |
| ATOM | 1147 | CD2 | TYR | A | 174 | −27.340 | 2.442 | −0.798 | 1.00 | 79.78 | C |
| ATOM | 1148 | CE1 | TYR | A | 174 | −28.838 | 1.110 | 1.111 | 1.00 | 81.50 | C |
| ATOM | 1149 | CE2 | TYR | A | 174 | −28.489 | 1.767 | −1.174 | 1.00 | 80.48 | C |
| ATOM | 1150 | CZ | TYR | A | 174 | −29.234 | 1.104 | −0.221 | 1.00 | 81.26 | C |
| ATOM | 1151 | OH | TYR | A | 174 | −30.365 | 0.439 | −0.601 | 1.00 | 79.71 | O |
| ATOM | 1152 | N | ARG | A | 175 | −24.709 | 0.070 | 0.457 | 1.00 | 82.91 | N |
| ATOM | 1153 | CA | ARG | A | 175 | −25.158 | −1.227 | 0.984 | 1.00 | 81.71 | C |
| ATOM | 1154 | C | ARG | A | 175 | −24.093 | −2.047 | 1.678 | 1.00 | 80.96 | C |
| ATOM | 1155 | O | ARG | A | 175 | −22.922 | −1.998 | 1.313 | 1.00 | 80.38 | O |
| ATOM | 1156 | CB | ARG | A | 175 | −25.819 | −2.057 | −0.136 | 1.00 | 82.53 | C |
| ATOM | 1157 | CG | ARG | A | 175 | −26.861 | −1.242 | −0.863 | 1.00 | 85.26 | C |
| ATOM | 1158 | CD | ARG | A | 175 | −28.068 | −1.948 | −1.318 | 1.00 | 83.28 | C |
| ATOM | 1159 | NE | ARG | A | 175 | −27.867 | −2.850 | −2.413 | 1.00 | 82.86 | N |
| ATOM | 1160 | CZ | ARG | A | 175 | −28.850 | −3.346 | −3.172 | 1.00 | 86.74 | C |
| ATOM | 1161 | NH1 | ARG | A | 175 | −30.142 | −3.019 | −2.963 | 1.00 | 84.23 | N |
| ATOM | 1162 | NH2 | ARG | A | 175 | −28.541 | −4.184 | −4.169 | 1.00 | 81.76 | N |
| ATOM | 1163 | N | ALA | A | 176 | −24.539 | −2.793 | 2.689 | 1.00 | 81.02 | N |
| ATOM | 1164 | CA | ALA | A | 176 | −23.696 | −3.687 | 3.454 | 1.00 | 81.16 | C |
| ATOM | 1165 | C | ALA | A | 176 | −23.664 | −5.020 | 2.737 | 1.00 | 81.72 | C |
| ATOM | 1166 | O | ALA | A | 176 | −24.541 | −5.308 | 1.920 | 1.00 | 81.33 | O |
| ATOM | 1167 | CB | ALA | A | 176 | −24.231 | −3.853 | 4.854 | 1.00 | 81.01 | C |
| ATOM | 1168 | N | THR | A | 177 | −22.651 | −5.821 | 3.056 | 1.00 | 81.43 | N |
| ATOM | 1169 | CA | THR | A | 177 | −22.421 | −7.128 | 2.422 | 1.00 | 80.81 | C |
| ATOM | 1170 | C | THR | A | 177 | −22.741 | −8.348 | 3.319 | 1.00 | 81.25 | C |
| ATOM | 1171 | O | THR | A | 177 | −22.430 | −9.481 | 2.947 | 1.00 | 81.14 | O |
| ATOM | 1172 | CB | THR | A | 177 | −20.959 | −7.215 | 1.944 | 1.00 | 80.88 | C |
| ATOM | 1173 | OG1 | THR | A | 177 | −20.080 | −7.111 | 3.071 | 1.00 | 80.59 | O |
| ATOM | 1174 | CG2 | THR | A | 177 | −20.656 | −6.090 | 0.961 | 1.00 | 80.78 | C |
| ATOM | 1175 | N | HIS | A | 178 | −23.358 | −8.123 | 4.482 | 1.00 | 80.75 | N |
| ATOM | 1176 | CA | HIS | A | 178 | −23.719 | −9.227 | 5.397 | 1.00 | 80.59 | C |
| ATOM | 1177 | C | HIS | A | 178 | −25.129 | −9.723 | 5.047 | 1.00 | 79.62 | C |
| ATOM | 1178 | O | HIS | A | 178 | −25.924 | −8.985 | 4.473 | 1.00 | 80.66 | O |
| ATOM | 1179 | CB | HIS | A | 178 | −23.574 | −8.824 | 6.878 | 1.00 | 80.59 | C |
| ATOM | 1180 | CG | HIS | A | 178 | −24.512 | −7.752 | 7.320 | 1.00 | 80.24 | C |
| ATOM | 1181 | ND1 | HIS | A | 178 | −24.229 | −6.410 | 7.189 | 1.00 | 85.34 | N |
| ATOM | 1182 | CD2 | HIS | A | 178 | −25.731 | −7.825 | 7.895 | 1.00 | 81.58 | C |
| ATOM | 1183 | CE1 | HIS | A | 178 | −25.238 | −5.702 | 7.664 | 1.00 | 86.20 | C |
| ATOM | 1184 | NE2 | HIS | A | 178 | −26.163 | −6.537 | 8.098 | 1.00 | 88.13 | N |
| ATOM | 1185 | N | GLN | A | 179 | −25.413 | −10.973 | 5.405 | 1.00 | 79.51 | N |
| ATOM | 1186 | CA | GLN | A | 179 | −26.652 | −11.670 | 4.994 | 1.00 | 79.05 | C |
| ATOM | 1187 | C | GLN | A | 179 | −27.968 | −11.024 | 5.453 | 1.00 | 77.54 | C |
| ATOM | 1188 | O | GLN | A | 179 | −28.903 | −10.937 | 4.667 | 1.00 | 76.07 | O |
| ATOM | 1189 | CB | GLN | A | 179 | −26.624 | −13.140 | 5.467 | 1.00 | 79.94 | C |
| ATOM | 1190 | CG | GLN | A | 179 | −27.540 | −14.079 | 4.668 | 1.00 | 82.48 | C |
| ATOM | 1191 | CD | GLN | A | 179 | −27.127 | −14.218 | 3.201 | 1.00 | 85.58 | C |
| ATOM | 1192 | OE1 | GLN | A | 179 | −25.963 | −14.006 | 2.838 | 1.00 | 84.07 | O |
| ATOM | 1193 | NE2 | GLN | A | 179 | −28.082 | −14.578 | 2.355 | 1.00 | 88.48 | N |
| ATOM | 1194 | N | GLU | A | 180 | −28.026 | −10.587 | 6.713 | 1.00 | 76.40 | N |
| ATOM | 1195 | CA | GLU | A | 180 | −29.224 | −9.915 | 7.278 | 1.00 | 76.08 | C |
| ATOM | 1196 | C | GLU | A | 180 | −29.656 | −8.694 | 6.441 | 1.00 | 74.97 | C |
| ATOM | 1197 | O | GLU | A | 180 | −30.854 | −8.437 | 6.268 | 1.00 | 72.77 | O |
| ATOM | 1198 | CB | GLU | A | 180 | −28.957 | −9.518 | 8.738 | 1.00 | 77.18 | C |
| ATOM | 1199 | CG | GLU | A | 180 | −30.098 | −8.829 | 9.499 | 1.00 | 78.62 | C |
| ATOM | 1200 | CD | GLU | A | 180 | −29.685 | −8.430 | 10.920 | 1.00 | 78.93 | C |
| ATOM | 1201 | OE1 | GLU | A | 180 | −30.024 | −7.303 | 11.336 | 1.00 | 77.22 | O |
| ATOM | 1202 | OE2 | GLU | A | 180 | −29.022 | −9.239 | 11.618 | 1.00 | 82.04 | O |
| ATOM | 1203 | N | ALA | A | 181 | −28.666 | −7.962 | 5.929 | 1.00 | 73.84 | N |
| ATOM | 1204 | CA | ALA | A | 181 | −28.887 | −6.814 | 5.061 | 1.00 | 74.58 | C |
| ATOM | 1205 | C | ALA | A | 181 | −29.359 | −7.291 | 3.699 | 1.00 | 74.81 | C |
| ATOM | 1206 | O | ALA | A | 181 | −30.389 | −6.828 | 3.201 | 1.00 | 74.62 | O |
| ATOM | 1207 | CB | ALA | A | 181 | −27.610 | −6.005 | 4.921 | 1.00 | 72.34 | C |

APPENDIX 1-continued

| | | | | | | | | | | |
|---|---|---|---|---|---|---|---|---|---|---|
| ATOM | 1208 | N | ILE | A | 182 | −28.592 | −8.218 | 3.110 | 1.00 | 76.12 | N |
| ATOM | 1209 | CA | ILE | A | 182 | −28.905 | −8.843 | 1.800 | 1.00 | 76.87 | C |
| ATOM | 1210 | C | ILE | A | 182 | −30.356 | −9.336 | 1.743 | 1.00 | 77.84 | C |
| ATOM | 1211 | O | ILE | A | 182 | −31.047 | −9.109 | 0.745 | 1.00 | 78.53 | O |
| ATOM | 1212 | CB | ILE | A | 182 | −27.924 | −10.003 | 1.453 | 1.00 | 76.51 | C |
| ATOM | 1213 | CG1 | ILE | A | 182 | −26.515 | −9.466 | 1.192 | 1.00 | 75.02 | C |
| ATOM | 1214 | CG2 | ILE | A | 182 | −28.387 | −10.756 | 0.226 | 1.00 | 76.30 | C |
| ATOM | 1215 | CD1 | ILE | A | 182 | −25.478 | −10.540 | 0.959 | 1.00 | 75.60 | C |
| ATOM | 1216 | N | ASN | A | 183 | −30.796 | −10.000 | 2.817 | 1.00 | 79.14 | N |
| ATOM | 1217 | CA | ASN | A | 183 | −32.185 | −10.442 | 2.958 | 1.00 | 79.97 | C |
| ATOM | 1218 | C | ASN | A | 183 | −33.152 | −9.263 | 2.924 | 1.00 | 81.18 | C |
| ATOM | 1219 | O | ASN | A | 183 | −34.160 | −9.323 | 2.232 | 1.00 | 81.85 | O |
| ATOM | 1220 | CB | ASN | A | 183 | −32.392 | −11.225 | 4.260 | 1.00 | 79.70 | C |
| ATOM | 1221 | CG | ASN | A | 183 | −31.725 | −12.586 | 4.246 | 1.00 | 78.69 | C |
| ATOM | 1222 | OD1 | ASN | A | 183 | −30.711 | −12.800 | 3.586 | 1.00 | 76.53 | O |
| ATOM | 1223 | ND2 | ASN | A | 183 | −32.301 | −13.522 | 4.984 | 1.00 | 78.92 | N |
| ATOM | 1224 | N | CYS | A | 184 | −32.835 | −8.200 | 3.671 | 1.00 | 81.90 | N |
| ATOM | 1225 | CA | CYS | A | 184 | −33.675 | −6.990 | 3.698 | 1.00 | 81.53 | C |
| ATOM | 1226 | C | CYS | A | 184 | −33.742 | −6.278 | 2.348 | 1.00 | 80.40 | C |
| ATOM | 1227 | O | CYS | A | 184 | −34.791 | −5.743 | 1.982 | 1.00 | 80.62 | O |
| ATOM | 1228 | CB | CYS | A | 184 | −33.189 | −5.995 | 4.751 | 1.00 | 82.03 | C |
| ATOM | 1229 | SG | CYS | A | 184 | −34.281 | −4.556 | 4.896 | 1.00 | 86.09 | S |
| ATOM | 1230 | N | TYR | A | 185 | −32.630 | −6.270 | 1.614 | 1.00 | 80.51 | N |
| ATOM | 1231 | CA | TYR | A | 185 | −32.588 | −5.626 | 0.289 | 1.00 | 80.30 | C |
| ATOM | 1232 | C | TYR | A | 185 | −33.500 | −6.328 | −0.693 | 1.00 | 80.59 | C |
| ATOM | 1233 | O | TYR | A | 185 | −34.322 | −5.683 | −1.354 | 1.00 | 82.14 | O |
| ATOM | 1234 | CB | TYR | A | 185 | −31.165 | −5.597 | −0.278 | 1.00 | 79.80 | C |
| ATOM | 1235 | CG | TYR | A | 185 | −30.177 | −4.798 | 0.552 | 1.00 | 80.24 | C |
| ATOM | 1236 | CD1 | TYR | A | 185 | −30.497 | −3.522 | 1.018 | 1.00 | 76.86 | C |
| ATOM | 1237 | CD2 | TYR | A | 185 | −28.923 | −5.313 | 0.866 | 1.00 | 79.73 | C |
| ATOM | 1238 | CE1 | TYR | A | 185 | −29.604 | −2.797 | 1.769 | 1.00 | 78.10 | C |
| ATOM | 1239 | CE2 | TYR | A | 185 | −28.021 | −4.589 | 1.618 | 1.00 | 79.03 | C |
| ATOM | 1240 | CZ | TYR | A | 185 | −28.365 | −3.334 | 2.066 | 1.00 | 78.33 | C |
| ATOM | 1241 | OH | TYR | A | 185 | −27.471 | −2.621 | 2.811 | 1.00 | 79.23 | O |
| ATOM | 1242 | N | ALA | A | 186 | −33.344 | −7.645 | −0.776 | 1.00 | 79.03 | N |
| ATOM | 1243 | CA | ALA | A | 186 | −34.189 | −8.489 | −1.622 | 1.00 | 78.43 | C |
| ATOM | 1244 | C | ALA | A | 186 | −35.659 | −8.474 | −1.178 | 1.00 | 78.71 | C |
| ATOM | 1245 | O | ALA | A | 186 | −36.557 | −8.506 | −2.023 | 1.00 | 79.49 | O |
| ATOM | 1246 | CB | ALA | A | 186 | −33.661 | −9.914 | −1.627 | 1.00 | 76.05 | C |
| ATOM | 1247 | N | GLU | A | 187 | −35.887 | −8.422 | 0.140 | 1.00 | 79.25 | N |
| ATOM | 1248 | CA | GLU | A | 187 | −37.237 | −8.399 | 0.713 | 1.00 | 79.62 | C |
| ATOM | 1249 | C | GLU | A | 187 | −37.976 | −7.085 | 0.400 | 1.00 | 79.69 | C |
| ATOM | 1250 | O | GLU | A | 187 | −37.549 | −5.998 | 0.814 | 1.00 | 80.47 | O |
| ATOM | 1251 | CB | GLU | A | 187 | −37.181 | −8.643 | 2.234 | 1.00 | 79.95 | C |
| ATOM | 1252 | CG | GLU | A | 187 | −38.523 | −8.617 | 2.992 | 1.00 | 82.26 | C |
| ATOM | 1253 | CD | GLU | A | 187 | −39.521 | −9.671 | 2.533 | 1.00 | 86.24 | C |
| ATOM | 1254 | OE1 | GLU | A | 187 | −39.137 | −10.643 | 1.845 | 1.00 | 92.89 | O |
| ATOM | 1255 | OE2 | GLU | A | 187 | −40.711 | −9.530 | 2.863 | 1.00 | 88.95 | O |
| ATOM | 1256 | N | GLU | A | 188 | −39.081 | −7.216 | −0.334 | 1.00 | 79.07 | N |
| ATOM | 1257 | CA | GLU | A | 188 | −39.930 | −6.085 | −0.751 | 1.00 | 79.55 | C |
| ATOM | 1258 | C | GLU | A | 188 | −40.619 | −5.361 | 0.404 | 1.00 | 79.89 | C |
| ATOM | 1259 | O | GLU | A | 188 | −40.897 | −4.161 | 0.292 | 1.00 | 79.15 | O |
| ATOM | 1260 | CB | GLU | A | 188 | −40.983 | −6.562 | −1.747 | 1.00 | 79.62 | C |
| ATOM | 1261 | CG | GLU | A | 188 | −42.048 | −7.458 | −1.121 | 1.00 | 83.66 | C |
| ATOM | 1262 | CD | GLU | A | 188 | −42.614 | −8.463 | −2.084 | 1.00 | 84.99 | C |
| ATOM | 1263 | OE1 | GLU | A | 188 | −42.812 | −8.122 | −3.268 | 1.00 | 95.21 | O |
| ATOM | 1264 | OE2 | GLU | A | 188 | −42.866 | −9.605 | −1.652 | 1.00 | 89.59 | O |
| ATOM | 1265 | N | THR | A | 189 | −40.891 | −6.089 | 1.496 | 1.00 | 77.96 | N |
| ATOM | 1266 | CA | THR | A | 189 | −41.533 | −5.512 | 2.676 | 1.00 | 75.91 | C |
| ATOM | 1267 | C | THR | A | 189 | −40.541 | −5.063 | 3.755 | 1.00 | 76.43 | C |
| ATOM | 1268 | O | THR | A | 189 | −40.961 | −4.656 | 4.836 | 1.00 | 76.97 | O |
| ATOM | 1269 | CB | THR | A | 189 | −42.562 | −6.481 | 3.300 | 1.00 | 75.78 | C |
| ATOM | 1270 | OG1 | THR | A | 189 | −41.883 | −7.617 | 3.843 | 1.00 | 74.95 | O |
| ATOM | 1271 | CG2 | THR | A | 189 | −43.580 | −6.923 | 2.252 | 1.00 | 70.98 | C |
| ATOM | 1272 | N | CYS | A | 190 | −39.242 | −5.131 | 3.464 | 1.00 | 78.00 | N |
| ATOM | 1273 | CA | CYS | A | 190 | −38.209 | −4.690 | 4.377 | 1.00 | 77.37 | C |
| ATOM | 1274 | C | CYS | A | 190 | −37.588 | −3.443 | 3.799 | 1.00 | 74.95 | C |
| ATOM | 1275 | O | CYS | A | 190 | −37.131 | −3.464 | 2.658 | 1.00 | 75.26 | O |
| ATOM | 1276 | CB | CYS | A | 190 | −37.136 | −5.755 | 4.545 | 1.00 | 79.47 | C |
| ATOM | 1277 | SG | CYS | A | 190 | −35.924 | −5.347 | 5.847 | 1.00 | 85.35 | S |
| ATOM | 1278 | N | CYS | A | 191 | −37.574 | −2.368 | 4.582 | 1.00 | 75.05 | N |
| ATOM | 1279 | CA | CYS | A | 191 | −36.955 | −1.110 | 4.175 | 1.00 | 77.17 | C |
| ATOM | 1280 | C | CYS | A | 191 | −36.140 | −0.537 | 5.329 | 1.00 | 77.29 | C |
| ATOM | 1281 | O | CYS | A | 191 | −36.450 | 0.523 | 5.856 | 1.00 | 81.42 | O |
| ATOM | 1282 | CB | CYS | A | 191 | −38.024 | −0.135 | 3.680 | 1.00 | 77.85 | C |
| ATOM | 1283 | SG | CYS | A | 191 | −37.383 | 1.370 | 2.899 | 1.00 | 80.61 | S |
| ATOM | 1284 | N | ASP | A | 192 | −35.091 | −1.270 | 5.703 | 1.00 | 78.03 | N |
| ATOM | 1285 | CA | ASP | A | 192 | −34.141 | −0.851 | 6.741 | 1.00 | 76.97 | C |
| ATOM | 1286 | C | ASP | A | 192 | −32.909 | −0.347 | 6.054 | 1.00 | 75.94 | C |
| ATOM | 1287 | O | ASP | A | 192 | −32.428 | −0.979 | 5.114 | 1.00 | 77.63 | O |

APPENDIX 1-continued

| ATOM | 1288 | CB  | ASP | A | 192 | −33.762 | −2.005 | 7.667  | 1.00 | 77.44 | C |
|------|------|-----|-----|---|-----|---------|--------|--------|------|-------|---|
| ATOM | 1289 | CG  | ASP | A | 192 | −34.889 | −2.419 | 8.586  | 1.00 | 80.00 | C |
| ATOM | 1290 | OD1 | ASP | A | 192 | −35.724 | −1.561 | 8.959  | 1.00 | 82.18 | O |
| ATOM | 1291 | OD2 | ASP | A | 192 | −34.941 | −3.619 | 8.943  | 1.00 | 80.09 | O |
| ATOM | 1292 | N   | PHE | A | 193 | −32.388 | 0.785  | 6.517  | 1.00 | 75.48 | N |
| ATOM | 1293 | CA  | PHE | A | 193 | −31.237 | 1.416  | 5.890  | 1.00 | 75.22 | C |
| ATOM | 1294 | C   | PHE | A | 193 | −29.909 | 0.865  | 6.443  | 1.00 | 75.43 | C |
| ATOM | 1295 | O   | PHE | A | 193 | −29.160 | 1.573  | 7.133  | 1.00 | 73.54 | O |
| ATOM | 1296 | CB  | PHE | A | 193 | −31.351 | 2.947  | 6.043  | 1.00 | 74.11 | C |
| ATOM | 1297 | CG  | PHE | A | 193 | −30.399 | 3.730  | 5.175  | 1.00 | 76.00 | C |
| ATOM | 1298 | CD1 | PHE | A | 193 | −30.300 | 3.471  | 3.793  | 1.00 | 76.25 | C |
| ATOM | 1299 | CD2 | PHE | A | 193 | −29.600 | 4.736  | 5.724  | 1.00 | 76.96 | C |
| ATOM | 1300 | CE1 | PHE | A | 193 | −29.428 | 4.189  | 2.984  | 1.00 | 73.80 | C |
| ATOM | 1301 | CE2 | PHE | A | 193 | −28.718 | 5.465  | 4.905  | 1.00 | 79.72 | C |
| ATOM | 1302 | CZ  | PHE | A | 193 | −28.638 | 5.183  | 3.528  | 1.00 | 75.51 | C |
| ATOM | 1303 | N   | PHE | A | 194 | −29.641 | −0.409 | 6.127  | 1.00 | 74.51 | N |
| ATOM | 1304 | CA  | PHE | A | 194 | −28.376 | −1.061 | 6.455  | 1.00 | 74.06 | C |
| ATOM | 1305 | C   | PHE | A | 194 | −27.340 | −0.493 | 5.527  | 1.00 | 74.74 | C |
| ATOM | 1306 | O   | PHE | A | 194 | −27.542 | −0.522 | 4.308  | 1.00 | 73.83 | O |
| ATOM | 1307 | CB  | PHE | A | 194 | −28.423 | −2.577 | 6.235  | 1.00 | 73.04 | C |
| ATOM | 1308 | CG  | PHE | A | 194 | −29.226 | −3.318 | 7.256  | 1.00 | 73.26 | C |
| ATOM | 1309 | CD1 | PHE | A | 194 | −28.674 | −3.630 | 8.499  | 1.00 | 75.81 | C |
| ATOM | 1310 | CD2 | PHE | A | 194 | −30.534 | −3.712 | 6.984  | 1.00 | 74.89 | C |
| ATOM | 1311 | CE1 | PHE | A | 194 | −29.412 | −4.320 | 9.457  | 1.00 | 74.15 | C |
| ATOM | 1312 | CE2 | PHE | A | 194 | −31.282 | −4.405 | 7.936  | 1.00 | 75.40 | C |
| ATOM | 1313 | CZ  | PHE | A | 194 | −30.720 | −4.709 | 9.176  | 1.00 | 74.86 | C |
| ATOM | 1314 | N   | THR | A | 195 | −26.241 | 0.022  | 6.087  | 1.00 | 73.91 | N |
| ATOM | 1315 | CA  | THR | A | 195 | −25.157 | 0.559  | 5.278  | 1.00 | 72.89 | C |
| ATOM | 1316 | C   | THR | A | 195 | −23.811 | −0.039 | 5.644  | 1.00 | 71.51 | C |
| ATOM | 1317 | O   | THR | A | 195 | −23.636 | −0.565 | 6.748  | 1.00 | 70.29 | O |
| ATOM | 1318 | CB  | THR | A | 195 | −25.034 | 2.092  | 5.403  | 1.00 | 73.36 | C |
| ATOM | 1319 | OG1 | THR | A | 195 | −24.316 | 2.431  | 6.598  | 1.00 | 75.79 | O |
| ATOM | 1320 | CG2 | THR | A | 195 | −26.415 | 2.762  | 5.409  | 1.00 | 75.39 | C |
| ATOM | 1321 | N   | ASN | A | 196 | −22.863 | 0.047  | 4.709  | 1.00 | 69.76 | N |
| ATOM | 1322 | CA  | ASN | A | 196 | −21.483 | −0.332 | 4.996  | 1.00 | 70.25 | C |
| ATOM | 1323 | C   | ASN | A | 196 | −20.870 | 0.823  | 5.783  | 1.00 | 70.56 | C |
| ATOM | 1324 | O   | ASN | A | 196 | −21.350 | 1.967  | 5.694  | 1.00 | 73.34 | O |
| ATOM | 1325 | CB  | ASN | A | 196 | −20.676 | −0.721 | 3.732  | 1.00 | 70.71 | C |
| ATOM | 1326 | CG  | ASN | A | 196 | −20.478 | 0.426  | 2.743  | 1.00 | 71.43 | C |
| ATOM | 1327 | OD1 | ASN | A | 196 | −19.940 | 1.481  | 3.071  | 1.00 | 74.37 | O |
| ATOM | 1328 | ND2 | ASN | A | 196 | −20.920 | 0.205  | 1.515  | 1.00 | 72.46 | N |
| ATOM | 1329 | N   | GLN | A | 197 | −19.824 | 0.524  | 6.544  | 1.00 | 69.71 | N |
| ATOM | 1330 | CA  | GLN | A | 197 | −19.195 | 1.507  | 7.446  | 1.00 | 69.84 | C |
| ATOM | 1331 | C   | GLN | A | 197 | −18.570 | 2.687  | 6.711  | 1.00 | 68.45 | C |
| ATOM | 1332 | O   | GLN | A | 197 | −18.745 | 3.832  | 7.137  | 1.00 | 68.34 | O |
| ATOM | 1333 | CB  | GLN | A | 197 | −18.141 | 0.829  | 8.319  | 1.00 | 70.49 | C |
| ATOM | 1334 | CG  | GLN | A | 197 | −18.723 | −0.221 | 9.264  | 1.00 | 73.78 | C |
| ATOM | 1335 | CD  | GLN | A | 197 | −17.662 | −1.017 | 9.977  | 1.00 | 75.55 | C |
| ATOM | 1336 | OE1 | GLN | A | 197 | −16.556 | −0.528 | 10.223 | 1.00 | 81.19 | O |
| ATOM | 1337 | NE2 | GLN | A | 197 | −17.988 | −2.262 | 10.319 | 1.00 | 83.68 | N |
| ATOM | 1338 | N   | ALA | A | 198 | −17.855 | 2.400  | 5.617  | 1.00 | 67.03 | N |
| ATOM | 1339 | CA  | ALA | A | 198 | −17.222 | 3.430  | 4.772  | 1.00 | 67.06 | C |
| ATOM | 1340 | C   | ALA | A | 198 | −18.229 | 4.480  | 4.309  | 1.00 | 68.00 | C |
| ATOM | 1341 | O   | ALA | A | 198 | −17.926 | 5.672  | 4.310  | 1.00 | 67.52 | O |
| ATOM | 1342 | CB  | ALA | A | 198 | −16.540 | 2.796  | 3.576  | 1.00 | 67.06 | C |
| ATOM | 1343 | N   | TYR | A | 199 | −19.420 | 4.027  | 3.916  | 1.00 | 67.41 | N |
| ATOM | 1344 | CA  | TYR | A | 199 | −20.503 | 4.925  | 3.544  | 1.00 | 68.01 | C |
| ATOM | 1345 | C   | TYR | A | 199 | −21.001 | 5.678  | 4.753  | 1.00 | 66.60 | C |
| ATOM | 1346 | O   | TYR | A | 199 | −21.162 | 6.889  | 4.697  | 1.00 | 64.41 | O |
| ATOM | 1347 | CB  | TYR | A | 199 | −21.685 | 4.168  | 2.935  | 1.00 | 69.88 | C |
| ATOM | 1348 | CG  | TYR | A | 199 | −22.897 | 5.054  | 2.714  | 1.00 | 67.04 | C |
| ATOM | 1349 | CD1 | TYR | A | 199 | −23.009 | 5.831  | 1.566  | 1.00 | 70.50 | C |
| ATOM | 1350 | CD2 | TYR | A | 199 | −23.932 | 5.113  | 3.655  | 1.00 | 69.18 | C |
| ATOM | 1351 | CE1 | TYR | A | 199 | −24.128 | 6.657  | 1.352  | 1.00 | 71.51 | C |
| ATOM | 1352 | CE2 | TYR | A | 199 | −25.051 | 5.933  | 3.453  | 1.00 | 72.40 | C |
| ATOM | 1353 | CZ  | TYR | A | 199 | −25.141 | 6.702  | 2.298  | 1.00 | 71.80 | C |
| ATOM | 1354 | OH  | TYR | A | 199 | −26.236 | 7.509  | 2.088  | 1.00 | 73.79 | O |
| ATOM | 1355 | N   | ALA | A | 200 | −21.245 | 4.942  | 5.840  | 1.00 | 67.80 | N |
| ATOM | 1356 | CA  | ALA | A | 200 | −21.723 | 5.531  | 7.100  | 1.00 | 66.98 | C |
| ATOM | 1357 | C   | ALA | A | 200 | −20.840 | 6.697  | 7.533  | 1.00 | 65.35 | C |
| ATOM | 1358 | O   | ALA | A | 200 | −21.354 | 7.739  | 7.890  | 1.00 | 62.59 | O |
| ATOM | 1359 | CB  | ALA | A | 200 | −21.789 | 4.486  | 8.183  | 1.00 | 67.92 | C |
| ATOM | 1360 | N   | ILE | A | 201 | −19.520 | 6.505  | 7.489  | 1.00 | 66.75 | N |
| ATOM | 1361 | CA  | ILE | A | 201 | −18.559 | 7.565  | 7.830  | 1.00 | 69.39 | C |
| ATOM | 1362 | C   | ILE | A | 201 | −18.514 | 8.680  | 6.785  | 1.00 | 70.99 | C |
| ATOM | 1363 | O   | ILE | A | 201 | −18.768 | 9.836  | 7.107  | 1.00 | 71.46 | O |
| ATOM | 1364 | CB  | ILE | A | 201 | −17.126 | 7.027  | 7.971  | 1.00 | 68.97 | C |
| ATOM | 1365 | CG1 | ILE | A | 201 | −16.998 | 6.142  | 9.210  | 1.00 | 70.83 | C |
| ATOM | 1366 | CG2 | ILE | A | 201 | −16.142 | 8.181  | 8.064  | 1.00 | 68.40 | C |
| ATOM | 1367 | CD1 | ILE | A | 201 | −15.610 | 5.530  | 9.383  | 1.00 | 71.18 | C |

APPENDIX 1-continued

| ATOM | 1368 | N | ALA | A | 202 | −18.191 | 8.311 | 5.542 | 1.00 | 71.53 | N |
|---|---|---|---|---|---|---|---|---|---|---|---|
| ATOM | 1369 | CA | ALA | A | 202 | −18.001 | 9.273 | 4.438 | 1.00 | 70.39 | C |
| ATOM | 1370 | C | ALA | A | 202 | −19.228 | 10.112 | 4.136 | 1.00 | 71.21 | C |
| ATOM | 1371 | O | ALA | A | 202 | −19.112 | 11.331 | 3.979 | 1.00 | 72.58 | O |
| ATOM | 1372 | CB | ALA | A | 202 | −17.558 | 8.555 | 3.177 | 1.00 | 69.73 | C |
| ATOM | 1373 | N | SER | A | 203 | −20.395 | 9.474 | 4.054 | 1.00 | 71.88 | N |
| ATOM | 1374 | CA | SER | A | 203 | −21.633 | 10.202 | 3.748 | 1.00 | 72.73 | C |
| ATOM | 1375 | C | SER | A | 203 | −22.030 | 11.160 | 4.861 | 1.00 | 75.38 | C |
| ATOM | 1376 | O | SER | A | 203 | −22.457 | 12.274 | 4.579 | 1.00 | 76.69 | O |
| ATOM | 1377 | CB | SER | A | 203 | −22.798 | 9.261 | 3.492 | 1.00 | 73.42 | C |
| ATOM | 1378 | OG | SER | A | 203 | −23.944 | 10.010 | 3.118 | 1.00 | 77.91 | O |
| ATOM | 1379 | N | SER | A | 204 | −21.890 | 10.730 | 6.114 | 1.00 | 72.53 | N |
| ATOM | 1380 | CA | SER | A | 204 | −22.266 | 11.570 | 7.250 | 1.00 | 71.77 | C |
| ATOM | 1381 | C | SER | A | 204 | −21.283 | 12.742 | 7.442 | 1.00 | 73.36 | C |
| ATOM | 1382 | O | SER | A | 204 | −21.695 | 13.822 | 7.863 | 1.00 | 73.43 | O |
| ATOM | 1383 | CB | SER | A | 204 | −22.428 | 10.728 | 8.525 | 1.00 | 69.52 | C |
| ATOM | 1384 | OG | SER | A | 204 | −21.292 | 9.941 | 8.776 | 1.00 | 76.74 | O |
| ATOM | 1385 | N | ILE | A | 205 | −19.998 | 12.537 | 7.137 | 1.00 | 73.22 | N |
| ATOM | 1386 | CA | ILE | A | 205 | −19.020 | 13.638 | 7.213 | 1.00 | 73.31 | C |
| ATOM | 1387 | C | ILE | A | 205 | −19.284 | 14.674 | 6.118 | 1.00 | 76.06 | C |
| ATOM | 1388 | O | ILE | A | 205 | −19.399 | 15.872 | 6.405 | 1.00 | 76.12 | O |
| ATOM | 1389 | CB | ILE | A | 205 | −17.569 | 13.147 | 7.126 | 1.00 | 72.39 | C |
| ATOM | 1390 | CG1 | ILE | A | 205 | −17.173 | 12.458 | 8.435 | 1.00 | 71.69 | C |
| ATOM | 1391 | CG2 | ILE | A | 205 | −16.625 | 14.303 | 6.876 | 1.00 | 70.67 | C |
| ATOM | 1392 | CD1 | ILE | A | 205 | −15.812 | 11.794 | 8.390 | 1.00 | 72.10 | C |
| ATOM | 1393 | N | VAL | A | 206 | −19.380 | 14.201 | 4.877 | 1.00 | 74.65 | N |
| ATOM | 1394 | CA | VAL | A | 206 | −19.591 | 15.081 | 3.713 | 1.00 | 77.11 | C |
| ATOM | 1395 | C | VAL | A | 206 | −20.972 | 15.757 | 3.665 | 1.00 | 75.89 | C |
| ATOM | 1396 | O | VAL | A | 206 | −21.071 | 16.933 | 3.317 | 1.00 | 75.71 | O |
| ATOM | 1397 | CB | VAL | A | 206 | −19.356 | 14.321 | 2.388 | 1.00 | 75.98 | C |
| ATOM | 1398 | CG1 | VAL | A | 206 | −19.647 | 15.210 | 1.194 | 1.00 | 77.29 | C |
| ATOM | 1399 | CG2 | VAL | A | 206 | −17.920 | 13.819 | 2.324 | 1.00 | 80.65 | C |
| ATOM | 1400 | N | SER | A | 207 | −22.023 | 15.025 | 4.009 | 1.00 | 76.66 | N |
| ATOM | 1401 | CA | SER | A | 207 | −23.377 | 15.585 | 3.972 | 1.00 | 77.79 | C |
| ATOM | 1402 | C | SER | A | 207 | −23.720 | 16.457 | 5.165 | 1.00 | 78.97 | C |
| ATOM | 1403 | O | SER | A | 207 | −24.437 | 17.437 | 4.995 | 1.00 | 83.06 | O |
| ATOM | 1404 | CB | SER | A | 207 | −24.420 | 14.488 | 3.922 | 1.00 | 78.06 | C |
| ATOM | 1405 | OG | SER | A | 207 | −24.231 | 13.633 | 2.814 | 1.00 | 83.89 | O |
| ATOM | 1406 | N | PHE | A | 208 | −23.216 | 16.103 | 6.356 | 1.00 | 79.98 | N |
| ATOM | 1407 | CA | PHE | A | 208 | −23.601 | 16.771 | 7.609 | 1.00 | 77.07 | C |
| ATOM | 1408 | C | PHE | A | 208 | −22.463 | 17.477 | 8.319 | 1.00 | 78.35 | C |
| ATOM | 1409 | O | PHE | A | 208 | −22.511 | 18.695 | 8.470 | 1.00 | 79.76 | O |
| ATOM | 1410 | CB | PHE | A | 208 | −24.254 | 15.753 | 8.552 | 1.00 | 76.98 | C |
| ATOM | 1411 | CG | PHE | A | 208 | −24.676 | 16.321 | 9.888 | 1.00 | 78.18 | C |
| ATOM | 1412 | CD1 | PHE | A | 208 | −25.792 | 17.141 | 9.984 | 1.00 | 77.60 | C |
| ATOM | 1413 | CD2 | PHE | A | 208 | −23.957 | 16.025 | 11.051 | 1.00 | 75.04 | C |
| ATOM | 1414 | CE1 | PHE | A | 208 | −26.190 | 17.668 | 11.216 | 1.00 | 77.26 | C |
| ATOM | 1415 | CE2 | PHE | A | 208 | −24.350 | 16.545 | 12.278 | 1.00 | 80.26 | C |
| ATOM | 1416 | CZ | PHE | A | 208 | −25.475 | 17.373 | 12.357 | 1.00 | 77.27 | C |
| ATOM | 1417 | N | TYR | A | 209 | −21.450 | 16.739 | 8.756 | 1.00 | 78.29 | N |
| ATOM | 1418 | CA | TYR | A | 209 | −20.386 | 17.351 | 9.593 | 1.00 | 78.96 | C |
| ATOM | 1419 | C | TYR | A | 209 | −19.583 | 18.463 | 8.941 | 1.00 | 78.89 | C |
| ATOM | 1420 | O | TYR | A | 209 | −19.222 | 19.422 | 9.625 | 1.00 | 79.13 | O |
| ATOM | 1421 | CB | TYR | A | 209 | −19.425 | 16.295 | 10.131 | 1.00 | 80.47 | C |
| ATOM | 1422 | CG | TYR | A | 209 | −20.047 | 15.425 | 11.181 | 1.00 | 82.05 | C |
| ATOM | 1423 | CD1 | TYR | A | 209 | −20.330 | 14.088 | 10.937 | 1.00 | 80.35 | C |
| ATOM | 1424 | CD2 | TYR | A | 209 | −20.360 | 15.948 | 12.440 | 1.00 | 84.46 | C |
| ATOM | 1425 | CE1 | TYR | A | 209 | −20.906 | 13.292 | 11.913 | 1.00 | 83.44 | C |
| ATOM | 1426 | CE2 | TYR | A | 209 | −20.936 | 15.163 | 13.424 | 1.00 | 85.84 | C |
| ATOM | 1427 | CZ | TYR | A | 209 | −21.208 | 13.835 | 13.159 | 1.00 | 85.25 | C |
| ATOM | 1428 | OH | TYR | A | 209 | −21.776 | 13.073 | 14.145 | 1.00 | 89.70 | O |
| ATOM | 1429 | N | VAL | A | 210 | −19.304 | 18.351 | 7.645 | 1.00 | 78.18 | N |
| ATOM | 1430 | CA | VAL | A | 210 | −18.557 | 19.404 | 6.944 | 1.00 | 77.41 | C |
| ATOM | 1431 | C | VAL | A | 210 | −19.350 | 20.740 | 6.944 | 1.00 | 77.38 | C |
| ATOM | 1432 | O | VAL | A | 210 | −18.853 | 21.716 | 7.495 | 1.00 | 80.02 | O |
| ATOM | 1433 | CB | VAL | A | 210 | −18.108 | 18.976 | 5.515 | 1.00 | 78.51 | C |
| ATOM | 1434 | CG1 | VAL | A | 210 | −17.758 | 20.202 | 4.653 | 1.00 | 73.94 | C |
| ATOM | 1435 | CG2 | VAL | A | 210 | −16.932 | 18.022 | 5.609 | 1.00 | 76.43 | C |
| ATOM | 1436 | N | PRO | A | 211 | −20.557 | 20.780 | 6.339 | 1.00 | 75.78 | N |
| ATOM | 1437 | CA | PRO | A | 211 | −21.304 | 22.033 | 6.379 | 1.00 | 76.70 | C |
| ATOM | 1438 | C | PRO | A | 211 | −21.721 | 22.509 | 7.793 | 1.00 | 78.77 | C |
| ATOM | 1439 | O | PRO | A | 211 | −21.917 | 23.707 | 7.967 | 1.00 | 81.95 | O |
| ATOM | 1440 | CB | PRO | A | 211 | −22.538 | 21.738 | 5.506 | 1.00 | 78.00 | C |
| ATOM | 1441 | CG | PRO | A | 211 | −22.687 | 20.307 | 5.514 | 1.00 | 77.13 | C |
| ATOM | 1442 | CD | PRO | A | 211 | −21.305 | 19.746 | 5.601 | 1.00 | 80.23 | C |
| ATOM | 1443 | N | LEU | A | 212 | −21.848 | 21.598 | 8.767 | 1.00 | 77.02 | N |
| ATOM | 1444 | CA | LEU | A | 212 | −22.178 | 21.965 | 10.159 | 1.00 | 75.25 | C |
| ATOM | 1445 | C | LEU | A | 212 | −21.034 | 22.723 | 10.815 | 1.00 | 75.40 | C |
| ATOM | 1446 | O | LEU | A | 212 | −21.248 | 23.765 | 11.404 | 1.00 | 76.71 | O |
| ATOM | 1447 | CB | LEU | A | 212 | −22.492 | 20.727 | 11.017 | 1.00 | 73.79 | C |

APPENDIX 1-continued

| ATOM | 1448 | CG | LEU | A | 212 | −22.759 | 20.906 | 12.537 | 1.00 | 77.60 | C |
|---|---|---|---|---|---|---|---|---|---|---|---|
| ATOM | 1449 | CD1 | LEU | A | 212 | −24.102 | 21.571 | 12.759 | 1.00 | 79.25 | C |
| ATOM | 1450 | CD2 | LEU | A | 212 | −22.691 | 19.558 | 13.306 | 1.00 | 70.72 | C |
| ATOM | 1451 | N | VAL | A | 213 | −19.826 | 22.183 | 10.711 | 1.00 | 76.14 | N |
| ATOM | 1452 | CA | VAL | A | 213 | −18.636 | 22.808 | 11.311 | 1.00 | 76.70 | C |
| ATOM | 1453 | C | VAL | A | 213 | −18.372 | 24.190 | 10.713 | 1.00 | 77.08 | C |
| ATOM | 1454 | O | VAL | A | 213 | −18.039 | 25.132 | 11.437 | 1.00 | 76.69 | O |
| ATOM | 1455 | CB | VAL | A | 213 | −17.380 | 21.915 | 11.146 | 1.00 | 79.00 | C |
| ATOM | 1456 | CG1 | VAL | A | 213 | −16.111 | 22.656 | 11.562 | 1.00 | 78.68 | C |
| ATOM | 1457 | CG2 | VAL | A | 213 | −17.534 | 20.627 | 11.955 | 1.00 | 77.70 | C |
| ATOM | 1458 | N | ILE | A | 214 | −18.528 | 24.295 | 9.396 | 1.00 | 74.65 | N |
| ATOM | 1459 | CA | ILE | A | 214 | −18.372 | 25.561 | 8.690 | 1.00 | 74.83 | C |
| ATOM | 1460 | C | ILE | A | 214 | −19.423 | 26.574 | 9.162 | 1.00 | 72.99 | C |
| ATOM | 1461 | O | ILE | A | 214 | −19.075 | 27.692 | 9.502 | 1.00 | 72.81 | O |
| ATOM | 1462 | CB | ILE | A | 214 | −18.480 | 25.384 | 7.144 | 1.00 | 73.17 | C |
| ATOM | 1463 | CG1 | ILE | A | 214 | −17.318 | 24.547 | 6.603 | 1.00 | 76.80 | C |
| ATOM | 1464 | CG2 | ILE | A | 214 | −18.501 | 26.748 | 6.450 | 1.00 | 71.35 | C |
| ATOM | 1465 | CD1 | ILE | A | 214 | −17.443 | 24.202 | 5.126 | 1.00 | 72.96 | C |
| ATOM | 1466 | N | MET | A | 215 | −20.692 | 26.159 | 9.171 | 1.00 | 73.55 | N |
| ATOM | 1467 | CA | MET | A | 215 | −21.824 | 26.990 | 9.611 | 1.00 | 75.44 | C |
| ATOM | 1468 | C | MET | A | 215 | −21.589 | 27.580 | 10.979 | 1.00 | 77.02 | C |
| ATOM | 1469 | O | MET | A | 215 | −21.690 | 28.787 | 11.150 | 1.00 | 79.77 | O |
| ATOM | 1470 | CB | MET | A | 215 | −23.099 | 26.153 | 9.675 | 1.00 | 74.74 | C |
| ATOM | 1471 | CG | MET | A | 215 | −24.374 | 26.874 | 10.124 | 1.00 | 73.35 | C |
| ATOM | 1472 | SD | MET | A | 215 | −25.653 | 25.672 | 10.545 | 1.00 | 82.79 | S |
| ATOM | 1473 | CE | MET | A | 215 | −25.102 | 25.185 | 12.188 | 1.00 | 78.98 | C |
| ATOM | 1474 | N | VAL | A | 216 | −21.281 | 26.709 | 11.938 | 1.00 | 73.57 | N |
| ATOM | 1475 | CA | VAL | A | 216 | −21.029 | 27.111 | 13.319 | 1.00 | 77.98 | C |
| ATOM | 1476 | C | VAL | A | 216 | −19.847 | 28.077 | 13.424 | 1.00 | 78.25 | C |
| ATOM | 1477 | O | VAL | A | 216 | −19.960 | 29.124 | 14.061 | 1.00 | 82.48 | O |
| ATOM | 1478 | CB | VAL | A | 216 | −20.760 | 25.888 | 14.249 | 1.00 | 74.95 | C |
| ATOM | 1479 | CG1 | VAL | A | 216 | −20.358 | 26.350 | 15.613 | 1.00 | 73.89 | C |
| ATOM | 1480 | CG2 | VAL | A | 216 | −21.995 | 24.992 | 14.334 | 1.00 | 72.42 | C |
| ATOM | 1481 | N | PHE | A | 217 | −18.724 | 27.724 | 12.802 | 1.00 | 78.36 | N |
| ATOM | 1482 | CA | PHE | A | 217 | −17.559 | 28.595 | 12.820 | 1.00 | 77.83 | C |
| ATOM | 1483 | C | PHE | A | 217 | −17.880 | 29.962 | 12.227 | 1.00 | 74.98 | C |
| ATOM | 1484 | O | PHE | A | 217 | −17.661 | 30.981 | 12.862 | 1.00 | 74.40 | O |
| ATOM | 1485 | CB | PHE | A | 217 | −16.394 | 27.992 | 12.054 | 1.00 | 80.26 | C |
| ATOM | 1486 | CG | PHE | A | 217 | −15.236 | 28.930 | 11.918 | 1.00 | 83.15 | C |
| ATOM | 1487 | CD1 | PHE | A | 217 | −14.381 | 29.152 | 12.994 | 1.00 | 87.33 | C |
| ATOM | 1488 | CD2 | PHE | A | 217 | −14.993 | 29.600 | 10.717 | 1.00 | 87.93 | C |
| ATOM | 1489 | CE1 | PHE | A | 217 | −13.296 | 30.029 | 12.881 | 1.00 | 85.31 | C |
| ATOM | 1490 | CE2 | PHE | A | 217 | −13.912 | 30.478 | 10.592 | 1.00 | 87.26 | C |
| ATOM | 1491 | CZ | PHE | A | 217 | −13.063 | 30.692 | 11.677 | 1.00 | 86.57 | C |
| ATOM | 1492 | N | VAL | A | 218 | −18.400 | 29.958 | 11.009 | 1.00 | 72.95 | N |
| ATOM | 1493 | CA | VAL | A | 218 | −18.693 | 31.202 | 10.299 | 1.00 | 72.35 | C |
| ATOM | 1494 | C | VAL | A | 218 | −19.739 | 32.039 | 11.007 | 1.00 | 70.18 | C |
| ATOM | 1495 | O | VAL | A | 218 | −19.547 | 33.238 | 11.123 | 1.00 | 72.08 | O |
| ATOM | 1496 | CB | VAL | A | 218 | −19.126 | 30.965 | 8.828 | 1.00 | 69.97 | C |
| ATOM | 1497 | CG1 | VAL | A | 218 | −19.608 | 32.264 | 8.189 | 1.00 | 63.51 | C |
| ATOM | 1498 | CG2 | VAL | A | 218 | −17.973 | 30.393 | 8.039 | 1.00 | 69.43 | C |
| ATOM | 1499 | N | TYR | A | 219 | −20.822 | 31.428 | 11.479 | 1.00 | 69.91 | N |
| ATOM | 1500 | CA | TYR | A | 219 | −21.867 | 32.204 | 12.154 | 1.00 | 70.79 | C |
| ATOM | 1501 | C | TYR | A | 219 | −21.482 | 32.646 | 13.561 | 1.00 | 72.41 | C |
| ATOM | 1502 | O | TYR | A | 219 | −22.135 | 33.532 | 14.094 | 1.00 | 73.85 | O |
| ATOM | 1503 | CB | TYR | A | 219 | −23.216 | 31.482 | 12.201 | 1.00 | 70.68 | C |
| ATOM | 1504 | CG | TYR | A | 219 | −24.373 | 32.468 | 12.149 | 1.00 | 72.35 | C |
| ATOM | 1505 | CD1 | TYR | A | 219 | −24.698 | 33.112 | 10.968 | 1.00 | 75.81 | C |
| ATOM | 1506 | CD2 | TYR | A | 219 | −25.136 | 32.755 | 13.263 | 1.00 | 77.93 | C |
| ATOM | 1507 | CE1 | TYR | A | 219 | −25.757 | 34.025 | 10.892 | 1.00 | 74.63 | C |
| ATOM | 1508 | CE2 | TYR | A | 219 | −26.203 | 33.673 | 13.190 | 1.00 | 70.80 | C |
| ATOM | 1509 | CZ | TYR | A | 219 | −26.499 | 34.292 | 12.013 | 1.00 | 79.33 | C |
| ATOM | 1510 | OH | TYR | A | 219 | −27.544 | 35.187 | 11.958 | 1.00 | 75.98 | O |
| ATOM | 1511 | N | SER | A | 220 | −20.451 | 32.053 | 14.170 | 1.00 | 71.26 | N |
| ATOM | 1512 | CA | SER | A | 220 | −19.982 | 32.579 | 15.456 | 1.00 | 72.46 | C |
| ATOM | 1513 | C | SER | A | 220 | −19.265 | 33.886 | 15.124 | 1.00 | 73.33 | C |
| ATOM | 1514 | O | SER | A | 220 | −19.384 | 34.833 | 15.876 | 1.00 | 71.17 | O |
| ATOM | 1515 | CB | SER | A | 220 | −19.110 | 31.593 | 16.240 | 1.00 | 71.03 | C |
| ATOM | 1516 | OG | SER | A | 220 | −17.988 | 31.169 | 15.514 | 1.00 | 78.76 | O |
| ATOM | 1517 | N | ARG | A | 221 | −18.539 | 33.924 | 13.990 | 1.00 | 71.00 | N |
| ATOM | 1518 | CA | ARG | A | 221 | −17.878 | 35.164 | 13.507 | 1.00 | 71.92 | C |
| ATOM | 1519 | C | ARG | A | 221 | −18.847 | 36.268 | 13.102 | 1.00 | 71.03 | C |
| ATOM | 1520 | O | ARG | A | 221 | −18.485 | 37.440 | 13.144 | 1.00 | 75.74 | O |
| ATOM | 1521 | CB | ARG | A | 221 | −16.940 | 34.887 | 12.319 | 1.00 | 73.28 | C |
| ATOM | 1522 | CG | ARG | A | 221 | −15.789 | 33.967 | 12.607 | 1.00 | 81.79 | C |
| ATOM | 1523 | CD | ARG | A | 221 | −14.737 | 34.643 | 13.460 | 1.00 | 91.32 | C |
| ATOM | 1524 | NE | ARG | A | 221 | −13.695 | 33.711 | 13.900 | 1.00 | 99.40 | N |
| ATOM | 1525 | CZ | ARG | A | 221 | −12.642 | 34.037 | 14.669 | 1.00 | 104.74 | C |
| ATOM | 1526 | NH1 | ARG | A | 221 | −12.463 | 35.296 | 15.107 | 1.00 | 108.58 | N |
| ATOM | 1527 | NH2 | ARG | A | 221 | −11.754 | 33.095 | 15.009 | 1.00 | 102.27 | N |

APPENDIX 1-continued

| | | | | | | | | | | |
|---|---|---|---|---|---|---|---|---|---|---|
| ATOM | 1528 | N | VAL | A | 222 | −20.065 | 35.898 | 12.705 | 1.00 | 72.12 | N |
| ATOM | 1529 | CA | VAL | A | 222 | −21.114 | 36.862 | 12.390 | 1.00 | 70.08 | C |
| ATOM | 1530 | C | VAL | A | 222 | −21.544 | 37.555 | 13.680 | 1.00 | 72.52 | C |
| ATOM | 1531 | O | VAL | A | 222 | −21.666 | 38.787 | 13.704 | 1.00 | 74.66 | O |
| ATOM | 1532 | CB | VAL | A | 222 | −22.314 | 36.199 | 11.688 | 1.00 | 69.66 | C |
| ATOM | 1533 | CG1 | VAL | A | 222 | −23.527 | 37.099 | 11.713 | 1.00 | 70.73 | C |
| ATOM | 1534 | CG2 | VAL | A | 222 | −21.940 | 35.844 | 10.245 | 1.00 | 74.61 | C |
| ATOM | 1535 | N | PHE | A | 223 | −21.771 | 36.782 | 14.752 | 1.00 | 72.29 | N |
| ATOM | 1536 | CA | PHE | A | 223 | −22.115 | 37.388 | 16.054 | 1.00 | 71.42 | C |
| ATOM | 1537 | C | PHE | A | 223 | −21.020 | 38.303 | 16.562 | 1.00 | 69.83 | C |
| ATOM | 1538 | O | PHE | A | 223 | −21.324 | 39.411 | 16.970 | 1.00 | 71.03 | O |
| ATOM | 1539 | CB | PHE | A | 223 | −22.461 | 36.334 | 17.105 | 1.00 | 72.71 | C |
| ATOM | 1540 | CG | PHE | A | 223 | −23.766 | 35.640 | 16.857 | 1.00 | 69.91 | C |
| ATOM | 1541 | CD1 | PHE | A | 223 | −24.927 | 36.370 | 16.563 | 1.00 | 71.96 | C |
| ATOM | 1542 | CD2 | PHE | A | 223 | −23.850 | 34.266 | 16.920 | 1.00 | 73.93 | C |
| ATOM | 1543 | CE1 | PHE | A | 223 | −26.121 | 35.741 | 16.338 | 1.00 | 73.93 | C |
| ATOM | 1544 | CE2 | PHE | A | 223 | −25.055 | 33.624 | 16.693 | 1.00 | 76.95 | C |
| ATOM | 1545 | CZ | PHE | A | 223 | −26.190 | 34.367 | 16.404 | 1.00 | 78.80 | C |
| ATOM | 1546 | N | GLN | A | 224 | −19.766 | 37.854 | 16.534 | 1.00 | 70.23 | N |
| ATOM | 1547 | CA | GLN | A | 224 | −18.632 | 38.724 | 16.916 | 1.00 | 71.28 | C |
| ATOM | 1548 | C | GLN | A | 224 | −18.655 | 40.034 | 16.155 | 1.00 | 72.34 | C |
| ATOM | 1549 | O | GLN | A | 224 | −18.462 | 41.077 | 16.742 | 1.00 | 76.18 | O |
| ATOM | 1550 | CB | GLN | A | 224 | −17.293 | 38.077 | 16.639 | 1.00 | 71.04 | C |
| ATOM | 1551 | CG | GLN | A | 224 | −17.007 | 36.807 | 17.433 | 1.00 | 82.15 | C |
| ATOM | 1552 | CD | GLN | A | 224 | −15.565 | 36.308 | 17.276 | 1.00 | 85.53 | C |
| ATOM | 1553 | OE1 | GLN | A | 224 | −14.706 | 36.986 | 16.673 | 1.00 | 85.57 | O |
| ATOM | 1554 | NE2 | GLN | A | 224 | −15.290 | 35.107 | 17.824 | 1.00 | 87.83 | N |
| ATOM | 1555 | N | GLU | A | 225 | −18.892 | 39.969 | 14.839 | 1.00 | 74.23 | N |
| ATOM | 1556 | CA | GLU | A | 225 | −18.986 | 41.187 | 14.026 | 1.00 | 73.90 | C |
| ATOM | 1557 | C | GLU | A | 225 | −20.161 | 42.043 | 14.442 | 1.00 | 72.00 | C |
| ATOM | 1558 | O | GLU | A | 225 | −19.987 | 43.221 | 14.670 | 1.00 | 69.39 | O |
| ATOM | 1559 | CB | GLU | A | 225 | −19.073 | 40.880 | 12.525 | 1.00 | 75.78 | C |
| ATOM | 1560 | CG | GLU | A | 225 | −17.713 | 40.806 | 11.881 | 1.00 | 85.48 | C |
| ATOM | 1561 | CD | GLU | A | 225 | −16.990 | 42.134 | 11.934 | 1.00 | 92.43 | C |
| ATOM | 1562 | OE1 | GLU | A | 225 | −17.670 | 43.174 | 11.759 | 1.00 | 86.05 | O |
| ATOM | 1563 | OE2 | GLU | A | 225 | −15.755 | 42.133 | 12.152 | 1.00 | 98.53 | O |
| ATOM | 1564 | N | ALA | A | 226 | −21.336 | 41.439 | 14.537 | 1.00 | 70.43 | N |
| ATOM | 1565 | CA | ALA | A | 226 | −22.521 | 42.145 | 14.988 | 1.00 | 71.14 | C |
| ATOM | 1566 | C | ALA | A | 226 | −22.238 | 42.861 | 16.326 | 1.00 | 70.13 | C |
| ATOM | 1567 | O | ALA | A | 226 | −22.513 | 44.040 | 16.455 | 1.00 | 69.11 | O |
| ATOM | 1568 | CB | ALA | A | 226 | −23.683 | 41.195 | 15.114 | 1.00 | 69.59 | C |
| ATOM | 1569 | N | LYS | A | 227 | −21.686 | 42.139 | 17.298 | 1.00 | 70.92 | N |
| ATOM | 1570 | CA | LYS | A | 227 | −21.345 | 42.716 | 18.619 | 1.00 | 72.35 | C |
| ATOM | 1571 | C | LYS | A | 227 | −20.374 | 43.880 | 18.510 | 1.00 | 70.68 | C |
| ATOM | 1572 | O | LYS | A | 227 | −20.498 | 44.860 | 19.238 | 1.00 | 71.56 | O |
| ATOM | 1573 | CB | LYS | A | 227 | −20.728 | 41.660 | 19.540 | 1.00 | 72.29 | C |
| ATOM | 1574 | CG | LYS | A | 227 | −20.673 | 42.077 | 21.027 | 1.00 | 77.11 | C |
| ATOM | 1575 | CD | LYS | A | 227 | −20.272 | 40.913 | 21.948 | 1.00 | 79.33 | C |
| ATOM | 1576 | CE | LYS | A | 227 | −20.366 | 41.295 | 23.457 | 1.00 | 89.68 | C |
| ATOM | 1577 | NZ | LYS | A | 227 | −19.211 | 42.084 | 23.975 | 1.00 | 91.63 | N |
| ATOM | 1578 | N | ARG | A | 228 | −19.419 | 43.749 | 17.591 | 1.00 | 71.06 | N |
| ATOM | 1579 | CA | ARG | A | 228 | −18.380 | 44.749 | 17.349 | 1.00 | 71.67 | C |
| ATOM | 1580 | C | ARG | A | 228 | −18.909 | 46.028 | 16.696 | 1.00 | 66.45 | C |
| ATOM | 1581 | O | ARG | A | 228 | −18.234 | 47.031 | 16.714 | 1.00 | 70.70 | O |
| ATOM | 1582 | CB | ARG | A | 228 | −17.271 | 44.142 | 16.486 | 1.00 | 73.73 | C |
| ATOM | 1583 | CG | ARG | A | 228 | −15.959 | 44.946 | 16.395 | 1.00 | 80.33 | C |
| ATOM | 1584 | CD | ARG | A | 228 | −15.060 | 44.487 | 15.239 | 1.00 | 85.20 | C |
| ATOM | 1585 | NE | ARG | A | 228 | −15.691 | 44.699 | 13.931 | 1.00 | 95.73 | N |
| ATOM | 1586 | CZ | ARG | A | 228 | −15.736 | 45.853 | 13.239 | 1.00 | 99.68 | C |
| ATOM | 1587 | NH1 | ARG | A | 228 | −15.178 | 46.979 | 13.702 | 1.00 | 98.15 | N |
| ATOM | 1588 | NH2 | ARG | A | 228 | −16.353 | 45.889 | 12.052 | 1.00 | 97.65 | N |
| ATOM | 1589 | N | GLN | A | 229 | −20.105 | 46.002 | 16.127 | 1.00 | 67.44 | N |
| ATOM | 1590 | CA | GLN | A | 229 | −20.718 | 47.217 | 15.562 | 1.00 | 69.07 | C |
| ATOM | 1591 | C | GLN | A | 229 | −21.324 | 48.107 | 16.630 | 1.00 | 68.99 | C |
| ATOM | 1592 | O | GLN | A | 229 | −21.550 | 49.299 | 16.388 | 1.00 | 73.07 | O |
| ATOM | 1593 | CB | GLN | A | 229 | −21.817 | 46.858 | 14.603 | 1.00 | 67.27 | C |
| ATOM | 1594 | CG | GLN | A | 229 | −21.328 | 46.085 | 13.403 | 1.00 | 79.11 | C |
| ATOM | 1595 | CD | GLN | A | 229 | −22.412 | 45.836 | 12.358 | 1.00 | 81.84 | C |
| ATOM | 1596 | OE1 | GLN | A | 229 | −22.097 | 45.437 | 11.233 | 1.00 | 98.22 | O |
| ATOM | 1597 | NE2 | GLN | A | 229 | −23.703 | 46.069 | 12.724 | 1.00 | 80.39 | N |
| ATOM | 1598 | N | LEU | A | 230 | −21.594 | 47.546 | 17.804 | 1.00 | 65.76 | N |
| ATOM | 1599 | CA | LEU | A | 230 | −22.180 | 48.318 | 18.887 | 1.00 | 66.37 | C |
| ATOM | 1600 | C | LEU | A | 230 | −21.228 | 49.424 | 19.268 | 1.00 | 62.49 | C |
| ATOM | 1601 | O | LEU | A | 230 | −20.068 | 49.184 | 19.517 | 1.00 | 63.24 | O |
| ATOM | 1602 | CB | LEU | A | 230 | −22.492 | 47.429 | 20.078 | 1.00 | 63.29 | C |
| ATOM | 1603 | CG | LEU | A | 230 | −23.526 | 46.346 | 19.805 | 1.00 | 63.55 | C |
| ATOM | 1604 | CD1 | LEU | A | 230 | −23.659 | 45.401 | 21.017 | 1.00 | 56.14 | C |
| ATOM | 1605 | CD2 | LEU | A | 230 | −24.867 | 46.998 | 19.398 | 1.00 | 63.01 | C |
| ATOM | 1606 | N | ASN | A | 1002 | −21.745 | 50.645 | 19.298 | 1.00 | 65.96 | N |
| ATOM | 1607 | CA | ASN | A | 1002 | −20.959 | 51.846 | 19.632 | 1.00 | 68.64 | C |

APPENDIX 1-continued

| | | | | | | | | | | |
|---|---|---|---|---|---|---|---|---|---|---|
| ATOM | 1608 | C | ASN | A | 1002 | −21.911 | 52.946 | 20.059 | 1.00 | 68.56 | C |
| ATOM | 1609 | O | ASN | A | 1002 | −23.125 | 52.706 | 20.134 | 1.00 | 70.46 | O |
| ATOM | 1610 | CB | ASN | A | 1002 | −20.114 | 52.260 | 18.442 | 1.00 | 68.39 | C |
| ATOM | 1611 | CG | ASN | A | 1002 | −20.935 | 52.517 | 17.224 | 1.00 | 74.98 | C |
| ATOM | 1612 | OD1 | ASN | A | 1002 | −22.100 | 52.934 | 17.313 | 1.00 | 65.74 | O |
| ATOM | 1613 | ND2 | ASN | A | 1002 | −20.342 | 52.273 | 16.058 | 1.00 | 67.18 | N |
| ATOM | 1614 | N | ILE | A | 1003 | −21.390 | 54.139 | 20.330 | 1.00 | 69.49 | N |
| ATOM | 1615 | CA | ILE | A | 1003 | −22.224 | 55.203 | 20.901 | 1.00 | 70.87 | C |
| ATOM | 1616 | C | ILE | A | 1003 | −23.404 | 55.572 | 20.013 | 1.00 | 70.78 | C |
| ATOM | 1617 | O | ILE | A | 1003 | −24.472 | 55.886 | 20.521 | 1.00 | 74.04 | O |
| ATOM | 1618 | CB | ILE | A | 1003 | −21.362 | 56.453 | 21.310 | 1.00 | 74.80 | C |
| ATOM | 1619 | CG1 | ILE | A | 1003 | −22.172 | 57.390 | 22.229 | 1.00 | 76.63 | C |
| ATOM | 1620 | CG2 | ILE | A | 1003 | −20.788 | 57.153 | 20.075 | 1.00 | 68.47 | C |
| ATOM | 1621 | CD1 | ILE | A | 1003 | −21.370 | 58.560 | 22.737 | 1.00 | 73.42 | C |
| ATOM | 1622 | N | PHE | A | 1004 | −23.204 | 55.527 | 18.695 | 1.00 | 73.63 | N |
| ATOM | 1623 | CA | PHE | A | 1004 | −24.261 | 55.801 | 17.719 | 1.00 | 72.72 | C |
| ATOM | 1624 | C | PHE | A | 1004 | −25.409 | 54.841 | 17.835 | 1.00 | 73.43 | C |
| ATOM | 1625 | O | PHE | A | 1004 | −26.574 | 55.255 | 17.872 | 1.00 | 71.77 | O |
| ATOM | 1626 | CB | PHE | A | 1004 | −23.679 | 55.727 | 16.309 | 1.00 | 75.62 | C |
| ATOM | 1627 | CG | PHE | A | 1004 | −24.689 | 55.716 | 15.236 | 1.00 | 71.84 | C |
| ATOM | 1628 | CD1 | PHE | A | 1004 | −25.453 | 56.848 | 14.979 | 1.00 | 82.28 | C |
| ATOM | 1629 | CD2 | PHE | A | 1004 | −24.892 | 54.570 | 14.452 | 1.00 | 82.90 | C |
| ATOM | 1630 | CE1 | PHE | A | 1004 | −26.423 | 56.843 | 13.943 | 1.00 | 77.44 | C |
| ATOM | 1631 | CE2 | PHE | A | 1004 | −25.865 | 54.564 | 13.410 | 1.00 | 71.41 | C |
| ATOM | 1632 | CZ | PHE | A | 1004 | −26.620 | 55.697 | 13.166 | 1.00 | 70.16 | C |
| ATOM | 1633 | N | GLU | A | 1005 | −25.074 | 53.559 | 17.889 | 1.00 | 72.98 | N |
| ATOM | 1634 | CA | GLU | A | 1005 | −26.063 | 52.517 | 18.064 | 1.00 | 72.41 | C |
| ATOM | 1635 | C | GLU | A | 1005 | −26.733 | 52.619 | 19.416 | 1.00 | 74.97 | C |
| ATOM | 1636 | O | GLU | A | 1005 | −27.949 | 52.434 | 19.517 | 1.00 | 74.19 | O |
| ATOM | 1637 | CB | GLU | A | 1005 | −25.418 | 51.130 | 17.931 | 1.00 | 72.97 | C |
| ATOM | 1638 | CG | GLU | A | 1005 | −24.759 | 50.844 | 16.561 | 1.00 | 75.62 | C |
| ATOM | 1639 | CD | GLU | A | 1005 | −25.713 | 51.008 | 15.396 | 1.00 | 84.27 | C |
| ATOM | 1640 | OE1 | GLU | A | 1005 | −26.925 | 50.899 | 15.640 | 1.00 | 91.81 | O |
| ATOM | 1641 | OE2 | GLU | A | 1005 | −25.261 | 51.243 | 14.247 | 1.00 | 80.28 | O |
| ATOM | 1642 | N | MET | A | 1006 | −25.939 | 52.913 | 20.453 | 1.00 | 71.72 | N |
| ATOM | 1643 | CA | MET | A | 1006 | −26.467 | 53.101 | 21.783 | 1.00 | 72.95 | C |
| ATOM | 1644 | C | MET | A | 1006 | −27.562 | 54.182 | 21.796 | 1.00 | 73.35 | C |
| ATOM | 1645 | O | MET | A | 1006 | −28.639 | 53.963 | 22.356 | 1.00 | 73.69 | O |
| ATOM | 1646 | CB | MET | A | 1006 | −25.315 | 53.438 | 22.773 | 1.00 | 73.49 | C |
| ATOM | 1647 | CG | MET | A | 1006 | −25.769 | 53.933 | 24.131 | 1.00 | 78.05 | C |
| ATOM | 1648 | SD | MET | A | 1006 | −24.447 | 54.468 | 25.254 | 1.00 | 74.91 | S |
| ATOM | 1649 | CE | MET | A | 1006 | −24.293 | 53.083 | 26.396 | 1.00 | 86.03 | C |
| ATOM | 1650 | N | LEU | A | 1007 | −27.286 | 55.335 | 21.179 | 1.00 | 72.95 | N |
| ATOM | 1651 | CA | LEU | A | 1007 | −28.235 | 56.464 | 21.209 | 1.00 | 73.25 | C |
| ATOM | 1652 | C | LEU | A | 1007 | −29.347 | 56.268 | 20.193 | 1.00 | 74.44 | C |
| ATOM | 1653 | O | LEU | A | 1007 | −30.441 | 56.795 | 20.352 | 1.00 | 75.83 | O |
| ATOM | 1654 | CB | LEU | A | 1007 | −27.539 | 57.814 | 21.003 | 1.00 | 71.83 | C |
| ATOM | 1655 | CG | LEU | A | 1007 | −26.953 | 58.593 | 22.197 | 1.00 | 76.11 | C |
| ATOM | 1656 | CD1 | LEU | A | 1007 | −28.031 | 58.916 | 23.248 | 1.00 | 80.06 | C |
| ATOM | 1657 | CD2 | LEU | A | 1007 | −25.786 | 57.886 | 22.829 | 1.00 | 73.36 | C |
| ATOM | 1658 | N | ARG | A | 1008 | −29.069 | 55.514 | 19.149 | 1.00 | 77.47 | N |
| ATOM | 1659 | CA | ARG | A | 1008 | −30.095 | 55.137 | 18.183 | 1.00 | 77.36 | C |
| ATOM | 1660 | C | ARG | A | 1008 | −31.138 | 54.231 | 18.865 | 1.00 | 76.88 | C |
| ATOM | 1661 | O | ARG | A | 1008 | −32.311 | 54.329 | 18.575 | 1.00 | 75.51 | O |
| ATOM | 1662 | CB | ARG | A | 1008 | −29.437 | 54.430 | 17.040 | 1.00 | 72.89 | C |
| ATOM | 1663 | CG | ARG | A | 1008 | −30.325 | 54.077 | 15.936 | 1.00 | 83.81 | C |
| ATOM | 1664 | CD | ARG | A | 1008 | −29.530 | 53.460 | 14.840 | 1.00 | 80.34 | C |
| ATOM | 1665 | NE | ARG | A | 1008 | −30.368 | 52.534 | 14.093 | 1.00 | 81.78 | N |
| ATOM | 1666 | CZ | ARG | A | 1008 | −29.944 | 51.431 | 13.485 | 1.00 | 85.98 | C |
| ATOM | 1667 | NH1 | ARG | A | 1008 | −28.660 | 51.081 | 13.524 | 1.00 | 80.09 | N |
| ATOM | 1668 | NH2 | ARG | A | 1008 | −30.823 | 50.660 | 12.823 | 1.00 | 93.61 | N |
| ATOM | 1669 | N | ILE | A | 1009 | −30.678 | 53.355 | 19.773 | 1.00 | 78.10 | N |
| ATOM | 1670 | CA | ILE | A | 1009 | −31.548 | 52.465 | 20.543 | 1.00 | 75.58 | C |
| ATOM | 1671 | C | ILE | A | 1009 | −32.251 | 53.251 | 21.658 | 1.00 | 78.69 | C |
| ATOM | 1672 | O | ILE | A | 1009 | −33.455 | 53.134 | 21.826 | 1.00 | 81.42 | O |
| ATOM | 1673 | CB | ILE | A | 1009 | −30.736 | 51.274 | 21.155 | 1.00 | 78.60 | C |
| ATOM | 1674 | CG1 | ILE | A | 1009 | −30.220 | 50.329 | 20.057 | 1.00 | 70.72 | C |
| ATOM | 1675 | CG2 | ILE | A | 1009 | −31.568 | 50.493 | 22.202 | 1.00 | 73.84 | C |
| ATOM | 1676 | CD1 | ILE | A | 1009 | −28.924 | 49.579 | 20.447 | 1.00 | 68.79 | C |
| ATOM | 1677 | N | ASP | A | 1010 | −31.492 | 54.049 | 22.412 | 1.00 | 81.55 | N |
| ATOM | 1678 | CA | ASP | A | 1010 | −32.048 | 54.813 | 23.555 | 1.00 | 80.99 | C |
| ATOM | 1679 | C | ASP | A | 1010 | −32.892 | 56.045 | 23.199 | 1.00 | 82.41 | C |
| ATOM | 1680 | O | ASP | A | 1010 | −33.892 | 56.302 | 23.876 | 1.00 | 83.53 | O |
| ATOM | 1681 | CB | ASP | A | 1010 | −30.918 | 55.254 | 24.486 | 1.00 | 79.05 | C |
| ATOM | 1682 | CG | ASP | A | 1010 | −30.273 | 54.103 | 25.216 | 1.00 | 81.30 | C |
| ATOM | 1683 | OD1 | ASP | A | 1010 | −30.918 | 53.076 | 25.354 | 1.00 | 79.79 | O |
| ATOM | 1684 | OD2 | ASP | A | 1010 | −29.110 | 54.217 | 25.660 | 1.00 | 68.53 | O |
| ATOM | 1685 | N | GLU | A | 1011 | −32.499 | 56.790 | 22.163 | 1.00 | 81.15 | N |
| ATOM | 1686 | CA | GLU | A | 1011 | −33.206 | 58.046 | 21.749 | 1.00 | 82.09 | C |
| ATOM | 1687 | C | GLU | A | 1011 | −34.075 | 57.898 | 20.499 | 1.00 | 82.84 | C |

APPENDIX 1-continued

| | | | | | | | | | | |
|---|---|---|---|---|---|---|---|---|---|---|
| ATOM | 1688 | O | GLU | A | 1011 | −35.124 | 58.541 | 20.397 | 1.00 | 86.08 | O |
| ATOM | 1689 | CB | GLU | A | 1011 | −32.189 | 59.197 | 21.548 | 1.00 | 85.07 | C |
| ATOM | 1690 | CG | GLU | A | 1011 | −32.748 | 60.535 | 20.987 | 1.00 | 86.91 | C |
| ATOM | 1691 | CD | GLU | A | 1011 | −33.834 | 61.166 | 21.857 | 1.00 | 92.06 | C |
| ATOM | 1692 | OE1 | GLU | A | 1011 | −33.791 | 60.980 | 23.098 | 1.00 | 92.05 | O |
| ATOM | 1693 | OE2 | GLU | A | 1011 | −34.736 | 61.855 | 21.291 | 1.00 | 82.39 | O |
| ATOM | 1694 | N | GLY | A | 1012 | −33.648 | 57.067 | 19.550 | 1.00 | 77.24 | N |
| ATOM | 1695 | CA | GLY | A | 1012 | −34.407 | 56.839 | 18.336 | 1.00 | 75.19 | C |
| ATOM | 1696 | C | GLY | A | 1012 | −33.925 | 57.768 | 17.246 | 1.00 | 74.64 | C |
| ATOM | 1697 | O | GLY | A | 1012 | −33.635 | 58.934 | 17.494 | 1.00 | 71.63 | O |
| ATOM | 1698 | N | LEU | A | 1013 | −33.841 | 57.245 | 16.032 | 1.00 | 74.33 | N |
| ATOM | 1699 | CA | LEU | A | 1013 | −33.402 | 58.024 | 14.892 | 1.00 | 73.75 | C |
| ATOM | 1700 | C | LEU | A | 1013 | −34.653 | 58.394 | 14.103 | 1.00 | 73.66 | C |
| ATOM | 1701 | O | LEU | A | 1013 | −35.397 | 57.511 | 13.670 | 1.00 | 72.82 | O |
| ATOM | 1702 | CB | LEU | A | 1013 | −32.419 | 57.214 | 14.060 | 1.00 | 73.46 | C |
| ATOM | 1703 | CG | LEU | A | 1013 | −31.520 | 58.014 | 13.118 | 1.00 | 77.16 | C |
| ATOM | 1704 | CD1 | LEU | A | 1013 | −30.400 | 57.161 | 12.611 | 1.00 | 81.09 | C |
| ATOM | 1705 | CD2 | LEU | A | 1013 | −32.304 | 58.573 | 11.978 | 1.00 | 75.18 | C |
| ATOM | 1706 | N | ARG | A | 1014 | −34.875 | 59.696 | 13.925 | 1.00 | 73.47 | N |
| ATOM | 1707 | CA | ARG | A | 1014 | −36.005 | 60.206 | 13.143 | 1.00 | 75.08 | C |
| ATOM | 1708 | C | ARG | A | 1014 | −35.492 | 60.915 | 11.894 | 1.00 | 73.46 | C |
| ATOM | 1709 | O | ARG | A | 1014 | −34.665 | 61.818 | 11.967 | 1.00 | 72.29 | O |
| ATOM | 1710 | CB | ARG | A | 1014 | −36.899 | 61.098 | 13.994 | 1.00 | 73.94 | C |
| ATOM | 1711 | CG | ARG | A | 1014 | −37.552 | 60.286 | 15.128 | 1.00 | 82.18 | C |
| ATOM | 1712 | CD | ARG | A | 1014 | −38.783 | 60.917 | 15.716 | 1.00 | 87.29 | C |
| ATOM | 1713 | NE | ARG | A | 1014 | −39.879 | 61.089 | 14.746 | 1.00 | 93.86 | N |
| ATOM | 1714 | CZ | ARG | A | 1014 | −41.129 | 61.469 | 15.053 | 1.00 | 92.93 | C |
| ATOM | 1715 | NH1 | ARG | A | 1014 | −41.488 | 61.729 | 16.323 | 1.00 | 95.92 | N |
| ATOM | 1716 | NH2 | ARG | A | 1014 | −42.038 | 61.591 | 14.080 | 1.00 | 92.74 | N |
| ATOM | 1717 | N | LEU | A | 1015 | −36.001 | 60.481 | 10.746 | 1.00 | 73.79 | N |
| ATOM | 1718 | CA | LEU | A | 1015 | −35.566 | 60.969 | 9.444 | 1.00 | 73.57 | C |
| ATOM | 1719 | C | LEU | A | 1015 | −36.284 | 62.239 | 9.033 | 1.00 | 74.92 | C |
| ATOM | 1720 | O | LEU | A | 1015 | −35.757 | 62.988 | 8.224 | 1.00 | 72.14 | O |
| ATOM | 1721 | CB | LEU | A | 1015 | −35.781 | 59.871 | 8.411 | 1.00 | 73.34 | C |
| ATOM | 1722 | CG | LEU | A | 1015 | −35.065 | 58.555 | 8.749 | 1.00 | 71.48 | C |
| ATOM | 1723 | CD1 | LEU | A | 1015 | −35.240 | 57.576 | 7.626 | 1.00 | 66.34 | C |
| ATOM | 1724 | CD2 | LEU | A | 1015 | −33.595 | 58.783 | 9.033 | 1.00 | 63.66 | C |
| ATOM | 1725 | N | LYS | A | 1016 | −37.480 | 62.472 | 9.593 | 1.00 | 77.95 | N |
| ATOM | 1726 | CA | LYS | A | 1016 | −38.274 | 63.678 | 9.327 | 1.00 | 75.82 | C |
| ATOM | 1727 | C | LYS | A | 1016 | −38.338 | 64.571 | 10.563 | 1.00 | 73.96 | C |
| ATOM | 1728 | O | LYS | A | 1016 | −38.379 | 64.065 | 11.680 | 1.00 | 71.82 | O |
| ATOM | 1729 | CB | LYS | A | 1016 | −39.688 | 63.302 | 8.908 | 1.00 | 75.21 | C |
| ATOM | 1730 | CG | LYS | A | 1016 | −39.744 | 62.451 | 7.649 | 1.00 | 79.49 | C |
| ATOM | 1731 | CD | LYS | A | 1016 | −41.159 | 62.214 | 7.176 | 1.00 | 77.17 | C |
| ATOM | 1732 | CE | LYS | A | 1016 | −41.160 | 61.358 | 5.900 | 1.00 | 81.57 | C |
| ATOM | 1733 | NZ | LYS | A | 1016 | −42.521 | 61.187 | 5.296 | 1.00 | 74.99 | N |
| ATOM | 1734 | N | ILE | A | 1017 | −38.347 | 65.889 | 10.334 | 1.00 | 73.18 | N |
| ATOM | 1735 | CA | ILE | A | 1017 | −38.511 | 66.900 | 11.372 | 1.00 | 72.14 | C |
| ATOM | 1736 | C | ILE | A | 1017 | −39.703 | 66.595 | 12.265 | 1.00 | 73.25 | C |
| ATOM | 1737 | O | ILE | A | 1017 | −40.764 | 66.207 | 11.774 | 1.00 | 74.28 | O |
| ATOM | 1738 | CB | ILE | A | 1017 | −38.705 | 68.320 | 10.765 | 1.00 | 71.53 | C |
| ATOM | 1739 | CG1 | ILE | A | 1017 | −37.391 | 68.862 | 10.210 | 1.00 | 74.05 | C |
| ATOM | 1740 | CG2 | ILE | A | 1017 | −39.204 | 69.308 | 11.788 | 1.00 | 70.34 | C |
| ATOM | 1741 | CD1 | ILE | A | 1017 | −37.443 | 70.318 | 9.833 | 1.00 | 73.51 | C |
| ATOM | 1742 | N | TYR | A | 1018 | −39.515 | 66.773 | 13.573 | 1.00 | 72.91 | N |
| ATOM | 1743 | CA | TYR | A | 1018 | −40.571 | 66.562 | 14.552 | 1.00 | 74.12 | C |
| ATOM | 1744 | C | TYR | A | 1018 | −40.391 | 67.540 | 15.700 | 1.00 | 73.99 | C |
| ATOM | 1745 | O | TYR | A | 1018 | −39.304 | 68.091 | 15.883 | 1.00 | 75.95 | O |
| ATOM | 1746 | CB | TYR | A | 1018 | −40.546 | 65.119 | 15.070 | 1.00 | 75.31 | C |
| ATOM | 1747 | CG | TYR | A | 1018 | −39.316 | 64.769 | 15.884 | 1.00 | 75.01 | C |
| ATOM | 1748 | CD1 | TYR | A | 1018 | −39.355 | 64.765 | 17.283 | 1.00 | 77.73 | C |
| ATOM | 1749 | CD2 | TYR | A | 1018 | −38.113 | 64.440 | 15.263 | 1.00 | 75.41 | C |
| ATOM | 1750 | CE1 | TYR | A | 1018 | −38.223 | 64.442 | 18.042 | 1.00 | 72.04 | C |
| ATOM | 1751 | CE2 | TYR | A | 1018 | −36.974 | 64.116 | 16.016 | 1.00 | 77.21 | C |
| ATOM | 1752 | CZ | TYR | A | 1018 | −37.042 | 64.120 | 17.403 | 1.00 | 76.64 | C |
| ATOM | 1753 | OH | TYR | A | 1018 | −35.923 | 63.800 | 18.142 | 1.00 | 79.46 | O |
| ATOM | 1754 | N | LYS | A | 1019 | −41.461 | 67.746 | 16.459 | 1.00 | 73.71 | N |
| ATOM | 1755 | CA | LYS | A | 1019 | −41.427 | 68.597 | 17.636 | 1.00 | 74.41 | C |
| ATOM | 1756 | C | LYS | A | 1019 | −41.056 | 67.729 | 18.826 | 1.00 | 75.37 | C |
| ATOM | 1757 | O | LYS | A | 1019 | −41.715 | 66.718 | 19.073 | 1.00 | 77.13 | O |
| ATOM | 1758 | CB | LYS | A | 1019 | −42.773 | 69.262 | 17.885 | 1.00 | 73.28 | C |
| ATOM | 1759 | CG | LYS | A | 1019 | −43.104 | 70.352 | 16.899 | 1.00 | 72.01 | C |
| ATOM | 1760 | CD | LYS | A | 1019 | −44.357 | 71.099 | 17.326 | 1.00 | 72.42 | C |
| ATOM | 1761 | CE | LYS | A | 1019 | −44.649 | 72.280 | 16.414 | 1.00 | 73.72 | C |
| ATOM | 1762 | NZ | LYS | A | 1019 | −45.910 | 72.993 | 16.796 | 1.00 | 71.74 | N |
| ATOM | 1763 | N | ASP | A | 1020 | −40.012 | 68.112 | 19.561 | 1.00 | 76.71 | N |
| ATOM | 1764 | CA | ASP | A | 1020 | −39.610 | 67.388 | 20.776 | 1.00 | 78.54 | C |
| ATOM | 1765 | C | ASP | A | 1020 | −40.629 | 67.615 | 21.913 | 1.00 | 78.53 | C |
| ATOM | 1766 | O | ASP | A | 1020 | −41.693 | 68.205 | 21.698 | 1.00 | 79.88 | O |
| ATOM | 1767 | CB | ASP | A | 1020 | −38.174 | 67.778 | 21.198 | 1.00 | 79.44 | C |

APPENDIX 1-continued

| ATOM | 1768 | CG | ASP | A | 1020 | −38.071 | 69.183 | 21.838 | 1.00 | 81.53 | C |
|---|---|---|---|---|---|---|---|---|---|---|---|
| ATOM | 1769 | OD1 | ASP | A | 1020 | −39.087 | 69.873 | 22.069 | 1.00 | 77.18 | O |
| ATOM | 1770 | OD2 | ASP | A | 1020 | −36.929 | 69.600 | 22.116 | 1.00 | 89.87 | O |
| ATOM | 1771 | N | THR | A | 1021 | −40.297 | 67.147 | 23.112 | 1.00 | 81.31 | N |
| ATOM | 1772 | CA | THR | A | 1021 | −41.163 | 67.303 | 24.299 | 1.00 | 81.40 | C |
| ATOM | 1773 | C | THR | A | 1021 | −41.464 | 68.771 | 24.674 | 1.00 | 81.89 | C |
| ATOM | 1774 | O | THR | A | 1021 | −42.562 | 69.085 | 25.152 | 1.00 | 83.48 | O |
| ATOM | 1775 | CB | THR | A | 1021 | −40.532 | 66.624 | 25.514 | 1.00 | 83.23 | C |
| ATOM | 1776 | OG1 | THR | A | 1021 | −39.212 | 67.149 | 25.716 | 1.00 | 86.46 | O |
| ATOM | 1777 | CG2 | THR | A | 1021 | −40.454 | 65.100 | 25.305 | 1.00 | 83.63 | C |
| ATOM | 1778 | N | GLU | A | 1022 | −40.488 | 69.653 | 24.447 | 1.00 | 81.25 | N |
| ATOM | 1779 | CA | GLU | A | 1022 | −40.617 | 71.091 | 24.720 | 1.00 | 80.42 | C |
| ATOM | 1780 | C | GLU | A | 1022 | −41.256 | 71.863 | 23.534 | 1.00 | 79.28 | C |
| ATOM | 1781 | O | GLU | A | 1022 | −41.339 | 73.093 | 23.576 | 1.00 | 79.62 | O |
| ATOM | 1782 | CB | GLU | A | 1022 | −39.243 | 71.710 | 25.032 | 1.00 | 81.04 | C |
| ATOM | 1783 | CG | GLU | A | 1022 | −38.301 | 70.940 | 26.011 | 1.00 | 82.43 | C |
| ATOM | 1784 | CD | GLU | A | 1022 | −38.788 | 70.891 | 27.448 | 1.00 | 92.01 | C |
| ATOM | 1785 | OE1 | GLU | A | 1022 | −39.749 | 71.611 | 27.806 | 1.00 | 94.63 | O |
| ATOM | 1786 | OE2 | GLU | A | 1022 | −38.192 | 70.117 | 28.231 | 1.00 | 97.00 | O |
| ATOM | 1787 | N | GLY | A | 1023 | −41.696 | 71.146 | 22.491 | 1.00 | 79.51 | N |
| ATOM | 1788 | CA | GLY | A | 1023 | −42.310 | 71.743 | 21.302 | 1.00 | 78.42 | C |
| ATOM | 1789 | C | GLY | A | 1023 | −41.324 | 72.232 | 20.244 | 1.00 | 78.89 | C |
| ATOM | 1790 | O | GLY | A | 1023 | −41.750 | 72.842 | 19.255 | 1.00 | 79.69 | O |
| ATOM | 1791 | N | TYR | A | 1024 | −40.021 | 71.971 | 20.436 | 1.00 | 77.49 | N |
| ATOM | 1792 | CA | TYR | A | 1024 | −38.981 | 72.476 | 19.532 | 1.00 | 76.94 | C |
| ATOM | 1793 | C | TYR | A | 1024 | −38.694 | 71.548 | 18.363 | 1.00 | 77.71 | C |
| ATOM | 1794 | O | TYR | A | 1024 | −38.686 | 70.321 | 18.524 | 1.00 | 79.61 | O |
| ATOM | 1795 | CB | TYR | A | 1024 | −37.663 | 72.699 | 20.269 | 1.00 | 77.27 | C |
| ATOM | 1796 | CG | TYR | A | 1024 | −37.711 | 73.692 | 21.400 | 1.00 | 79.68 | C |
| ATOM | 1797 | CD1 | TYR | A | 1024 | −38.145 | 74.987 | 21.192 | 1.00 | 81.27 | C |
| ATOM | 1798 | CD2 | TYR | A | 1024 | −37.313 | 73.337 | 22.684 | 1.00 | 79.56 | C |
| ATOM | 1799 | CE1 | TYR | A | 1024 | −38.189 | 75.913 | 22.232 | 1.00 | 83.68 | C |
| ATOM | 1800 | CE2 | TYR | A | 1024 | −37.353 | 74.253 | 23.736 | 1.00 | 78.83 | C |
| ATOM | 1801 | CZ | TYR | A | 1024 | −37.792 | 75.541 | 23.503 | 1.00 | 80.59 | C |
| ATOM | 1802 | OH | TYR | A | 1024 | −37.836 | 76.457 | 24.534 | 1.00 | 83.58 | O |
| ATOM | 1803 | N | TYR | A | 1025 | −38.452 | 72.145 | 17.191 | 1.00 | 74.53 | N |
| ATOM | 1804 | CA | TYR | A | 1025 | −38.176 | 71.387 | 15.969 | 1.00 | 73.53 | C |
| ATOM | 1805 | C | TYR | A | 1025 | −36.849 | 70.657 | 16.050 | 1.00 | 68.58 | C |
| ATOM | 1806 | O | TYR | A | 1025 | −35.801 | 71.285 | 16.188 | 1.00 | 69.06 | O |
| ATOM | 1807 | CB | TYR | A | 1025 | −38.195 | 72.295 | 14.736 | 1.00 | 71.74 | C |
| ATOM | 1808 | CG | TYR | A | 1025 | −39.564 | 72.806 | 14.416 | 1.00 | 70.34 | C |
| ATOM | 1809 | CD1 | TYR | A | 1025 | −39.924 | 74.104 | 14.717 | 1.00 | 71.87 | C |
| ATOM | 1810 | CD2 | TYR | A | 1025 | −40.510 | 71.983 | 13.810 | 1.00 | 71.28 | C |
| ATOM | 1811 | CE1 | TYR | A | 1025 | −41.186 | 74.577 | 14.423 | 1.00 | 77.57 | C |
| ATOM | 1812 | CE2 | TYR | A | 1025 | −41.783 | 72.445 | 13.509 | 1.00 | 70.46 | C |
| ATOM | 1813 | CZ | TYR | A | 1025 | −42.118 | 73.747 | 13.819 | 1.00 | 72.50 | C |
| ATOM | 1814 | OH | TYR | A | 1025 | −43.366 | 74.222 | 13.531 | 1.00 | 73.02 | O |
| ATOM | 1815 | N | THR | A | 1026 | −36.923 | 69.330 | 15.960 | 1.00 | 68.83 | N |
| ATOM | 1816 | CA | THR | A | 1026 | −35.783 | 68.431 | 16.129 | 1.00 | 69.83 | C |
| ATOM | 1817 | C | THR | A | 1026 | −35.730 | 67.408 | 15.000 | 1.00 | 71.01 | C |
| ATOM | 1818 | O | THR | A | 1026 | −36.752 | 67.153 | 14.338 | 1.00 | 75.69 | O |
| ATOM | 1819 | CB | THR | A | 1026 | −35.922 | 67.741 | 17.500 | 1.00 | 68.73 | C |
| ATOM | 1820 | OG1 | THR | A | 1026 | −36.033 | 68.752 | 18.502 | 1.00 | 71.36 | O |
| ATOM | 1821 | CG2 | THR | A | 1026 | −34.750 | 66.824 | 17.843 | 1.00 | 65.86 | C |
| ATOM | 1822 | N | ILE | A | 1027 | −34.552 | 66.825 | 14.769 | 1.00 | 69.80 | N |
| ATOM | 1823 | CA | ILE | A | 1027 | −34.397 | 65.788 | 13.737 | 1.00 | 72.31 | C |
| ATOM | 1824 | C | ILE | A | 1027 | −33.259 | 64.836 | 14.091 | 1.00 | 73.35 | C |
| ATOM | 1825 | O | ILE | A | 1027 | −32.339 | 65.215 | 14.794 | 1.00 | 74.44 | O |
| ATOM | 1826 | CB | ILE | A | 1027 | −34.153 | 66.428 | 12.350 | 1.00 | 71.44 | C |
| ATOM | 1827 | CG1 | ILE | A | 1027 | −34.482 | 65.443 | 11.224 | 1.00 | 73.60 | C |
| ATOM | 1828 | CG2 | ILE | A | 1027 | −32.713 | 66.934 | 12.235 | 1.00 | 69.68 | C |
| ATOM | 1829 | CD1 | ILE | A | 1027 | −34.540 | 66.100 | 9.855 | 1.00 | 69.11 | C |
| ATOM | 1830 | N | GLY | A | 1028 | −33.331 | 63.596 | 13.601 | 1.00 | 72.50 | N |
| ATOM | 1831 | CA | GLY | A | 1028 | −32.287 | 62.599 | 13.863 | 1.00 | 71.73 | C |
| ATOM | 1832 | C | GLY | A | 1028 | −32.366 | 62.107 | 15.292 | 1.00 | 71.31 | C |
| ATOM | 1833 | O | GLY | A | 1028 | −33.455 | 61.891 | 15.807 | 1.00 | 70.02 | O |
| ATOM | 1834 | N | ILE | A | 1029 | −31.202 | 61.935 | 15.918 | 1.00 | 73.01 | N |
| ATOM | 1835 | CA | ILE | A | 1029 | −31.090 | 61.460 | 17.295 | 1.00 | 72.52 | C |
| ATOM | 1836 | C | ILE | A | 1029 | −31.167 | 62.687 | 18.232 | 1.00 | 74.59 | C |
| ATOM | 1837 | O | ILE | A | 1029 | −30.158 | 63.152 | 18.782 | 1.00 | 77.27 | O |
| ATOM | 1838 | CB | ILE | A | 1029 | −29.786 | 60.637 | 17.526 | 1.00 | 72.24 | C |
| ATOM | 1839 | CG1 | ILE | A | 1029 | −29.696 | 59.446 | 16.569 | 1.00 | 71.48 | C |
| ATOM | 1840 | CG2 | ILE | A | 1029 | −29.716 | 60.140 | 18.998 | 1.00 | 70.08 | C |
| ATOM | 1841 | CD1 | ILE | A | 1029 | −28.290 | 58.898 | 16.365 | 1.00 | 72.58 | C |
| ATOM | 1842 | N | GLY | A | 1030 | −32.378 | 63.195 | 18.397 | 1.00 | 72.49 | N |
| ATOM | 1843 | CA | GLY | A | 1030 | −32.622 | 64.375 | 19.197 | 1.00 | 72.04 | C |
| ATOM | 1844 | C | GLY | A | 1030 | −31.760 | 65.582 | 18.861 | 1.00 | 73.16 | C |
| ATOM | 1845 | O | GLY | A | 1030 | −31.349 | 66.291 | 19.755 | 1.00 | 72.16 | O |
| ATOM | 1846 | N | HIS | A | 1031 | −31.480 | 65.821 | 17.574 | 1.00 | 75.22 | N |
| ATOM | 1847 | CA | HIS | A | 1031 | −30.705 | 67.007 | 17.192 | 1.00 | 74.36 | C |

APPENDIX 1-continued

| | | | | | | | | | | |
|---|---|---|---|---|---|---|---|---|---|---|
| ATOM | 1848 | C | HIS | A | 1031 | −31.668 | 68.175 | 17.134 | 1.00 | 75.22 | C |
| ATOM | 1849 | O | HIS | A | 1031 | −32.614 | 68.137 | 16.371 | 1.00 | 78.88 | O |
| ATOM | 1850 | CB | HIS | A | 1031 | −29.985 | 66.864 | 15.840 | 1.00 | 76.09 | C |
| ATOM | 1851 | CG | HIS | A | 1031 | −29.190 | 68.068 | 15.470 | 1.00 | 74.73 | C |
| ATOM | 1852 | ND1 | HIS | A | 1031 | −27.828 | 68.140 | 15.644 | 1.00 | 73.37 | N |
| ATOM | 1853 | CD2 | HIS | A | 1031 | −29.568 | 69.255 | 14.941 | 1.00 | 70.52 | C |
| ATOM | 1854 | CE1 | HIS | A | 1031 | −27.397 | 69.320 | 15.234 | 1.00 | 72.05 | C |
| ATOM | 1855 | NE2 | HIS | A | 1031 | −28.434 | 70.016 | 14.805 | 1.00 | 73.60 | N |
| ATOM | 1856 | N | LEU | A | 1032 | −31.420 | 69.209 | 17.937 | 1.00 | 74.86 | N |
| ATOM | 1857 | CA | LEU | A | 1032 | −32.271 | 70.400 | 17.966 | 1.00 | 75.57 | C |
| ATOM | 1858 | C | LEU | A | 1032 | −31.871 | 71.334 | 16.840 | 1.00 | 75.37 | C |
| ATOM | 1859 | O | LEU | A | 1032 | −30.681 | 71.654 | 16.690 | 1.00 | 76.52 | O |
| ATOM | 1860 | CB | LEU | A | 1032 | −32.148 | 71.137 | 19.305 | 1.00 | 74.42 | C |
| ATOM | 1861 | CG | LEU | A | 1032 | −33.092 | 72.326 | 19.545 | 1.00 | 76.35 | C |
| ATOM | 1862 | CD1 | LEU | A | 1032 | −34.490 | 71.821 | 19.722 | 1.00 | 81.83 | C |
| ATOM | 1863 | CD2 | LEU | A | 1032 | −32.682 | 73.124 | 20.760 | 1.00 | 73.47 | C |
| ATOM | 1864 | N | LEU | A | 1033 | −32.857 | 71.770 | 16.057 | 1.00 | 74.07 | N |
| ATOM | 1865 | CA | LEU | A | 1033 | −32.610 | 72.675 | 14.928 | 1.00 | 73.31 | C |
| ATOM | 1866 | C | LEU | A | 1033 | −32.684 | 74.147 | 15.331 | 1.00 | 72.89 | C |
| ATOM | 1867 | O | LEU | A | 1033 | −31.789 | 74.937 | 15.003 | 1.00 | 70.82 | O |
| ATOM | 1868 | CB | LEU | A | 1033 | −33.595 | 72.374 | 13.787 | 1.00 | 73.71 | C |
| ATOM | 1869 | CG | LEU | A | 1033 | −33.380 | 71.032 | 13.099 | 1.00 | 68.93 | C |
| ATOM | 1870 | CD1 | LEU | A | 1033 | −34.527 | 70.727 | 12.146 | 1.00 | 71.95 | C |
| ATOM | 1871 | CD2 | LEU | A | 1033 | −32.023 | 71.025 | 12.372 | 1.00 | 66.34 | C |
| ATOM | 1872 | N | THR | A | 1034 | −33.751 | 74.502 | 16.039 | 1.00 | 73.89 | N |
| ATOM | 1873 | CA | THR | A | 1034 | −33.986 | 75.873 | 16.494 | 1.00 | 71.83 | C |
| ATOM | 1874 | C | THR | A | 1034 | −35.070 | 75.849 | 17.538 | 1.00 | 73.47 | C |
| ATOM | 1875 | O | THR | A | 1034 | −35.849 | 74.896 | 17.591 | 1.00 | 74.91 | O |
| ATOM | 1876 | CB | THR | A | 1034 | −34.439 | 76.792 | 15.325 | 1.00 | 71.67 | C |
| ATOM | 1877 | OG1 | THR | A | 1034 | −34.731 | 78.108 | 15.807 | 1.00 | 67.14 | O |
| ATOM | 1878 | CG2 | THR | A | 1034 | −35.685 | 76.231 | 14.634 | 1.00 | 67.88 | C |
| ATOM | 1879 | N | LYS | A | 1035 | −35.120 | 76.892 | 18.365 | 1.00 | 73.16 | N |
| ATOM | 1880 | CA | LYS | A | 1035 | −36.190 | 77.037 | 19.352 | 1.00 | 74.56 | C |
| ATOM | 1881 | C | LYS | A | 1035 | −37.402 | 77.824 | 18.786 | 1.00 | 74.05 | C |
| ATOM | 1882 | O | LYS | A | 1035 | −38.435 | 77.955 | 19.456 | 1.00 | 73.29 | O |
| ATOM | 1883 | CB | LYS | A | 1035 | −35.669 | 77.666 | 20.656 | 1.00 | 75.36 | C |
| ATOM | 1884 | CG | LYS | A | 1035 | −34.711 | 76.751 | 21.441 | 1.00 | 74.77 | C |
| ATOM | 1885 | CD | LYS | A | 1035 | −34.455 | 77.236 | 22.866 | 1.00 | 77.28 | C |
| ATOM | 1886 | CE | LYS | A | 1035 | −33.836 | 78.641 | 22.924 | 1.00 | 82.03 | C |
| ATOM | 1887 | NZ | LYS | A | 1035 | −33.484 | 79.060 | 24.331 | 1.00 | 81.98 | N |
| ATOM | 1888 | N | SER | A | 1036 | −37.256 | 78.330 | 17.559 | 1.00 | 73.73 | N |
| ATOM | 1889 | CA | SER | A | 1036 | −38.296 | 79.089 | 16.869 | 1.00 | 73.96 | C |
| ATOM | 1890 | C | SER | A | 1036 | −39.540 | 78.248 | 16.553 | 1.00 | 73.14 | C |
| ATOM | 1891 | O | SER | A | 1036 | −39.420 | 77.055 | 16.331 | 1.00 | 75.32 | O |
| ATOM | 1892 | CB | SER | A | 1036 | −37.713 | 79.649 | 15.561 | 1.00 | 74.91 | C |
| ATOM | 1893 | OG | SER | A | 1036 | −38.688 | 80.260 | 14.743 | 1.00 | 72.52 | O |
| ATOM | 1894 | N | PRO | A | 1037 | −40.740 | 78.874 | 16.532 | 1.00 | 73.94 | N |
| ATOM | 1895 | CA | PRO | A | 1037 | −41.968 | 78.169 | 16.153 | 1.00 | 73.36 | C |
| ATOM | 1896 | C | PRO | A | 1037 | −42.157 | 78.061 | 14.632 | 1.00 | 74.22 | C |
| ATOM | 1897 | O | PRO | A | 1037 | −43.072 | 77.365 | 14.184 | 1.00 | 76.00 | O |
| ATOM | 1898 | CB | PRO | A | 1037 | −43.054 | 79.058 | 16.732 | 1.00 | 72.94 | C |
| ATOM | 1899 | CG | PRO | A | 1037 | −42.497 | 80.415 | 16.588 | 1.00 | 73.18 | C |
| ATOM | 1900 | CD | PRO | A | 1037 | −41.032 | 80.284 | 16.861 | 1.00 | 73.91 | C |
| ATOM | 1901 | N | SER | A | 1038 | −41.308 | 78.744 | 13.855 | 1.00 | 73.88 | N |
| ATOM | 1902 | CA | SER | A | 1038 | −41.346 | 78.688 | 12.406 | 1.00 | 73.57 | C |
| ATOM | 1903 | C | SER | A | 1038 | −40.709 | 77.399 | 11.934 | 1.00 | 74.14 | C |
| ATOM | 1904 | O | SER | A | 1038 | −39.552 | 77.122 | 12.271 | 1.00 | 73.16 | O |
| ATOM | 1905 | CB | SER | A | 1038 | −40.594 | 79.872 | 11.797 | 1.00 | 73.20 | C |
| ATOM | 1906 | OG | SER | A | 1038 | −40.486 | 79.739 | 10.391 | 1.00 | 72.62 | O |
| ATOM | 1907 | N | LEU | A | 1039 | −41.463 | 76.617 | 11.163 | 1.00 | 72.03 | N |
| ATOM | 1908 | CA | LEU | A | 1039 | −40.961 | 75.378 | 10.590 | 1.00 | 72.88 | C |
| ATOM | 1909 | C | LEU | A | 1039 | −39.905 | 75.704 | 9.557 | 1.00 | 72.75 | C |
| ATOM | 1910 | O | LEU | A | 1039 | −38.836 | 75.100 | 9.543 | 1.00 | 74.58 | O |
| ATOM | 1911 | CB | LEU | A | 1039 | −42.092 | 74.581 | 9.944 | 1.00 | 72.16 | C |
| ATOM | 1912 | CG | LEU | A | 1039 | −41.717 | 73.267 | 9.243 | 1.00 | 71.92 | C |
| ATOM | 1913 | CD1 | LEU | A | 1039 | −41.053 | 72.299 | 10.198 | 1.00 | 68.87 | C |
| ATOM | 1914 | CD2 | LEU | A | 1039 | −42.951 | 72.627 | 8.601 | 1.00 | 71.51 | C |
| ATOM | 1915 | N | ASN | A | 1040 | −40.218 | 76.665 | 8.694 | 1.00 | 74.45 | N |
| ATOM | 1916 | CA | ASN | A | 1040 | −39.282 | 77.148 | 7.665 | 1.00 | 74.48 | C |
| ATOM | 1917 | C | ASN | A | 1040 | −37.918 | 77.589 | 8.246 | 1.00 | 74.80 | C |
| ATOM | 1918 | O | ASN | A | 1040 | −36.899 | 77.499 | 7.561 | 1.00 | 76.00 | O |
| ATOM | 1919 | CB | ASN | A | 1040 | −39.937 | 78.277 | 6.838 | 1.00 | 74.13 | C |
| ATOM | 1920 | CG | ASN | A | 1040 | −41.135 | 77.779 | 5.985 | 1.00 | 73.14 | C |
| ATOM | 1921 | OD1 | ASN | A | 1040 | −41.183 | 76.619 | 5.555 | 1.00 | 70.14 | O |
| ATOM | 1922 | ND2 | ASN | A | 1040 | −42.095 | 78.665 | 5.748 | 1.00 | 66.32 | N |
| ATOM | 1923 | N | ALA | A | 1041 | −37.918 | 78.058 | 9.500 | 1.00 | 74.86 | N |
| ATOM | 1924 | CA | ALA | A | 1041 | −36.689 | 78.402 | 10.228 | 1.00 | 75.02 | C |
| ATOM | 1925 | C | ALA | A | 1041 | −35.886 | 77.139 | 10.604 | 1.00 | 75.73 | C |
| ATOM | 1926 | O | ALA | A | 1041 | −34.664 | 77.155 | 10.555 | 1.00 | 75.98 | O |
| ATOM | 1927 | CB | ALA | A | 1041 | −37.011 | 79.220 | 11.466 | 1.00 | 73.60 | C |

APPENDIX 1-continued

| | | | | | | | | | | |
|---|---|---|---|---|---|---|---|---|---|---|
| ATOM | 1928 | N | ALA | A | 1042 | −36.583 | 76.061 | 10.975 | 1.00 | 75.31 | N |
| ATOM | 1929 | CA | ALA | A | 1042 | −35.953 | 74.762 | 11.236 | 1.00 | 74.13 | C |
| ATOM | 1930 | C | ALA | A | 1042 | −35.329 | 74.212 | 9.956 | 1.00 | 75.51 | C |
| ATOM | 1931 | O | ALA | A | 1042 | −34.152 | 73.844 | 9.946 | 1.00 | 75.22 | O |
| ATOM | 1932 | CB | ALA | A | 1042 | −36.969 | 73.782 | 11.779 | 1.00 | 73.73 | C |
| ATOM | 1933 | N | LYS | A | 1043 | −36.135 | 74.164 | 8.887 | 1.00 | 75.74 | N |
| ATOM | 1934 | CA | LYS | A | 1043 | −35.689 | 73.728 | 7.547 | 1.00 | 76.54 | C |
| ATOM | 1935 | C | LYS | A | 1043 | −34.445 | 74.481 | 7.067 | 1.00 | 76.74 | C |
| ATOM | 1936 | O | LYS | A | 1043 | −33.526 | 73.869 | 6.530 | 1.00 | 78.09 | O |
| ATOM | 1937 | CB | LYS | A | 1043 | −36.823 | 73.893 | 6.527 | 1.00 | 75.43 | C |
| ATOM | 1938 | CG | LYS | A | 1043 | −37.946 | 72.879 | 6.697 | 1.00 | 76.23 | C |
| ATOM | 1939 | CD | LYS | A | 1043 | −39.136 | 73.199 | 5.806 | 1.00 | 82.58 | C |
| ATOM | 1940 | CE | LYS | A | 1043 | −40.094 | 72.010 | 5.671 | 1.00 | 85.26 | C |
| ATOM | 1941 | NZ | LYS | A | 1043 | −40.465 | 71.420 | 6.980 | 1.00 | 90.37 | N |
| ATOM | 1942 | N | SER | A | 1044 | −34.430 | 75.798 | 7.267 | 1.00 | 75.27 | N |
| ATOM | 1943 | CA | SER | A | 1044 | −33.272 | 76.626 | 6.931 | 1.00 | 75.10 | C |
| ATOM | 1944 | C | SER | A | 1044 | −32.023 | 76.175 | 7.694 | 1.00 | 75.62 | C |
| ATOM | 1945 | O | SER | A | 1044 | −30.957 | 76.023 | 7.097 | 1.00 | 77.80 | O |
| ATOM | 1946 | CB | SER | A | 1044 | −33.557 | 78.096 | 7.232 | 1.00 | 75.53 | C |
| ATOM | 1947 | OG | SER | A | 1044 | −32.465 | 78.910 | 6.848 | 1.00 | 75.67 | O |
| ATOM | 1948 | N | GLU | A | 1045 | −32.166 | 75.966 | 9.006 | 1.00 | 73.82 | N |
| ATOM | 1949 | CA | GLU | A | 1045 | −31.062 | 75.471 | 9.836 | 1.00 | 73.20 | C |
| ATOM | 1950 | C | GLU | A | 1045 | −30.641 | 74.064 | 9.456 | 1.00 | 71.02 | C |
| ATOM | 1951 | O | GLU | A | 1045 | −29.448 | 73.752 | 9.494 | 1.00 | 71.07 | O |
| ATOM | 1952 | CB | GLU | A | 1045 | −31.427 | 75.494 | 11.331 | 1.00 | 71.62 | C |
| ATOM | 1953 | CG | GLU | A | 1045 | −31.659 | 76.884 | 11.923 | 1.00 | 73.11 | C |
| ATOM | 1954 | CD | GLU | A | 1045 | −30.431 | 77.762 | 11.949 | 1.00 | 76.79 | C |
| ATOM | 1955 | OE1 | GLU | A | 1045 | −29.308 | 77.260 | 11.747 | 1.00 | 80.04 | O |
| ATOM | 1956 | OE2 | GLU | A | 1045 | −30.595 | 78.980 | 12.177 | 1.00 | 85.26 | O |
| ATOM | 1957 | N | LEU | A | 1046 | −31.615 | 73.224 | 9.100 | 1.00 | 70.49 | N |
| ATOM | 1958 | CA | LEU | A | 1046 | −31.342 | 71.839 | 8.710 | 1.00 | 73.29 | C |
| ATOM | 1959 | C | LEU | A | 1046 | −30.492 | 71.807 | 7.455 | 1.00 | 73.52 | C |
| ATOM | 1960 | O | LEU | A | 1046 | −29.453 | 71.144 | 7.434 | 1.00 | 74.73 | O |
| ATOM | 1961 | CB | LEU | A | 1046 | −32.644 | 71.064 | 8.469 | 1.00 | 75.19 | C |
| ATOM | 1962 | CG | LEU | A | 1046 | −32.556 | 69.562 | 8.130 | 1.00 | 73.72 | C |
| ATOM | 1963 | CD1 | LEU | A | 1046 | −31.881 | 68.775 | 9.243 | 1.00 | 74.36 | C |
| ATOM | 1964 | CD2 | LEU | A | 1046 | −33.942 | 69.000 | 7.851 | 1.00 | 73.43 | C |
| ATOM | 1965 | N | ASP | A | 1047 | −30.945 | 72.529 | 6.426 | 1.00 | 72.94 | N |
| ATOM | 1966 | CA | ASP | A | 1047 | −30.225 | 72.645 | 5.148 | 1.00 | 75.39 | C |
| ATOM | 1967 | C | ASP | A | 1047 | −28.812 | 73.161 | 5.343 | 1.00 | 74.85 | C |
| ATOM | 1968 | O | ASP | A | 1047 | −27.875 | 72.634 | 4.758 | 1.00 | 76.38 | O |
| ATOM | 1969 | CB | ASP | A | 1047 | −30.953 | 73.595 | 4.160 | 1.00 | 74.34 | C |
| ATOM | 1970 | CG | ASP | A | 1047 | −32.327 | 73.076 | 3.713 | 1.00 | 75.72 | C |
| ATOM | 1971 | OD1 | ASP | A | 1047 | −32.707 | 71.938 | 4.072 | 1.00 | 72.63 | O |
| ATOM | 1972 | OD2 | ASP | A | 1047 | −33.029 | 73.824 | 2.995 | 1.00 | 80.04 | O |
| ATOM | 1973 | N | LYS | A | 1048 | −28.677 | 74.193 | 6.168 | 1.00 | 75.86 | N |
| ATOM | 1974 | CA | LYS | A | 1048 | −27.379 | 74.779 | 6.494 | 1.00 | 75.59 | C |
| ATOM | 1975 | C | LYS | A | 1048 | −26.464 | 73.779 | 7.248 | 1.00 | 75.44 | C |
| ATOM | 1976 | O | LYS | A | 1048 | −25.241 | 73.810 | 7.088 | 1.00 | 75.09 | O |
| ATOM | 1977 | CB | LYS | A | 1048 | −27.603 | 76.061 | 7.296 | 1.00 | 75.61 | C |
| ATOM | 1978 | CG | LYS | A | 1048 | −26.368 | 76.896 | 7.555 | 1.00 | 77.43 | C |
| ATOM | 1979 | CD | LYS | A | 1048 | −26.729 | 78.377 | 7.838 | 1.00 | 78.34 | C |
| ATOM | 1980 | CE | LYS | A | 1048 | −27.671 | 78.567 | 9.048 | 1.00 | 80.49 | C |
| ATOM | 1981 | NZ | LYS | A | 1048 | −27.074 | 78.073 | 10.322 | 1.00 | 79.34 | N |
| ATOM | 1982 | N | ALA | A | 1049 | −27.073 | 72.903 | 8.055 | 1.00 | 73.58 | N |
| ATOM | 1983 | CA | ALA | A | 1049 | −26.345 | 71.870 | 8.804 | 1.00 | 74.82 | C |
| ATOM | 1984 | C | ALA | A | 1049 | −25.950 | 70.699 | 7.909 | 1.00 | 75.13 | C |
| ATOM | 1985 | O | ALA | A | 1049 | −24.797 | 70.271 | 7.913 | 1.00 | 75.27 | O |
| ATOM | 1986 | CB | ALA | A | 1049 | −27.188 | 71.364 | 9.973 | 1.00 | 73.33 | C |
| ATOM | 1987 | N | ILE | A | 1050 | −26.924 | 70.194 | 7.152 | 1.00 | 73.31 | N |
| ATOM | 1988 | CA | ILE | A | 1050 | −26.746 | 69.038 | 6.255 | 1.00 | 73.24 | C |
| ATOM | 1989 | C | ILE | A | 1050 | −25.994 | 69.378 | 4.951 | 1.00 | 72.49 | C |
| ATOM | 1990 | O | ILE | A | 1050 | −25.155 | 68.602 | 4.500 | 1.00 | 72.34 | O |
| ATOM | 1991 | CB | ILE | A | 1050 | −28.124 | 68.397 | 5.931 | 1.00 | 73.95 | C |
| ATOM | 1992 | CG1 | ILE | A | 1050 | −28.758 | 67.828 | 7.207 | 1.00 | 72.34 | C |
| ATOM | 1993 | CG2 | ILE | A | 1050 | −27.996 | 67.297 | 4.907 | 1.00 | 70.31 | C |
| ATOM | 1994 | CD1 | ILE | A | 1050 | −27.968 | 66.650 | 7.819 | 1.00 | 75.79 | C |
| ATOM | 1995 | N | GLY | A | 1051 | −26.304 | 70.530 | 4.362 | 1.00 | 70.45 | N |
| ATOM | 1996 | CA | GLY | A | 1051 | −25.628 | 71.022 | 3.152 | 1.00 | 69.29 | C |
| ATOM | 1997 | C | GLY | A | 1051 | −26.371 | 70.810 | 1.841 | 1.00 | 68.84 | C |
| ATOM | 1998 | O | GLY | A | 1051 | −25.741 | 70.624 | 0.800 | 1.00 | 64.99 | O |
| ATOM | 1999 | N | ARG | A | 1052 | −27.703 | 70.841 | 1.900 | 1.00 | 66.56 | N |
| ATOM | 2000 | CA | ARG | A | 1052 | −28.563 | 70.680 | 0.730 | 1.00 | 67.90 | C |
| ATOM | 2001 | C | ARG | A | 1052 | −29.995 | 71.012 | 1.090 | 1.00 | 68.30 | C |
| ATOM | 2002 | O | ARG | A | 1052 | −30.309 | 71.175 | 2.261 | 1.00 | 71.80 | O |
| ATOM | 2003 | CB | ARG | A | 1052 | −28.502 | 69.251 | 0.162 | 1.00 | 66.98 | C |
| ATOM | 2004 | CG | ARG | A | 1052 | −28.971 | 68.148 | 1.076 | 1.00 | 72.44 | C |
| ATOM | 2005 | CD | ARG | A | 1052 | −29.034 | 66.833 | 0.330 | 1.00 | 70.28 | C |
| ATOM | 2006 | NE | ARG | A | 1052 | −29.469 | 65.745 | 1.210 | 1.00 | 74.46 | N |
| ATOM | 2007 | CZ | ARG | A | 1052 | −30.740 | 65.449 | 1.540 | 1.00 | 75.81 | C |

APPENDIX 1-continued

| ATOM | 2008 | NH1 | ARG | A | 1052 | −31.772 | 66.146 | 1.076 | 1.00 | 75.31 | N |
|---|---|---|---|---|---|---|---|---|---|---|---|
| ATOM | 2009 | NH2 | ARG | A | 1052 | −30.991 | 64.430 | 2.354 | 1.00 | 78.34 | N |
| ATOM | 2010 | N | ASN | A | 1053 | −30.856 | 71.108 | 0.083 | 1.00 | 67.63 | N |
| ATOM | 2011 | CA | ASN | A | 1053 | −32.289 | 71.307 | 0.299 | 1.00 | 69.73 | C |
| ATOM | 2012 | C | ASN | A | 1053 | −32.876 | 69.984 | 0.719 | 1.00 | 69.35 | C |
| ATOM | 2013 | O | ASN | A | 1053 | −33.005 | 69.075 | −0.095 | 1.00 | 69.80 | O |
| ATOM | 2014 | CB | ASN | A | 1053 | −32.996 | 71.829 | −0.957 | 1.00 | 70.79 | C |
| ATOM | 2015 | CG | ASN | A | 1053 | −32.759 | 73.310 | −1.201 | 1.00 | 72.54 | C |
| ATOM | 2016 | OD1 | ASN | A | 1053 | −33.223 | 73.847 | −2.196 | 1.00 | 78.00 | O |
| ATOM | 2017 | ND2 | ASN | A | 1053 | −32.037 | 73.975 | −0.292 | 1.00 | 81.34 | N |
| ATOM | 2018 | N | THR | A | 1054 | −33.228 | 69.880 | 1.996 | 1.00 | 72.38 | N |
| ATOM | 2019 | CA | THR | A | 1054 | −33.753 | 68.647 | 2.552 | 1.00 | 72.53 | C |
| ATOM | 2020 | C | THR | A | 1054 | −35.266 | 68.588 | 2.510 | 1.00 | 73.02 | C |
| ATOM | 2021 | O | THR | A | 1054 | −35.826 | 67.516 | 2.305 | 1.00 | 77.21 | O |
| ATOM | 2022 | CB | THR | A | 1054 | −33.251 | 68.458 | 3.982 | 1.00 | 71.32 | C |
| ATOM | 2023 | OG1 | THR | A | 1054 | −33.557 | 69.619 | 4.758 | 1.00 | 71.59 | O |
| ATOM | 2024 | CG2 | THR | A | 1054 | −31.748 | 68.254 | 3.981 | 1.00 | 73.10 | C |
| ATOM | 2025 | N | ASN | A | 1055 | −35.908 | 69.737 | 2.702 | 1.00 | 75.24 | N |
| ATOM | 2026 | CA | ASN | A | 1055 | −37.360 | 69.842 | 2.815 | 1.00 | 76.78 | C |
| ATOM | 2027 | C | ASN | A | 1055 | −37.876 | 69.053 | 4.046 | 1.00 | 76.94 | C |
| ATOM | 2028 | O | ASN | A | 1055 | −38.985 | 68.522 | 4.044 | 1.00 | 82.59 | O |
| ATOM | 2029 | CB | ASN | A | 1055 | −38.062 | 69.398 | 1.517 | 1.00 | 76.21 | C |
| ATOM | 2030 | CG | ASN | A | 1055 | −39.511 | 69.867 | 1.431 | 1.00 | 78.54 | C |
| ATOM | 2031 | OD1 | ASN | A | 1055 | −39.930 | 70.812 | 2.109 | 1.00 | 77.71 | O |
| ATOM | 2032 | ND2 | ASN | A | 1055 | −40.285 | 69.199 | 0.587 | 1.00 | 87.37 | N |
| ATOM | 2033 | N | GLY | A | 1056 | −37.054 | 68.984 | 5.091 | 1.00 | 76.49 | N |
| ATOM | 2034 | CA | GLY | A | 1056 | −37.403 | 68.283 | 6.314 | 1.00 | 76.60 | C |
| ATOM | 2035 | C | GLY | A | 1056 | −36.995 | 66.832 | 6.409 | 1.00 | 74.80 | C |
| ATOM | 2036 | O | GLY | A | 1056 | −37.028 | 66.298 | 7.489 | 1.00 | 77.03 | O |
| ATOM | 2037 | N | VAL | A | 1057 | −36.610 | 66.192 | 5.301 | 1.00 | 74.21 | N |
| ATOM | 2038 | CA | VAL | A | 1057 | −36.246 | 64.770 | 5.320 | 1.00 | 73.68 | C |
| ATOM | 2039 | C | VAL | A | 1057 | −34.745 | 64.554 | 5.095 | 1.00 | 73.15 | C |
| ATOM | 2040 | O | VAL | A | 1057 | −34.181 | 65.114 | 4.151 | 1.00 | 77.13 | O |
| ATOM | 2041 | CB | VAL | A | 1057 | −37.029 | 63.981 | 4.261 | 1.00 | 72.56 | C |
| ATOM | 2042 | CG1 | VAL | A | 1057 | −36.711 | 62.498 | 4.368 | 1.00 | 74.94 | C |
| ATOM | 2043 | CG2 | VAL | A | 1057 | −38.523 | 64.201 | 4.432 | 1.00 | 70.86 | C |
| ATOM | 2044 | N | ILE | A | 1058 | −34.120 | 63.742 | 5.963 | 1.00 | 71.83 | N |
| ATOM | 2045 | CA | ILE | A | 1058 | −32.698 | 63.347 | 5.843 | 1.00 | 71.92 | C |
| ATOM | 2046 | C | ILE | A | 1058 | −32.520 | 61.833 | 5.872 | 1.00 | 73.30 | C |
| ATOM | 2047 | O | ILE | A | 1058 | −33.382 | 61.111 | 6.370 | 1.00 | 76.64 | O |
| ATOM | 2048 | CB | ILE | A | 1058 | −31.815 | 63.953 | 6.956 | 1.00 | 67.96 | C |
| ATOM | 2049 | CG1 | ILE | A | 1058 | −32.220 | 63.448 | 8.364 | 1.00 | 71.45 | C |
| ATOM | 2050 | CG2 | ILE | A | 1058 | −31.883 | 65.457 | 6.899 | 1.00 | 65.81 | C |
| ATOM | 2051 | CD1 | ILE | A | 1058 | −31.205 | 63.816 | 9.445 | 1.00 | 65.73 | C |
| ATOM | 2052 | N | THR | A | 1059 | −31.392 | 61.362 | 5.343 | 1.00 | 72.25 | N |
| ATOM | 2053 | CA | THR | A | 1059 | −31.070 | 59.932 | 5.345 | 1.00 | 71.10 | C |
| ATOM | 2054 | C | THR | A | 1059 | −30.533 | 59.545 | 6.712 | 1.00 | 70.11 | C |
| ATOM | 2055 | O | THR | A | 1059 | −30.166 | 60.405 | 7.495 | 1.00 | 71.12 | O |
| ATOM | 2056 | CB | THR | A | 1059 | −29.990 | 59.595 | 4.353 | 1.00 | 70.42 | C |
| ATOM | 2057 | OG1 | THR | A | 1059 | −28.775 | 60.228 | 4.776 | 1.00 | 67.63 | O |
| ATOM | 2058 | CG2 | THR | A | 1059 | −30.377 | 60.056 | 2.874 | 1.00 | 63.19 | C |
| ATOM | 2059 | N | LYS | A | 1060 | −30.493 | 58.244 | 6.972 | 1.00 | 70.88 | N |
| ATOM | 2060 | CA | LYS | A | 1060 | −29.950 | 57.684 | 8.208 | 1.00 | 71.95 | C |
| ATOM | 2061 | C | LYS | A | 1060 | −28.481 | 58.087 | 8.416 | 1.00 | 72.94 | C |
| ATOM | 2062 | O | LYS | A | 1060 | −28.082 | 58.452 | 9.536 | 1.00 | 71.54 | O |
| ATOM | 2063 | CB | LYS | A | 1060 | −30.074 | 56.151 | 8.215 | 1.00 | 70.63 | C |
| ATOM | 2064 | CG | LYS | A | 1060 | −29.325 | 55.466 | 9.387 | 1.00 | 75.49 | C |
| ATOM | 2065 | CD | LYS | A | 1060 | −29.500 | 53.953 | 9.419 | 1.00 | 73.88 | C |
| ATOM | 2066 | CE | LYS | A | 1060 | −28.422 | 53.322 | 10.308 | 1.00 | 71.79 | C |
| ATOM | 2067 | NZ | LYS | A | 1060 | −28.584 | 51.848 | 10.427 | 1.00 | 80.16 | N |
| ATOM | 2068 | N | ASP | A | 1061 | −27.706 | 58.010 | 7.330 | 1.00 | 68.84 | N |
| ATOM | 2069 | CA | ASP | A | 1061 | −26.282 | 58.339 | 7.320 | 1.00 | 68.20 | C |
| ATOM | 2070 | C | ASP | A | 1061 | −26.043 | 59.814 | 7.586 | 1.00 | 66.58 | C |
| ATOM | 2071 | O | ASP | A | 1061 | −25.076 | 60.148 | 8.255 | 1.00 | 70.66 | O |
| ATOM | 2072 | CB | ASP | A | 1061 | −25.622 | 57.923 | 5.983 | 1.00 | 64.64 | C |
| ATOM | 2073 | CG | ASP | A | 1061 | −25.572 | 56.386 | 5.788 | 1.00 | 73.92 | C |
| ATOM | 2074 | OD1 | ASP | A | 1061 | −25.501 | 55.619 | 6.782 | 1.00 | 83.01 | O |
| ATOM | 2075 | OD2 | ASP | A | 1061 | −25.603 | 55.935 | 4.630 | 1.00 | 82.92 | O |
| ATOM | 2076 | N | GLU | A | 1062 | −26.909 | 60.687 | 7.071 | 1.00 | 60.10 | N |
| ATOM | 2077 | CA | GLU | A | 1062 | −26.856 | 62.113 | 7.437 | 1.00 | 62.56 | C |
| ATOM | 2078 | C | GLU | A | 1062 | −27.203 | 62.317 | 8.955 | 1.00 | 64.45 | C |
| ATOM | 2079 | O | GLU | A | 1062 | −26.559 | 63.127 | 9.619 | 1.00 | 62.28 | O |
| ATOM | 2080 | CB | GLU | A | 1062 | −27.770 | 62.910 | 6.572 | 1.00 | 60.74 | C |
| ATOM | 2081 | CG | GLU | A | 1062 | −27.243 | 63.018 | 5.142 | 1.00 | 60.93 | C |
| ATOM | 2082 | CD | GLU | A | 1062 | −28.230 | 63.606 | 4.198 | 1.00 | 68.90 | C |
| ATOM | 2083 | OE1 | GLU | A | 1062 | −29.446 | 63.498 | 4.488 | 1.00 | 67.42 | O |
| ATOM | 2084 | OE2 | GLU | A | 1062 | −27.795 | 64.182 | 3.155 | 1.00 | 73.08 | O |
| ATOM | 2085 | N | ALA | A | 1063 | −28.197 | 61.590 | 9.485 | 1.00 | 64.40 | N |
| ATOM | 2086 | CA | ALA | A | 1063 | −28.494 | 61.647 | 10.955 | 1.00 | 68.01 | C |
| ATOM | 2087 | C | ALA | A | 1063 | −27.251 | 61.296 | 11.748 | 1.00 | 69.72 | C |

APPENDIX 1-continued

| ATOM | 2088 | O | ALA | A | 1063 | −26.948 | 61.940 | 12.745 | 1.00 | 79.20 | O |
|---|---|---|---|---|---|---|---|---|---|---|---|
| ATOM | 2089 | CB | ALA | A | 1063 | −29.637 | 60.723 | 11.331 | 1.00 | 65.57 | C |
| ATOM | 2090 | N | GLU | A | 1064 | −26.529 | 60.269 | 11.298 | 1.00 | 73.91 | N |
| ATOM | 2091 | CA | GLU | A | 1064 | −25.261 | 59.873 | 11.920 | 1.00 | 71.50 | C |
| ATOM | 2092 | C | GLU | A | 1064 | −24.218 | 60.973 | 11.815 | 1.00 | 72.04 | C |
| ATOM | 2093 | O | GLU | A | 1064 | −23.465 | 61.158 | 12.747 | 1.00 | 76.73 | O |
| ATOM | 2094 | CB | GLU | A | 1064 | −24.746 | 58.584 | 11.294 | 1.00 | 70.30 | C |
| ATOM | 2095 | CG | GLU | A | 1064 | −23.391 | 58.090 | 11.772 | 1.00 | 71.10 | C |
| ATOM | 2096 | CD | GLU | A | 1064 | −23.012 | 56.715 | 11.195 | 1.00 | 81.17 | C |
| ATOM | 2097 | OE1 | GLU | A | 1064 | −23.711 | 56.194 | 10.251 | 1.00 | 87.16 | O |
| ATOM | 2098 | OE2 | GLU | A | 1064 | −22.006 | 56.150 | 11.688 | 1.00 | 89.77 | O |
| ATOM | 2099 | N | LYS | A | 1065 | −24.168 | 61.701 | 10.695 | 1.00 | 73.67 | N |
| ATOM | 2100 | CA | LYS | A | 1065 | −23.204 | 62.821 | 10.568 | 1.00 | 73.69 | C |
| ATOM | 2101 | C | LYS | A | 1065 | −23.466 | 63.903 | 11.620 | 1.00 | 70.10 | C |
| ATOM | 2102 | O | LYS | A | 1065 | −22.553 | 64.325 | 12.310 | 1.00 | 68.11 | O |
| ATOM | 2103 | CB | LYS | A | 1065 | −23.232 | 63.461 | 9.190 | 1.00 | 75.31 | C |
| ATOM | 2104 | CG | LYS | A | 1065 | −22.891 | 62.546 | 8.022 | 1.00 | 80.59 | C |
| ATOM | 2105 | CD | LYS | A | 1065 | −21.422 | 62.223 | 7.938 | 1.00 | 85.80 | C |
| ATOM | 2106 | CE | LYS | A | 1065 | −21.098 | 61.379 | 6.680 | 1.00 | 81.37 | C |
| ATOM | 2107 | NZ | LYS | A | 1065 | −21.661 | 61.944 | 5.425 | 1.00 | 72.55 | N |
| ATOM | 2108 | N | LEU | A | 1066 | −24.718 | 64.335 | 11.723 | 1.00 | 69.54 | N |
| ATOM | 2109 | CA | LEU | A | 1066 | −25.133 | 65.305 | 12.748 | 1.00 | 71.70 | C |
| ATOM | 2110 | C | LEU | A | 1066 | −24.854 | 64.804 | 14.165 | 1.00 | 70.08 | C |
| ATOM | 2111 | O | LEU | A | 1066 | −24.476 | 65.572 | 15.033 | 1.00 | 68.08 | O |
| ATOM | 2112 | CB | LEU | A | 1066 | −26.621 | 65.605 | 12.636 | 1.00 | 71.78 | C |
| ATOM | 2113 | CG | LEU | A | 1066 | −27.056 | 66.466 | 11.468 | 1.00 | 76.18 | C |
| ATOM | 2114 | CD1 | LEU | A | 1066 | −28.565 | 66.357 | 11.261 | 1.00 | 78.42 | C |
| ATOM | 2115 | CD2 | LEU | A | 1066 | −26.625 | 67.899 | 11.715 | 1.00 | 77.95 | C |
| ATOM | 2116 | N | PHE | A | 1067 | −25.049 | 63.513 | 14.373 | 1.00 | 71.17 | N |
| ATOM | 2117 | CA | PHE | A | 1067 | −24.844 | 62.899 | 15.673 | 1.00 | 71.75 | C |
| ATOM | 2118 | C | PHE | A | 1067 | −23.383 | 62.902 | 16.104 | 1.00 | 71.56 | C |
| ATOM | 2119 | O | PHE | A | 1067 | −23.098 | 63.171 | 17.275 | 1.00 | 76.85 | O |
| ATOM | 2120 | CB | PHE | A | 1067 | −25.378 | 61.480 | 15.669 | 1.00 | 74.38 | C |
| ATOM | 2121 | CG | PHE | A | 1067 | −25.046 | 60.740 | 16.880 | 1.00 | 75.45 | C |
| ATOM | 2122 | CD1 | PHE | A | 1067 | −25.810 | 60.897 | 18.012 | 1.00 | 78.29 | C |
| ATOM | 2123 | CD2 | PHE | A | 1067 | −23.957 | 59.877 | 16.909 | 1.00 | 81.22 | C |
| ATOM | 2124 | CE1 | PHE | A | 1067 | −25.509 | 60.221 | 19.138 | 1.00 | 77.84 | C |
| ATOM | 2125 | CE2 | PHE | A | 1067 | −23.650 | 59.194 | 18.043 | 1.00 | 81.99 | C |
| ATOM | 2126 | CZ | PHE | A | 1067 | −24.425 | 59.361 | 19.165 | 1.00 | 78.68 | C |
| ATOM | 2127 | N | ASN | A | 1068 | −22.464 | 62.611 | 15.188 | 1.00 | 72.06 | N |
| ATOM | 2128 | CA | ASN | A | 1068 | −21.035 | 62.658 | 15.520 | 1.00 | 72.87 | C |
| ATOM | 2129 | C | ASN | A | 1068 | −20.611 | 64.092 | 15.888 | 1.00 | 74.75 | C |
| ATOM | 2130 | O | ASN | A | 1068 | −19.722 | 64.272 | 16.716 | 1.00 | 76.41 | O |
| ATOM | 2131 | CB | ASN | A | 1068 | −20.134 | 62.151 | 14.400 | 1.00 | 70.30 | C |
| ATOM | 2132 | CG | ASN | A | 1068 | −20.477 | 60.741 | 13.936 | 1.00 | 77.74 | C |
| ATOM | 2133 | OD1 | ASN | A | 1068 | −20.902 | 59.903 | 14.722 | 1.00 | 71.67 | O |
| ATOM | 2134 | ND2 | ASN | A | 1068 | −20.286 | 60.479 | 12.617 | 1.00 | 72.67 | N |
| ATOM | 2135 | N | GLN | A | 1069 | −21.244 | 65.094 | 15.275 | 1.00 | 73.62 | N |
| ATOM | 2136 | CA | GLN | A | 1069 | −20.982 | 66.487 | 15.631 | 1.00 | 73.62 | C |
| ATOM | 2137 | C | GLN | A | 1069 | −21.541 | 66.803 | 17.020 | 1.00 | 73.06 | C |
| ATOM | 2138 | O | GLN | A | 1069 | −20.874 | 67.455 | 17.802 | 1.00 | 68.92 | O |
| ATOM | 2139 | CB | GLN | A | 1069 | −21.586 | 67.449 | 14.634 | 1.00 | 71.42 | C |
| ATOM | 2140 | CG | GLN | A | 1069 | −20.967 | 67.379 | 13.249 | 1.00 | 81.86 | C |
| ATOM | 2141 | CD | GLN | A | 1069 | −21.717 | 68.235 | 12.239 | 1.00 | 81.55 | C |
| ATOM | 2142 | OE1 | GLN | A | 1069 | −22.504 | 69.116 | 12.614 | 1.00 | 87.86 | O |
| ATOM | 2143 | NE2 | GLN | A | 1069 | −21.480 | 67.980 | 10.948 | 1.00 | 91.37 | N |
| ATOM | 2144 | N | ASP | A | 1070 | −22.759 | 66.341 | 17.304 | 1.00 | 69.64 | N |
| ATOM | 2145 | CA | ASP | A | 1070 | −23.362 | 66.549 | 18.615 | 1.00 | 70.15 | C |
| ATOM | 2146 | C | ASP | A | 1070 | −22.510 | 65.879 | 19.689 | 1.00 | 70.56 | C |
| ATOM | 2147 | O | ASP | A | 1070 | −22.272 | 66.486 | 20.737 | 1.00 | 71.26 | O |
| ATOM | 2148 | CB | ASP | A | 1070 | −24.795 | 66.038 | 18.664 | 1.00 | 68.69 | C |
| ATOM | 2149 | CG | ASP | A | 1070 | −25.742 | 66.828 | 17.756 | 1.00 | 77.13 | C |
| ATOM | 2150 | OD1 | ASP | A | 1070 | −25.444 | 67.997 | 17.392 | 1.00 | 75.90 | O |
| ATOM | 2151 | OD2 | ASP | A | 1070 | −26.794 | 66.277 | 17.400 | 1.00 | 74.40 | O |
| ATOM | 2152 | N | VAL | A | 1071 | −22.058 | 64.649 | 19.426 | 1.00 | 67.27 | N |
| ATOM | 2153 | CA | VAL | A | 1071 | −21.150 | 63.948 | 20.341 | 1.00 | 69.23 | C |
| ATOM | 2154 | C | VAL | A | 1071 | −19.906 | 64.780 | 20.577 | 1.00 | 70.51 | C |
| ATOM | 2155 | O | VAL | A | 1071 | −19.509 | 64.968 | 21.714 | 1.00 | 71.56 | O |
| ATOM | 2156 | CB | VAL | A | 1071 | −20.737 | 62.563 | 19.820 | 1.00 | 66.16 | C |
| ATOM | 2157 | CG1 | VAL | A | 1071 | −19.561 | 62.086 | 20.548 | 1.00 | 63.68 | C |
| ATOM | 2158 | CG2 | VAL | A | 1071 | −21.887 | 61.570 | 19.952 | 1.00 | 68.51 | C |
| ATOM | 2159 | N | ASP | A | 1072 | −19.294 | 65.280 | 19.500 | 1.00 | 74.44 | N |
| ATOM | 2160 | CA | ASP | A | 1072 | −18.128 | 66.154 | 19.623 | 1.00 | 73.07 | C |
| ATOM | 2161 | C | ASP | A | 1072 | −18.410 | 67.321 | 20.555 | 1.00 | 74.85 | C |
| ATOM | 2162 | O | ASP | A | 1072 | −17.628 | 67.585 | 21.464 | 1.00 | 78.47 | O |
| ATOM | 2163 | CB | ASP | A | 1072 | −17.688 | 66.703 | 18.269 | 1.00 | 77.99 | C |
| ATOM | 2164 | CG | ASP | A | 1072 | −16.502 | 67.645 | 18.387 | 1.00 | 82.49 | C |
| ATOM | 2165 | OD1 | ASP | A | 1072 | −15.355 | 67.156 | 18.521 | 1.00 | 93.79 | O |
| ATOM | 2166 | OD2 | ASP | A | 1072 | −16.730 | 68.874 | 18.341 | 1.00 | 88.07 | O |
| ATOM | 2167 | N | ALA | A | 1073 | −19.530 | 68.003 | 20.316 | 1.00 | 70.34 | N |

APPENDIX 1-continued

| | | | | | | | | | | |
|---|---|---|---|---|---|---|---|---|---|---|
| ATOM | 2168 | CA | ALA | A | 1073 | −19.981 | 69.126 | 21.153 | 1.00 | 71.13 | C |
| ATOM | 2169 | C | ALA | A | 1073 | −20.178 | 68.742 | 22.643 | 1.00 | 72.31 | C |
| ATOM | 2170 | O | ALA | A | 1073 | −19.771 | 69.495 | 23.520 | 1.00 | 72.64 | O |
| ATOM | 2171 | CB | ALA | A | 1073 | −21.261 | 69.675 | 20.620 | 1.00 | 68.05 | C |
| ATOM | 2172 | N | ALA | A | 1074 | −20.797 | 67.584 | 22.890 | 1.00 | 69.54 | N |
| ATOM | 2173 | CA | ALA | A | 1074 | −21.085 | 67.096 | 24.244 | 1.00 | 71.93 | C |
| ATOM | 2174 | C | ALA | A | 1074 | −19.795 | 66.903 | 25.028 | 1.00 | 72.36 | C |
| ATOM | 2175 | O | ALA | A | 1074 | −19.684 | 67.378 | 26.149 | 1.00 | 77.33 | O |
| ATOM | 2176 | CB | ALA | A | 1074 | −21.851 | 65.807 | 24.193 | 1.00 | 71.13 | C |
| ATOM | 2177 | N | VAL | A | 1075 | −18.836 | 66.207 | 24.415 | 1.00 | 72.46 | N |
| ATOM | 2178 | CA | VAL | A | 1075 | −17.511 | 65.973 | 24.995 | 1.00 | 74.25 | C |
| ATOM | 2179 | C | VAL | A | 1075 | −16.752 | 67.262 | 25.348 | 1.00 | 74.70 | C |
| ATOM | 2180 | O | VAL | A | 1075 | −16.163 | 67.345 | 26.429 | 1.00 | 74.40 | O |
| ATOM | 2181 | CB | VAL | A | 1075 | −16.648 | 65.102 | 24.073 | 1.00 | 74.74 | C |
| ATOM | 2182 | CG1 | VAL | A | 1075 | −15.208 | 65.076 | 24.539 | 1.00 | 75.33 | C |
| ATOM | 2183 | CG2 | VAL | A | 075 | −17.205 | 63.696 | 24.033 | 1.00 | 76.41 | C |
| ATOM | 2184 | N | ARG | A | 1076 | −16.768 | 68.246 | 24.455 | 1.00 | 72.53 | N |
| ATOM | 2185 | CA | ARG | A | 1076 | −16.124 | 69.546 | 24.726 | 1.00 | 74.21 | C |
| ATOM | 2186 | C | ARG | A | 1076 | −16.766 | 70.230 | 25.911 | 1.00 | 74.53 | C |
| ATOM | 2187 | O | ARG | A | 1076 | −16.070 | 70.838 | 26.735 | 1.00 | 74.38 | O |
| ATOM | 2188 | CB | ARG | A | 1076 | −16.204 | 70.487 | 23.533 | 1.00 | 70.53 | C |
| ATOM | 2189 | CG | ARG | A | 1076 | −15.356 | 70.070 | 22.367 | 1.00 | 76.54 | C |
| ATOM | 2190 | CD | ARG | A | 1076 | −15.465 | 71.070 | 21.205 | 1.00 | 82.85 | C |
| ATOM | 2191 | NE | ARG | A | 1076 | −15.065 | 70.430 | 19.951 | 1.00 | 91.84 | N |
| ATOM | 2192 | CZ | ARG | A | 1076 | −13.802 | 70.183 | 19.569 | 1.00 | 96.99 | C |
| ATOM | 2193 | NH1 | ARG | A | 1076 | −12.746 | 70.517 | 20.334 | 1.00 | 97.76 | N |
| ATOM | 2194 | NH2 | ARG | A | 1076 | −13.580 | 69.588 | 18.393 | 1.00 | 103.37 | N |
| ATOM | 2195 | N | GLY | A | 1077 | −18.091 | 70.120 | 25.977 | 1.00 | 72.90 | N |
| ATOM | 2196 | CA | GLY | A | 1077 | −18.865 | 70.656 | 27.059 | 1.00 | 73.02 | C |
| ATOM | 2197 | C | GLY | A | 1077 | −18.543 | 69.995 | 28.392 | 1.00 | 72.32 | C |
| ATOM | 2198 | O | GLY | A | 1077 | −18.322 | 70.690 | 29.387 | 1.00 | 73.12 | O |
| ATOM | 2199 | N | ILE | A | 1078 | −18.523 | 68.661 | 28.399 | 1.00 | 72.41 | N |
| ATOM | 2200 | CA | ILE | A | 1078 | −18.104 | 67.858 | 29.564 | 1.00 | 73.34 | C |
| ATOM | 2201 | C | ILE | A | 1078 | −16.739 | 68.293 | 30.083 | 1.00 | 71.54 | C |
| ATOM | 2202 | O | ILE | A | 1078 | −16.577 | 68.522 | 31.280 | 1.00 | 76.16 | O |
| ATOM | 2203 | CB | ILE | A | 1078 | −18.044 | 66.363 | 29.210 | 1.00 | 74.38 | C |
| ATOM | 2204 | CG1 | ILE | A | 1078 | −19.453 | 65.757 | 29.198 | 1.00 | 79.15 | C |
| ATOM | 2205 | CG2 | ILE | A | 1078 | −17.205 | 65.616 | 30.174 | 1.00 | 64.66 | C |
| ATOM | 2206 | CD1 | ILE | A | 1078 | −19.514 | 64.385 | 28.554 | 1.00 | 75.65 | C |
| ATOM | 2207 | N | LEU | A | 1079 | −15.775 | 68.407 | 29.177 | 1.00 | 72.22 | N |
| ATOM | 2208 | CA | LEU | A | 1079 | −14.407 | 68.819 | 29.512 | 1.00 | 73.11 | C |
| ATOM | 2209 | C | LEU | A | 1079 | −14.278 | 70.275 | 30.001 | 1.00 | 73.92 | C |
| ATOM | 2210 | O | LEU | A | 1079 | −13.281 | 70.613 | 30.627 | 1.00 | 78.75 | O |
| ATOM | 2211 | CB | LEU | A | 1079 | −13.462 | 68.578 | 28.317 | 1.00 | 72.14 | C |
| ATOM | 2212 | CG | LEU | A | 1079 | −13.192 | 67.115 | 27.909 | 1.00 | 72.35 | C |
| ATOM | 2213 | CD1 | LEU | A | 1079 | −12.301 | 67.074 | 26.679 | 1.00 | 59.40 | C |
| ATOM | 2214 | CD2 | LEU | A | 1079 | −12.543 | 66.309 | 29.031 | 1.00 | 62.86 | C |
| ATOM | 2215 | N | ARG | A | 1080 | −15.269 | 71.118 | 29.714 | 1.00 | 73.61 | N |
| ATOM | 2216 | CA | ARG | A | 1080 | −15.330 | 72.490 | 30.251 | 1.00 | 74.19 | C |
| ATOM | 2217 | C | ARG | A | 1080 | −16.039 | 72.537 | 31.609 | 1.00 | 72.82 | C |
| ATOM | 2218 | O | ARG | A | 1080 | −15.894 | 73.505 | 32.331 | 1.00 | 72.73 | O |
| ATOM | 2219 | CB | ARG | A | 1080 | −16.061 | 73.439 | 29.301 | 1.00 | 74.26 | C |
| ATOM | 2220 | CG | ARG | A | 1080 | −15.236 | 73.955 | 28.140 | 1.00 | 79.49 | C |
| ATOM | 2221 | CD | ARG | A | 1080 | −15.964 | 75.121 | 27.460 | 1.00 | 79.38 | C |
| ATOM | 2222 | NE | ARG | A | 1080 | −17.260 | 74.691 | 26.922 | 1.00 | 88.39 | N |
| ATOM | 2223 | CZ | ARG | A | 1080 | −17.535 | 74.387 | 25.636 | 1.00 | 87.86 | C |
| ATOM | 2224 | NH1 | ARG | A | 1080 | −16.608 | 74.451 | 24.665 | 1.00 | 87.22 | N |
| ATOM | 2225 | NH2 | ARG | A | 1080 | −18.777 | 74.009 | 25.314 | 1.00 | 81.94 | N |
| ATOM | 2226 | N | ASN | A | 1081 | −16.800 | 71.495 | 31.946 | 1.00 | 72.20 | N |
| ATOM | 2227 | CA | ASN | A | 1081 | −17.553 | 71.464 | 33.183 | 1.00 | 70.14 | C |
| ATOM | 2228 | C | ASN | A | 1081 | −16.680 | 70.903 | 34.293 | 1.00 | 70.99 | C |
| ATOM | 2229 | O | ASN | A | 1081 | −16.295 | 69.733 | 34.252 | 1.00 | 70.87 | O |
| ATOM | 2230 | CB | ASN | A | 1081 | −18.817 | 70.642 | 33.002 | 1.00 | 68.83 | C |
| ATOM | 2231 | CG | ASN | A | 1081 | −19.789 | 70.813 | 34.137 | 1.00 | 74.52 | C |
| ATOM | 2232 | OD1 | ASN | A | 1081 | −19.521 | 70.405 | 35.275 | 1.00 | 81.88 | O |
| ATOM | 2233 | ND2 | ASN | A | 1081 | −20.937 | 71.417 | 33.848 | 1.00 | 65.69 | N |
| ATOM | 2234 | N | ALA | A | 1082 | −16.374 | 71.750 | 35.281 | 1.00 | 69.81 | N |
| ATOM | 2235 | CA | ALA | A | 1082 | −15.539 | 71.386 | 36.459 | 1.00 | 71.34 | C |
| ATOM | 2236 | C | ALA | A | 1082 | −15.942 | 70.101 | 37.203 | 1.00 | 70.68 | C |
| ATOM | 2237 | O | ALA | A | 1082 | −15.081 | 69.426 | 37.748 | 1.00 | 77.40 | O |
| ATOM | 2238 | CB | ALA | A | 1082 | −15.508 | 72.546 | 37.451 | 1.00 | 64.36 | C |
| ATOM | 2239 | N | LYS | A | 1083 | −17.233 | 69.784 | 37.213 | 1.00 | 68.55 | N |
| ATOM | 2240 | CA | LYS | A | 1083 | −17.776 | 68.623 | 37.931 | 1.00 | 69.05 | C |
| ATOM | 2241 | C | LYS | A | 1083 | −17.798 | 67.337 | 37.093 | 1.00 | 72.30 | C |
| ATOM | 2242 | O | LYS | A | 1083 | −17.732 | 66.243 | 37.649 | 1.00 | 76.42 | O |
| ATOM | 2243 | CB | LYS | A | 1083 | −19.193 | 68.923 | 38.398 | 1.00 | 70.45 | C |
| ATOM | 2244 | CG | LYS | A | 1083 | −19.359 | 70.297 | 39.063 | 1.00 | 75.92 | C |
| ATOM | 2245 | CD | LYS | A | 1083 | −20.720 | 70.447 | 39.698 | 1.00 | 81.44 | C |
| ATOM | 2246 | CE | LYS | A | 1083 | −20.926 | 71.864 | 40.217 | 1.00 | 85.50 | C |
| ATOM | 2247 | NZ | LYS | A | 1083 | −22.148 | 71.994 | 41.068 | 1.00 | 88.29 | N |

APPENDIX 1-continued

| | | | | | | | | | | |
|---|---|---|---|---|---|---|---|---|---|---|
| ATOM | 2248 | N | LEU | A | 1084 | −17.891 | 67.460 | 35.765 | 1.00 | 68.40 | N |
| ATOM | 2249 | CA | LEU | A | 1084 | −17.898 | 66.286 | 34.894 | 1.00 | 70.90 | C |
| ATOM | 2250 | C | LEU | A | 1084 | −16.518 | 65.924 | 34.402 | 1.00 | 70.17 | C |
| ATOM | 2251 | O | LEU | A | 1084 | −16.247 | 64.740 | 34.205 | 1.00 | 72.79 | O |
| ATOM | 2252 | CB | LEU | A | 1084 | −18.843 | 66.497 | 33.694 | 1.00 | 68.64 | C |
| ATOM | 2253 | CG | LEU | A | 1084 | −20.304 | 66.801 | 34.051 | 1.00 | 71.12 | C |
| ATOM | 2254 | CD1 | LEU | A | 1084 | −21.213 | 66.916 | 32.787 | 1.00 | 59.19 | C |
| ATOM | 2255 | CD2 | LEU | A | 1084 | −20.847 | 65.747 | 35.010 | 1.00 | 56.68 | C |
| ATOM | 2256 | N | LYS | A | 1085 | −15.650 | 66.917 | 34.205 | 1.00 | 68.34 | N |
| ATOM | 2257 | CA | LYS | A | 1085 | −14.316 | 66.663 | 33.652 | 1.00 | 68.63 | C |
| ATOM | 2258 | C | LYS | A | 1085 | −13.538 | 65.559 | 34.383 | 1.00 | 68.76 | C |
| ATOM | 2259 | O | LYS | A | 1085 | −13.070 | 64.643 | 33.723 | 1.00 | 75.06 | O |
| ATOM | 2260 | CB | LYS | A | 1085 | −13.482 | 67.951 | 33.565 | 1.00 | 67.89 | C |
| ATOM | 2261 | CG | LYS | A | 1085 | −12.110 | 67.770 | 32.917 | 1.00 | 69.24 | C |
| ATOM | 2262 | CD | LYS | A | 1085 | −11.322 | 69.054 | 32.925 | 1.00 | 72.42 | C |
| ATOM | 2263 | CE | LYS | A | 1085 | −10.040 | 68.905 | 32.138 | 1.00 | 77.84 | C |
| ATOM | 2264 | NZ | LYS | A | 1085 | −9.131 | 67.881 | 32.745 | 1.00 | 85.14 | N |
| ATOM | 2265 | N | PRO | A | 1086 | −13.399 | 65.636 | 35.740 | 1.00 | 69.24 | N |
| ATOM | 2266 | CA | PRO | A | 1086 | −12.637 | 64.586 | 36.440 | 1.00 | 69.18 | C |
| ATOM | 2267 | C | PRO | A | 1086 | −13.226 | 63.190 | 36.261 | 1.00 | 68.97 | C |
| ATOM | 2268 | O | PRO | A | 1086 | −12.488 | 62.197 | 36.199 | 1.00 | 69.99 | O |
| ATOM | 2269 | CB | PRO | A | 1086 | −12.771 | 64.966 | 37.923 | 1.00 | 67.72 | C |
| ATOM | 2270 | CG | PRO | A | 1086 | −13.201 | 66.357 | 37.950 | 1.00 | 72.53 | C |
| ATOM | 2271 | CD | PRO | A | 1086 | −13.918 | 66.646 | 36.679 | 1.00 | 66.17 | C |
| ATOM | 2272 | N | VAL | A | 1087 | −14.549 | 63.136 | 36.184 | 1.00 | 68.84 | N |
| ATOM | 2273 | CA | VAL | A | 1087 | −15.265 | 61.885 | 36.092 | 1.00 | 72.28 | C |
| ATOM | 2274 | C | VAL | A | 1087 | −14.985 | 61.291 | 34.743 | 1.00 | 73.91 | C |
| ATOM | 2275 | O | VAL | A | 1087 | −14.480 | 60.176 | 34.672 | 1.00 | 77.11 | O |
| ATOM | 2276 | CB | VAL | A | 1087 | −16.769 | 62.062 | 36.305 | 1.00 | 72.36 | C |
| ATOM | 2277 | CG1 | VAL | A | 1087 | −17.431 | 60.720 | 36.368 | 1.00 | 78.50 | C |
| ATOM | 2278 | CG2 | VAL | A | 1087 | −17.032 | 62.832 | 37.602 | 1.00 | 75.48 | C |
| ATOM | 2279 | N | TYR | A | 1088 | −15.310 | 62.047 | 33.691 | 1.00 | 76.42 | N |
| ATOM | 2280 | CA | TYR | A | 1088 | −15.087 | 61.660 | 32.290 | 1.00 | 74.22 | C |
| ATOM | 2281 | C | TYR | A | 1088 | −13.655 | 61.241 | 32.054 | 1.00 | 73.79 | C |
| ATOM | 2282 | O | TYR | A | 1088 | −13.414 | 60.184 | 31.502 | 1.00 | 71.26 | O |
| ATOM | 2283 | CB | TYR | A | 1088 | −15.420 | 62.840 | 31.382 | 1.00 | 76.80 | C |
| ATOM | 2284 | CG | TYR | A | 1088 | −15.345 | 62.536 | 29.909 | 1.00 | 78.30 | C |
| ATOM | 2285 | CD1 | TYR | A | 1088 | −16.447 | 61.994 | 29.225 | 1.00 | 82.88 | C |
| ATOM | 2286 | CD2 | TYR | A | 1088 | −14.181 | 62.787 | 29.185 | 1.00 | 82.17 | C |
| ATOM | 2287 | CE1 | TYR | A | 1088 | −16.368 | 61.712 | 27.838 | 1.00 | 78.90 | C |
| ATOM | 2288 | CE2 | TYR | A | 1088 | −14.102 | 62.511 | 27.823 | 1.00 | 73.71 | C |
| ATOM | 2289 | CZ | TYR | A | 1088 | −15.199 | 61.976 | 27.162 | 1.00 | 71.96 | C |
| ATOM | 2290 | OH | TYR | A | 1088 | −15.099 | 61.705 | 25.804 | 1.00 | 90.19 | O |
| ATOM | 2291 | N | ASP | A | 1089 | −12.708 | 62.082 | 32.483 | 1.00 | 73.28 | N |
| ATOM | 2292 | CA | ASP | A | 1089 | −11.262 | 61.780 | 32.399 | 1.00 | 72.57 | C |
| ATOM | 2293 | C | ASP | A | 1089 | −10.880 | 60.403 | 32.936 | 1.00 | 71.20 | C |
| ATOM | 2294 | O | ASP | A | 1089 | −9.987 | 59.755 | 32.407 | 1.00 | 70.55 | O |
| ATOM | 2295 | CB | ASP | A | 1089 | −10.438 | 62.802 | 33.208 | 1.00 | 72.85 | C |
| ATOM | 2296 | CG | ASP | A | 1089 | −10.162 | 64.118 | 32.468 | 1.00 | 79.93 | C |
| ATOM | 2297 | OD1 | ASP | A | 1089 | −10.551 | 64.287 | 31.274 | 1.00 | 78.98 | O |
| ATOM | 2298 | OD2 | ASP | A | 1089 | −9.528 | 65.004 | 33.120 | 1.00 | 69.59 | O |
| ATOM | 2299 | N | SER | A | 1090 | −11.562 | 59.969 | 33.993 | 1.00 | 72.25 | N |
| ATOM | 2300 | CA | SER | A | 1090 | −11.244 | 58.711 | 34.670 | 1.00 | 71.13 | C |
| ATOM | 2301 | C | SER | A | 1090 | −11.893 | 57.495 | 34.027 | 1.00 | 69.01 | C |
| ATOM | 2302 | O | SER | A | 1090 | −11.411 | 56.383 | 34.199 | 1.00 | 69.79 | O |
| ATOM | 2303 | CB | SER | A | 1090 | −11.684 | 58.791 | 36.124 | 1.00 | 67.58 | C |
| ATOM | 2304 | OG | SER | A | 1090 | −13.085 | 58.665 | 36.232 | 1.00 | 65.84 | O |
| ATOM | 2305 | N | LEU | A | 1091 | −12.979 | 57.703 | 33.293 | 1.00 | 72.26 | N |
| ATOM | 2306 | CA | LEU | A | 1091 | −13.727 | 56.593 | 32.729 | 1.00 | 70.30 | C |
| ATOM | 2307 | C | LEU | A | 1091 | −13.092 | 56.023 | 31.462 | 1.00 | 73.59 | C |
| ATOM | 2308 | O | LEU | A | 1091 | −12.420 | 56.715 | 30.705 | 1.00 | 75.14 | O |
| ATOM | 2309 | CB | LEU | A | 1091 | −15.172 | 57.014 | 32.457 | 1.00 | 73.21 | C |
| ATOM | 2310 | CG | LEU | A | 1091 | −16.060 | 57.298 | 33.687 | 1.00 | 69.70 | C |
| ATOM | 2311 | CD1 | LEU | A | 1091 | −17.374 | 57.869 | 33.211 | 1.00 | 74.59 | C |
| ATOM | 2312 | CD2 | LEU | A | 1091 | −16.287 | 56.051 | 34.482 | 1.00 | 61.23 | C |
| ATOM | 2313 | N | ASP | A | 1092 | −13.324 | 54.735 | 31.257 | 1.00 | 73.36 | N |
| ATOM | 2314 | CA | ASP | A | 1092 | −12.955 | 54.046 | 30.017 | 1.00 | 74.54 | C |
| ATOM | 2315 | C | ASP | A | 1092 | −13.910 | 54.480 | 28.927 | 1.00 | 72.07 | C |
| ATOM | 2316 | O | ASP | A | 1092 | −14.938 | 55.088 | 29.230 | 1.00 | 69.09 | O |
| ATOM | 2317 | CB | ASP | A | 1092 | −13.093 | 52.547 | 30.180 | 1.00 | 74.48 | C |
| ATOM | 2318 | CG | ASP | A | 1092 | −14.502 | 52.157 | 30.522 | 1.00 | 82.40 | C |
| ATOM | 2319 | OD1 | ASP | A | 1092 | −15.393 | 52.059 | 29.643 | 1.00 | 78.10 | O |
| ATOM | 2320 | OD2 | ASP | A | 1092 | −14.702 | 51.956 | 31.702 | 1.00 | 93.39 | O |
| ATOM | 2321 | N | ALA | A | 1093 | −13.561 | 54.156 | 27.677 | 1.00 | 71.26 | N |
| ATOM | 2322 | CA | ALA | A | 1093 | −14.332 | 54.530 | 26.455 | 1.00 | 72.91 | C |
| ATOM | 2323 | C | ALA | A | 1093 | −15.817 | 54.185 | 26.482 | 1.00 | 72.49 | C |
| ATOM | 2324 | O | ALA | A | 1093 | −16.642 | 55.016 | 26.143 | 1.00 | 77.77 | O |
| ATOM | 2325 | CB | ALA | A | 1093 | −13.682 | 53.884 | 25.213 | 1.00 | 68.92 | C |
| ATOM | 2326 | N | VAL | A | 1094 | −16.152 | 52.959 | 26.882 | 1.00 | 74.25 | N |
| ATOM | 2327 | CA | VAL | A | 1094 | −17.566 | 52.517 | 26.970 | 1.00 | 76.09 | C |

APPENDIX 1-continued

| | | | | | | | | | | |
|---|---|---|---|---|---|---|---|---|---|---|
| ATOM | 2328 | C | VAL | A | 1094 | −18.388 | 53.297 | 28.021 | 1.00 | 74.99 | C |
| ATOM | 2329 | O | VAL | A | 1094 | −19.550 | 53.686 | 27.760 | 1.00 | 74.98 | O |
| ATOM | 2330 | CB | VAL | A | 1094 | −17.680 | 51.014 | 27.268 | 1.00 | 77.56 | C |
| ATOM | 2331 | CG1 | VAL | A | 1094 | −19.124 | 50.634 | 27.518 | 1.00 | 80.02 | C |
| ATOM | 2332 | CG2 | VAL | A | 1094 | −17.091 | 50.192 | 26.098 | 1.00 | 77.82 | C |
| ATOM | 2333 | N | ARG | A | 1095 | −17.804 | 53.527 | 29.192 | 1.00 | 74.55 | N |
| ATOM | 2334 | CA | ARG | A | 1095 | −18.502 | 54.306 | 30.245 | 1.00 | 72.87 | C |
| ATOM | 2335 | C | ARG | A | 1095 | −18.564 | 55.792 | 29.877 | 1.00 | 70.86 | C |
| ATOM | 2336 | O | ARG | A | 1095 | −19.529 | 56.471 | 30.224 | 1.00 | 70.60 | O |
| ATOM | 2337 | CB | ARG | A | 1095 | −17.855 | 54.090 | 31.598 | 1.00 | 74.90 | C |
| ATOM | 2338 | CG | ARG | A | 1095 | −17.944 | 52.648 | 32.049 | 1.00 | 74.88 | C |
| ATOM | 2339 | CD | ARG | A | 1095 | −17.456 | 52.519 | 33.465 | 1.00 | 76.13 | C |
| ATOM | 2340 | NE | ARG | A | 1095 | −17.765 | 51.222 | 34.039 | 1.00 | 68.67 | N |
| ATOM | 2341 | CZ | ARG | A | 1095 | −17.035 | 50.111 | 33.935 | 1.00 | 75.88 | C |
| ATOM | 2342 | NH1 | ARG | A | 1095 | −15.900 | 50.077 | 33.261 | 1.00 | 77.10 | N |
| ATOM | 2343 | NH2 | ARG | A | 1095 | −17.456 | 48.999 | 34.523 | 1.00 | 78.82 | N |
| ATOM | 2344 | N | ARG | A | 1096 | −17.550 | 56.304 | 29.176 | 1.00 | 70.40 | N |
| ATOM | 2345 | CA | ARG | A | 1096 | −17.646 | 57.654 | 28.616 | 1.00 | 72.78 | C |
| ATOM | 2346 | C | ARG | A | 1096 | −18.895 | 57.781 | 27.683 | 1.00 | 75.95 | C |
| ATOM | 2347 | O | ARG | A | 1096 | −19.603 | 58.790 | 27.741 | 1.00 | 76.20 | O |
| ATOM | 2348 | CB | ARG | A | 1096 | −16.382 | 58.032 | 27.849 | 1.00 | 74.96 | C |
| ATOM | 2349 | CG | ARG | A | 1096 | −15.212 | 58.381 | 28.729 | 1.00 | 76.80 | C |
| ATOM | 2350 | CD | ARG | A | 1096 | −13.987 | 58.699 | 27.888 | 1.00 | 73.69 | C |
| ATOM | 2351 | NE | ARG | A | 1096 | −12.821 | 58.877 | 28.724 | 1.00 | 75.05 | N |
| ATOM | 2352 | CZ | ARG | A | 1096 | −11.617 | 59.276 | 28.334 | 1.00 | 76.09 | C |
| ATOM | 2353 | NH1 | ARG | A | 1096 | −11.358 | 59.568 | 27.062 | 1.00 | 79.66 | N |
| ATOM | 2354 | NH2 | ARG | A | 1096 | −10.642 | 59.388 | 29.244 | 1.00 | 73.76 | N |
| ATOM | 2355 | N | ALA | A | 1097 | −19.154 | 56.767 | 26.842 | 1.00 | 74.52 | N |
| ATOM | 2356 | CA | ALA | A | 1097 | −20.381 | 56.762 | 25.993 | 1.00 | 75.40 | C |
| ATOM | 2357 | C | ALA | A | 1097 | −21.606 | 56.787 | 26.899 | 1.00 | 74.68 | C |
| ATOM | 2358 | O | ALA | A | 1097 | −22.596 | 57.444 | 26.594 | 1.00 | 75.19 | O |
| ATOM | 2359 | CB | ALA | A | 1097 | −20.428 | 55.556 | 25.084 | 1.00 | 65.57 | C |
| ATOM | 2360 | N | ALA | A | 1098 | −21.538 | 56.068 | 28.019 | 1.00 | 77.29 | N |
| ATOM | 2361 | CA | ALA | A | 1098 | −22.627 | 56.110 | 29.004 | 1.00 | 77.63 | C |
| ATOM | 2362 | C | ALA | A | 1098 | −22.855 | 57.549 | 29.425 | 1.00 | 75.46 | C |
| ATOM | 2363 | O | ALA | A | 1098 | −23.953 | 58.037 | 29.306 | 1.00 | 77.90 | O |
| ATOM | 2364 | CB | ALA | A | 1098 | −22.319 | 55.252 | 30.201 | 1.00 | 72.80 | C |
| ATOM | 2365 | N | LEU | A | 1099 | −21.808 | 58.215 | 29.906 | 1.00 | 74.27 | N |
| ATOM | 2366 | CA | LEU | A | 1099 | −21.935 | 59.610 | 30.389 | 1.00 | 73.67 | C |
| ATOM | 2367 | C | LEU | A | 1099 | −22.493 | 60.542 | 29.329 | 1.00 | 73.73 | C |
| ATOM | 2368 | O | LEU | A | 1099 | −23.412 | 61.328 | 29.602 | 1.00 | 73.92 | O |
| ATOM | 2369 | CB | LEU | A | 1099 | −20.590 | 60.144 | 30.886 | 1.00 | 76.16 | C |
| ATOM | 2370 | CG | LEU | A | 1099 | −20.612 | 61.381 | 31.794 | 1.00 | 76.75 | C |
| ATOM | 2371 | CD1 | LEU | A | 1099 | −21.495 | 61.167 | 33.000 | 1.00 | 72.22 | C |
| ATOM | 2372 | CD2 | LEU | A | 1099 | −19.187 | 61.741 | 32.236 | 1.00 | 66.69 | C |
| ATOM | 2373 | N | ILE | A | 1100 | −21.941 | 60.454 | 28.115 | 1.00 | 72.03 | N |
| ATOM | 2374 | CA | ILE | A | 1100 | −22.430 | 61.252 | 26.986 | 1.00 | 70.39 | C |
| ATOM | 2375 | C | ILE | A | 1100 | −23.908 | 60.998 | 26.758 | 1.00 | 69.34 | C |
| ATOM | 2376 | O | ILE | A | 1100 | −24.674 | 61.941 | 26.552 | 1.00 | 70.67 | O |
| ATOM | 2377 | CB | ILE | A | 1100 | −21.672 | 60.964 | 25.677 | 1.00 | 74.51 | C |
| ATOM | 2378 | CG1 | ILE | A | 1100 | −20.208 | 61.411 | 25.789 | 1.00 | 74.12 | C |
| ATOM | 2379 | CG2 | ILE | A | 1100 | −22.368 | 61.684 | 24.523 | 1.00 | 66.55 | C |
| ATOM | 2380 | CD1 | ILE | A | 1100 | −19.273 | 60.643 | 24.910 | 1.00 | 71.96 | C |
| ATOM | 2381 | N | ASN | A | 1101 | −24.305 | 59.727 | 26.798 | 1.00 | 69.64 | N |
| ATOM | 2382 | CA | ASN | A | 1101 | −25.716 | 59.340 | 26.656 | 1.00 | 71.15 | C |
| ATOM | 2383 | C | ASN | A | 1101 | −26.587 | 60.154 | 27.596 | 1.00 | 73.26 | C |
| ATOM | 2384 | O | ASN | A | 1101 | −27.606 | 60.720 | 27.158 | 1.00 | 73.01 | O |
| ATOM | 2385 | CB | ASN | A | 1101 | −25.859 | 57.819 | 26.880 | 1.00 | 74.91 | C |
| ATOM | 2386 | CG | ASN | A | 1101 | −27.242 | 57.286 | 26.621 | 1.00 | 72.41 | C |
| ATOM | 2387 | OD1 | ASN | A | 1101 | −28.218 | 57.895 | 26.974 | 1.00 | 68.21 | O |
| ATOM | 2388 | ND2 | ASN | A | 1101 | −27.321 | 56.110 | 25.995 | 1.00 | 66.91 | N |
| ATOM | 2389 | N | MET | A | 1102 | −26.191 | 60.217 | 28.876 | 1.00 | 73.18 | N |
| ATOM | 2390 | CA | MET | A | 1102 | −26.922 | 60.986 | 29.894 | 1.00 | 73.53 | C |
| ATOM | 2391 | C | MET | A | 1102 | −26.897 | 62.472 | 29.579 | 1.00 | 72.72 | C |
| ATOM | 2392 | O | MET | A | 1102 | −27.909 | 63.130 | 29.719 | 1.00 | 75.34 | O |
| ATOM | 2393 | CB | MET | A | 1102 | −26.341 | 60.788 | 31.315 | 1.00 | 69.92 | C |
| ATOM | 2394 | CG | MET | A | 1102 | −26.311 | 59.343 | 31.846 | 1.00 | 71.61 | C |
| ATOM | 2395 | SD | MET | A | 1102 | −25.639 | 59.205 | 33.558 | 1.00 | 75.01 | S |
| ATOM | 2396 | CE | MET | A | 1102 | −26.903 | 60.133 | 34.436 | 1.00 | 72.22 | C |
| ATOM | 2397 | N | VAL | A | 1103 | −25.743 | 62.997 | 29.160 | 1.00 | 73.08 | N |
| ATOM | 2398 | CA | VAL | A | 1103 | −25.650 | 64.430 | 28.774 | 1.00 | 75.10 | C |
| ATOM | 2399 | C | VAL | A | 1103 | −26.605 | 64.736 | 27.585 | 1.00 | 74.50 | C |
| ATOM | 2400 | O | VAL | A | 1103 | −27.280 | 65.769 | 27.587 | 1.00 | 74.33 | O |
| ATOM | 2401 | CB | VAL | A | 1103 | −24.203 | 64.859 | 28.445 | 1.00 | 74.63 | C |
| ATOM | 2402 | CG1 | VAL | A | 1103 | −24.181 | 66.214 | 27.773 | 1.00 | 74.66 | C |
| ATOM | 2403 | CG2 | VAL | A | 1103 | −23.345 | 64.892 | 29.715 | 1.00 | 73.28 | C |
| ATOM | 2404 | N | PHE | A | 1104 | −26.648 | 63.838 | 26.598 | 1.00 | 72.50 | N |
| ATOM | 2405 | CA | PHE | A | 1104 | −27.641 | 63.937 | 25.507 | 1.00 | 77.14 | C |
| ATOM | 2406 | C | PHE | A | 1104 | −29.050 | 64.133 | 26.087 | 1.00 | 77.59 | C |
| ATOM | 2407 | O | PHE | A | 1104 | −29.746 | 65.023 | 25.684 | 1.00 | 78.04 | O |

APPENDIX 1-continued

| | | | | | | | | | | |
|---|---|---|---|---|---|---|---|---|---|---|
| ATOM | 2408 | CB  | PHE | A | 1104 | −27.615 | 62.712 | 24.557 | 1.00 | 78.31 | C |
| ATOM | 2409 | CG  | PHE | A | 1104 | −26.870 | 62.933 | 23.259 | 1.00 | 81.99 | C |
| ATOM | 2410 | CD1 | PHE | A | 1104 | −25.489 | 63.029 | 23.238 | 1.00 | 78.79 | C |
| ATOM | 2411 | CD2 | PHE | A | 1104 | −27.580 | 63.037 | 22.027 | 1.00 | 90.20 | C |
| ATOM | 2412 | CE1 | PHE | A | 1104 | −24.800 | 63.227 | 22.021 | 1.00 | 77.16 | C |
| ATOM | 2413 | CE2 | PHE | A | 1104 | −26.910 | 63.237 | 20.821 | 1.00 | 84.00 | C |
| ATOM | 2414 | CZ  | PHE | A | 1104 | −25.509 | 63.332 | 20.823 | 1.00 | 86.09 | C |
| ATOM | 2415 | N   | GLN | A | 1105 | −29.446 | 63.296 | 27.039 | 1.00 | 76.01 | N |
| ATOM | 2416 | CA  | GLN | A | 1105 | −30.818 | 63.335 | 27.575 | 1.00 | 75.44 | C |
| ATOM | 2417 | C   | GLN | A | 1105 | −31.159 | 64.480 | 28.544 | 1.00 | 74.63 | C |
| ATOM | 2418 | O   | GLN | A | 1105 | −32.249 | 65.043 | 28.455 | 1.00 | 75.26 | O |
| ATOM | 2419 | CB  | GLN | A | 1105 | −31.100 | 62.012 | 28.270 | 1.00 | 77.85 | C |
| ATOM | 2420 | CG  | GLN | A | 1105 | −32.567 | 61.757 | 28.615 | 1.00 | 75.54 | C |
| ATOM | 2421 | CD  | GLN | A | 1105 | −32.781 | 60.378 | 29.168 | 1.00 | 75.71 | C |
| ATOM | 2422 | OE1 | GLN | A | 1105 | −31.834 | 59.620 | 29.340 | 1.00 | 71.29 | O |
| ATOM | 2423 | NE2 | GLN | A | 1105 | −34.025 | 60.039 | 29.450 | 1.00 | 70.96 | N |
| ATOM | 2424 | N   | MET | A | 1106 | −30.250 | 64.819 | 29.456 | 1.00 | 76.62 | N |
| ATOM | 2425 | CA  | MET | A | 1106 | −30.529 | 65.838 | 30.524 | 1.00 | 77.20 | C |
| ATOM | 2426 | C   | MET | A | 1106 | −29.666 | 67.100 | 30.498 | 1.00 | 75.43 | C |
| ATOM | 2427 | O   | MET | A | 1106 | −29.901 | 68.010 | 31.296 | 1.00 | 78.05 | O |
| ATOM | 2428 | CB  | MET | A | 1106 | −30.319 | 65.216 | 31.902 | 1.00 | 79.39 | C |
| ATOM | 2429 | CG  | MET | A | 1106 | −30.886 | 63.832 | 32.124 | 1.00 | 85.85 | C |
| ATOM | 2430 | SD  | MET | A | 1106 | −30.091 | 63.064 | 33.542 | 1.00 | 85.72 | S |
| ATOM | 2431 | CE  | MET | A | 1106 | −29.933 | 61.419 | 32.917 | 1.00 | 81.10 | C |
| ATOM | 2432 | N   | GLY | A | 1107 | −28.675 | 67.166 | 29.609 | 1.00 | 75.52 | N |
| ATOM | 2433 | CA  | GLY | A | 1107 | −27.748 | 68.294 | 29.560 | 1.00 | 76.26 | C |
| ATOM | 2434 | C   | GLY | A | 1107 | −26.702 | 68.166 | 30.651 | 1.00 | 78.60 | C |
| ATOM | 2435 | O   | GLY | A | 1107 | −26.827 | 67.330 | 31.555 | 1.00 | 78.11 | O |
| ATOM | 2436 | N   | GLU | A | 1108 | −25.666 | 68.993 | 30.573 | 1.00 | 79.86 | N |
| ATOM | 2437 | CA  | GLU | A | 1108 | −24.556 | 68.931 | 31.548 | 1.00 | 82.66 | C |
| ATOM | 2438 | C   | GLU | A | 1108 | −24.966 | 69.224 | 32.966 | 1.00 | 82.97 | C |
| ATOM | 2439 | O   | GLU | A | 1108 | −24.495 | 68.560 | 33.891 | 1.00 | 86.76 | O |
| ATOM | 2440 | CB  | GLU | A | 1108 | −23.454 | 69.901 | 31.185 | 1.00 | 82.78 | C |
| ATOM | 2441 | CG  | GLU | A | 1108 | −22.714 | 69.512 | 29.969 | 1.00 | 86.49 | C |
| ATOM | 2442 | CD  | GLU | A | 1108 | −21.722 | 70.556 | 29.554 | 1.00 | 90.68 | C |
| ATOM | 2443 | OE1 | GLU | A | 1108 | −21.148 | 71.271 | 30.409 | 1.00 | 90.93 | O |
| ATOM | 2444 | OE2 | GLU | A | 1108 | −21.523 | 70.659 | 28.348 | 1.00 | 103.73 | O |
| ATOM | 2445 | N   | THR | A | 1109 | −25.837 | 70.214 | 33.132 | 1.00 | 82.33 | N |
| ATOM | 2446 | CA  | THR | A | 1109 | −26.324 | 70.597 | 34.451 | 1.00 | 80.83 | C |
| ATOM | 2447 | C   | THR | A | 1109 | −27.061 | 69.455 | 35.112 | 1.00 | 79.03 | C |
| ATOM | 2448 | O   | THR | A | 1109 | −26.755 | 69.098 | 36.247 | 1.00 | 84.70 | O |
| ATOM | 2449 | CB  | THR | A | 1109 | −27.270 | 71.802 | 34.386 | 1.00 | 79.62 | C |
| ATOM | 2450 | OG1 | THR | A | 1109 | −26.591 | 72.907 | 33.776 | 1.00 | 80.39 | O |
| ATOM | 2451 | CG2 | THR | A | 1109 | −27.731 | 72.196 | 35.790 | 1.00 | 81.01 | C |
| ATOM | 2452 | N   | GLY | A | 1110 | −28.028 | 68.889 | 34.395 | 1.00 | 78.14 | N |
| ATOM | 2453 | CA  | GLY | A | 1110 | −28.794 | 67.749 | 34.888 | 1.00 | 77.59 | C |
| ATOM | 2454 | C   | GLY | A | 1110 | −27.893 | 66.637 | 35.399 | 1.00 | 76.91 | C |
| ATOM | 2455 | O   | GLY | A | 1110 | −28.147 | 66.069 | 36.450 | 1.00 | 77.84 | O |
| ATOM | 2456 | N   | VAL | A | 1111 | −26.838 | 66.348 | 34.639 | 1.00 | 74.81 | N |
| ATOM | 2457 | CA  | VAL | A | 1111 | −25.901 | 65.274 | 34.952 | 1.00 | 73.76 | C |
| ATOM | 2458 | C   | VAL | A | 1111 | −24.901 | 65.663 | 36.063 | 1.00 | 74.74 | C |
| ATOM | 2459 | O   | VAL | A | 1111 | −24.475 | 64.809 | 36.863 | 1.00 | 70.56 | O |
| ATOM | 2460 | CB  | VAL | A | 1111 | −25.094 | 64.844 | 33.715 | 1.00 | 68.49 | C |
| ATOM | 2461 | CG1 | VAL | A | 1111 | −24.173 | 63.695 | 34.081 | 1.00 | 64.99 | C |
| ATOM | 2462 | CG2 | VAL | A | 1111 | −26.023 | 64.438 | 32.582 | 1.00 | 68.09 | C |
| ATOM | 2463 | N   | ALA | A | 1112 | −24.531 | 66.949 | 36.096 | 1.00 | 74.29 | N |
| ATOM | 2464 | CA  | ALA | A | 1112 | −23.631 | 67.491 | 37.119 | 1.00 | 77.63 | C |
| ATOM | 2465 | C   | ALA | A | 1112 | −24.255 | 67.423 | 38.496 | 1.00 | 77.53 | C |
| ATOM | 2466 | O   | ALA | A | 1112 | −23.542 | 67.410 | 39.483 | 1.00 | 82.24 | O |
| ATOM | 2467 | CB  | ALA | A | 1112 | −23.256 | 68.931 | 36.798 | 1.00 | 77.58 | C |
| ATOM | 2468 | N   | GLY | A | 1113 | −25.591 | 67.381 | 38.553 | 1.00 | 79.76 | N |
| ATOM | 2469 | CA  | GLY | A | 1113 | −26.323 | 67.270 | 39.808 | 1.00 | 77.64 | C |
| ATOM | 2470 | C   | GLY | A | 1113 | −26.267 | 65.900 | 40.461 | 1.00 | 78.25 | C |
| ATOM | 2471 | O   | GLY | A | 1113 | −26.687 | 65.780 | 41.588 | 1.00 | 76.50 | O |
| ATOM | 2472 | N   | PHE | A | 1114 | −25.757 | 64.861 | 39.774 | 1.00 | 77.88 | N |
| ATOM | 2473 | CA  | PHE | A | 1114 | −25.586 | 63.533 | 40.383 | 1.00 | 76.03 | C |
| ATOM | 2474 | C   | PHE | A | 1114 | −24.276 | 63.500 | 41.179 | 1.00 | 75.36 | C |
| ATOM | 2475 | O   | PHE | A | 1114 | −23.399 | 62.693 | 40.887 | 1.00 | 73.89 | O |
| ATOM | 2476 | CB  | PHE | A | 1114 | −25.559 | 62.437 | 39.310 | 1.00 | 81.97 | C |
| ATOM | 2477 | CG  | PHE | A | 1114 | −26.845 | 62.247 | 38.594 | 1.00 | 84.39 | C |
| ATOM | 2478 | CD1 | PHE | A | 1114 | −27.906 | 61.609 | 39.202 | 1.00 | 93.33 | C |
| ATOM | 2479 | CD2 | PHE | A | 1114 | −27.001 | 62.696 | 37.310 | 1.00 | 90.99 | C |
| ATOM | 2480 | CE1 | PHE | A | 1114 | −29.108 | 61.433 | 38.521 | 1.00 | 91.37 | C |
| ATOM | 2481 | CE2 | PHE | A | 1114 | −28.187 | 62.526 | 36.627 | 1.00 | 91.29 | C |
| ATOM | 2482 | CZ  | PHE | A | 1114 | −29.244 | 61.894 | 37.229 | 1.00 | 89.69 | C |
| ATOM | 2483 | N   | THR | A | 1115 | −24.139 | 64.364 | 42.186 | 1.00 | 70.77 | N |
| ATOM | 2484 | CA  | THR | A | 1115 | −22.860 | 64.550 | 42.845 | 1.00 | 71.53 | C |
| ATOM | 2485 | C   | THR | A | 1115 | −22.292 | 63.256 | 43.420 | 1.00 | 72.52 | C |
| ATOM | 2486 | O   | THR | A | 1115 | −21.124 | 62.964 | 43.206 | 1.00 | 74.92 | O |
| ATOM | 2487 | CB  | THR | A | 1115 | −22.950 | 65.613 | 43.957 | 1.00 | 74.18 | C |

APPENDIX 1-continued

| | | | | | | | | | | |
|---|---|---|---|---|---|---|---|---|---|---|
| ATOM | 2488 | OG1 | THR | A | 1115 | −23.638 | 66.761 | 43.454 | 1.00 | 81.29 | O |
| ATOM | 2489 | CG2 | THR | A | 1115 | −21.562 | 66.027 | 44.419 | 1.00 | 65.46 | C |
| ATOM | 2490 | N | ASN | A | 1116 | −23.112 | 62.494 | 44.138 | 1.00 | 73.53 | N |
| ATOM | 2491 | CA | ASN | A | 1116 | −22.644 | 61.260 | 44.779 | 1.00 | 74.43 | C |
| ATOM | 2492 | C | ASN | A | 1116 | −22.327 | 60.176 | 43.753 | 1.00 | 74.36 | C |
| ATOM | 2493 | O | ASN | A | 1116 | −21.286 | 59.523 | 43.854 | 1.00 | 73.98 | O |
| ATOM | 2494 | CB | ASN | A | 1116 | −23.652 | 60.723 | 45.803 | 1.00 | 76.08 | C |
| ATOM | 2495 | CG | ASN | A | 1116 | −23.916 | 61.701 | 46.958 | 1.00 | 81.08 | C |
| ATOM | 2496 | OD1 | ASN | A | 1116 | −22.994 | 62.125 | 47.647 | 1.00 | 76.24 | O |
| ATOM | 2497 | ND2 | ASN | A | 1116 | −25.181 | 62.050 | 47.163 | 1.00 | 82.05 | N |
| ATOM | 2498 | N | SER | A | 1117 | −23.218 | 59.986 | 42.776 | 1.00 | 71.66 | N |
| ATOM | 2499 | CA | SER | A | 1117 | −22.990 | 59.014 | 41.697 | 1.00 | 71.35 | C |
| ATOM | 2500 | C | SER | A | 1117 | −21.736 | 59.307 | 40.895 | 1.00 | 72.60 | C |
| ATOM | 2501 | O | SER | A | 1117 | −21.010 | 58.386 | 40.567 | 1.00 | 73.79 | O |
| ATOM | 2502 | CB | SER | A | 1117 | −24.170 | 58.962 | 40.748 | 1.00 | 74.52 | C |
| ATOM | 2503 | OG | SER | A | 1117 | −25.271 | 58.329 | 41.351 | 1.00 | 74.10 | O |
| ATOM | 2504 | N | LEU | A | 1118 | −21.484 | 60.580 | 40.586 | 1.00 | 74.22 | N |
| ATOM | 2505 | CA | LEU | A | 1118 | −20.253 | 60.997 | 39.863 | 1.00 | 74.12 | C |
| ATOM | 2506 | C | LEU | A | 1118 | −18.961 | 60.660 | 40.618 | 1.00 | 73.96 | C |
| ATOM | 2507 | O | LEU | A | 1118 | −17.984 | 60.195 | 40.025 | 1.00 | 78.17 | O |
| ATOM | 2508 | CB | LEU | A | 1118 | −20.299 | 62.503 | 39.566 | 1.00 | 74.92 | C |
| ATOM | 2509 | CG | LEU | A | 1118 | −21.337 | 62.937 | 38.500 | 1.00 | 77.06 | C |
| ATOM | 2510 | CD1 | LEU | A | 1118 | −21.516 | 64.484 | 38.518 | 1.00 | 79.91 | C |
| ATOM | 2511 | CD2 | LEU | A | 1118 | −20.950 | 62.456 | 37.120 | 1.00 | 79.15 | C |
| ATOM | 2512 | N | ARG | A | 1119 | −18.972 | 60.901 | 41.917 | 1.00 | 73.81 | N |
| ATOM | 2513 | CA | ARG | A | 1119 | −17.857 | 60.571 | 42.806 | 1.00 | 76.37 | C |
| ATOM | 2514 | C | ARG | A | 1119 | −17.586 | 59.069 | 42.837 | 1.00 | 73.72 | C |
| ATOM | 2515 | O | ARG | A | 1119 | −16.439 | 58.633 | 42.760 | 1.00 | 71.54 | O |
| ATOM | 2516 | CB | ARG | A | 1119 | −18.179 | 61.041 | 44.229 | 1.00 | 72.72 | C |
| ATOM | 2517 | CG | ARG | A | 1119 | −17.067 | 60.873 | 45.241 | 1.00 | 81.26 | C |
| ATOM | 2518 | CD | ARG | A | 1119 | −17.608 | 60.978 | 46.712 | 1.00 | 88.03 | C |
| ATOM | 2519 | NE | ARG | A | 1119 | −18.622 | 62.027 | 46.876 | 1.00 | 97.80 | N |
| ATOM | 2520 | CZ | ARG | A | 1119 | −18.387 | 63.350 | 46.852 | 1.00 | 107.35 | C |
| ATOM | 2521 | NH1 | ARG | A | 1119 | −17.149 | 63.849 | 46.666 | 1.00 | 110.91 | N |
| ATOM | 2522 | NH2 | ARG | A | 1119 | −19.407 | 64.207 | 47.016 | 1.00 | 108.55 | N |
| ATOM | 2523 | N | MET | A | 1120 | −18.653 | 58.296 | 42.958 | 1.00 | 72.40 | N |
| ATOM | 2524 | CA | MET | A | 1120 | −18.554 | 56.843 | 42.948 | 1.00 | 75.44 | C |
| ATOM | 2525 | C | MET | A | 1120 | −18.059 | 56.323 | 41.610 | 1.00 | 72.59 | C |
| ATOM | 2526 | O | MET | A | 1120 | −17.199 | 55.455 | 41.580 | 1.00 | 74.45 | O |
| ATOM | 2527 | CB | MET | A | 1120 | −19.884 | 56.228 | 43.338 | 1.00 | 74.73 | C |
| ATOM | 2528 | CG | MET | A | 1120 | −20.116 | 56.407 | 44.861 | 1.00 | 79.31 | C |
| ATOM | 2529 | SD | MET | A | 1120 | −21.698 | 55.810 | 45.341 | 1.00 | 86.73 | S |
| ATOM | 2530 | CE | MET | A | 1120 | −22.843 | 56.943 | 44.571 | 1.00 | 82.05 | C |
| ATOM | 2531 | N | LEU | A | 1121 | −18.592 | 56.851 | 40.516 | 1.00 | 70.51 | N |
| ATOM | 2532 | CA | LEU | A | 1121 | −18.067 | 56.495 | 39.211 | 1.00 | 73.43 | C |
| ATOM | 2533 | C | LEU | A | 1121 | −16.581 | 56.816 | 39.149 | 1.00 | 71.65 | C |
| ATOM | 2534 | O | LEU | A | 1121 | −15.810 | 55.970 | 38.728 | 1.00 | 74.87 | O |
| ATOM | 2535 | CB | LEU | A | 1121 | −18.802 | 57.213 | 38.086 | 1.00 | 67.49 | C |
| ATOM | 2536 | CG | LEU | A | 1121 | −20.247 | 56.734 | 37.877 | 1.00 | 72.80 | C |
| ATOM | 2537 | CD1 | LEU | A | 1121 | −20.990 | 57.724 | 36.968 | 1.00 | 65.17 | C |
| ATOM | 2538 | CD2 | LEU | A | 1121 | −20.343 | 55.241 | 37.364 | 1.00 | 62.04 | C |
| ATOM | 2539 | N | GLN | A | 1122 | −16.186 | 58.020 | 39.565 | 1.00 | 69.51 | N |
| ATOM | 2540 | CA | GLN | A | 1122 | −14.760 | 58.419 | 39.551 | 1.00 | 69.43 | C |
| ATOM | 2541 | C | GLN | A | 1122 | −13.852 | 57.422 | 40.302 | 1.00 | 69.96 | C |
| ATOM | 2542 | O | GLN | A | 1122 | −12.726 | 57.188 | 39.889 | 1.00 | 72.67 | O |
| ATOM | 2543 | CB | GLN | A | 1122 | −14.602 | 59.828 | 40.123 | 1.00 | 69.75 | C |
| ATOM | 2544 | CG | GLN | A | 1122 | −13.203 | 60.432 | 39.975 | 1.00 | 73.87 | C |
| ATOM | 2545 | CD | GLN | A | 1122 | −13.125 | 61.883 | 40.443 | 1.00 | 79.31 | C |
| ATOM | 2546 | OE1 | GLN | A | 1122 | −14.139 | 62.505 | 40.758 | 1.00 | 88.60 | O |
| ATOM | 2547 | NE2 | GLN | A | 1122 | −11.907 | 62.426 | 40.490 | 1.00 | 84.85 | N |
| ATOM | 2548 | N | GLN | A | 1123 | −14.364 | 56.850 | 41.395 | 1.00 | 66.33 | N |
| ATOM | 2549 | CA | GLN | A | 1123 | −13.659 | 55.833 | 42.182 | 1.00 | 71.40 | C |
| ATOM | 2550 | C | GLN | A | 1123 | −13.857 | 54.373 | 41.688 | 1.00 | 70.37 | C |
| ATOM | 2551 | O | GLN | A | 1123 | −13.323 | 53.450 | 42.300 | 1.00 | 68.04 | O |
| ATOM | 2552 | CB | GLN | A | 1123 | −14.083 | 55.958 | 43.662 | 1.00 | 66.15 | C |
| ATOM | 2553 | CG | GLN | A | 1123 | −13.701 | 57.318 | 44.267 | 1.00 | 65.21 | C |
| ATOM | 2554 | CD | GLN | A | 1123 | −14.267 | 57.566 | 45.652 | 1.00 | 69.71 | C |
| ATOM | 2555 | OE1 | GLN | A | 1123 | −15.294 | 57.018 | 46.035 | 1.00 | 77.32 | O |
| ATOM | 2556 | NE2 | GLN | A | 1123 | −13.585 | 58.404 | 46.411 | 1.00 | 63.29 | N |
| ATOM | 2557 | N | LYS | A | 1124 | −14.609 | 54.174 | 40.604 | 1.00 | 69.50 | N |
| ATOM | 2558 | CA | LYS | A | 1124 | −14.896 | 52.830 | 40.066 | 1.00 | 74.09 | C |
| ATOM | 2559 | C | LYS | A | 1124 | −15.719 | 51.959 | 41.048 | 1.00 | 75.70 | C |
| ATOM | 2560 | O | LYS | A | 1124 | −15.562 | 50.733 | 41.084 | 1.00 | 75.06 | O |
| ATOM | 2561 | CB | LYS | A | 1124 | −13.603 | 52.089 | 39.688 | 1.00 | 79.02 | C |
| ATOM | 2562 | CG | LYS | A | 1124 | −12.571 | 52.892 | 38.892 | 1.00 | 83.65 | C |
| ATOM | 2563 | CD | LYS | A | 1124 | −12.682 | 52.701 | 37.399 | 1.00 | 89.63 | C |
| ATOM | 2564 | CE | LYS | A | 1124 | −11.978 | 53.758 | 36.540 | 1.00 | 92.96 | C |
| ATOM | 2565 | NZ | LYS | A | 1124 | −12.833 | 55.011 | 36.416 | 1.00 | 104.91 | N |
| ATOM | 2566 | N | ARG | A | 1125 | −16.586 | 52.609 | 41.828 | 1.00 | 74.41 | N |
| ATOM | 2567 | CA | ARG | A | 1125 | −17.489 | 51.958 | 42.758 | 1.00 | 73.39 | C |

APPENDIX 1-continued

| | | | | | | | | | |
|---|---|---|---|---|---|---|---|---|---|
| ATOM | 2568 | C | ARG | A | 1125 | −18.787 | 51.862 | 41.975 | 1.00 | 72.92 | C |
| ATOM | 2569 | O | ARG | A | 1125 | −19.755 | 52.569 | 42.238 | 1.00 | 75.78 | O |
| ATOM | 2570 | CB | ARG | A | 1125 | −17.625 | 52.765 | 44.049 | 1.00 | 72.14 | C |
| ATOM | 2571 | CG | ARG | A | 1125 | −16.304 | 52.959 | 44.776 | 1.00 | 74.10 | C |
| ATOM | 2572 | CD | ARG | A | 1125 | −16.448 | 53.860 | 45.974 | 1.00 | 76.04 | C |
| ATOM | 2573 | NE | ARG | A | 1125 | −17.144 | 53.226 | 47.096 | 1.00 | 83.94 | N |
| ATOM | 2574 | CZ | ARG | A | 1125 | −17.567 | 53.859 | 48.203 | 1.00 | 87.62 | C |
| ATOM | 2575 | NH1 | ARG | A | 1125 | −17.373 | 55.179 | 48.365 | 1.00 | 91.97 | N |
| ATOM | 2576 | NH2 | ARG | A | 1125 | −18.195 | 53.171 | 49.172 | 1.00 | 84.34 | N |
| ATOM | 2577 | N | TRP | A | 1126 | −18.778 | 50.963 | 41.005 | 1.00 | 74.20 | N |
| ATOM | 2578 | CA | TRP | A | 1126 | −19.839 | 50.847 | 39.981 | 1.00 | 72.97 | C |
| ATOM | 2579 | C | TRP | A | 1126 | −21.220 | 50.507 | 40.541 | 1.00 | 71.90 | C |
| ATOM | 2580 | O | TRP | A | 1126 | −22.203 | 51.187 | 40.232 | 1.00 | 67.72 | O |
| ATOM | 2581 | CB | TRP | A | 1126 | −19.473 | 49.781 | 38.959 | 1.00 | 69.76 | C |
| ATOM | 2582 | CG | TRP | A | 1126 | −18.124 | 49.894 | 38.335 | 1.00 | 70.87 | C |
| ATOM | 2583 | CD1 | TRP | A | 1126 | −17.183 | 48.917 | 38.255 | 1.00 | 66.79 | C |
| ATOM | 2584 | CD2 | TRP | A | 1126 | −17.564 | 51.047 | 37.699 | 1.00 | 70.96 | C |
| ATOM | 2585 | NE1 | TRP | A | 1126 | −16.068 | 49.386 | 37.610 | 1.00 | 69.94 | N |
| ATOM | 2586 | CE2 | TRP | A | 1126 | −16.280 | 50.692 | 37.260 | 1.00 | 70.31 | C |
| ATOM | 2587 | CE3 | TRP | A | 1126 | −18.026 | 52.351 | 37.457 | 1.00 | 71.68 | C |
| ATOM | 2588 | CZ2 | TRP | A | 1126 | −15.460 | 51.576 | 36.600 | 1.00 | 74.24 | C |
| ATOM | 2589 | CZ3 | TRP | A | 1126 | −17.205 | 53.235 | 36.801 | 1.00 | 71.20 | C |
| ATOM | 2590 | CH2 | TRP | A | 1126 | −15.939 | 52.850 | 36.379 | 1.00 | 73.75 | C |
| ATOM | 2591 | N | ASP | A | 1127 | −21.273 | 49.458 | 41.357 | 1.00 | 72.11 | N |
| ATOM | 2592 | CA | ASP | A | 1127 | −22.537 | 49.012 | 41.994 | 1.00 | 74.28 | C |
| ATOM | 2593 | C | ASP | A | 1127 | −23.168 | 50.100 | 42.830 | 1.00 | 72.96 | C |
| ATOM | 2594 | O | ASP | A | 1127 | −24.377 | 50.283 | 42.781 | 1.00 | 77.35 | O |
| ATOM | 2595 | CB | ASP | A | 1127 | −22.326 | 47.768 | 42.874 | 1.00 | 73.85 | C |
| ATOM | 2596 | CG | ASP | A | 1127 | −22.177 | 46.475 | 42.065 | 1.00 | 80.36 | C |
| ATOM | 2597 | OD1 | ASP | A | 1127 | −22.034 | 46.530 | 40.836 | 1.00 | 81.11 | O |
| ATOM | 2598 | OD2 | ASP | A | 1127 | −22.204 | 45.386 | 42.681 | 1.00 | 97.24 | O |
| ATOM | 2599 | N | GLU | A | 1128 | −22.349 | 50.813 | 43.586 | 1.00 | 70.74 | N |
| ATOM | 2600 | CA | GLU | A | 1128 | −22.840 | 51.886 | 44.452 | 1.00 | 72.33 | C |
| ATOM | 2601 | C | GLU | A | 1128 | −23.299 | 53.089 | 43.646 | 1.00 | 70.63 | C |
| ATOM | 2602 | O | GLU | A | 1128 | −24.276 | 53.740 | 44.017 | 1.00 | 70.95 | O |
| ATOM | 2603 | CB | GLU | A | 1128 | −21.764 | 52.293 | 45.420 | 1.00 | 70.41 | C |
| ATOM | 2604 | CG | GLU | A | 1128 | −21.384 | 51.186 | 46.364 | 1.00 | 79.81 | C |
| ATOM | 2605 | CD | GLU | A | 1128 | −20.232 | 51.570 | 47.219 | 1.00 | 81.59 | C |
| ATOM | 2606 | OE1 | GLU | A | 1128 | −20.445 | 52.476 | 48.059 | 1.00 | 90.24 | O |
| ATOM | 2607 | OE2 | GLU | A | 1128 | −19.131 | 50.969 | 47.053 | 1.00 | 85.83 | O |
| ATOM | 2608 | N | ALA | A | 1129 | −22.587 | 53.372 | 42.561 | 1.00 | 67.55 | N |
| ATOM | 2609 | CA | ALA | A | 1129 | −23.000 | 54.375 | 41.574 | 1.00 | 71.98 | C |
| ATOM | 2610 | C | ALA | A | 1129 | −24.378 | 54.000 | 41.058 | 1.00 | 70.13 | C |
| ATOM | 2611 | O | ALA | A | 1129 | −25.263 | 54.827 | 41.057 | 1.00 | 76.48 | O |
| ATOM | 2612 | CB | ALA | A | 1129 | −21.989 | 54.462 | 40.410 | 1.00 | 65.05 | C |
| ATOM | 2613 | N | ALA | A | 1130 | −24.534 | 52.742 | 40.634 | 1.00 | 72.74 | N |
| ATOM | 2614 | CA | ALA | A | 1130 | −25.821 | 52.182 | 40.126 | 1.00 | 70.99 | C |
| ATOM | 2615 | C | ALA | A | 1130 | −26.956 | 52.249 | 41.142 | 1.00 | 70.01 | C |
| ATOM | 2616 | O | ALA | A | 1130 | −28.122 | 52.487 | 40.776 | 1.00 | 68.38 | O |
| ATOM | 2617 | CB | ALA | A | 1130 | −25.623 | 50.735 | 39.676 | 1.00 | 66.12 | C |
| ATOM | 2618 | N | VAL | A | 1131 | −26.632 | 52.039 | 42.416 | 1.00 | 68.58 | N |
| ATOM | 2619 | CA | VAL | A | 1131 | −27.663 | 52.124 | 43.473 | 1.00 | 67.85 | C |
| ATOM | 2620 | C | VAL | A | 1131 | −28.222 | 53.535 | 43.503 | 1.00 | 69.11 | C |
| ATOM | 2621 | O | VAL | A | 1131 | −29.445 | 53.719 | 43.551 | 1.00 | 67.62 | O |
| ATOM | 2622 | CB | VAL | A | 1131 | −27.149 | 51.685 | 44.851 | 1.00 | 69.41 | C |
| ATOM | 2623 | CG1 | VAL | A | 1131 | −28.070 | 52.236 | 46.024 | 1.00 | 60.58 | C |
| ATOM | 2624 | CG2 | VAL | A | 1131 | −27.016 | 50.147 | 44.886 | 1.00 | 64.52 | C |
| ATOM | 2625 | N | ASN | A | 1132 | −27.323 | 54.517 | 43.466 | 1.00 | 71.57 | N |
| ATOM | 2626 | CA | ASN | A | 1132 | −27.706 | 55.935 | 43.510 | 1.00 | 73.21 | C |
| ATOM | 2627 | C | ASN | A | 1132 | −28.408 | 56.412 | 42.232 | 1.00 | 70.74 | C |
| ATOM | 2628 | O | ASN | A | 1132 | −29.422 | 57.104 | 42.307 | 1.00 | 68.21 | O |
| ATOM | 2629 | CB | ASN | A | 1132 | −26.486 | 56.817 | 43.828 | 1.00 | 72.85 | C |
| ATOM | 2630 | CG | ASN | A | 1132 | −26.112 | 56.776 | 45.296 | 1.00 | 78.49 | C |
| ATOM | 2631 | OD1 | ASN | A | 1132 | −26.088 | 57.807 | 45.962 | 1.00 | 83.67 | O |
| ATOM | 2632 | ND2 | ASN | A | 1132 | −25.822 | 55.588 | 45.808 | 1.00 | 84.32 | N |
| ATOM | 2633 | N | LEU | A | 1133 | −27.869 | 56.040 | 41.076 | 1.00 | 69.80 | N |
| ATOM | 2634 | CA | LEU | A | 1133 | −28.465 | 56.421 | 39.798 | 1.00 | 72.25 | C |
| ATOM | 2635 | C | LEU | A | 1133 | −29.883 | 55.859 | 39.633 | 1.00 | 73.77 | C |
| ATOM | 2636 | O | LEU | A | 1133 | −30.748 | 56.528 | 39.065 | 1.00 | 78.51 | O |
| ATOM | 2637 | CB | LEU | A | 1133 | −27.569 | 55.971 | 38.637 | 1.00 | 74.37 | C |
| ATOM | 2638 | CG | LEU | A | 1133 | −26.186 | 56.632 | 38.565 | 1.00 | 74.55 | C |
| ATOM | 2639 | CD1 | LEU | A | 1133 | −25.327 | 56.045 | 37.436 | 1.00 | 81.95 | C |
| ATOM | 2640 | CD2 | LEU | A | 1133 | −26.336 | 58.139 | 38.408 | 1.00 | 79.93 | C |
| ATOM | 2641 | N | ALA | A | 1134 | −30.121 | 54.639 | 40.132 | 1.00 | 72.16 | N |
| ATOM | 2642 | CA | ALA | A | 1134 | −31.455 | 54.022 | 40.090 | 1.00 | 71.47 | C |
| ATOM | 2643 | C | ALA | A | 1134 | −32.505 | 54.776 | 40.950 | 1.00 | 72.41 | C |
| ATOM | 2644 | O | ALA | A | 1134 | −33.701 | 54.586 | 40.741 | 1.00 | 70.87 | O |
| ATOM | 2645 | CB | ALA | A | 1134 | −31.378 | 52.533 | 40.511 | 1.00 | 68.95 | C |
| ATOM | 2646 | N | LYS | A | 1135 | −32.052 | 55.620 | 41.901 | 1.00 | 68.74 | N |
| ATOM | 2647 | CA | LYS | A | 1135 | −32.946 | 56.436 | 42.773 | 1.00 | 72.99 | C |

APPENDIX 1-continued

| ATOM | 2648 | C | LYS | A | 1135 | −33.266 | 57.857 | 42.231 | 1.00 | 72.10 | C |
|---|---|---|---|---|---|---|---|---|---|---|---|
| ATOM | 2649 | O | LYS | A | 1135 | −33.585 | 58.762 | 43.000 | 1.00 | 74.92 | O |
| ATOM | 2650 | CB | LYS | A | 1135 | −32.343 | 56.536 | 44.199 | 1.00 | 69.32 | C |
| ATOM | 2651 | CG | LYS | A | 1135 | −32.402 | 55.253 | 45.012 | 1.00 | 76.21 | C |
| ATOM | 2652 | CD | LYS | A | 1135 | −31.674 | 55.410 | 46.367 | 1.00 | 77.13 | C |
| ATOM | 2653 | CE | LYS | A | 1135 | −31.950 | 54.245 | 47.310 | 1.00 | 77.91 | C |
| ATOM | 2654 | NZ | LYS | A | 1135 | −30.938 | 54.134 | 48.434 | 1.00 | 77.31 | N |
| ATOM | 2655 | N | SER | A | 1136 | −33.185 | 58.051 | 40.916 | 1.00 | 76.65 | N |
| ATOM | 2656 | CA | SER | A | 1136 | −33.404 | 59.364 | 40.298 | 1.00 | 74.00 | C |
| ATOM | 2657 | C | SER | A | 1136 | −34.753 | 59.516 | 39.594 | 1.00 | 76.99 | C |
| ATOM | 2658 | O | SER | A | 1136 | −35.464 | 58.536 | 39.320 | 1.00 | 79.35 | O |
| ATOM | 2659 | CB | SER | A | 1136 | −32.289 | 59.635 | 39.304 | 1.00 | 75.82 | C |
| ATOM | 2660 | OG | SER | A | 1136 | −32.139 | 58.573 | 38.368 | 1.00 | 74.98 | O |
| ATOM | 2661 | N | ARG | A | 1137 | −35.081 | 60.775 | 39.313 | 1.00 | 74.80 | N |
| ATOM | 2662 | CA | ARG | A | 1137 | −36.216 | 61.141 | 38.485 | 1.00 | 72.91 | C |
| ATOM | 2663 | C | ARG | A | 1137 | −35.965 | 60.639 | 37.043 | 1.00 | 71.62 | C |
| ATOM | 2664 | O | ARG | A | 1137 | −36.884 | 60.312 | 36.325 | 1.00 | 70.32 | O |
| ATOM | 2665 | CB | ARG | A | 1137 | −36.395 | 62.661 | 38.504 | 1.00 | 71.58 | C |
| ATOM | 2666 | CG | ARG | A | 1137 | −37.567 | 63.220 | 37.702 | 1.00 | 76.14 | C |
| ATOM | 2667 | CD | ARG | A | 1137 | −38.896 | 62.715 | 38.231 | 1.00 | 84.99 | C |
| ATOM | 2668 | NE | ARG | A | 1137 | −40.034 | 63.267 | 37.497 | 1.00 | 85.80 | N |
| ATOM | 2669 | CZ | ARG | A | 1137 | −41.305 | 62.894 | 37.664 | 1.00 | 83.56 | C |
| ATOM | 2670 | NH1 | ARG | A | 1137 | −41.640 | 61.951 | 38.547 | 1.00 | 74.66 | N |
| ATOM | 2671 | NH2 | ARG | A | 1137 | −42.263 | 63.469 | 36.933 | 1.00 | 88.55 | N |
| ATOM | 2672 | N | TRP | A | 1138 | −34.703 | 60.592 | 36.651 | 1.00 | 70.67 | N |
| ATOM | 2673 | CA | TRP | A | 1138 | −34.289 | 60.023 | 35.392 | 1.00 | 72.64 | C |
| ATOM | 2674 | C | TRP | A | 1138 | −34.759 | 58.569 | 35.248 | 1.00 | 74.44 | C |
| ATOM | 2675 | O | TRP | A | 1138 | −35.428 | 58.233 | 34.279 | 1.00 | 74.91 | O |
| ATOM | 2676 | CB | TRP | A | 1138 | −32.778 | 60.118 | 35.298 | 1.00 | 72.63 | C |
| ATOM | 2677 | CG | TRP | A | 1138 | −32.166 | 59.434 | 34.164 | 1.00 | 72.19 | C |
| ATOM | 2678 | CD1 | TRP | A | 1138 | −32.556 | 59.491 | 32.862 | 1.00 | 72.21 | C |
| ATOM | 2679 | CD2 | TRP | A | 1138 | −31.024 | 58.574 | 34.207 | 1.00 | 68.92 | C |
| ATOM | 2680 | NE1 | TRP | A | 1138 | −31.724 | 58.713 | 32.092 | 1.00 | 73.58 | N |
| ATOM | 2681 | CE2 | TRP | A | 1138 | −30.780 | 58.139 | 32.887 | 1.00 | 67.95 | C |
| ATOM | 2682 | CE3 | TRP | A | 1138 | −30.190 | 58.125 | 35.223 | 1.00 | 66.16 | C |
| ATOM | 2683 | CZ2 | TRP | A | 1138 | −29.749 | 57.293 | 32.570 | 1.00 | 69.41 | C |
| ATOM | 2684 | CZ3 | TRP | A | 1138 | −29.142 | 57.262 | 34.893 | 1.00 | 71.01 | C |
| ATOM | 2685 | CH2 | TRP | A | 1138 | −28.934 | 56.863 | 33.600 | 1.00 | 71.24 | C |
| ATOM | 2686 | N | TYR | A | 1139 | −34.407 | 57.727 | 36.212 | 1.00 | 73.44 | N |
| ATOM | 2687 | CA | TYR | A | 1139 | −34.828 | 56.318 | 36.196 | 1.00 | 70.88 | C |
| ATOM | 2688 | C | TYR | A | 1139 | −36.337 | 56.170 | 36.397 | 1.00 | 71.38 | C |
| ATOM | 2689 | O | TYR | A | 1139 | −36.940 | 55.218 | 35.922 | 1.00 | 72.03 | O |
| ATOM | 2690 | CB | TYR | A | 1139 | −34.064 | 55.516 | 37.258 | 1.00 | 74.06 | C |
| ATOM | 2691 | CG | TYR | A | 1139 | −34.530 | 54.095 | 37.404 | 1.00 | 70.82 | C |
| ATOM | 2692 | CD1 | TYR | A | 1139 | −34.012 | 53.101 | 36.601 | 1.00 | 76.39 | C |
| ATOM | 2693 | CD2 | TYR | A | 1139 | −35.496 | 53.746 | 38.351 | 1.00 | 76.13 | C |
| ATOM | 2694 | CE1 | TYR | A | 1139 | −34.429 | 51.793 | 36.720 | 1.00 | 73.02 | C |
| ATOM | 2695 | CE2 | TYR | A | 1139 | −35.923 | 52.436 | 38.481 | 1.00 | 79.81 | C |
| ATOM | 2696 | CZ | TYR | A | 1139 | −35.376 | 51.461 | 37.651 | 1.00 | 77.76 | C |
| ATOM | 2697 | OH | TYR | A | 1139 | −35.772 | 50.154 | 37.747 | 1.00 | 78.31 | O |
| ATOM | 2698 | N | ASN | A | 1140 | −36.943 | 57.111 | 37.106 | 1.00 | 72.72 | N |
| ATOM | 2699 | CA | ASN | A | 1140 | −38.381 | 57.111 | 37.312 | 1.00 | 71.50 | C |
| ATOM | 2700 | C | ASN | A | 1140 | −39.175 | 57.391 | 36.028 | 1.00 | 70.46 | C |
| ATOM | 2701 | O | ASN | A | 1140 | −40.307 | 56.929 | 35.882 | 1.00 | 72.15 | O |
| ATOM | 2702 | CB | ASN | A | 1140 | −38.755 | 58.172 | 38.338 | 1.00 | 68.60 | C |
| ATOM | 2703 | CG | ASN | A | 1140 | −40.230 | 58.240 | 38.572 | 1.00 | 72.49 | C |
| ATOM | 2704 | OD1 | ASN | A | 1140 | −40.864 | 59.264 | 38.335 | 1.00 | 72.97 | O |
| ATOM | 2705 | ND2 | ASN | A | 1140 | −40.801 | 57.138 | 39.040 | 1.00 | 83.45 | N |
| ATOM | 2706 | N | GLN | A | 1141 | −38.573 | 58.145 | 35.111 | 1.00 | 71.15 | N |
| ATOM | 2707 | CA | GLN | A | 1141 | −39.248 | 58.616 | 33.896 | 1.00 | 71.46 | C |
| ATOM | 2708 | C | GLN | A | 1141 | −38.919 | 57.755 | 32.677 | 1.00 | 72.46 | C |
| ATOM | 2709 | O | GLN | A | 1141 | −39.828 | 57.378 | 31.930 | 1.00 | 69.45 | O |
| ATOM | 2710 | CB | GLN | A | 1141 | −38.887 | 60.091 | 33.663 | 1.00 | 71.54 | C |
| ATOM | 2711 | CG | GLN | A | 1141 | −39.493 | 61.040 | 34.694 | 1.00 | 74.06 | C |
| ATOM | 2712 | CD | GLN | A | 1141 | −40.987 | 61.142 | 34.576 | 1.00 | 84.66 | C |
| ATOM | 2713 | OE1 | GLN | A | 1141 | −41.726 | 60.867 | 35.539 | 1.00 | 72.30 | O |
| ATOM | 2714 | NE2 | GLN | A | 1141 | −41.461 | 61.535 | 33.387 | 1.00 | 78.96 | N |
| ATOM | 2715 | N | THR | A | 1142 | −37.633 | 57.454 | 32.490 | 1.00 | 69.68 | N |
| ATOM | 2716 | CA | THR | A | 1142 | −37.167 | 56.582 | 31.409 | 1.00 | 71.24 | C |
| ATOM | 2717 | C | THR | A | 1142 | −36.399 | 55.382 | 31.997 | 1.00 | 71.57 | C |
| ATOM | 2718 | O | THR | A | 1142 | −35.177 | 55.274 | 31.783 | 1.00 | 73.67 | O |
| ATOM | 2719 | CB | THR | A | 1142 | −36.318 | 57.373 | 30.396 | 1.00 | 73.10 | C |
| ATOM | 2720 | OG1 | THR | A | 1142 | −35.335 | 58.134 | 31.100 | 1.00 | 65.73 | O |
| ATOM | 2721 | CG2 | THR | A | 1142 | −37.223 | 58.326 | 29.569 | 1.00 | 63.92 | C |
| ATOM | 2722 | N | PRO | A | 1143 | −37.120 | 54.475 | 32.744 | 1.00 | 68.91 | N |
| ATOM | 2723 | CA | PRO | A | 1143 | −36.537 | 53.299 | 33.404 | 1.00 | 67.95 | C |
| ATOM | 2724 | C | PRO | A | 1143 | −35.762 | 52.372 | 32.497 | 1.00 | 71.67 | C |
| ATOM | 2725 | O | PRO | A | 1143 | −34.638 | 52.018 | 32.834 | 1.00 | 70.47 | O |
| ATOM | 2726 | CB | PRO | A | 1143 | −37.760 | 52.553 | 33.937 | 1.00 | 70.48 | C |
| ATOM | 2727 | CG | PRO | A | 1143 | −38.920 | 53.137 | 33.252 | 1.00 | 70.91 | C |

APPENDIX 1-continued

| ATOM | 2728 | CD | PRO | A | 1143 | −38.570 | 54.528 | 33.001 | 1.00 | 68.98 | C |
|---|---|---|---|---|---|---|---|---|---|---|---|
| ATOM | 2729 | N | ASN | A | 1144 | −36.357 | 51.993 | 31.361 | 1.00 | 70.87 | N |
| ATOM | 2730 | CA | ASN | A | 1144 | −35.706 | 51.083 | 30.410 | 1.00 | 71.14 | C |
| ATOM | 2731 | C | ASN | A | 1144 | −34.382 | 51.613 | 29.946 | 1.00 | 72.08 | C |
| ATOM | 2732 | O | ASN | A | 1144 | −33.369 | 50.921 | 30.071 | 1.00 | 71.77 | O |
| ATOM | 2733 | CB | ASN | A | 1144 | −36.582 | 50.818 | 29.180 | 1.00 | 71.11 | C |
| ATOM | 2734 | CG | ASN | A | 1144 | −37.859 | 50.077 | 29.515 | 1.00 | 74.27 | C |
| ATOM | 2735 | OD1 | ASN | A | 1144 | −37.919 | 49.323 | 30.480 | 1.00 | 76.06 | O |
| ATOM | 2736 | ND2 | ASN | A | 1144 | −38.895 | 50.288 | 28.709 | 1.00 | 86.76 | N |
| ATOM | 2737 | N | ARG | A | 1145 | −34.388 | 52.837 | 29.409 | 1.00 | 70.29 | N |
| ATOM | 2738 | CA | ARG | A | 1145 | −33.147 | 53.500 | 28.979 | 1.00 | 69.78 | C |
| ATOM | 2739 | C | ARG | A | 1145 | −32.142 | 53.627 | 30.132 | 1.00 | 70.79 | C |
| ATOM | 2740 | O | ARG | A | 1145 | −30.950 | 53.299 | 29.984 | 1.00 | 71.02 | O |
| ATOM | 2741 | CB | ARG | A | 1145 | −33.450 | 54.880 | 28.462 | 1.00 | 69.40 | C |
| ATOM | 2742 | CG | ARG | A | 1145 | −32.215 | 55.697 | 28.103 | 1.00 | 72.46 | C |
| ATOM | 2743 | CD | ARG | A | 1145 | −32.619 | 56.971 | 27.368 | 1.00 | 71.18 | C |
| ATOM | 2744 | NE | ARG | A | 1145 | −31.446 | 57.732 | 26.931 | 1.00 | 74.68 | N |
| ATOM | 2745 | CZ | ARG | A | 1145 | −31.488 | 58.840 | 26.186 | 1.00 | 81.63 | C |
| ATOM | 2746 | NH1 | ARG | A | 1145 | −32.661 | 59.353 | 25.769 | 1.00 | 76.56 | N |
| ATOM | 2747 | NH2 | ARG | A | 1145 | −30.354 | 59.453 | 25.844 | 1.00 | 80.74 | N |
| ATOM | 2748 | N | ALA | A | 1146 | −32.632 | 54.105 | 31.272 | 1.00 | 68.56 | N |
| ATOM | 2749 | CA | ALA | A | 1146 | −31.782 | 54.265 | 32.437 | 1.00 | 70.12 | C |
| ATOM | 2750 | C | ALA | A | 1146 | −31.211 | 52.906 | 32.844 | 1.00 | 68.68 | C |
| ATOM | 2751 | O | ALA | A | 1146 | −30.039 | 52.815 | 33.194 | 1.00 | 70.80 | O |
| ATOM | 2752 | CB | ALA | A | 1146 | −32.534 | 54.894 | 33.547 | 1.00 | 66.71 | C |
| ATOM | 2753 | N | LYS | A | 1147 | −32.029 | 51.862 | 32.786 | 1.00 | 69.92 | N |
| ATOM | 2754 | CA | LYS | A | 1147 | −31.583 | 50.524 | 33.161 | 1.00 | 72.10 | C |
| ATOM | 2755 | C | LYS | A | 1147 | −30.365 | 50.177 | 32.322 | 1.00 | 72.04 | C |
| ATOM | 2756 | O | LYS | A | 1147 | −29.317 | 49.794 | 32.881 | 1.00 | 66.93 | O |
| ATOM | 2757 | CB | LYS | A | 1147 | −32.712 | 49.514 | 32.992 | 1.00 | 73.45 | C |
| ATOM | 2758 | CG | LYS | A | 1147 | −32.536 | 48.177 | 33.665 | 1.00 | 78.51 | C |
| ATOM | 2759 | CD | LYS | A | 1147 | −33.835 | 47.348 | 33.477 | 1.00 | 82.18 | C |
| ATOM | 2760 | CE | LYS | A | 1147 | −33.762 | 45.956 | 34.103 | 1.00 | 93.88 | C |
| ATOM | 2761 | NZ | LYS | A | 1147 | −33.816 | 45.967 | 35.617 | 1.00 | 96.78 | N |
| ATOM | 2762 | N | ARG | A | 1148 | −30.494 | 50.323 | 30.986 | 1.00 | 73.00 | N |
| ATOM | 2763 | CA | ARG | A | 1148 | −29.393 | 50.016 | 30.051 | 1.00 | 70.89 | C |
| ATOM | 2764 | C | ARG | A | 1148 | −28.135 | 50.860 | 30.239 | 1.00 | 74.78 | C |
| ATOM | 2765 | O | ARG | A | 1148 | −27.034 | 50.334 | 30.098 | 1.00 | 80.02 | O |
| ATOM | 2766 | CB | ARG | A | 1148 | −29.832 | 50.150 | 28.590 | 1.00 | 72.03 | C |
| ATOM | 2767 | CG | ARG | A | 1148 | −30.780 | 49.068 | 28.099 | 1.00 | 70.33 | C |
| ATOM | 2768 | CD | ARG | A | 1148 | −30.936 | 49.102 | 26.596 | 1.00 | 72.06 | C |
| ATOM | 2769 | NE | ARG | A | 1148 | −31.674 | 50.290 | 26.158 | 1.00 | 71.65 | N |
| ATOM | 2770 | CZ | ARG | A | 1148 | −33.006 | 50.391 | 26.084 | 1.00 | 72.14 | C |
| ATOM | 2771 | NH1 | ARG | A | 1148 | −33.801 | 49.382 | 26.416 | 1.00 | 78.11 | N |
| ATOM | 2772 | NH2 | ARG | A | 1148 | −33.568 | 51.523 | 25.671 | 1.00 | 71.64 | N |
| ATOM | 2773 | N | VAL | A | 1149 | −28.270 | 52.150 | 30.547 | 1.00 | 74.24 | N |
| ATOM | 2774 | CA | VAL | A | 1149 | −27.072 | 52.990 | 30.752 | 1.00 | 71.90 | C |
| ATOM | 2775 | C | VAL | A | 1149 | −26.399 | 52.632 | 32.098 | 1.00 | 74.21 | C |
| ATOM | 2776 | O | VAL | A | 1149 | −25.188 | 52.478 | 32.164 | 1.00 | 77.27 | O |
| ATOM | 2777 | CB | VAL | A | 1149 | −27.374 | 54.510 | 30.676 | 1.00 | 78.88 | C |
| ATOM | 2778 | CG1 | VAL | A | 1149 | −26.122 | 55.316 | 31.006 | 1.00 | 78.08 | C |
| ATOM | 2779 | CG2 | VAL | A | 1149 | −27.939 | 54.922 | 29.282 | 1.00 | 63.48 | C |
| ATOM | 2780 | N | ILE | A | 1150 | −27.182 | 52.498 | 33.158 | 1.00 | 70.73 | N |
| ATOM | 2781 | CA | ILE | A | 1150 | −26.623 | 52.164 | 34.467 | 1.00 | 70.91 | C |
| ATOM | 2782 | C | ILE | A | 1150 | −25.901 | 50.823 | 34.437 | 1.00 | 69.25 | C |
| ATOM | 2783 | O | ILE | A | 1150 | −24.744 | 50.727 | 34.864 | 1.00 | 74.32 | O |
| ATOM | 2784 | CB | ILE | A | 1150 | −27.689 | 52.145 | 35.570 | 1.00 | 71.99 | C |
| ATOM | 2785 | CG1 | ILE | A | 1150 | −28.264 | 53.541 | 35.793 | 1.00 | 69.99 | C |
| ATOM | 2786 | CG2 | ILE | A | 1150 | −27.077 | 51.645 | 36.848 | 1.00 | 70.14 | C |
| ATOM | 2787 | CD1 | ILE | A | 1150 | −29.550 | 53.539 | 36.637 | 1.00 | 76.32 | C |
| ATOM | 2788 | N | THR | A | 1151 | −26.578 | 49.793 | 33.938 | 1.00 | 67.61 | N |
| ATOM | 2789 | CA | THR | A | 1151 | −25.954 | 48.476 | 33.707 | 1.00 | 67.20 | C |
| ATOM | 2790 | C | THR | A | 1151 | −24.648 | 48.608 | 32.920 | 1.00 | 70.88 | C |
| ATOM | 2791 | O | THR | A | 1151 | −23.683 | 47.887 | 33.190 | 1.00 | 74.26 | O |
| ATOM | 2792 | CB | THR | A | 1151 | −26.876 | 47.558 | 32.905 | 1.00 | 68.20 | C |
| ATOM | 2793 | OG1 | THR | A | 1151 | −28.158 | 47.491 | 33.541 | 1.00 | 72.09 | O |
| ATOM | 2794 | CG2 | THR | A | 1151 | −26.270 | 46.158 | 32.776 | 1.00 | 64.27 | C |
| ATOM | 2795 | N | THR | A | 1152 | −24.619 | 49.527 | 31.941 | 1.00 | 67.75 | N |
| ATOM | 2796 | CA | THR | A | 1152 | −23.399 | 49.788 | 31.157 | 1.00 | 70.23 | C |
| ATOM | 2797 | C | THR | A | 1152 | −22.322 | 50.417 | 32.042 | 1.00 | 69.27 | C |
| ATOM | 2798 | O | THR | A | 1152 | −21.145 | 50.068 | 31.924 | 1.00 | 71.67 | O |
| ATOM | 2799 | CB | THR | A | 1152 | −23.676 | 50.696 | 29.941 | 1.00 | 66.28 | C |
| ATOM | 2800 | OG1 | THR | A | 1152 | −24.680 | 50.076 | 29.121 | 1.00 | 70.58 | O |
| ATOM | 2801 | CG2 | THR | A | 1152 | −22.396 | 50.939 | 29.157 | 1.00 | 69.86 | C |
| ATOM | 2802 | N | PHE | A | 1153 | −22.719 | 51.337 | 32.913 | 1.00 | 68.71 | N |
| ATOM | 2803 | CA | PHE | A | 1153 | −21.791 | 51.796 | 33.990 | 1.00 | 74.06 | C |
| ATOM | 2804 | C | PHE | A | 1153 | −21.345 | 50.649 | 34.890 | 1.00 | 70.59 | C |
| ATOM | 2805 | O | PHE | A | 1153 | −20.232 | 50.662 | 35.389 | 1.00 | 76.73 | O |
| ATOM | 2806 | CB | PHE | A | 1153 | −22.391 | 52.892 | 34.872 | 1.00 | 71.58 | C |
| ATOM | 2807 | CG | PHE | A | 1153 | −22.359 | 54.274 | 34.258 | 1.00 | 75.33 | C |

APPENDIX 1-continued

| | | | | | | | | | | |
|---|---|---|---|---|---|---|---|---|---|---|
| ATOM | 2808 | CD1 | PHE | A | 1153 | −21.180 | 54.807 | 33.778 | 1.00 | 76.55 | C |
| ATOM | 2809 | CD2 | PHE | A | 1153 | −23.508 | 55.034 | 34.170 | 1.00 | 79.26 | C |
| ATOM | 2810 | CE1 | PHE | A | 1153 | −21.147 | 56.059 | 33.224 | 1.00 | 73.15 | C |
| ATOM | 2811 | CE2 | PHE | A | 1153 | −23.479 | 56.282 | 33.622 | 1.00 | 72.03 | C |
| ATOM | 2812 | CZ | PHE | A | 1153 | −22.296 | 56.799 | 33.147 | 1.00 | 71.84 | C |
| ATOM | 2813 | N | ARG | A | 1154 | −22.198 | 49.655 | 35.108 | 1.00 | 70.31 | N |
| ATOM | 2814 | CA | ARG | A | 1154 | −21.801 | 48.490 | 35.940 | 1.00 | 72.56 | C |
| ATOM | 2815 | C | ARG | A | 1154 | −20.774 | 47.559 | 35.312 | 1.00 | 74.07 | C |
| ATOM | 2816 | O | ARG | A | 1154 | −19.826 | 47.158 | 35.994 | 1.00 | 75.46 | O |
| ATOM | 2817 | CB | ARG | A | 1154 | −23.013 | 47.661 | 36.354 | 1.00 | 71.60 | C |
| ATOM | 2818 | CG | ARG | A | 1154 | −23.926 | 48.392 | 37.315 | 1.00 | 78.93 | C |
| ATOM | 2819 | CD | ARG | A | 1154 | −24.313 | 47.484 | 38.485 | 1.00 | 80.49 | C |
| ATOM | 2820 | NE | ARG | A | 1154 | −25.312 | 46.492 | 38.126 | 1.00 | 81.98 | N |
| ATOM | 2821 | CZ | ARG | A | 1154 | −25.657 | 45.436 | 38.870 | 1.00 | 84.48 | C |
| ATOM | 2822 | NH1 | ARG | A | 1154 | −25.082 | 45.186 | 40.063 | 1.00 | 90.99 | N |
| ATOM | 2823 | NH2 | ARG | A | 1154 | −26.595 | 44.601 | 38.421 | 1.00 | 88.13 | N |
| ATOM | 2824 | N | THR | A | 1155 | −20.956 | 47.219 | 34.029 | 1.00 | 73.12 | N |
| ATOM | 2825 | CA | THR | A | 1155 | −20.095 | 46.232 | 33.346 | 1.00 | 74.07 | C |
| ATOM | 2826 | C | THR | A | 1155 | −18.969 | 46.828 | 32.501 | 1.00 | 76.10 | C |
| ATOM | 2827 | O | THR | A | 1155 | −17.912 | 46.218 | 32.361 | 1.00 | 76.98 | O |
| ATOM | 2828 | CB | THR | A | 1155 | −20.940 | 45.324 | 32.422 | 1.00 | 75.54 | C |
| ATOM | 2829 | OG1 | THR | A | 1155 | −21.368 | 46.063 | 31.251 | 1.00 | 76.27 | O |
| ATOM | 2830 | CG2 | THR | A | 1155 | −22.152 | 44.777 | 33.176 | 1.00 | 73.31 | C |
| ATOM | 2831 | N | GLY | A | 1156 | −19.185 | 48.008 | 31.936 | 1.00 | 75.88 | N |
| ATOM | 2832 | CA | GLY | A | 1156 | −18.198 | 48.591 | 31.038 | 1.00 | 76.99 | C |
| ATOM | 2833 | C | GLY | A | 1156 | −18.113 | 47.829 | 29.703 | 1.00 | 78.89 | C |
| ATOM | 2834 | O | GLY | A | 1156 | −17.054 | 47.785 | 29.073 | 1.00 | 77.75 | O |
| ATOM | 2835 | N | THR | A | 1157 | −19.240 | 47.235 | 29.297 | 1.00 | 79.45 | N |
| ATOM | 2836 | CA | THR | A | 1157 | −19.388 | 46.573 | 28.025 | 1.00 | 75.30 | C |
| ATOM | 2837 | C | THR | A | 1157 | −20.713 | 47.007 | 27.435 | 1.00 | 76.85 | C |
| ATOM | 2838 | O | THR | A | 1157 | −21.568 | 47.591 | 28.121 | 1.00 | 72.71 | O |
| ATOM | 2839 | CB | THR | A | 1157 | −19.491 | 45.069 | 28.150 | 1.00 | 77.35 | C |
| ATOM | 2840 | OG1 | THR | A | 1157 | −20.771 | 44.747 | 28.718 | 1.00 | 78.06 | O |
| ATOM | 2841 | CG2 | THR | A | 1157 | −18.332 | 44.460 | 29.016 | 1.00 | 73.49 | C |
| ATOM | 2842 | N | TRP | A | 1158 | −20.880 | 46.706 | 26.149 | 1.00 | 75.57 | N |
| ATOM | 2843 | CA | TRP | A | 1158 | −22.102 | 47.000 | 25.412 | 1.00 | 72.41 | C |
| ATOM | 2844 | C | TRP | A | 1158 | −23.213 | 45.956 | 25.579 | 1.00 | 72.74 | C |
| ATOM | 2845 | O | TRP | A | 1158 | −24.243 | 46.070 | 24.904 | 1.00 | 74.46 | O |
| ATOM | 2846 | CB | TRP | A | 1158 | −21.769 | 47.101 | 23.927 | 1.00 | 76.07 | C |
| ATOM | 2847 | CG | TRP | A | 1158 | −20.844 | 48.147 | 23.646 | 1.00 | 74.03 | C |
| ATOM | 2848 | CD1 | TRP | A | 1158 | −19.563 | 48.007 | 23.274 | 1.00 | 71.12 | C |
| ATOM | 2849 | CD2 | TRP | A | 1158 | −21.107 | 49.539 | 23.717 | 1.00 | 72.83 | C |
| ATOM | 2850 | NE1 | TRP | A | 1158 | −18.986 | 49.238 | 23.096 | 1.00 | 76.80 | N |
| ATOM | 2851 | CE2 | TRP | A | 1158 | −19.916 | 50.200 | 23.362 | 1.00 | 66.00 | C |
| ATOM | 2852 | CE3 | TRP | A | 1158 | −22.238 | 50.297 | 24.049 | 1.00 | 74.60 | C |
| ATOM | 2853 | CZ2 | TRP | A | 1158 | −19.811 | 51.582 | 23.322 | 1.00 | 71.92 | C |
| ATOM | 2854 | CZ3 | TRP | A | 1158 | −22.138 | 51.673 | 24.012 | 1.00 | 76.31 | C |
| ATOM | 2855 | CH2 | TRP | A | 1158 | −20.927 | 52.307 | 23.649 | 1.00 | 74.45 | C |
| ATOM | 2856 | N | ASP | A | 1159 | −23.019 | 44.955 | 26.460 | 1.00 | 72.02 | N |
| ATOM | 2857 | CA | ASP | A | 1159 | −23.967 | 43.835 | 26.664 | 1.00 | 71.28 | C |
| ATOM | 2858 | C | ASP | A | 1159 | −25.450 | 44.207 | 26.837 | 1.00 | 72.00 | C |
| ATOM | 2859 | O | ASP | A | 1159 | −26.316 | 43.422 | 26.450 | 1.00 | 73.98 | O |
| ATOM | 2860 | CB | ASP | A | 1159 | −23.527 | 42.966 | 27.852 | 1.00 | 73.56 | C |
| ATOM | 2861 | CG | ASP | A | 1159 | −22.254 | 42.143 | 27.570 | 1.00 | 78.31 | C |
| ATOM | 2862 | OD1 | ASP | A | 1159 | −21.715 | 42.178 | 26.450 | 1.00 | 78.77 | O |
| ATOM | 2863 | OD2 | ASP | A | 1159 | −21.791 | 41.449 | 28.499 | 1.00 | 92.78 | O |
| ATOM | 2864 | N | ALA | A | 1160 | −25.746 | 45.381 | 27.405 | 1.00 | 72.33 | N |
| ATOM | 2865 | CA | ALA | A | 1160 | −27.154 | 45.828 | 27.567 | 1.00 | 72.44 | C |
| ATOM | 2866 | C | ALA | A | 1160 | −27.815 | 46.215 | 26.238 | 1.00 | 72.65 | C |
| ATOM | 2867 | O | ALA | A | 1160 | −29.037 | 46.285 | 26.169 | 1.00 | 75.90 | O |
| ATOM | 2868 | CB | ALA | A | 1160 | −27.254 | 46.998 | 28.560 | 1.00 | 69.43 | C |
| ATOM | 2869 | N | TYR | A | 1161 | −27.010 | 46.465 | 25.200 | 1.00 | 73.56 | N |
| ATOM | 2870 | CA | TYR | A | 1161 | −27.500 | 46.850 | 23.870 | 1.00 | 70.85 | C |
| ATOM | 2871 | C | TYR | A | 1161 | −27.500 | 45.693 | 22.845 | 1.00 | 71.12 | C |
| ATOM | 2872 | O | TYR | A | 1161 | −27.779 | 45.928 | 21.684 | 1.00 | 74.87 | O |
| ATOM | 2873 | CB | TYR | A | 1161 | −26.712 | 48.067 | 23.381 | 1.00 | 70.71 | C |
| ATOM | 2874 | CG | TYR | A | 1161 | −26.977 | 49.224 | 24.282 | 1.00 | 69.57 | C |
| ATOM | 2875 | CD1 | TYR | A | 1161 | −28.020 | 50.090 | 24.037 | 1.00 | 67.53 | C |
| ATOM | 2876 | CD2 | TYR | A | 1161 | −26.187 | 49.451 | 25.400 | 1.00 | 71.83 | C |
| ATOM | 2877 | CE1 | TYR | A | 1161 | −28.269 | 51.157 | 24.878 | 1.00 | 69.80 | C |
| ATOM | 2878 | CE2 | TYR | A | 1161 | −26.432 | 50.509 | 26.236 | 1.00 | 64.36 | C |
| ATOM | 2879 | CZ | TYR | A | 1161 | −27.470 | 51.366 | 25.980 | 1.00 | 73.12 | C |
| ATOM | 2880 | OH | TYR | A | 1161 | −27.695 | 52.436 | 26.850 | 1.00 | 77.23 | O |
| ATOM | 2881 | N | LYS | A | 263 | −27.193 | 44.468 | 23.289 | 1.00 | 68.62 | N |
| ATOM | 2882 | CA | LYS | A | 263 | −27.211 | 43.302 | 22.437 | 1.00 | 68.39 | C |
| ATOM | 2883 | C | LYS | A | 263 | −28.617 | 42.992 | 22.039 | 1.00 | 68.68 | C |
| ATOM | 2884 | O | LYS | A | 263 | −29.497 | 43.032 | 22.873 | 1.00 | 71.28 | O |
| ATOM | 2885 | CB | LYS | A | 263 | −26.716 | 42.052 | 23.152 | 1.00 | 70.24 | C |
| ATOM | 2886 | CG | LYS | A | 263 | −25.247 | 41.957 | 23.391 | 1.00 | 76.63 | C |
| ATOM | 2887 | CD | LYS | A | 263 | −24.916 | 40.567 | 23.966 | 1.00 | 77.14 | C |

APPENDIX 1-continued

| ATOM | 2888 | CE  | LYS | A | 263 | −23.433 | 40.257 | 23.926 | 1.00 | 86.04 | C |
| ATOM | 2889 | NZ  | LYS | A | 263 | −23.139 | 38.781 | 24.083 | 1.00 | 88.05 | N |
| ATOM | 2890 | N   | PHE | A | 264 | −28.823 | 42.683 | 20.766 | 1.00 | 66.31 | N |
| ATOM | 2891 | CA  | PHE | A | 264 | −30.129 | 42.267 | 20.240 | 1.00 | 67.14 | C |
| ATOM | 2892 | C   | PHE | A | 264 | −31.247 | 43.272 | 20.499 | 1.00 | 66.08 | C |
| ATOM | 2893 | O   | PHE | A | 264 | −32.385 | 42.892 | 20.754 | 1.00 | 66.16 | O |
| ATOM | 2894 | CB  | PHE | A | 264 | −30.490 | 40.877 | 20.774 | 1.00 | 65.00 | C |
| ATOM | 2895 | CG  | PHE | A | 264 | −29.455 | 39.843 | 20.461 | 1.00 | 68.77 | C |
| ATOM | 2896 | CD1 | PHE | A | 264 | −28.761 | 39.182 | 21.465 | 1.00 | 69.39 | C |
| ATOM | 2897 | CD2 | PHE | A | 264 | −29.166 | 39.530 | 19.135 | 1.00 | 69.77 | C |
| ATOM | 2898 | CE1 | PHE | A | 264 | −27.800 | 38.223 | 21.148 | 1.00 | 67.15 | C |
| ATOM | 2899 | CE2 | PHE | A | 264 | −28.210 | 38.578 | 18.825 | 1.00 | 68.88 | C |
| ATOM | 2900 | CZ  | PHE | A | 264 | −27.531 | 37.925 | 19.832 | 1.00 | 67.43 | C |
| ATOM | 2901 | N   | CYS | A | 265 | −30.891 | 44.551 | 20.430 | 1.00 | 66.76 | N |
| ATOM | 2902 | CA  | CYS | A | 265 | −31.837 | 45.636 | 20.494 | 1.00 | 66.33 | C |
| ATOM | 2903 | C   | CYS | A | 265 | −32.192 | 46.034 | 19.051 | 1.00 | 66.21 | C |
| ATOM | 2904 | O   | CYS | A | 265 | −33.355 | 46.217 | 18.742 | 1.00 | 67.25 | O |
| ATOM | 2905 | CB  | CYS | A | 265 | −31.269 | 46.818 | 21.274 | 1.00 | 65.09 | C |
| ATOM | 2906 | SG  | CYS | A | 265 | −31.066 | 46.521 | 23.110 | 1.00 | 69.25 | S |
| ATOM | 2907 | N   | LEU | A | 266 | −31.183 | 46.163 | 18.186 | 1.00 | 63.62 | N |
| ATOM | 2908 | CA  | LEU | A | 266 | −31.385 | 46.560 | 16.806 | 1.00 | 65.11 | C |
| ATOM | 2909 | C   | LEU | A | 266 | −32.130 | 45.487 | 16.037 | 1.00 | 65.91 | C |
| ATOM | 2910 | O   | LEU | A | 266 | −31.815 | 44.312 | 16.172 | 1.00 | 65.41 | O |
| ATOM | 2911 | CB  | LEU | A | 266 | −30.044 | 46.787 | 16.116 | 1.00 | 63.47 | C |
| ATOM | 2912 | CG  | LEU | A | 266 | −29.137 | 47.928 | 16.567 | 1.00 | 66.69 | C |
| ATOM | 2913 | CD1 | LEU | A | 266 | −27.791 | 47.827 | 15.848 | 1.00 | 64.50 | C |
| ATOM | 2914 | CD2 | LEU | A | 266 | −29.796 | 49.271 | 16.325 | 1.00 | 66.85 | C |
| ATOM | 2915 | N   | LYS | A | 267 | −33.112 | 45.898 | 15.238 | 1.00 | 68.75 | N |
| ATOM | 2916 | CA  | LYS | A | 267 | −33.870 | 44.973 | 14.350 | 1.00 | 71.90 | C |
| ATOM | 2917 | C   | LYS | A | 267 | −32.973 | 44.007 | 13.566 | 1.00 | 69.09 | C |
| ATOM | 2918 | O   | LYS | A | 267 | −33.274 | 42.829 | 13.463 | 1.00 | 72.39 | O |
| ATOM | 2919 | CB  | LYS | A | 267 | −34.768 | 45.762 | 13.373 | 1.00 | 74.97 | C |
| ATOM | 2920 | CG  | LYS | A | 267 | −34.008 | 46.721 | 12.419 | 1.00 | 82.81 | C |
| ATOM | 2921 | CD  | LYS | A | 267 | −34.913 | 47.656 | 11.634 | 1.00 | 84.17 | C |
| ATOM | 2922 | CE  | LYS | A | 267 | −34.071 | 48.658 | 10.816 | 1.00 | 88.72 | C |
| ATOM | 2923 | NZ  | LYS | A | 267 | −34.904 | 49.777 | 10.290 | 1.00 | 88.47 | N |
| ATOM | 2924 | N   | GLU | A | 268 | −31.877 | 44.519 | 13.024 | 1.00 | 68.14 | N |
| ATOM | 2925 | CA  | GLU | A | 268 | −30.929 | 43.706 | 12.257 | 1.00 | 68.69 | C |
| ATOM | 2926 | C   | GLU | A | 268 | −30.232 | 42.665 | 13.125 | 1.00 | 69.97 | C |
| ATOM | 2927 | O   | GLU | A | 268 | −30.010 | 41.554 | 12.679 | 1.00 | 71.10 | O |
| ATOM | 2928 | CB  | GLU | A | 268 | −29.897 | 44.568 | 11.492 | 1.00 | 71.25 | C |
| ATOM | 2929 | CG  | GLU | A | 268 | −29.063 | 45.591 | 12.318 | 1.00 | 82.60 | C |
| ATOM | 2930 | CD  | GLU | A | 268 | −29.720 | 46.975 | 12.491 | 1.00 | 84.41 | C |
| ATOM | 2931 | OE1 | GLU | A | 268 | −30.934 | 47.164 | 12.219 | 1.00 | 81.45 | O |
| ATOM | 2932 | OE2 | GLU | A | 268 | −28.992 | 47.877 | 12.911 | 1.00 | 83.78 | O |
| ATOM | 2933 | N   | HIS | A | 269 | −29.891 | 43.023 | 14.366 | 1.00 | 70.32 | N |
| ATOM | 2934 | CA  | HIS | A | 269 | −29.274 | 42.065 | 15.287 | 1.00 | 68.22 | C |
| ATOM | 2935 | C   | HIS | A | 269 | −30.290 | 41.039 | 15.757 | 1.00 | 66.82 | C |
| ATOM | 2936 | O   | HIS | A | 269 | −29.946 | 39.856 | 15.882 | 1.00 | 65.02 | O |
| ATOM | 2937 | CB  | HIS | A | 269 | −28.612 | 42.794 | 16.451 | 1.00 | 71.92 | C |
| ATOM | 2938 | CG  | HIS | A | 269 | −27.390 | 43.554 | 16.047 | 1.00 | 71.60 | C |
| ATOM | 2939 | ND1 | HIS | A | 269 | −26.547 | 44.134 | 16.958 | 1.00 | 68.24 | N |
| ATOM | 2940 | CD2 | HIS | A | 269 | −26.867 | 43.824 | 14.824 | 1.00 | 75.13 | C |
| ATOM | 2941 | CE1 | HIS | A | 269 | −25.557 | 44.734 | 16.325 | 1.00 | 73.61 | C |
| ATOM | 2942 | NE2 | HIS | A | 269 | −25.725 | 44.562 | 15.027 | 1.00 | 78.78 | N |
| ATOM | 2943 | N   | LYS | A | 270 | −31.526 | 41.477 | 16.014 | 1.00 | 64.48 | N |
| ATOM | 2944 | CA  | LYS | A | 270 | −32.619 | 40.536 | 16.296 | 1.00 | 67.98 | C |
| ATOM | 2945 | C   | LYS | A | 270 | −32.761 | 39.521 | 15.146 | 1.00 | 68.82 | C |
| ATOM | 2946 | O   | LYS | A | 270 | −32.861 | 38.328 | 15.394 | 1.00 | 66.36 | O |
| ATOM | 2947 | CB  | LYS | A | 270 | −33.948 | 41.247 | 16.519 | 1.00 | 66.79 | C |
| ATOM | 2948 | CG  | LYS | A | 270 | −33.987 | 42.127 | 17.773 | 1.00 | 73.23 | C |
| ATOM | 2949 | CD  | LYS | A | 270 | −35.412 | 42.556 | 18.088 | 1.00 | 71.51 | C |
| ATOM | 2950 | CE  | LYS | A | 270 | −35.487 | 43.405 | 19.345 | 1.00 | 75.87 | C |
| ATOM | 2951 | NZ  | LYS | A | 270 | −35.017 | 42.669 | 20.545 | 1.00 | 77.55 | N |
| ATOM | 2952 | N   | ALA | A | 271 | −32.764 | 40.009 | 13.897 | 1.00 | 69.99 | N |
| ATOM | 2953 | CA  | ALA | A | 271 | −32.855 | 39.121 | 12.713 | 1.00 | 71.38 | C |
| ATOM | 2954 | C   | ALA | A | 271 | −31.731 | 38.111 | 12.727 | 1.00 | 71.12 | C |
| ATOM | 2955 | O   | ALA | A | 271 | −31.975 | 36.946 | 12.466 | 1.00 | 73.66 | O |
| ATOM | 2956 | CB  | ALA | A | 271 | −32.855 | 39.918 | 11.399 | 1.00 | 64.88 | C |
| ATOM | 2957 | N   | LEU | A | 272 | −30.502 | 38.548 | 13.034 | 1.00 | 72.07 | N |
| ATOM | 2958 | CA  | LEU | A | 272 | −29.359 | 37.599 | 13.151 | 1.00 | 74.58 | C |
| ATOM | 2959 | C   | LEU | A | 272 | −29.561 | 36.513 | 14.240 | 1.00 | 75.85 | C |
| ATOM | 2960 | O   | LEU | A | 272 | −29.137 | 35.367 | 14.051 | 1.00 | 81.93 | O |
| ATOM | 2961 | CB  | LEU | A | 272 | −28.025 | 38.324 | 13.408 | 1.00 | 73.91 | C |
| ATOM | 2962 | CG  | LEU | A | 272 | −27.406 | 39.228 | 12.329 | 1.00 | 78.65 | C |
| ATOM | 2963 | CD1 | LEU | A | 272 | −26.129 | 39.864 | 12.873 | 1.00 | 79.09 | C |
| ATOM | 2964 | CD2 | LEU | A | 272 | −27.118 | 38.465 | 11.080 | 1.00 | 65.55 | C |
| ATOM | 2965 | N   | LYS | A | 273 | −30.195 | 36.864 | 15.358 | 1.00 | 76.42 | N |
| ATOM | 2966 | CA  | LYS | A | 273 | −30.509 | 35.866 | 16.403 | 1.00 | 77.14 | C |
| ATOM | 2967 | C   | LYS | A | 273 | −31.512 | 34.845 | 15.857 | 1.00 | 77.91 | C |

APPENDIX 1-continued

| ATOM | 2968 | O   | LYS | A | 273 | −31.346 | 33.663 | 16.083 | 1.00 | 76.67 | O |
| --- | --- | --- | --- | --- | --- | --- | --- | --- | --- | --- | --- |
| ATOM | 2969 | CB  | LYS | A | 273 | −31.049 | 36.529 | 17.656 | 1.00 | 78.11 | C |
| ATOM | 2970 | CG  | LYS | A | 273 | −31.226 | 35.608 | 18.867 | 1.00 | 80.19 | C |
| ATOM | 2971 | CD  | LYS | A | 273 | −31.473 | 36.443 | 20.100 | 1.00 | 79.05 | C |
| ATOM | 2972 | CE  | LYS | A | 273 | −31.752 | 35.624 | 21.329 | 1.00 | 82.30 | C |
| ATOM | 2973 | NZ  | LYS | A | 273 | −31.953 | 36.544 | 22.492 | 1.00 | 84.12 | N |
| ATOM | 2974 | N   | THR | A | 274 | −32.541 | 35.313 | 15.139 | 1.00 | 80.30 | N |
| ATOM | 2975 | CA  | THR | A | 274 | −33.525 | 34.414 | 14.487 | 1.00 | 78.23 | C |
| ATOM | 2976 | C   | THR | A | 274 | −32.827 | 33.369 | 13.651 | 1.00 | 76.51 | C |
| ATOM | 2977 | O   | THR | A | 274 | −33.082 | 32.191 | 13.826 | 1.00 | 75.03 | O |
| ATOM | 2978 | CB  | THR | A | 274 | −34.520 | 35.166 | 13.564 | 1.00 | 81.00 | C |
| ATOM | 2979 | OG1 | THR | A | 274 | −35.198 | 36.197 | 14.293 | 1.00 | 83.35 | O |
| ATOM | 2980 | CG2 | THR | A | 274 | −35.553 | 34.206 | 12.963 | 1.00 | 79.62 | C |
| ATOM | 2981 | N   | LEU | A | 275 | −31.950 | 33.800 | 12.754 | 1.00 | 73.92 | N |
| ATOM | 2982 | CA  | LEU | A | 275 | −31.183 | 32.862 | 11.925 | 1.00 | 74.39 | C |
| ATOM | 2983 | C   | LEU | A | 275 | −30.330 | 31.927 | 12.779 | 1.00 | 75.45 | C |
| ATOM | 2984 | O   | LEU | A | 275 | −30.279 | 30.721 | 12.524 | 1.00 | 76.13 | O |
| ATOM | 2985 | CB  | LEU | A | 275 | −30.301 | 33.605 | 10.922 | 1.00 | 75.70 | C |
| ATOM | 2986 | CG  | LEU | A | 275 | −30.975 | 34.417 | 9.808 | 1.00 | 75.16 | C |
| ATOM | 2987 | CD1 | LEU | A | 275 | −29.909 | 35.169 | 8.981 | 1.00 | 67.26 | C |
| ATOM | 2988 | CD2 | LEU | A | 275 | −31.846 | 33.533 | 8.910 | 1.00 | 70.95 | C |
| ATOM | 2989 | N   | GLY | A | 276 | −29.663 | 32.476 | 13.797 | 1.00 | 78.78 | N |
| ATOM | 2990 | CA  | GLY | A | 276 | −28.890 | 31.661 | 14.740 | 1.00 | 73.44 | C |
| ATOM | 2991 | C   | GLY | A | 276 | −29.740 | 30.605 | 15.422 | 1.00 | 73.61 | C |
| ATOM | 2992 | O   | GLY | A | 276 | −29.247 | 29.515 | 15.743 | 1.00 | 74.08 | O |
| ATOM | 2993 | N   | ILE | A | 277 | −31.017 | 30.921 | 15.645 | 1.00 | 73.26 | N |
| ATOM | 2994 | CA  | ILE | A | 277 | −31.955 | 29.987 | 16.286 | 1.00 | 76.95 | C |
| ATOM | 2995 | C   | ILE | A | 277 | −32.354 | 28.862 | 15.334 | 1.00 | 75.85 | C |
| ATOM | 2996 | O   | ILE | A | 277 | −32.540 | 27.720 | 15.768 | 1.00 | 77.29 | O |
| ATOM | 2997 | CB  | ILE | A | 277 | −33.202 | 30.721 | 16.866 | 1.00 | 74.67 | C |
| ATOM | 2998 | CG1 | ILE | A | 277 | −32.797 | 31.558 | 18.081 | 1.00 | 76.85 | C |
| ATOM | 2999 | CG2 | ILE | A | 277 | −34.275 | 29.747 | 17.287 | 1.00 | 72.00 | C |
| ATOM | 3000 | CD1 | ILE | A | 277 | −33.970 | 32.239 | 18.788 | 1.00 | 76.44 | C |
| ATOM | 3001 | N   | ILE | A | 278 | −32.481 | 29.188 | 14.048 | 1.00 | 79.83 | N |
| ATOM | 3002 | CA  | ILE | A | 278 | −32.787 | 28.208 | 13.010 | 1.00 | 77.27 | C |
| ATOM | 3003 | C   | ILE | A | 278 | −31.630 | 27.225 | 12.931 | 1.00 | 79.77 | C |
| ATOM | 3004 | O   | ILE | A | 278 | −31.833 | 26.004 | 12.877 | 1.00 | 80.80 | O |
| ATOM | 3005 | CB  | ILE | A | 278 | −33.004 | 28.892 | 11.637 | 1.00 | 77.96 | C |
| ATOM | 3006 | CG1 | ILE | A | 278 | −34.244 | 29.798 | 11.651 | 1.00 | 79.43 | C |
| ATOM | 3007 | CG2 | ILE | A | 278 | −33.174 | 27.888 | 10.557 | 1.00 | 78.57 | C |
| ATOM | 3008 | CD1 | ILE | A | 278 | −35.544 | 29.087 | 11.775 | 1.00 | 83.47 | C |
| ATOM | 3009 | N   | MET | A | 279 | −30.412 | 27.761 | 12.933 | 1.00 | 79.21 | N |
| ATOM | 3010 | CA  | MET | A | 279 | −29.206 | 26.942 | 12.826 | 1.00 | 77.35 | C |
| ATOM | 3011 | C   | MET | A | 279 | −29.019 | 26.044 | 14.018 | 1.00 | 75.85 | C |
| ATOM | 3012 | O   | MET | A | 279 | −28.798 | 24.844 | 13.852 | 1.00 | 73.53 | O |
| ATOM | 3013 | CB  | MET | A | 279 | −27.982 | 27.830 | 12.632 | 1.00 | 76.42 | C |
| ATOM | 3014 | CG  | MET | A | 279 | −27.992 | 28.535 | 11.284 | 1.00 | 79.03 | C |
| ATOM | 3015 | SD  | MET | A | 279 | −26.852 | 29.897 | 11.156 | 1.00 | 80.66 | S |
| ATOM | 3016 | CE  | MET | A | 279 | −27.061 | 30.304 | 9.407 | 1.00 | 79.86 | C |
| ATOM | 3017 | N   | GLY | A | 280 | −29.112 | 26.625 | 15.214 | 1.00 | 78.82 | N |
| ATOM | 3018 | CA  | GLY | A | 280 | −28.937 | 25.880 | 16.463 | 1.00 | 76.24 | C |
| ATOM | 3019 | C   | GLY | A | 280 | −29.970 | 24.785 | 16.660 | 1.00 | 79.31 | C |
| ATOM | 3020 | O   | GLY | A | 280 | −29.640 | 23.694 | 17.120 | 1.00 | 80.01 | O |
| ATOM | 3021 | N   | THR | A | 281 | −31.219 | 25.084 | 16.309 | 1.00 | 80.59 | N |
| ATOM | 3022 | CA  | THR | A | 281 | −32.309 | 24.123 | 16.408 | 1.00 | 78.83 | C |
| ATOM | 3023 | C   | THR | A | 281 | −32.057 | 22.935 | 15.492 | 1.00 | 77.28 | C |
| ATOM | 3024 | O   | THR | A | 281 | −32.190 | 21.801 | 15.923 | 1.00 | 76.07 | O |
| ATOM | 3025 | CB  | THR | A | 281 | −33.657 | 24.780 | 16.070 | 1.00 | 81.71 | C |
| ATOM | 3026 | OG1 | THR | A | 281 | −33.964 | 25.771 | 17.065 | 1.00 | 79.40 | O |
| ATOM | 3027 | CG2 | THR | A | 281 | −34.769 | 23.760 | 16.038 | 1.00 | 82.36 | C |
| ATOM | 3028 | N   | PHE | A | 282 | −31.694 | 23.205 | 14.237 | 1.00 | 79.67 | N |
| ATOM | 3029 | CA  | PHE | A | 282 | −31.347 | 22.147 | 13.279 | 1.00 | 77.00 | C |
| ATOM | 3030 | C   | PHE | A | 282 | −30.221 | 21.282 | 13.817 | 1.00 | 76.25 | C |
| ATOM | 3031 | O   | PHE | A | 282 | −30.266 | 20.069 | 13.697 | 1.00 | 73.80 | O |
| ATOM | 3032 | CB  | PHE | A | 282 | −30.917 | 22.731 | 11.930 | 1.00 | 77.95 | C |
| ATOM | 3033 | CG  | PHE | A | 282 | −30.691 | 21.679 | 10.853 | 1.00 | 76.73 | C |
| ATOM | 3034 | CD1 | PHE | A | 282 | −31.723 | 21.314 | 9.995 | 1.00 | 75.49 | C |
| ATOM | 3035 | CD2 | PHE | A | 282 | −29.460 | 21.064 | 10.706 | 1.00 | 76.37 | C |
| ATOM | 3036 | CE1 | PHE | A | 282 | −31.526 | 20.343 | 8.997 | 1.00 | 76.36 | C |
| ATOM | 3037 | CE2 | PHE | A | 282 | −29.254 | 20.097 | 9.720 | 1.00 | 84.43 | C |
| ATOM | 3038 | CZ  | PHE | A | 282 | −30.297 | 19.737 | 8.857 | 1.00 | 76.69 | C |
| ATOM | 3039 | N   | THR | A | 283 | −29.214 | 21.923 | 14.406 | 1.00 | 77.11 | N |
| ATOM | 3040 | CA  | THR | A | 283 | −28.058 | 21.218 | 14.945 | 1.00 | 76.40 | C |
| ATOM | 3041 | C   | THR | A | 283 | −28.460 | 20.311 | 16.078 | 1.00 | 76.62 | C |
| ATOM | 3042 | O   | THR | A | 283 | −28.105 | 19.152 | 16.073 | 1.00 | 76.69 | O |
| ATOM | 3043 | CB  | THR | A | 283 | −26.981 | 22.183 | 15.448 | 1.00 | 76.06 | C |
| ATOM | 3044 | OG1 | THR | A | 283 | −26.544 | 23.023 | 14.367 | 1.00 | 80.64 | O |
| ATOM | 3045 | CG2 | THR | A | 283 | −25.784 | 21.412 | 16.018 | 1.00 | 75.59 | C |
| ATOM | 3046 | N   | LEU | A | 284 | −29.203 | 20.844 | 17.041 | 1.00 | 78.59 | N |
| ATOM | 3047 | CA  | LEU | A | 284 | −29.636 | 20.065 | 18.204 | 1.00 | 77.27 | C |

APPENDIX 1-continued

| | | | | | | | | | | |
|---|---|---|---|---|---|---|---|---|---|---|
| ATOM | 3048 | C | LEU | A | 284 | −30.578 | 18.920 | 17.845 | 1.00 | 77.57 | C |
| ATOM | 3049 | O | LEU | A | 284 | −30.560 | 17.886 | 18.500 | 1.00 | 76.25 | O |
| ATOM | 3050 | CB | LEU | A | 284 | −30.300 | 20.986 | 19.236 | 1.00 | 80.83 | C |
| ATOM | 3051 | CG | LEU | A | 284 | −29.359 | 22.013 | 19.916 | 1.00 | 89.13 | C |
| ATOM | 3052 | CD1 | LEU | A | 284 | −30.162 | 23.029 | 20.724 | 1.00 | 93.20 | C |
| ATOM | 3053 | CD2 | LEU | A | 284 | −28.290 | 21.337 | 20.801 | 1.00 | 91.45 | C |
| ATOM | 3054 | N | CYS | A | 285 | −31.395 | 19.108 | 16.806 | 1.00 | 77.86 | N |
| ATOM | 3055 | CA | CYS | A | 285 | −32.341 | 18.073 | 16.367 | 1.00 | 76.99 | C |
| ATOM | 3056 | C | CYS | A | 285 | −31.677 | 16.920 | 15.620 | 1.00 | 75.92 | C |
| ATOM | 3057 | O | CYS | A | 285 | −32.095 | 15.782 | 15.783 | 1.00 | 75.32 | O |
| ATOM | 3058 | CB | CYS | A | 285 | −33.462 | 18.678 | 15.513 | 1.00 | 76.74 | C |
| ATOM | 3059 | SG | CYS | A | 285 | −34.727 | 19.541 | 16.511 | 1.00 | 86.35 | S |
| ATOM | 3060 | N | TRP | A | 286 | −30.657 | 17.219 | 14.810 | 1.00 | 76.29 | N |
| ATOM | 3061 | CA | TRP | A | 286 | −29.938 | 16.192 | 14.020 | 1.00 | 75.01 | C |
| ATOM | 3062 | C | TRP | A | 286 | −28.635 | 15.671 | 14.635 | 1.00 | 75.15 | C |
| ATOM | 3063 | O | TRP | A | 286 | −28.250 | 14.544 | 14.330 | 1.00 | 75.31 | O |
| ATOM | 3064 | CB | TRP | A | 286 | −29.641 | 16.703 | 12.599 | 1.00 | 72.75 | C |
| ATOM | 3065 | CG | TRP | A | 286 | −30.853 | 16.738 | 11.766 | 1.00 | 70.37 | C |
| ATOM | 3066 | CD1 | TRP | A | 286 | −31.543 | 17.832 | 11.381 | 1.00 | 69.67 | C |
| ATOM | 3067 | CD2 | TRP | A | 286 | −31.533 | 15.613 | 11.212 | 1.00 | 67.81 | C |
| ATOM | 3068 | NE1 | TRP | A | 286 | −32.621 | 17.469 | 10.614 | 1.00 | 76.08 | N |
| ATOM | 3069 | CE2 | TRP | A | 286 | −32.636 | 16.107 | 10.496 | 1.00 | 67.36 | C |
| ATOM | 3070 | CE3 | TRP | A | 286 | −31.314 | 14.228 | 11.254 | 1.00 | 69.38 | C |
| ATOM | 3071 | CZ2 | TRP | A | 286 | −33.523 | 15.274 | 9.822 | 1.00 | 73.52 | C |
| ATOM | 3072 | CZ3 | TRP | A | 286 | −32.202 | 13.391 | 10.581 | 1.00 | 71.27 | C |
| ATOM | 3073 | CH2 | TRP | A | 286 | −33.291 | 13.920 | 9.875 | 1.00 | 72.45 | C |
| ATOM | 3074 | N | LEU | A | 287 | −27.958 | 16.454 | 15.474 | 1.00 | 71.19 | N |
| ATOM | 3075 | CA | LEU | A | 287 | −26.645 | 16.020 | 16.001 | 1.00 | 72.17 | C |
| ATOM | 3076 | C | LEU | A | 287 | −26.669 | 14.651 | 16.667 | 1.00 | 70.61 | C |
| ATOM | 3077 | O | LEU | A | 287 | −25.822 | 13.834 | 16.347 | 1.00 | 73.46 | O |
| ATOM | 3078 | CB | LEU | A | 287 | −26.019 | 17.049 | 16.953 | 1.00 | 74.35 | C |
| ATOM | 3079 | CG | LEU | A | 287 | −24.542 | 16.884 | 17.277 | 1.00 | 76.88 | C |
| ATOM | 3080 | CD1 | LEU | A | 287 | −23.682 | 16.964 | 16.013 | 1.00 | 78.66 | C |
| ATOM | 3081 | CD2 | LEU | A | 287 | −24.130 | 17.956 | 18.279 | 1.00 | 79.06 | C |
| ATOM | 3082 | N | PRO | A | 288 | −27.627 | 14.395 | 17.583 | 1.00 | 69.58 | N |
| ATOM | 3083 | CA | PRO | A | 288 | −27.682 | 13.074 | 18.227 | 1.00 | 68.99 | C |
| ATOM | 3084 | C | PRO | A | 288 | −27.767 | 11.903 | 17.248 | 1.00 | 68.90 | C |
| ATOM | 3085 | O | PRO | A | 288 | −27.052 | 10.906 | 17.406 | 1.00 | 67.39 | O |
| ATOM | 3086 | CB | PRO | A | 288 | −28.979 | 13.140 | 19.057 | 1.00 | 68.33 | C |
| ATOM | 3087 | CG | PRO | A | 288 | −29.207 | 14.546 | 19.305 | 1.00 | 66.28 | C |
| ATOM | 3088 | CD | PRO | A | 288 | −28.701 | 15.269 | 18.091 | 1.00 | 70.69 | C |
| ATOM | 3089 | N | PHE | A | 289 | −28.641 | 12.042 | 16.255 | 1.00 | 67.58 | N |
| ATOM | 3090 | CA | PHE | A | 289 | −28.807 | 11.038 | 15.217 | 1.00 | 67.91 | C |
| ATOM | 3091 | C | PHE | A | 289 | −27.479 | 10.746 | 14.519 | 1.00 | 69.22 | C |
| ATOM | 3092 | O | PHE | A | 289 | −27.072 | 9.576 | 14.412 | 1.00 | 68.30 | O |
| ATOM | 3093 | CB | PHE | A | 289 | −29.853 | 11.505 | 14.189 | 1.00 | 69.82 | C |
| ATOM | 3094 | CG | PHE | A | 289 | −30.014 | 10.578 | 13.047 | 1.00 | 67.38 | C |
| ATOM | 3095 | CD1 | PHE | A | 289 | −30.850 | 9.475 | 13.157 | 1.00 | 64.32 | C |
| ATOM | 3096 | CD2 | PHE | A | 289 | −29.335 | 10.795 | 11.859 | 1.00 | 71.12 | C |
| ATOM | 3097 | CE1 | PHE | A | 289 | −31.008 | 8.610 | 12.114 | 1.00 | 70.14 | C |
| ATOM | 3098 | CE2 | PHE | A | 289 | −29.489 | 9.926 | 10.798 | 1.00 | 76.34 | C |
| ATOM | 3099 | CZ | PHE | A | 289 | −30.327 | 8.829 | 10.923 | 1.00 | 75.79 | C |
| ATOM | 3100 | N | PHE | A | 290 | −26.818 | 11.811 | 14.052 | 1.00 | 69.03 | N |
| ATOM | 3101 | CA | PHE | A | 290 | −25.522 | 11.686 | 13.347 | 1.00 | 70.29 | C |
| ATOM | 3102 | C | PHE | A | 290 | −24.346 | 11.254 | 14.222 | 1.00 | 70.41 | C |
| ATOM | 3103 | O | PHE | A | 290 | −23.386 | 10.677 | 13.697 | 1.00 | 72.74 | O |
| ATOM | 3104 | CB | PHE | A | 290 | −25.180 | 12.971 | 12.585 | 1.00 | 73.06 | C |
| ATOM | 3105 | CG | PHE | A | 290 | −25.942 | 13.108 | 11.295 | 1.00 | 73.80 | C |
| ATOM | 3106 | CD1 | PHE | A | 290 | −27.103 | 13.864 | 11.226 | 1.00 | 70.64 | C |
| ATOM | 3107 | CD2 | PHE | A | 290 | −25.494 | 12.467 | 10.149 | 1.00 | 76.58 | C |
| ATOM | 3108 | CE1 | PHE | A | 290 | −27.800 | 13.990 | 10.058 | 1.00 | 79.74 | C |
| ATOM | 3109 | CE2 | PHE | A | 290 | −26.191 | 12.586 | 8.960 | 1.00 | 75.30 | C |
| ATOM | 3110 | CZ | PHE | A | 290 | −27.349 | 13.352 | 8.914 | 1.00 | 77.36 | C |
| ATOM | 3111 | N | ILE | A | 291 | −24.404 | 11.522 | 15.528 | 1.00 | 69.93 | N |
| ATOM | 3112 | CA | ILE | A | 291 | −23.391 | 11.003 | 16.454 | 1.00 | 71.11 | C |
| ATOM | 3113 | C | ILE | A | 291 | −23.517 | 9.476 | 16.516 | 1.00 | 72.55 | C |
| ATOM | 3114 | O | ILE | A | 291 | −22.507 | 8.765 | 16.534 | 1.00 | 76.20 | O |
| ATOM | 3115 | CB | ILE | A | 291 | −23.511 | 11.621 | 17.873 | 1.00 | 71.52 | C |
| ATOM | 3116 | CG1 | ILE | A | 291 | −23.073 | 13.081 | 17.853 | 1.00 | 73.15 | C |
| ATOM | 3117 | CG2 | ILE | A | 291 | −22.642 | 10.888 | 18.894 | 1.00 | 65.02 | C |
| ATOM | 3118 | CD1 | ILE | A | 291 | −23.309 | 13.807 | 19.140 | 1.00 | 72.16 | C |
| ATOM | 3119 | N | VAL | A | 292 | −24.757 | 8.984 | 16.545 | 1.00 | 74.02 | N |
| ATOM | 3120 | CA | VAL | A | 292 | −25.023 | 7.539 | 16.619 | 1.00 | 74.95 | C |
| ATOM | 3121 | C | VAL | A | 292 | −24.586 | 6.782 | 15.340 | 1.00 | 73.29 | C |
| ATOM | 3122 | O | VAL | A | 292 | −24.192 | 5.619 | 15.426 | 1.00 | 74.16 | O |
| ATOM | 3123 | CB | VAL | A | 292 | −26.505 | 7.253 | 16.998 | 1.00 | 74.89 | C |
| ATOM | 3124 | CG1 | VAL | A | 292 | −26.814 | 5.775 | 16.915 | 1.00 | 73.02 | C |
| ATOM | 3125 | CG2 | VAL | A | 292 | −26.781 | 7.774 | 18.427 | 1.00 | 73.75 | C |
| ATOM | 3126 | N | ASN | A | 293 | −24.651 | 7.431 | 14.176 | 1.00 | 73.79 | N |
| ATOM | 3127 | CA | ASN | A | 293 | −24.112 | 6.835 | 12.936 | 1.00 | 72.79 | C |

APPENDIX 1-continued

| | | | | | | | | | | |
|---|---|---|---|---|---|---|---|---|---|---|
| ATOM | 3128 | C | ASN | A | 293 | −22.641 | 6.495 | 13.085 | 1.00 | 71.66 | C |
| ATOM | 3129 | O | ASN | A | 293 | −22.206 | 5.409 | 12.709 | 1.00 | 72.11 | O |
| ATOM | 3130 | CB | ASN | A | 293 | −24.250 | 7.782 | 11.745 | 1.00 | 72.08 | C |
| ATOM | 3131 | CG | ASN | A | 293 | −25.673 | 7.961 | 11.287 | 1.00 | 76.70 | C |
| ATOM | 3132 | OD1 | ASN | A | 293 | −26.584 | 7.306 | 11.777 | 1.00 | 77.56 | O |
| ATOM | 3133 | ND2 | ASN | A | 293 | −25.871 | 8.863 | 10.327 | 1.00 | 72.62 | N |
| ATOM | 3134 | N | ILE | A | 294 | −21.887 | 7.435 | 13.639 | 1.00 | 70.24 | N |
| ATOM | 3135 | CA | ILE | A | 294 | −20.451 | 7.272 | 13.833 | 1.00 | 71.74 | C |
| ATOM | 3136 | C | ILE | A | 294 | −20.156 | 6.296 | 14.963 | 1.00 | 71.03 | C |
| ATOM | 3137 | O | ILE | A | 294 | −19.288 | 5.437 | 14.807 | 1.00 | 69.26 | O |
| ATOM | 3138 | CB | ILE | A | 294 | −19.784 | 8.608 | 14.115 | 1.00 | 71.93 | C |
| ATOM | 3139 | CG1 | ILE | A | 294 | −19.878 | 9.502 | 12.885 | 1.00 | 71.27 | C |
| ATOM | 3140 | CG2 | ILE | A | 294 | −18.313 | 8.421 | 14.498 | 1.00 | 72.08 | C |
| ATOM | 3141 | CD1 | ILE | A | 294 | −19.391 | 10.862 | 13.168 | 1.00 | 79.13 | C |
| ATOM | 3142 | N | VAL | A | 295 | −20.872 | 6.426 | 16.088 | 1.00 | 71.55 | N |
| ATOM | 3143 | CA | VAL | A | 295 | −20.735 | 5.484 | 17.234 | 1.00 | 70.36 | C |
| ATOM | 3144 | C | VAL | A | 295 | −20.932 | 4.029 | 16.782 | 1.00 | 69.42 | C |
| ATOM | 3145 | O | VAL | A | 295 | −20.224 | 3.142 | 17.243 | 1.00 | 66.44 | O |
| ATOM | 3146 | CB | VAL | A | 295 | −21.720 | 5.835 | 18.396 | 1.00 | 70.22 | C |
| ATOM | 3147 | CG1 | VAL | A | 295 | −21.803 | 4.721 | 19.419 | 1.00 | 68.33 | C |
| ATOM | 3148 | CG2 | VAL | A | 295 | −21.304 | 7.125 | 19.065 | 1.00 | 71.01 | C |
| ATOM | 3149 | N | HIS | A | 296 | −21.890 | 3.805 | 15.878 | 1.00 | 69.19 | N |
| ATOM | 3150 | CA | HIS | A | 296 | −22.128 | 2.462 | 15.311 | 1.00 | 71.67 | C |
| ATOM | 3151 | C | HIS | A | 296 | −21.079 | 1.977 | 14.297 | 1.00 | 72.30 | C |
| ATOM | 3152 | O | HIS | A | 296 | −21.022 | 0.785 | 13.996 | 1.00 | 72.47 | O |
| ATOM | 3153 | CB | HIS | A | 296 | −23.545 | 2.349 | 14.737 | 1.00 | 72.70 | C |
| ATOM | 3154 | CG | HIS | A | 296 | −24.591 | 2.269 | 15.795 | 1.00 | 77.53 | C |
| ATOM | 3155 | ND1 | HIS | A | 296 | −24.369 | 1.632 | 16.991 | 1.00 | 78.84 | N |
| ATOM | 3156 | CD2 | HIS | A | 296 | −25.859 | 2.736 | 15.848 | 1.00 | 85.05 | C |
| ATOM | 3157 | CE1 | HIS | A | 296 | −25.448 | 1.710 | 17.733 | 1.00 | 78.27 | C |
| ATOM | 3158 | NE2 | HIS | A | 296 | −26.370 | 2.373 | 17.069 | 1.00 | 81.35 | N |
| ATOM | 3159 | N | VAL | A | 297 | −20.267 | 2.893 | 13.781 | 1.00 | 73.43 | N |
| ATOM | 3160 | CA | VAL | A | 297 | −19.118 | 2.535 | 12.948 | 1.00 | 73.61 | C |
| ATOM | 3161 | C | VAL | A | 297 | −17.993 | 2.051 | 13.878 | 1.00 | 72.62 | C |
| ATOM | 3162 | O | VAL | A | 297 | −17.220 | 1.165 | 13.505 | 1.00 | 73.05 | O |
| ATOM | 3163 | CB | VAL | A | 297 | −18.653 | 3.713 | 12.050 | 1.00 | 73.85 | C |
| ATOM | 3164 | CG1 | VAL | A | 297 | −17.424 | 3.338 | 11.238 | 1.00 | 72.56 | C |
| ATOM | 3165 | CG2 | VAL | A | 297 | −19.786 | 4.139 | 11.127 | 1.00 | 72.80 | C |
| ATOM | 3166 | N | ILE | A | 298 | −17.912 | 2.636 | 15.082 | 1.00 | 72.35 | N |
| ATOM | 3167 | CA | ILE | A | 298 | −16.930 | 2.236 | 16.097 | 1.00 | 73.03 | C |
| ATOM | 3168 | C | ILE | A | 298 | −17.351 | 0.886 | 16.688 | 1.00 | 73.53 | C |
| ATOM | 3169 | O | ILE | A | 298 | −16.612 | −0.099 | 16.597 | 1.00 | 74.08 | O |
| ATOM | 3170 | CB | ILE | A | 298 | −16.780 | 3.288 | 17.246 | 1.00 | 73.65 | C |
| ATOM | 3171 | CG1 | ILE | A | 298 | −16.402 | 4.687 | 16.716 | 1.00 | 76.60 | C |
| ATOM | 3172 | CG2 | ILE | A | 298 | −15.757 | 2.827 | 18.255 | 1.00 | 73.25 | C |
| ATOM | 3173 | CD1 | ILE | A | 298 | −15.059 | 4.764 | 16.007 | 1.00 | 80.21 | C |
| ATOM | 3174 | N | GLN | A | 299 | −18.542 | 0.864 | 17.290 | 1.00 | 73.48 | N |
| ATOM | 3175 | CA | GLN | A | 299 | −19.132 | −0.345 | 17.862 | 1.00 | 74.55 | C |
| ATOM | 3176 | C | GLN | A | 299 | −20.619 | −0.354 | 17.524 | 1.00 | 75.17 | C |
| ATOM | 3177 | O | GLN | A | 299 | −21.368 | 0.466 | 18.040 | 1.00 | 77.55 | O |
| ATOM | 3178 | CB | GLN | A | 299 | −18.917 | −0.401 | 19.378 | 1.00 | 75.38 | C |
| ATOM | 3179 | CG | GLN | A | 299 | −19.532 | −1.630 | 20.086 | 1.00 | 76.95 | C |
| ATOM | 3180 | CD | GLN | A | 299 | −18.993 | −2.963 | 19.563 | 1.00 | 80.36 | C |
| ATOM | 3181 | OE1 | GLN | A | 299 | −17.801 | −3.255 | 19.675 | 1.00 | 81.59 | O |
| ATOM | 3182 | NE2 | GLN | A | 299 | −19.883 | −3.778 | 18.992 | 1.00 | 79.18 | N |
| ATOM | 3183 | N | ASP | A | 300 | −21.035 | −1.282 | 16.662 | 1.00 | 75.16 | N |
| ATOM | 3184 | CA | ASP | A | 300 | −22.420 | −1.357 | 16.206 | 1.00 | 76.26 | C |
| ATOM | 3185 | C | ASP | A | 300 | −23.306 | −1.994 | 17.284 | 1.00 | 76.70 | C |
| ATOM | 3186 | O | ASP | A | 300 | −22.818 | −2.756 | 18.121 | 1.00 | 75.98 | O |
| ATOM | 3187 | CB | ASP | A | 300 | −22.492 | −2.145 | 14.883 | 1.00 | 76.84 | C |
| ATOM | 3188 | CG | ASP | A | 300 | −23.781 | −1.873 | 14.069 | 1.00 | 78.37 | C |
| ATOM | 3189 | OD1 | ASP | A | 300 | −24.504 | −0.874 | 14.303 | 1.00 | 80.03 | O |
| ATOM | 3190 | OD2 | ASP | A | 300 | −24.068 | −2.688 | 13.168 | 1.00 | 83.02 | O |
| ATOM | 3191 | N | ASN | A | 301 | −24.601 | −1.661 | 17.248 | 1.00 | 76.86 | N |
| ATOM | 3192 | CA | ASN | A | 301 | −25.633 | −2.196 | 18.177 | 1.00 | 76.17 | C |
| ATOM | 3193 | C | ASN | A | 301 | −25.536 | −1.740 | 19.656 | 1.00 | 75.65 | C |
| ATOM | 3194 | O | ASN | A | 301 | −26.220 | −2.290 | 20.520 | 1.00 | 76.59 | O |
| ATOM | 3195 | CB | ASN | A | 301 | −25.700 | −3.741 | 18.089 | 1.00 | 75.63 | C |
| ATOM | 3196 | CG | ASN | A | 301 | −26.022 | −4.235 | 16.690 | 1.00 | 74.71 | C |
| ATOM | 3197 | OD1 | ASN | A | 301 | −26.917 | −3.714 | 16.030 | 1.00 | 64.90 | O |
| ATOM | 3198 | ND2 | ASN | A | 301 | −25.291 | −5.246 | 16.233 | 1.00 | 75.78 | N |
| ATOM | 3199 | N | LEU | A | 302 | −24.700 | −0.743 | 19.938 | 1.00 | 76.35 | N |
| ATOM | 3200 | CA | LEU | A | 302 | −24.547 | −0.197 | 21.298 | 1.00 | 78.80 | C |
| ATOM | 3201 | C | LEU | A | 302 | −25.815 | 0.534 | 21.817 | 1.00 | 79.26 | C |
| ATOM | 3202 | O | LEU | A | 302 | −26.074 | 0.566 | 23.018 | 1.00 | 80.59 | O |
| ATOM | 3203 | CB | LEU | A | 302 | −23.350 | 0.764 | 21.335 | 1.00 | 79.16 | C |
| ATOM | 3204 | CG | LEU | A | 302 | −22.832 | 1.213 | 22.703 | 1.00 | 79.37 | C |
| ATOM | 3205 | CD1 | LEU | A | 302 | −22.199 | 0.039 | 23.438 | 1.00 | 77.36 | C |
| ATOM | 3206 | CD2 | LEU | A | 302 | −21.839 | 2.351 | 22.545 | 1.00 | 79.97 | C |
| ATOM | 3207 | N | ILE | A | 303 | −26.572 | 1.105 | 20.888 | 1.00 | 79.64 | N |

APPENDIX 1-continued

| ATOM | 3208 | CA | ILE | A | 303 | −27.765 | 1.886 | 21.120 | 1.00 | 80.47 | C |
| ATOM | 3209 | C | ILE | A | 303 | −28.881 | 1.166 | 20.393 | 1.00 | 80.12 | C |
| ATOM | 3210 | O | ILE | A | 303 | −28.747 | 0.854 | 19.208 | 1.00 | 80.56 | O |
| ATOM | 3211 | CB | ILE | A | 303 | −27.623 | 3.313 | 20.573 | 1.00 | 79.71 | C |
| ATOM | 3212 | CG1 | ILE | A | 303 | −26.513 | 4.056 | 21.326 | 1.00 | 80.55 | C |
| ATOM | 3213 | CG2 | ILE | A | 303 | −28.930 | 4.068 | 20.708 | 1.00 | 78.77 | C |
| ATOM | 3214 | CD1 | ILE | A | 303 | −26.243 | 5.427 | 20.826 | 1.00 | 83.25 | C |
| ATOM | 3215 | N | ARG | A | 304 | −29.973 | 0.910 | 21.111 | 1.00 | 81.10 | N |
| ATOM | 3216 | CA | ARG | A | 304 | −31.132 | 0.177 | 20.596 | 1.00 | 83.66 | C |
| ATOM | 3217 | C | ARG | A | 304 | −31.686 | 0.776 | 19.310 | 1.00 | 82.48 | C |
| ATOM | 3218 | O | ARG | A | 304 | −31.542 | 1.977 | 19.070 | 1.00 | 83.57 | O |
| ATOM | 3219 | CB | ARG | A | 304 | −32.265 | 0.192 | 21.608 | 1.00 | 84.33 | C |
| ATOM | 3220 | CG | ARG | A | 304 | −31.969 | −0.426 | 22.966 | 1.00 | 91.17 | C |
| ATOM | 3221 | CD | ARG | A | 304 | −33.142 | −0.227 | 23.870 | 1.00 | 96.90 | C |
| ATOM | 3222 | NE | ARG | A | 304 | −34.321 | −0.914 | 23.347 | 1.00 | 107.82 | N |
| ATOM | 3223 | CZ | ARG | A | 304 | −35.556 | −0.820 | 23.845 | 1.00 | 114.88 | C |
| ATOM | 3224 | NH1 | ARG | A | 304 | −35.826 | −0.056 | 24.909 | 1.00 | 119.98 | N |
| ATOM | 3225 | NH2 | ARG | A | 304 | −36.539 | −1.505 | 23.268 | 1.00 | 117.19 | N |
| ATOM | 3226 | N | LYS | A | 305 | −32.317 | −0.069 | 18.496 | 1.00 | 80.96 | N |
| ATOM | 3227 | CA | LYS | A | 305 | −32.950 | 0.369 | 17.249 | 1.00 | 82.83 | C |
| ATOM | 3228 | C | LYS | A | 305 | −34.024 | 1.432 | 17.501 | 1.00 | 82.19 | C |
| ATOM | 3229 | O | LYS | A | 305 | −34.122 | 2.399 | 16.751 | 1.00 | 83.88 | O |
| ATOM | 3230 | CB | LYS | A | 305 | −33.573 | −0.819 | 16.514 | 1.00 | 82.92 | C |
| ATOM | 3231 | CG | LYS | A | 305 | −34.091 | −0.499 | 15.109 | 1.00 | 86.35 | C |
| ATOM | 3232 | CD | LYS | A | 305 | −34.754 | −1.709 | 14.472 | 1.00 | 87.13 | C |
| ATOM | 3233 | CE | LYS | A | 305 | −35.417 | −1.329 | 13.154 | 1.00 | 88.05 | C |
| ATOM | 3234 | NZ | LYS | A | 305 | −36.147 | −2.481 | 12.552 | 1.00 | 91.16 | N |
| ATOM | 3235 | N | GLU | A | 306 | −34.813 | 1.237 | 18.553 | 1.00 | 79.77 | N |
| ATOM | 3236 | CA | GLU | A | 306 | −35.888 | 2.166 | 18.928 | 1.00 | 78.91 | C |
| ATOM | 3237 | C | GLU | A | 306 | −35.388 | 3.534 | 19.354 | 1.00 | 75.42 | C |
| ATOM | 3238 | O | GLU | A | 306 | −36.083 | 4.526 | 19.156 | 1.00 | 73.51 | O |
| ATOM | 3239 | CB | GLU | A | 306 | −36.707 | 1.586 | 20.062 | 1.00 | 80.27 | C |
| ATOM | 3240 | CG | GLU | A | 306 | −37.464 | 0.323 | 19.682 | 1.00 | 88.15 | C |
| ATOM | 3241 | CD | GLU | A | 306 | −38.035 | −0.379 | 20.876 | 1.00 | 92.42 | C |
| ATOM | 3242 | OE1 | GLU | A | 306 | −38.087 | 0.245 | 21.964 | 1.00 | 103.55 | O |
| ATOM | 3243 | OE2 | GLU | A | 306 | −38.436 | −1.560 | 20.740 | 1.00 | 104.10 | O |
| ATOM | 3244 | N | VAL | A | 307 | −34.191 | 3.586 | 19.938 | 1.00 | 74.31 | N |
| ATOM | 3245 | CA | VAL | A | 307 | −33.579 | 4.864 | 20.314 | 1.00 | 73.09 | C |
| ATOM | 3246 | C | VAL | A | 307 | −33.126 | 5.563 | 19.040 | 1.00 | 72.26 | C |
| ATOM | 3247 | O | VAL | A | 307 | −33.415 | 6.740 | 18.854 | 1.00 | 74.87 | O |
| ATOM | 3248 | CB | VAL | A | 307 | −32.398 | 4.703 | 21.330 | 1.00 | 71.64 | C |
| ATOM | 3249 | CG1 | VAL | A | 307 | −31.597 | 5.986 | 21.441 | 1.00 | 63.03 | C |
| ATOM | 3250 | CG2 | VAL | A | 307 | −32.925 | 4.287 | 22.703 | 1.00 | 68.24 | C |
| ATOM | 3251 | N | TYR | A | 308 | −32.423 | 4.833 | 18.177 | 1.00 | 71.72 | N |
| ATOM | 3252 | CA | TYR | A | 308 | −31.955 | 5.366 | 16.892 | 1.00 | 72.58 | C |
| ATOM | 3253 | C | TYR | A | 308 | −33.106 | 5.892 | 16.025 | 1.00 | 72.20 | C |
| ATOM | 3254 | O | TYR | A | 308 | −32.981 | 6.951 | 15.414 | 1.00 | 72.72 | O |
| ATOM | 3255 | CB | TYR | A | 308 | −31.184 | 4.294 | 16.135 | 1.00 | 75.16 | C |
| ATOM | 3256 | CG | TYR | A | 308 | −30.534 | 4.770 | 14.855 | 1.00 | 75.61 | C |
| ATOM | 3257 | CD1 | TYR | A | 308 | −30.984 | 4.338 | 13.610 | 1.00 | 83.25 | C |
| ATOM | 3258 | CD2 | TYR | A | 308 | −29.470 | 5.650 | 14.894 | 1.00 | 77.87 | C |
| ATOM | 3259 | CE1 | TYR | A | 308 | −30.378 | 4.780 | 12.435 | 1.00 | 82.87 | C |
| ATOM | 3260 | CE2 | TYR | A | 308 | −28.859 | 6.098 | 13.747 | 1.00 | 74.78 | C |
| ATOM | 3261 | CZ | TYR | A | 308 | −29.313 | 5.663 | 12.513 | 1.00 | 80.83 | C |
| ATOM | 3262 | OH | TYR | A | 308 | −28.716 | 6.100 | 11.357 | 1.00 | 79.13 | O |
| ATOM | 3263 | N | ILE | A | 309 | −34.214 | 5.152 | 15.979 | 1.00 | 70.18 | N |
| ATOM | 3264 | CA | ILE | A | 309 | −35.412 | 5.593 | 15.251 | 1.00 | 71.74 | C |
| ATOM | 3265 | C | ILE | A | 309 | −35.959 | 6.873 | 15.863 | 1.00 | 72.46 | C |
| ATOM | 3266 | O | ILE | A | 309 | −36.272 | 7.798 | 15.139 | 1.00 | 73.87 | O |
| ATOM | 3267 | CB | ILE | A | 309 | −36.519 | 4.520 | 15.243 | 1.00 | 70.27 | C |
| ATOM | 3268 | CG1 | ILE | A | 309 | −36.141 | 3.375 | 14.316 | 1.00 | 69.96 | C |
| ATOM | 3269 | CG2 | ILE | A | 309 | −37.839 | 5.100 | 14.781 | 1.00 | 68.79 | C |
| ATOM | 3270 | CD1 | ILE | A | 309 | −36.987 | 2.145 | 14.516 | 1.00 | 72.32 | C |
| ATOM | 3271 | N | LEU | A | 310 | −36.067 | 6.917 | 17.195 | 1.00 | 74.30 | N |
| ATOM | 3272 | CA | LEU | A | 310 | −36.561 | 8.109 | 17.895 | 1.00 | 73.71 | C |
| ATOM | 3273 | C | LEU | A | 310 | −35.682 | 9.324 | 17.619 | 1.00 | 75.46 | C |
| ATOM | 3274 | O | LEU | A | 310 | −36.208 | 10.416 | 17.414 | 1.00 | 76.09 | O |
| ATOM | 3275 | CB | LEU | A | 310 | −36.677 | 7.873 | 19.405 | 1.00 | 76.16 | C |
| ATOM | 3276 | CG | LEU | A | 310 | −37.103 | 9.087 | 20.269 | 1.00 | 79.17 | C |
| ATOM | 3277 | CD1 | LEU | A | 310 | −38.353 | 9.787 | 19.699 | 1.00 | 80.03 | C |
| ATOM | 3278 | CD2 | LEU | A | 310 | −37.344 | 8.666 | 21.710 | 1.00 | 74.92 | C |
| ATOM | 3279 | N | LEU | A | 311 | −34.358 | 9.142 | 17.612 | 1.00 | 74.63 | N |
| ATOM | 3280 | CA | LEU | A | 311 | −33.436 | 10.249 | 17.271 | 1.00 | 73.90 | C |
| ATOM | 3281 | C | LEU | A | 311 | −33.611 | 10.744 | 15.829 | 1.00 | 73.58 | C |
| ATOM | 3282 | O | LEU | A | 311 | −33.346 | 11.904 | 15.546 | 1.00 | 75.24 | O |
| ATOM | 3283 | CB | LEU | A | 311 | −31.976 | 9.857 | 17.497 | 1.00 | 71.95 | C |
| ATOM | 3284 | CG | LEU | A | 311 | −31.583 | 9.468 | 18.926 | 1.00 | 74.42 | C |
| ATOM | 3285 | CD1 | LEU | A | 311 | −30.094 | 9.202 | 18.969 | 1.00 | 78.05 | C |
| ATOM | 3286 | CD2 | LEU | A | 311 | −31.960 | 10.525 | 19.951 | 1.00 | 79.68 | C |
| ATOM | 3287 | N | ASN | A | 312 | −34.053 | 9.862 | 14.932 | 1.00 | 73.28 | N |

APPENDIX 1-continued

| | | | | | | | | | | |
|---|---|---|---|---|---|---|---|---|---|---|
| ATOM | 3288 | CA | ASN | A | 312 | −34.337 | 10.228 | 13.551 | 1.00 | 74.59 | C |
| ATOM | 3289 | C | ASN | A | 312 | −35.602 | 11.076 | 13.491 | 1.00 | 74.96 | C |
| ATOM | 3290 | O | ASN | A | 312 | −35.654 | 12.057 | 12.741 | 1.00 | 76.71 | O |
| ATOM | 3291 | CB | ASN | A | 312 | −34.490 | 8.970 | 12.679 | 1.00 | 73.89 | C |
| ATOM | 3292 | CG | ASN | A | 312 | −34.276 | 9.231 | 11.170 | 1.00 | 75.40 | C |
| ATOM | 3293 | OD1 | ASN | A | 312 | −33.933 | 8.302 | 10.439 | 1.00 | 75.69 | O |
| ATOM | 3294 | ND2 | ASN | A | 312 | −34.471 | 10.471 | 10.709 | 1.00 | 73.01 | N |
| ATOM | 3295 | N | TRP | A | 313 | −36.614 | 10.702 | 14.275 | 1.00 | 75.65 | N |
| ATOM | 3296 | CA | TRP | A | 313 | −37.880 | 11.461 | 14.327 | 1.00 | 73.90 | C |
| ATOM | 3297 | C | TRP | A | 313 | −37.748 | 12.844 | 14.967 | 1.00 | 74.02 | C |
| ATOM | 3298 | O | TRP | A | 313 | −38.556 | 13.726 | 14.676 | 1.00 | 74.92 | O |
| ATOM | 3299 | CB | TRP | A | 313 | −38.988 | 10.634 | 14.986 | 1.00 | 75.64 | C |
| ATOM | 3300 | CG | TRP | A | 313 | −39.562 | 9.768 | 13.984 | 1.00 | 77.34 | C |
| ATOM | 3301 | CD1 | TRP | A | 313 | −39.070 | 8.583 | 13.548 | 1.00 | 77.95 | C |
| ATOM | 3302 | CD2 | TRP | A | 313 | −40.757 | 10.004 | 13.254 | 1.00 | 77.66 | C |
| ATOM | 3303 | NE1 | TRP | A | 313 | −39.885 | 8.056 | 12.589 | 1.00 | 77.47 | N |
| ATOM | 3304 | CE2 | TRP | A | 313 | −40.935 | 8.910 | 12.384 | 1.00 | 79.44 | C |
| ATOM | 3305 | CE3 | TRP | A | 313 | −41.701 | 11.037 | 13.247 | 1.00 | 76.72 | C |
| ATOM | 3306 | CZ2 | TRP | A | 313 | −42.025 | 8.813 | 11.509 | 1.00 | 79.40 | C |
| ATOM | 3307 | CZ3 | TRP | A | 313 | −42.790 | 10.944 | 12.374 | 1.00 | 78.33 | C |
| ATOM | 3308 | CH2 | TRP | A | 313 | −42.940 | 9.835 | 11.518 | 1.00 | 77.48 | C |
| ATOM | 3309 | N | ILE | A | 314 | −36.742 | 13.024 | 15.822 | 1.00 | 71.91 | N |
| ATOM | 3310 | CA | ILE | A | 314 | −36.411 | 14.336 | 16.368 | 1.00 | 71.31 | C |
| ATOM | 3311 | C | ILE | A | 314 | −35.847 | 15.185 | 15.213 | 1.00 | 71.78 | C |
| ATOM | 3312 | O | ILE | A | 314 | −36.108 | 16.396 | 15.114 | 1.00 | 72.42 | O |
| ATOM | 3313 | CB | ILE | A | 314 | −35.406 | 14.239 | 17.546 | 1.00 | 69.93 | C |
| ATOM | 3314 | CG1 | ILE | A | 314 | −36.040 | 13.519 | 18.735 | 1.00 | 69.22 | C |
| ATOM | 3315 | CG2 | ILE | A | 314 | −34.975 | 15.611 | 18.002 | 1.00 | 66.77 | C |
| ATOM | 3316 | CD1 | ILE | A | 314 | −35.054 | 13.195 | 19.841 | 1.00 | 70.69 | C |
| ATOM | 3317 | N | GLY | A | 315 | −35.072 | 14.536 | 14.350 | 1.00 | 71.45 | N |
| ATOM | 3318 | CA | GLY | A | 315 | −34.603 | 15.150 | 13.118 | 1.00 | 73.83 | C |
| ATOM | 3319 | C | GLY | A | 315 | −35.780 | 15.520 | 12.237 | 1.00 | 73.35 | C |
| ATOM | 3320 | O | GLY | A | 315 | −35.913 | 16.673 | 11.866 | 1.00 | 71.64 | O |
| ATOM | 3321 | N | TYR | A | 316 | −36.634 | 14.545 | 11.909 | 1.00 | 74.36 | N |
| ATOM | 3322 | CA | TYR | A | 316 | −37.825 | 14.800 | 11.050 | 1.00 | 74.23 | C |
| ATOM | 3323 | C | TYR | A | 316 | −38.668 | 15.970 | 11.526 | 1.00 | 75.48 | C |
| ATOM | 3324 | O | TYR | A | 316 | −38.949 | 16.889 | 10.754 | 1.00 | 76.19 | O |
| ATOM | 3325 | CB | TYR | A | 316 | −38.746 | 13.570 | 10.960 | 1.00 | 74.65 | C |
| ATOM | 3326 | CG | TYR | A | 316 | −38.256 | 12.359 | 10.139 | 1.00 | 77.26 | C |
| ATOM | 3327 | CD1 | TYR | A | 316 | −38.869 | 11.121 | 10.288 | 1.00 | 77.77 | C |
| ATOM | 3328 | CD2 | TYR | A | 316 | −37.200 | 12.448 | 9.231 | 1.00 | 75.43 | C |
| ATOM | 3329 | CE1 | TYR | A | 316 | −38.459 | 10.025 | 9.571 | 1.00 | 71.53 | C |
| ATOM | 3330 | CE2 | TYR | A | 316 | −36.787 | 11.358 | 8.514 | 1.00 | 78.76 | C |
| ATOM | 3331 | CZ | TYR | A | 316 | −37.420 | 10.148 | 8.688 | 1.00 | 77.38 | C |
| ATOM | 3332 | OH | TYR | A | 316 | −37.015 | 9.061 | 7.979 | 1.00 | 77.21 | O |
| ATOM | 3333 | N | VAL | A | 317 | −39.057 | 15.910 | 12.801 | 1.00 | 74.20 | N |
| ATOM | 3334 | CA | VAL | A | 317 | −39.872 | 16.934 | 13.466 | 1.00 | 72.51 | C |
| ATOM | 3335 | C | VAL | A | 317 | −39.316 | 18.355 | 13.330 | 1.00 | 72.64 | C |
| ATOM | 3336 | O | VAL | A | 317 | −40.086 | 19.311 | 13.253 | 1.00 | 72.17 | O |
| ATOM | 3337 | CB | VAL | A | 317 | −40.088 | 16.560 | 14.984 | 1.00 | 72.14 | C |
| ATOM | 3338 | CG1 | VAL | A | 317 | −40.336 | 17.760 | 15.804 | 1.00 | 74.78 | C |
| ATOM | 3339 | CG2 | VAL | A | 317 | −41.253 | 15.603 | 15.111 | 1.00 | 69.59 | C |
| ATOM | 3340 | N | ASN | A | 318 | −37.988 | 18.491 | 13.296 | 1.00 | 74.61 | N |
| ATOM | 3341 | CA | ASN | A | 318 | −37.342 | 19.793 | 13.078 | 1.00 | 75.44 | C |
| ATOM | 3342 | C | ASN | A | 318 | −37.882 | 20.548 | 11.857 | 1.00 | 75.25 | C |
| ATOM | 3343 | O | ASN | A | 318 | −37.912 | 21.779 | 11.844 | 1.00 | 72.63 | O |
| ATOM | 3344 | CB | ASN | A | 318 | −35.843 | 19.645 | 12.910 | 1.00 | 74.36 | C |
| ATOM | 3345 | CG | ASN | A | 318 | −35.171 | 20.958 | 12.635 | 1.00 | 79.05 | C |
| ATOM | 3346 | OD1 | ASN | A | 318 | −35.023 | 21.806 | 13.522 | 1.00 | 80.80 | O |
| ATOM | 3347 | ND2 | ASN | A | 318 | −34.761 | 21.142 | 11.396 | 1.00 | 83.57 | N |
| ATOM | 3348 | N | SER | A | 319 | −38.308 | 19.798 | 10.836 | 1.00 | 75.32 | N |
| ATOM | 3349 | CA | SER | A | 319 | −38.951 | 20.365 | 9.640 | 1.00 | 76.04 | C |
| ATOM | 3350 | C | SER | A | 319 | −40.218 | 21.194 | 9.925 | 1.00 | 76.24 | C |
| ATOM | 3351 | O | SER | A | 319 | −40.670 | 21.930 | 9.046 | 1.00 | 77.32 | O |
| ATOM | 3352 | CB | SER | A | 319 | −39.285 | 19.245 | 8.635 | 1.00 | 74.82 | C |
| ATOM | 3353 | OG | SER | A | 319 | −38.120 | 18.509 | 8.281 | 1.00 | 77.99 | O |
| ATOM | 3354 | N | GLY | A | 320 | −40.782 | 21.078 | 11.133 | 1.00 | 75.25 | N |
| ATOM | 3355 | CA | GLY | A | 320 | −41.934 | 21.857 | 11.544 | 1.00 | 74.43 | C |
| ATOM | 3356 | C | GLY | A | 320 | −41.642 | 23.110 | 12.350 | 1.00 | 76.72 | C |
| ATOM | 3357 | O | GLY | A | 320 | −42.562 | 23.884 | 12.581 | 1.00 | 78.81 | O |
| ATOM | 3358 | N | PHE | A | 321 | −40.391 | 23.328 | 12.777 | 1.00 | 75.79 | N |
| ATOM | 3359 | CA | PHE | A | 321 | −40.076 | 24.440 | 13.706 | 1.00 | 77.01 | C |
| ATOM | 3360 | C | PHE | A | 321 | −39.761 | 25.780 | 13.112 | 1.00 | 77.35 | C |
| ATOM | 3361 | O | PHE | A | 321 | −40.178 | 26.799 | 13.680 | 1.00 | 75.78 | O |
| ATOM | 3362 | CB | PHE | A | 321 | −38.912 | 24.051 | 14.634 | 1.00 | 78.53 | C |
| ATOM | 3363 | CG | PHE | A | 321 | −39.192 | 22.851 | 15.497 | 1.00 | 78.83 | C |
| ATOM | 3364 | CD1 | PHE | A | 321 | −38.154 | 22.005 | 15.857 | 1.00 | 82.01 | C |
| ATOM | 3365 | CD2 | PHE | A | 321 | −40.490 | 22.551 | 15.953 | 1.00 | 81.40 | C |
| ATOM | 3366 | CE1 | PHE | A | 321 | −38.383 | 20.891 | 16.650 | 1.00 | 81.76 | C |
| ATOM | 3367 | CE2 | PHE | A | 321 | −40.722 | 21.446 | 16.740 | 1.00 | 83.47 | C |

APPENDIX 1-continued

| | | | | | | | | | | |
|---|---|---|---|---|---|---|---|---|---|---|
| ATOM | 3368 | CZ | PHE | A | 321 | −39.667 | 20.614 | 17.091 | 1.00 | 85.30 | C |
| ATOM | 3369 | N | ASN | A | 322 | −39.040 | 25.807 | 11.996 | 1.00 | 77.86 | N |
| ATOM | 3370 | CA | ASN | A | 322 | −38.637 | 27.082 | 11.381 | 1.00 | 78.02 | C |
| ATOM | 3371 | C | ASN | A | 322 | −39.785 | 28.061 | 11.142 | 1.00 | 78.43 | C |
| ATOM | 3372 | O | ASN | A | 322 | −39.620 | 29.237 | 11.440 | 1.00 | 77.20 | O |
| ATOM | 3373 | CB | ASN | A | 322 | −37.866 | 26.856 | 10.087 | 1.00 | 79.19 | C |
| ATOM | 3374 | CG | ASN | A | 322 | −36.531 | 26.208 | 10.315 | 1.00 | 81.79 | C |
| ATOM | 3375 | OD1 | ASN | A | 322 | −36.158 | 25.901 | 11.455 | 1.00 | 74.61 | O |
| ATOM | 3376 | ND2 | ASN | A | 322 | −35.791 | 25.989 | 9.229 | 1.00 | 85.04 | N |
| ATOM | 3377 | N | PRO | A | 323 | −40.941 | 27.582 | 10.609 | 1.00 | 78.55 | N |
| ATOM | 3378 | CA | PRO | A | 323 | −42.088 | 28.479 | 10.469 | 1.00 | 79.23 | C |
| ATOM | 3379 | C | PRO | A | 323 | −42.469 | 29.179 | 11.779 | 1.00 | 80.55 | C |
| ATOM | 3380 | O | PRO | A | 323 | −42.795 | 30.367 | 11.751 | 1.00 | 83.61 | O |
| ATOM | 3381 | CB | PRO | A | 323 | −43.200 | 27.542 | 9.997 | 1.00 | 80.04 | C |
| ATOM | 3382 | CG | PRO | A | 323 | −42.474 | 26.473 | 9.266 | 1.00 | 79.60 | C |
| ATOM | 3383 | CD | PRO | A | 323 | −41.271 | 26.232 | 10.104 | 1.00 | 78.83 | C |
| ATOM | 3384 | N | LEU | A | 324 | −42.426 | 28.454 | 12.899 | 1.00 | 80.72 | N |
| ATOM | 3385 | CA | LEU | A | 324 | −42.689 | 29.050 | 14.233 | 1.00 | 81.22 | C |
| ATOM | 3386 | C | LEU | A | 324 | −41.580 | 30.013 | 14.651 | 1.00 | 78.60 | C |
| ATOM | 3387 | O | LEU | A | 324 | −41.851 | 31.053 | 15.230 | 1.00 | 77.91 | O |
| ATOM | 3388 | CB | LEU | A | 324 | −42.847 | 27.970 | 15.310 | 1.00 | 83.48 | C |
| ATOM | 3389 | CG | LEU | A | 324 | −44.017 | 27.003 | 15.125 | 1.00 | 90.04 | C |
| ATOM | 3390 | CD1 | LEU | A | 324 | −43.821 | 25.727 | 15.948 | 1.00 | 91.90 | C |
| ATOM | 3391 | CD2 | LEU | A | 324 | −45.329 | 27.707 | 15.474 | 1.00 | 93.47 | C |
| ATOM | 3392 | N | ILE | A | 325 | −40.334 | 29.656 | 14.355 | 1.00 | 77.22 | N |
| ATOM | 3393 | CA | ILE | A | 325 | −39.186 | 30.504 | 14.689 | 1.00 | 76.61 | C |
| ATOM | 3394 | C | ILE | A | 325 | −39.244 | 31.830 | 13.907 | 1.00 | 75.96 | C |
| ATOM | 3395 | O | ILE | A | 325 | −38.791 | 32.850 | 14.407 | 1.00 | 76.16 | O |
| ATOM | 3396 | CB | ILE | A | 325 | −37.837 | 29.776 | 14.433 | 1.00 | 76.87 | C |
| ATOM | 3397 | CG1 | ILE | A | 325 | −37.701 | 28.520 | 15.328 | 1.00 | 77.05 | C |
| ATOM | 3398 | CG2 | ILE | A | 325 | −36.654 | 30.701 | 14.689 | 1.00 | 73.66 | C |
| ATOM | 3399 | CD1 | ILE | A | 325 | −36.611 | 27.536 | 14.870 | 1.00 | 70.46 | C |
| ATOM | 3400 | N | TYR | A | 326 | −39.803 | 31.815 | 12.690 | 1.00 | 76.28 | N |
| ATOM | 3401 | CA | TYR | A | 326 | −39.934 | 33.054 | 11.884 | 1.00 | 76.44 | C |
| ATOM | 3402 | C | TYR | A | 326 | −40.978 | 34.017 | 12.416 | 1.00 | 73.86 | C |
| ATOM | 3403 | O | TYR | A | 326 | −40.991 | 35.153 | 11.992 | 1.00 | 77.86 | O |
| ATOM | 3404 | CB | TYR | A | 326 | −40.242 | 32.772 | 10.409 | 1.00 | 77.72 | C |
| ATOM | 3405 | CG | TYR | A | 326 | −39.240 | 31.893 | 9.701 | 1.00 | 77.26 | C |
| ATOM | 3406 | CD1 | TYR | A | 326 | −39.666 | 30.889 | 8.847 | 1.00 | 77.44 | C |
| ATOM | 3407 | CD2 | TYR | A | 326 | −37.865 | 32.057 | 9.885 | 1.00 | 81.33 | C |
| ATOM | 3408 | CE1 | TYR | A | 326 | −38.764 | 30.077 | 8.194 | 1.00 | 78.66 | C |
| ATOM | 3409 | CE2 | TYR | A | 326 | −36.961 | 31.248 | 9.236 | 1.00 | 83.58 | C |
| ATOM | 3410 | CZ | TYR | A | 326 | −37.423 | 30.258 | 8.389 | 1.00 | 80.70 | C |
| ATOM | 3411 | OH | TYR | A | 326 | −36.541 | 29.451 | 7.742 | 1.00 | 81.84 | O |
| ATOM | 3412 | N | CYS | A | 327 | −41.848 | 33.582 | 13.332 | 1.00 | 72.88 | N |
| ATOM | 3413 | CA | CYS | A | 327 | −42.782 | 34.496 | 13.999 | 1.00 | 76.25 | C |
| ATOM | 3414 | C | CYS | A | 327 | −42.064 | 35.537 | 14.905 | 1.00 | 78.27 | C |
| ATOM | 3415 | O | CYS | A | 327 | −42.684 | 36.508 | 15.330 | 1.00 | 79.91 | O |
| ATOM | 3416 | CB | CYS | A | 327 | −43.827 | 33.729 | 14.805 | 1.00 | 77.89 | C |
| ATOM | 3417 | SG | CYS | A | 327 | −44.970 | 32.742 | 13.778 | 1.00 | 82.26 | S |
| ATOM | 3418 | N | ARG | A | 328 | −40.770 | 35.320 | 15.191 | 1.00 | 79.14 | N |
| ATOM | 3419 | CA | ARG | A | 328 | −39.919 | 36.324 | 15.832 | 1.00 | 79.59 | C |
| ATOM | 3420 | C | ARG | A | 328 | −39.781 | 37.596 | 14.984 | 1.00 | 79.99 | C |
| ATOM | 3421 | O | ARG | A | 328 | −39.581 | 38.680 | 15.524 | 1.00 | 79.93 | O |
| ATOM | 3422 | CB | ARG | A | 328 | −38.515 | 35.771 | 16.078 | 1.00 | 77.25 | C |
| ATOM | 3423 | CG | ARG | A | 328 | −38.423 | 34.646 | 17.130 | 1.00 | 76.09 | C |
| ATOM | 3424 | CD | ARG | A | 328 | −36.998 | 34.067 | 17.220 | 1.00 | 77.31 | C |
| ATOM | 3425 | NE | ARG | A | 328 | −36.006 | 35.129 | 17.048 | 1.00 | 75.58 | N |
| ATOM | 3426 | CZ | ARG | A | 328 | −35.537 | 35.945 | 17.985 | 1.00 | 81.23 | C |
| ATOM | 3427 | NH1 | ARG | A | 328 | −35.953 | 35.859 | 19.252 | 1.00 | 74.46 | N |
| ATOM | 3428 | NH2 | ARG | A | 328 | −34.631 | 36.866 | 17.640 | 1.00 | 81.80 | N |
| ATOM | 3429 | N | SER | A | 329 | −39.885 | 37.449 | 13.659 | 1.00 | 82.57 | N |
| ATOM | 3430 | CA | SER | A | 329 | −39.788 | 38.574 | 12.743 | 1.00 | 84.20 | C |
| ATOM | 3431 | C | SER | A | 329 | −41.107 | 39.324 | 12.711 | 1.00 | 84.79 | C |
| ATOM | 3432 | O | SER | A | 329 | −42.151 | 38.687 | 12.597 | 1.00 | 88.37 | O |
| ATOM | 3433 | CB | SER | A | 329 | −39.460 | 38.097 | 11.335 | 1.00 | 84.66 | C |
| ATOM | 3434 | OG | SER | A | 329 | −39.465 | 39.190 | 10.429 | 1.00 | 90.44 | O |
| ATOM | 3435 | N | PRO | A | 330 | −41.076 | 40.675 | 12.814 | 1.00 | 86.62 | N |
| ATOM | 3436 | CA | PRO | A | 330 | −42.339 | 41.415 | 12.685 | 1.00 | 85.84 | C |
| ATOM | 3437 | C | PRO | A | 330 | −42.905 | 41.369 | 11.253 | 1.00 | 86.45 | C |
| ATOM | 3438 | O | PRO | A | 330 | −44.103 | 41.466 | 11.079 | 1.00 | 85.67 | O |
| ATOM | 3439 | CB | PRO | A | 330 | −41.960 | 42.851 | 13.080 | 1.00 | 85.22 | C |
| ATOM | 3440 | CG | PRO | A | 330 | −40.597 | 42.764 | 13.669 | 1.00 | 85.83 | C |
| ATOM | 3441 | CD | PRO | A | 330 | −39.946 | 41.595 | 13.045 | 1.00 | 85.56 | C |
| ATOM | 3442 | N | ASP | A | 331 | −42.031 | 41.216 | 10.256 | 1.00 | 87.75 | N |
| ATOM | 3443 | CA | ASP | A | 331 | −42.440 | 41.127 | 8.854 | 1.00 | 88.35 | C |
| ATOM | 3444 | C | ASP | A | 331 | −43.160 | 39.831 | 8.516 | 1.00 | 88.54 | C |
| ATOM | 3445 | O | ASP | A | 331 | −44.180 | 39.865 | 7.824 | 1.00 | 87.13 | O |
| ATOM | 3446 | CB | ASP | A | 331 | −41.225 | 41.268 | 7.929 | 1.00 | 91.75 | C |
| ATOM | 3447 | CG | ASP | A | 331 | −40.585 | 42.640 | 8.000 | 1.00 | 99.65 | C |

APPENDIX 1-continued

| | | | | | | | | | | |
|---|---|---|---|---|---|---|---|---|---|---|
| ATOM | 3448 | OD1 | ASP | A | 331 | −41.152 | 43.526 | 8.660 | 1.00 | 101.57 | O |
| ATOM | 3449 | OD2 | ASP | A | 331 | −39.507 | 42.825 | 7.387 | 1.00 | 108.72 | O |
| ATOM | 3450 | N | PHE | A | 332 | −42.638 | 38.697 | 8.992 | 1.00 | 87.91 | N |
| ATOM | 3451 | CA | PHE | A | 332 | −43.306 | 37.387 | 8.759 | 1.00 | 85.83 | C |
| ATOM | 3452 | C | PHE | A | 332 | −44.596 | 37.298 | 9.525 | 1.00 | 84.97 | C |
| ATOM | 3453 | O | PHE | A | 332 | −45.583 | 36.811 | 9.006 | 1.00 | 85.85 | O |
| ATOM | 3454 | CB | PHE | A | 332 | −42.419 | 36.206 | 9.142 | 1.00 | 83.02 | C |
| ATOM | 3455 | CG | PHE | A | 332 | −41.421 | 35.848 | 8.099 | 1.00 | 81.58 | C |
| ATOM | 3456 | CD1 | PHE | A | 332 | −40.184 | 36.470 | 8.064 | 1.00 | 79.60 | C |
| ATOM | 3457 | CD2 | PHE | A | 332 | −41.719 | 34.884 | 7.141 | 1.00 | 82.96 | C |
| ATOM | 3458 | CE1 | PHE | A | 332 | −39.251 | 36.138 | 7.092 | 1.00 | 83.90 | C |
| ATOM | 3459 | CE2 | PHE | A | 332 | −40.794 | 34.541 | 6.159 | 1.00 | 81.77 | C |
| ATOM | 3460 | CZ | PHE | A | 332 | −39.558 | 35.166 | 6.132 | 1.00 | 84.78 | C |
| ATOM | 3461 | N | ARG | A | 333 | −44.567 | 37.772 | 10.764 | 1.00 | 85.64 | N |
| ATOM | 3462 | CA | ARG | A | 333 | −45.742 | 37.795 | 11.618 | 1.00 | 86.23 | C |
| ATOM | 3463 | C | ARG | A | 333 | −46.875 | 38.603 | 10.964 | 1.00 | 85.68 | C |
| ATOM | 3464 | O | ARG | A | 333 | −48.015 | 38.171 | 11.005 | 1.00 | 85.47 | O |
| ATOM | 3465 | CB | ARG | A | 333 | −45.357 | 38.362 | 12.963 | 1.00 | 86.76 | C |
| ATOM | 3466 | CG | ARG | A | 333 | −46.383 | 38.222 | 14.059 | 1.00 | 90.70 | C |
| ATOM | 3467 | CD | ARG | A | 333 | −45.671 | 38.263 | 15.407 | 1.00 | 93.90 | C |
| ATOM | 3468 | NE | ARG | A | 333 | −44.710 | 39.377 | 15.472 | 1.00 | 100.54 | N |
| ATOM | 3469 | CZ | ARG | A | 333 | −43.693 | 39.490 | 16.335 | 1.00 | 103.24 | C |
| ATOM | 3470 | NH1 | ARG | A | 333 | −43.449 | 38.553 | 17.262 | 1.00 | 104.89 | N |
| ATOM | 3471 | NH2 | ARG | A | 333 | −42.899 | 40.566 | 16.271 | 1.00 | 102.64 | N |
| ATOM | 3472 | N | ILE | A | 334 | −46.534 | 39.755 | 10.373 | 1.00 | 84.51 | N |
| ATOM | 3473 | CA | ILE | A | 334 | −47.472 | 40.580 | 9.584 | 1.00 | 83.97 | C |
| ATOM | 3474 | C | ILE | A | 334 | −47.898 | 39.862 | 8.316 | 1.00 | 82.02 | C |
| ATOM | 3475 | O | ILE | A | 334 | −49.077 | 39.871 | 7.963 | 1.00 | 86.53 | O |
| ATOM | 3476 | CB | ILE | A | 334 | −46.862 | 41.959 | 9.211 | 1.00 | 85.26 | C |
| ATOM | 3477 | CG1 | ILE | A | 334 | −46.777 | 42.860 | 10.444 | 1.00 | 85.90 | C |
| ATOM | 3478 | CG2 | ILE | A | 334 | −47.692 | 42.668 | 8.142 | 1.00 | 82.88 | C |
| ATOM | 3479 | CD1 | ILE | A | 334 | −45.791 | 44.015 | 10.287 | 1.00 | 88.19 | C |
| ATOM | 3480 | N | ALA | A | 335 | −46.934 | 39.248 | 7.635 | 1.00 | 80.09 | N |
| ATOM | 3481 | CA | ALA | A | 335 | −47.202 | 38.470 | 6.433 | 1.00 | 79.44 | C |
| ATOM | 3482 | C | ALA | A | 335 | −48.199 | 37.345 | 6.719 | 1.00 | 78.78 | C |
| ATOM | 3483 | O | ALA | A | 335 | −49.207 | 37.251 | 6.057 | 1.00 | 78.15 | O |
| ATOM | 3484 | CB | ALA | A | 335 | −45.911 | 37.896 | 5.876 | 1.00 | 78.92 | C |
| ATOM | 3485 | N | PHE | A | 336 | −47.896 | 36.511 | 7.714 | 1.00 | 78.39 | N |
| ATOM | 3486 | CA | PHE | A | 336 | −48.760 | 35.372 | 8.092 | 1.00 | 77.87 | C |
| ATOM | 3487 | C | PHE | A | 336 | −50.184 | 35.751 | 8.427 | 1.00 | 77.70 | C |
| ATOM | 3488 | O | PHE | A | 336 | −51.116 | 35.205 | 7.847 | 1.00 | 75.76 | O |
| ATOM | 3489 | CB | PHE | A | 336 | −48.198 | 34.602 | 9.301 | 1.00 | 77.26 | C |
| ATOM | 3490 | CG | PHE | A | 336 | −46.852 | 33.943 | 9.072 | 1.00 | 77.36 | C |
| ATOM | 3491 | CD1 | PHE | A | 336 | −46.408 | 33.562 | 7.796 | 1.00 | 78.61 | C |
| ATOM | 3492 | CD2 | PHE | A | 336 | −46.024 | 33.695 | 10.152 | 1.00 | 76.74 | C |
| ATOM | 3493 | CE1 | PHE | A | 336 | −45.180 | 32.962 | 7.621 | 1.00 | 76.21 | C |
| ATOM | 3494 | CE2 | PHE | A | 336 | −44.787 | 33.089 | 9.974 | 1.00 | 78.36 | C |
| ATOM | 3495 | CZ | PHE | A | 336 | −44.372 | 32.724 | 8.700 | 1.00 | 76.78 | C |
| ATOM | 3496 | N | GLN | A | 337 | −50.346 | 36.681 | 9.363 | 1.00 | 78.23 | N |
| ATOM | 3497 | CA | GLN | A | 337 | −51.691 | 37.124 | 9.792 | 1.00 | 79.51 | C |
| ATOM | 3498 | C | GLN | A | 337 | −52.549 | 37.711 | 8.642 | 1.00 | 78.03 | C |
| ATOM | 3499 | O | GLN | A | 337 | −53.778 | 37.646 | 8.694 | 1.00 | 78.24 | O |
| ATOM | 3500 | CB | GLN | A | 337 | −51.609 | 38.081 | 10.997 | 1.00 | 80.74 | C |
| ATOM | 3501 | CG | GLN | A | 337 | −50.870 | 39.391 | 10.802 | 1.00 | 86.86 | C |
| ATOM | 3502 | CD | GLN | A | 337 | −50.613 | 40.113 | 12.143 | 1.00 | 89.20 | C |
| ATOM | 3503 | OE1 | GLN | A | 337 | −51.317 | 39.877 | 13.127 | 1.00 | 97.34 | O |
| ATOM | 3504 | NE2 | GLN | A | 337 | −49.610 | 40.989 | 12.177 | 1.00 | 94.24 | N |
| ATOM | 3505 | N | GLU | A | 338 | −51.900 | 38.271 | 7.622 | 1.00 | 76.38 | N |
| ATOM | 3506 | CA | GLU | A | 338 | −52.591 | 38.694 | 6.411 | 1.00 | 74.47 | C |
| ATOM | 3507 | C | GLU | A | 338 | −53.085 | 37.448 | 5.670 | 1.00 | 73.86 | C |
| ATOM | 3508 | O | GLU | A | 338 | −54.258 | 37.370 | 5.282 | 1.00 | 73.06 | O |
| ATOM | 3509 | CB | GLU | A | 338 | −51.659 | 39.512 | 5.516 | 1.00 | 75.29 | C |
| ATOM | 3510 | CG | GLU | A | 338 | −52.343 | 40.279 | 4.365 | 1.00 | 79.56 | C |
| ATOM | 3511 | CD | GLU | A | 338 | −52.695 | 39.442 | 3.113 | 1.00 | 85.28 | C |
| ATOM | 3512 | OE1 | GLU | A | 338 | −52.500 | 38.207 | 3.087 | 1.00 | 91.20 | O |
| ATOM | 3513 | OE2 | GLU | A | 338 | −53.176 | 40.048 | 2.131 | 1.00 | 89.12 | O |
| ATOM | 3514 | N | LEU | A | 339 | −52.177 | 36.488 | 5.477 | 1.00 | 70.47 | N |
| ATOM | 3515 | CA | LEU | A | 339 | −52.475 | 35.242 | 4.763 | 1.00 | 71.14 | C |
| ATOM | 3516 | C | LEU | A | 339 | −53.527 | 34.375 | 5.463 | 1.00 | 72.95 | C |
| ATOM | 3517 | O | LEU | A | 339 | −54.255 | 33.650 | 4.793 | 1.00 | 74.46 | O |
| ATOM | 3518 | CB | LEU | A | 339 | −51.209 | 34.406 | 4.567 | 1.00 | 68.65 | C |
| ATOM | 3519 | CG | LEU | A | 339 | −50.055 | 35.021 | 3.778 | 1.00 | 69.52 | C |
| ATOM | 3520 | CD1 | LEU | A | 339 | −48.805 | 34.139 | 3.935 | 1.00 | 68.79 | C |
| ATOM | 3521 | CD2 | LEU | A | 339 | −50.411 | 35.225 | 2.315 | 1.00 | 62.62 | C |
| ATOM | 3522 | N | LEU | A | 340 | −53.599 | 34.455 | 6.796 | 1.00 | 74.28 | N |
| ATOM | 3523 | CA | LEU | A | 340 | −54.598 | 33.718 | 7.588 | 1.00 | 75.08 | C |
| ATOM | 3524 | C | LEU | A | 340 | −55.848 | 34.573 | 7.901 | 1.00 | 76.80 | C |
| ATOM | 3525 | O | LEU | A | 340 | −56.573 | 34.280 | 8.860 | 1.00 | 76.39 | O |
| ATOM | 3526 | CB | LEU | A | 340 | −53.960 | 33.174 | 8.878 | 1.00 | 74.68 | C |
| ATOM | 3527 | CG | LEU | A | 340 | −52.763 | 32.233 | 8.701 | 1.00 | 73.84 | C |

APPENDIX 1-continued

| | | | | | | | | | | |
|---|---|---|---|---|---|---|---|---|---|---|
| ATOM | 3528 | CD1 | LEU | A | 340 | −52.150 | 31.887 | 10.048 | 1.00 | 73.83 | C |
| ATOM | 3529 | CD2 | LEU | A | 340 | −53.167 | 30.976 | 7.982 | 1.00 | 73.24 | C |
| ATOM | 3530 | N | CYS | A | 341 | −56.083 | 35.619 | 7.088 | 1.00 | 79.59 | N |
| ATOM | 3531 | CA | CYS | A | 341 | −57.280 | 36.477 | 7.152 | 1.00 | 80.75 | C |
| ATOM | 3532 | C | CYS | A | 341 | −57.536 | 37.089 | 8.530 | 1.00 | 81.21 | C |
| ATOM | 3533 | O | CYS | A | 341 | −58.613 | 36.911 | 9.114 | 1.00 | 81.97 | O |
| ATOM | 3534 | CB | CYS | A | 341 | −58.500 | 35.683 | 6.674 | 1.00 | 81.26 | C |
| ATOM | 3535 | SG | CYS | A | 341 | −58.243 | 34.889 | 5.079 | 1.00 | 88.24 | S |
| ATOM | 3536 | N | LEU | A | 342 | −56.533 | 37.809 | 9.031 | 1.00 | 81.84 | N |
| ATOM | 3537 | CA | LEU | A | 342 | −56.598 | 38.483 | 10.333 | 1.00 | 82.60 | C |
| ATOM | 3538 | C | LEU | A | 342 | −56.370 | 39.993 | 10.158 | 1.00 | 83.35 | C |
| ATOM | 3539 | O | LEU | A | 342 | −55.715 | 40.650 | 10.971 | 1.00 | 85.10 | O |
| ATOM | 3540 | CB | LEU | A | 342 | −55.575 | 37.878 | 11.303 | 1.00 | 82.19 | C |
| ATOM | 3541 | CG | LEU | A | 342 | −55.513 | 36.347 | 11.407 | 1.00 | 82.55 | C |
| ATOM | 3542 | CD1 | LEU | A | 342 | −54.415 | 35.913 | 12.368 | 1.00 | 82.95 | C |
| ATOM | 3543 | CD2 | LEU | A | 342 | −56.851 | 35.782 | 11.838 | 1.00 | 83.45 | C |
| TER | 3544 | | LEU | A | 342 | | | | | | |
| HETATM | 3545 | C1 | MAL | A | 401 | −30.433 | 67.551 | 22.604 | 1.00 | 116.54 | C |
| HETATM | 3546 | C2 | MAL | A | 401 | −29.508 | 68.271 | 21.613 | 1.00 | 116.67 | C |
| HETATM | 3547 | C3 | MAL | A | 401 | −28.286 | 67.466 | 21.250 | 1.00 | 115.67 | C |
| HETATM | 3548 | C4 | MAL | A | 401 | −27.437 | 67.774 | 22.475 | 1.00 | 113.35 | C |
| HETATM | 3549 | C5 | MAL | A | 401 | −28.222 | 67.326 | 23.742 | 1.00 | 114.16 | C |
| HETATM | 3550 | C6 | MAL | A | 401 | −27.467 | 67.821 | 24.997 | 1.00 | 112.25 | C |
| HETATM | 3551 | O1 | MAL | A | 401 | −30.860 | 66.152 | 22.481 | 1.00 | 118.82 | O |
| HETATM | 3552 | O2 | MAL | A | 401 | −30.196 | 68.896 | 20.430 | 1.00 | 113.17 | O |
| HETATM | 3553 | O3 | MAL | A | 401 | −27.692 | 67.923 | 20.042 | 1.00 | 118.88 | O |
| HETATM | 3554 | O4 | MAL | A | 401 | −26.151 | 67.133 | 22.417 | 1.00 | 110.96 | O |
| HETATM | 3555 | O5 | MAL | A | 401 | −29.640 | 67.723 | 23.796 | 1.00 | 116.03 | O |
| HETATM | 3556 | O6 | MAL | A | 401 | −28.329 | 68.191 | 26.091 | 1.00 | 111.18 | O |
| HETATM | 3557 | C1' | MAL | A | 401 | −34.225 | 64.365 | 24.555 | 1.00 | 118.64 | C |
| HETATM | 3558 | C2' | MAL | A | 401 | −34.062 | 65.875 | 24.695 | 1.00 | 118.98 | C |
| HETATM | 3559 | C3' | MAL | A | 401 | −33.053 | 66.497 | 23.732 | 1.00 | 118.89 | C |
| HETATM | 3560 | C4' | MAL | A | 401 | −31.773 | 65.653 | 23.533 | 1.00 | 118.41 | C |
| HETATM | 3561 | C5' | MAL | A | 401 | −32.192 | 64.169 | 23.329 | 1.00 | 117.27 | C |
| HETATM | 3562 | C6' | MAL | A | 401 | −31.044 | 63.164 | 23.154 | 1.00 | 114.49 | C |
| HETATM | 3563 | O1' | MAL | A | 401 | −34.905 | 63.850 | 25.705 | 1.00 | 115.98 | O |
| HETATM | 3564 | O2' | MAL | A | 401 | −35.328 | 66.510 | 24.463 | 1.00 | 120.41 | O |
| HETATM | 3565 | O3' | MAL | A | 401 | −32.803 | 67.771 | 24.346 | 1.00 | 118.98 | O |
| HETATM | 3566 | O5' | MAL | A | 401 | −32.951 | 63.737 | 24.467 | 1.00 | 118.26 | O |
| HETATM | 3567 | O6' | MAL | A | 401 | −31.319 | 61.889 | 23.781 | 1.00 | 101.09 | O |
| HETATM | 3568 | S | SO4 | A | 402 | −30.549 | 40.587 | 1.840 | 1.00 | 88.35 | S |
| HETATM | 3569 | O1 | SO4 | A | 402 | −31.012 | 40.657 | 0.449 | 1.00 | 91.49 | O |
| HETATM | 3570 | O2 | SO4 | A | 402 | −31.341 | 41.518 | 2.648 | 1.00 | 79.98 | O |
| HETATM | 3571 | O3 | SO4 | A | 402 | −30.747 | 39.233 | 2.389 | 1.00 | 86.89 | O |
| HETATM | 3572 | O4 | SO4 | A | 402 | −29.136 | 40.942 | 1.808 | 1.00 | 79.16 | O |
| HETATM | 3573 | S | SO4 | A | 403 | −34.529 | 39.154 | 20.841 | 1.00 | 91.42 | S |
| HETATM | 3574 | O1 | SO4 | A | 403 | −35.518 | 40.193 | 21.131 | 1.00 | 84.45 | O |
| HETATM | 3575 | O2 | SO4 | A | 403 | −33.296 | 39.334 | 21.612 | 1.00 | 93.22 | O |
| HETATM | 3576 | O3 | SO4 | A | 403 | −35.078 | 37.875 | 21.232 | 1.00 | 84.98 | O |
| HETATM | 3577 | O4 | SO4 | A | 403 | −34.193 | 39.246 | 19.438 | 1.00 | 95.59 | O |
| HETATM | 3578 | S | SO4 | A | 404 | −26.677 | 61.410 | 43.667 | 1.00 | 79.61 | S |
| HETATM | 3579 | O1 | SO4 | A | 404 | −26.224 | 60.482 | 42.637 | 1.00 | 81.00 | O |
| HETATM | 3580 | O2 | SO4 | A | 404 | −27.968 | 62.001 | 43.315 | 1.00 | 78.07 | O |
| HETATM | 3581 | O3 | SO4 | A | 404 | −26.852 | 60.655 | 44.907 | 1.00 | 85.67 | O |
| HETATM | 3582 | O4 | SO4 | A | 404 | −25.700 | 62.487 | 43.819 | 1.00 | 76.33 | O |
| HETATM | 3583 | S | SO4 | A | 405 | −38.222 | 54.167 | 28.613 | 1.00 | 76.15 | S |
| HETATM | 3584 | O1 | SO4 | A | 405 | −36.815 | 54.454 | 28.371 | 1.00 | 62.35 | O |
| HETATM | 3585 | O2 | SO4 | A | 405 | −38.708 | 53.202 | 27.628 | 1.00 | 74.38 | O |
| HETATM | 3586 | O3 | SO4 | A | 405 | −38.392 | 53.561 | 29.925 | 1.00 | 77.47 | O |
| HETATM | 3587 | O4 | SO4 | A | 405 | −38.983 | 55.412 | 28.536 | 1.00 | 74.20 | O |
| HETATM | 3588 | S | SO4 | A | 406 | −14.626 | 46.742 | 34.955 | 1.00 | 133.97 | S |
| HETATM | 3589 | O1 | SO4 | A | 406 | −14.905 | 46.888 | 33.527 | 1.00 | 132.94 | O |
| HETATM | 3590 | O2 | SO4 | A | 406 | −15.870 | 46.485 | 35.690 | 1.00 | 131.52 | O |
| HETATM | 3591 | O3 | SO4 | A | 406 | −13.744 | 45.588 | 35.141 | 1.00 | 137.48 | O |
| HETATM | 3592 | O4 | SO4 | A | 406 | −13.968 | 47.953 | 35.460 | 1.00 | 129.69 | O |
| HETATM | 3593 | S | SO4 | A | 407 | −39.375 | 59.242 | 10.957 | 1.00 | 103.03 | S |
| HETATM | 3594 | O1 | SO4 | A | 407 | −38.112 | 58.591 | 10.589 | 1.00 | 100.34 | O |
| HETATM | 3595 | O2 | SO4 | A | 407 | −40.365 | 59.029 | 9.899 | 1.00 | 104.55 | O |
| HETATM | 3596 | O3 | SO4 | A | 407 | −39.865 | 58.663 | 12.211 | 1.00 | 107.47 | O |
| HETATM | 3597 | O4 | SO4 | A | 407 | −39.174 | 60.683 | 11.138 | 1.00 | 106.88 | O |
| HETATM | 3598 | O17 | CAU | A | 408 | −33.477 | 10.957 | 8.170 | 1.00 | 50.96 | O |
| HETATM | 3599 | C16 | CAU | A | 408 | −32.267 | 10.230 | 8.041 | 1.00 | 45.65 | C |
| HETATM | 3600 | C18 | CAU | A | 408 | −32.478 | 8.951 | 7.225 | 1.00 | 51.24 | C |
| HETATM | 3601 | N19 | CAU | A | 408 | −33.702 | 8.250 | 7.600 | 1.00 | 54.99 | N |
| HETATM | 3602 | C20 | CAU | A | 408 | −33.806 | 6.805 | 7.498 | 1.00 | 60.13 | C |
| HETATM | 3603 | C21 | CAU | A | 408 | −33.533 | 6.385 | 6.055 | 1.00 | 66.62 | C |
| HETATM | 3604 | C22 | CAU | A | 408 | −35.184 | 6.350 | 7.988 | 1.00 | 59.87 | C |
| HETATM | 3605 | C15 | CAU | A | 408 | −31.242 | 11.105 | 7.364 | 1.00 | 46.24 | C |
| HETATM | 3606 | O14 | CAU | A | 408 | −30.049 | 10.367 | 7.182 | 1.00 | 51.01 | O |
| HETATM | 3607 | C13 | CAU | A | 408 | −28.931 | 10.857 | 6.581 | 1.00 | 52.29 | C |

APPENDIX 1-continued

| | | | | | | | | | | |
|---|---|---|---|---|---|---|---|---|---|---|
| HETATM | 3608 | C12 | CAU | A | 408 | −28.911 | 12.133 | 6.005 | 1.00 | 56.44 | C |
| HETATM | 3609 | C11 | CAU | A | 408 | −27.768 | 12.628 | 5.393 | 1.00 | 56.29 | C |
| HETATM | 3610 | O10 | CAU | A | 408 | −26.608 | 11.875 | 5.332 | 1.00 | 54.90 | C |
| HETATM | 3611 | C8 | CAU | A | 408 | −26.565 | 10.625 | 5.875 | 1.00 | 54.68 | C |
| HETATM | 3612 | C9 | CAU | A | 408 | −27.768 | 10.108 | 6.517 | 1.00 | 53.44 | C |
| HETATM | 3613 | N7 | CAU | A | 408 | −25.593 | 9.657 | 5.974 | 1.00 | 57.07 | N |
| HETATM | 3614 | C3 | CAU | A | 408 | −26.096 | 8.561 | 6.637 | 1.00 | 55.09 | C |
| HETATM | 3615 | C4 | CAU | A | 408 | −27.482 | 8.863 | 6.976 | 1.00 | 53.66 | C |
| HETATM | 3616 | C2 | CAU | A | 408 | −25.589 | 7.338 | 7.009 | 1.00 | 54.54 | C |
| HETATM | 3617 | C1 | CAU | A | 408 | −26.395 | 6.432 | 7.689 | 1.00 | 56.87 | C |
| HETATM | 3618 | C6 | CAU | A | 408 | −27.717 | 6.731 | 8.006 | 1.00 | 56.28 | C |
| HETATM | 3619 | C5 | CAU | A | 408 | −28.269 | 7.948 | 7.652 | 1.00 | 56.42 | C |
| HETATM | 3620 | C1 | BU1 | A | 409 | −26.142 | 41.424 | 19.127 | 1.00 | 52.74 | C |
| HETATM | 3621 | C2 | BU1 | A | 409 | −24.673 | 41.194 | 19.349 | 1.00 | 50.50 | C |
| HETATM | 3622 | C3 | BU1 | A | 409 | −24.361 | 39.703 | 19.256 | 1.00 | 58.68 | C |
| HETATM | 3623 | C4 | BU1 | A | 409 | −23.639 | 39.193 | 20.492 | 1.00 | 60.90 | C |
| HETATM | 3624 | O5 | BU1 | A | 409 | −26.449 | 42.812 | 19.063 | 1.00 | 46.89 | O |
| HETATM | 3625 | O6 | BU1 | A | 409 | −23.397 | 37.796 | 20.358 | 1.00 | 65.39 | O |
| HETATM | 3626 | C1 | BU1 | A | 410 | −25.492 | 26.523 | 17.727 | 1.00 | 80.96 | C |
| HETATM | 3627 | C2 | BU1 | A | 410 | −25.259 | 26.818 | 16.240 | 1.00 | 75.39 | C |
| HETATM | 3628 | C3 | BU1 | A | 410 | −25.569 | 28.286 | 15.904 | 1.00 | 72.90 | C |
| HETATM | 3629 | C4 | BU1 | A | 410 | −24.368 | 29.076 | 15.393 | 1.00 | 70.20 | C |
| HETATM | 3630 | O5 | BU1 | A | 410 | −25.036 | 25.202 | 18.096 | 1.00 | 82.37 | O |
| HETATM | 3631 | O6 | BU1 | A | 410 | −23.728 | 29.769 | 16.468 | 1.00 | 72.23 | O |
| HETATM | 3632 | C1 | ACM | A | 411 | −33.365 | 45.116 | 23.775 | 1.00 | 72.09 | C |
| HETATM | 3633 | O | ACM | A | 411 | −34.580 | 45.100 | 23.784 | 1.00 | 74.74 | O |
| HETATM | 3634 | N | ACM | A | 411 | −32.677 | 43.981 | 23.897 | 1.00 | 71.73 | N |
| HETATM | 3635 | C2 | ACM | A | 411 | −32.587 | 46.397 | 23.626 | 1.00 | 69.99 | C |
| HETATM | 3636 | C1 | CLR | A | 412 | −36.292 | 27.653 | −4.352 | 1.00 | 98.97 | C |
| HETATM | 3637 | C2 | CLR | A | 412 | −36.571 | 29.133 | −4.591 | 1.00 | 98.10 | C |
| HETATM | 3638 | C3 | CLR | A | 412 | −35.425 | 29.793 | −5.354 | 1.00 | 98.91 | C |
| HETATM | 3639 | C4 | CLR | A | 412 | −34.965 | 29.038 | −6.627 | 1.00 | 98.80 | C |
| HETATM | 3640 | C5 | CLR | A | 412 | −35.001 | 27.515 | −6.513 | 1.00 | 99.38 | C |
| HETATM | 3641 | C6 | CLR | A | 412 | −34.088 | 26.785 | −7.209 | 1.00 | 99.72 | C |
| HETATM | 3642 | C7 | CLR | A | 412 | −34.017 | 25.259 | −7.204 | 1.00 | 98.91 | C |
| HETATM | 3643 | C8 | CLR | A | 412 | −35.275 | 24.631 | −6.633 | 1.00 | 99.40 | C |
| HETATM | 3644 | C9 | CLR | A | 412 | −35.651 | 25.377 | −5.337 | 1.00 | 99.32 | C |
| HETATM | 3645 | C10 | CLR | A | 412 | −36.050 | 26.846 | −5.645 | 1.00 | 100.31 | C |
| HETATM | 3646 | C11 | CLR | A | 412 | −36.707 | 24.655 | −4.466 | 1.00 | 96.50 | C |
| HETATM | 3647 | C12 | CLR | A | 412 | −36.536 | 23.143 | −4.365 | 1.00 | 96.65 | C |
| HETATM | 3648 | C13 | CLR | A | 412 | −36.329 | 22.495 | −5.719 | 1.00 | 100.10 | C |
| HETATM | 3649 | C14 | CLR | A | 412 | −35.100 | 23.138 | −6.353 | 1.00 | 101.09 | C |
| HETATM | 3650 | C15 | CLR | A | 412 | −34.782 | 22.237 | −7.542 | 1.00 | 101.42 | C |
| HETATM | 3651 | C16 | CLR | A | 412 | −35.217 | 20.837 | −7.081 | 1.00 | 101.37 | C |
| HETATM | 3652 | C17 | CLR | A | 412 | −35.995 | 21.000 | −5.758 | 1.00 | 100.60 | C |
| HETATM | 3653 | C18 | CLR | A | 412 | −37.562 | 22.726 | −6.571 | 1.00 | 103.09 | C |
| HETATM | 3654 | C19 | CLR | A | 412 | −37.268 | 26.936 | −6.512 | 1.00 | 102.37 | C |
| HETATM | 3655 | C20 | CLR | A | 412 | −37.144 | 19.961 | −5.632 | 1.00 | 100.25 | C |
| HETATM | 3656 | C21 | CLR | A | 412 | −38.032 | 20.187 | −4.406 | 1.00 | 98.50 | C |
| HETATM | 3657 | C22 | CLR | A | 412 | −36.561 | 18.538 | −5.657 | 1.00 | 101.01 | C |
| HETATM | 3658 | C23 | CLR | A | 412 | −37.437 | 17.457 | −5.012 | 1.00 | 103.22 | C |
| HETATM | 3659 | C24 | CLR | A | 412 | −36.748 | 16.094 | −5.099 | 1.00 | 105.36 | C |
| HETATM | 3660 | C25 | CLR | A | 412 | −37.535 | 15.014 | −5.853 | 1.00 | 107.48 | C |
| HETATM | 3661 | C26 | CLR | A | 412 | −36.571 | 14.080 | −6.591 | 1.00 | 107.73 | C |
| HETATM | 3662 | C27 | CLR | A | 412 | −38.402 | 14.192 | −4.899 | 1.00 | 106.61 | C |
| HETATM | 3663 | O1 | CLR | A | 412 | −35.828 | 31.158 | −5.664 | 1.00 | 99.70 | O |
| HETATM | 3664 | C1 | CLR | A | 413 | −52.083 | 29.442 | 3.198 | 1.00 | 84.76 | C |
| HETATM | 3665 | C2 | CLR | A | 413 | −52.244 | 30.951 | 3.100 | 1.00 | 85.75 | C |
| HETATM | 3666 | C3 | CLR | A | 413 | −53.214 | 31.296 | 1.956 | 1.00 | 84.48 | C |
| HETATM | 3667 | C4 | CLR | A | 413 | −54.606 | 30.718 | 2.233 | 1.00 | 82.59 | C |
| HETATM | 3668 | C5 | CLR | A | 413 | −54.424 | 29.218 | 2.245 | 1.00 | 86.97 | C |
| HETATM | 3669 | C6 | CLR | A | 413 | −55.171 | 28.468 | 1.400 | 1.00 | 86.01 | C |
| HETATM | 3670 | C7 | CLR | A | 413 | −55.077 | 26.968 | 1.309 | 1.00 | 88.00 | C |
| HETATM | 3671 | C8 | CLR | A | 413 | −54.340 | 26.362 | 2.487 | 1.00 | 89.33 | C |
| HETATM | 3672 | C9 | CLR | A | 413 | −53.087 | 27.161 | 2.862 | 1.00 | 88.72 | C |
| HETATM | 3673 | C10 | CLR | A | 413 | −53.399 | 28.636 | 3.214 | 1.00 | 85.54 | C |
| HETATM | 3674 | C11 | CLR | A | 413 | −52.265 | 26.440 | 3.959 | 1.00 | 87.79 | C |
| HETATM | 3675 | C12 | CLR | A | 413 | −51.961 | 24.981 | 3.616 | 1.00 | 90.38 | C |
| HETATM | 3676 | C13 | CLR | A | 413 | −53.219 | 24.202 | 3.283 | 1.00 | 90.23 | C |
| HETATM | 3677 | C14 | CLR | A | 413 | −53.904 | 24.933 | 2.142 | 1.00 | 92.32 | C |
| HETATM | 3678 | C15 | CLR | A | 413 | −54.976 | 23.971 | 1.668 | 1.00 | 92.65 | C |
| HETATM | 3679 | C16 | CLR | A | 413 | −54.282 | 22.616 | 1.827 | 1.00 | 93.79 | C |
| HETATM | 3680 | C17 | CLR | A | 413 | −53.018 | 22.820 | 2.693 | 1.00 | 91.53 | C |
| HETATM | 3681 | C18 | CLR | A | 413 | −54.156 | 24.093 | 4.499 | 1.00 | 87.86 | C |
| HETATM | 3682 | C19 | CLR | A | 413 | −54.039 | 28.774 | 4.595 | 1.00 | 82.64 | C |
| HETATM | 3683 | C20 | CLR | A | 413 | −52.772 | 21.624 | 3.653 | 1.00 | 91.51 | C |
| HETATM | 3684 | C21 | CLR | A | 413 | −51.815 | 21.878 | 4.816 | 1.00 | 89.13 | C |
| HETATM | 3685 | C22 | CLR | A | 413 | −52.233 | 20.430 | 2.857 | 1.00 | 91.91 | C |
| HETATM | 3686 | C23 | CLR | A | 413 | −52.841 | 19.099 | 3.296 | 1.00 | 93.30 | C |
| HETATM | 3687 | C24 | CLR | A | 413 | −52.459 | 17.993 | 2.311 | 1.00 | 92.99 | C |

APPENDIX 1-continued

| | | | | | | | | | | |
|---|---|---|---|---|---|---|---|---|---|---|
| HETATM | 3688 | C25 | CLR | A | 413 | −51.938 | 16.746 | 3.002 | 1.00 | 92.39 | C |
| HETATM | 3689 | C26 | CLR | A | 413 | −52.059 | 15.541 | 2.076 | 1.00 | 94.36 | C |
| HETATM | 3690 | C27 | CLR | A | 413 | −50.499 | 16.952 | 3.460 | 1.00 | 89.59 | C |
| HETATM | 3691 | O1 | CLR | A | 413 | −53.334 | 32.684 | 1.607 | 1.00 | 81.53 | O |
| HETATM | 3692 | C1 | CLR | A | 414 | −41.706 | 27.953 | −4.419 | 1.00 | 114.97 | C |
| HETATM | 3693 | C2 | CLR | A | 414 | −41.768 | 29.448 | −4.709 | 1.00 | 114.73 | C |
| HETATM | 3694 | C3 | CLR | A | 414 | −40.664 | 29.838 | −5.694 | 1.00 | 114.23 | C |
| HETATM | 3695 | C4 | CLR | A | 414 | −40.711 | 29.022 | −7.000 | 1.00 | 115.07 | C |
| HETATM | 3696 | C5 | CLR | A | 414 | −40.836 | 27.528 | −6.714 | 1.00 | 115.29 | C |
| HETATM | 3697 | C6 | CLR | A | 414 | −40.069 | 26.669 | −7.418 | 1.00 | 115.44 | C |
| HETATM | 3698 | C7 | CLR | A | 414 | −40.081 | 25.169 | −7.226 | 1.00 | 116.17 | C |
| HETATM | 3699 | C8 | CLR | A | 414 | −41.303 | 24.678 | −6.473 | 1.00 | 115.82 | C |
| HETATM | 3700 | C9 | CLR | A | 414 | −41.567 | 25.570 | −5.252 | 1.00 | 114.14 | C |
| HETATM | 3701 | C10 | CLR | A | 414 | −41.815 | 27.052 | −5.652 | 1.00 | 114.08 | C |
| HETATM | 3702 | C11 | CLR | A | 414 | −42.685 | 24.996 | −4.348 | 1.00 | 113.90 | C |
| HETATM | 3703 | C12 | CLR | A | 414 | −42.459 | 23.526 | −3.999 | 1.00 | 115.68 | C |
| HETATM | 3704 | C13 | CLR | A | 414 | −42.294 | 22.667 | −5.238 | 1.00 | 115.89 | C |
| HETATM | 3705 | C14 | CLR | A | 414 | −41.123 | 23.217 | −6.042 | 1.00 | 116.05 | C |
| HETATM | 3706 | C15 | CLR | A | 414 | −40.935 | 22.171 | −7.143 | 1.00 | 117.57 | C |
| HETATM | 3707 | C16 | CLR | A | 414 | −41.285 | 20.849 | −6.450 | 1.00 | 117.86 | C |
| HETATM | 3708 | C17 | CLR | A | 414 | −41.874 | 21.195 | −5.060 | 1.00 | 116.61 | C |
| HETATM | 3709 | C18 | CLR | A | 414 | −43.602 | 22.724 | −6.051 | 1.00 | 114.74 | C |
| HETATM | 3710 | C19 | CLR | A | 414 | −43.197 | 27.247 | −6.285 | 1.00 | 114.74 | C |
| HETATM | 3711 | C20 | CLR | A | 414 | −42.937 | 20.193 | −4.516 | 1.00 | 116.12 | C |
| HETATM | 3712 | C21 | CLR | A | 414 | −43.284 | 20.508 | −3.065 | 1.00 | 114.86 | C |
| HETATM | 3713 | C22 | CLR | A | 414 | −42.503 | 18.733 | −4.603 | 1.00 | 115.06 | C |
| HETATM | 3714 | C23 | CLR | A | 414 | −43.586 | 17.708 | −4.216 | 1.00 | 115.00 | C |
| HETATM | 3715 | C24 | CLR | A | 414 | −42.985 | 16.411 | −3.662 | 1.00 | 113.44 | C |
| HETATM | 3716 | C25 | CLR | A | 414 | −42.272 | 15.571 | −4.726 | 1.00 | 113.32 | C |
| HETATM | 3717 | C26 | CLR | A | 414 | −40.869 | 16.077 | −5.018 | 1.00 | 111.52 | C |
| HETATM | 3718 | C27 | CLR | A | 414 | −42.204 | 14.107 | −4.309 | 1.00 | 112.05 | C |
| HETATM | 3719 | O1 | CLR | A | 414 | −40.674 | 31.263 | −5.966 | 1.00 | 114.05 | O |
| HETATM | 3720 | C1 | PLM | A | 415 | −57.959 | 33.303 | 4.949 | 1.00 | 94.70 | C |
| HETATM | 3721 | O2 | PLM | A | 415 | −57.047 | 33.732 | 4.211 | 1.00 | 99.49 | O |
| HETATM | 3722 | C2 | PLM | A | 415 | −58.012 | 31.828 | 5.279 | 1.00 | 93.74 | C |
| HETATM | 3723 | C3 | PLM | A | 415 | −59.131 | 31.125 | 4.492 | 1.00 | 92.47 | C |
| HETATM | 3724 | C4 | PLM | A | 415 | −58.642 | 29.982 | 3.590 | 1.00 | 91.37 | C |
| HETATM | 3725 | C5 | PLM | A | 415 | −59.532 | 28.742 | 3.701 | 1.00 | 89.98 | C |
| HETATM | 3726 | C6 | PLM | A | 415 | −59.310 | 27.816 | 2.505 | 1.00 | 88.93 | C |
| HETATM | 3727 | C7 | PLM | A | 415 | −60.003 | 26.467 | 2.677 | 1.00 | 86.74 | C |
| HETATM | 3728 | C8 | PLM | A | 415 | −59.012 | 25.330 | 2.467 | 1.00 | 86.47 | C |
| HETATM | 3729 | C9 | PLM | A | 415 | −59.709 | 23.971 | 2.504 | 1.00 | 88.96 | C |
| HETATM | 3730 | CA | PLM | A | 415 | −58.837 | 22.893 | 3.156 | 1.00 | 90.43 | C |
| HETATM | 3731 | CB | PLM | A | 415 | −59.094 | 21.474 | 2.622 | 1.00 | 94.25 | C |
| HETATM | 3732 | CC | PLM | A | 415 | −57.863 | 20.775 | 2.016 | 1.00 | 96.09 | C |
| HETATM | 3733 | CD | PLM | A | 415 | −57.471 | 19.483 | 2.752 | 1.00 | 100.00 | C |
| HETATM | 3734 | CE | PLM | A | 415 | −56.635 | 18.544 | 1.872 | 1.00 | 101.35 | C |
| HETATM | 3735 | CF | PLM | A | 415 | −56.391 | 17.207 | 2.576 | 1.00 | 101.14 | C |
| HETATM | 3736 | CG | PLM | A | 415 | −55.695 | 16.199 | 1.664 | 1.00 | 99.15 | C |
| HETATM | 3737 | C35 | 12P | A | 416 | −12.915 | 54.897 | 17.807 | 1.00 | 109.60 | C |
| HETATM | 3738 | O34 | 12P | A | 416 | −13.949 | 54.683 | 18.777 | 1.00 | 110.80 | O |
| HETATM | 3739 | C33 | 12P | A | 416 | −13.451 | 54.394 | 20.091 | 1.00 | 108.13 | C |
| HETATM | 3740 | C32 | 12P | A | 416 | −13.568 | 55.622 | 20.982 | 1.00 | 105.37 | C |
| HETATM | 3741 | O31 | 12P | A | 416 | −12.299 | 56.022 | 21.539 | 1.00 | 101.39 | O |
| HETATM | 3742 | C30 | 12P | A | 416 | −12.283 | 57.340 | 22.133 | 1.00 | 102.00 | C |
| HETATM | 3743 | C29 | 12P | A | 416 | −13.231 | 57.476 | 23.346 | 1.00 | 99.93 | C |
| HETATM | 3744 | O28 | 12P | A | 416 | −14.580 | 57.575 | 22.874 | 1.00 | 94.22 | O |
| HETATM | 3745 | C27 | 12P | A | 416 | −15.580 | 58.132 | 23.720 | 1.00 | 91.37 | C |
| HETATM | 3746 | C26 | 12P | A | 416 | −16.528 | 58.912 | 22.820 | 1.00 | 89.49 | C |
| HETATM | 3747 | O25 | 12P | A | 416 | −15.752 | 59.825 | 22.016 | 1.00 | 91.31 | O |
| HETATM | 3748 | C24 | 12P | A | 416 | −16.081 | 59.833 | 20.621 | 1.00 | 89.90 | C |
| HETATM | 3749 | C23 | 12P | A | 416 | −14.998 | 60.574 | 19.838 | 1.00 | 88.02 | C |
| HETATM | 3750 | O22 | 12P | A | 416 | −14.838 | 61.904 | 20.352 | 1.00 | 86.45 | O |
| HETATM | 3751 | C21 | 12P | A | 416 | −15.839 | 62.838 | 19.944 | 1.00 | 77.75 | C |
| HETATM | 3752 | C20 | 12P | A | 416 | −15.146 | 63.916 | 19.149 | 1.00 | 82.56 | C |
| HETATM | 3753 | O19 | 12P | A | 416 | −14.005 | 64.462 | 19.834 | 1.00 | 79.81 | O |
| HETATM | 3754 | C18 | 12P | A | 416 | −14.323 | 65.263 | 20.988 | 1.00 | 86.00 | C |
| HETATM | 3755 | C17 | 12P | A | 416 | −13.223 | 66.275 | 21.332 | 1.00 | 87.84 | C |
| HETATM | 3756 | O16 | 12P | A | 416 | −11.998 | 65.967 | 20.653 | 1.00 | 93.31 | O |
| HETATM | 3757 | C15 | 12P | A | 416 | −11.011 | 65.354 | 21.493 | 1.00 | 96.79 | C |
| HETATM | 3758 | O | HOH | A | 501 | −23.201 | 38.168 | 1.127 | 1.00 | 60.95 | O |
| HETATM | 3759 | O | HOH | A | 502 | −28.322 | 45.445 | 19.106 | 1.00 | 62.27 | O |
| HETATM | 3760 | O | HOH | A | 503 | −25.663 | 51.540 | 11.557 | 1.00 | 73.63 | O |
| HETATM | 3761 | O | HOH | A | 504 | −18.403 | 54.490 | 20.568 | 1.00 | 49.22 | O |
| HETATM | 3762 | O | HOH | A | 505 | −28.865 | 62.967 | 14.476 | 1.00 | 49.07 | O |
| HETATM | 3763 | O | HOH | A | 506 | −38.344 | 25.395 | 6.999 | 1.00 | 53.60 | O |
| HETATM | 3764 | O | HOH | A | 507 | −24.235 | 47.669 | 28.279 | 1.00 | 58.12 | O |
| HETATM | 3765 | O | HOH | A | 508 | −29.566 | 58.644 | 29.505 | 1.00 | 53.32 | O |
| HETATM | 3766 | O | HOH | A | 509 | −9.129 | 65.077 | 35.788 | 1.00 | 53.82 | O |
| HETATM | 3767 | O | HOH | A | 510 | −31.588 | 56.235 | 5.270 | 1.00 | 54.83 | O |

APPENDIX 1-continued

| | | | | | | | | | | |
|---|---|---|---|---|---|---|---|---|---|---|
| HETATM | 3768 | O | HOH | A | 511 | −33.767 | −0.936 | 2.970 | 1.00 | 76.89 | O |
| HETATM | 3769 | O | HOH | A | 512 | −36.831 | 52.163 | 25.686 | 1.00 | 59.37 | O |
| HETATM | 3770 | O | HOH | A | 513 | −20.293 | 51.784 | 5.369 | 1.00 | 57.17 | O |
| HETATM | 3771 | O | HOH | A | 514 | −33.710 | 48.038 | 30.053 | 1.00 | 55.19 | O |
| HETATM | 3772 | O | HOH | A | 515 | −27.498 | 71.737 | 31.097 | 1.00 | 72.77 | O |
| HETATM | 3773 | O | HOH | A | 516 | −38.419 | 75.003 | 17.409 | 1.00 | 63.18 | O |
| HETATM | 3774 | O | HOH | A | 517 | −13.008 | 52.291 | 33.720 | 1.00 | 54.29 | O |
| HETATM | 3775 | O | HOH | A | 518 | −25.417 | 49.449 | 2.526 | 1.00 | 84.88 | O |
| HETATM | 3776 | O | HOH | A | 519 | −44.492 | 24.103 | 10.594 | 1.00 | 70.04 | O |
| HETATM | 3777 | O | HOH | A | 520 | −53.192 | 34.656 | −0.012 | 0.50 | 68.32 | O |
| HETATM | 3778 | O | HOH | A | 521 | −33.730 | 52.334 | 13.531 | 1.00 | 71.71 | O |
| HETATM | 3779 | O | HOH | A | 522 | −19.401 | 44.894 | 11.284 | 1.00 | 82.98 | O |
| HETATM | 3780 | O | HOH | A | 523 | −20.706 | −4.455 | 5.029 | 1.00 | 74.00 | O |
| HETATM | 3781 | O | HOH | A | 524 | −18.878 | 44.843 | 24.435 | 1.00 | 71.79 | O |
| HETATM | 3782 | O | HOH | A | 525 | −26.266 | 47.546 | 12.074 | 1.00 | 96.88 | O |
| HETATM | 3783 | O | HOH | A | 526 | −35.818 | 54.612 | 25.448 | 1.00 | 65.23 | O |
| HETATM | 3784 | O | HOH | A | 527 | −27.911 | 63.928 | 17.098 | 1.00 | 56.73 | O |
| HETATM | 3785 | O | HOH | A | 528 | −34.136 | 24.300 | 12.374 | 1.00 | 64.85 | O |
| HETATM | 3786 | O | HOH | A | 529 | −31.485 | 13.403 | 16.427 | 1.00 | 55.45 | O |
| HETATM | 3787 | O | HOH | A | 530 | −33.229 | 46.525 | 27.509 | 1.00 | 62.72 | O |
| HETATM | 3788 | O | HOH | A | 531 | −37.000 | 56.927 | 26.470 | 1.00 | 69.85 | O |
| HETATM | 3789 | O | HOH | A | 532 | −38.272 | 23.691 | 9.991 | 1.00 | 74.37 | O |
| HETATM | 3790 | O | HOH | A | 533 | −23.738 | 45.700 | 30.214 | 1.00 | 70.87 | O |
| HETATM | 3791 | O | HOH | A | 534 | −35.547 | 18.917 | 9.368 | 1.00 | 68.76 | O |
| HETATM | 3792 | O | HOH | A | 535 | −27.520 | 46.018 | 35.709 | 1.00 | 73.73 | O |
| HETATM | 3793 | O | HOH | A | 536 | −11.169 | 52.639 | 27.107 | 1.00 | 53.63 | O |
| HETATM | 3794 | O | HOH | A | 537 | −35.161 | 36.603 | 6.920 | 1.00 | 84.70 | O |
| HETATM | 3795 | O | HOH | A | 538 | −13.331 | 64.631 | 16.826 | 1.00 | 78.41 | O |
| HETATM | 3796 | O | HOH | A | 539 | −15.737 | 37.989 | 13.501 | 1.00 | 74.20 | O |
| HETATM | 3797 | O | HOH | A | 540 | −17.612 | 49.885 | 19.741 | 1.00 | 67.69 | O |
| HETATM | 3798 | O | HOH | A | 541 | −28.871 | 56.041 | 4.930 | 1.00 | 62.51 | O |
| HETATM | 3799 | O | HOH | A | 542 | −18.100 | 62.470 | 17.192 | 1.00 | 64.11 | O |
| HETATM | 3800 | O | HOH | A | 543 | −39.876 | 5.502 | 10.338 | 1.00 | 78.73 | O |
| HETATM | 3801 | O | HOH | A | 544 | −39.732 | −5.317 | −4.531 | 1.00 | 75.67 | O |
| HETATM | 3802 | O | HOH | A | 545 | −19.865 | 59.621 | 17.222 | 1.00 | 67.78 | O |
| HETATM | 3803 | O | HOH | A | 546 | −37.397 | 27.672 | 6.120 | 1.00 | 59.62 | O |
| HETATM | 3804 | O | HOH | A | 547 | −19.199 | 49.833 | 44.410 | 1.00 | 55.49 | O |
| HETATM | 3805 | O | HOH | A | 548 | −35.618 | 21.645 | 8.827 | 1.00 | 61.27 | O |
| CONECT | 597 | 1283 | | | | | | | | | |
| CONECT | 1229 | 1277 | | | | | | | | | |
| CONECT | 1277 | 1229 | | | | | | | | | |
| CONECT | 1283 | 597 | | | | | | | | | |
| CONECT | 2906 | 3635 | | | | | | | | | |
| CONECT | 3535 | 3720 | | | | | | | | | |
| CONECT | 3545 | 3546 | 3551 | 3555 | | | | | | | |
| CONECT | 3546 | 3545 | 3547 | 3552 | | | | | | | |
| CONECT | 3547 | 3546 | 3548 | 3553 | | | | | | | |
| CONECT | 3548 | 3547 | 3549 | 3554 | | | | | | | |
| CONECT | 3549 | 3548 | 3550 | 3555 | | | | | | | |
| CONECT | 3550 | 3549 | 3556 | | | | | | | | |
| CONECT | 3551 | 3545 | 3560 | | | | | | | | |
| CONECT | 3552 | 3546 | | | | | | | | | |
| CONECT | 3553 | 3547 | | | | | | | | | |
| CONECT | 3554 | 3548 | | | | | | | | | |
| CONECT | 3555 | 3545 | 3549 | | | | | | | | |
| CONECT | 3556 | 3550 | | | | | | | | | |
| CONECT | 3557 | 3558 | 3563 | 3566 | | | | | | | |
| CONECT | 3558 | 3557 | 3559 | 3564 | | | | | | | |
| CONECT | 3559 | 3558 | 3560 | 3565 | | | | | | | |
| CONECT | 3560 | 3551 | 3559 | 3561 | | | | | | | |
| CONECT | 3561 | 3560 | 3562 | 3566 | | | | | | | |
| CONECT | 3562 | 3561 | 3567 | | | | | | | | |
| CONECT | 3563 | 3557 | | | | | | | | | |
| CONECT | 3564 | 3558 | | | | | | | | | |
| CONECT | 3565 | 3559 | | | | | | | | | |
| CONECT | 3566 | 3557 | 3561 | | | | | | | | |
| CONECT | 3567 | 3562 | | | | | | | | | |
| CONECT | 3568 | 3569 | 3570 | 3571 | 3572 | | | | | | |
| CONECT | 3569 | 3568 | | | | | | | | | |
| CONECT | 3570 | 3568 | | | | | | | | | |
| CONECT | 3571 | 3568 | | | | | | | | | |
| CONECT | 3572 | 3568 | | | | | | | | | |
| CONECT | 3573 | 3574 | 3575 | 3576 | 3577 | | | | | | |
| CONECT | 3574 | 3573 | | | | | | | | | |
| CONECT | 3575 | 3573 | | | | | | | | | |
| CONECT | 3576 | 3573 | | | | | | | | | |
| CONECT | 3577 | 3573 | | | | | | | | | |
| CONECT | 3578 | 3579 | 3580 | 3581 | 3582 | | | | | | |
| CONECT | 3579 | 3578 | | | | | | | | | |
| CONECT | 3580 | 3578 | | | | | | | | | |

APPENDIX 1-continued

| | | | | | |
|---|---|---|---|---|---|
| CONECT | 3581 | 3578 | | | |
| CONECT | 3582 | 3578 | | | |
| CONECT | 3583 | 3584 | 3585 | 3586 | 3587 |
| CONECT | 3584 | 3583 | | | |
| CONECT | 3585 | 3583 | | | |
| CONECT | 3586 | 3583 | | | |
| CONECT | 3587 | 3583 | | | |
| CONECT | 3588 | 3589 | 3590 | 3591 | 3592 |
| CONECT | 3589 | 3588 | | | |
| CONECT | 3590 | 3588 | | | |
| CONECT | 3591 | 3588 | | | |
| CONECT | 3592 | 3588 | | | |
| CONECT | 3593 | 3594 | 3595 | 3596 | 3597 |
| CONECT | 3594 | 3593 | | | |
| CONECT | 3595 | 3593 | | | |
| CONECT | 3596 | 3593 | | | |
| CONECT | 3597 | 3593 | | | |
| CONECT | 3598 | 3599 | | | |
| CONECT | 3599 | 3598 | 3600 | 3605 | |
| CONECT | 3600 | 3599 | 3601 | | |
| CONECT | 3601 | 3600 | 3602 | | |
| CONECT | 3602 | 3601 | 3603 | 3604 | |
| CONECT | 3603 | 3602 | | | |
| CONECT | 3604 | 3602 | | | |
| CONECT | 3605 | 3599 | 3606 | | |
| CONECT | 3606 | 3605 | 3607 | | |
| CONECT | 3607 | 3606 | 3608 | 3612 | |
| CONECT | 3608 | 3607 | 3609 | | |
| CONECT | 3609 | 3608 | 3610 | | |
| CONECT | 3610 | 3609 | 3611 | | |
| CONECT | 3611 | 3610 | 3612 | 3613 | |
| CONECT | 3612 | 3607 | 3611 | 3615 | |
| CONECT | 3613 | 3611 | 3614 | | |
| CONECT | 3614 | 3613 | 3615 | 3616 | |
| CONECT | 3615 | 3612 | 3614 | 3619 | |
| CONECT | 3616 | 3614 | 3617 | | |
| CONECT | 3617 | 3616 | 3618 | | |
| CONECT | 3618 | 3617 | 3619 | | |
| CONECT | 3619 | 3615 | 3618 | | |
| CONECT | 3620 | 3621 | 3624 | | |
| CONECT | 3621 | 3620 | 3622 | | |
| CONECT | 3622 | 3621 | 3623 | | |
| CONECT | 3623 | 3622 | 3625 | | |
| CONECT | 3624 | 3620 | | | |
| CONECT | 3625 | 3623 | | | |
| CONECT | 3626 | 3627 | 3630 | | |
| CONECT | 3627 | 3626 | 3628 | | |
| CONECT | 3628 | 3627 | 3629 | | |
| CONECT | 3629 | 3628 | 3631 | | |
| CONECT | 3630 | 3626 | | | |
| CONECT | 3631 | 3629 | | | |
| CONECT | 3632 | 3633 | 3634 | 3635 | |
| CONECT | 3633 | 3632 | | | |
| CONECT | 3634 | 3632 | | | |
| CONECT | 3635 | 2906 | 3632 | | |
| CONECT | 3636 | 3637 | 3645 | | |
| CONECT | 3637 | 3636 | 3638 | | |
| CONECT | 3638 | 3637 | 3639 | 3663 | |
| CONECT | 3639 | 3638 | 3640 | | |
| CONECT | 3640 | 3639 | 3641 | 3645 | |
| CONECT | 3641 | 3640 | 3642 | | |
| CONECT | 3642 | 3641 | 3643 | | |
| CONECT | 3643 | 3642 | 3644 | 3649 | |
| CONECT | 3644 | 3643 | 3645 | 3646 | |
| CONECT | 3645 | 3636 | 3640 | 3644 | 3654 |
| CONECT | 3646 | 3644 | 3647 | | |
| CONECT | 3647 | 3646 | 3648 | | |
| CONECT | 3648 | 3647 | 3649 | 3652 | 3653 |
| CONECT | 3649 | 3643 | 3648 | 3650 | |
| CONECT | 3650 | 3649 | 3651 | | |
| CONECT | 3651 | 3650 | 3652 | | |
| CONECT | 3652 | 3648 | 3651 | 3655 | |
| CONECT | 3653 | 3648 | | | |
| CONECT | 3654 | 3645 | | | |
| CONECT | 3655 | 3652 | 3656 | 3657 | |
| CONECT | 3656 | 3655 | | | |
| CONECT | 3657 | 3655 | 3658 | | |
| CONECT | 3658 | 3657 | 3659 | | |
| CONECT | 3659 | 3658 | 3660 | | |
| CONECT | 3660 | 3659 | 3661 | 3662 | |

APPENDIX 1-continued

| | | | | |
|---|---|---|---|---|
| CONECT | 3661 | 3660 | | |
| CONECT | 3662 | 3660 | | |
| CONECT | 3663 | 3638 | | |
| CONECT | 3664 | 3665 | 3673 | |
| CONECT | 3665 | 3664 | 3666 | |
| CONECT | 3666 | 3665 | 3667 | 3691 |
| CONECT | 3667 | 3666 | 3668 | |
| CONECT | 3668 | 3667 | 3669 | 3673 |
| CONECT | 3669 | 3668 | 3670 | |
| CONECT | 3670 | 3669 | 3671 | |
| CONECT | 3671 | 3670 | 3672 | 3677 |
| CONECT | 3672 | 3671 | 3673 | 3674 |
| CONECT | 3673 | 3664 | 3668 | 3672 | 3682 |
| CONECT | 3674 | 3672 | 3675 | |
| CONECT | 3675 | 3674 | 3676 | |
| CONECT | 3676 | 3675 | 3677 | 3680 | 3681 |
| CONECT | 3677 | 3671 | 3676 | 3678 |
| CONECT | 3678 | 3677 | 3679 | |
| CONECT | 3679 | 3678 | 3680 | |
| CONECT | 3680 | 3676 | 3679 | 3683 |
| CONECT | 3681 | 3676 | | |
| CONECT | 3682 | 3673 | | |
| CONECT | 3683 | 3680 | 3684 | 3685 |
| CONECT | 3684 | 3683 | | |
| CONECT | 3685 | 3683 | 3686 | |
| CONECT | 3686 | 3685 | 3687 | |
| CONECT | 3687 | 3686 | 3688 | |
| CONECT | 3688 | 3687 | 3689 | 3690 |
| CONECT | 3689 | 3688 | | |
| CONECT | 3690 | 3688 | | |
| CONECT | 3691 | 3666 | | |
| CONECT | 3692 | 3693 | 3701 | |
| CONECT | 3693 | 3692 | 3694 | |
| CONECT | 3694 | 3693 | 3695 | 3719 |
| CONECT | 3695 | 3694 | 3696 | |
| CONECT | 3696 | 3695 | 3697 | 3701 |
| CONECT | 3697 | 3696 | 3698 | |
| CONECT | 3698 | 3697 | 3699 | |
| CONECT | 3699 | 3698 | 3700 | 3705 |
| CONECT | 3700 | 3699 | 3701 | 3702 |
| CONECT | 3701 | 3692 | 3696 | 3700 | 3710 |
| CONECT | 3702 | 3700 | 3703 | |
| CONECT | 3703 | 3702 | 3704 | |
| CONECT | 3704 | 3703 | 3705 | 3708 | 3709 |
| CONECT | 3705 | 3699 | 3704 | 3706 |
| CONECT | 3706 | 3705 | 3707 | |
| CONECT | 3707 | 3706 | 3708 | |
| CONECT | 3708 | 3704 | 3707 | 3711 |
| CONECT | 3709 | 3704 | | |
| CONECT | 3710 | 3701 | | |
| CONECT | 3711 | 3708 | 3712 | 3713 |
| CONECT | 3712 | 3711 | | |
| CONECT | 3713 | 3711 | 3714 | |
| CONECT | 3714 | 3713 | 3715 | |
| CONECT | 3715 | 3714 | 3716 | |
| CONECT | 3716 | 3715 | 3717 | 3718 |
| CONECT | 3717 | 3716 | | |
| CONECT | 3718 | 3716 | | |
| CONECT | 3719 | 3694 | | |
| CONECT | 3720 | 3535 | 3721 | 3722 |
| CONECT | 3721 | 3720 | | |
| CONECT | 3722 | 3720 | 3723 | |
| CONECT | 3723 | 3722 | 3724 | |
| CONECT | 3724 | 3723 | 3725 | |
| CONECT | 3725 | 3724 | 3726 | |
| CONECT | 3726 | 3725 | 3727 | |
| CONECT | 3727 | 3726 | 3728 | |
| CONECT | 3728 | 3727 | 3729 | |
| CONECT | 3729 | 3728 | 3730 | |
| CONECT | 3730 | 3729 | 3731 | |
| CONECT | 3731 | 3730 | 3732 | |
| CONECT | 3732 | 3731 | 3733 | |
| CONECT | 3733 | 3732 | 3734 | |
| CONECT | 3734 | 3733 | 3735 | |
| CONECT | 3735 | 3734 | 3736 | |
| CONECT | 3736 | 3735 | | |
| CONECT | 3737 | 3738 | | |
| CONECT | 3738 | 3737 | 3739 | |
| CONECT | 3739 | 3738 | 3740 | |
| CONECT | 3740 | 3739 | 3741 | |

APPENDIX 1-continued

```
CONECT    3741   3740   3742
CONECT    3742   3741   3743
CONECT    3743   3742   3744
CONECT    3744   3743   3745
CONECT    3745   3744   3746
CONECT    3746   3745   3747
CONECT    3747   3746   3748
CONECT    3748   3747   3749
CONECT    3749   3748   3750
CONECT    3750   3749   3751
CONECT    3751   3750   3752
CONECT    3752   3751   3753
CONECT    3753   3752   3754
CONECT    3754   3753   3755
CONECT    3755   3754   3756
CONECT    3756   3755   3757
CONECT    3757   3756
MASTER     455      0     16     19      4      0     18      6   3804      1    219     39
END
```

The invention claimed is:

1. A composition for lipidic cubic phase crystallization of a membrane protein, comprising
    a polyethylene glycol or modified polyethylene glycol, wherein said polyethylene glycol has an average molecular weight of 300 to 2,000;
    0.1 to 0.5 M of a salt;
    a host lipid, wherein said host lipid is a monoacylglycerol;
    a lipid additive, wherein said lipid additive is a sterol, and wherein said sterol is present at a concentration of 5-20% w/w in said host lipid;
    a buffer, wherein said buffer has a pH between 4.5-8.0; and 1 to 100 mg/ml of a membrane protein.

2. The composition of claim 1, wherein said salt is selected from the group consisting of a sulfate salt, a citrate salt, a malonate salt, a tartrate salt, an acetate salt, and a formate salt.

3. The composition of claim 2, wherein said salt is present at a concentration of 0.1-0.2 M.

4. The composition of claim 1, wherein said buffer is present at a concentration of 0.05-0.5 M.

5. The composition of claim 1, further comprising an alcohol present at a concentration of 1-10% v/v.

6. The composition of claim 5, wherein said alcohol is present at a concentration of 5-7% v/v.

7. The composition of claim 5, wherein said alcohol is a diol or triol.

8. The composition of claim 1 wherein said host lipid is selected from the group consisting of monopalmitolein, monovaccenin and monoolein.

9. The composition of claim 1 wherein said protein to be crystallized in said composition is present at a concentration of 40-60 mg/mL.

10. The composition of claim 1 wherein said membrane protein is a G-protein coupled receptor.

11. The composition of claim 1, wherein said membrane protein comprises a $\beta_2$AR protein.

12. The composition of claim 11, further comprising a ligand selected from the group consisting of carazolol, timolol, alprenolol, and clenbutorol.

13. A method of generating crystals of a membrane protein comprising:
    mixing a lipid additive with a host lipid to form a lipid mixture, wherein said host lipid is a monoacylglycerol, and wherein said lipid additive is a sterol, and wherein said lipid additive is 5 to 20% w/w in said host lipid; and
    combining said lipid mixture with a membrane protein solution to form a protein-lipid mixture, wherein said membrane protein is present in said protein-lipid mixture at a concentration of between 1 and 100 mg/ml; and
    overlaying said protein-lipid mixture with a precipitant solution, wherein said precipitant solution comprises a polyethylene glycol or modified polyethylene glycol, wherein said polyethylene glycol has an average molecular weight of 300 to 2000; 0.1 to 0.5 M of a salt; and a buffer, wherein said buffer has a pH between 4.5-8.0.

14. A method of screening a crystal of a GPCR present in a liquid cubic phase composition comprising:
    preparing a lipidic cubic phase composition, wherein said composition comprises a G-protein coupled receptor (GPCR) protein, a polyethylene glycol or modified polyethylene glycol, wherein said polyethylene glycol has an average molecular weight of 300 to 2,000; 0.1 to 0.5 M of a salt; a host lipid, wherein said host lipid is a monoacylglycerol; a lipid additive, wherein said lipid additive is a sterol and wherein said sterol is present at a concentration of 5-20% w/w in said host lipid; and a buffer, wherein said buffer has a pH between 4.5-8.0; and
    exposing said composition to a first X-ray beam and determining a change in direction or intensity of said first X-ray beam;
    exposing said composition to a second beam and determining a change in direction or intensity of said second X-ray beam;
    identifying an area where said GPCR crystal is present in said composition; and
    exposing said identified area to at least a third X-ray beam.

* * * * *

UNITED STATES PATENT AND TRADEMARK OFFICE
CERTIFICATE OF CORRECTION

PATENT NO. : 8,252,899 B2  
APPLICATION NO. : 12/739134  
DATED : August 28, 2012  
INVENTOR(S) : Stevens et al.

Page 1 of 1

It is certified that error appears in the above-identified patent and that said Letters Patent is hereby corrected as shown below:

In the Specification

Column 1, Lines 15-24, the paragraph STATEMENT AS TO FEDERALLY SPONSORED RESEARCH should be changed to:
-- STATEMENT OF GOVERNMENT LICENSE RIGHTS
This invention was made with government support under grant numbers GM073197, GM074691, and GM062411 awarded by the National Institutes of Health. The government has certain rights in the invention. --

Signed and Sealed this  
Seventh Day of April, 2020

Andrei Iancu  
*Director of the United States Patent and Trademark Office*